(12) United States Patent
Kimura et al.

(10) Patent No.: US 7,829,580 B2
(45) Date of Patent: Nov. 9, 2010

(54) CYCLIC AMINE DERIVATIVE HAVING HETEROARYL RING

(75) Inventors: Tomio Kimura, Tokyo (JP); Naoki Tanaka, Tokyo (JP); Atsuhiro Sugidachi, Tokyo (JP); Toshiyuki Konosu, Tokyo (JP)

(73) Assignee: Sankyo Company, Ltd., Tokyo (JP)

( * ) Notice: Subject to any disclaimer, the term of this patent is extended or adjusted under 35 U.S.C. 154(b) by 820 days.

(21) Appl. No.: 11/442,429

(22) Filed: May 26, 2006

(65) Prior Publication Data

US 2006/0270706 A1 Nov. 30, 2006

(51) Int. Cl.
*A61K 31/445* (2006.01)
*C07D 211/54* (2006.01)

(52) U.S. Cl. .................. 514/317; 514/252; 514/255; 514/256; 514/316; 514/323; 514/326; 514/331; 544/238; 544/333; 544/405; 546/194; 546/201; 546/209; 546/210

(58) Field of Classification Search ............... 514/252, 514/255, 256, 316, 317, 323, 326, 331; 544/238, 544/333, 405; 546/194, 201, 209, 210
See application file for complete search history.

(56) References Cited

U.S. PATENT DOCUMENTS

| | | | |
|---|---|---|---|
| 5,750,754 A | 5/1998 | Mills | |
| 6,087,379 A | 7/2000 | Asai et al. | |
| 6,610,708 B1 | 8/2003 | Asai et al. | |
| 2004/0254376 A1 | 12/2004 | Suzuki et al. | |
| 2006/0270706 A1* | 11/2006 | Kimura et al. | 514/317 |
| 2009/0306059 A1* | 12/2009 | Kimura et al. | 514/227.8 |

FOREIGN PATENT DOCUMENTS

| | | |
|---|---|---|
| JP | 11-310570 | 11/1999 |
| JP | 11-315020 | 11/1999 |
| JP | 3088016 | 7/2000 |
| JP | 10-120649 | 2/2002 |
| JP | 2007-001974 | * 11/2007 |
| WO | WO 94/22835 | 10/1994 |
| WO | WO 02/085850 | 10/2002 |

OTHER PUBLICATIONS

Wyngaarden et al. "Cecil Textbook of medicine" p. 247 (1983).*
definition "prodrug" MedicieNet.com (2009) (1 page from internet).*
Kimura et al. "preparation of cyclic amine . . . " CA 145:505461 (2006).*
Kimura et al "Preparation of cyclic amine . . . " CA 146:121973 (2007).*
Kimura et al. "preparation of cyclic amine . . . " CA 149:128750 (2008).*
Web definition of prodrug (2010).*

International Search Report for International Application No. PCT/JP2004/017974, date of mailing International Search Report: Feb. 15, 2005.
U.S. Appl. No. 11/915,522, filed Nov. 26, 2007, Kimura, et al.
Supplementary European Search Report for European Application No. 06 74 6885 as issued Mar. 11, 2010; which is the European application of the related U.S. Appl. No. 11/915,522.
English Abstract of JP 11-315052.
Search Report and Written Opinion for Singapore Application No. 200718118-3 as issued May 26, 2009; which is the Singapore application of the related U.S. Appl. No. 11/915,522.
Sugidachi, A., et al., "Antiplatelet action of R-99224, an active metabolite of a novel thienopyridine-type Gi-linked P2T antagonist, CS-747", British Journal of Pharmacology (2001), 132, pp. 47-54.
Sugidachi, A., et al., "The in vivo pharmacological profile of CS-747, a novel antiplatelet agent with platelet ADP receptor antagonist properties", British Journal of Pharmacology (2000), 129, pp. 1439-1446.
Pereillo, J., et al., "Structure and Stereochemistry of the Active Metabolite of Clopidogrel", Drug Metabolism and Disposition, 2002, The American Society of Pharmacology and Experimental Therapeutics, DMD 30, pp. 1288-1295.
Born et al., "The aggregation of Blood Platelets." *The Journal of Physiology*, vol. 168, 178, 1963.
T. W. Green et al., "Protective Groups in Organic Synthesis, Third Edition", John Wiley & Sons, Inc. (1999)—in particular pp. 17-245 and 369-493.
S. Reddy, et al.: Tetrahedron Letters, 41: 6285-6288, (2000).
Caprie Steering Committee. "A randomised, blinded, trial of clopidogrel versus aspirin in patients at risk of ischaemic events (Caprie)", *The Lancet*, 348:1329-39 (1996).
"Cecil Textbook of Medicine" sixteenth edition; eds. Wyngaarden, J.B. and Smith L.H.; W.B. Saunders Company. p. 247. (1983).
English Translation of the International Preliminary Report on Patentability together with the Written Opinion of the International Search Authority as issued in Application PCT/JP2004/017974, dated Jul. 24, 2006; which is the corresponding PCT application.

(Continued)

*Primary Examiner*—Celia Chang
(74) *Attorney, Agent, or Firm*—Brandon T. Schurter; Locke Lord Bissell & Liddell

(57) ABSTRACT

A compound having the general formula (I)

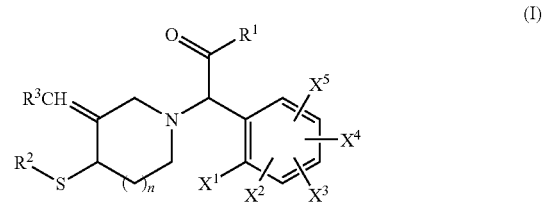

(I)

wherein $R^1$ represents C1-C6 alkyl, etc., $R^2$ represents hydrogen, C2-C7 alkanoyl, C7-C11 arylcarbonyl, the formula $R^4$—$(CH_2)_r$—, etc., $R^3$ represents C6-C10 aryl, etc., $X^1$, $X^2$, $X^3$, $X^4$ and $X^5$ each independently represents hydrogen, halogen, etc., and n represents an integer of 0 to 2, pharmacologically acceptable salts thereof or prodrugs thereof. They have excellent inhibition of platelet activation, etc. and are useful as a prophylactic or therapeutic agents for diseases related to thrombus or embolus formation.

72 Claims, No Drawings

OTHER PUBLICATIONS

International Search Report as issued in Application PCT/JP2004/017974, dated Feb. 15, 2005; which is the corresponding PCT application.

English Translation of the International Preliminary Report on Patentability together with the Written Opinion of the International Search Authority as issued in Application PCT/JP2006/310556, dated Nov. 29, 2007; which is the International application of the related U.S. Appl. No. 11/915,522.

International Search Report as issued in Application PCT/JP2006/310556, dated Jul. 25, 2006; which is the International application of the related U.S. Appl. No. 11/915,522.

* cited by examiner

CYCLIC AMINE DERIVATIVE HAVING HETEROARYL RING

This application claims the benefit under 35 U.S.C. §120 and under 35 U.S.C. §365(c) of PCT/JP2004/017974, which was filed Nov. 26, 2004 designating the U.S., and claims the benefit under 35 U.S.C. §119(a)-(d) of Japanese Patent Application 2003-399960, filed Nov. 28, 2003. The contents of the prior applications are hereby incorporated by reference in their entirety.

TECHNICAL FIELD

The present invention relates to compounds which exhibit activity in the inhibition of platelet aggregation, pharmacologically acceptable salts thereof and prodrugs thereof.

BACKGROUND OF THE INVENTION

Recently, the number of patients with cardiovascular diseases associated with aging of the population and changes of eating habits and lifestyle has risen markedly. Since thrombotic diseases such as cerebral infarction, myocardial infarction and peripheral circulatory disorders have not only high morbidity but also result in poor prognosis and limitation on activities of daily living, patients with these disorders have an undue burden of personal and social disability. It is well known that the direct causes of these diseases are angiostenosis caused by thrombus induced by platelet activation (adhesion to damaged areas of blood vessels, release of physiologically active substances, clot formation, and so on) and ischemia associated with angiostenosis. Thus, antithrombotic agents that inhibit platelet activation play important roles in preventing the occurrence and recurrence of these diseases as well as in their treatment. Furthermore, these agents are considered to become more and more important in the future as the number of patients with thrombotic diseases increases.

Several biological substances related to platelet aggregation, such as adenosine 5'-diphosphate (ADP), thromboxane $A_2$ (TXA$_2$), collagen, serotonin (5-HT) and the like, are known. Moreover, P2Y$_1$ and P2Y$_{12}$ receptors are known as ADP receptors. Some existing antithrombotic agents act by exerting antagonistic action against these receptors. Examples of such antithrombotic agents are ticlopidine and clopidogrel, which have thienopyridine structures.

In addition, compounds as described in WO98/08811 or WO99/43648 are known as compounds having non-thienopyridine structures and antagonistic action against ADP receptors. However, there are certain problems in that these compounds are chemically unstable or only weakly active.

SUMMARY OF THE INVENTION

The compounds of the present invention are chemically stable and exert excellent platelet anticoagulation activities and inhibiting action against thrombosis formation. Furthermore, the compounds of the present invention exert the said actions with short onset latencies and exhibit low toxicities. Thus, the compounds of the present invention may be useful in the prophylactic, prevention of recurrence, and therapeutic settings (particularly the latter) against diseases induced by platelet activation such as thrombosis formation and platelet coagulation and releasing responses of platelets, for example in percutaneous coronary intervention (PCI), angioplasty, endarterectomy, restenosis after stenting, acute coronary syndrome, stable and unstable angina, myocardial infarction, atrial fibrillation, cerebral ischemic attack, cerebral infarction, and atherosclerosis and diseases induced by thrombosis formation or embolus formation that are associated with diabetes mellitus, peripheral arterial disease, heparin-induced thrombocytopenia (HIT), thrombotic thrombocytopenic purpura (TTP), antiphospholipid antibody syndrome, venous thrombosis, and ichorrhemia.

DETAILED DESCRIPTION OF THE INVENTION

To create novel antithrombotic agents, the present inventors have diligently explored chemically stable compounds having non-thienopyridine structures and activity in the inhibition of platelet aggregation, and found that compounds having the general formula (I) of the present invention, pharmacologically acceptable salts thereof and prodrugs thereof have desirable characteristics, and thus completed the present invention.

The present invention provides pharmaceutical compositions comprising compounds having the general formula (I), pharmacologically acceptable salts thereof and prodrugs thereof, as active ingredients (particularly pharmaceutical compositions for prophylactic or therapeutic agents for diseases related to thrombus or embolus formation), use of compounds having the general formula (I), pharmacologically acceptable salts thereof and prodrugs thereof to manufacture pharmaceutical compositions (particularly pharmaceutical compositions for prophylactic or therapeutic agents for diseases related to thrombus or embolus formation) and prophylactic or therapeutic methods for diseases (particularly diseases related to thrombus or embolus formation) by administration of compounds having the general formula (I), pharmacologically acceptable salts thereof and prodrugs thereof to warm-blooded animals (especially humans) at pharmacologically effective doses.

The present invention relates the compound having the general formula (I) shown below,

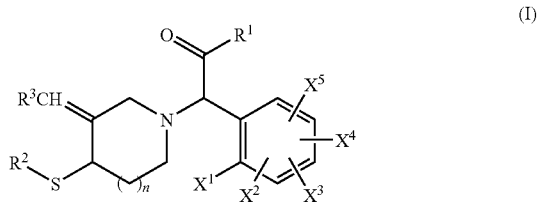

[wherein, $R^1$ represents a hydrogen atom, a C1-C6 alkyl group which may be substituted (said substituent group represents a halogen atom or a C1-C6 alkoxy group), a C3-C6 cycloalkyl group which may be substituted (said substituent group represents a halogen atom or a C1-C6 alkoxy group), a C1-C6 alkoxy group which may be substituted (said substituent group represents a halogen atom or a C1-C6 alkoxy group) or a C6-C10 aryl group which may be substituted (said substituent group represents a halogen atom, a C1-C6 alkyl group, a C1-C6 alkoxy group, a cyano group or a nitro group);

$R^2$ represents a hydrogen atom, a C1-C7 alkanoyl group, a C7-C11 arylcarbonyl group, a group of formula $R^4$—(CH$_2$)$_l$—CO— (wherein $R^4$ represents a C1-C6 alkoxy group, an amino group, a C1-C6 alkylamino group, a di-(C1-C6 alkyl)amino group or a carboxyl group; and l represents an integer of from 0 to 4), a C6-C10 arylsulfonyl group, a C7-C16 alkylarylsulfonyl group, a C1-C6 alkylsulfanyl group or a C1-C6 alkylsulfanyl group substituted with 1 or 2 substituents selected from a group consisting of "an amino group, a carboxyl group, a C1-C6 acylamino group and a C2-C7 alkoxycarbonyl group";

$R^3$ represents a C6-C10 aryl group, a C6-C10 aryl group substituted with from 1 to 5 substituents selected from <Substituent group α>, a heteroaryl group or a heteroaryl group substituted with from 1 to 5 substituents selected from <Substituent group α>;

$X^1$, $X^2$, $X^3$, $X^4$ and $X^5$ represent independently a hydrogen atom, a halogen atom, an amino group, a carboxyl group, a carbamoyl group, a cyano group, a nitro group, a C1-C6 alkyl group, a halogeno C1-C6 alkyl group, a C1-C6 alkoxy group or a halogeno C1-C6 alkoxy group;

n represents an integer of from 0 to 2; and

<Substituent group α> is defined by:

a halogen atom, an amino group, a carboxyl group, a carbamoyl group, a cyano group, a nitro group, a C1-C6 alkyl group, a halogeno C1-C6 alkyl group, a C1-C6 alkyl group substituted with heteroaryl group(s), a C1-C6 alkoxy group, a halogeno C1-C6 alkoxy group, a hydroxy C1-C6 alkyl group, a C2-C12 alkoxyalkyl group, a C2-C7 alkanoyl group, a C4-C7 cycloalkylcarbonyl group, a C1-C6 alkylamino group, a di-(C1-C6 alkyl)amino group, a C2-C7 alkylcarbamoyl group, a di-(C1-C6 alkyl)carbamoyl group, a group of formula $R^5$—CO—CHR$^6$—(CH$_2$)$_m$— (wherein $R^5$ represents a hydroxyl group, an amino group, a C1-C6 alkyl group, a C1-C6 alkylamino group, a di-(C1-C6 alkyl)amino group, a hydroxyamino group, a C1-C6 alkoxyamino group or a C1-C6 alkoxy group;

$R^6$ represents a hydrogen atom, a C1-C6 alkyl group, a C2-C7 carboxyalkyl group or a C3-C13 alkoxycarbonylalkyl group; and m represents an integer of from 0 to 5) and a sulfamoyl C1-C6 alkyl group], pharmacologically acceptable salts thereof and prodrugs thereof.

A compound having the general formula (I) shown above, pharmacologically acceptable salts thereof and prodrugs thereof are preferably (1) a compound wherein $R^1$ represents a C1-C6 alkyl group, a halogeno C1-C6 alkyl group, a C3-C6 cycloalkyl group, a halogeno C3-C6 cycloalkyl group or a C1-C6 alkoxy group, pharmacologically acceptable salts thereof or prodrugs thereof;

(2) a compound wherein $R^1$ represents a C3-C6 cycloalkyl group, a halogeno C3-C6 cycloalkyl group or a C1-C6 alkoxy group, pharmacologically acceptable salts thereof or prodrugs thereof;

(3) a compound wherein $R^1$ represents a C3-C6 cycloalkyl group or a C1-C6 alkoxy group, pharmacologically acceptable salts thereof or prodrugs thereof;

(4) a compound wherein $R^1$ represents a cyclopropyl group or a methoxy group, pharmacologically acceptable salts thereof or prodrugs thereof;

(5) a compound wherein $R^1$ represents a cyclopropyl group, pharmacologically acceptable salts thereof or prodrugs thereof;

(6) a compound wherein $R^2$ represents a hydrogen atom or a C2-C7 alkanoyl group, pharmacologically acceptable salts thereof or prodrugs thereof;

(7) a compound wherein $R^2$ represents a hydrogen atom or an acetyl group, pharmacologically acceptable salts thereof or prodrugs thereof;

(8) a compound wherein $R^2$ represents a hydrogen atom, pharmacologically acceptable salts thereof or prodrugs thereof;

(9) a compound wherein $R^3$ represents a heteroaryl group or a heteroaryl group substituted with 1 or 2 substituents selected from <Substituent group α>, pharmacologically acceptable salts thereof or prodrugs thereof;

(10) a compound wherein $R^3$ represents a heteroaryl group or a heteroaryl group substituted with one substituent selected from <Substituent group α>, pharmacologically acceptable salts thereof or prodrugs thereof;

(11) a compound wherein $R^3$ represents a heteroaryl group substituted with one substituent selected from <Substituent group α>, pharmacologically acceptable salts thereof or prodrugs thereof;

(12) a compound wherein $R^3$ represents a heteroaryl group substituted with one substituent selected from <Substituent group α>, and said substituent selected from <Substituent group α> represents a group of formula $R^5$—CO—CHR$^6$—(CH$_2$)$_m$— (wherein $R^5$ represents a hydroxyl group, an amino group, a C1-C6 alkyl group, a C1-C6 alkylamino group, a di-(C1-C6 alkyl)amino group, a hydroxyamino group, a C1-C6 alkoxyamino group or a C1-C6 alkoxy group; $R^6$ represents a hydrogen atom; and m represents an integer of from 0 to 5), pharmacologically acceptable salts thereof or prodrugs thereof;

(13) a compound wherein $R^3$ represents a heteroaryl group substituted with one substituent selected from <Substituent group α>, and said substituent selected from <Substituent group α> represents a group of formula $R^5$—CO—CHR$^6$—(CH$_2$)$_m$— (wherein $R^5$ represents a hydroxyl group, a hydroxyamino group, a C1-C6 alkoxyamino group or a C1-C6 alkoxy group; $R^6$ represents a hydrogen atom; and m represents an integer of from 0 to 5), pharmacologically acceptable salts thereof or prodrugs thereof;

(14) a compound wherein $R^3$ represents a heteroaryl group substituted with one substituent selected from <Substituent group α>, and said substituent selected from <Substituent group α> represents a group of formula $R^5$—CO—CHR$^6$—(CH$_2$)$_m$— (wherein $R^5$ represents a hydroxyl group; $R^6$ represents a hydrogen atom; and m represents an integer of from 0 to 2), pharmacologically acceptable salts thereof or prodrugs thereof;

(15) a compound wherein a heteroaryl group of $R^3$ represents a furyl group, thienyl group, pyrrolyl group, pyrazolyl group, imidazolyl group, oxazolyl group, isoxazolyl group, thiazolyl group, triazolyl group, tetrazolyl group, thiadiazolyl group, oxadiazolyl group, pyridyl group, pyridazinyl group, pyrimidinyl group, pyrazinyl group, indolyl group or quinolyl group, pharmacologically acceptable salts thereof or prodrugs thereof;

(16) a compound wherein a heteroaryl group of $R^3$ represents a pyrrolyl group, pyrazolyl group, imidazolyl group, triazolyl group or tetrazolyl group, pharmacologically acceptable salts thereof or prodrugs thereof;

(17) a compound wherein a heteroaryl group of $R^3$ represents a pyrazolyl group, triazolyl group or tetrazolyl group, pharmacologically acceptable salts thereof or prodrugs thereof;

(18) a compound wherein $R^3$ represents a 1-(carboxymethyl)-1H-pyrazol-3-yl, 1-(2-carboxyethyl)-1H-pyrazol-3-yl, 1-(3-carboxypropyl)-1H-pyrazol-3-yl, 1-(carboxymethyl)-1H-pyrazol-4-yl, 1-(2-carboxyethyl)-1H-pyrazol-4-yl, 1-(3-carboxypropyl)-1H-pyrazol-4-yl, 1-(carboxymethyl)-1H-1,2,3-triazol-4-yl, 1-(2-carboxyethyl)-1H-1,2,3-triazol-4-yl, 1-(3-carboxypropyl)-1H-1,2,3-triazol-4-yl, 1-(4-carboxybutyl)-1H-1,2,3-triazol-4-yl, 1-(carboxymethyl)-1H-1,2,3-triazol-5-yl, 1-(2-carboxyethyl)-1H-1,2,3-triazol-5-yl, 1-(3-carboxypropyl)-1H-1,2,3-triazol-5-yl, 1-(4-carboxybutyl)-1H-1,2,3-triazol-5-yl, 2-(carboxymethyl)-2H-1,2,3-triazol-4-yl, 2-(2-carboxyethyl)-2H-1,2,3-triazol-4-yl, 2-(3-carboxypropyl)-2H-1,2,3-triazol-4-yl, 1-(carboxymethyl)-1H-tetrazol-5-yl, 1-(2-carboxyethyl)-1H-tetrazol-5-yl, 1-(3-carboxypropyl)-1H-tetrazol-5-yl, 1-(4-carboxybutyl)-1H-tetrazol-5-yl, 2-(carboxymethyl)-2H-tetrazol-5-yl, 2-(2-carboxyethyl)-2H-tetrazol-5-yl, 2-(3-carboxypropyl)-2H-tetrazol-5-yl or 2-(4-carboxybutyl)-2H-tetrazol-5-yl group, pharmacologically acceptable salts thereof or prodrugs thereof;

(19) a compound wherein $X^1$, $X^2$, $X^3$, $X^4$ and $X^5$ represent independently a hydrogen atom or a halogen atom, pharmacologically acceptable salts thereof or prodrugs thereof;

(20) a compound wherein $X^1$ and $X^2$ represent independently a hydrogen atom or a halogen atom, and $X^3$, $X^4$ and $X^5$ represent a hydrogen atom, pharmacologically acceptable salts thereof or prodrugs thereof;

(21) a compound wherein $X^1$ represents a halogen atom, and $X^2$, $X^3$, $X^4$ and $X^5$ represent a hydrogen atom, pharmacologically acceptable salts thereof or prodrugs thereof;

(22) a compound wherein $X^1$ represents a fluorine atom, and $X^2$, $X^3$, $X^4$ and $X^5$ represent a hydrogen atom, pharmacologically acceptable salts thereof or prodrugs thereof;

(23) a compound wherein n represents 0 or 1, pharmacologically acceptable salts thereof or prodrugs thereof; or

(24) a compound wherein n represents 1, pharmacologically acceptable salts thereof or prodrugs thereof.

Further, in each group of (1)-(5), (6)-(8), (9)-(18), (19)-(22) and (23)-(24) described above, a more preferable compound is shown as the number increases [the same concept is applied to each group of (25)-(28) described below]. A compound obtained by selecting $R^1$ from each group of (1)-(5), $R^2$ from each group of (6)-(8), $R^3$ from each group of (9)-(18), $X^1$, $X^2$, $X^3$, $X^4$ and $X^5$ from each group of (19)-(22) and n from each group of (23)-(24), respectively, followed by arbitrarily combining these selected groups is also preferable, and can be, for example, the following:

(25) a compound wherein $R^1$ represents a C3-C6 cycloalkyl group or a C1-C6 alkoxy group;

$R^2$ represents a hydrogen atom or a C2-C7 alkanoyl group;

$R^3$ represents a heteroaryl group substituted with one substituent selected from <Substituent group α>, said substituent selected from <Substituent group α> represents a group of formula $R^5$—CO—CHR$^6$—(CH$_2$)$_m$— (wherein $R^5$ represents a hydroxyl group, a hydroxyamino group, a C1-C6 alkoxyamino group or a C1-C6 alkoxy group; $R^6$ represents a hydrogen atom; and m represents an integer of from 0 to 5), and a heteroaryl group of $R^3$ represents a pyrrolyl group, pyrazolyl group, imidazolyl group, triazolyl group or tetrazolyl group;

$X^1$ and $X^2$ represent independently a hydrogen atom or a halogen atom;

$X^3$, $X^4$ and $X^5$ represent a hydrogen atom; and n represents 0 or 1, pharmacologically acceptable salts thereof or prodrugs thereof;

(26) a compound wherein $R^1$ represents a cyclopropyl group or a methoxy group;

$R^2$ represents a hydrogen atom or an acetyl group;

$R^3$ represents a heteroaryl group substituted with one substituent selected from <Substituent group α>, said substituent selected from <Substituent group α> represents a group of formula $R^5$—CO—CHR$^6$—(CH$_2$)$_m$— (wherein $R^5$ represents a hydroxyl group, a hydroxyamino group, a C1-C6 alkoxyamino group or a C1-C6 alkoxy group; $R^6$ represents a hydrogen atom; and m represents an integer of from 0 to 5), and a heteroaryl group of $R^3$ represents a pyrrolyl group, pyrazolyl group, imidazolyl group, triazolyl group or tetrazolyl group;

$X^1$ represents a halogen atom;

$X^2$, $X^3$, $X^4$ and $X^5$ represent a hydrogen atom; and n represents 1, pharmacologically acceptable salts thereof or prodrugs thereof;

(27) a compound wherein $R^1$ represents a cyclopropyl group or a methoxy group;

$R^2$ represents a hydrogen atom;

$R^3$ represents a heteroaryl group substituted with one substituent selected from <Substituent group α>, said substituent selected from <Substituent group α> represents a group of formula $R^5$—CO—CHR$^6$—(CH$_2$)$_m$— (wherein $R^5$ represents a hydroxyl group; $R^6$ represents a hydrogen atom; and m represents an integer of from 0 to 2), a heteroaryl group of $R^3$ represents a pyrazolyl group, triazolyl group or tetrazolyl group;

$X^1$ represents a fluorine atom;

$X^2$, $X^3$, $X^4$ and $X^5$ represent a hydrogen atom; and n represents 1, pharmacologically acceptable salts thereof or prodrugs thereof; or

(28) a compound wherein $R^1$ represents a cyclopropyl group or a methoxy group;

$R^2$ represents a hydrogen atom;

$R^3$ represents a 1-(carboxymethyl)-1H-pyrazol-3-yl, 1-(2-carboxyethyl)-1H-pyrazol-3-yl, 1-(3-carboxypropyl)-1H-pyrazol-3-yl, 1-(carboxymethyl)-1H-pyrazol-4-yl, 1-(2-carboxyethyl)-1H-pyrazol-4-yl, 1-(3-carboxypropyl)-1H-pyrazol-4-yl, 1-(carboxymethyl)-1H-1,2,3-triazol-4-yl, 1-(2-carboxyethyl)-1H-1,2,3-triazol-4-yl, 1-(3-carboxypropyl)-1H-1,2,3-triazol-4-yl, 1-(4-carboxybutyl)-1H-1,2,3-triazol-4-yl, 1-(carboxymethyl)-1H-1,2,3-triazol-5-yl, 1-(2-carboxyethyl)-1H-1,2,3-triazol-5-yl, 1-(3-carboxypropyl)-1H-1,2,3-triazol-5-yl, 1-(4-carboxybutyl)-1H-1,2,3-triazol-5-yl, 2-(carboxymethyl)-2H-1,2,3-triazol-4-yl, 2-(2-carboxyethyl)-2H-1,2,3-triazol-4-yl, 2-(3-carboxypropyl)-2H-1,2,3-triazol-4-yl, 1-(carboxymethyl)-1H-tetrazol-5-yl, 1-(2-carboxyethyl)-1H-tetrazol-5-yl, 1-(3-carboxypropyl)-1H-tetrazol-5-yl, 1-(4-carboxybutyl)-1H-tetrazol-5-yl, 2-(carboxymethyl)-2H-tetrazol-5-yl, 2-(2-carboxyethyl)-2H-tetrazol-5-yl, 2-(3-carboxypropyl)-2H-tetrazol-5-yl or 2-(4-carboxybutyl)-2H-tetrazol-5-yl group;

$X^1$ represents a fluorine atom;

$X^2$, $X^3$, $X^4$ and $X^5$ represent a hydrogen atom; and n represents 1, pharmacologically acceptable salts thereof or prodrugs thereof.

Furthermore, another aspect of the present invention relates to a medicament containing the compound, pharmacologically acceptable salts thereof or prodrugs thereof described in (1)-(28) above (preferably an antithrombotic agent).

The compound having the general formula (I') shown below,

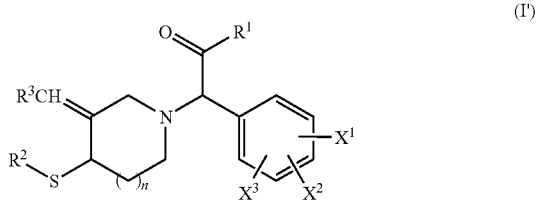

(I')

[wherein, $R^1$ represents a C1-C6 alkyl group, a halogeno C1-C6 alkyl group, a C3-C6 cycloalkyl group, a halogeno C3-C6 cycloalkyl group, a C1-C6 alkoxy group, a halogeno C1-C6 alkoxy group, a C6-C10 aryl group or a halogeno C6-C10 aryl group;

$R^2$ represents a hydrogen atom, a C2-C7 alkanoyl group, a C7-C11 arylcarbonyl group, a group of formula $R^4$—$(CH_2)_l$—CO— (wherein $R^4$ represents a C1-C6 alkoxy group, an amino group, a C1-C6 alkylamino group, a di-(C1-C6 alkyl)amino group or a carboxyl group; and l represents an integer of from 0 to 4), a C6-C10 arylsulfonyl group, a C7-C16 alkylarylsulfonyl group, a C1-C6 alkylsulfanyl group or a C1-C6 alkylsulfanyl group substituted with 1 or 2 substituents selected from a group consisting of "an amino group, a carboxyl group, a C1-C6 acylamino group and a C2-C7 alkoxycarbonyl group";

$R^3$ represents a C6-C10 aryl group, a C6-C10 aryl group substituted with from 1 to 2 substituents selected from <Substituent group α'>, a heteroaryl group or a heteroaryl group substituted with 1 or 2 substituents selected from <Substituent group α'>; and $X^1$, $X^2$ and $X^3$ represent independently a hydrogen atom, a halogen atom, an amino group, a carboxyl group, a carbamoyl group, a cyano group, a nitro group, a C1-C6 alkyl group, a halogeno C1-C6 alkyl group, a C1-C6 alkoxy group or a halogeno C1-C6 alkoxy group;

n represents an integer of from 0 to 2; and

<Substituent group α'> is defined by:

a halogen atom, an amino group, a carboxyl group, a carbamoyl group, a cyano group, a nitro group, a C1-C6 alkyl group, a halogeno C1-C6 alkyl group, a C1-C6 alkyl group substituted with heteroaryl group(s), a C1-C6 alkoxy group, a halogeno C1-C6 alkoxy group, a C2-C12 alkoxyalkyl group, a C2-C7 alkanoyl group, a C4-C7 cycloalkylcarbonyl group, a C1-C6 alkylamino group, a di-(C1-C6 alkyl)amino group, a C2-C7 alkylcarbamoyl group, a di-(C1-C6 alkyl)carbamoyl group, a group of formula $R^5$—CO—$CHR^6$—$(CH_2)_n$— (wherein $R^5$ represents a hydroxyl group, an amino group, a C1-C6 alkyl group, a C1-C6 alkylamino group, a di-(C1-C6 alkyl)amino group, a HO—NH— group or a C1-C6 alkoxy group; $R^6$ represents a hydrogen atom, a C1-C6 alkyl group, a C2-C7 carboxyalkyl group or a C3-C13 alkoxycarbonyla- lkyl group, and m represents an integer of from 0 to 5) and a sulfamoyl C1-C6 alkyl group], pharmacologically acceptable salts thereof and prodrugs thereof are also preferable.

The "C1-C6 alkyl group" in the general formula (I) shown above can be, for example, a straight or branched chain alkyl group having from 1 to 6 carbon atoms such as a methyl, ethyl, propyl, isopropyl, butyl, isobutyl, s-butyl, t-butyl, pentyl, isopentyl, 2-methylbutyl, neopentyl, 1-ethylpropyl, hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group, and is preferably a straight or branched chain alkyl group having from 1 to 4 carbon atoms, and more preferably a methyl group.

The "halogeno C1-C6 alkyl group" in the general formula (I) shown above indicates a group wherein said "C1-C6 alkyl group" is substituted with halogen atom(s), and can be, for example, a trifluoromethyl, trichloromethyl, difluoromethyl, dichloromethyl, dibromomethyl, fluoromethyl, 2,2,2-trifluoroethyl, 2,2,2-trichloroethyl, 2-bromoethyl, 2-chloroethyl, 2-fluoroethyl, 2-iodoethyl, 3-chloropropyl, 4-fluorobutyl, 6-iodohexyl or 2,2-dibromoethyl group, and is preferably a trifluoromethyl group.

The "C3-C6 cycloalkyl group" in the general formula (I) shown above can be, for example, a 3- to 6-membered saturated cyclic hydrocarbon group such as a cyclopropyl, cyclobutyl, cyclopentyl or cyclohexyl group, and is preferably a cyclopropyl group.

The "halogeno C3-C6 cycloalkyl group" in the general formula (I) shown above indicates a group wherein said "C3-C6 cycloalkyl group" is substituted with halogen atom(s), and can be, for example, a 2-fluorocyclopropyl, 2-chlorocyclopropyl, 2-fluorocyclopentyl, 2-chlorocyclopentyl, 2-fluorocyclohexyl or 2-chlorocyclohexyl group, and is preferably a 2-fluorocyclopropyl group.

The "C1-C6 alkoxy group" in the general formula (I) shown above indicates a group wherein said "C1-C6 alkyl group" is bonded to an oxygen atom, and can be, for example, a straight or branched chain alkoxy group having from 1 to 6 carbon atoms such as a methoxy, ethoxy, n-propoxy, isopropoxy, n-butoxy, isobutoxy, s-butoxy, t-butoxy, n-pentyloxy, isopentyloxy, 2-methylbutoxy, neopentyloxy, n-hexyloxy, 4-methylpentyloxy, 3-methylpentyloxy, 2-methylpentyloxy, 3,3-dimethylbutoxy, 2,2-dimethylbutoxy, 1,1-dimethylbutoxy, 1,2-dimethylbutoxy, 1,3-dimethylbutoxy or 2,3-dimethylbutoxy group, and is preferably a straight or branched chain alkoxy group having from 1 to 4 carbon atoms, and more preferably a methoxy or ethoxy group.

The "halogeno C1-C6 alkoxy group" in the general formula (I) shown above indicates a group wherein said "C1-C6 alkoxy group" is substituted with halogen atom(s), and can be, for example, a trifluoromethoxy, trichloromethoxy, difluoromethoxy, dichloromethoxy, dibromomethoxy, fluoromethoxy, 2,2,2-trichloroethoxy, 2,2,2-trifluoroethoxy, 2-bromoethoxy, 2-chloroethoxy, 2-fluoroethoxy or 2,2-dibromoethoxy group, and is preferably a 2-bromoethoxy, 2-chloroethoxy and 2-fluoroethoxy group.

The "C6-C10 aryl group" in the general formula (I) shown above can be, for example, an aromatic hydrocarbon group having from 6 to 10 carbon atoms such as a phenyl or naphthyl group, and is preferably a phenyl group.

The "halogeno C6-C10 aryl group" in the general formula (I) shown above indicates a group wherein said "C1-C10 aryl group" is substituted with halogen atom(s), and can be, for example, a 4-chlorophenyl, 4-fluorophenyl, 2,4-dichlorophenyl or 2,4-difluorophenyl group, and is preferably a 4-chlorophenyl group.

The "C2-C7 alkanoyl group" in the general formula (I) shown above can be, for example, a straight or branched chain alkanoyl group having from 2 to 7 carbon atoms such as an acetyl, propionyl, butyryl, isobutyryl, pentanoyl, pivaloyl, valeryl, isovaleryl, hexanoyl or heptanoyl group, and is preferably an acetyl group.

The "C7-C11 arylcarbonyl group" in the general formula (I) shown above indicates a group wherein said "C6-C10 aryl group" is bonded to a carbonyl group, and can be, for example, a benzoyl, α-naphthoyl or β-naphthoyl group, and is preferably a benzoyl group.

The "C1-C6 alkylamino group" in the general formula (I) shown above indicates a group wherein said "C1-C6 alkyl group" is bonded to an amino group, and can be, for example, a straight or branched chain alkylamino group having from 1 to 6 carbon atoms such as a methylamino, ethylamino, propylamino, isopropylamino, butylamino, isobutylamino, s-butylamino, t-butylamino, pentylamino, isopentylamino, 2-methylbutylamino, neopentylamino, 1-ethylpropylamino, hexylamino, isohexylamino, 4-methylpentylamino, 3-methylpentylamino, 2-methylpentylamino, 1-methylpentylamino, 3,3-dimethylbutylamino, 2,2-dimethylbutylamino, 1,1-dimethylbutylamino, 1,2-dimethylbutylamino, 1,3-dimethylbutylamino, 2,3-dimethylbutylamino or 2-ethylbutylamino group, and is preferably a straight or branched chain alkylamino group having from 1 to 4 carbon atoms, and more preferably a methylamino group.

The "di-(C1-C6 alkyl)amino group" in the general formula (I) shown above indicates a group wherein an amino group is substituted with two "C1-C6 alkyl groups", and can be, for example, a dimethylamino, methylethylamino, diethylamino, di-n-propylamino, diisopropylamino N-(n-propyl)-N-ethylamino, di-n-butylamino, diisobutylamino, di-s-butylamino, di-t-butylamino, di-n-pentylamino, diisopentylamino, di-2-methylbutylamino, dineopentylamino, di-1-ethylpropylamino, di-n-hexylamino, diisohexylamino, di-4-methylpentylamino, di-3-methylpentylamino, di-2-methylpentylamino, di-1-methylpentylamino, di-3,3-dimethylbutylamino, di-2,2-dimethylbutylamino, di-1,1-dimethylbutylamino, di-1,2-dimethylbutylamino, di-1,3-dimethylbutylamino, di-2,3-dimethylbutylamino or di-2-ethylbutylamino group, and is preferably a dimethylamino, methylethylamino or diethylamino group.

The "C6-C10 arylsulfonyl group" in the general formula (I) shown above indicates a group wherein said "C6-C10 aryl group" is bonded to a sulfonyl group, and can be, for example, a benzenesulfonyl, α-naphthalenesulfonyl or β-naphthalenesulfonyl group, and is preferably a phenylsulfonyl group.

The "C7-C16 alkylarylsulfonyl group" in the general formula (I) shown above indicates a group wherein said "C1-C6 alkyl group" is bonded to said "C6-C10 arylsulfonyl group", and can be, for example, 2-methylbenzenesulfonyl, 3-methylbenzenesulfonyl, 4-methylbenzenesulfonyl, 2-ethylbenzenesulfonyl, 3-ethylbenzenesulfonyl, 4-ethylbenzenesulfonyl, 2,4,6-trimethylbenzenesulfonyl, 3,4,5-trimethylbenzenesulfonyl, 2-n-propylbenzenesulfonyl, 4-n-propylbenzenesulfonyl, 2-isopropylbenzenesulfonyl, 4-isopropylbenzenesulfonyl, 2-butylbenzenesulfonyl or 4-butylbenzenesulfonyl group, and is preferably a 4-methylbenzenesulfonyl group.

The "C1-C6 alkylsulfanyl group" in the general formula (I) shown above indicates a group wherein said "C1-C6 alkyl group" is bonded to a sulfur atom, and can be, for example, a straight or branched chain alkylsulfanyl group having from 1 to 6 carbon atoms such as a methylsulfanyl, ethylsulfanyl, n-propylsulfanyl, isopropylsulfanyl, n-butylsulfanyl, isobutylsulfanyl, s-butylsulfanyl, t-butylsulfanyl, n-pentylsulfanyl, isopentylsulfanyl, 2-methylbutylsulfanyl, neopentylsulfanyl, 1-ethylpropylsulfanyl, n-hexylsulfanyl, isohexylsulfanyl, 4-methylpentylsulfanyl, 3-methylpentylsulfanyl, 2-methylpentylsulfanyl, 1-methylpentylsulfanyl, 3,3-dimethylbutylsulfanyl, 2,2-dimethylbutylsulfanyl, 1,1-dimethylbutylsulfanyl, 1,2-dimethylbutylsulfanyl, 1,3-dimethylbutylsulfanyl, 2,3-dimethylbutylsulfanyl or 2-ethylbutylsulfanyl group, and is preferably a straight or branched chain alkylsulfanyl group having from 1 to 4 carbon atoms, and more preferably a methylsulfanyl group.

The "C1-C6 acylamino group" in the general formula (I) shown above indicates a straight or branched chain acylamino group having from 1 to 6 carbon atoms such as a formylamino, acetylamino, propionylamino, butyrylamino, isobutyrylamino, pentanoylamino, pivaloylamino, valerylamino, isovalerylamino or hexanoylamino group, and is preferably an acetylamino group.

The "C2-C7 alkoxycarbonyl group" in the general formula (I) shown above indicates a straight or branched chain alkoxycabonyl group having from 2 to 7 carbon atoms such as a methoxycarbonyl, ethoxycarbonyl, n-propoxycarbonyl, isopropoxycarbonyl, n-butoxycarbonyl, isobutoxycarbonyl, s-butoxycarbonyl, t-butoxycarbonyl, n-pentyloxycarbonyl, isopentyloxycarbonyl, 2-methylbutoxycarbonyl, neopentyloxycarbonyl, n-hexyloxycarbonyl, 4-methylpentyloxycarbonyl, 3-methylpentyloxycarbonyl, 2-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl or 2,3-dimethylbutoxycarbonyl group, and is preferably a methoxycarbonyl or ethoxycarbonyl group.

The "heteroaryl group" in the general formula (I) shown above can be, for example, a 5- to 7-membered aromatic heterocyclic group containing from 1 to 4 heteroatoms selected from sulfur atom(s), oxygen atom(s) and/or nitrogen atom(s) such as a furyl, thienyl, pyrrolyl, pyrazolyl, imidazolyl, oxazolyl, isoxazolyl, thiazolyl, isothiazolyl, triazolyl, tetrazolyl, thiadiazolyl, oxadiazolyl, pyranyl, pyridyl, pyridazinyl, pyrimidinyl or pyrazinyl group, or an aromatic heterocyclic group fused with other cyclic groups such as an isoindolyl, indolyl, isoquinolyl or quinolyl group, and is preferably a 5- to 7-membered aromatic heterocyclic group containing at least one of nitrogen atom, and more preferably a pyrazolyl, triazolyl or tetrazolyl group.

The "hydroxy C1-C6 alkyl group" in the general formula (I) shown above indicates a group wherein said "C1-C6 alkyl group" is substituted with hydroxyl group(s), and can be, for example, a hydroxymethyl, 1-hydroxyethyl, 2-hydroxyethyl, 1-hydroxy-2-methylethyl, 2-hydroxy-2-methylethyl, 1-hydroxypropyl, 2-hydroxypropyl, 3-hydroxypropyl, 1-hydroxybutyl, 2-hydroxybutyl, 3-hydroxybutyl, 4-hydroxybutyl, 5-hydroxypentyl or 6-hydroxyhexyl group, and is preferably a hydroxymethyl, 2-hydroxyethyl or 3-hydroxypropyl group.

The "C2-C12 alkoxyalkyl group" in the general formula (I) shown above indicates a group wherein said "C1-C6 alkoxy group" is bonded to said "C1-C6 alkyl group", and can be, for example, a methoxymethyl, ethoxymethyl, n-propoxymethyl, isopropoxymethyl, n-butoxymethyl, isobutoxymethyl, s-butoxymethyl, t-butoxymethyl, n-pentyloxymethyl, isopentyloxymethyl, 2-methylbutoxymethyl, neopentyloxymethyl, n-hexyloxymethyl, 4-methylpentyloxymethyl, 3-methylpentyloxymethyl, 2-methylpentyloxymethyl, 3,3-dimethylbutoxymethyl, 2,2-dimethylbutoxymethyl, 1,1-dimethylbutoxymethyl, 1,2-dimethylbutoxymethyl, 1,3- dimethylbutoxymethyl, 2,3-dimethylbutoxymethyl, 2-methoxyethyl, 2-ethoxyethyl, 2-(n-propoxy)ethyl, 2-(isopropoxy)ethyl, 2-(n-butoxy)ethyl, 2-(isobutoxy)ethyl, 2-(s-butoxy)ethyl, 2-(t-butoxy)ethyl, 2-(n-pentyloxy)ethyl, 2-(isopentyloxy)ethyl, 2-(2-methylbutoxy)ethyl, 2-(neopentyloxy)ethyl, 2-(n-hexyloxy)ethyl, 2-(4-methylpentyloxy)ethyl, 2-(3-methylpentyloxy)ethyl, 2-(2-methylpentyloxy)ethyl, 2-(3,3-dimethylbutoxy)ethyl, 2,2-dimethylbutoxyethyl, 1,1-dimethylbutoxyethyl, 1,2-dimethylbutoxyethyl, 1,3-dimethylbutoxyethyl or 2,3-dimethylbutoxyethyl group, and is preferably a straight or branched chain alkoxyalkyl group having from 2 to 4 carbon atoms, and more preferably a methoxymethyl or methoxyethyl group.

The "C4-C7 cycloalkylcarbonyl group" in the general formula (I) shown above indicates a group wherein said "C3-C6 cycloalkyl group" is bonded to a carbonyl group", and can be, for example, a cyclopropylcarbonyl, cyclobutylcarbonyl, cyclopentylcarbonyl or cyclohexylcarbonyl group, and is preferably a cyclopropylcarbonyl group.

The "C2-C7 alkylcarbamoyl group" in the general formula (I) shown above indicates a group wherein said "C1-C6 alkyl group" is bonded to a carbamoyl group", and can be, for example, a methylcarbamoyl, ethylcarbamoyl, propylcarbamoyl, isopropylcarbamoyl, butylcarbamoyl, isobutylcarbamoyl, s-butylcarbamoyl, t-butylcarbamoyl, pentylcarbamoyl, isopentylcarbamoyl, 2-methylbutylcarbamoyl, neopentylcarbamoyl, 1-ethylpropylcarbamoyl, hexylcarbamoyl, isohexylcarbamoyl, 4-methylpentylcarbamoyl, 3-methylpentylcarbamoyl, 2-methylpentylcarbamoyl, 1-methylpentylcarbamoyl, 3,3-dimethylbutylcarbamoyl, 2,2-dimethylbutylcarbamoyl, 1,1-dimethylbutylcarbamoyl, 1,2-dimethylbutylcarbamoyl, 1,3-dimethylbutylcarbamoyl, 2,3-dimethylbutylcarbamoyl or 2-ethylbutylcarbamoyl group, and is preferably an alkylcarbamoyl group having from 2 to 5 carbon atoms, and more preferably a methylcarbamoyl or ethylcarbamoyl group.

The "di-(C1-C6 alkyl)carbamoyl group" in the general formula (I) shown above indicates a group wherein a carbamoyl group is substituted with two "C1-C6 alkyl groups", and can be, for example, a dimethylcarbamoyl, methylethylcarbamoyl, diethylcarbamoyl, di-n-propylcarbamoyl, diisopropylcarbamoyl, N-(n-propyl)-N-ethylcarbamoyl, di-n-butylcarbamoyl, diisobutylcarbamoyl, di-s-butylcarbamoyl, di-t-butylcarbamoyl, di-n-pentylcarbamoyl, diisopentylcarbamoyl, di-2-methylbutylcarbamoyl, dineopentylcarbamoyl, di-1-ethylpropylcarbamoyl, di-n-hexylcarbamoyl, diisohexylcarbamoyl, di-4-methylpentylcarbamoyl, di-3-methylpentylcarbamoyl, di-2-methylpentylcarbamoyl, di-1-methylpentylcarbamoyl, di-3,3-dimethylbutylcarbamoyl, di-2,2-dimethylbutylcarbamoyl, di-1,1-dimethylbutylcarbamoyl, di-1,2-dimethylbutylcarbamoyl, di-1,3-dimethylbutylcarbamoyl, di-2,3-dimethylbutylcarbamoyl or di-2-ethylbutylcarbamoyl group, and is preferably a dimethylcarbamoyl, methylethylcarbamoyl or diethylcarbamoyl group.

The "C1-C6 alkoxyamino group" in the general formula (I) shown above indicates a group wherein the oxygen atom of a hydroxyamino group is substituted with said "C1-C6 alkyl group", and can be, for example, a methoxyamino, ethoxyamino, n-propoxyamino, isopropoxyamino, n-butoxyamino, isobutoxyamino, s-butoxyamino, t-butoxyamino, n-pentyloxyamino, isopentyloxyamino, 2-methylbutoxyamino, neopentyloxyamino, n-hexyloxyamino, 4-methylpentyloxyamino, 3-methylpentyloxyamino, 2-methylpentyloxyamino, 3,3-dimethylbutoxyamino, 2,2-dimethylbutoxyamino, 1,1-dimethylbutoxyamino, 1,2-dimethylbutoxyamino, 1,3-dimethylbutoxyamino or 2,3-dimethylbutoxyamino group, and is preferably a methoxyamino group.

The "C2-C7 carboxyalkyl group" in the general formula (I) shown above indicates a group wherein said "C1-C6 alkyl group" is substituted with carboxyl group(s), and can be, for example, a carboxymethyl, 1-carboxyethyl, 1-carboxypropyl, 1-carboxybutyl, 1-carboxypentyl, 1-ethyl-1-carboxypropyl, 1-carboxyhexyl, 2-carboxyethyl, 2-carboxypropyl, 2-carboxybutyl, 2-carboxypentyl, 1-ethyl-2-carboxypropyl, 3-carboxypropyl, 4-carboxybutyl, 5-carboxypentyl or 6-carboxyhexyl group, and is preferably a carboxymethyl or 2-carboxyethyl group.

The "C3-C13 alkoxycarbonylalkyl group" in the general formula (I) shown above indicates a group wherein said "C1-C6 alkyl group" is substituted with said "C2-C7 alkoxycarbonyl group", and can be, for example, a methoxycarbonylmethyl, 2-methoxycarbonylethyl, 3-methoxycarbonylpropyl, 4-methoxycarbonylbutyl, 5-methoxycarbonylpentyl, 1-ethyl-1-methoxycarbonylpropyl, 6-methoxycarbonylhexyl, 2-methoxycarbonylpropyl, 2-methoxycarbonylbutyl, 2-methoxycarbonylpentyl, 1-ethyl-2-methoxycarbonylpropyl, ethoxycarbonylmethyl, 3-ethoxycarbonylpropyl, 4-ethoxycarbonylbutyl, 5-ethoxycarbonylpentyl, 1-ethyl-1-ethoxycarbonylpropyl, 6-ethoxycarbonylhexyl, 2-ethoxycarbonylethyl, 2-ethoxycarbonylpropyl, 2-ethoxycarbonylbutyl, 2-ethoxycarbonylpentyl, 1-ethyl-2-ethoxycarbonylpropyl, propoxycarbonylmethyl, butoxycarbonylmethyl or t-butoxycarbonylmethyl group, and is preferably a methoxycarbonylmethyl, 2-methoxycarbonylethyl, ethoxycarbonylmethyl or 2-ethoxycarbonylethyl group.

The "halogen atom" in the general formula (I) shown above can be, for example, a fluorine atom, chlorine atom, bromine atom or iodine atom, and is preferably a fluorine atom or chlorine atom, and more preferably a fluorine atom.

In the compounds (I) of the present invention, optical isomers due to the asymmetric carbon atom contained in their structures (including diastereomers) may be present, and additionally, geometrical isomers due to the carbon-carbon double bond may be also present in same compounds. The present invention encompasses all of these isomers. The geometric structure of the double bond to which the $R^3$ group is bonded is preferred to be the E-isomer.

As some compounds (I) of the present invention have various groups such as a sulfanyl group, a carboxyl group, a hydroxyl group or an amino group in their structure, the "prodrug thereof" means a derivative in which any of such groups is modified by an appropriate functional group that can be cleaved by a biological process such as hydrolysis in vivo. In these cases, it can be determined whether the derivative is "an appropriate functional group that can be cleaved by a biological process such as hydrolysis in vivo" or not according to whether the original compound or a pharmacologically acceptable salt thereof generated can be detected, by administering the derivative to an experimental animal such as a rat or a mouse by an intravenous injection, subcutaneous injection or oral administration, and measuring a body fluid of the animal thereafter.

When the compounds (I) of the present invention contain a sulfanyl group in their structures, the functional group employed for forming a prodrug thereof is not particularly restricted, and can be, for example, an "aliphatic acyl group", including an alkanoyl group such as a formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl or henicosanoyl group, an alkylcarbonyl group substituted with a carboxyl group such as a succinoyl, glutaroyl or adipoyl group, a carbonyl group substituted with a halogeno lower alkyl group such as a chloroacetyl, dichloroacetyl, trichloroacetyl or trifluoroacetyl group, a saturated cyclic hydrocarbon-carbonyl group such as a cyclopropylcarbonyl, cyclobutylcarbonyl, cyclopentylcarbonyl, cyclohexylcarbonyl, cycloheptylcarbonyl or cyclooctylcarbonyl group, an alkylcarbonyl group substituted with lower alkoxy group(s) such as a methoxyacetyl group, and an unsaturated alkylcarbonyl group such as a (E)-2-methyl-2-butenoyl group (preferably a C1-C6 alkanoyl group); a "carbonyloxyalkyl group", including an oxodioxolenylmethyl group such as a (5-methyl-2-oxo-1,3-dioxolen-4-yl)methyl or (5-phenyl-2-oxo-1,3-dioxolen-4-yl)methyl group; an "aromatic acyl group", including an arylcarbonyl group such as a benzoyl, α-naphthoyl, β-naphthoyl, pyridoyl, thienoyl or furoyl group, a halogeno arylcarbonyl group such as a 2-bromobenzoyl or 4-chlorobenzoyl group, an arylcarbonyl group substituted with lower alkyl group(s) such as a 2,4,6-trimethylbenzoyl or 4-toluoyl group, a lower alkoxylated arylcarbonyl group such as a 4-anisoyl group, an arylcarbonyl group substituted with carboxyl group(s) such as a 2-carboxybenzoyl, 3-carboxybenzoyl or 4-carboxybenzoyl group, a nitrated arylcarbonyl group such as a 4-nitrobenzoyl or 2-nitrobenzoyl group, an arylcarbonyl group substituted with lower alkoxycarbonyl group(s) such as a 2-(methoxycarbonyl)benzoyl group, and an arylcarbonyl group substituted with aryl group(s) such as a 4-phenylbenzoyl group; an "aralkylcarbonyl group", including a carbonyl group substituted with a lower alkyl group which is substituted with from 1 to 3 aryl groups such as a phenylacetyl, α-naphthylpropionyl, β-naphthylbutyryl, diphenylisobutyryl, triphenylacetyl, α-naphthyldiphenylisobutyryl or 9-anthrylpentanoyl group, and a lower alkylcarbonyl group substituted with from 1 to 3 aryl groups, of which the aryl ring is substituted with lower alkyl group(s), lower alkoxy group(s), nitro group(s), halogen atom(s) or cyano group(s), such as a 4-methylphenylacetyl, 2,4,6-trimethylphenylformyl, 3,4,5-trimethylphenylbutyryl, 4-methoxyphenylisobutyryl, 4-methoxyphenyldiphenylpivaloyl, 2-nitrophenylacetyl, 4-nitrophenylpropionyl, 4-chlorophenylbutyryl, 4-bromophenylacetyl or 4-cyanophenylpentanoyl group; a "tetrahydropyranyl or tetrahydrothiopyranyl group" such as a tetrahydropyran-2-yl, 3-bromotetrahydropyran-2-yl, 4-methoxytetrahydropyran-4-yl, tetrahydrothiopyran-2-yl or 4-methoxytetrahydrothiopyran-4-yl group; a "tetrahydrofuranyl or tetrahydrothiofuranyl group" such as a tetrahydrofuran-2-yl or tetrahydrothiofuran-2-yl group; an "alkoxymethyl group", including a lower alkoxymethyl group such as a methoxymethyl, 1,1-dimethyl-1-methoxymethyl, ethoxymethyl, propoxymethyl, isopropoxymethyl, butoxymethyl or t-butoxymethyl group, a lower alkoxymethyl group substituted with lower alkoxy group(s) such as a 2-methoxyethoxymethyl group, and a halogeno lower alkoxymethyl group such as a 2,2,2-trichloroethoxymethyl or bis(2-chloroethoxy)methyl group; a "substituted ethyl group", including a lower alkoxylated ethyl group such as a 1-ethoxyethyl or 1-(isopropoxy)ethyl group, and a halogenated ethyl group such as a 2,2,2-trichloroethyl group; an "aralkyl group", including a lower alkyl group substituted with from 1 to 3 aryl groups such as a benzyl, α-naphthylmethyl, β-naphthylmethyl, diphenylmethyl, triphenylmethyl, α-naphthyldiphenylmethyl or 9-anthrylmethyl group, and a lower alkyl group substituted with from 1 to 3 aryl groups, of which an aryl ring is substituted with lower alkyl group(s), lower alkoxy group(s), nitro group(s), halogen atom(s) or cyano group(s), such as a 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl or 4-cyanobenzyl group; an "alkoxycarbonyl group", including a lower alkoxycarbonyl group such as a methoxycarbonyl, ethoxycarbonyl, t-butoxycarbonyl or isobutoxycarbonyl group, and a lower alkoxycarbonyl group substituted with halogen atom(s) or tri-lower alkylsilyl group(s) such as a 2,2,2-trichloroethoxycarbonyl or 2-trimethylsilylethoxycarbonyl group; an "alkenyloxycarbonyl group" such as a vinyloxycarbonyl or allyloxycarbonyl group; an "aralkyloxycarbonyl group", of which an aryl ring may be substituted with 1 or 2 substituents selected from lower alkoxy group(s) or nitro group(s), such as a benzyloxycarbonyl, 4-methoxybenzyloxycarbonyl, 3,4-dimethoxybenzyloxycarbonyl, 2-nitrobenzyloxycarbonyl or 4-nitrobenzyloxycarbonyl group; a straight or branched chain alkylsulfanyl group having from 1 to 6 carbon atoms such as a methylsulfanyl, ethylsulfanyl, n-propylsulfanyl, isopropylsulfanyl, n-butylsulfanyl, isobutylsulfanyl, s-butylsulfanyl, t-butylsulfanyl, n-pentylsulfanyl, isopentylsulfanyl, 2-methylbutylsulfanyl, neopentylsulfanyl, 1-ethylpropylsulfanyl, n-hexylsulfanyl, isohexylsulfanyl, 4-methylpentylsulfanyl, 3-methylpentylsulfanyl, 2-methylpentylsulfanyl, 1-methylpentylsulfanyl, 3,3-dimethylbutylsulfanyl, 2,2-dimethylbutylsulfanyl, 1,1-dimethylbutylsulfanyl, 1,2-dimethylbutylsulfanyl, 1,3-dimethylbutylsulfanyl, 2,3-dimethylbutylsulfanyl or 2-ethylbutylsulfanyl group; or an "aminoacyl group of an α-amino acid" such as a phenylalanine, and is preferably a group which forms a pharmacologically acceptable ester such as an "aliphatic acyl group" or an "aromatic acyl group", or a "C1-C6 alkylsulfanyl group" such as a methylsulfanyl, ethylsulfanyl, n-propylsulfanyl, isopropylsulfanyl, n-butylsulfanyl, isobutylsulfanyl, s-butylsulfanyl, or t-butylsulfanyl group, more preferably a group which forms a pharmacologically acceptable ester, particularly preferably a "C1-C6 alkanoyl group" such as a formyl, acetyl, propionyl, butyryl, isobutyryl, pentanoyl or pivaloyl group, and most preferably an acetyl group.

When the compounds (I) of the present invention contain a carboxyl group in their structures, the functional group employed for forming a prodrug thereof can be, for example, a "lower alkyl group" such as a methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl or 2-ethylbutyl group (preferably a C1-C6 alkyl group); an "alkoxy lower alkyl group", including a lower alkoxy lower alkyl group such as a methoxymethyl, 1-ethoxyethyl, 1-methyl-1-methoxyethyl, 1-(isopropoxy)ethyl, 2-methoxyethyl, 2-ethoxyethyl, 1,1-dimethyl-1-methoxymethyl, ethoxymethyl, n-propoxymethyl, isopropoxymethyl, n-butoxymethyl or tert-butoxymethyl group, a lower alkoxylated lower alkoxy lower alkyl group such as a 2-methoxyethoxymethyl group, an "aryl" oxy "lower alkyl group" such as a phenoxymethyl group, and a halogenated lower alkoxy lower alkyl group such as a 2,2,2-trichloroethoxymethyl or bis(2-chloroethoxy)methyl group; a "lower alkoxy" carbonyl "lower alkyl group" such as a methoxycarbonylmethyl group; a cyano "lower alkyl group" such as a cyanomethyl or 2-cyanoethyl group; a "lower alkyl" thiomethyl group such as a methylthiomethyl or ethylthiomethyl group; an "aryl" thiomethyl group such as a phenylthiomethyl or naphthylthiomethyl group; a "lower alkyl" sulfonyl "lower alkyl group", which may be substituted with halogen atom(s), such as a 2-methanesulfonylethyl or 2-trifluoromethanesulfonylethyl group; an "aryl" sulfonyl "lower alkyl group" such as a 2-benzenesulfonylethyl or 2-toluenesulfonylethyl group; an acyloxy "lower alkyl group", including an "aliphatic acyl" oxy "lower alkyl group" such as a formyloxymethyl, acetoxymethyl, propionyloxymethyl, butyryloxymethyl, pivaloyloxymethyl, valeryloxymethyl, isovaleryloxymethyl, hexanoyloxymethyl, 1-formyloxyethyl, 1-acetoxyethyl, 1-propionyloxyethyl, 1-butyryloxyethyl, 1-pivaloyloxyethyl, 1-valeryloxyethyl, 1-isovaleryloxyethyl, 1-hexanoyloxyethyl, 2-formyloxyethyl, 2-acetoxyethyl, 2-propionyloxyethyl, 2-butyryloxyethyl, 2-pivaloyloxyethyl, 2-valeryloxyethyl, 2-isovaleryloxyethyl, 2-hexanoyloxyethyl, 1-formyloxypropyl, 1-acetoxypropyl, 1-propionyloxypropyl, 1-butyryloxypropyl, 1-pivaloyloxypropyl, 1-valeryloxypropyl, 1-isovaleryloxypropyl, 1-hexanoyloxypropyl, 1-acetoxybutyl, 1-propionyloxybutyl, 1-butyryloxybutyl, 1-pivaloyloxybutyl, 1-acetoxypentyl, 1-propionyloxypentyl, 1-butyryloxypentyl, 1-pivaloyloxypentyl or 1-pivaloyloxyhexyl group, a "cycloalkyl" carbonyloxy "lower alkyl group" such as a cyclopentanoyloxymethyl, cyclohexanoyloxymethyl, 1-cyclopentanoyloxyethyl, 1-cyclohexanoyloxyethyl, 1-cyclopentanoyloxypropyl, 1-cyclohexanoyloxypropyl, 1-cyclopentanoyloxybutyl or 1-cyclohexanoyloxybutyl group, and an "aromatic acyl" oxy "lower alkyl group" such as a benzoyloxymethyl group; an "(alkoxycarbonyloxy)alkyl group" such as a methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, pentyloxycarbonyloxymethyl, hexyloxycarbonyloxymethyl, cylohexyloxycarbonyloxymethyl, cylohexyloxycarbonyloxy(cyclohexyl)methyl, 1-(methoxycarbonyloxy)ethyl, 1-(ethoxycarbonyloxy)ethyl, 1-propoxycarbonyloxyethyl, 1-(isopropoxycarbonyloxy)ethyl, 1-butoxycarbonyloxyethyl, 1-isobutoxycarbonyloxyethyl, 1-(tert-butoxycarbonyloxy)ethyl, 1-pentyloxycarbonyloxyethyl, 1-hexyloxycarbonyloxyethyl, 1-cyclopentyloxycarbonyloxyethyl, 1-cyclopentyloxycarbonyloxypropyl, 1-cyclohexyloxycarbonyloxypropyl, 1-cyclopentyloxycarbonyloxybutyl, 1-cyclohexyloxycarbonyloxybutyl, 1-(cyclohexyloxycarbonyloxy)ethyl, 1-(ethoxycarbonyloxy)propyl, 2-methoxycarbonyloxyethyl, 2-ethoxycarbonyloxyethyl, 2-propoxycarbonyloxyethyl, 2-isopropoxycarbonyloxyethyl, 2-butoxycarbonyloxyethyl, 2-isobutoxycarbonyloxyethyl, 2-pentyloxycarbonyloxyethyl, 2-hexyloxycarbonyloxyethyl, 1-methoxycarbonyloxypropyl, 1-ethoxycarbonyloxypropyl, 1-propoxycarbonyloxypropyl, 1-isopropoxycarbonyloxypropyl, 1-butoxycarbonyloxypropyl, 1-isobutoxycarbonyloxypropyl, 1-pentyloxycarbonyloxypropyl, 1-hexyloxycarbonyloxypropyl, 1-methoxycarbonyloxybutyl, 1-ethoxycarbonyloxybutyl, 1-propoxycarbonyloxybutyl, 1-isopropoxycarbonyloxybutyl, 1-butoxycarbonyloxybutyl, 1-isobutoxycarbonyloxybutyl, 1-methoxycarbonyloxypentyl, 1-ethoxycarbonyloxypentyl, 1-methoxycarbonyloxyhexyl or 1-ethoxycarbonyloxyhexyl group; a "carbonyloxyalkyl group", including an oxodioxolenylmethyl group such as a (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl or (5-butyl-2-oxo-1,3-dioxolen-4-yl)methyl group; a "phthalidyl group" such as a phthalidyl, dimethylphthalidyl or dimethoxyphthalidyl group; an "aryl group" such as a phenyl or indanyl group; a "carboxyalkyl group" such as a carboxymethyl group; or a "residual group forming an amino acid amide" such as a phenylalanine, and is preferably a group which forms pharmacologically acceptable esters such as an "alkyl group", "alkoxyalkyl group", "carbonyloxyalkyl group" or (alkoxycarbonyloxy)alkyl group, more preferably a "C1-C6 alkyl group" such as a methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl or 1-methylpentyl group, and particularly preferably a methyl or ethyl group.

When the compounds (I) of the present invention contain a hydroxyl group in their structures, the functional group employed for forming a prodrug thereof can be, for example, an "aliphatic acyl group", including an alkyl carbonyl group such as a formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, icosanoyl or henicosanoyl group, a carboxylated alkylcarbonyl group such as a succinoyl, glutaroyl or adipoyl group, a halogeno lower alkylcarbonyl group such as a chloroacetyl, dichloroacetyl, trichloroacetyl or trifluoroacetyl group, a lower alkoxy lower alkylcarbonyl group such as a methoxyacetyl group, and an unsaturated alkylcarbonyl group such as a (E)-2-methyl-2-butenoyl group (preferably a C1-C6 alkanoyl group); an "aromatic acyl group", including an arylcarbonyl group such as a benzoyl, α-naphthoyl or β-naphthoyl group, a halogeno arylcarbonyl group such as a 2-bromobenzoyl or 4-chlorobenzoyl group, a lower alkylated arylcarbonyl group such as a 2,4,6-trimethylbenzoyl or 4-toluoyl group, a lower alkoxylated arylcarbonyl group such as a 4-anisoyl group, a carboxylated arylcarbonyl group such as a 2-carboxybenzoyl, 3-carboxybenzoyl or 4-carboxybenzoyl group, a nitrated arylcarbonyl group such as a 4-nitrobenzoyl or 2-nitrobenzoyl group, a lower alkoxycarbonylated arylcarbonyl group such as a 2-(methoxycarbonyl)benzoyl group, and an arylated arylcarbonyl group such as a 4-phenylbenzoyl group; an acyloxyalkyl group such as a ethylcarbonyloxymethyl, pivaloyloxymethyl, dimethylaminoacetyloxymethyl or 1-acetoxyethyl group; a 1-(alkoxycarbonyloxy)alkyl group such as a 1-(methoxycarbonyloxy)ethyl, 1-(ethoxycarbonyloxy)ethyl, ethoxycarbonyloxymethyl, 1-(isopropoxycarbonyloxy)ethyl, 1-(t-butoxycarbonyloxy)ethyl, 1-(ethoxycarbonyloxy)propyl or 1-(cyclohexyloxycarbonyloxy)ethyl group; a phthalidyl group; a "carbonyloxyalkyl group", including an oxodioxolenylmethyl group such as a 4-methyl-oxodioxolenylmethyl, 4-phenyl-oxodioxolenylmethyl or oxodioxolenylmethyl group; a "residual group of a salt of a succinic acid half-ester"; a "residual group of a salt of a phosphoric acid ester"; a "residual group forming an amino acid ester"; a carbamoyl group; a carbamoyl group substituted with 1 or 2 lower alkyl groups; or a "carbonyloxyalkyloxycarbonyl group" such as a pivaloyloxymethoxycarbonyl group, and is preferably a group which forms a pharmacologically acceptable ester such as an "aliphatic acyl group" or an "aromatic acyl group", more preferably a "C1-C6 alkanoyl group" such as an acetyl, propionyl, butyryl, isobutyryl, pentanoyl or pivaloyl group, and particularly preferably an acetyl group.

When the compounds (I) of the present invention contain an amino group in their structures, the functional group employed for forming a prodrug thereof can be, for example, an aliphatic acyl group consisting of: an alkanoyl group such as a formyl, acetyl, propionyl, butyryl, isobutyryl, pentanoyl, pivaloyl, valeryl, isovaleryl, octanoyl, lauroyl, palmitoyl or stearoyl group, a halogeno lower alkylcarbonyl group such as a chloroacetyl, dichloroacetyl, trichloroacetyl or trifluoroacetyl group, a lower alkoxy lower alkylcarbonyl group such as a methoxyacetyl group, and an unsaturated alkylcarbonyl group such as a (E)-2-methyl-2-butenoyl group (preferably a C1-C6 alkanoyl group); an aromatic acyl group consisting of: an arylcarbonyl group such as a benzoyl, α-naphthoyl or β-naphthoyl group, a halogeno arylcarbonyl group such as a 2-bromobenzoyl or 4-chlorobenzoyl group, a lower alkylated arylcarbonyl group such as a 2,4,6-trimethylbenzoyl or 4-toluoyl group, a lower alkoxylated arylcarbonyl group such as a 4-anisoyl group, a nitrated arylcarbonyl group such as a 4-nitrobenzoyl or 2-nitrobenzoyl group, a lower alkoxycarbonylated arylcarbonyl group such as a 2-(methoxycarbonyl)benzoyl group, and an arylated arylcarbonyl group such as a 4-phenylbenzoyl group; an alkoxycarbonyl group, including a lower alkoxycarbonyl group such as a methoxycarbonyl, ethoxycarbonyl, t-butoxycarbonyl or isobutoxycarbonyl group, and a lower alkoxycarbonyl group substituted with halogen atom(s) or tri-lower alkylsilyl group(s) such as a 2,2,2-trichloroethoxycarbonyl or 2-trimethylsilylethoxycarbonyl group; an alkenyloxycarbonyl group such as a vinyloxycarbonyl or allyloxycarbonyl group; and an aryloxycarbonyl group, of which an aryl ring may be substituted with 1 or 2 substituents selected from lower alkoxy group(s), nitro group(s) and halogen atom(s), such as a phenoxycarbonyl, 4-methoxyphenoxycarbonyl, 3,4-dimethoxyphenoxycarbonyl, 2-nitrophenoxycarbonyl, 4-nitrophenoxycarbonyl or 4-fluorophenoxycarbonyl group, and is preferably a C1-C6 alkanoyl group.

The "prodrug" of the compounds having the formula (I) is preferably pharmacologically acceptable esters thereof that are prepared by converting the sulfanyl group, carboxyl group or hydroxyl group contained in said compounds, respectively.

The "pharmacologically acceptable salts thereof" mean a salt that is prepared from the compounds (I) of the present invention. Such salt is preferably a metal salt, including an alkali metal salt such as sodium salt, potassium salt or lithium salt, an alkaline earth metal salt such as calcium salt or magnesium salt, an aluminium salt, an iron salt, a zinc salt, a copper salt, a nickel salt and a cobalt salt; an amine salt, including an inorganic salt such as ammonium salt, and an organic salt such as t-octylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N, N'-dibenzylethylenediamine salt, chloroprocaine salt, procaine salt, diethanolamine salt, N-benzylphenethylamine salt, piperazine salt, tetramethylammonium salt or tris(hydroxymethyl)aminomethane salt; an inorganic acid salt, including a hydrohalogenic acid salt such as hydrofluoride, hydrochloride, hydrobromide or hydroiodide, a nitrate, a perchlorate, a sulfate and a phosphate; a lower alkanesulfonate such as methanesulfonate, trifluoromethanesulfonate or ethanesulfonate; an arylsulfonate such as benzenesulfonate or p-toluenesulfonate; an organic acid salt such as acetate, malate, fumarate, succinate, citrate, tartrate, oxalate or maleate; or an amino acid salt such as glycine salt, lysine salt, arginine salt, ornithine salt, glutamic acid salt or aspartic acid salt, and more preferably an inorganic acid salt.

Furthermore, the compounds (I) of the present invention can exist as a hydrate thereof.

The preferred examples of the compounds of general formula (I) can be specifically shown in Tables 1-6, but the scope of the present invention should not be limited to these compounds.

The meaning of the abbreviations in the following Tables is shown below.

Ac: acetyl group

Me: methyl group

Et: ethyl group

N-AcCys: N-acetylcysteinyl group

Ph: phenyl group

2-Thi: 2-thienyl group

3-Thi: 3-thienyl group

2-Fur: 2-furyl group

3-Fur: 3-furyl group

3-Pyza: pyrazol-3-yl group

4-Pyza: pyrazol-4-yl group

5-Pyza: pyrazol-5-yl group 1,3,4-dMePyza: 1,3-dimethylpyrazol-4-yl group 1,3,5-dMePyza: 1,3-dimethylpyrazol-5-yl group 2-Thiz: 1,3-thiazol-2-yl group 4-Thiz: 1,3-thiazol-4-yl group 5-Thiz: 1,3-thiazol-5-yl group 4,2-NH$_2$Thiz: 4-amino-1,3-thiazol-2-yl group 2,4-NH$_2$Thiz: 2-amino-1,3-thiazol-4-yl group 2,5-NH$_2$Thiz: 2-amino-1,3-thiazol-5-yl group 2-Imid: imidazol-2-yl group 4-Imid: imidazol-4-yl group 5-Imid: imidazol-5-yl group Tez: tetrazol-5-yl group 4-Triz$_1$: 1,2,3-triazol-4-yl group 3-Triz$_2$: 1,2,4-triazol-3-yl group 2-Pyr: 2-pyridyl group 3-Pyr: 3-pyridyl group 4-Pyr: 4-pyridyl group 6,2-MePyr: 6-methylpyridin-2-yl group 2-Oxa: 1,3-oxazol-2-yl group 4-Oxa: 1,3-oxazol-4-yl group 5-Oxa: 1,3-oxazol-5-yl group 3-Isox: isoxazol-3-yl group 4-Isox: isoxazol-4-yl group 5-Isox: isoxazol-5-yl group 4-αThiad: 1,2,3-thiadiazol-4-yl group 5-αThiad: 1,2,3-thiadiazol-5-yl group 3-βThiad: 1,2,4-thiadiazol-3-yl group 5-βThiad: 1,2,4-thiadiazol-5-yl group 3-γThiad: 1,2,5-thiadiazol-3-yl group 3-Ind: indol-3-yl group 3-Quin: 3-quinolyl group 3-Pyzn: pyridazin-3-yl group 4-Pyzn: pyridazin-4-yl group 4-αOxdad: 1,2,3-oxadiazol-4-yl group 5-αOxdad: 1,2,3-oxadiazol-5-yl group 3-βOxdad: 1,2,4-oxadiazol-3-yl group 5-βOxdad: 1,2,4-oxadiazol-5-yl group 3-γOxdad: 1,2,5-oxadiazol-3-yl group 2-Pyrr: 2-pyrrol-2-yl group 3-Pyrr: 2-pyrrol-3-yl group 2-Pyz: pyrazin-2-yl group 2-Pym: pyrimidin-2-yl group 4-Pym: pyrimidin-4-yl group 5-Pym: pyrimidin-5-yl group

TABLE 1

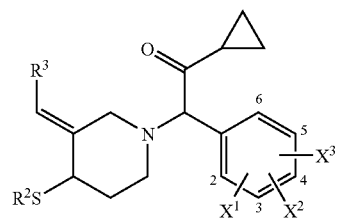

| Compd. No. | $R^2$ | $R^3$ | $X^1$ | $X^2$ | $X^3$ |
|---|---|---|---|---|---|
| 1-1 | H | Ph | 2-F | H | H |
| 1-2 | Ac | Ph | 2-F | H | H |
| 1-3 | H | Ph | 2-F | 4-F | H |
| 1-4 | Ac | Ph | 2-F | 4-F | H |
| 1-5 | H | 2-Thi | 2-F | H | H |
| 1-6 | Ac | 2-Thi | 2-F | H | H |
| 1-7 | H | 2-Thi | 2-F | 4-F | H |
| 1-8 | Ac | 2-Thi | 2-F | 4-F | H |
| 1-9 | H | 3-Thi | 2-F | H | H |
| 1-10 | Ac | 3-Thi | 2-F | H | H |
| 1-11 | H | 3-Thi | 2-F | 4-F | H |
| 1-12 | Ac | 3-Thi | 2-F | 4-F | H |
| 1-13 | H | 2-Fur | 2-F | H | H |
| 1-14 | Ac | 2-Fur | 2-F | H | H |
| 1-15 | H | 2-Fur | 2-F | 4-F | H |
| 1-16 | Ac | 2-Fur | 2-F | 4-F | H |
| 1-17 | H | 3-Fur | 2-F | H | H |
| 1-18 | Ac | 3-Fur | 2-F | H | H |
| 1-19 | H | 3-Fur | 2-F | 4-F | H |
| 1-20 | Ac | 3-Fur | 2-F | 4-F | H |
| 1-21 | H | 3-Pyza | 2-F | H | H |
| 1-22 | Ac | 3-Pyza | 2-F | H | H |
| 1-23 | H | 3-Pyza | 2-F | 4-F | H |
| 1-24 | Ac | 3-Pyza | 2-F | 4-F | H |
| 1-25 | H | 4-Pyza | 2-F | H | H |
| 1-26 | Ac | 4-Pyza | 2-F | H | H |
| 1-27 | H | 4-Pyza | 2-F | 4-F | H |
| 1-28 | Ac | 4-Pyza | 2-F | 4-F | H |
| 1-29 | H | 2-Thiz | 2-F | H | H |

TABLE 1-continued

| Compd. No. | $R^2$ | $R^3$ | $X^1$ | $X^2$ | $X^3$ |
|---|---|---|---|---|---|
| 1-30 | Ac | 2-Thiz | 2-F | H | H |
| 1-31 | H | 2-Thiz | 2-F | 4-F | H |
| 1-32 | Ac | 2-Thiz | 2-F | 4-F | H |
| 1-33 | H | 4-Thiz | 2-F | H | H |
| 1-34 | Ac | 4-Thiz | 2-F | H | H |
| 1-35 | H | 4-Thiz | 2-F | 4-F | H |
| 1-36 | Ac | 4-Thiz | 2-F | 4-F | H |
| 1-37 | H | 5-Thiz | 2-F | H | H |
| 1-38 | Ac | 5-Thiz | 2-F | H | H |
| 1-39 | H | 5-Thiz | 2-F | 4-F | H |
| 1-40 | Ac | 5-Thiz | 2-F | 4-F | H |
| 1-41 | H | 2-Imid | 2-F | H | H |
| 1-42 | Ac | 2-Imid | 2-F | H | H |
| 1-43 | H | 2-Imid | 2-F | 4-F | H |
| 1-44 | Ac | 2-Imid | 2-F | 4-F | H |
| 1-45 | H | 4-Imid | 2-F | H | H |
| 1-46 | Ac | 4-Imid | 2-F | H | H |
| 1-47 | H | 4-Imid | 2-F | 4-F | H |
| 1-48 | Ac | 4-Imid | 2-F | 4-F | H |
| 1-49 | H | 4-Triz$_1$ | 2-F | H | H |
| 1-50 | Ac | 4-Triz$_1$ | 2-F | H | H |
| 1-51 | H | 4-Triz$_1$ | 2-F | 4-F | H |
| 1-52 | Ac | 4-Triz$_1$ | 2-F | 4-F | H |
| 1-53 | H | 3-Triz$_2$ | 2-F | H | H |
| 1-54 | Ac | 3-Triz$_2$ | 2-F | H | H |
| 1-55 | H | 3-Triz$_2$ | 2-F | 4-F | H |
| 1-56 | Ac | 3-Triz$_2$ | 2-F | 4-F | H |
| 1-57 | H | Tez | 2-F | H | H |
| 1-58 | Ac | Tez | 2-F | H | H |
| 1-59 | H | Tez | 2-F | 4-F | H |
| 1-60 | Ac | Tez | 2-F | 4-F | H |
| 1-61 | H | 2-Pyr | 2-F | H | H |
| 1-62 | Ac | 2-Pyr | 2-F | H | H |
| 1-63 | H | 2-Pyr | 2-F | 4-F | H |
| 1-64 | Ac | 2-Pyr | 2-F | 4-F | H |
| 1-65 | H | 6,2-MePyr | 2-F | H | H |
| 1-66 | Ac | 6,2-MePyr | 2-F | H | H |
| 1-67 | H | 6,2-MePyr | 2-F | 4-F | H |
| 1-68 | Ac | 6,2-MePyr | 2-F | 4-F | H |
| 1-69 | H | 3-Pyr | 2-F | H | H |
| 1-70 | Ac | 3-Pyr | 2-F | H | H |
| 1-71 | H | 3-Pyr | 2-F | 4-F | H |
| 1-72 | Ac | 3-Pyr | 2-F | 4-F | H |
| 1-73 | H | 4-Pyr | 2-F | H | H |
| 1-74 | Ac | 4-Pyr | 2-F | H | H |
| 1-75 | H | 4-Pyr | 2-F | 4-F | H |
| 1-76 | Ac | 4-Pyr | 2-F | 4-F | H |
| 1-77 | H | 2-Oxa | 2-F | H | H |
| 1-78 | Ac | 2-Oxa | 2-F | H | H |
| 1-79 | H | 2-Oxa | 2-F | 4-F | H |
| 1-80 | Ac | 2-Oxa | 2-F | 4-F | H |
| 1-81 | H | 4-Oxa | 2-F | H | H |
| 1-82 | Ac | 4-Oxa | 2-F | H | H |
| 1-83 | H | 4-Oxa | 2-F | 4-F | H |
| 1-84 | Ac | 4-Oxa | 2-F | 4-F | H |
| 1-85 | H | 5-Oxa | 2-F | H | H |
| 1-86 | Ac | 5-Oxa | 2-F | H | H |
| 1-87 | H | 5-Oxa | 2-F | 4-F | H |
| 1-88 | Ac | 5-Oxa | 2-F | 4-F | H |
| 1-89 | H | 3-Isox | 2-F | H | H |
| 1-90 | Ac | 3-Isox | 2-F | H | H |
| 1-91 | H | 3-Isox | 2-F | 4-F | H |
| 1-92 | Ac | 3-Isox | 2-F | 4-F | H |
| 1-93 | H | 4-Isox | 2-F | H | H |

TABLE 1-continued

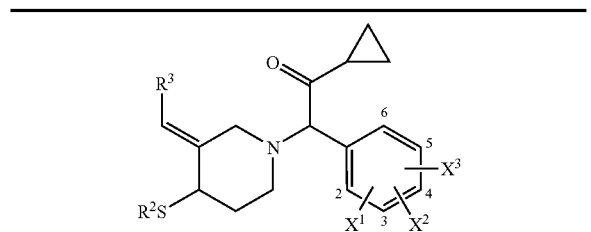

| Compd. No. | $R^2$ | $R^3$ | $X^1$ | $X^2$ | $X^3$ |
|---|---|---|---|---|---|
| 1-94 | Ac | 4-Isox | 2-F | H | H |
| 1-95 | H | 4-Isox | 2-F | 4-F | H |
| 1-96 | Ac | 4-Isox | 2-F | 4-F | H |
| 1-97 | H | 5-Isox | 2-F | H | H |
| 1-98 | Ac | 5-Isox | 2-F | H | H |
| 1-99 | H | 5-Isox | 2-F | 4-F | H |
| 1-100 | Ac | 5-Isox | 2-F | 4-F | H |
| 1-101 | H | 2-Pyz | 2-F | H | H |
| 1-102 | Ac | 2-Pyz | 2-F | H | H |
| 1-103 | H | 2-Pyz | 2-F | 4-F | H |
| 1-104 | Ac | 2-Pyz | 2-F | 4-F | H |
| 1-105 | H | 2-Pym | 2-F | H | H |
| 1-106 | Ac | 2-Pym | 2-F | H | H |
| 1-107 | H | 2-Pym | 2-F | 4-F | H |
| 1-108 | Ac | 2-Pym | 2-F | 4-F | H |
| 1-109 | H | 4-Pym | 2-F | H | H |
| 1-110 | Ac | 4-Pym | 2-F | H | H |
| 1-111 | H | 4-Pym | 2-F | 4-F | H |
| 1-112 | Ac | 4-Pym | 2-F | 4-F | H |
| 1-113 | H | 5-Pym | 2-F | H | H |
| 1-114 | Ac | 5-Pym | 2-F | H | H |
| 1-115 | H | 5-Pym | 2-F | 4-F | H |
| 1-116 | Ac | 5-Pym | 2-F | 4-F | H |
| 1-117 | H | 3-Pyzn | 2-F | H | H |
| 1-118 | Ac | 3-Pyzn | 2-F | H | H |
| 1-119 | H | 3-Pyzn | 2-F | 4-F | H |
| 1-120 | Ac | 3-Pyzn | 2-F | 4-F | H |
| 1-121 | H | 4-Pyzn | 2-F | H | H |
| 1-122 | Ac | 4-Pyzn | 2-F | H | H |
| 1-123 | H | 4-Pyzn | 2-F | 4-F | H |
| 1-124 | Ac | 4-Pyzn | 2-F | 4-F | H |
| 1-125 | H | 4-αThiad | 2-F | H | H |
| 1-126 | Ac | 4-αThiad | 2-F | H | H |
| 1-127 | H | 4-αThiad | 2-F | 4-F | H |
| 1-128 | Ac | 4-αThiad | 2-F | 4-F | H |
| 1-129 | H | 5-αThiad | 2-F | H | H |
| 1-130 | Ac | 5-αThiad | 2-F | H | H |
| 1-131 | H | 5-αThiad | 2-F | 4-F | H |
| 1-132 | Ac | 5-αThiad | 2-F | 4-F | H |
| 1-133 | H | 3-βThiad | 2-F | H | H |
| 1-134 | Ac | 3-βThiad | 2-F | H | H |
| 1-135 | H | 3-βThiad | 2-F | 4-F | H |
| 1-136 | Ac | 3-βThiad | 2-F | 4-F | H |
| 1-137 | H | 5-βThiad | 2-F | H | H |
| 1-138 | Ac | 5-βThiad | 2-F | H | H |
| 1-139 | H | 5-βThiad | 2-F | 4-F | H |
| 1-140 | Ac | 5-βThiad | 2-F | 4-F | H |
| 1-141 | H | 3-γThiad | 2-F | H | H |
| 1-142 | Ac | 3-γThiad | 2-F | H | H |
| 1-143 | H | 3-γThiad | 2-F | 4-F | H |
| 1-144 | Ac | 3-γThiad | 2-F | 4-F | H |
| 1-145 | H | 4-αOxdad | 2-F | H | H |
| 1-146 | Ac | 4-αOxdad | 2-F | H | H |
| 1-147 | H | 4-αOxdad | 2-F | 4-F | H |
| 1-148 | Ac | 4-αOxdad | 2-F | 4-F | H |
| 1-149 | H | 5-αOxdad | 2-F | H | H |
| 1-150 | Ac | 5-αOxdad | 2-F | H | H |
| 1-151 | H | 5-αOxdad | 2-F | 4-F | H |
| 1-152 | Ac | 5-αOxdad | 2-F | 4-F | H |
| 1-153 | H | 3-βOxdad | 2-F | H | H |
| 1-154 | Ac | 3-βOxdad | 2-F | H | H |
| 1-155 | H | 3-βOxdad | 2-F | 4-F | H |
| 1-156 | Ac | 3-βOxdad | 2-F | 4-F | H |
| 1-157 | H | 5-βOxdad | 2-F | H | H |
| 1-158 | Ac | 5-βOxdad | 2-F | H | H |
| 1-159 | H | 5-βOxdad | 2-F | 4-F | H |
| 1-160 | Ac | 5-βOxdad | 2-F | 4-F | H |
| 1-161 | H | 3-γOxdad | 2-F | H | H |
| 1-162 | Ac | 3-γOxdad | 2-F | H | H |
| 1-163 | H | 3-γOxdad | 2-F | 4-F | H |
| 1-164 | Ac | 3-γOxdad | 2-F | 4-F | H |
| 1-165 | H | 3-Ind | 2-F | H | H |
| 1-166 | Ac | 3-Ind | 2-F | H | H |
| 1-167 | H | 3-Ind | 2-F | 4-F | H |
| 1-168 | Ac | 3-Ind | 2-F | 4-F | H |
| 1-169 | H | 3-Quin | 2-F | H | H |
| 1-170 | Ac | 3-Quin | 2-F | H | H |
| 1-171 | H | 3-Quin | 2-F | 4-F | H |
| 1-172 | Ac | 3-Quin | 2-F | 4-F | H |
| 1-173 | H | 1,3,4-dMePyza | 2-F | H | H |
| 1-174 | Ac | 1,3,4-dMePyza | 2-F | H | H |
| 1-175 | H | 1,3,4-dMePyza | 2-F | 4-F | H |
| 1-176 | Ac | 1,3,4-dMePyza | 2-F | 4-F | H |
| 1-177 | H | 1,3,5-dMePyza | 2-F | H | H |
| 1-178 | Ac | 1,3,5-dMePyza | 2-F | H | H |
| 1-179 | H | 1,3,5-dMePyza | 2-F | 4-F | H |
| 1-180 | Ac | 1,3,5-dMePyza | 2-F | 4-F | H |
| 1-181 | H | 4-Imid | 2-F | 5-F | H |
| 1-182 | Ac | 4-Imid | 2-F | 5-F | H |
| 1-183 | H | 4-Imid | 2-F | 4-F | 5-F |
| 1-184 | Ac | 4-Imid | 2-F | 4-F | 5-F |
| 1-185 | H | 4-Imid | 2-F | 3-F | 4-F |
| 1-186 | Ac | 4-Imid | 2-F | 3-F | 4-F |
| 1-187 | Me₂CHCO— | 4-αThiad | 2-F | H | H |
| 1-188 | MeOCH₂CO— | 4-αThiad | 2-F | H | H |
| 1-189 | NH₂CH₂CO— | 4-αThiad | 2-F | H | H |
| 1-190 | NMe₂CH₂CO— | 4-αThiad | 2-F | H | H |
| 1-191 | N-AcCys- | 4-αThiad | 2-F | H | H |
| 1-192 | HOOC(CH₂)₂CO— | 4-αThiad | 2-F | H | H |
| 1-193 | Ts | 4-αThiad | 2-F | H | H |
| 1-194 | H | 4,2-NH₂Thiz | 2-F | H | H |
| 1-195 | Ac | 4,2-NH₂Thiz | 2-F | H | H |
| 1-196 | H | 4,2-NH₂Thiz | 2-F | 4-F | H |
| 1-197 | Ac | 4,2-NH₂Thiz | 2-F | 4-F | H |
| 1-198 | H | 2,4-NH₂Thiz | 2-F | H | H |
| 1-199 | Ac | 2,4-NH₂Thiz | 2-F | H | H |
| 1-200 | H | 2,4-NH₂Thiz | 2-F | 4-F | H |
| 1-201 | Ac | 2,4-NH₂Thiz | 2-F | 4-F | H |
| 1-202 | H | 2,5-NH₂Thiz | 2-F | H | H |
| 1-203 | Ac | 2,5-NH₂Thiz | 2-F | H | H |
| 1-204 | H | 2,5-NH₂Thiz | 2-F | 4-F | H |
| 1-205 | Ac | 2,5-NH₂Thiz | 2-F | 4-F | H |
| 1-206 | H | 5(3)-(carboxymethyl)-1H-pyrazole-3(5)-yl | 2-F | H | H |
| 1-207 | Ac | 5(3)-(carboxymethyl)-1H-pyrazole-3-(5)-yl | 2-F | H | H |
| 1-208 | H | 5(3)-(ethoxycarbonylmethyl)-1H-pyrazole-3(5)-yl | 2-F | H | H |
| 1-209 | Ac | 5(3)-(ethoxycarbonylmethyl)-1H-pyrazole-3(5)-yl | 2-F | H | H |
| 1-210 | H | 5-carboxy-1H-1,2,3-triazole-4-yl | 2-F | H | H |
| 1-211 | Ac | 5-carboxy-1H-1,2,3-triazole-4-yl | 2-F | H | H |
| 1-212 | H | 5-(ethoxycarbonyl)-1H-1,2,3-triazole-4-yl | 2-F | H | H |

TABLE 1-continued

[Structure: R³ group, cyclopropyl ketone, piperidine with R²S substituent, phenyl ring with X¹, X², X³ positions labeled 2,3,4,5,6]

| Compd. No. | R² | R³ | X¹ | X² | X³ |
|---|---|---|---|---|---|
| 1-213 | Ac | 5-(ethoxycarbonyl)-1H-1,2,3-triazole-4-yl | 2-F | H | H |
| 1-214 | H | 5-carboxy-2-(3-carboxypropyl)-2H-1,2,3-triazole-4-yl | 2-F | H | H |
| 1-215 | Ac | 5-carboxy-2-(3-carboxypropyl)-2H-1,2,3-triazole-4-yl | 2-F | H | H |
| 1-216 | H | 2-(3-carboxypropyl)-5-(ethoxycarbonyl)-2H-1,2,3-triazole-4-yl | 2-F | H | H |
| 1-217 | Ac | 2-(3-carboxypropyl)-5-(ethoxycarbonyl)-2H-1,2,3-triazole-4-yl | 2-F | H | H |
| 1-218 | H | 5-(ethoxycarbonyl)-2-[3-(ethoxycarbonyl)propyl]-2H-1,2,3-triazole-4-yl | 2-F | H | H |
| 1-219 | Ac | 5-(ethoxycarbonyl)-2-[3-(ethoxycarbonyl)propyl]-2H-1,2,3-triazole-4-yl | 2-F | H | H |
| 1-220 | H | 5-carboxy-2-[3-(ethoxy-carbonyl)propyl]-2H-1,2,3-triazole-4-yl | 2-F | H | H |
| 1-221 | Ac | 5-carboxy-2-[3-(ethoxy-carbonyl)propyl]-2H 1,2,3-triazole-4-yl | 2-F | H | H |

When the R³ group shown in Table 1 is the pyrazolyl group, triazolyl group and terazolyl group, the tautomers due to the hydrogen atom position are present. The exemplification compounds shown above include all of these tautomers.

TABLE 2

[General structure with Htcy-N-R group, piperidine, cyclopropyl ketone, phenyl with X¹,X²,X³]

Htcy groups: 3-Pyza, 4-Pyza, 5-Pyza, 2-Pyrr, 3-Pyrr, 2-Imid, 4-Imid, 5-Imid, 4-αTriz, 5-αTriz, 3-βTriz, 5-βTriz, 3-γTriz, 2-δTriz, Tez₂, Tez₁

| Compd. No. | R² | Htcy | R | X¹ | X² | X³ |
|---|---|---|---|---|---|---|
| 2-1 | H | 3-Pyza | Me | 2-F | H | H |
| 2-2 | Ac | 3-Pyza | Me | 2-F | H | H |
| 2-3 | H | 3-Pyza | Me | 2-F | 4-F | H |
| 2-4 | Ac | 3-Pyza | Me | 2-F | 4-F | H |
| 2-5 | H | 3-Pyza | Et | 2-F | H | H |
| 2-6 | Ac | 3-Pyza | Et | 2-F | H | H |
| 2-7 | H | 3-Pyza | Et | 2-F | 4-F | H |
| 2-8 | Ac | 3-Pyza | Et | 2-F | 4-F | H |
| 2-9 | H | 3-Pyza | Ac | 2-F | H | H |
| 2-10 | Ac | 3-Pyza | Ac | 2-F | H | H |
| 2-11 | H | 3-Pyza | Ac | 2-F | 4-F | H |
| 2-12 | Ac | 3-Pyza | Ac | 2-F | 4-F | H |
| 2-13 | H | 3-Pyza | —CH₂COOH | 2-F | H | H |
| 2-14 | Ac | 3-Pyza | —CH₂COOH | 2-F | H | H |
| 2-15 | H | 3-Pyza | —CH₂COOH | 2-F | 4-F | H |
| 2-16 | Ac | 3-Pyza | —CH₂COOH | 2-F | 4-F | H |
| 2-17 | H | 3-Pyza | —(CH₂)₂COOH | 2-F | H | H |
| 2-18 | Ac | 3-Pyza | —(CH₂)₂COOH | 2-F | H | H |
| 2-19 | H | 3-Pyza | —(CH₂)₂COOH | 2-F | 4-F | H |
| 2-20 | Ac | 3-Pyza | —(CH₂)₂COOH | 2-F | 4-F | H |
| 2-21 | H | 3-Pyza | —(CH₂)₃COOH | 2-F | H | H |
| 2-22 | Ac | 3-Pyza | —(CH₂)₃COOH | 2-F | H | H |
| 2-23 | H | 3-Pyza | —(CH₂)₃COOH | 2-F | 4-F | H |
| 2-24 | Ac | 3-Pyza | —(CH₂)₃COOH | 2-F | 4-F | H |
| 2-25 | H | 3-Pyza | —(CH₂)₄COOH | 2-F | H | H |
| 2-26 | Ac | 3-Pyza | —(CH₂)₄COOH | 2-F | H | H |
| 2-27 | H | 3-Pyza | —(CH₂)₄COOH | 2-F | 4-F | H |
| 2-28 | Ac | 3-Pyza | —(CH₂)₂COOH | 2-F | 4-F | H |
| 2-29 | H | 3-Pyza | —CH₂COOMe | 2-F | H | H |
| 2-30 | Ac | 3-Pyza | —CH₂COOMe | 2-F | H | H |
| 2-31 | H | 3-Pyza | —CH₂COOMe | 2-F | 4-F | H |
| 2-32 | Ac | 3-Pyza | —CH₂COOMe | 2-F | 4-F | H |
| 2-33 | H | 3-Pyza | —(CH₂)₂COOMe | 2-F | H | H |
| 2-34 | Ac | 3-Pyza | —(CH₂)₂COOMe | 2-F | H | H |
| 2-35 | H | 3-Pyza | —(CH₂)₂COOMe | 2-F | 4-F | H |
| 2-36 | Ac | 3-Pyza | —(CH₂)₂COOMe | 2-F | 4-F | H |
| 2-37 | H | 3-Pyza | —(CH₂)₃COOMe | 2-F | H | H |
| 2-38 | Ac | 3-Pyza | —(CH₂)₃COOMe | 2-F | H | H |
| 2-39 | H | 3-Pyza | —(CH₂)₃COOMe | 2-F | 4-F | H |
| 2-40 | Ac | 3-Pyza | —(CH₂)₃COOMe | 2-F | 4-F | H |
| 2-41 | H | 3-Pyza | —(CH₂)₄COOMe | 2-F | H | H |
| 2-42 | Ac | 3-Pyza | —(CH₂)₄COOMe | 2-F | H | H |
| 2-43 | H | 3-Pyza | —(CH₂)₄COOMe | 2-F | 4-F | H |
| 2-44 | Ac | 3-Pyza | —(CH₂)₄COOMe | 2-F | 4-F | H |
| 2-45 | H | 3-Pyza | —CH₂COOEt | 2-F | H | H |
| 2-46 | Ac | 3-Pyza | —CH₂COOEt | 2-F | H | H |

TABLE 2-continued

| | | | | | | |
|---|---|---|---|---|---|---|
| 2-47 | H | 3-Pyza | —CH$_2$COOEt | 2-F | H | H |
| 2-48 | Ac | 3-Pyza | —CH$_2$COOEt | 2-F | 4-F | H |
| 2-49 | H | 3-Pyza | —(CH$_2$)$_2$COOEt | 2-F | H | H |
| 2-50 | Ac | 3-Pyza | —(CH$_2$)$_2$COOEt | 2-F | H | H |
| 2-51 | H | 3-Pyza | —(CH$_2$)$_2$COOEt | 2-F | 4-F | H |
| 2-52 | Ac | 3-Pyza | —(CH$_2$)$_2$COOEt | 2-F | 4-F | H |
| 2-53 | H | 3-Pyza | —(CH$_2$)$_3$COOEt | 2-F | H | H |
| 2-54 | Ac | 3-Pyza | —(CH$_2$)$_3$COOEt | 2-F | H | H |
| 2-55 | H | 3-Pyza | —(CH$_2$)$_3$COOEt | 2-F | 4-F | H |
| 2-56 | Ac | 3-Pyza | —(CH$_2$)$_3$COOEt | 2-F | 4-F | H |
| 2-57 | H | 3-Pyza | —(CH$_2$)$_4$COOEt | 2-F | H | H |
| 2-58 | Ac | 3-Pyza | —(CH$_2$)$_4$COOEt | 2-F | H | H |
| 2-59 | H | 3-Pyza | —(CH$_2$)$_4$COOEt | 2-F | 4-F | H |
| 2-60 | Ac | 3-Pyza | —(CH$_2$)$_4$COOEt | 2-F | 4-F | H |
| 2-61 | H | 3-Pyza | —CH$_2$COOPr | 2-F | H | H |
| 2-62 | Ac | 3-Pyza | —CH$_2$COOPr | 2-F | H | H |
| 2-63 | H | 3-Pyza | —CH$_2$COOPr | 2-F | 4-F | H |
| 2-64 | Ac | 3-Pyza | —CH$_2$COOPr | 2-F | 4-F | H |
| 2-65 | H | 3-Pyza | —(CH$_2$)$_2$COOPr | 2-F | H | H |
| 2-66 | Ac | 3-Pyza | —(CH$_2$)$_2$COOPr | 2-F | H | H |
| 2-67 | H | 3-Pyza | —(CH$_2$)$_2$COOPr | 2-F | 4-F | H |
| 2-68 | Ac | 3-Pyza | —(CH$_2$)$_2$COOPr | 2-F | 4-F | H |
| 2-69 | H | 3-Pyza | —CH$_2$COOBu | 2-F | H | H |
| 2-70 | Ac | 3-Pyza | —CH$_2$COOBu | 2-F | H | H |
| 2-71 | H | 3-Pyza | —CH$_2$COOBu | 2-F | 4-F | H |
| 2-72 | Ac | 3-Pyza | —CH$_2$COOBu | 2-F | 4-F | H |
| 2-73 | H | 3-Pyza | —(CH$_2$)$_2$COOBu | 2-F | H | H |
| 2-74 | Ac | 3-Pyza | —(CH$_2$)$_2$COOBu | 2-F | H | H |
| 2-75 | H | 3-Pyza | —(CH$_2$)$_2$COOBu | 2-F | 4-F | H |
| 2-76 | Ac | 3-Pyza | —(CH$_2$)$_2$COOBu | 2-F | 4-F | H |
| 2-77 | H | 3-Pyza | —CH$_2$COO$^t$Bu | 2-F | H | H |
| 2-78 | Ac | 3-Pyza | —CH$_2$COO$^t$Bu | 2-F | H | H |
| 2-79 | H | 3-Pyza | —CH$_2$COO$^t$Bu | 2-F | 4-F | H |
| 2-80 | Ac | 3-Pyza | —CH$_2$COO$^t$Bu | 2-F | 4-F | H |
| 2-81 | H | 3-Pyza | —(CH$_2$)$_2$COO$^t$Bu | 2-F | H | H |
| 2-82 | Ac | 3-Pyza | —(CH$_2$)$_2$COO$^t$Bu | 2-F | H | H |
| 2-83 | H | 3-Pyza | —(CH$_2$)$_2$COO$^t$Bu | 2-F | 4-F | H |
| 2-84 | Ac | 3-Pyza | —(CH$_2$)$_2$COO$^t$Bu | 2-F | 4-F | H |
| 2-85 | H | 3-Pyza | —CH$_2$CONHOH | 2-F | H | H |
| 2-86 | Ac | 3-Pyza | —CH$_2$CONHOH | 2-F | H | H |
| 2-87 | H | 3-Pyza | —CH$_2$CONHOH | 2-F | 4-F | H |
| 2-88 | Ac | 3-Pyza | —CH$_2$CONHOH | 2-F | 4-F | H |
| 2-89 | H | 3-Pyza | —(CH$_2$)$_2$CONHOH | 2-F | H | H |
| 2-90 | Ac | 3-Pyza | —(CH$_2$)$_2$CONHOH | 2-F | H | H |
| 2-91 | H | 3-Pyza | —(CH$_2$)$_2$CONHOH | 2-F | 4-F | H |
| 2-92 | Ac | 3-Pyza | —(CH$_2$)$_2$CONHOH | 2-F | 4-F | H |
| 2-93 | H | 3-Pyza | —(CH$_2$)$_3$CONHOH | 2-F | H | H |
| 2-94 | Ac | 3-Pyza | —(CH$_2$)$_3$CONHOH | 2-F | H | H |
| 2-95 | H | 3-Pyza | —(CH$_2$)$_3$CONHOH | 2-F | 4-F | H |
| 2-96 | Ac | 3-Pyza | —(CH$_2$)$_3$CONHOH | 2-F | 4-F | H |
| 2-97 | H | 3-Pyza | —(CH$_2$)$_4$CONHOH | 2-F | H | H |
| 2-98 | Ac | 3-Pyza | —(CH$_2$)$_4$CONHOH | 2-F | H | H |
| 2-99 | H | 3-Pyza | —(CH$_2$)$_4$CONHOH | 2-F | 4-F | H |
| 2-100 | Ac | 3-Pyza | —(CH$_2$)$_4$CONHOH | 2-F | 4-F | H |
| 2-101 | H | 3-Pyza | —CH$_2$CONH$_2$ | 2-F | H | H |
| 2-102 | Ac | 3-Pyza | —CH$_2$CONH$_2$ | 2-F | H | H |
| 2-103 | H | 3-Pyza | —CH$_2$CONH$_2$ | 2-F | 4-F | H |
| 2-104 | Ac | 3-Pyza | —CH$_2$CONH$_2$ | 2-F | 4-F | H |
| 2-105 | H | 3-Pyza | —(CH$_2$)$_2$CONH$_2$ | 2-F | H | H |
| 2-106 | Ac | 3-Pyza | —(CH$_2$)$_2$CONH$_2$ | 2-F | H | H |
| 2-107 | H | 3-Pyza | —(CH$_2$)$_2$CONH$_2$ | 2-F | 4-F | H |
| 2-108 | Ac | 3-Pyza | —(CH$_2$)$_2$CONH$_2$ | 2-F | 4-F | H |
| 2-109 | H | 3-Pyza | —CH$_2$CONHMe | 2-F | H | H |
| 2-110 | Ac | 3-Pyza | —CH$_2$CONHMe | 2-F | H | H |
| 2-111 | H | 3-Pyza | —CH$_2$CONHMe | 2-F | 4-F | H |
| 2-112 | Ac | 3-Pyza | —CH$_2$CONHMe | 2-F | 4-F | H |
| 2-113 | H | 3-Pyza | —(CH$_2$)$_2$CONHMe | 2-F | H | H |
| 2-114 | Ac | 3-Pyza | —(CH$_2$)$_2$CONHMe | 2-F | H | H |
| 2-115 | H | 3-Pyza | —(CH$_2$)$_2$CONHMe | 2-F | 4-F | H |
| 2-116 | Ac | 3-Pyza | —(CH$_2$)$_2$CONHMe | 2-F | 4-F | H |
| 2-117 | H | 3-Pyza | —CH$_2$CONMe$_2$ | 2-F | H | H |
| 2-118 | Ac | 3-Pyza | —CH$_2$CONMe$_2$ | 2-F | H | H |
| 2-119 | H | 3-Pyza | —CH$_2$CONMe$_2$ | 2-F | 4-F | H |
| 2-120 | Ac | 3-Pyza | —CH$_2$CONMe$_2$ | 2-F | 4-F | H |
| 2-121 | H | 3-Pyza | —(CH$_2$)$_2$CONMe$_2$ | 2-F | H | H |
| 2-122 | Ac | 3-Pyza | —(CH$_2$)$_2$CONMe$_2$ | 2-F | H | H |
| 2-123 | H | 3-Pyza | —(CH$_2$)$_2$CONMe$_2$ | 2-F | 4-F | H |
| 2-124 | Ac | 3-Pyza | —(CH$_2$)$_2$CONMe$_2$ | 2-F | 4-F | H |
| 2-125 | H | 3-Pyza | —CH$_2$SO$_2$NH$_2$ | 2-F | H | H |
| 2-126 | Ac | 3-Pyza | —CH$_2$SO$_2$NH$_2$ | 2-F | H | H |
| 2-127 | H | 3-Pyza | —CH$_2$SO$_2$NH$_2$ | 2-F | 4-F | H |
| 2-128 | Ac | 3-Pyza | —CH$_2$SO$_2$NH$_2$ | 2-F | 4-F | H |
| 2-129 | H | 3-Pyza | —(CH$_2$)$_2$SO$_2$NH$_2$ | 2-F | H | H |
| 2-130 | Ac | 3-Pyza | —(CH$_2$)$_2$SO$_2$NH$_2$ | 2-F | H | H |
| 2-131 | H | 3-Pyza | —(CH$_2$)$_2$SO$_2$NH$_2$ | 2-F | 4-F | H |
| 2-132 | Ac | 3-Pyza | —(CH$_2$)$_2$SO$_2$NH$_2$ | 2-F | 4-F | H |
| 2-133 | H | 3-Pyza | —CH$_2$COEt | 2-F | H | H |
| 2-134 | Ac | 3-Pyza | —CH$_2$COEt | 2-F | H | H |
| 2-135 | H | 3-Pyza | —CH$_2$COEt | 2-F | 4-F | H |
| 2-136 | Ac | 3-Pyza | —CH$_2$COEt | 2-F | 4-F | H |
| 2-137 | H | 3-Pyza | —(CH$_2$)$_2$COEt | 2-F | H | H |
| 2-138 | Ac | 3-Pyza | —(CH$_2$)$_2$COEt | 2-F | H | H |
| 2-139 | H | 3-Pyza | —(CH$_2$)$_2$COEt | 2-F | 4-F | H |
| 2-140 | Ac | 3-Pyza | —(CH$_2$)$_2$COEt | 2-F | 4-F | H |
| 2-141 | H | 3-Pyza | —CH(COOEt)CH$_2$COOEt | 2-F | H | H |
| 2-142 | Ac | 3-Pyza | —CH(COOEt)CH$_2$COOEt | 2-F | H | H |
| 2-143 | H | 3-Pyza | —CH(COOEt)CH$_2$COOEt | 2-F | 4-F | H |
| 2-144 | Ac | 3-Pyza | —CH(COOEt)CH$_2$COOEt | 2-F | 4-F | H |
| 2-145 | H | 3-Pyza | —CH$_2$-(4-Thiz) | 2-F | H | H |
| 2-146 | Ac | 3-Pyza | —CH$_2$-(4-Thiz) | 2-F | H | H |
| 2-147 | H | 3-Pyza | —CH$_2$-(4-Thiz) | 2-F | 4-F | H |
| 2-148 | Ac | 3-Pyza | —CH$_2$-(4-Thiz) | 2-F | 4-F | H |
| 2-149 | H | 3-Pyza | —(CH$_2$)$_2$-(4-Thiz) | 2-F | H | H |
| 2-150 | Ac | 3-Pyza | —(CH$_2$)$_2$-(4-Thiz) | 2-F | H | H |
| 2-151 | H | 3-Pyza | —(CH$_2$)$_2$-(4-Thiz) | 2-F | 4-F | H |
| 2-152 | Ac | 3-Pyza | —(CH$_2$)$_2$-(4-Thiz) | 2-F | 4-F | H |
| 2-153 | H | 3-Pyza | —CH$_2$OH | 2-F | H | H |
| 2-154 | Ac | 3-Pyza | —CH$_2$OH | 2-F | H | H |
| 2-155 | H | 3-Pyza | —CH$_2$OH | 2-F | 4-F | H |
| 2-156 | Ac | 3-Pyza | —CH$_2$OH | 2-F | 4-F | H |
| 2-157 | H | 3-Pyza | —(CH$_2$)$_2$OH | 2-F | H | H |
| 2-158 | Ac | 3-Pyza | —(CH$_2$)$_2$OH | 2-F | H | H |
| 2-159 | H | 3-Pyza | —(CH$_2$)$_2$OH | 2-F | 4-F | H |
| 2-160 | Ac | 3-Pyza | —(CH$_2$)$_2$OH | 2-F | 4-F | H |
| 2-161 | H | 3-Pyza | —CH$_2$OMe | 2-F | H | H |
| 2-162 | Ac | 3-Pyza | —CH$_2$OMe | 2-F | H | H |
| 2-163 | H | 3-Pyza | —CH$_2$OMe | 2-F | 4-F | H |
| 2-164 | Ac | 3-Pyza | —CH$_2$OMe | 2-F | 4-F | H |
| 2-165 | H | 3-Pyza | —(CH$_2$)$_2$OMe | 2-F | H | H |
| 2-166 | Ac | 3-Pyza | —(CH$_2$)$_2$OMe | 2-F | H | H |
| 2-167 | H | 3-Pyza | —(CH$_2$)$_2$OMe | 2-F | 4-F | H |
| 2-168 | Ac | 3-Pyza | —(CH$_2$)$_2$OMe | 2-F | 4-F | H |
| 2-169 | H | 4-Pyza | Me | 2-F | H | H |
| 2-170 | Ac | 4-Pyza | Me | 2-F | H | H |
| 2-171 | H | 4-Pyza | Me | 2-F | 4-F | H |
| 2-172 | Ac | 4-Pyza | Me | 2-F | 4-F | H |
| 2-173 | H | 4-Pyza | Et | 2-F | H | H |
| 2-174 | Ac | 4-Pyza | Et | 2-F | H | H |
| 2-175 | H | 4-Pyza | Et | 2-F | 4-F | H |
| 2-176 | Ac | 4-Pyza | Et | 2-F | 4-F | H |
| 2-177 | H | 4-Pyza | Ac | 2-F | H | H |
| 2-178 | Ac | 4-Pyza | Ac | 2-F | H | H |
| 2-179 | H | 4-Pyza | Ac | 2-F | 4-F | H |
| 2-180 | Ac | 4-Pyza | Ac | 2-F | 4-F | H |
| 2-181 | H | 4-Pyza | —CH$_2$COOH | 2-F | H | H |
| 2-182 | Ac | 4-Pyza | —CH$_2$COOH | 2-F | H | H |
| 2-183 | H | 4-Pyza | —CH$_2$COOH | 2-F | 4-F | H |
| 2-184 | Ac | 4-Pyza | —CH$_2$COOH | 2-F | 4-F | H |
| 2-185 | H | 4-Pyza | —(CH$_2$)$_2$COOH | 2-F | H | H |
| 2-186 | Ac | 4-Pyza | —(CH$_2$)$_2$COOH | 2-F | H | H |
| 2-187 | H | 4-Pyza | —(CH$_2$)$_2$COOH | 2-F | 4-F | H |
| 2-188 | Ac | 4-Pyza | —(CH$_2$)$_2$COOH | 2-F | 4-F | H |
| 2-189 | H | 4-Pyza | —(CH$_2$)$_3$COOH | 2-F | H | H |
| 2-190 | Ac | 4-Pyza | —(CH$_2$)$_3$COOH | 2-F | H | H |
| 2-191 | H | 4-Pyza | —(CH$_2$)$_3$COOH | 2-F | 4-F | H |
| 2-192 | Ac | 4-Pyza | —(CH$_2$)$_3$COOH | 2-F | 4-F | H |
| 2-193 | H | 4-Pyza | —(CH$_2$)$_4$COOH | 2-F | H | H |
| 2-194 | Ac | 4-Pyza | —(CH$_2$)$_4$COOH | 2-F | H | H |
| 2-195 | H | 4-Pyza | —(CH$_2$)$_4$COOH | 2-F | 4-F | H |
| 2-196 | Ac | 4-Pyza | —(CH$_2$)$_4$COOH | 2-F | 4-F | H |
| 2-197 | H | 4-Pyza | —CH$_2$COOMe | 2-F | H | H |
| 2-198 | Ac | 4-Pyza | —CH$_2$COOMe | 2-F | H | H |
| 2-199 | H | 4-Pyza | —CH$_2$COOMe | 2-F | 4-F | H |
| 2-200 | Ac | 4-Pyza | —CH$_2$COOMe | 2-F | 4-F | H |
| 2-201 | H | 4-Pyza | —(CH$_2$)$_2$COOMe | 2-F | H | H |
| 2-202 | Ac | 4-Pyza | —(CH$_2$)$_2$COOMe | 2-F | H | H |
| 2-203 | H | 4-Pyza | —(CH$_2$)$_2$COOMe | 2-F | 4-F | H |
| 2-204 | Ac | 4-Pyza | —(CH$_2$)$_2$COOMe | 2-F | 4-F | H |

TABLE 2-continued

| | | | | | | |
|---|---|---|---|---|---|---|
| 2-205 | H | 4-Pyza | —(CH$_2$)$_3$COOMe | 2-F | H | H |
| 2-206 | Ac | 4-Pyza | —(CH$_2$)$_3$COOMe | 2-F | H | H |
| 2-207 | H | 4-Pyza | —(CH$_2$)$_3$COOMe | 2-F | 4-F | H |
| 2-208 | Ac | 4-Pyza | —(CH$_2$)$_3$COOMe | 2-F | 4-F | H |
| 2-209 | H | 4-Pyza | —(CH$_2$)$_4$COOMe | 2-F | H | H |
| 2-210 | Ac | 4-Pyza | —(CH$_2$)$_4$COOMe | 2-F | H | H |
| 2-211 | H | 4-Pyza | —(CH$_2$)$_4$COOMe | 2-F | 4-F | H |
| 2-212 | Ac | 4-Pyza | —(CH$_2$)$_4$COOMe | 2-F | 4-F | H |
| 2-213 | H | 4-Pyza | —CH$_2$COOEt | 2-F | H | H |
| 2-214 | Ac | 4-Pyza | —CH$_2$COOEt | 2-F | H | H |
| 2-215 | H | 4-Pyza | —CH$_2$COOEt | 2-F | 4-F | H |
| 2-216 | Ac | 4-Pyza | —CH$_2$COOEt | 2-F | 4-F | H |
| 2-217 | H | 4-Pyza | —(CH$_2$)$_2$COOEt | 2-F | H | H |
| 2-218 | Ac | 4-Pyza | —(CH$_2$)$_2$COOEt | 2-F | H | H |
| 2-219 | H | 4-Pyza | —(CH$_2$)$_2$COOEt | 2-F | 4-F | H |
| 2-220 | Ac | 4-Pyza | —(CH$_2$)$_2$COOEt | 2-F | 4-F | H |
| 2-221 | H | 4-Pyza | —(CH$_2$)$_3$COOEt | 2-F | H | H |
| 2-222 | Ac | 4-Pyza | —(CH$_2$)$_3$COOEt | 2-F | H | H |
| 2-223 | H | 4-Pyza | —(CH$_2$)$_3$COOEt | 2-F | 4-F | H |
| 2-224 | Ac | 4-Pyza | —(CH$_2$)$_3$COOEt | 2-F | 4-F | H |
| 2-225 | H | 4-Pyza | —(CH$_2$)$_4$COOEt | 2-F | H | H |
| 2-226 | Ac | 4-Pyza | —(CH$_2$)$_4$COOEt | 2-F | H | H |
| 2-227 | H | 4-Pyza | —(CH$_2$)$_4$COOEt | 2-F | 4-F | H |
| 2-228 | Ac | 4-Pyza | —(CH$_2$)$_4$COOEt | 2-F | 4-F | H |
| 2-229 | H | 4-Pyza | —CH$_2$COOPr | 2-F | H | H |
| 2-230 | Ac | 4-Pyza | —CH$_2$COOPr | 2-F | H | H |
| 2-231 | H | 4-Pyza | —CH$_2$COOPr | 2-F | 4-F | H |
| 2-232 | Ac | 4-Pyza | —CH$_2$COOPr | 2-F | 4-F | H |
| 2-233 | H | 4-Pyza | —(CH$_2$)$_2$COOPr | 2-F | H | H |
| 2-234 | Ac | 4-Pyza | —(CH$_2$)$_2$COOPr | 2-F | H | H |
| 2-235 | H | 4-Pyza | —(CH$_2$)$_2$COOPr | 2-F | 4-F | H |
| 2-236 | Ac | 4-Pyza | —(CH$_2$)$_2$COOPr | 2-F | 4-F | H |
| 2-237 | H | 4-Pyza | —CH$_2$COOBu | 2-F | H | H |
| 2-238 | Ac | 4-Pyza | —CH$_2$COOBu | 2-F | H | H |
| 2-239 | H | 4-Pyza | —CH$_2$COOBu | 2-F | 4-F | H |
| 2-240 | Ac | 4-Pyza | —CH$_2$COOBu | 2-F | 4-F | H |
| 2-241 | H | 4-Pyza | —(CH$_2$)$_2$COOBu | 2-F | H | H |
| 2-242 | Ac | 4-Pyza | —(CH$_2$)$_2$COOBu | 2-F | H | H |
| 2-243 | H | 4-Pyza | —(CH$_2$)$_2$COOBu | 2-F | 4-F | H |
| 2-244 | Ac | 4-Pyza | —(CH$_2$)$_2$COOBu | 2-F | 4-F | H |
| 2-245 | H | 4-Pyza | —CH$_2$COO$^t$Bu | 2-F | H | H |
| 2-246 | Ac | 4-Pyza | —CH$_2$COO$^t$Bu | 2-F | H | H |
| 2-247 | H | 4-Pyza | —CH$_2$COO$^t$Bu | 2-F | 4-F | H |
| 2-248 | Ac | 4-Pyza | —CH$_2$COO$^t$Bu | 2-F | 4-F | H |
| 2-249 | H | 4-Pyza | —(CH$_2$)$_2$COO$^t$Bu | 2-F | H | H |
| 2-250 | Ac | 4-Pyza | —(CH$_2$)$_2$COO$^t$Bu | 2-F | H | H |
| 2-251 | H | 4-Pyza | —(CH$_2$)$_2$COO$^t$Bu | 2-F | 4-F | H |
| 2-252 | Ac | 4-Pyza | —(CH$_2$)$_2$COO$^t$Bu | 2-F | 4-F | H |
| 2-253 | H | 4-Pyza | —CH$_2$CONHOH | 2-F | H | H |
| 2-254 | Ac | 4-Pyza | —CH$_2$CONHOH | 2-F | H | H |
| 2-255 | H | 4-Pyza | —CH$_2$CONHOH | 2-F | 4-F | H |
| 2-256 | Ac | 4-Pyza | —CH$_2$CONHOH | 2-F | 4-F | H |
| 2-257 | H | 4-Pyza | —(CH$_2$)$_2$CONHOH | 2-F | H | H |
| 2-258 | Ac | 4-Pyza | —(CH$_2$)$_2$CONHOH | 2-F | H | H |
| 2-259 | H | 4-Pyza | —(CH$_2$)$_2$CONHOH | 2-F | 4-F | H |
| 2-260 | Ac | 4-Pyza | —(CH$_2$)$_2$CONHOH | 2-F | 4-F | H |
| 2-261 | H | 4-Pyza | —(CH$_2$)$_3$CONHOH | 2-F | H | H |
| 2-262 | Ac | 4-Pyza | —(CH$_2$)$_3$CONHOH | 2-F | H | H |
| 2-263 | H | 4-Pyza | —(CH$_2$)$_3$CONHOH | 2-F | 4-F | H |
| 2-264 | Ac | 4-Pyza | —(CH$_2$)$_3$CONHOH | 2-F | 4-F | H |
| 2-265 | H | 4-Pyza | —(CH$_2$)$_4$CONHOH | 2-F | H | H |
| 2-266 | Ac | 4-Pyza | —(CH$_2$)$_4$CONHOH | 2-F | H | H |
| 2-267 | H | 4-Pyza | —(CH$_2$)$_4$CONHOH | 2-F | 4-F | H |
| 2-268 | Ac | 4-Pyza | —(CH$_2$)$_4$CONHOH | 2-F | 4-F | H |
| 2-269 | H | 4-Pyza | —CH$_2$CONH$_2$ | 2-F | H | H |
| 2-270 | Ac | 4-Pyza | —CH$_2$CONH$_2$ | 2-F | H | H |
| 2-271 | H | 4-Pyza | —CH$_2$CONH$_2$ | 2-F | 4-F | H |
| 2-272 | Ac | 4-Pyza | —CH$_2$CONH$_2$ | 2-F | 4-F | H |
| 2-273 | H | 4-Pyza | —(CH$_2$)$_2$CONH$_2$ | 2-F | H | H |
| 2-274 | Ac | 4-Pyza | —(CH$_2$)$_2$CONH$_2$ | 2-F | H | H |
| 2-275 | H | 4-Pyza | —(CH$_2$)$_2$CONH$_2$ | 2-F | 4-F | H |
| 2-276 | Ac | 4-Pyza | —(CH$_2$)$_2$CONH$_2$ | 2-F | 4-F | H |
| 2-277 | H | 4-Pyza | —CH$_2$CONHMe | 2-F | H | H |
| 2-278 | Ac | 4-Pyza | —CH$_2$CONHMe | 2-F | H | H |
| 2-279 | H | 4-Pyza | —CH$_2$CONHMe | 2-F | 4-F | H |
| 2-280 | Ac | 4-Pyza | —CH$_2$CONHMe | 2-F | 4-F | H |
| 2-281 | H | 4-Pyza | —(CH$_2$)$_2$CONHMe | 2-F | H | H |
| 2-282 | Ac | 4-Pyza | —(CH$_2$)$_2$CONHMe | 2-F | H | H |
| 2-283 | H | 4-Pyza | —(CH$_2$)$_2$CONHMe | 2-F | 4-F | H |
| 2-284 | Ac | 4-Pyza | —(CH$_2$)$_2$CONHMe | 2-F | 4-F | H |
| 2-285 | H | 4-Pyza | —CH$_2$CONMe$_2$ | 2-F | H | H |
| 2-286 | Ac | 4-Pyza | —CH$_2$CONMe$_2$ | 2-F | H | H |
| 2-287 | H | 4-Pyza | —CH$_2$CONMe$_2$ | 2-F | 4-F | H |
| 2-288 | Ac | 4-Pyza | —CH$_2$CONMe$_2$ | 2-F | 4-F | H |
| 2-289 | H | 4-Pyza | —(CH$_2$)$_2$CONMe$_2$ | 2-F | H | H |
| 2-290 | Ac | 4-Pyza | —(CH$_2$)$_2$CONMe$_2$ | 2-F | H | H |
| 2-291 | H | 4-Pyza | —(CH$_2$)$_2$CONMe$_2$ | 2-F | 4-F | H |
| 2-292 | Ac | 4-Pyza | —(CH$_2$)$_2$CONMe$_2$ | 2-F | 4-F | H |
| 2-293 | H | 4-Pyza | —CH$_2$SO$_2$NH$_2$ | 2-F | H | H |
| 2-294 | Ac | 4-Pyza | —CH$_2$SO$_2$NH$_2$ | 2-F | H | H |
| 2-295 | H | 4-Pyza | —CH$_2$SO$_2$NH$_2$ | 2-F | 4-F | H |
| 2-296 | Ac | 4-Pyza | —CH$_2$SO$_2$NH$_2$ | 2-F | 4-F | H |
| 2-297 | H | 4-Pyza | —(CH$_2$)$_2$SO$_2$NH$_2$ | 2-F | H | H |
| 2-298 | Ac | 4-Pyza | —(CH$_2$)$_2$SO$_2$NH$_2$ | 2-F | H | H |
| 2-299 | H | 4-Pyza | —(CH$_2$)$_2$SO$_2$NH$_2$ | 2-F | 4-F | H |
| 2-300 | Ac | 4-Pyza | —(CH$_2$)$_2$SO$_2$NH$_2$ | 2-F | 4-F | H |
| 2-301 | H | 4-Pyza | —CH$_2$COEt | 2-F | H | H |
| 2-302 | Ac | 4-Pyza | —CH$_2$COEt | 2-F | H | H |
| 2-303 | H | 4-Pyza | —CH$_2$COEt | 2-F | 4-F | H |
| 2-304 | Ac | 4-Pyza | —CH$_2$COEt | 2-F | 4-F | H |
| 2-305 | H | 4-Pyza | —(CH$_2$)$_2$COEt | 2-F | H | H |
| 2-306 | Ac | 4-Pyza | —(CH$_2$)$_2$COEt | 2-F | H | H |
| 2-307 | H | 4-Pyza | —(CH$_2$)$_2$COEt | 2-F | 4-F | H |
| 2-308 | Ac | 4-Pyza | —(CH$_2$)$_2$COEt | 2-F | 4-F | H |
| 2-309 | H | 4-Pyza | —CH(COOEt)CH$_2$COOEt | 2-F | H | H |
| 2-310 | Ac | 4-Pyza | —CH(COOEt)CH$_2$COOEt | 2-F | H | H |
| 2-311 | H | 4-Pyza | —CH(COOEt)CH$_2$COOEt | 2-F | 4-F | H |
| 2-312 | Ac | 4-Pyza | —CH(COOEt)CH$_2$COOEt | 2-F | 4-F | H |
| 2-313 | H | 4-Pyza | —CH$_2$-(4-Thiz) | 2-F | H | H |
| 2-314 | Ac | 4-Pyza | —CH$_2$-(4-Thiz) | 2-F | H | H |
| 2-315 | H | 4-Pyza | —CH$_2$-(4-Thiz) | 2-F | 4-F | H |
| 2-316 | Ac | 4-Pyza | —CH$_2$-(4-Thiz) | 2-F | 4-F | H |
| 2-317 | H | 4-Pyza | —(CH$_2$)$_2$-(4-Thiz) | 2-F | H | H |
| 2-318 | Ac | 4-Pyza | —(CH$_2$)$_2$-(4-Thiz) | 2-F | H | H |
| 2-319 | H | 4-Pyza | —(CH$_2$)$_2$-(4-Thiz) | 2-F | 4-F | H |
| 2-320 | Ac | 4-Pyza | —(CH$_2$)$_2$-(4-Thiz) | 2-F | 4-F | H |
| 2-321 | H | 4-Pyza | —CH$_2$OH | 2-F | H | H |
| 2-322 | Ac | 4-Pyza | —CH$_2$OH | 2-F | H | H |
| 2-323 | H | 4-Pyza | —CH$_2$OH | 2-F | 4-F | H |
| 2-324 | Ac | 4-Pyza | —CH$_2$OH | 2-F | 4-F | H |
| 2-325 | H | 4-Pyza | —(CH$_2$)$_2$OH | 2-F | H | H |
| 2-326 | Ac | 4-Pyza | —(CH$_2$)$_2$OH | 2-F | H | H |
| 2-327 | H | 4-Pyza | —(CH$_2$)$_2$OH | 2-F | 4-F | H |
| 2-328 | Ac | 4-Pyza | —(CH$_2$)$_2$OH | 2-F | 4-F | H |
| 2-329 | H | 4-Pyza | —CH$_2$OMe | 2-F | H | H |
| 2-330 | Ac | 4-Pyza | —CH$_2$OMe | 2-F | H | H |
| 2-331 | H | 4-Pyza | —CH$_2$OMe | 2-F | 4-F | H |
| 2-332 | Ac | 4-Pyza | —CH$_2$OMe | 2-F | 4-F | H |
| 2-333 | H | 4-Pyza | —(CH$_2$)$_2$OMe | 2-F | H | H |
| 2-334 | Ac | 4-Pyza | —(CH$_2$)$_2$OMe | 2-F | H | H |
| 2-335 | H | 4-Pyza | —(CH$_2$)$_2$OMe | 2-F | 4-F | H |
| 2-336 | Ac | 4-Pyza | —(CH$_2$)$_2$OMe | 2-F | 4-F | H |
| 2-337 | H | 5-Pyza | Me | 2-F | H | H |
| 2-338 | Ac | 5-Pyza | Me | 2-F | H | H |
| 2-339 | H | 5-Pyza | Me | 2-F | 4-F | H |
| 2-340 | Ac | 5-Pyza | Me | 2-F | 4-F | H |
| 2-341 | H | 5-Pyza | Et | 2-F | H | H |
| 2-342 | Ac | 5-Pyza | Et | 2-F | H | H |
| 2-343 | H | 5-Pyza | Et | 2-F | 4-F | H |
| 2-344 | Ac | 5-Pyza | Et | 2-F | 4-F | H |
| 2-345 | H | 5-Pyza | Ac | 2-F | H | H |
| 2-346 | Ac | 5-Pyza | Ac | 2-F | H | H |
| 2-347 | H | 5-Pyza | Ac | 2-F | 4-F | H |
| 2-348 | Ac | 5-Pyza | Ac | 2-F | 4-F | H |
| 2-349 | H | 5-Pyza | —CH$_2$COOH | 2-F | H | H |
| 2-350 | Ac | 5-Pyza | —CH$_2$COOH | 2-F | H | H |
| 2-351 | H | 5-Pyza | —CH$_2$COOH | 2-F | 4-F | H |
| 2-352 | Ac | 5-Pyza | —CH$_2$COOH | 2-F | 4-F | H |
| 2-353 | H | 5-Pyza | —(CH$_2$)$_2$COOH | 2-F | H | H |
| 2-354 | Ac | 5-Pyza | —(CH$_2$)$_2$COOH | 2-F | H | H |
| 2-355 | H | 5-Pyza | —(CH$_2$)$_2$COOH | 2-F | 4-F | H |
| 2-356 | Ac | 5-Pyza | —(CH$_2$)$_2$COOH | 2-F | 4-F | H |
| 2-357 | H | 5-Pyza | —(CH$_2$)$_3$COOH | 2-F | H | H |
| 2-358 | Ac | 5-Pyza | —(CH$_2$)$_3$COOH | 2-F | H | H |
| 2-359 | H | 5-Pyza | —(CH$_2$)$_3$COOH | 2-F | 4-F | H |
| 2-360 | Ac | 5-Pyza | —(CH$_2$)$_3$COOH | 2-F | 4-F | H |
| 2-361 | H | 5-Pyza | —(CH$_2$)$_4$COOH | 2-F | H | H |
| 2-362 | Ac | 5-Pyza | —(CH$_2$)$_4$COOH | 2-F | H | H |

TABLE 2-continued

| | | | | | | |
|---|---|---|---|---|---|---|
| 2-363 | H | 5-Pyza | —(CH₂)₄COOH | 2-F | H | H |
| 2-364 | Ac | 5-Pyza | —(CH₂)₄COOH | 2-F | 4-F | H |
| 2-365 | H | 5-Pyza | —CH₂COOMe | 2-F | H | H |
| 2-366 | Ac | 5-Pyza | —CH₂COOMe | 2-F | H | H |
| 2-367 | H | 5-Pyza | —CH₂COOMe | 2-F | 4-F | H |
| 2-368 | Ac | 5-Pyza | —CH₂COOMe | 2-F | 4-F | H |
| 2-369 | H | 5-Pyza | —(CH₂)₂COOMe | 2-F | H | H |
| 2-370 | Ac | 5-Pyza | —(CH₂)₂COOMe | 2-F | H | H |
| 2-371 | H | 5-Pyza | —(CH₂)₂COOMe | 2-F | 4-F | H |
| 2-372 | Ac | 5-Pyza | —(CH₂)₂COOMe | 2-F | 4-F | H |
| 2-373 | H | 5-Pyza | —(CH₂)₃COOMe | 2-F | H | H |
| 2-374 | Ac | 5-Pyza | —(CH₂)₃COOMe | 2-F | H | H |
| 2-375 | H | 5-Pyza | —(CH₂)₃COOMe | 2-F | 4-F | H |
| 2-376 | Ac | 5-Pyza | —(CH₂)₃COOMe | 2-F | 4-F | H |
| 2-377 | H | 5-Pyza | —(CH₂)₄COOMe | 2-F | H | H |
| 2-378 | Ac | 5-Pyza | —(CH₂)₄COOMe | 2-F | H | H |
| 2-379 | H | 5-Pyza | —(CH₂)₄COOMe | 2-F | 4-F | H |
| 2-380 | Ac | 5-Pyza | —(CH₂)₄COOMe | 2-F | 4-F | H |
| 2-381 | H | 5-Pyza | —CH₂COOEt | 2-F | H | H |
| 2-382 | Ac | 5-Pyza | —CH₂COOEt | 2-F | H | H |
| 2-383 | H | 5-Pyza | —CH₂COOEt | 2-F | 4-F | H |
| 2-384 | Ac | 5-Pyza | —CH₂COOEt | 2-F | 4-F | H |
| 2-385 | H | 5-Pyza | —(CH₂)₂COOEt | 2-F | H | H |
| 2-386 | Ac | 5-Pyza | —(CH₂)₂COOEt | 2-F | H | H |
| 2-387 | H | 5-Pyza | —(CH₂)₂COOEt | 2-F | 4-F | H |
| 2-388 | Ac | 5-Pyza | —(CH₂)₂COOEt | 2-F | 4-F | H |
| 2-389 | H | 5-Pyza | —(CH₂)₃COOEt | 2-F | H | H |
| 2-390 | Ac | 5-Pyza | —(CH₂)₃COOEt | 2-F | H | H |
| 2-391 | H | 5-Pyza | —(CH₂)₃COOEt | 2-F | 4-F | H |
| 2-392 | Ac | 5-Pyza | —(CH₂)₃COOEt | 2-F | 4-F | H |
| 2-393 | H | 5-Pyza | —(CH₂)₄COOEt | 2-F | H | H |
| 2-394 | Ac | 5-Pyza | —(CH₂)₄COOEt | 2-F | H | H |
| 2-395 | H | 5-Pyza | —(CH₂)₄COOEt | 2-F | 4-F | H |
| 2-396 | Ac | 5-Pyza | —(CH₂)₄COOEt | 2-F | 4-F | H |
| 2-397 | H | 5-Pyza | —CH₂COOPr | 2-F | H | H |
| 2-398 | Ac | 5-Pyza | —CH₂COOPr | 2-F | H | H |
| 2-399 | H | 5-Pyza | —CH₂COOPr | 2-F | 4-F | H |
| 2-400 | Ac | 5-Pyza | —CH₂COOPr | 2-F | 4-F | H |
| 2-401 | H | 5-Pyza | —(CH₂)₂COOPr | 2-F | H | H |
| 2-402 | Ac | 5-Pyza | —(CH₂)₂COOPr | 2-F | H | H |
| 2-403 | H | 5-Pyza | —(CH₂)₂COOPr | 2-F | 4-F | H |
| 2-404 | Ac | 5-Pyza | —(CH₂)₂COOPr | 2-F | 4-F | H |
| 2-405 | H | 5-Pyza | —CH₂COOBu | 2-F | H | H |
| 2-406 | Ac | 5-Pyza | —CH₂COOBu | 2-F | H | H |
| 2-407 | H | 5-Pyza | —CH₂COOBu | 2-F | 4-F | H |
| 2-408 | Ac | 5-Pyza | —CH₂COOBu | 2-F | 4-F | H |
| 2-409 | H | 5-Pyza | —(CH₂)₂COOBu | 2-F | H | H |
| 2-410 | Ac | 5-Pyza | —(CH₂)₂COOBu | 2-F | H | H |
| 2-411 | H | 5-Pyza | —(CH₂)₂COOBu | 2-F | 4-F | H |
| 2-412 | Ac | 5-Pyza | —(CH₂)₂COOBu | 2-F | 4-F | H |
| 2-413 | H | 5-Pyza | —CH₂COOᵗBu | 2-F | H | H |
| 2-414 | Ac | 5-Pyza | —CH₂COOᵗBu | 2-F | H | H |
| 2-415 | H | 5-Pyza | —CH₂COOᵗBu | 2-F | 4-F | H |
| 2-416 | Ac | 5-Pyza | —CH₂COOᵗBu | 2-F | 4-F | H |
| 2-417 | H | 5-Pyza | —(CH₂)₂COOᵗBu | 2-F | H | H |
| 2-418 | Ac | 5-Pyza | —(CH₂)₂COOᵗBu | 2-F | H | H |
| 2-419 | H | 5-Pyza | —(CH₂)₂COOᵗBu | 2-F | 4-F | H |
| 2-420 | Ac | 5-Pyza | —(CH₂)₂COOᵗBu | 2-F | 4-F | H |
| 2-421 | H | 5-Pyza | —CH₂CONHOH | 2-F | H | H |
| 2-422 | Ac | 5-Pyza | —CH₂CONHOH | 2-F | H | H |
| 2-423 | H | 5-Pyza | —CH₂CONHOH | 2-F | 4-F | H |
| 2-424 | Ac | 5-Pyza | —CH₂CONHOH | 2-F | 4-F | H |
| 2-425 | H | 5-Pyza | —(CH₂)₂CONHOH | 2-F | H | H |
| 2-426 | Ac | 5-Pyza | —(CH₂)₂CONHOH | 2-F | H | H |
| 2-427 | H | 5-Pyza | —(CH₂)₂CONHOH | 2-F | 4-F | H |
| 2-428 | Ac | 5-Pyza | —(CH₂)₂CONHOH | 2-F | 4-F | H |
| 2-429 | H | 5-Pyza | —(CH₂)₃CONHOH | 2-F | H | H |
| 2-430 | Ac | 5-Pyza | —(CH₂)₃CONHOH | 2-F | H | H |
| 2-431 | H | 5-Pyza | —(CH₂)₃CONHOH | 2-F | 4-F | H |
| 2-432 | Ac | 5-Pyza | —(CH₂)₃CONHOH | 2-F | 4-F | H |
| 2-433 | H | 5-Pyza | —(CH₂)₄CONHOH | 2-F | H | H |
| 2-434 | Ac | 5-Pyza | —(CH₂)₄CONHOH | 2-F | H | H |
| 2-435 | H | 5-Pyza | —(CH₂)₄CONHOH | 2-F | 4-F | H |
| 2-436 | Ac | 5-Pyza | —(CH₂)₄CONHOH | 2-F | 4-F | H |
| 2-437 | H | 5-Pyza | —CH₂CONH₂ | 2-F | H | H |
| 2-438 | Ac | 5-Pyza | —CH₂CONH₂ | 2-F | H | H |
| 2-439 | H | 5-Pyza | —CH₂CONH₂ | 2-F | 4-F | H |
| 2-440 | Ac | 5-Pyza | —CH₂CONH₂ | 2-F | 4-F | H |
| 2-441 | H | 5-Pyza | —(CH₂)₂CONH₂ | 2-F | H | H |
| 2-442 | Ac | 5-Pyza | —(CH₂)₂CONH₂ | 2-F | H | H |
| 2-443 | H | 5-Pyza | —(CH₂)₂CONH₂ | 2-F | 4-F | H |
| 2-444 | Ac | 5-Pyza | —(CH₂)₂CONH₂ | 2-F | 4-F | H |
| 2-445 | H | 5-Pyza | —CH₂CONHMe | 2-F | H | H |
| 2-446 | Ac | 5-Pyza | —CH₂CONHMe | 2-F | H | H |
| 2-447 | H | 5-Pyza | —CH₂CONHMe | 2-F | 4-F | H |
| 2-448 | Ac | 5-Pyza | —CH₂CONHMe | 2-F | 4-F | H |
| 2-449 | H | 5-Pyza | —(CH₂)₂CONHMe | 2-F | H | H |
| 2-450 | Ac | 5-Pyza | —(CH₂)₂CONHMe | 2-F | H | H |
| 2-451 | H | 5-Pyza | —(CH₂)₂CONHMe | 2-F | 4-F | H |
| 2-452 | Ac | 5-Pyza | —(CH₂)₂CONHMe | 2-F | 4-F | H |
| 2-453 | H | 5-Pyza | —CH₂CONMe₂ | 2-F | H | H |
| 2-454 | Ac | 5-Pyza | —CH₂CONMe₂ | 2-F | H | H |
| 2-455 | H | 5-Pyza | —CH₂CONMe₂ | 2-F | 4-F | H |
| 2-456 | Ac | 5-Pyza | —CH₂CONMe₂ | 2-F | 4-F | H |
| 2-457 | H | 5-Pyza | —(CH₂)₂CONMe₂ | 2-F | H | H |
| 2-458 | Ac | 5-Pyza | —(CH₂)₂CONMe₂ | 2-F | H | H |
| 2-459 | H | 5-Pyza | —(CH₂)₂CONMe₂ | 2-F | 4-F | H |
| 2-460 | Ac | 5-Pyza | —(CH₂)₂CONMe₂ | 2-F | 4-F | H |
| 2-461 | H | 5-Pyza | —CH₂SO₂NH₂ | 2-F | H | H |
| 2-462 | Ac | 5-Pyza | —CH₂SO₂NH₂ | 2-F | H | H |
| 2-463 | H | 5-Pyza | —CH₂SO₂NH₂ | 2-F | 4-F | H |
| 2-464 | Ac | 5-Pyza | —CH₂SO₂NH₂ | 2-F | 4-F | H |
| 2-465 | H | 5-Pyza | —(CH₂)₂SO₂NH₂ | 2-F | H | H |
| 2-466 | Ac | 5-Pyza | —(CH₂)₂SO₂NH₂ | 2-F | H | H |
| 2-467 | H | 5-Pyza | —(CH₂)₂SO₂NH₂ | 2-F | 4-F | H |
| 2-468 | Ac | 5-Pyza | —(CH₂)₂SO₂NH₂ | 2-F | 4-F | H |
| 2-469 | H | 5-Pyza | —CH₂COEt | 2-F | H | H |
| 2-470 | Ac | 5-Pyza | —CH₂COEt | 2-F | H | H |
| 2-471 | H | 5-Pyza | —CH₂COEt | 2-F | 4-F | H |
| 2-472 | Ac | 5-Pyza | —CH₂COEt | 2-F | 4-F | H |
| 2-473 | H | 5-Pyza | —(CH₂)₂COEt | 2-F | H | H |
| 2-474 | Ac | 5-Pyza | —(CH₂)₂COEt | 2-F | H | H |
| 2-475 | H | 5-Pyza | —(CH₂)₂COEt | 2-F | 4-F | H |
| 2-476 | Ac | 5-Pyza | —(CH₂)₂COEt | 2-F | 4-F | H |
| 2-477 | H | 5-Pyza | —CH(COOEt)CH₂COOEt | 2-F | H | H |
| 2-478 | Ac | 5-Pyza | —CH(COOEt)CH₂COOEt | 2-F | H | H |
| 2-479 | H | 5-Pyza | —CH(COOEt)CH₂COOEt | 2-F | 4-F | H |
| 2-480 | Ac | 5-Pyza | —CH(COOEt)CH₂COOEt | 2-F | 4-F | H |
| 2-481 | H | 5-Pyza | —CH₂-(4-Thiz) | 2-F | H | H |
| 2-482 | Ac | 5-Pyza | —CH₂-(4-Thiz) | 2-F | H | H |
| 2-483 | H | 5-Pyza | —CH₂-(4-Thiz) | 2-F | 4-F | H |
| 2-484 | Ac | 5-Pyza | —CH₂-(4-Thiz) | 2-F | 4-F | H |
| 2-485 | H | 5-Pyza | —(CH₂)₂-(4-Thiz) | 2-F | H | H |
| 2-486 | Ac | 5-Pyza | —(CH₂)₂-(4-Thiz) | 2-F | H | H |
| 2-487 | H | 5-Pyza | —(CH₂)₂-(4-Thiz) | 2-F | 4-F | H |
| 2-488 | Ac | 5-Pyza | —(CH₂)₂-(4-Thiz) | 2-F | 4-F | H |
| 2-489 | H | 5-Pyza | —CH₂OH | 2-F | H | H |
| 2-490 | Ac | 5-Pyza | —CH₂OH | 2-F | H | H |
| 2-491 | H | 5-Pyza | —CH₂OH | 2-F | 4-F | H |
| 2-492 | Ac | 5-Pyza | —CH₂OH | 2-F | 4-F | H |
| 2-493 | H | 5-Pyza | —(CH₂)₂OH | 2-F | H | H |
| 2-494 | Ac | 5-Pyza | —(CH₂)₂OH | 2-F | H | H |
| 2-495 | H | 5-Pyza | —(CH₂)₂OH | 2-F | 4-F | H |
| 2-496 | Ac | 5-Pyza | —(CH₂)₂OH | 2-F | 4-F | H |
| 2-497 | H | 5-Pyza | —CH₂OMe | 2-F | H | H |
| 2-498 | Ac | 5-Pyza | —CH₂OMe | 2-F | H | H |
| 2-499 | H | 5-Pyza | —CH₂OMe | 2-F | 4-F | H |
| 2-500 | Ac | 5-Pyza | —CH₂OMe | 2-F | 4-F | H |
| 2-501 | H | 5-Pyza | —(CH₂)₂OMe | 2-F | H | H |
| 2-502 | Ac | 5-Pyza | —(CH₂)₂OMe | 2-F | H | H |
| 2-503 | H | 5-Pyza | —(CH₂)₂OMe | 2-F | 4-F | H |
| 2-504 | Ac | 5-Pyza | —(CH₂)₂OMe | 2-F | 4-F | H |
| 2-505 | H | 2-Pyrr | Me | 2-F | H | H |
| 2-506 | Ac | 2-Pyrr | Me | 2-F | H | H |
| 2-507 | H | 2-Pyrr | Me | 2-F | 4-F | H |
| 2-508 | Ac | 2-Pyrr | Me | 2-F | 4-F | H |
| 2-509 | H | 2-Pyrr | Et | 2-F | H | H |
| 2-510 | Ac | 2-Pyrr | Et | 2-F | H | H |
| 2-511 | H | 2-Pyrr | Et | 2-F | 4-F | H |
| 2-512 | Ac | 2-Pyrr | Et | 2-F | 4-F | H |
| 2-513 | H | 2-Pyrr | —CH₂COOH | 2-F | H | H |
| 2-514 | Ac | 2-Pyrr | —CH₂COOH | 2-F | H | H |
| 2-515 | H | 2-Pyrr | —CH₂COOH | 2-F | 4-F | H |
| 2-516 | Ac | 2-Pyrr | —CH₂COOH | 2-F | 4-F | H |
| 2-517 | H | 2-Pyrr | —(CH₂)₂COOH | 2-F | H | H |
| 2-518 | Ac | 2-Pyrr | —(CH₂)₂COOH | 2-F | H | H |
| 2-519 | H | 2-Pyrr | —(CH₂)₂COOH | 2-F | 4-F | H |
| 2-520 | Ac | 2-Pyrr | —(CH₂)₂COOH | 2-F | 4-F | H |

TABLE 2-continued

| | | | | | | |
|---|---|---|---|---|---|---|
| 2-521 | H | 2-Pyrr | —(CH₂)₃COOH | 2-F | H | H |
| 2-522 | Ac | 2-Pyrr | —(CH₂)₃COOH | 2-F | H | H |
| 2-523 | H | 2-Pyrr | —(CH₂)₃COOH | 2-F | 4-F | H |
| 2-524 | Ac | 2-Pyrr | —(CH₂)₃COOH | 2-F | 4-F | H |
| 2-525 | H | 2-Pyrr | —(CH₂)₄COOH | 2-F | H | H |
| 2-526 | Ac | 2-Pyrr | —(CH₂)₄COOH | 2-F | H | H |
| 2-527 | H | 2-Pyrr | —(CH₂)₄COOH | 2-F | 4-F | H |
| 2-528 | Ac | 2-Pyrr | —(CH₂)₄COOH | 2-F | 4-F | H |
| 2-529 | H | 2-Pyrr | —CH₂COOMe | 2-F | H | H |
| 2-530 | Ac | 2-Pyrr | —CH₂COOMe | 2-F | H | H |
| 2-531 | H | 2-Pyrr | —CH₂COOMe | 2-F | 4-F | H |
| 2-532 | Ac | 2-Pyrr | —CH₂COOMe | 2-F | 4-F | H |
| 2-533 | H | 2-Pyrr | —(CH₂)₂COOMe | 2-F | H | H |
| 2-534 | Ac | 2-Pyrr | —(CH₂)₂COOMe | 2-F | H | H |
| 2-535 | H | 2-Pyrr | —(CH₂)₂COOMe | 2-F | 4-F | H |
| 2-536 | Ac | 2-Pyrr | —(CH₂)₂COOMe | 2-F | 4-F | H |
| 2-537 | H | 2-Pyrr | —(CH₂)₃COOMe | 2-F | H | H |
| 2-538 | Ac | 2-Pyrr | —(CH₂)₃COOMe | 2-F | H | H |
| 2-539 | H | 2-Pyrr | —(CH₂)₃COOMe | 2-F | 4-F | H |
| 2-540 | Ac | 2-Pyrr | —(CH₂)₃COOMe | 2-F | 4-F | H |
| 2-541 | H | 2-Pyrr | —(CH₂)₄COOMe | 2-F | H | H |
| 2-542 | Ac | 2-Pyrr | —(CH₂)₄COOMe | 2-F | H | H |
| 2-543 | H | 2-Pyrr | —(CH₂)₄COOMe | 2-F | 4-F | H |
| 2-544 | Ac | 2-Pyrr | —(CH₂)₄COOMe | 2-F | 4-F | H |
| 2-545 | H | 2-Pyrr | —CH₂COOEt | 2-F | H | H |
| 2-546 | Ac | 2-Pyrr | —CH₂COOEt | 2-F | H | H |
| 2-547 | H | 2-Pyrr | —CH₂COOEt | 2-F | 4-F | H |
| 2-548 | Ac | 2-Pyrr | —CH₂COOEt | 2-F | 4-F | H |
| 2-549 | H | 2-Pyrr | —(CH₂)₂COOEt | 2-F | H | H |
| 2-550 | Ac | 2-Pyrr | —(CH₂)₂COOEt | 2-F | H | H |
| 2-551 | H | 2-Pyrr | —(CH₂)₂COOEt | 2-F | 4-F | H |
| 2-552 | Ac | 2-Pyrr | —(CH₂)₂COOEt | 2-F | 4-F | H |
| 2-553 | H | 2-Pyrr | —(CH₂)₃COOEt | 2-F | H | H |
| 2-554 | Ac | 2-Pyrr | —(CH₂)₃COOEt | 2-F | H | H |
| 2-555 | H | 2-Pyrr | —(CH₂)₃COOEt | 2-F | 4-F | H |
| 2-556 | Ac | 2-Pyrr | —(CH₂)₃COOEt | 2-F | 4-F | H |
| 2-557 | H | 2-Pyrr | —(CH₂)₄COOEt | 2-F | H | H |
| 2-558 | Ac | 2-Pyrr | —(CH₂)₄COOEt | 2-F | H | H |
| 2-559 | H | 2-Pyrr | —(CH₂)₄COOEt | 2-F | 4-F | H |
| 2-560 | Ac | 2-Pyrr | —(CH₂)₄COOEt | 2-F | 4-F | H |
| 2-561 | H | 2-Pyrr | —CH₂COOPr | 2-F | H | H |
| 2-562 | Ac | 2-Pyrr | —CH₂COOPr | 2-F | H | H |
| 2-563 | H | 2-Pyrr | —CH₂COOPr | 2-F | 4-F | H |
| 2-564 | Ac | 2-Pyrr | —CH₂COOPr | 2-F | 4-F | H |
| 2-565 | H | 2-Pyrr | —(CH₂)₂COOPr | 2-F | H | H |
| 2-566 | Ac | 2-Pyrr | —(CH₂)₂COOPr | 2-F | H | H |
| 2-567 | H | 2-Pyrr | —(CH₂)₂COOPr | 2-F | 4-F | H |
| 2-568 | Ac | 2-Pyrr | —(CH₂)₂COOPr | 2-F | 4-F | H |
| 2-569 | H | 2-Pyrr | —CH₂COOBu | 2-F | H | H |
| 2-570 | Ac | 2-Pyrr | —CH₂COOBu | 2-F | H | H |
| 2-571 | H | 2-Pyrr | —CH₂COOBu | 2-F | 4-F | H |
| 2-572 | Ac | 2-Pyrr | —CH₂COOBu | 2-F | 4-F | H |
| 2-573 | H | 2-Pyrr | —(CH₂)₂COOBu | 2-F | H | H |
| 2-574 | Ac | 2-Pyrr | —(CH₂)₂COOBu | 2-F | H | H |
| 2-575 | H | 2-Pyrr | —(CH₂)₂COOBu | 2-F | 4-F | H |
| 2-576 | Ac | 2-Pyrr | —(CH₂)₂COOBu | 2-F | 4-F | H |
| 2-577 | H | 2-Pyrr | —CH₂COOᵗBu | 2-F | H | H |
| 2-578 | Ac | 2-Pyrr | —CH₂COOᵗBu | 2-F | H | H |
| 2-579 | H | 2-Pyrr | —CH₂COOᵗBu | 2-F | 4-F | H |
| 2-580 | Ac | 2-Pyrr | —CH₂COOᵗBu | 2-F | 4-F | H |
| 2-581 | H | 2-Pyrr | —(CH₂)₂COOᵗBu | 2-F | H | H |
| 2-582 | Ac | 2-Pyrr | —(CH₂)₂COOᵗBu | 2-F | H | H |
| 2-583 | H | 2-Pyrr | —(CH₂)₂COOᵗBu | 2-F | 4-F | H |
| 2-584 | Ac | 2-Pyrr | —(CH₂)₂COOᵗBu | 2-F | 4-F | H |
| 2-585 | H | 2-Pyrr | —CH₂CONHOH | 2-F | H | H |
| 2-586 | Ac | 2-Pyrr | —CH₂CONHOH | 2-F | H | H |
| 2-587 | H | 2-Pyrr | —CH₂CONHOH | 2-F | 4-F | H |
| 2-588 | Ac | 2-Pyrr | —CH₂CONHOH | 2-F | 4-F | H |
| 2-589 | H | 2-Pyrr | —(CH₂)₂CONHOH | 2-F | H | H |
| 2-590 | Ac | 2-Pyrr | —(CH₂)₂CONHOH | 2-F | H | H |
| 2-591 | H | 2-Pyrr | —(CH₂)₂CONHOH | 2-F | 4-F | H |
| 2-592 | Ac | 2-Pyrr | —(CH₂)₂CONHOH | 2-F | 4-F | H |
| 2-593 | H | 2-Pyrr | —(CH₂)₃CONHOH | 2-F | H | H |
| 2-594 | Ac | 2-Pyrr | —(CH₂)₃CONHOH | 2-F | H | H |
| 2-595 | H | 2-Pyrr | —(CH₂)₃CONHOH | 2-F | 4-F | H |
| 2-596 | Ac | 2-Pyrr | —(CH₂)₃CONHOH | 2-F | 4-F | H |
| 2-597 | H | 2-Pyrr | —(CH₂)₄CONHOH | 2-F | H | H |
| 2-598 | Ac | 2-Pyrr | —(CH₂)₄CONHOH | 2-F | H | H |
| 2-599 | H | 2-Pyrr | —(CH₂)₄CONHOH | 2-F | 4-F | H |
| 2-600 | Ac | 2-Pyrr | —(CH₂)₄CONHOH | 2-F | 4-F | H |
| 2-601 | H | 2-Pyrr | —CH₂CONH₂ | 2-F | H | H |
| 2-602 | Ac | 2-Pyrr | —CH₂CONH₂ | 2-F | H | H |
| 2-603 | H | 2-Pyrr | —CH₂CONH₂ | 2-F | 4-F | H |
| 2-604 | Ac | 2-Pyrr | —CH₂CONH₂ | 2-F | 4-F | H |
| 2-605 | H | 2-Pyrr | —(CH₂)₂CONH₂ | 2-F | H | H |
| 2-606 | Ac | 2-Pyrr | —(CH₂)₂CONH₂ | 2-F | H | H |
| 2-607 | H | 2-Pyrr | —(CH₂)₂CONH₂ | 2-F | 4-F | H |
| 2-608 | Ac | 2-Pyrr | —(CH₂)₂CONH₂ | 2-F | 4-F | H |
| 2-609 | H | 2-Pyrr | —CH₂CONHMe | 2-F | H | H |
| 2-610 | Ac | 2-Pyrr | —CH₂CONHMe | 2-F | H | H |
| 2-611 | H | 2-Pyrr | —CH₂CONHMe | 2-F | 4-F | H |
| 2-612 | Ac | 2-Pyrr | —CH₂CONHMe | 2-F | 4-F | H |
| 2-613 | H | 2-Pyrr | —(CH₂)₂CONHMe | 2-F | H | H |
| 2-614 | Ac | 2-Pyrr | —(CH₂)₂CONHMe | 2-F | H | H |
| 2-615 | H | 2-Pyrr | —(CH₂)₂CONHMe | 2-F | 4-F | H |
| 2-616 | Ac | 2-Pyrr | —(CH₂)₂CONHMe | 2-F | 4-F | H |
| 2-617 | H | 2-Pyrr | —CH₂CONMe₂ | 2-F | H | H |
| 2-618 | Ac | 2-Pyrr | —CH₂CONMe₂ | 2-F | H | H |
| 2-619 | H | 2-Pyrr | —CH₂CONMe₂ | 2-F | 4-F | H |
| 2-620 | Ac | 2-Pyrr | —CH₂CONMe₂ | 2-F | 4-F | H |
| 2-621 | H | 2-Pyrr | —(CH₂)₂CONMe₂ | 2-F | H | H |
| 2-622 | Ac | 2-Pyrr | —(CH₂)₂CONMe₂ | 2-F | H | H |
| 2-623 | H | 2-Pyrr | —(CH₂)₂CONMe₂ | 2-F | 4-F | H |
| 2-624 | Ac | 2-Pyrr | —(CH₂)₂CONMe₂ | 2-F | 4-F | H |
| 2-625 | H | 2-Pyrr | —CH₂SO₂NH₂ | 2-F | H | H |
| 2-626 | Ac | 2-Pyrr | —CH₂SO₂NH₂ | 2-F | H | H |
| 2-627 | H | 2-Pyrr | —CH₂SO₂NH₂ | 2-F | 4-F | H |
| 2-628 | Ac | 2-Pyrr | —CH₂SO₂NH₂ | 2-F | 4-F | H |
| 2-629 | H | 2-Pyrr | —(CH₂)₂SO₂NH₂ | 2-F | H | H |
| 2-630 | Ac | 2-Pyrr | —(CH₂)₂SO₂NH₂ | 2-F | H | H |
| 2-631 | H | 2-Pyrr | —(CH₂)₂SO₂NH₂ | 2-F | 4-F | H |
| 2-632 | Ac | 2-Pyrr | —(CH₂)₂SO₂NH₂ | 2-F | 4-F | H |
| 2-633 | H | 3-Pyrr | Me | 2-F | H | H |
| 2-634 | Ac | 3-Pyrr | Me | 2-F | H | H |
| 2-635 | H | 3-Pyrr | Me | 2-F | 4-F | H |
| 2-636 | Ac | 3-Pyrr | Me | 2-F | 4-F | H |
| 2-637 | H | 3-Pyrr | Et | 2-F | H | H |
| 2-638 | Ac | 3-Pyrr | Et | 2-F | H | H |
| 2-639 | H | 3-Pyrr | Et | 2-F | 4-F | H |
| 2-640 | Ac | 3-Pyrr | Et | 2-F | 4-F | H |
| 2-641 | H | 3-Pyrr | —CH₂COOH | 2-F | H | H |
| 2-642 | Ac | 3-Pyrr | —CH₂COOH | 2-F | H | H |
| 2-643 | H | 3-Pyrr | —CH₂COOH | 2-F | 4-F | H |
| 2-644 | Ac | 3-Pyrr | —CH₂COOH | 2-F | 4-F | H |
| 2-645 | H | 3-Pyrr | —(CH₂)₂COOH | 2-F | H | H |
| 2-646 | Ac | 3-Pyrr | —(CH₂)₂COOH | 2-F | H | H |
| 2-647 | H | 3-Pyrr | —(CH₂)₂COOH | 2-F | 4-F | H |
| 2-648 | Ac | 3-Pyrr | —(CH₂)₂COOH | 2-F | 4-F | H |
| 2-649 | H | 3-Pyrr | —(CH₂)₃COOH | 2-F | H | H |
| 2-650 | Ac | 3-Pyrr | —(CH₂)₃COOH | 2-F | H | H |
| 2-651 | H | 3-Pyrr | —(CH₂)₃COOH | 2-F | 4-F | H |
| 2-652 | Ac | 3-Pyrr | —(CH₂)₃COOH | 2-F | 4-F | H |
| 2-653 | H | 3-Pyrr | —(CH₂)₄COOH | 2-F | H | H |
| 2-654 | Ac | 3-Pyrr | —(CH₂)₄COOH | 2-F | H | H |
| 2-655 | H | 3-Pyrr | —(CH₂)₄COOH | 2-F | 4-F | H |
| 2-656 | Ac | 3-Pyrr | —(CH₂)₄COOH | 2-F | 4-F | H |
| 2-657 | H | 3-Pyrr | —CH₂COOMe | 2-F | H | H |
| 2-658 | Ac | 3-Pyrr | —CH₂COOMe | 2-F | H | H |
| 2-659 | H | 3-Pyrr | —CH₂COOMe | 2-F | 4-F | H |
| 2-660 | Ac | 3-Pyrr | —CH₂COOMe | 2-F | 4-F | H |
| 2-661 | H | 3-Pyrr | —(CH₂)₂COOMe | 2-F | H | H |
| 2-662 | Ac | 3-Pyrr | —(CH₂)₂COOMe | 2-F | H | H |
| 2-663 | H | 3-Pyrr | —(CH₂)₂COOMe | 2-F | 4-F | H |
| 2-664 | Ac | 3-Pyrr | —(CH₂)₂COOMe | 2-F | 4-F | H |
| 2-665 | H | 3-Pyrr | —(CH₂)₃COOMe | 2-F | H | H |
| 2-666 | Ac | 3-Pyrr | —(CH₂)₃COOMe | 2-F | H | H |
| 2-667 | H | 3-Pyrr | —(CH₂)₃COOMe | 2-F | 4-F | H |
| 2-668 | Ac | 3-Pyrr | —(CH₂)₃COOMe | 2-F | 4-F | H |
| 2-669 | H | 3-Pyrr | —(CH₂)₄COOMe | 2-F | H | H |
| 2-670 | Ac | 3-Pyrr | —(CH₂)₄COOMe | 2-F | H | H |
| 2-671 | H | 3-Pyrr | —(CH₂)₄COOMe | 2-F | 4-F | H |
| 2-672 | Ac | 3-Pyrr | —(CH₂)₄COOMe | 2-F | 4-F | H |
| 2-673 | H | 3-Pyrr | —CH₂COOEt | 2-F | H | H |
| 2-674 | Ac | 3-Pyrr | —CH₂COOEt | 2-F | H | H |
| 2-675 | H | 3-Pyrr | —CH₂COOEt | 2-F | 4-F | H |
| 2-676 | Ac | 3-Pyrr | —CH₂COOEt | 2-F | 4-F | H |
| 2-677 | H | 3-Pyrr | —(CH₂)₂COOEt | 2-F | H | H |
| 2-678 | Ac | 3-Pyrr | —(CH₂)₂COOEt | 2-F | H | H |

TABLE 2-continued

| | | | | | | |
|---|---|---|---|---|---|---|
| 2-679 | H | 3-Pyrr | —(CH$_2$)$_2$COOEt | 2-F | 4-F | H |
| 2-680 | Ac | 3-Pyrr | —(CH$_2$)$_2$COOEt | 2-F | 4-F | H |
| 2-681 | H | 3-Pyrr | —(CH$_2$)$_3$COOEt | 2-F | H | H |
| 2-682 | Ac | 3-Pyrr | —(CH$_2$)$_3$COOEt | 2-F | H | H |
| 2-683 | H | 3-Pyrr | —(CH$_2$)$_3$COOEt | 2-F | 4-F | H |
| 2-684 | Ac | 3-Pyrr | —(CH$_2$)$_3$COOEt | 2-F | 4-F | H |
| 2-685 | H | 3-Pyrr | —(CH$_2$)$_4$COOEt | 2-F | H | H |
| 2-686 | Ac | 3-Pyrr | —(CH$_2$)$_4$COOEt | 2-F | H | H |
| 2-687 | H | 3-Pyrr | —(CH$_2$)$_4$COOEt | 2-F | 4-F | H |
| 2-688 | Ac | 3-Pyrr | —(CH$_2$)$_4$COOEt | 2-F | 4-F | H |
| 2-689 | H | 3-Pyrr | —CH$_2$COOPr | 2-F | H | H |
| 2-690 | Ac | 3-Pyrr | —CH$_2$COOPr | 2-F | H | H |
| 2-691 | H | 3-Pyrr | —CH$_2$COOPr | 2-F | 4-F | H |
| 2-692 | Ac | 3-Pyrr | —CH$_2$COOPr | 2-F | 4-F | H |
| 2-693 | H | 3-Pyrr | —(CH$_2$)$_2$COOPr | 2-F | H | H |
| 2-694 | Ac | 3-Pyrr | —(CH$_2$)$_2$COOPr | 2-F | H | H |
| 2-695 | H | 3-Pyrr | —(CH$_2$)$_2$COOPr | 2-F | 4-F | H |
| 2-696 | Ac | 3-Pyrr | —(CH$_2$)$_2$COOPr | 2-F | 4-F | H |
| 2-697 | H | 3-Pyrr | —CH$_2$COOBu | 2-F | H | H |
| 2-698 | Ac | 3-Pyrr | —CH$_2$COOBu | 2-F | H | H |
| 2-699 | H | 3-Pyrr | —CH$_2$COOBu | 2-F | 4-F | H |
| 2-700 | Ac | 3-Pyrr | —CH$_2$COOBu | 2-F | 4-F | H |
| 2-701 | H | 3-Pyrr | —(CH$_2$)$_2$COOBu | 2-F | H | H |
| 2-702 | Ac | 3-Pyrr | —(CH$_2$)$_2$COOBu | 2-F | H | H |
| 2-703 | H | 3-Pyrr | —(CH$_2$)$_2$COOBu | 2-F | 4-F | H |
| 2-704 | Ac | 3-Pyrr | —(CH$_2$)$_2$COOBu | 2-F | 4-F | H |
| 2-705 | H | 3-Pyrr | —CH$_2$COO$^t$Bu | 2-F | H | H |
| 2-706 | Ac | 3-Pyrr | —CH$_2$COO$^t$Bu | 2-F | H | H |
| 2-707 | H | 3-Pyrr | —CH$_2$COO$^t$Bu | 2-F | 4-F | H |
| 2-708 | Ac | 3-Pyrr | —CH$_2$COO$^t$Bu | 2-F | 4-F | H |
| 2-709 | H | 3-Pyrr | —(CH$_2$)$_2$COO$^t$Bu | 2-F | H | H |
| 2-710 | Ac | 3-Pyrr | —(CH$_2$)$_2$COO$^t$Bu | 2-F | H | H |
| 2-711 | H | 3-Pyrr | —(CH$_2$)$_2$COO$^t$Bu | 2-F | 4-F | H |
| 2-712 | Ac | 3-Pyrr | —(CH$_2$)$_2$COO$^t$Bu | 2-F | 4-F | H |
| 2-713 | H | 3-Pyrr | —CH$_2$CONHOH | 2-F | H | H |
| 2-714 | Ac | 3-Pyrr | —CH$_2$CONHOH | 2-F | H | H |
| 2-715 | H | 3-Pyrr | —CH$_2$CONHOH | 2-F | 4-F | H |
| 2-716 | Ac | 3-Pyrr | —CH$_2$CONHOH | 2-F | 4-F | H |
| 2-717 | H | 3-Pyrr | —(CH$_2$)$_2$CONHOH | 2-F | H | H |
| 2-718 | Ac | 3-Pyrr | —(CH$_2$)$_2$CONHOH | 2-F | H | H |
| 2-719 | H | 3-Pyrr | —(CH$_2$)$_2$CONHOH | 2-F | 4-F | H |
| 2-720 | Ac | 3-Pyrr | —(CH$_2$)$_2$CONHOH | 2-F | 4-F | H |
| 2-721 | H | 3-Pyrr | —(CH$_2$)$_3$CONHOH | 2-F | H | H |
| 2-722 | Ac | 3-Pyrr | —(CH$_2$)$_3$CONHOH | 2-F | H | H |
| 2-723 | H | 3-Pyrr | —(CH$_2$)$_3$CONHOH | 2-F | 4-F | H |
| 2-724 | Ac | 3-Pyrr | —(CH$_2$)$_3$CONHOH | 2-F | 4-F | H |
| 2-725 | H | 3-Pyrr | —(CH$_2$)$_4$CONHOH | 2-F | H | H |
| 2-726 | Ac | 3-Pyrr | —(CH$_2$)$_4$CONHOH | 2-F | H | H |
| 2-727 | H | 3-Pyrr | —(CH$_2$)$_4$CONHOH | 2-F | 4-F | H |
| 2-728 | Ac | 3-Pyrr | —(CH$_2$)$_4$CONHOH | 2-F | 4-F | H |
| 2-729 | H | 3-Pyrr | —CH$_2$CONH$_2$ | 2-F | H | H |
| 2-730 | Ac | 3-Pyrr | —CH$_2$CONH$_2$ | 2-F | H | H |
| 2-731 | H | 3-Pyrr | —CH$_2$CONH$_2$ | 2-F | 4-F | H |
| 2-732 | Ac | 3-Pyrr | —CH$_2$CONH$_2$ | 2-F | 4-F | H |
| 2-733 | H | 3-Pyrr | —(CH$_2$)$_2$CONH$_2$ | 2-F | H | H |
| 2-734 | Ac | 3-Pyrr | —(CH$_2$)$_2$CONH$_2$ | 2-F | H | H |
| 2-735 | H | 3-Pyrr | —(CH$_2$)$_2$CONH$_2$ | 2-F | 4-F | H |
| 2-736 | Ac | 3-Pyrr | —(CH$_2$)$_2$CONH$_2$ | 2-F | 4-F | H |
| 2-737 | H | 3-Pyrr | —CH$_2$CONHMe | 2-F | H | H |
| 2-738 | Ac | 3-Pyrr | —CH$_2$CONHMe | 2-F | H | H |
| 2-739 | H | 3-Pyrr | —CH$_2$CONHMe | 2-F | 4-F | H |
| 2-740 | Ac | 3-Pyrr | —CH$_2$CONHMe | 2-F | 4-F | H |
| 2-741 | H | 3-Pyrr | —(CH$_2$)$_2$CONHMe | 2-F | H | H |
| 2-742 | Ac | 3-Pyrr | —(CH$_2$)$_2$CONHMe | 2-F | H | H |
| 2-743 | H | 3-Pyrr | —(CH$_2$)$_2$CONHMe | 2-F | 4-F | H |
| 2-744 | Ac | 3-Pyrr | —(CH$_2$)$_2$CONHMe | 2-F | 4-F | H |
| 2-745 | H | 3-Pyrr | —CH$_2$CONMe$_2$ | 2-F | H | H |
| 2-746 | Ac | 3-Pyrr | —CH$_2$CONMe$_2$ | 2-F | H | H |
| 2-747 | H | 3-Pyrr | —CH$_2$CONMe$_2$ | 2-F | 4-F | H |
| 2-748 | Ac | 3-Pyrr | —CH$_2$CONMe$_2$ | 2-F | 4-F | H |
| 2-749 | H | 3-Pyrr | —(CH$_2$)$_2$CONMe$_2$ | 2-F | H | H |
| 2-750 | Ac | 3-Pyrr | —(CH$_2$)$_2$CONMe$_2$ | 2-F | H | H |
| 2-751 | H | 3-Pyrr | —(CH$_2$)$_2$CONMe$_2$ | 2-F | 4-F | H |
| 2-752 | Ac | 3-Pyrr | —(CH$_2$)$_2$CONMe$_2$ | 2-F | 4-F | H |
| 2-753 | H | 3-Pyrr | —CH$_2$SO$_2$NH$_2$ | 2-F | H | H |
| 2-754 | Ac | 3-Pyrr | —CH$_2$SO$_2$NH$_2$ | 2-F | H | H |
| 2-755 | H | 3-Pyrr | —CH$_2$SO$_2$NH$_2$ | 2-F | 4-F | H |
| 2-756 | Ac | 3-Pyrr | —CH$_2$SO$_2$NH$_2$ | 2-F | 4-F | H |
| 2-757 | H | 3-Pyrr | —(CH$_2$)$_2$SO$_2$NH$_2$ | 2-F | H | H |
| 2-758 | Ac | 3-Pyrr | —(CH$_2$)$_2$SO$_2$NH$_2$ | 2-F | H | H |
| 2-759 | H | 3-Pyrr | —(CH$_2$)$_2$SO$_2$NH$_2$ | 2-F | 4-F | H |
| 2-760 | Ac | 3-Pyrr | —(CH$_2$)$_2$SO$_2$NH$_2$ | 2-F | 4-F | H |
| 2-761 | H | 2-Imid | Me | 2-F | H | H |
| 2-762 | Ac | 2-Imid | Me | 2-F | H | H |
| 2-763 | H | 2-Imid | Me | 2-F | 4-F | H |
| 2-764 | Ac | 2-Imid | Me | 2-F | 4-F | H |
| 2-765 | H | 2-Imid | Et | 2-F | H | H |
| 2-766 | Ac | 2-Imid | Et | 2-F | H | H |
| 2-767 | H | 2-Imid | Et | 2-F | 4-F | H |
| 2-768 | Ac | 2-Imid | Et | 2-F | 4-F | H |
| 2-769 | H | 2-Imid | —CH$_2$COOH | 2-F | H | H |
| 2-770 | Ac | 2-Imid | —CH$_2$COOH | 2-F | H | H |
| 2-771 | H | 2-Imid | —CH$_2$COOH | 2-F | 4-F | H |
| 2-772 | Ac | 2-Imid | —CH$_2$COOH | 2-F | 4-F | H |
| 2-773 | H | 2-Imid | —(CH$_2$)$_2$COOH | 2-F | H | H |
| 2-774 | Ac | 2-Imid | —(CH$_2$)$_2$COOH | 2-F | H | H |
| 2-775 | H | 2-Imid | —(CH$_2$)$_2$COOH | 2-F | 4-F | H |
| 2-776 | Ac | 2-Imid | —(CH$_2$)$_2$COOH | 2-F | 4-F | H |
| 2-777 | H | 2-Imid | —(CH$_2$)$_3$COOH | 2-F | H | H |
| 2-778 | Ac | 2-Imid | —(CH$_2$)$_3$COOH | 2-F | H | H |
| 2-779 | H | 2-Imid | —(CH$_2$)$_3$COOH | 2-F | 4-F | H |
| 2-780 | Ac | 2-Imid | —(CH$_2$)$_3$COOH | 2-F | 4-F | H |
| 2-781 | H | 2-Imid | —(CH$_2$)$_4$COOH | 2-F | H | H |
| 2-782 | Ac | 2-Imid | —(CH$_2$)$_4$COOH | 2-F | H | H |
| 2-783 | H | 2-Imid | —(CH$_2$)$_4$COOH | 2-F | 4-F | H |
| 2-784 | Ac | 2-Imid | —(CH$_2$)$_4$COOH | 2-F | 4-F | H |
| 2-785 | H | 2-Imid | —CH$_2$COOMe | 2-F | H | H |
| 2-786 | Ac | 2-Imid | —CH$_2$COOMe | 2-F | H | H |
| 2-787 | H | 2-Imid | —CH$_2$COOMe | 2-F | 4-F | H |
| 2-788 | Ac | 2-Imid | —CH$_2$COOMe | 2-F | 4-F | H |
| 2-789 | H | 2-Imid | —(CH$_2$)$_2$COOMe | 2-F | H | H |
| 2-790 | Ac | 2-Imid | —(CH$_2$)$_2$COOMe | 2-F | H | H |
| 2-791 | H | 2-Imid | —(CH$_2$)$_2$COOMe | 2-F | 4-F | H |
| 2-792 | Ac | 2-Imid | —(CH$_2$)$_2$COOMe | 2-F | 4-F | H |
| 2-793 | H | 2-Imid | —(CH$_2$)$_3$COOMe | 2-F | H | H |
| 2-794 | Ac | 2-Imid | —(CH$_2$)$_3$COOMe | 2-F | H | H |
| 2-795 | H | 2-Imid | —(CH$_2$)$_3$COOMe | 2-F | 4-F | H |
| 2-796 | Ac | 2-Imid | —(CH$_2$)$_3$COOMe | 2-F | 4-F | H |
| 2-797 | H | 2-Imid | —(CH$_2$)$_4$COOMe | 2-F | H | H |
| 2-798 | Ac | 2-Imid | —(CH$_2$)$_4$COOMe | 2-F | H | H |
| 2-799 | H | 2-Imid | —(CH$_2$)$_4$COOMe | 2-F | 4-F | H |
| 2-800 | Ac | 2-Imid | —(CH$_2$)$_4$COOMe | 2-F | 4-F | H |
| 2-801 | H | 2-Imid | —CH$_2$COOEt | 2-F | H | H |
| 2-802 | Ac | 2-Imid | —CH$_2$COOEt | 2-F | H | H |
| 2-803 | H | 2-Imid | —CH$_2$COOEt | 2-F | 4-F | H |
| 2-804 | Ac | 2-Imid | —CH$_2$COOEt | 2-F | 4-F | H |
| 2-805 | H | 2-Imid | —(CH$_2$)$_2$COOEt | 2-F | H | H |
| 2-806 | Ac | 2-Imid | —(CH$_2$)$_2$COOEt | 2-F | H | H |
| 2-807 | H | 2-Imid | —(CH$_2$)$_2$COOEt | 2-F | 4-F | H |
| 2-808 | Ac | 2-Imid | —(CH$_2$)$_2$COOEt | 2-F | 4-F | H |
| 2-809 | H | 2-Imid | —(CH$_2$)$_3$COOEt | 2-F | H | H |
| 2-810 | Ac | 2-Imid | —(CH$_2$)$_3$COOEt | 2-F | H | H |
| 2-811 | H | 2-Imid | —(CH$_2$)$_3$COOEt | 2-F | 4-F | H |
| 2-812 | Ac | 2-Imid | —(CH$_2$)$_3$COOEt | 2-F | 4-F | H |
| 2-813 | H | 2-Imid | —(CH$_2$)$_4$COOEt | 2-F | H | H |
| 2-814 | Ac | 2-Imid | —(CH$_2$)$_4$COOEt | 2-F | H | H |
| 2-815 | H | 2-Imid | —(CH$_2$)$_4$COOEt | 2-F | 4-F | H |
| 2-816 | Ac | 2-Imid | —(CH$_2$)$_4$COOEt | 2-F | 4-F | H |
| 2-817 | H | 2-Imid | —CH$_2$COOPr | 2-F | H | H |
| 2-818 | Ac | 2-Imid | —CH$_2$COOPr | 2-F | H | H |
| 2-819 | H | 2-Imid | —CH$_2$COOPr | 2-F | 4-F | H |
| 2-820 | Ac | 2-Imid | —CH$_2$COOPr | 2-F | 4-F | H |
| 2-821 | H | 2-Imid | —(CH$_2$)$_2$COOPr | 2-F | H | H |
| 2-822 | Ac | 2-Imid | —(CH$_2$)$_2$COOPr | 2-F | H | H |
| 2-823 | H | 2-Imid | —(CH$_2$)$_2$COOPr | 2-F | 4-F | H |
| 2-824 | Ac | 2-Imid | —(CH$_2$)$_2$COOPr | 2-F | 4-F | H |
| 2-825 | H | 2-Imid | —CH$_2$COOBu | 2-F | H | H |
| 2-826 | Ac | 2-Imid | —CH$_2$COOBu | 2-F | H | H |
| 2-827 | H | 2-Imid | —CH$_2$COOBu | 2-F | 4-F | H |
| 2-828 | Ac | 2-Imid | —CH$_2$COOBu | 2-F | 4-F | H |
| 2-829 | H | 2-Imid | —(CH$_2$)$_2$COOBu | 2-F | H | H |
| 2-830 | Ac | 2-Imid | —(CH$_2$)$_2$COOBu | 2-F | H | H |
| 2-831 | H | 2-Imid | —(CH$_2$)$_2$COOBu | 2-F | 4-F | H |
| 2-832 | Ac | 2-Imid | —(CH$_2$)$_2$COOBu | 2-F | 4-F | H |
| 2-833 | H | 2-Imid | —CH$_2$COO$^t$Bu | 2-F | H | H |
| 2-834 | Ac | 2-Imid | —CH$_2$COO$^t$Bu | 2-F | H | H |
| 2-835 | H | 2-Imid | —CH$_2$COO$^t$Bu | 2-F | 4-F | H |
| 2-836 | Ac | 2-Imid | —CH$_2$COO$^t$Bu | 2-F | 4-F | H |

TABLE 2-continued

| | | | | | |
|---|---|---|---|---|---|
| 2-837 | H | 2-Imid | —(CH$_2$)$_2$COO$^t$Bu | 2-F | H H |
| 2-838 | Ac | 2-Imid | —(CH$_2$)$_2$COO$^t$Bu | 2-F | H H |
| 2-839 | H | 2-Imid | —(CH$_2$)$_2$COO$^t$Bu | 2-F | 4-F H |
| 2-840 | Ac | 2-Imid | —(CH$_2$)$_2$COO$^t$Bu | 2-F | 4-F H |
| 2-841 | H | 2-Imid | —CH$_2$CONHOH | 2-F | H H |
| 2-842 | Ac | 2-Imid | —CH$_2$CONHOH | 2-F | H H |
| 2-843 | H | 2-Imid | —CH$_2$CONHOH | 2-F | 4-F H |
| 2-844 | Ac | 2-Imid | —CH$_2$CONHOH | 2-F | 4-F H |
| 2-845 | H | 2-Imid | —(CH$_2$)$_2$CONHOH | 2-F | H H |
| 2-846 | Ac | 2-Imid | —(CH$_2$)$_2$CONHOH | 2-F | H H |
| 2-847 | H | 2-Imid | —(CH$_2$)$_2$CONHOH | 2-F | 4-F H |
| 2-848 | Ac | 2-Imid | —(CH$_2$)$_2$CONHOH | 2-F | 4-F H |
| 2-849 | H | 2-Imid | —(CH$_2$)$_3$CONHOH | 2-F | H H |
| 2-850 | Ac | 2-Imid | —(CH$_2$)$_3$CONHOH | 2-F | H H |
| 2-851 | H | 2-Imid | —(CH$_2$)$_3$CONHOH | 2-F | 4-F H |
| 2-852 | Ac | 2-Imid | —(CH$_2$)$_3$CONHOH | 2-F | 4-F H |
| 2-853 | H | 2-Imid | —(CH$_2$)$_4$CONHOH | 2-F | H H |
| 2-854 | Ac | 2-Imid | —(CH$_2$)$_4$CONHOH | 2-F | H H |
| 2-855 | H | 2-Imid | —(CH$_2$)$_4$CONHOH | 2-F | 4-F H |
| 2-856 | Ac | 2-Imid | —(CH$_2$)$_4$CONHOH | 2-F | 4-F H |
| 2-857 | H | 2-Imid | —CH$_2$CONH$_2$ | 2-F | H H |
| 2-858 | Ac | 2-Imid | —CH$_2$CONH$_2$ | 2-F | H H |
| 2-859 | H | 2-Imid | —CH$_2$CONH$_2$ | 2-F | 4-F H |
| 2-860 | Ac | 2-Imid | —CH$_2$CONH$_2$ | 2-F | 4-F H |
| 2-861 | H | 2-Imid | —(CH$_2$)$_2$CONH$_2$ | 2-F | H H |
| 2-862 | Ac | 2-Imid | —(CH$_2$)$_2$CONH$_2$ | 2-F | H H |
| 2-863 | H | 2-Imid | —(CH$_2$)$_2$CONH$_2$ | 2-F | 4-F H |
| 2-864 | Ac | 2-Imid | —(CH$_2$)$_2$CONH$_2$ | 2-F | 4-F H |
| 2-865 | H | 2-Imid | —CH$_2$CONHMe | 2-F | H H |
| 2-866 | Ac | 2-Imid | —CH$_2$CONHMe | 2-F | H H |
| 2-867 | H | 2-Imid | —CH$_2$CONHMe | 2-F | 4-F H |
| 2-868 | Ac | 2-Imid | —CH$_2$CONHMe | 2-F | 4-F H |
| 2-869 | H | 2-Imid | —(CH$_2$)$_2$CONHMe | 2-F | H H |
| 2-870 | Ac | 2-Imid | —(CH$_2$)$_2$CONHMe | 2-F | H H |
| 2-871 | H | 2-Imid | —(CH$_2$)$_2$CONHMe | 2-F | 4-F H |
| 2-872 | Ac | 2-Imid | —(CH$_2$)$_2$CONHMe | 2-F | 4-F H |
| 2-873 | H | 2-Imid | —CH$_2$CONMe$_2$ | 2-F | H H |
| 2-874 | Ac | 2-Imid | —CH$_2$CONMe$_2$ | 2-F | H H |
| 2-875 | H | 2-Imid | —CH$_2$CONMe$_2$ | 2-F | 4-F H |
| 2-876 | Ac | 2-Imid | —CH$_2$CONMe$_2$ | 2-F | 4-F H |
| 2-877 | H | 2-Imid | —(CH$_2$)$_2$CONMe$_2$ | 2-F | H H |
| 2-878 | Ac | 2-Imid | —(CH$_2$)$_2$CONMe$_2$ | 2-F | H H |
| 2-879 | H | 2-Imid | —(CH$_2$)$_2$CONMe$_2$ | 2-F | 4-F H |
| 2-880 | Ac | 2-Imid | —(CH$_2$)$_2$CONMe$_2$ | 2-F | 4-F H |
| 2-881 | H | 2-Imid | —CH$_2$SO$_2$NH$_2$ | 2-F | H H |
| 2-882 | Ac | 2-Imid | —CH$_2$SO$_2$NH$_2$ | 2-F | H H |
| 2-883 | H | 2-Imid | —CH$_2$SO$_2$NH$_2$ | 2-F | 4-F H |
| 2-884 | Ac | 2-Imid | —CH$_2$SO$_2$NH$_2$ | 2-F | 4-F H |
| 2-885 | H | 2-Imid | —(CH$_2$)$_2$SO$_2$NH$_2$ | 2-F | H H |
| 2-886 | Ac | 2-Imid | —(CH$_2$)$_2$SO$_2$NH$_2$ | 2-F | H H |
| 2-887 | H | 2-Imid | —(CH$_2$)$_2$SO$_2$NH$_2$ | 2-F | 4-F H |
| 2-888 | Ac | 2-Imid | —(CH$_2$)$_2$SO$_2$NH$_2$ | 2-F | 4-F H |
| 2-889 | H | 4-Imid | Me | 2-F | H H |
| 2-890 | Ac | 4-Imid | Me | 2-F | H H |
| 2-891 | H | 4-Imid | Me | 2-F | 4-F H |
| 2-892 | Ac | 4-Imid | Me | 2-F | 4-F H |
| 2-893 | H | 4-Imid | Et | 2-F | H H |
| 2-894 | Ac | 4-Imid | Et | 2-F | H H |
| 2-895 | H | 4-Imid | Et | 2-F | 4-F H |
| 2-896 | Ac | 4-Imid | Et | 2-F | 4-F H |
| 2-897 | H | 4-Imid | —CH$_2$COOH | 2-F | H H |
| 2-898 | Ac | 4-Imid | —CH$_2$COOH | 2-F | H H |
| 2-899 | H | 4-Imid | —CH$_2$COOH | 2-F | 4-F H |
| 2-900 | Ac | 4-Imid | —CH$_2$COOH | 2-F | 4-F H |
| 2-901 | H | 4-Imid | —(CH$_2$)$_2$COOH | 2-F | H H |
| 2-902 | Ac | 4-Imid | —(CH$_2$)$_2$COOH | 2-F | H H |
| 2-903 | H | 4-Imid | —(CH$_2$)$_2$COOH | 2-F | 4-F H |
| 2-904 | Ac | 4-Imid | —(CH$_2$)$_2$COOH | 2-F | 4-F H |
| 2-905 | H | 4-Imid | —(CH$_2$)$_3$COOH | 2-F | H H |
| 2-906 | Ac | 4-Imid | —(CH$_2$)$_3$COOH | 2-F | H H |
| 2-907 | H | 4-Imid | —(CH$_2$)$_3$COOH | 2-F | 4-F H |
| 2-908 | Ac | 4-Imid | —(CH$_2$)$_3$COOH | 2-F | 4-F H |
| 2-909 | H | 4-Imid | —(CH$_2$)$_4$COOH | 2-F | H H |
| 2-910 | Ac | 4-Imid | —(CH$_2$)$_4$COOH | 2-F | H H |
| 2-911 | H | 4-Imid | —(CH$_2$)$_4$COOH | 2-F | 4-F H |
| 2-912 | Ac | 4-Imid | —(CH$_2$)$_4$COOH | 2-F | 4-F H |
| 2-913 | H | 4-Imid | —CH$_2$COOMe | 2-F | H H |
| 2-914 | Ac | 4-Imid | —CH$_2$COOMe | 2-F | H H |
| 2-915 | H | 4-Imid | —CH$_2$COOMe | 2-F | 4-F H |
| 2-916 | Ac | 4-Imid | —CH$_2$COOMe | 2-F | 4-F H |
| 2-917 | H | 4-Imid | —(CH$_2$)$_2$COOMe | 2-F | H H |
| 2-918 | Ac | 4-Imid | —(CH$_2$)$_2$COOMe | 2-F | H H |
| 2-919 | H | 4-Imid | —(CH$_2$)$_2$COOMe | 2-F | 4-F H |
| 2-920 | Ac | 4-Imid | —(CH$_2$)$_2$COOMe | 2-F | 4-F H |
| 2-921 | H | 4-Imid | —(CH$_2$)$_3$COOMe | 2-F | H H |
| 2-922 | Ac | 4-Imid | —(CH$_2$)$_3$COOMe | 2-F | H H |
| 2-923 | H | 4-Imid | —(CH$_2$)$_3$COOMe | 2-F | 4-F H |
| 2-924 | Ac | 4-Imid | —(CH$_2$)$_3$COOMe | 2-F | 4-F H |
| 2-925 | H | 4-Imid | —(CH$_2$)$_4$COOMe | 2-F | H H |
| 2-926 | Ac | 4-Imid | —(CH$_2$)$_4$COOMe | 2-F | H H |
| 2-927 | H | 4-Imid | —(CH$_2$)$_4$COOMe | 2-F | 4-F H |
| 2-928 | Ac | 4-Imid | —(CH$_2$)$_4$COOMe | 2-F | 4-F H |
| 2-929 | H | 4-Imid | —CH$_2$COOEt | 2-F | H H |
| 2-930 | Ac | 4-Imid | —CH$_2$COOEt | 2-F | H H |
| 2-931 | H | 4-Imid | —CH$_2$COOEt | 2-F | 4-F H |
| 2-932 | Ac | 4-Imid | —CH$_2$COOEt | 2-F | 4-F H |
| 2-933 | H | 4-Imid | —(CH$_2$)$_2$COOEt | 2-F | H H |
| 2-934 | Ac | 4-Imid | —(CH$_2$)$_2$COOEt | 2-F | H H |
| 2-935 | H | 4-Imid | —(CH$_2$)$_2$COOEt | 2-F | 4-F H |
| 2-936 | Ac | 4-Imid | —(CH$_2$)$_2$COOEt | 2-F | 4-F H |
| 2-937 | H | 4-Imid | —(CH$_2$)$_3$COOEt | 2-F | H H |
| 2-938 | Ac | 4-Imid | —(CH$_2$)$_3$COOEt | 2-F | H H |
| 2-939 | H | 4-Imid | —(CH$_2$)$_3$COOEt | 2-F | 4-F H |
| 2-940 | Ac | 4-Imid | —(CH$_2$)$_3$COOEt | 2-F | 4-F H |
| 2-941 | H | 4-Imid | —(CH$_2$)$_4$COOEt | 2-F | H H |
| 2-942 | Ac | 4-Imid | —(CH$_2$)$_4$COOEt | 2-F | H H |
| 2-943 | H | 4-Imid | —(CH$_2$)$_4$COOEt | 2-F | 4-F H |
| 2-944 | Ac | 4-Imid | —(CH$_2$)$_4$COOEt | 2-F | 4-F H |
| 2-945 | H | 4-Imid | —CH$_2$COOPr | 2-F | H H |
| 2-946 | Ac | 4-Imid | —CH$_2$COOPr | 2-F | H H |
| 2-947 | H | 4-Imid | —CH$_2$COOPr | 2-F | 4-F H |
| 2-948 | Ac | 4-Imid | —CH$_2$COOPr | 2-F | 4-F H |
| 2-949 | H | 4-Imid | —(CH$_2$)$_2$COOPr | 2-F | H H |
| 2-950 | Ac | 4-Imid | —(CH$_2$)$_2$COOPr | 2-F | H H |
| 2-951 | H | 4-Imid | —(CH$_2$)$_2$COOPr | 2-F | 4-F H |
| 2-952 | Ac | 4-Imid | —(CH$_2$)$_2$COOPr | 2-F | 4-F H |
| 2-953 | H | 4-Imid | —CH$_2$COOBu | 2-F | H H |
| 2-954 | Ac | 4-Imid | —CH$_2$COOBu | 2-F | H H |
| 2-955 | H | 4-Imid | —CH$_2$COOBu | 2-F | 4-F H |
| 2-956 | Ac | 4-Imid | —CH$_2$COOBu | 2-F | 4-F H |
| 2-957 | H | 4-Imid | —(CH$_2$)$_2$COOBu | 2-F | H H |
| 2-958 | Ac | 4-Imid | —(CH$_2$)$_2$COOBu | 2-F | H H |
| 2-959 | H | 4-Imid | —(CH$_2$)$_2$COOBu | 2-F | 4-F H |
| 2-960 | Ac | 4-Imid | —(CH$_2$)$_2$COOBu | 2-F | 4-F H |
| 2-961 | H | 4-Imid | —CH$_2$COO$^t$Bu | 2-F | H H |
| 2-962 | Ac | 4-Imid | —CH$_2$COO$^t$Bu | 2-F | H H |
| 2-963 | H | 4-Imid | —CH$_2$COO$^t$Bu | 2-F | 4-F H |
| 2-964 | Ac | 4-Imid | —CH$_2$COO$^t$Bu | 2-F | 4-F H |
| 2-965 | H | 4-Imid | —(CH$_2$)$_2$COO$^t$Bu | 2-F | H H |
| 2-966 | Ac | 4-Imid | —(CH$_2$)$_2$COO$^t$Bu | 2-F | H H |
| 2-967 | H | 4-Imid | —(CH$_2$)$_2$COO$^t$Bu | 2-F | 4-F H |
| 2-968 | Ac | 4-Imid | —(CH$_2$)$_2$COO$^t$Bu | 2-F | 4-F H |
| 2-969 | H | 4-Imid | —CH$_2$CONHOH | 2-F | H H |
| 2-970 | Ac | 4-Imid | —CH$_2$CONHOH | 2-F | H H |
| 2-971 | H | 4-Imid | —CH$_2$CONHOH | 2-F | 4-F H |
| 2-972 | Ac | 4-Imid | —CH$_2$CONHOH | 2-F | 4-F H |
| 2-973 | H | 4-Imid | —(CH$_2$)$_2$CONHOH | 2-F | H H |
| 2-974 | Ac | 4-Imid | —(CH$_2$)$_2$CONHOH | 2-F | H H |
| 2-975 | H | 4-Imid | —(CH$_2$)$_2$CONHOH | 2-F | 4-F H |
| 2-976 | Ac | 4-Imid | —(CH$_2$)$_2$CONHOH | 2-F | 4-F H |
| 2-977 | H | 4-Imid | —(CH$_2$)$_3$CONHOH | 2-F | H H |
| 2-978 | Ac | 4-Imid | —(CH$_2$)$_3$CONHOH | 2-F | H H |
| 2-979 | H | 4-Imid | —(CH$_2$)$_3$CONHOH | 2-F | 4-F H |
| 2-980 | Ac | 4-Imid | —(CH$_2$)$_3$CONHOH | 2-F | 4-F H |
| 2-981 | H | 4-Imid | —(CH$_2$)$_4$CONHOH | 2-F | H H |
| 2-982 | Ac | 4-Imid | —(CH$_2$)$_4$CONHOH | 2-F | H H |
| 2-983 | H | 4-Imid | —(CH$_2$)$_4$CONHOH | 2-F | 4-F H |
| 2-984 | Ac | 4-Imid | —(CH$_2$)$_4$CONHOH | 2-F | 4-F H |
| 2-985 | H | 4-Imid | —CH$_2$CONH$_2$ | 2-F | H H |
| 2-986 | Ac | 4-Imid | —CH$_2$CONH$_2$ | 2-F | H H |
| 2-987 | H | 4-Imid | —CH$_2$CONH$_2$ | 2-F | 4-F H |
| 2-988 | Ac | 4-Imid | —CH$_2$CONH$_2$ | 2-F | 4-F H |
| 2-989 | H | 4-Imid | —(CH$_2$)$_2$CONH$_2$ | 2-F | H H |
| 2-990 | Ac | 4-Imid | —(CH$_2$)$_2$CONH$_2$ | 2-F | H H |
| 2-991 | H | 4-Imid | —(CH$_2$)$_2$CONH$_2$ | 2-F | 4-F H |
| 2-992 | Ac | 4-Imid | —(CH$_2$)$_2$CONH$_2$ | 2-F | 4-F H |
| 2-993 | H | 4-Imid | —CH$_2$CONHMe | 2-F | H H |
| 2-994 | Ac | 4-Imid | —CH$_2$CONHMe | 2-F | H H |

TABLE 2-continued

| | | | | | | |
|---|---|---|---|---|---|---|
| 2-995 | H | 4-Imid | —CH$_2$CONHMe | 2-F | H | H |
| 2-996 | Ac | 4-Imid | —CH$_2$CONHMe | 2-F | H | H |
| 2-997 | H | 4-Imid | —(CH$_2$)$_2$CONHMe | 2-F | H | H |
| 2-998 | Ac | 4-Imid | —(CH$_2$)$_2$CONHMe | 2-F | H | H |
| 2-999 | H | 4-Imid | —(CH$_2$)$_2$CONHMe | 2-F | 4-F | H |
| 2-1000 | Ac | 4-Imid | —(CH$_2$)$_2$CONHMe | 2-F | 4-F | H |
| 2-1001 | H | 4-Imid | —CH$_2$CONMe$_2$ | 2-F | H | H |
| 2-1002 | Ac | 4-Imid | —CH$_2$CONMe$_2$ | 2-F | H | H |
| 2-1003 | H | 4-Imid | —CH$_2$CONMe$_2$ | 2-F | 4-F | H |
| 2-1004 | Ac | 4-Imid | —CH$_2$CONMe$_2$ | 2-F | 4-F | H |
| 2-1005 | H | 4-Imid | —(CH$_2$)$_2$CONMe$_2$ | 2-F | H | H |
| 2-1006 | Ac | 4-Imid | —(CH$_2$)$_2$CONMe$_2$ | 2-F | H | H |
| 2-1007 | H | 4-Imid | —(CH$_2$)$_2$CONMe$_2$ | 2-F | 4-F | H |
| 2-1008 | Ac | 4-Imid | —(CH$_2$)$_2$CONMe$_2$ | 2-F | 4-F | H |
| 2-1009 | H | 4-Imid | —CH$_2$SO$_2$NH$_2$ | 2-F | H | H |
| 2-1010 | Ac | 4-Imid | —CH$_2$SO$_2$NH$_2$ | 2-F | H | H |
| 2-1011 | H | 4-Imid | —CH$_2$SO$_2$NH$_2$ | 2-F | 4-F | H |
| 2-1012 | Ac | 4-Imid | —CH$_2$SO$_2$NH$_2$ | 2-F | 4-F | H |
| 2-1013 | H | 4-Imid | —(CH$_2$)$_2$SO$_2$NH$_2$ | 2-F | H | H |
| 2-1014 | Ac | 4-Imid | —(CH$_2$)$_2$SO$_2$NH$_2$ | 2-F | H | H |
| 2-1015 | H | 4-Imid | —(CH$_2$)$_2$SO$_2$NH$_2$ | 2-F | 4-F | H |
| 2-1016 | Ac | 4-Imid | —(CH$_2$)$_2$SO$_2$NH$_2$ | 2-F | 4-F | H |
| 2-1017 | H | 5-Imid | Me | 2-F | H | H |
| 2-1018 | Ac | 5-Imid | Me | 2-F | H | H |
| 2-1019 | H | 5-Imid | Me | 2-F | 4-F | H |
| 2-1020 | Ac | 5-Imid | Me | 2-F | 4-F | H |
| 2-1021 | H | 5-Imid | Et | 2-F | H | H |
| 2-1022 | Ac | 5-Imid | Et | 2-F | H | H |
| 2-1023 | H | 5-Imid | Et | 2-F | 4-F | H |
| 2-1024 | Ac | 5-Imid | Et | 2-F | 4-F | H |
| 2-1025 | H | 5-Imid | —CH$_2$COOH | 2-F | H | H |
| 2-1026 | Ac | 5-Imid | —CH$_2$COOH | 2-F | H | H |
| 2-1027 | H | 5-Imid | —CH$_2$COOH | 2-F | 4-F | H |
| 2-1028 | Ac | 5-Imid | —CH$_2$COOH | 2-F | 4-F | H |
| 2-1029 | H | 5-Imid | —(CH$_2$)$_2$COOH | 2-F | H | H |
| 2-1030 | Ac | 5-Imid | —(CH$_2$)$_2$COOH | 2-F | H | H |
| 2-1031 | H | 5-Imid | —(CH$_2$)$_2$COOH | 2-F | 4-F | H |
| 2-1032 | Ac | 5-Imid | —(CH$_2$)$_2$COOH | 2-F | 4-F | H |
| 2-1033 | H | 5-Imid | —(CH$_2$)$_3$COOH | 2-F | H | H |
| 2-1034 | Ac | 5-Imid | —(CH$_2$)$_3$COOH | 2-F | H | H |
| 2-1035 | H | 5-Imid | —(CH$_2$)$_3$COOH | 2-F | 4-F | H |
| 2-1036 | Ac | 5-Imid | —(CH$_2$)$_3$COOH | 2-F | 4-F | H |
| 2-1037 | H | 5-Imid | —(CH$_2$)$_4$COOH | 2-F | H | H |
| 2-1038 | Ac | 5-Imid | —(CH$_2$)$_4$COOH | 2-F | H | H |
| 2-1039 | H | 5-Imid | —(CH$_2$)$_4$COOH | 2-F | 4-F | H |
| 2-1040 | Ac | 5-Imid | —(CH$_2$)$_4$COOH | 2-F | 4-F | H |
| 2-1041 | H | 5-Imid | —CH$_2$COOMe | 2-F | H | H |
| 2-1042 | Ac | 5-Imid | —CH$_2$COOMe | 2-F | H | H |
| 2-1043 | H | 5-Imid | —CH$_2$COOMe | 2-F | 4-F | H |
| 2-1044 | Ac | 5-Imid | —CH$_2$COOMe | 2-F | 4-F | H |
| 2-1045 | H | 5-Imid | —(CH$_2$)$_2$COOMe | 2-F | H | H |
| 2-1046 | Ac | 5-Imid | —(CH$_2$)$_2$COOMe | 2-F | H | H |
| 2-1047 | H | 5-Imid | —(CH$_2$)$_2$COOMe | 2-F | 4-F | H |
| 2-1048 | Ac | 5-Imid | —(CH$_2$)$_2$COOMe | 2-F | 4-F | H |
| 2-1049 | H | 5-Imid | —(CH$_2$)$_3$COOMe | 2-F | H | H |
| 2-1050 | Ac | 5-Imid | —(CH$_2$)$_3$COOMe | 2-F | H | H |
| 2-1051 | H | 5-Imid | —(CH$_2$)$_3$COOMe | 2-F | 4-F | H |
| 2-1052 | Ac | 5-Imid | —(CH$_2$)$_3$COOMe | 2-F | 4-F | H |
| 2-1053 | H | 5-Imid | —(CH$_2$)$_4$COOMe | 2-F | H | H |
| 2-1054 | Ac | 5-Imid | —(CH$_2$)$_4$COOMe | 2-F | H | H |
| 2-1055 | H | 5-Imid | —(CH$_2$)$_4$COOMe | 2-F | 4-F | H |
| 2-1056 | Ac | 5-Imid | —(CH$_2$)$_4$COOMe | 2-F | 4-F | H |
| 2-1057 | H | 5-Imid | —CH$_2$COOEt | 2-F | H | H |
| 2-1058 | Ac | 5-Imid | —CH$_2$COOEt | 2-F | H | H |
| 2-1059 | H | 5-Imid | —CH$_2$COOEt | 2-F | 4-F | H |
| 2-1060 | Ac | 5-Imid | —CH$_2$COOEt | 2-F | 4-F | H |
| 2-1061 | H | 5-Imid | —(CH$_2$)$_2$COOEt | 2-F | H | H |
| 2-1062 | Ac | 5-Imid | —(CH$_2$)$_2$COOEt | 2-F | H | H |
| 2-1063 | H | 5-Imid | —(CH$_2$)$_2$COOEt | 2-F | 4-F | H |
| 2-1064 | Ac | 5-Imid | —(CH$_2$)$_2$COOEt | 2-F | 4-F | H |
| 2-1065 | H | 5-Imid | —(CH$_2$)$_3$COOEt | 2-F | H | H |
| 2-1066 | Ac | 5-Imid | —(CH$_2$)$_3$COOEt | 2-F | H | H |
| 2-1067 | H | 5-Imid | —(CH$_2$)$_3$COOEt | 2-F | 4-F | H |
| 2-1068 | Ac | 5-Imid | —(CH$_2$)$_3$COOEt | 2-F | 4-F | H |
| 2-1069 | H | 5-Imid | —(CH$_2$)$_4$COOEt | 2-F | H | H |
| 2-1070 | Ac | 5-Imid | —(CH$_2$)$_4$COOEt | 2-F | H | H |
| 2-1071 | H | 5-Imid | —(CH$_2$)$_4$COOEt | 2-F | 4-F | H |
| 2-1072 | Ac | 5-Imid | —(CH$_2$)$_4$COOEt | 2-F | 4-F | H |
| 2-1073 | H | 5-Imid | —CH$_2$COOPr | 2-F | H | H |
| 2-1074 | Ac | 5-Imid | —CH$_2$COOPr | 2-F | H | H |
| 2-1075 | H | 5-Imid | —CH$_2$COOPr | 2-F | 4-F | H |
| 2-1076 | Ac | 5-Imid | —CH$_2$COOPr | 2-F | 4-F | H |
| 2-1077 | H | 5-Imid | —(CH$_2$)$_2$COOPr | 2-F | H | H |
| 2-1078 | Ac | 5-Imid | —(CH$_2$)$_2$COOPr | 2-F | H | H |
| 2-1079 | H | 5-Imid | —(CH$_2$)$_2$COOPr | 2-F | 4-F | H |
| 2-1080 | Ac | 5-Imid | —(CH$_2$)$_2$COOPr | 2-F | 4-F | H |
| 2-1081 | H | 5-Imid | —CH$_2$COOBu | 2-F | H | H |
| 2-1082 | Ac | 5-Imid | —CH$_2$COOBu | 2-F | H | H |
| 2-1083 | H | 5-Imid | —CH$_2$COOBu | 2-F | 4-F | H |
| 2-1084 | Ac | 5-Imid | —CH$_2$COOBu | 2-F | 4-F | H |
| 2-1085 | H | 5-Imid | —(CH$_2$)$_2$COOBu | 2-F | H | H |
| 2-1086 | Ac | 5-Imid | —(CH$_2$)$_2$COOBu | 2-F | H | H |
| 2-1087 | H | 5-Imid | —(CH$_2$)$_2$COOBu | 2-F | 4-F | H |
| 2-1088 | Ac | 5-Imid | —(CH$_2$)$_2$COOBu | 2-F | 4-F | H |
| 2-1089 | H | 5-Imid | —CH$_2$COO$^t$Bu | 2-F | H | H |
| 2-1090 | Ac | 5-Imid | —CH$_2$COO$^t$Bu | 2-F | H | H |
| 2-1091 | H | 5-Imid | —CH$_2$COO$^t$Bu | 2-F | 4-F | H |
| 2-1092 | Ac | 5-Imid | —CH$_2$COO$^t$Bu | 2-F | 4-F | H |
| 2-1093 | H | 5-Imid | —(CH$_2$)$_2$COO$^t$Bu | 2-F | H | H |
| 2-1094 | Ac | 5-Imid | —(CH$_2$)$_2$COO$^t$Bu | 2-F | H | H |
| 2-1095 | H | 5-Imid | —(CH$_2$)$_2$COO$^t$Bu | 2-F | 4-F | H |
| 2-1096 | Ac | 5-Imid | —(CH$_2$)$_2$COO$^t$Bu | 2-F | 4-F | H |
| 2-1097 | H | 5-Imid | —CH$_2$CONHOH | 2-F | H | H |
| 2-1098 | Ac | 5-Imid | —CH$_2$CONHOH | 2-F | H | H |
| 2-1099 | H | 5-Imid | —CH$_2$CONHOH | 2-F | 4-F | H |
| 2-1100 | Ac | 5-Imid | —CH$_2$CONHOH | 2-F | 4-F | H |
| 2-1101 | H | 5-Imid | —(CH$_2$)$_2$CONHOH | 2-F | H | H |
| 2-1102 | Ac | 5-Imid | —(CH$_2$)$_2$CONHOH | 2-F | H | H |
| 2-1103 | H | 5-Imid | —(CH$_2$)$_2$CONHOH | 2-F | 4-F | H |
| 2-1104 | Ac | 5-Imid | —(CH$_2$)$_2$CONHOH | 2-F | 4-F | H |
| 2-1105 | H | 5-Imid | —(CH$_2$)$_3$CONHOH | 2-F | H | H |
| 2-1106 | Ac | 5-Imid | —(CH$_2$)$_3$CONHOH | 2-F | H | H |
| 2-1107 | H | 5-Imid | —(CH$_2$)$_3$CONHOH | 2-F | 4-F | H |
| 2-1108 | Ac | 5-Imid | —(CH$_2$)$_3$CONHOH | 2-F | 4-F | H |
| 2-1109 | H | 5-Imid | —(CH$_2$)$_4$CONHOH | 2-F | H | H |
| 2-1110 | Ac | 5-Imid | —(CH$_2$)$_4$CONHOH | 2-F | H | H |
| 2-1111 | H | 5-Imid | —(CH$_2$)$_4$CONHOH | 2-F | 4-F | H |
| 2-1112 | Ac | 5-Imid | —(CH$_2$)$_4$CONHOH | 2-F | 4-F | H |
| 2-1113 | H | 5-Imid | —CH$_2$CONH$_2$ | 2-F | H | H |
| 2-1114 | Ac | 5-Imid | —CH$_2$CONH$_2$ | 2-F | H | H |
| 2-1115 | H | 5-Imid | —CH$_2$CONH$_2$ | 2-F | 4-F | H |
| 2-1116 | Ac | 5-Imid | —CH$_2$CONH$_2$ | 2-F | 4-F | H |
| 2-1117 | H | 5-Imid | —(CH$_2$)$_2$CONH$_2$ | 2-F | H | H |
| 2-1118 | Ac | 5-Imid | —(CH$_2$)$_2$CONH$_2$ | 2-F | H | H |
| 2-1119 | H | 5-Imid | —(CH$_2$)$_2$CONH$_2$ | 2-F | 4-F | H |
| 2-1120 | Ac | 5-Imid | —(CH$_2$)$_2$CONH$_2$ | 2-F | 4-F | H |
| 2-1121 | H | 5-Imid | —CH$_2$CONHMe | 2-F | H | H |
| 2-1122 | Ac | 5-Imid | —CH$_2$CONHMe | 2-F | H | H |
| 2-1123 | H | 5-Imid | —CH$_2$CONHMe | 2-F | 4-F | H |
| 2-1124 | Ac | 5-Imid | —CH$_2$CONHMe | 2-F | 4-F | H |
| 2-1125 | H | 5-Imid | —(CH$_2$)$_2$CONHMe | 2-F | H | H |
| 2-1126 | Ac | 5-Imid | —(CH$_2$)$_2$CONHMe | 2-F | H | H |
| 2-1127 | H | 5-Imid | —(CH$_2$)$_2$CONHMe | 2-F | 4-F | H |
| 2-1128 | Ac | 5-Imid | —(CH$_2$)$_2$CONHMe | 2-F | 4-F | H |
| 2-1129 | H | 5-Imid | —CH$_2$CONMe$_2$ | 2-F | H | H |
| 2-1130 | Ac | 5-Imid | —CH$_2$CONMe$_2$ | 2-F | H | H |
| 2-1131 | H | 5-Imid | —CH$_2$CONMe$_2$ | 2-F | 4-F | H |
| 2-1132 | Ac | 5-Imid | —CH$_2$CONMe$_2$ | 2-F | 4-F | H |
| 2-1133 | H | 5-Imid | —(CH$_2$)$_2$CONMe$_2$ | 2-F | H | H |
| 2-1134 | Ac | 5-Imid | —(CH$_2$)$_2$CONMe$_2$ | 2-F | H | H |
| 2-1135 | H | 5-Imid | —(CH$_2$)$_2$CONMe$_2$ | 2-F | 4-F | H |
| 2-1136 | Ac | 5-Imid | —(CH$_2$)$_2$CONMe$_2$ | 2-F | 4-F | H |
| 2-1137 | H | 5-Imid | —CH$_2$SO$_2$NH$_2$ | 2-F | H | H |
| 2-1138 | Ac | 5-Imid | —CH$_2$SO$_2$NH$_2$ | 2-F | H | H |
| 2-1139 | H | 5-Imid | —CH$_2$SO$_2$NH$_2$ | 2-F | 4-F | H |
| 2-1140 | Ac | 5-Imid | —CH$_2$SO$_2$NH$_2$ | 2-F | 4-F | H |
| 2-1141 | H | 5-Imid | —(CH$_2$)$_2$SO$_2$NH$_2$ | 2-F | H | H |
| 2-1142 | Ac | 5-Imid | —(CH$_2$)$_2$SO$_2$NH$_2$ | 2-F | H | H |
| 2-1143 | H | 5-Imid | —(CH$_2$)$_2$SO$_2$NH$_2$ | 2-F | 4-F | H |
| 2-1144 | Ac | 5-Imid | —(CH$_2$)$_2$SO$_2$NH$_2$ | 2-F | 4-F | H |
| 2-1145 | H | 4-αTriz | —CH$_2$COOH | 2-F | H | H |
| 2-1146 | Ac | 4-αTriz | —CH$_2$COOH | 2-F | H | H |
| 2-1147 | H | 4-αTriz | —CH$_2$COOH | 2-F | 4-F | H |
| 2-1148 | Ac | 4-αTriz | —CH$_2$COOH | 2-F | 4-F | H |
| 2-1149 | H | 4-αTriz | —(CH$_2$)$_2$COOH | 2-F | H | H |
| 2-1150 | Ac | 4-αTriz | —(CH$_2$)$_2$COOH | 2-F | H | H |
| 2-1151 | H | 4-αTriz | —(CH$_2$)$_2$COOH | 2-F | 4-F | H |
| 2-1152 | Ac | 4-αTriz | —(CH$_2$)$_2$COOH | 2-F | 4-F | H |

TABLE 2-continued

| | | | | | | |
|---|---|---|---|---|---|---|
| 2-1153 | H | 4-αTriz | —(CH₂)₃COOH | 2-F | H | H |
| 2-1154 | Ac | 4-αTriz | —(CH₂)₃COOH | 2-F | H | H |
| 2-1155 | H | 4-αTriz | —(CH₂)₃COOH | 2-F | 4-F | H |
| 2-1156 | Ac | 4-αTriz | —(CH₂)₃COOH | 2-F | 4-F | H |
| 2-1157 | H | 4-αTriz | —(CH₂)₄COOH | 2-F | H | H |
| 2-1158 | Ac | 4-αTriz | —(CH₂)₄COOH | 2-F | H | H |
| 2-1159 | H | 4-αTriz | —(CH₂)₄COOH | 2-F | 4-F | H |
| 2-1160 | Ac | 4-αTriz | —(CH₂)₄COOH | 2-F | 4-F | H |
| 2-1161 | H | 4-αTriz | —CH₂COOMe | 2-F | H | H |
| 2-1162 | Ac | 4-αTriz | —CH₂COOMe | 2-F | H | H |
| 2-1163 | H | 4-αTriz | —CH₂COOMe | 2-F | 4-F | H |
| 2-1164 | Ac | 4-αTriz | —CH₂COOMe | 2-F | 4-F | H |
| 2-1165 | H | 4-αTriz | —(CH₂)₂COOMe | 2-F | H | H |
| 2-1166 | Ac | 4-αTriz | —(CH₂)₂COOMe | 2-F | H | H |
| 2-1167 | H | 4-αTriz | —(CH₂)₂COOMe | 2-F | 4-F | H |
| 2-1168 | Ac | 4-αTriz | —(CH₂)₂COOMe | 2-F | 4-F | H |
| 2-1169 | H | 4-αTriz | —(CH₂)₃COOMe | 2-F | H | H |
| 2-1170 | Ac | 4-αTriz | —(CH₂)₃COOMe | 2-F | H | H |
| 2-1171 | H | 4-αTriz | —(CH₂)₃COOMe | 2-F | 4-F | H |
| 2-1172 | Ac | 4-αTriz | —(CH₂)₃COOMe | 2-F | 4-F | H |
| 2-1173 | H | 4-αTriz | —(CH₂)₄COOMe | 2-F | H | H |
| 2-1174 | Ac | 4-αTriz | —(CH₂)₄COOMe | 2-F | H | H |
| 2-1175 | H | 4-αTriz | —(CH₂)₄COOMe | 2-F | 4-F | H |
| 2-1176 | Ac | 4-αTriz | —(CH₂)₄COOMe | 2-F | 4-F | H |
| 2-1177 | H | 4-αTriz | —CH₂COOEt | 2-F | H | H |
| 2-1178 | Ac | 4-αTriz | —CH₂COOEt | 2-F | H | H |
| 2-1179 | H | 4-αTriz | —CH₂COOEt | 2-F | 4-F | H |
| 2-1180 | Ac | 4-αTriz | —CH₂COOEt | 2-F | 4-F | H |
| 2-1181 | H | 4-αTriz | —(CH₂)₂COOEt | 2-F | H | H |
| 2-1182 | Ac | 4-αTriz | —(CH₂)₂COOEt | 2-F | H | H |
| 2-1183 | H | 4-αTriz | —(CH₂)₂COOEt | 2-F | 4-F | H |
| 2-1184 | Ac | 4-αTriz | —(CH₂)₂COOEt | 2-F | 4-F | H |
| 2-1185 | H | 4-αTriz | —(CH₂)₃COOEt | 2-F | H | H |
| 2-1186 | Ac | 4-αTriz | —(CH₂)₃COOEt | 2-F | H | H |
| 2-1187 | H | 4-αTriz | —(CH₂)₃COOEt | 2-F | 4-F | H |
| 2-1188 | Ac | 4-αTriz | —(CH₂)₃COOEt | 2-F | 4-F | H |
| 2-1189 | H | 4-αTriz | —(CH₂)₄COOEt | 2-F | H | H |
| 2-1190 | Ac | 4-αTriz | —(CH₂)₄COOEt | 2-F | H | H |
| 2-1191 | H | 4-αTriz | —(CH₂)₄COOEt | 2-F | 4-F | H |
| 2-1192 | Ac | 4-αTriz | —(CH₂)₄COOEt | 2-F | 4-F | H |
| 2-1193 | H | 4-αTriz | —CH₂CONHOH | 2-F | H | H |
| 2-1194 | Ac | 4-αTriz | —CH₂CONHOH | 2-F | H | H |
| 2-1195 | H | 4-αTriz | —CH₂CONHOH | 2-F | 4-F | H |
| 2-1196 | Ac | 4-αTriz | —CH₂CONHOH | 2-F | 4-F | H |
| 2-1197 | H | 4-αTriz | —(CH₂)₂CONHOH | 2-F | H | H |
| 2-1198 | Ac | 4-αTriz | —(CH₂)₂CONHOH | 2-F | H | H |
| 2-1199 | H | 4-αTriz | —(CH₂)₂CONHOH | 2-F | 4-F | H |
| 2-1200 | Ac | 4-αTriz | —(CH₂)₂CONHOH | 2-F | 4-F | H |
| 2-1201 | H | 4-αTriz | —(CH₂)₃CONHOH | 2-F | H | H |
| 2-1202 | Ac | 4-αTriz | —(CH₂)₃CONHOH | 2-F | H | H |
| 2-1203 | H | 4-αTriz | —(CH₂)₃CONHOH | 2-F | 4-F | H |
| 2-1204 | Ac | 4-αTriz | —(CH₂)₃CONHOH | 2-F | 4-F | H |
| 2-1205 | H | 4-αTriz | —(CH₂)₄CONHOH | 2-F | H | H |
| 2-1206 | Ac | 4-αTriz | —(CH₂)₄CONHOH | 2-F | H | H |
| 2-1207 | H | 4-αTriz | —(CH₂)₄CONHOH | 2-F | 4-F | H |
| 2-1208 | Ac | 4-αTriz | —(CH₂)₄CONHOH | 2-F | 4-F | H |
| 2-1209 | H | 5-αTriz | —CH₂COOH | 2-F | H | H |
| 2-1210 | Ac | 5-αTriz | —CH₂COOH | 2-F | H | H |
| 2-1211 | H | 5-αTriz | —CH₂COOH | 2-F | 4-F | H |
| 2-1212 | Ac | 5-αTriz | —CH₂COOH | 2-F | 4-F | H |
| 2-1213 | H | 5-αTriz | —(CH₂)₂COOH | 2-F | H | H |
| 2-1214 | Ac | 5-αTriz | —(CH₂)₂COOH | 2-F | H | H |
| 2-1215 | H | 5-αTriz | —(CH₂)₂COOH | 2-F | 4-F | H |
| 2-1216 | Ac | 5-αTriz | —(CH₂)₂COOH | 2-F | 4-F | H |
| 2-1217 | H | 5-αTriz | —(CH₂)₃COOH | 2-F | H | H |
| 2-1218 | Ac | 5-αTriz | —(CH₂)₃COOH | 2-F | H | H |
| 2-1219 | H | 5-αTriz | —(CH₂)₃COOH | 2-F | 4-F | H |
| 2-1220 | Ac | 5-αTriz | —(CH₂)₃COOH | 2-F | 4-F | H |
| 2-1221 | H | 5-αTriz | —(CH₂)₄COOH | 2-F | H | H |
| 2-1222 | Ac | 5-αTriz | —(CH₂)₄COOH | 2-F | H | H |
| 2-1223 | H | 5-αTriz | —(CH₂)₄COOH | 2-F | 4-F | H |
| 2-1224 | Ac | 5-αTriz | —(CH₂)₄COOH | 2-F | 4-F | H |
| 2-1225 | H | 5-αTriz | —CH₂COOMe | 2-F | H | H |
| 2-1226 | Ac | 5-αTriz | —CH₂COOMe | 2-F | H | H |
| 2-1227 | H | 5-αTriz | —CH₂COOMe | 2-F | 4-F | H |
| 2-1228 | Ac | 5-αTriz | —CH₂COOMe | 2-F | 4-F | H |
| 2-1229 | H | 5-αTriz | —(CH₂)₂COOMe | 2-F | H | H |
| 2-1230 | Ac | 5-αTriz | —(CH₂)₂COOMe | 2-F | H | H |
| 2-1231 | H | 5-αTriz | —(CH₂)₂COOMe | 2-F | 4-F | H |
| 2-1232 | Ac | 5-αTriz | —(CH₂)₂COOMe | 2-F | 4-F | H |
| 2-1233 | H | 5-αTriz | —(CH₂)₃COOMe | 2-F | H | H |
| 2-1234 | Ac | 5-αTriz | —(CH₂)₃COOMe | 2-F | H | H |
| 2-1235 | H | 5-αTriz | —(CH₂)₃COOMe | 2-F | 4-F | H |
| 2-1236 | Ac | 5-αTriz | —(CH₂)₃COOMe | 2-F | 4-F | H |
| 2-1237 | H | 5-αTriz | —(CH₂)₄COOMe | 2-F | H | H |
| 2-1238 | Ac | 5-αTriz | —(CH₂)₄COOMe | 2-F | H | H |
| 2-1239 | H | 5-αTriz | —(CH₂)₄COOMe | 2-F | 4-F | H |
| 2-1240 | Ac | 5-αTriz | —(CH₂)₄COOMe | 2-F | 4-F | H |
| 2-1241 | H | 5-αTriz | —CH₂COOEt | 2-F | H | H |
| 2-1242 | Ac | 5-αTriz | —CH₂COOEt | 2-F | H | H |
| 2-1243 | H | 5-αTriz | —CH₂COOEt | 2-F | 4-F | H |
| 2-1244 | Ac | 5-αTriz | —CH₂COOEt | 2-F | 4-F | H |
| 2-1245 | H | 5-αTriz | —(CH₂)₂COOEt | 2-F | H | H |
| 2-1246 | Ac | 5-αTriz | —(CH₂)₂COOEt | 2-F | H | H |
| 2-1247 | H | 5-αTriz | —(CH₂)₂COOEt | 2-F | 4-F | H |
| 2-1248 | Ac | 5-αTriz | —(CH₂)₂COOEt | 2-F | 4-F | H |
| 2-1249 | H | 5-αTriz | —(CH₂)₃COOEt | 2-F | H | H |
| 2-1250 | Ac | 5-αTriz | —(CH₂)₃COOEt | 2-F | H | H |
| 2-1251 | H | 5-αTriz | —(CH₂)₃COOEt | 2-F | 4-F | H |
| 2-1252 | Ac | 5-αTriz | —(CH₂)₃COOEt | 2-F | 4-F | H |
| 2-1253 | H | 5-αTriz | —(CH₂)₄COOEt | 2-F | H | H |
| 2-1254 | Ac | 5-αTriz | —(CH₂)₄COOEt | 2-F | H | H |
| 2-1255 | H | 5-αTriz | —(CH₂)₄COOEt | 2-F | 4-F | H |
| 2-1256 | Ac | 5-αTriz | —(CH₂)₄COOEt | 2-F | 4-F | H |
| 2-1257 | H | 5-αTriz | —CH₂CONHOH | 2-F | H | H |
| 2-1258 | Ac | 5-αTriz | —CH₂CONHOH | 2-F | H | H |
| 2-1259 | H | 5-αTriz | —CH₂CONHOH | 2-F | 4-F | H |
| 2-1260 | Ac | 5-αTriz | —CH₂CONHOH | 2-F | 4-F | H |
| 2-1261 | H | 5-αTriz | —(CH₂)₂CONHOH | 2-F | H | H |
| 2-1262 | Ac | 5-αTriz | —(CH₂)₂CONHOH | 2-F | H | H |
| 2-1263 | H | 5-αTriz | —(CH₂)₂CONHOH | 2-F | 4-F | H |
| 2-1264 | Ac | 5-αTriz | —(CH₂)₂CONHOH | 2-F | 4-F | H |
| 2-1265 | H | 5-αTriz | —(CH₂)₃CONHOH | 2-F | H | H |
| 2-1266 | Ac | 5-αTriz | —(CH₂)₃CONHOH | 2-F | H | H |
| 2-1267 | H | 5-αTriz | —(CH₂)₃CONHOH | 2-F | 4-F | H |
| 2-1268 | Ac | 5-αTriz | —(CH₂)₃CONHOH | 2-F | 4-F | H |
| 2-1269 | H | 5-αTriz | —(CH₂)₄CONHOH | 2-F | H | H |
| 2-1270 | Ac | 5-αTriz | —(CH₂)₄CONHOH | 2-F | H | H |
| 2-1271 | H | 5-αTriz | —(CH₂)₄CONHOH | 2-F | 4-F | H |
| 2-1272 | Ac | 5-αTriz | —(CH₂)₄CONHOH | 2-F | 4-F | H |
| 2-1273 | H | 3-βTriz | —CH₂COOH | 2-F | H | H |
| 2-1274 | Ac | 3-βTriz | —CH₂COOH | 2-F | H | H |
| 2-1275 | H | 3-βTriz | —CH₂COOH | 2-F | 4-F | H |
| 2-1276 | Ac | 3-βTriz | —CH₂COOH | 2-F | 4-F | H |
| 2-1277 | H | 3-βTriz | —(CH₂)₂COOH | 2-F | H | H |
| 2-1278 | Ac | 3-βTriz | —(CH₂)₂COOH | 2-F | H | H |
| 2-1279 | H | 3-βTriz | —(CH₂)₂COOH | 2-F | 4-F | H |
| 2-1280 | Ac | 3-βTriz | —(CH₂)₂COOH | 2-F | 4-F | H |
| 2-1281 | H | 3-βTriz | —(CH₂)₃COOH | 2-F | H | H |
| 2-1282 | Ac | 3-βTriz | —(CH₂)₃COOH | 2-F | H | H |
| 2-1283 | H | 3-βTriz | —(CH₂)₃COOH | 2-F | 4-F | H |
| 2-1284 | Ac | 3-βTriz | —(CH₂)₃COOH | 2-F | 4-F | H |
| 2-1285 | H | 3-βTriz | —(CH₂)₄COOH | 2-F | H | H |
| 2-1286 | Ac | 3-βTriz | —(CH₂)₄COOH | 2-F | H | H |
| 2-1287 | H | 3-βTriz | —(CH₂)₄COOH | 2-F | 4-F | H |
| 2-1288 | Ac | 3-βTriz | —(CH₂)₄COOH | 2-F | 4-F | H |
| 2-1289 | H | 3-βTriz | —CH₂COOMe | 2-F | H | H |
| 2-1290 | Ac | 3-βTriz | —CH₂COOMe | 2-F | H | H |
| 2-1291 | H | 3-βTriz | —CH₂COOMe | 2-F | 4-F | H |
| 2-1292 | Ac | 3-βTriz | —CH₂COOMe | 2-F | 4-F | H |
| 2-1293 | H | 3-βTriz | —(CH₂)₂COOMe | 2-F | H | H |
| 2-1294 | Ac | 3-βTriz | —(CH₂)₂COOMe | 2-F | H | H |
| 2-1295 | H | 3-βTriz | —(CH₂)₂COOMe | 2-F | 4-F | H |
| 2-1296 | Ac | 3-βTriz | —(CH₂)₂COOMe | 2-F | 4-F | H |
| 2-1297 | H | 3-βTriz | —(CH₂)₃COOMe | 2-F | H | H |
| 2-1298 | Ac | 3-βTriz | —(CH₂)₃COOMe | 2-F | H | H |
| 2-1299 | H | 3-βTriz | —(CH₂)₃COOMe | 2-F | 4-F | H |
| 2-1300 | Ac | 3-βTriz | —(CH₂)₃COOMe | 2-F | 4-F | H |
| 2-1301 | H | 3-βTriz | —(CH₂)₄COOMe | 2-F | H | H |
| 2-1302 | Ac | 3-βTriz | —(CH₂)₄COOMe | 2-F | H | H |
| 2-1303 | H | 3-βTriz | —(CH₂)₄COOMe | 2-F | 4-F | H |
| 2-1304 | Ac | 3-βTriz | —(CH₂)₄COOMe | 2-F | 4-F | H |
| 2-1305 | H | 3-βTriz | —CH₂COOEt | 2-F | H | H |
| 2-1306 | Ac | 3-βTriz | —CH₂COOEt | 2-F | H | H |
| 2-1307 | H | 3-βTriz | —CH₂COOEt | 2-F | 4-F | H |
| 2-1308 | Ac | 3-βTriz | —CH₂COOEt | 2-F | 4-F | H |
| 2-1309 | H | 3-βTriz | —(CH₂)₂COOEt | 2-F | H | H |
| 2-1310 | Ac | 3-βTriz | —(CH₂)₂COOEt | 2-F | H | H |

TABLE 2-continued

| | | | | | | |
|---|---|---|---|---|---|---|
| 2-1311 | H | 3-βTriz | —(CH$_2$)$_2$COOEt | 2-F | 4-F | H |
| 2-1312 | Ac | 3-βTriz | —(CH$_2$)$_2$COOEt | 2-F | 4-F | H |
| 2-1313 | H | 3-βTriz | —(CH$_2$)$_3$COOEt | 2-F | H | H |
| 2-1314 | Ac | 3-βTriz | —(CH$_2$)$_3$COOEt | 2-F | H | H |
| 2-1315 | H | 3-βTriz | —(CH$_2$)$_3$COOEt | 2-F | 4-F | H |
| 2-1316 | Ac | 3-βTriz | —(CH$_2$)$_3$COOEt | 2-F | 4-F | H |
| 2-1317 | H | 3-βTriz | —(CH$_2$)$_4$COOEt | 2-F | H | H |
| 2-1318 | Ac | 3-βTriz | —(CH$_2$)$_4$COOEt | 2-F | H | H |
| 2-1319 | H | 3-βTriz | —(CH$_2$)$_4$COOEt | 2-F | 4-F | H |
| 2-1320 | Ac | 3-βTriz | —(CH$_2$)$_4$COOEt | 2-F | 4-F | H |
| 2-1321 | H | 3-βTriz | —CH$_2$CONHOH | 2-F | H | H |
| 2-1322 | Ac | 3-βTriz | —CH$_2$CONHOH | 2-F | H | H |
| 2-1323 | H | 3-βTriz | —CH$_2$CONHOH | 2-F | 4-F | H |
| 2-1324 | Ac | 3-βTriz | —CH$_2$CONHOH | 2-F | 4-F | H |
| 2-1325 | H | 3-βTriz | —(CH$_2$)$_2$CONHOH | 2-F | H | H |
| 2-1326 | Ac | 3-βTriz | —(CH$_2$)$_2$CONHOH | 2-F | H | H |
| 2-1327 | H | 3-βTriz | —(CH$_2$)$_2$CONHOH | 2-F | 4-F | H |
| 2-1328 | Ac | 3-βTriz | —(CH$_2$)$_2$CONHOH | 2-F | 4-F | H |
| 2-1329 | H | 3-βTriz | —(CH$_2$)$_3$CONHOH | 2-F | H | H |
| 2-1330 | Ac | 3-βTriz | —(CH$_2$)$_3$CONHOH | 2-F | H | H |
| 2-1331 | H | 3-βTriz | —(CH$_2$)$_3$CONHOH | 2-F | 4-F | H |
| 2-1332 | Ac | 3-βTriz | —(CH$_2$)$_3$CONHOH | 2-F | 4-F | H |
| 2-1333 | H | 3-βTriz | —(CH$_2$)$_4$CONHOH | 2-F | H | H |
| 2-1334 | Ac | 3-βTriz | —(CH$_2$)$_4$CONHOH | 2-F | H | H |
| 2-1335 | H | 3-βTriz | —(CH$_2$)$_4$CONHOH | 2-F | 4-F | H |
| 2-1336 | Ac | 3-βTriz | —(CH$_2$)$_4$CONHOH | 2-F | 4-F | H |
| 2-1337 | H | 5-βTriz | —CH$_2$COOH | 2-F | H | H |
| 2-1338 | Ac | 5-βTriz | —CH$_2$COOH | 2-F | H | H |
| 2-1339 | H | 5-βTriz | —CH$_2$COOH | 2-F | 4-F | H |
| 2-1340 | Ac | 5-βTriz | —CH$_2$COOH | 2-F | 4-F | H |
| 2-1341 | H | 5-βTriz | —(CH$_2$)$_2$COOH | 2-F | H | H |
| 2-1342 | Ac | 5-βTriz | —(CH$_2$)$_2$COOH | 2-F | H | H |
| 2-1343 | H | 5-βTriz | —(CH$_2$)$_2$COOH | 2-F | 4-F | H |
| 2-1344 | Ac | 5-βTriz | —(CH$_2$)$_2$COOH | 2-F | 4-F | H |
| 2-1345 | H | 5-βTriz | —(CH$_2$)$_3$COOH | 2-F | H | H |
| 2-1346 | Ac | 5-βTriz | —(CH$_2$)$_3$COOH | 2-F | H | H |
| 2-1347 | H | 5-βTriz | —(CH$_2$)$_3$COOH | 2-F | 4-F | H |
| 2-1348 | Ac | 5-βTriz | —(CH$_2$)$_3$COOH | 2-F | 4-F | H |
| 2-1349 | H | 5-βTriz | —(CH$_2$)$_4$COOH | 2-F | H | H |
| 2-1350 | Ac | 5-βTriz | —(CH$_2$)$_4$COOH | 2-F | H | H |
| 2-1351 | H | 5-βTriz | —(CH$_2$)$_4$COOH | 2-F | 4-F | H |
| 2-1352 | Ac | 5-βTriz | —(CH$_2$)$_4$COOH | 2-F | 4-F | H |
| 2-1353 | H | 5-βTriz | —CH$_2$COOMe | 2-F | H | H |
| 2-1354 | Ac | 5-βTriz | —CH$_2$COOMe | 2-F | H | H |
| 2-1355 | H | 5-βTriz | —CH$_2$COOMe | 2-F | 4-F | H |
| 2-1356 | Ac | 5-βTriz | —CH$_2$COOMe | 2-F | 4-F | H |
| 2-1357 | H | 5-βTriz | —(CH$_2$)$_2$COOMe | 2-F | H | H |
| 2-1358 | Ac | 5-βTriz | —(CH$_2$)$_2$COOMe | 2-F | H | H |
| 2-1359 | H | 5-βTriz | —(CH$_2$)$_2$COOMe | 2-F | 4-F | H |
| 2-1360 | Ac | 5-βTriz | —(CH$_2$)$_2$COOMe | 2-F | 4-F | H |
| 2-1361 | H | 5-βTriz | —(CH$_2$)$_3$COOMe | 2-F | H | H |
| 2-1362 | Ac | 5-βTriz | —(CH$_2$)$_3$COOMe | 2-F | H | H |
| 2-1363 | H | 5-βTriz | —(CH$_2$)$_3$COOMe | 2-F | 4-F | H |
| 2-1364 | Ac | 5-βTriz | —(CH$_2$)$_3$COOMe | 2-F | 4-F | H |
| 2-1365 | H | 5-βTriz | —(CH$_2$)$_4$COOMe | 2-F | H | H |
| 2-1366 | Ac | 5-βTriz | —(CH$_2$)$_4$COOMe | 2-F | H | H |
| 2-1367 | H | 5-βTriz | —(CH$_2$)$_4$COOMe | 2-F | 4-F | H |
| 2-1368 | Ac | 5-βTriz | —(CH$_2$)$_4$COOMe | 2-F | 4-F | H |
| 2-1369 | H | 5-βTriz | —CH$_2$COOEt | 2-F | H | H |
| 2-1370 | Ac | 5-βTriz | —CH$_2$COOEt | 2-F | H | H |
| 2-1371 | H | 5-βTriz | —CH$_2$COOEt | 2-F | 4-F | H |
| 2-1372 | Ac | 5-βTriz | —CH$_2$COOEt | 2-F | 4-F | H |
| 2-1373 | H | 5-βTriz | —(CH$_2$)$_2$COOEt | 2-F | H | H |
| 2-1374 | Ac | 5-βTriz | —(CH$_2$)$_2$COOEt | 2-F | H | H |
| 2-1375 | H | 5-βTriz | —(CH$_2$)$_2$COOEt | 2-F | 4-F | H |
| 2-1376 | Ac | 5-βTriz | —(CH$_2$)$_2$COOEt | 2-F | 4-F | H |
| 2-1377 | H | 5-βTriz | —(CH$_2$)$_3$COOEt | 2-F | H | H |
| 2-1378 | Ac | 5-βTriz | —(CH$_2$)$_3$COOEt | 2-F | H | H |
| 2-1379 | H | 5-βTriz | —(CH$_2$)$_3$COOEt | 2-F | 4-F | H |
| 2-1380 | Ac | 5-βTriz | —(CH$_2$)$_3$COOEt | 2-F | 4-F | H |
| 2-1381 | H | 5-βTriz | —(CH$_2$)$_4$COOEt | 2-F | H | H |
| 2-1382 | Ac | 5-βTriz | —(CH$_2$)$_4$COOEt | 2-F | H | H |
| 2-1383 | H | 5-βTriz | —(CH$_2$)$_4$COOEt | 2-F | 4-F | H |
| 2-1384 | Ac | 5-βTriz | —(CH$_2$)$_4$COOEt | 2-F | 4-F | H |
| 2-1385 | H | 5-βTriz | —CH$_2$CONHOH | 2-F | H | H |
| 2-1386 | Ac | 5-βTriz | —CH$_2$CONHOH | 2-F | H | H |
| 2-1387 | H | 5-βTriz | —CH$_2$CONHOH | 2-F | 4-F | H |
| 2-1388 | Ac | 5-βTriz | —CH$_2$CONHOH | 2-F | 4-F | H |
| 2-1389 | H | 5-βTriz | —(CH$_2$)$_2$CONHOH | 2-F | H | H |
| 2-1390 | Ac | 5-βTriz | —(CH$_2$)$_2$CONHOH | 2-F | H | H |
| 2-1391 | H | 5-βTriz | —(CH$_2$)$_2$CONHOH | 2-F | 4-F | H |
| 2-1392 | Ac | 5-βTriz | —(CH$_2$)$_2$CONHOH | 2-F | 4-F | H |
| 2-1393 | H | 5-βTriz | —(CH$_2$)$_3$CONHOH | 2-F | H | H |
| 2-1394 | Ac | 5-βTriz | —(CH$_2$)$_3$CONHOH | 2-F | H | H |
| 2-1395 | H | 5-βTriz | —(CH$_2$)$_3$CONHOH | 2-F | 4-F | H |
| 2-1396 | Ac | 5-βTriz | —(CH$_2$)$_3$CONHOH | 2-F | 4-F | H |
| 2-1397 | H | 5-βTriz | —(CH$_2$)$_4$CONHOH | 2-F | H | H |
| 2-1398 | Ac | 5-βTriz | —(CH$_2$)$_4$CONHOH | 2-F | H | H |
| 2-1399 | H | 5-βTriz | —(CH$_2$)$_4$CONHOH | 2-F | 4-F | H |
| 2-1400 | Ac | 5-βTriz | —(CH$_2$)$_4$CONHOH | 2-F | 4-F | H |
| 2-1401 | H | 3-γTriz | —CH$_2$COOH | 2-F | H | H |
| 2-1402 | Ac | 3-γTriz | —CH$_2$COOH | 2-F | H | H |
| 2-1403 | H | 3-γTriz | —CH$_2$COOH | 2-F | 4-F | H |
| 2-1404 | Ac | 3-γTriz | —CH$_2$COOH | 2-F | 4-F | H |
| 2-1405 | H | 3-γTriz | —(CH$_2$)$_2$COOH | 2-F | H | H |
| 2-1406 | Ac | 3-γTriz | —(CH$_2$)$_2$COOH | 2-F | H | H |
| 2-1407 | H | 3-γTriz | —(CH$_2$)$_2$COOH | 2-F | 4-F | H |
| 2-1408 | Ac | 3-γTriz | —(CH$_2$)$_2$COOH | 2-F | 4-F | H |
| 2-1409 | H | 3-γTriz | —(CH$_2$)$_3$COOH | 2-F | H | H |
| 2-1410 | Ac | 3-γTriz | —(CH$_2$)$_3$COOH | 2-F | H | H |
| 2-1411 | H | 3-γTriz | —(CH$_2$)$_3$COOH | 2-F | 4-F | H |
| 2-1412 | Ac | 3-γTriz | —(CH$_2$)$_3$COOH | 2-F | 4-F | H |
| 2-1413 | H | 3-γTriz | —(CH$_2$)$_4$COOH | 2-F | H | H |
| 2-1414 | Ac | 3-γTriz | —(CH$_2$)$_4$COOH | 2-F | H | H |
| 2-1415 | H | 3-γTriz | —(CH$_2$)$_4$COOH | 2-F | 4-F | H |
| 2-1416 | Ac | 3-γTriz | —(CH$_2$)$_4$COOH | 2-F | 4-F | H |
| 2-1417 | H | 3-γTriz | —CH$_2$COOMe | 2-F | H | H |
| 2-1418 | Ac | 3-γTriz | —CH$_2$COOMe | 2-F | H | H |
| 2-1419 | H | 3-γTriz | —CH$_2$COOMe | 2-F | 4-F | H |
| 2-1420 | Ac | 3-γTriz | —CH$_2$COOMe | 2-F | 4-F | H |
| 2-1421 | H | 3-γTriz | —(CH$_2$)$_2$COOMe | 2-F | H | H |
| 2-1422 | Ac | 3-γTriz | —(CH$_2$)$_2$COOMe | 2-F | H | H |
| 2-1423 | H | 3-γTriz | —(CH$_2$)$_2$COOMe | 2-F | 4-F | H |
| 2-1424 | Ac | 3-γTriz | —(CH$_2$)$_2$COOMe | 2-F | 4-F | H |
| 2-1425 | H | 3-γTriz | —(CH$_2$)$_3$COOMe | 2-F | H | H |
| 2-1426 | Ac | 3-γTriz | —(CH$_2$)$_3$COOMe | 2-F | H | H |
| 2-1427 | H | 3-γTriz | —(CH$_2$)$_3$COOMe | 2-F | 4-F | H |
| 2-1428 | Ac | 3-γTriz | —(CH$_2$)$_3$COOMe | 2-F | 4-F | H |
| 2-1429 | H | 3-γTriz | —(CH$_2$)$_4$COOMe | 2-F | H | H |
| 2-1430 | Ac | 3-γTriz | —(CH$_2$)$_4$COOMe | 2-F | H | H |
| 2-1431 | H | 3-γTriz | —(CH$_2$)$_4$COOMe | 2-F | 4-F | H |
| 2-1432 | Ac | 3-γTriz | —(CH$_2$)$_4$COOMe | 2-F | 4-F | H |
| 2-1433 | H | 3-γTriz | —CH$_2$COOEt | 2-F | H | H |
| 2-1434 | Ac | 3-γTriz | —CH$_2$COOEt | 2-F | H | H |
| 2-1435 | H | 3-γTriz | —CH$_2$COOEt | 2-F | 4-F | H |
| 2-1436 | Ac | 3-γTriz | —CH$_2$COOEt | 2-F | 4-F | H |
| 2-1437 | H | 3-γTriz | —(CH$_2$)$_2$COOEt | 2-F | H | H |
| 2-1438 | Ac | 3-γTriz | —(CH$_2$)$_2$COOEt | 2-F | H | H |
| 2-1439 | H | 3-γTriz | —(CH$_2$)$_2$COOEt | 2-F | 4-F | H |
| 2-1440 | Ac | 3-γTriz | —(CH$_2$)$_2$COOEt | 2-F | 4-F | H |
| 2-1441 | H | 3-γTriz | —(CH$_2$)$_3$COOEt | 2-F | H | H |
| 2-1442 | Ac | 3-γTriz | —(CH$_2$)$_3$COOEt | 2-F | H | H |
| 2-1443 | H | 3-γTriz | —(CH$_2$)$_3$COOEt | 2-F | 4-F | H |
| 2-1444 | Ac | 3-γTriz | —(CH$_2$)$_3$COOEt | 2-F | 4-F | H |
| 2-1445 | H | 3-γTriz | —(CH$_2$)$_4$COOEt | 2-F | H | H |
| 2-1446 | Ac | 3-γTriz | —(CH$_2$)$_4$COOEt | 2-F | H | H |
| 2-1447 | H | 3-γTriz | —(CH$_2$)$_4$COOEt | 2-F | 4-F | H |
| 2-1448 | Ac | 3-γTriz | —(CH$_2$)$_4$COOEt | 2-F | 4-F | H |
| 2-1449 | H | 3-γTriz | —CH$_2$CONHOH | 2-F | H | H |
| 2-1450 | Ac | 3-γTriz | —CH$_2$CONHOH | 2-F | H | H |
| 2-1451 | H | 3-γTriz | —CH$_2$CONHOH | 2-F | 4-F | H |
| 2-1452 | Ac | 3-γTriz | —CH$_2$CONHOH | 2-F | 4-F | H |
| 2-1453 | H | 3-γTriz | —(CH$_2$)$_2$CONHOH | 2-F | H | H |
| 2-1454 | Ac | 3-γTriz | —(CH$_2$)$_2$CONHOH | 2-F | H | H |
| 2-1455 | H | 3-γTriz | —(CH$_2$)$_2$CONHOH | 2-F | 4-F | H |
| 2-1456 | Ac | 3-γTriz | —(CH$_2$)$_2$CONHOH | 2-F | 4-F | H |
| 2-1457 | H | 3-γTriz | —(CH$_2$)$_3$CONHOH | 2-F | H | H |
| 2-1458 | Ac | 3-γTriz | —(CH$_2$)$_3$CONHOH | 2-F | H | H |
| 2-1459 | H | 3-γTriz | —(CH$_2$)$_3$CONHOH | 2-F | 4-F | H |
| 2-1460 | Ac | 3-γTriz | —(CH$_2$)$_3$CONHOH | 2-F | 4-F | H |
| 2-1461 | H | 3-γTriz | —(CH$_2$)$_4$CONHOH | 2-F | H | H |
| 2-1462 | Ac | 3-γTriz | —(CH$_2$)$_4$CONHOH | 2-F | H | H |
| 2-1463 | H | 3-γTriz | —(CH$_2$)$_4$CONHOH | 2-F | 4-F | H |
| 2-1464 | Ac | 3-γTriz | —(CH$_2$)$_4$CONHOH | 2-F | 4-F | H |
| 2-1465 | H | 2-δTriz | —CH$_2$COOH | 2-F | H | H |
| 2-1466 | Ac | 2-δTriz | —CH$_2$COOH | 2-F | H | H |
| 2-1467 | H | 2-δTriz | —CH$_2$COOH | 2-F | 4-F | H |
| 2-1468 | Ac | 2-δTriz | —CH$_2$COOH | 2-F | 4-F | H |

TABLE 2-continued

| | | | | | | |
|---|---|---|---|---|---|---|
| 2-1469 | H | 2-δTriz | —(CH₂)₂COOH | 2-F | H | H |
| 2-1470 | Ac | 2-δTriz | —(CH₂)₂COOH | 2-F | H | H |
| 2-1471 | H | 2-δTriz | —(CH₂)₂COOH | 2-F | 4-F | H |
| 2-1472 | Ac | 2-δTriz | —(CH₂)₂COOH | 2-F | 4-F | H |
| 2-1473 | H | 2-δTriz | —(CH₂)₂COOH | 2-F | H | H |
| 2-1474 | Ac | 2-δTriz | —(CH₂)₂COOH | 2-F | H | H |
| 2-1475 | H | 2-δTriz | —(CH₂)₂COOH | 2-F | 4-F | H |
| 2-1476 | Ac | 2-δTriz | —(CH₂)₂COOH | 2-F | 4-F | H |
| 2-1477 | H | 2-δTriz | —(CH₂)₄COOH | 2-F | H | H |
| 2-1478 | Ac | 2-δTriz | —(CH₂)₄COOH | 2-F | H | H |
| 2-1479 | H | 2-δTriz | —(CH₂)₄COOH | 2-F | 4-F | H |
| 2-1480 | Ac | 2-δTriz | —(CH₂)₄COOH | 2-F | 4-F | H |
| 2-1481 | H | 2-δTriz | —CH₂COOMe | 2-F | H | H |
| 2-1482 | Ac | 2-δTriz | —CH₂COOMe | 2-F | H | H |
| 2-1483 | H | 2-δTriz | —CH₂COOMe | 2-F | 4-F | H |
| 2-1484 | Ac | 2-δTriz | —CH₂COOMe | 2-F | 4-F | H |
| 2-1485 | H | 2-δTriz | —(CH₂)₂COOMe | 2-F | H | H |
| 2-1486 | Ac | 2-δTriz | —(CH₂)₂COOMe | 2-F | H | H |
| 2-1487 | H | 2-δTriz | —(CH₂)₂COOMe | 2-F | 4-F | H |
| 2-1488 | Ac | 2-δTriz | —(CH₂)₂COOMe | 2-F | 4-F | H |
| 2-1489 | H | 2-δTriz | —(CH₂)₃COOMe | 2-F | H | H |
| 2-1490 | Ac | 2-δTriz | —(CH₂)₃COOMe | 2-F | H | H |
| 2-1491 | H | 2-δTriz | —(CH₂)₃COOMe | 2-F | 4-F | H |
| 2-1492 | Ac | 2-δTriz | —(CH₂)₃COOMe | 2-F | 4-F | H |
| 2-1493 | H | 2-δTriz | —(CH₂)₄COOMe | 2-F | H | H |
| 2-1494 | Ac | 2-δTriz | —(CH₂)₄COOMe | 2-F | H | H |
| 2-1495 | H | 2-δTriz | —(CH₂)₄COOMe | 2-F | 4-F | H |
| 2-1496 | Ac | 2-δTriz | —(CH₂)₄COOMe | 2-F | 4-F | H |
| 2-1497 | H | 2-δTriz | —CH₂COOEt | 2-F | H | H |
| 2-1498 | Ac | 2-δTriz | —CH₂COOEt | 2-F | H | H |
| 2-1499 | H | 2-δTriz | —CH₂COOEt | 2-F | 4-F | H |
| 2-1500 | Ac | 2-δTriz | —CH₂COOEt | 2-F | 4-F | H |
| 2-1501 | H | 2-δTriz | —(CH₂)₂COOEt | 2-F | H | H |
| 2-1502 | Ac | 2-δTriz | —(CH₂)₂COOEt | 2-F | H | H |
| 2-1503 | H | 2-δTriz | —(CH₂)₂COOEt | 2-F | 4-F | H |
| 2-1504 | Ac | 2-δTriz | —(CH₂)₂COOEt | 2-F | 4-F | H |
| 2-1505 | H | 2-δTriz | —(CH₂)₃COOEt | 2-F | H | H |
| 2-1506 | Ac | 2-δTriz | —(CH₂)₃COOEt | 2-F | H | H |
| 2-1507 | H | 2-δTriz | —(CH₂)₃COOEt | 2-F | 4-F | H |
| 2-1508 | Ac | 2-δTriz | —(CH₂)₃COOEt | 2-F | 4-F | H |
| 2-1509 | H | 2-δTriz | —(CH₂)₄COOEt | 2-F | H | H |
| 2-1510 | Ac | 2-δTriz | —(CH₂)₄COOEt | 2-F | H | H |
| 2-1511 | H | 2-δTriz | —(CH₂)₄COOEt | 2-F | 4-F | H |
| 2-1512 | Ac | 2-δTriz | —(CH₂)₄COOEt | 2-F | 4-F | H |
| 2-1513 | H | 2-δTriz | —CH₂CONHOH | 2-F | H | H |
| 2-1514 | Ac | 2-δTriz | —CH₂CONHOH | 2-F | H | H |
| 2-1515 | H | 2-δTriz | —CH₂CONHOH | 2-F | 4-F | H |
| 2-1516 | Ac | 2-δTriz | —CH₂CONHOH | 2-F | 4-F | H |
| 2-1517 | H | 2-δTriz | —(CH₂)₂CONHOH | 2-F | H | H |
| 2-1518 | Ac | 2-δTriz | —(CH₂)₂CONHOH | 2-F | H | H |
| 2-1519 | H | 2-δTriz | —(CH₂)₂CONHOH | 2-F | 4-F | H |
| 2-1520 | Ac | 2-δTriz | —(CH₂)₂CONHOH | 2-F | 4-F | H |
| 2-1521 | H | 2-δTriz | —(CH₂)₃CONHOH | 2-F | H | H |
| 2-1522 | Ac | 2-δTriz | —(CH₂)₃CONHOH | 2-F | H | H |
| 2-1523 | H | 2-δTriz | —(CH₂)₃CONHOH | 2-F | 4-F | H |
| 2-1524 | Ac | 2-δTriz | —(CH₂)₃CONHOH | 2-F | 4-F | H |
| 2-1525 | H | 2-δTriz | —(CH₂)₄CONHOH | 2-F | H | H |
| 2-1526 | Ac | 2-δTriz | —(CH₂)₄CONHOH | 2-F | H | H |
| 2-1527 | H | 2-δTriz | —(CH₂)₄CONHOH | 2-F | 4-F | H |
| 2-1528 | Ac | 2-δTriz | —(CH₂)₄CONHOH | 2-F | 4-F | H |
| 2-1529 | H | Tez₁ | —CH₂COOH | 2-F | H | H |
| 2-1530 | Ac | Tez₁ | —CH₂COOH | 2-F | H | H |
| 2-1531 | H | Tez₁ | —CH₂COOH | 2-F | 4-F | H |
| 2-1532 | Ac | Tez₁ | —CH₂COOH | 2-F | 4-F | H |
| 2-1533 | H | Tez₁ | —(CH₂)₂COOH | 2-F | H | H |
| 2-1534 | Ac | Tez₁ | —(CH₂)₂COOH | 2-F | H | H |
| 2-1535 | H | Tez₁ | —(CH₂)₂COOH | 2-F | 4-F | H |
| 2-1536 | Ac | Tez₁ | —(CH₂)₂COOH | 2-F | 4-F | H |
| 2-1537 | H | Tez₁ | —(CH₂)₃COOH | 2-F | H | H |
| 2-1538 | Ac | Tez₁ | —(CH₂)₃COOH | 2-F | H | H |
| 2-1539 | H | Tez₁ | —(CH₂)₃COOH | 2-F | 4-F | H |
| 2-1540 | Ac | Tez₁ | —(CH₂)₃COOH | 2-F | 4-F | H |
| 2-1541 | H | Tez₁ | —(CH₂)₄COOH | 2-F | H | H |
| 2-1542 | Ac | Tez₁ | —(CH₂)₄COOH | 2-F | H | H |
| 2-1543 | H | Tez₁ | —(CH₂)₄COOH | 2-F | 4-F | H |
| 2-1544 | Ac | Tez₁ | —(CH₂)₄COOH | 2-F | 4-F | H |
| 2-1545 | H | Tez₁ | —CH₂COOMe | 2-F | H | H |
| 2-1546 | Ac | Tez₁ | —CH₂COOMe | 2-F | H | H |
| 2-1547 | H | Tez₁ | —CH₂COOMe | 2-F | 4-F | H |
| 2-1548 | Ac | Tez₁ | —CH₂COOMe | 2-F | 4-F | H |
| 2-1549 | H | Tez₁ | —(CH₂)₂COOMe | 2-F | H | H |
| 2-1550 | Ac | Tez₁ | —(CH₂)₂COOMe | 2-F | H | H |
| 2-1551 | H | Tez₁ | —(CH₂)₂COOMe | 2-F | 4-F | H |
| 2-1552 | Ac | Tez₁ | —(CH₂)₂COOMe | 2-F | 4-F | H |
| 2-1553 | H | Tez₁ | —(CH₂)₃COOMe | 2-F | H | H |
| 2-1554 | Ac | Tez₁ | —(CH₂)₃COOMe | 2-F | H | H |
| 2-1555 | H | Tez₁ | —(CH₂)₃COOMe | 2-F | 4-F | H |
| 2-1556 | Ac | Tez₁ | —(CH₂)₃COOMe | 2-F | 4-F | H |
| 2-1557 | H | Tez₁ | —(CH₂)₄COOMe | 2-F | H | H |
| 2-1558 | Ac | Tez₁ | —(CH₂)₄COOMe | 2-F | H | H |
| 2-1559 | H | Tez₁ | —(CH₂)₄COOMe | 2-F | 4-F | H |
| 2-1560 | Ac | Tez₁ | —(CH₂)₄COOMe | 2-F | 4-F | H |
| 2-1561 | H | Tez₁ | —CH₂COOEt | 2-F | H | H |
| 2-1562 | Ac | Tez₁ | —CH₂COOEt | 2-F | H | H |
| 2-1563 | H | Tez₁ | —CH₂COOEt | 2-F | 4-F | H |
| 2-1564 | Ac | Tez₁ | —CH₂COOEt | 2-F | 4-F | H |
| 2-1565 | H | Tez₁ | —(CH₂)₂COOEt | 2-F | H | H |
| 2-1566 | Ac | Tez₁ | —(CH₂)₂COOEt | 2-F | H | H |
| 2-1567 | H | Tez₁ | —(CH₂)₂COOEt | 2-F | 4-F | H |
| 2-1568 | Ac | Tez₁ | —(CH₂)₂COOEt | 2-F | 4-F | H |
| 2-1569 | H | Tez₁ | —(CH₂)₃COOEt | 2-F | H | H |
| 2-1570 | Ac | Tez₁ | —(CH₂)₃COOEt | 2-F | H | H |
| 2-1571 | H | Tez₁ | —(CH₂)₃COOEt | 2-F | 4-F | H |
| 2-1572 | Ac | Tez₁ | —(CH₂)₃COOEt | 2-F | 4-F | H |
| 2-1573 | H | Tez₁ | —(CH₂)₄COOEt | 2-F | H | H |
| 2-1574 | Ac | Tez₁ | —(CH₂)₄COOEt | 2-F | H | H |
| 2-1575 | H | Tez₁ | —(CH₂)₄COOEt | 2-F | 4-F | H |
| 2-1576 | Ac | Tez₁ | —(CH₂)₄COOEt | 2-F | 4-F | H |
| 2-1577 | H | Tez₁ | —CH₂CONHOH | 2-F | H | H |
| 2-1578 | Ac | Tez₁ | —CH₂CONHOH | 2-F | H | H |
| 2-1579 | H | Tez₁ | —CH₂CONHOH | 2-F | 4-F | H |
| 2-1580 | Ac | Tez₁ | —CH₂CONHOH | 2-F | 4-F | H |
| 2-1581 | H | Tez₁ | —(CH₂)₂CONHOH | 2-F | H | H |
| 2-1582 | Ac | Tez₁ | —(CH₂)₂CONHOH | 2-F | H | H |
| 2-1583 | H | Tez₁ | —(CH₂)₂CONHOH | 2-F | 4-F | H |
| 2-1584 | Ac | Tez₁ | —(CH₂)₂CONHOH | 2-F | 4-F | H |
| 2-1585 | H | Tez₁ | —(CH₂)₃CONHOH | 2-F | H | H |
| 2-1586 | Ac | Tez₁ | —(CH₂)₃CONHOH | 2-F | H | H |
| 2-1587 | H | Tez₁ | —(CH₂)₃CONHOH | 2-F | 4-F | H |
| 2-1588 | Ac | Tez₁ | —(CH₂)₃CONHOH | 2-F | 4-F | H |
| 2-1589 | H | Tez₁ | —(CH₂)₄CONHOH | 2-F | H | H |
| 2-1590 | Ac | Tez₁ | —(CH₂)₄CONHOH | 2-F | H | H |
| 2-1591 | H | Tez₁ | —(CH₂)₄CONHOH | 2-F | 4-F | H |
| 2-1592 | Ac | Tez₁ | —(CH₂)₄CONHOH | 2-F | 4-F | H |
| 2-1593 | H | Tez₂ | —CH₂COOH | 2-F | H | H |
| 2-1594 | Ac | Tez₂ | —CH₂COOH | 2-F | H | H |
| 2-1595 | H | Tez₂ | —CH₂COOH | 2-F | 4-F | H |
| 2-1596 | Ac | Tez₂ | —CH₂COOH | 2-F | 4-F | H |
| 2-1597 | H | Tez₂ | —(CH₂)₂COOH | 2-F | H | H |
| 2-1598 | Ac | Tez₂ | —(CH₂)₂COOH | 2-F | H | H |
| 2-1599 | H | Tez₂ | —(CH₂)₂COOH | 2-F | 4-F | H |
| 2-1600 | Ac | Tez₂ | —(CH₂)₂COOH | 2-F | 4-F | H |
| 2-1601 | H | Tez₂ | —(CH₂)₃COOH | 2-F | H | H |
| 2-1602 | Ac | Tez₂ | —(CH₂)₃COOH | 2-F | H | H |
| 2-1603 | H | Tez₂ | —(CH₂)₃COOH | 2-F | 4-F | H |
| 2-1604 | Ac | Tez₂ | —(CH₂)₃COOH | 2-F | 4-F | H |
| 2-1605 | H | Tez₂ | —(CH₂)₄COOH | 2-F | H | H |
| 2-1606 | Ac | Tez₂ | —(CH₂)₄COOH | 2-F | H | H |
| 2-1607 | H | Tez₂ | —(CH₂)₄COOH | 2-F | 4-F | H |
| 2-1608 | Ac | Tez₂ | —(CH₂)₄COOH | 2-F | 4-F | H |
| 2-1609 | H | Tez₂ | —CH₂COOMe | 2-F | H | H |
| 2-1610 | Ac | Tez₂ | —CH₂COOMe | 2-F | H | H |
| 2-1611 | H | Tez₂ | —CH₂COOMe | 2-F | 4-F | H |
| 2-1612 | Ac | Tez₂ | —CH₂COOMe | 2-F | 4-F | H |
| 2-1613 | H | Tez₂ | —(CH₂)₂COOMe | 2-F | H | H |
| 2-1614 | Ac | Tez₂ | —(CH₂)₂COOMe | 2-F | H | H |
| 2-1615 | H | Tez₂ | —(CH₂)₂COOMe | 2-F | 4-F | H |
| 2-1616 | Ac | Tez₂ | —(CH₂)₂COOMe | 2-F | 4-F | H |
| 2-1617 | H | Tez₂ | —(CH₂)₃COOMe | 2-F | H | H |
| 2-1618 | Ac | Tez₂ | —(CH₂)₃COOMe | 2-F | H | H |
| 2-1619 | H | Tez₂ | —(CH₂)₃COOMe | 2-F | 4-F | H |
| 2-1620 | Ac | Tez₂ | —(CH₂)₃COOMe | 2-F | 4-F | H |
| 2-1621 | H | Tez₂ | —(CH₂)₄COOMe | 2-F | H | H |
| 2-1622 | Ac | Tez₂ | —(CH₂)₄COOMe | 2-F | H | H |
| 2-1623 | H | Tez₂ | —(CH₂)₄COOMe | 2-F | 4-F | H |
| 2-1624 | Ac | Tez₂ | —(CH₂)₄COOMe | 2-F | 4-F | H |
| 2-1625 | H | Tez₂ | —CH₂COOEt | 2-F | H | H |
| 2-1626 | Ac | Tez₂ | —CH₂COOEt | 2-F | H | H |

TABLE 2-continued

| | | | | | | |
|---|---|---|---|---|---|---|
| 2-1627 | H | Tez$_2$ | —CH$_2$COOEt | 2-F | H | H |
| 2-1628 | Ac | Tez$_2$ | —CH$_2$COOEt | 2-F | H | H |
| 2-1629 | H | Tez$_2$ | —(CH$_2$)$_2$COOEt | 2-F | H | H |
| 2-1630 | Ac | Tez$_2$ | —(CH$_2$)$_2$COOEt | 2-F | H | H |
| 2-1631 | H | Tez$_2$ | —(CH$_2$)$_2$COOEt | 2-F | 4-F | H |
| 2-1632 | Ac | Tez$_2$ | —(CH$_2$)$_2$COOEt | 2-F | 4-F | H |
| 2-1633 | H | Tez$_2$ | —(CH$_2$)$_3$COOEt | 2-F | H | H |
| 2-1634 | Ac | Tez$_2$ | —(CH$_2$)$_3$COOEt | 2-F | H | H |
| 2-1635 | H | Tez$_2$ | —(CH$_2$)$_3$COOEt | 2-F | 4-F | H |
| 2-1636 | Ac | Tez$_2$ | —(CH$_2$)$_3$COOEt | 2-F | 4-F | H |
| 2-1637 | H | Tez$_2$ | —(CH$_2$)$_4$COOEt | 2-F | H | H |
| 2-1638 | Ac | Tez$_2$ | —(CH$_2$)$_4$COOEt | 2-F | H | H |
| 2-1639 | H | Tez$_2$ | —(CH$_2$)$_4$COOEt | 2-F | 4-F | H |
| 2-1640 | Ac | Tez$_2$ | —(CH$_2$)$_4$COOEt | 2-F | 4-F | H |
| 2-1641 | H | Tez$_2$ | —CH$_2$CONHOH | 2-F | H | H |
| 2-1642 | Ac | Tez$_2$ | —CH$_2$CONHOH | 2-F | H | H |
| 2-1643 | H | Tez$_2$ | —CH$_2$CONHOH | 2-F | 4-F | H |
| 2-1644 | Ac | Tez$_2$ | —CH$_2$CONHOH | 2-F | 4-F | H |
| 2-1645 | H | Tez$_2$ | —(CH$_2$)$_2$CONHOH | 2-F | H | H |
| 2-1646 | Ac | Tez$_2$ | —(CH$_2$)$_2$CONHOH | 2-F | H | H |
| 2-1647 | H | Tez$_2$ | —(CH$_2$)$_2$CONHOH | 2-F | 4-F | H |
| 2-1648 | Ac | Tez$_2$ | —(CH$_2$)$_2$CONHOH | 2-F | 4-F | H |
| 2-1649 | H | Tez$_2$ | —(CH$_2$)$_3$CONHOH | 2-F | H | H |
| 2-1650 | Ac | Tez$_2$ | —(CH$_2$)$_3$CONHOH | 2-F | H | H |
| 2-1651 | H | Tez$_2$ | —(CH$_2$)$_3$CONHOH | 2-F | 4-F | H |
| 2-1652 | Ac | Tez$_2$ | —(CH$_2$)$_3$CONHOH | 2-F | 4-F | H |
| 2-1653 | H | Tez$_2$ | —(CH$_2$)$_4$CONHOH | 2-F | H | H |
| 2-1654 | Ac | Tez$_2$ | —(CH$_2$)$_4$CONHOH | 2-F | H | H |
| 2-1655 | H | Tez$_2$ | —(CH$_2$)$_4$CONHOH | 2-F | 4-F | H |
| 2-1656 | Ac | Tez$_2$ | —(CH$_2$)$_4$CONHOH | 2-F | 4-F | H |
| 2-1657 | H | 3-Pyza | —CH$_2$NH$_2$ | 2-F | H | H |
| 2-1658 | Ac | 3-Pyza | —CH$_2$NH$_2$ | 2-F | H | H |
| 2-1659 | H | 3-Pyza | —CH$_2$NH$_2$ | 2-F | 4-F | H |
| 2-1660 | Ac | 3-Pyza | —CH$_2$NH$_2$ | 2-F | 4-F | H |
| 2-1661 | H | 3-Pyza | —(CH$_2$)$_2$NH$_2$ | 2-F | H | H |
| 2-1662 | Ac | 3-Pyza | —(CH$_2$)$_2$NH$_2$ | 2-F | H | H |
| 2-1663 | H | 3-Pyza | —(CH$_2$)$_2$NH$_2$ | 2-F | 4-F | H |
| 2-1664 | Ac | 3-Pyza | —(CH$_2$)$_2$NH$_2$ | 2-F | 4-F | H |
| 2-1665 | H | 3-Pyza | —CH$_2$CONHOMe | 2-F | H | H |
| 2-1666 | Ac | 3-Pyza | —CH$_2$CONHOMe | 2-F | H | H |
| 2-1667 | H | 3-Pyza | —CH$_2$CONHOMe | 2-F | 4-F | H |
| 2-1668 | Ac | 3-Pyza | —CH$_2$CONHOMe | 2-F | 4-F | H |
| 2-1669 | H | 3-Pyza | —(CH$_2$)$_2$CONHOMe | 2-F | H | H |
| 2-1670 | Ac | 3-Pyza | —(CH$_2$)$_2$CONHOMe | 2-F | H | H |
| 2-1671 | H | 3-Pyza | —(CH$_2$)$_2$CONHOMe | 2-F | 4-F | H |
| 2-1672 | Ac | 3-Pyza | —(CH$_2$)$_2$CONHOMe | 2-F | 4-F | H |
| 2-1673 | H | 3-Pyza | —CH$_2$-Tez | 2-F | H | H |
| 2-1674 | Ac | 3-Pyza | —CH$_2$-Tez | 2-F | H | H |
| 2-1675 | H | 3-Pyza | —CH$_2$-Tez | 2-F | 4-F | H |
| 2-1676 | Ac | 3-Pyza | —CH$_2$-Tez | 2-F | 4-F | H |
| 2-1677 | H | 3-Pyza | —CH$_2$-2-Pyr | 2-F | H | H |
| 2-1678 | Ac | 3-Pyza | —CH$_2$-2-Pyr | 2-F | H | H |
| 2-1679 | H | 3-Pyza | —CH$_2$-2-Pyr | 2-F | 4-F | H |
| 2-1680 | Ac | 3-Pyza | —CH$_2$-2-Pyr | 2-F | 4-F | H |
| 2-1681 | H | 4-αTriz | —CH$_2$CONHOMe | 2-F | H | H |
| 2-1682 | Ac | 4-αTriz | —CH$_2$CONHOMe | 2-F | H | H |
| 2-1683 | H | 4-αTriz | —CH$_2$CONHOMe | 2-F | 4-F | H |
| 2-1684 | Ac | 4-αTriz | —CH$_2$CONHOMe | 2-F | 4-F | H |
| 2-1685 | H | 4-αTriz | —(CH$_2$)$_2$CONHOMe | 2-F | H | H |
| 2-1686 | Ac | 4-αTriz | —(CH$_2$)$_2$CONHOMe | 2-F | H | H |
| 2-1687 | H | 4-αTriz | —(CH$_2$)$_2$CONHOMe | 2-F | 4-F | H |
| 2-1688 | Ac | 4-αTriz | —(CH$_2$)$_2$CONHOMe | 2-F | 4-F | H |
| 2-1689 | H | 4-αTriz | —(CH$_2$)$_3$CONHOMe | 2-F | H | H |
| 2-1690 | Ac | 4-αTriz | —(CH$_2$)$_3$CONHOMe | 2-F | H | H |
| 2-1691 | H | 4-αTriz | —(CH$_2$)$_3$CONHOMe | 2-F | 4-F | H |
| 2-1692 | Ac | 4-αTriz | —(CH$_2$)$_3$CONHOMe | 2-F | 4-F | H |
| 2-1693 | H | 4-αTriz | —(CH$_2$)$_4$CONHOMe | 2-F | H | H |
| 2-1694 | Ac | 4-αTriz | —(CH$_2$)$_4$CONHOMe | 2-F | H | H |
| 2-1695 | H | 4-αTriz | —(CH$_2$)$_4$CONHOMe | 2-F | 4-F | H |
| 2-1696 | Ac | 4-αTriz | —(CH$_2$)$_4$CONHOMe | 2-F | 4-F | H |
| 2-1697 | H | 4-αTriz | —CH$_2$CONHOEt | 2-F | H | H |
| 2-1698 | Ac | 4-αTriz | —CH$_2$CONHOEt | 2-F | H | H |
| 2-1699 | H | 4-αTriz | —CH$_2$CONHOEt | 2-F | 4-F | H |
| 2-1700 | Ac | 4-αTriz | —CH$_2$CONHOEt | 2-F | 4-F | H |
| 2-1701 | H | 4-αTriz | —(CH$_2$)$_2$CONHOEt | 2-F | H | H |
| 2-1702 | Ac | 4-αTriz | —(CH$_2$)$_2$CONHOEt | 2-F | H | H |
| 2-1703 | H | 4-αTriz | —(CH$_2$)$_2$CONHOEt | 2-F | 4-F | H |
| 2-1704 | Ac | 4-αTriz | —(CH$_2$)$_2$CONHOEt | 2-F | 4-F | H |
| 2-1705 | H | 4-αTriz | —(CH$_2$)$_3$CONHOEt | 2-F | H | H |
| 2-1706 | Ac | 4-αTriz | —(CH$_2$)$_3$CONHOEt | 2-F | H | H |
| 2-1707 | H | 4-αTriz | —(CH$_2$)$_3$CONHOEt | 2-F | 4-F | H |
| 2-1708 | Ac | 4-αTriz | —(CH$_2$)$_3$CONHOEt | 2-F | 4-F | H |
| 2-1709 | H | 5-αTriz | —CH$_2$CONHOMe | 2-F | H | H |
| 2-1710 | Ac | 5-αTriz | —CH$_2$CONHOMe | 2-F | H | H |
| 2-1711 | H | 5-αTriz | —CH$_2$CONHOMe | 2-F | 4-F | H |
| 2-1712 | Ac | 5-αTriz | —CH$_2$CONHOMe | 2-F | 4-F | H |
| 2-1713 | H | 5-αTriz | —(CH$_2$)$_2$CONHOMe | 2-F | H | H |
| 2-1714 | Ac | 5-αTriz | —(CH$_2$)$_2$CONHOMe | 2-F | H | H |
| 2-1715 | H | 5-αTriz | —(CH$_2$)$_2$CONHOMe | 2-F | 4-F | H |
| 2-1716 | Ac | 5-αTriz | —(CH$_2$)$_2$CONHOMe | 2-F | 4-F | H |
| 2-1717 | H | 5-αTriz | —(CH$_2$)$_3$CONHOMe | 2-F | H | H |
| 2-1718 | Ac | 5-αTriz | —(CH$_2$)$_3$CONHOMe | 2-F | H | H |
| 2-1719 | H | 5-αTriz | —(CH$_2$)$_3$CONHOMe | 2-F | 4-F | H |
| 2-1720 | Ac | 5-αTriz | —(CH$_2$)$_3$CONHOMe | 2-F | 4-F | H |
| 2-1721 | H | 5-αTriz | —(CH$_2$)$_4$CONHOMe | 2-F | H | H |
| 2-1722 | Ac | 5-αTriz | —(CH$_2$)$_4$CONHOMe | 2-F | H | H |
| 2-1723 | H | 5-αTriz | —(CH$_2$)$_4$CONHOMe | 2-F | 4-F | H |
| 2-1724 | Ac | 5-αTriz | —(CH$_2$)$_4$CONHOMe | 2-F | 4-F | H |
| 2-1725 | H | 3-Pyza | H | 2-Cl | H | H |
| 2-1726 | Ac | 3-Pyza | H | 2-Cl | H | H |
| 2-1727 | H | 3-Pyza | Ac | 2-Cl | H | H |
| 2-1728 | Ac | 3-Pyza | Ac | 2-Cl | H | H |
| 2-1729 | H | 3-Pyza | —CH$_2$COOH | 2-Cl | H | H |
| 2-1730 | Ac | 3-Pyza | —CH$_2$COOH | 2-Cl | H | H |
| 2-1731 | H | 3-Pyza | —(CH$_2$)$_2$COOH | 2-Cl | H | H |
| 2-1732 | Ac | 3-Pyza | —(CH$_2$)$_2$COOH | 2-Cl | H | H |
| 2-1733 | H | 3-Pyza | —(CH$_2$)$_3$COOH | 2-Cl | H | H |
| 2-1734 | Ac | 3-Pyza | —(CH$_2$)$_3$COOH | 2-Cl | H | H |
| 2-1735 | H | 3-Pyza | —(CH$_2$)$_4$COOH | 2-Cl | H | H |
| 2-1736 | Ac | 3-Pyza | —(CH$_2$)$_4$COOH | 2-Cl | H | H |
| 2-1737 | H | 3-Pyza | —CH$_2$COOMe | 2-Cl | H | H |
| 2-1738 | Ac | 3-Pyza | —CH$_2$COOMe | 2-Cl | H | H |
| 2-1739 | H | 3-Pyza | —(CH$_2$)$_2$COOMe | 2-Cl | H | H |
| 2-1740 | Ac | 3-Pyza | —(CH$_2$)$_2$COOMe | 2-Cl | H | H |
| 2-1741 | H | 3-Pyza | —CH$_2$COOEt | 2-Cl | H | H |
| 2-1742 | Ac | 3-Pyza | —CH$_2$COOEt | 2-Cl | H | H |
| 2-1743 | H | 3-Pyza | —(CH$_2$)$_2$COOEt | 2-Cl | H | H |
| 2-1744 | Ac | 3-Pyza | —(CH$_2$)$_2$COOEt | 2-Cl | H | H |
| 2-1745 | H | 4-Pyza | —CH$_2$COOH | 2-Cl | H | H |
| 2-1746 | Ac | 4-Pyza | —CH$_2$COOH | 2-Cl | H | H |
| 2-1747 | H | 4-Pyza | —(CH$_2$)$_2$COOH | 2-Cl | H | H |
| 2-1748 | Ac | 4-Pyza | —(CH$_2$)$_2$COOH | 2-Cl | H | H |
| 2-1749 | H | 4-Pyza | —(CH$_2$)$_3$COOH | 2-Cl | H | H |
| 2-1750 | Ac | 4-Pyza | —(CH$_2$)$_3$COOH | 2-Cl | H | H |
| 2-1751 | H | 4-Pyza | —(CH$_2$)$_4$COOH | 2-Cl | H | H |
| 2-1752 | Ac | 4-Pyza | —(CH$_2$)$_4$COOH | 2-Cl | H | H |
| 2-1753 | H | 5-Pyza | —CH$_2$COOMe | 2-Cl | H | H |
| 2-1754 | Ac | 5-Pyza | —CH$_2$COOMe | 2-Cl | H | H |
| 2-1755 | H | 5-Pyza | —(CH$_2$)$_2$COOMe | 2-Cl | H | H |
| 2-1756 | Ac | 5-Pyza | —(CH$_2$)$_2$COOMe | 2-Cl | H | H |
| 2-1757 | H | 5-Pyza | —CH$_2$COOEt | 2-Cl | H | H |
| 2-1758 | Ac | 5-Pyza | —CH$_2$COOEt | 2-Cl | H | H |
| 2-1759 | H | 5-Pyza | —(CH$_2$)$_2$COOEt | 2-Cl | H | H |
| 2-1760 | Ac | 5-Pyza | —(CH$_2$)$_2$COOEt | 2-Cl | H | H |
| 2-1761 | H | 5-Pyza | —CH$_2$COOH | 2-Cl | H | H |
| 2-1762 | Ac | 5-Pyza | —CH$_2$COOH | 2-Cl | H | H |
| 2-1763 | H | 5-Pyza | —(CH$_2$)$_2$COOH | 2-Cl | H | H |
| 2-1764 | Ac | 5-Pyza | —(CH$_2$)$_2$COOH | 2-Cl | H | H |
| 2-1765 | H | 5-Pyza | —(CH$_2$)$_3$COOH | 2-Cl | H | H |
| 2-1766 | Ac | 5-Pyza | —(CH$_2$)$_3$COOH | 2-Cl | H | H |
| 2-1767 | H | 5-Pyza | —(CH$_2$)$_4$COOH | 2-Cl | H | H |
| 2-1768 | Ac | 5-Pyza | —(CH$_2$)$_4$COOH | 2-Cl | H | H |
| 2-1769 | H | 4-αTriz | H | 2-Cl | H | H |
| 2-1770 | Ac | 4-αTriz | H | 2-Cl | H | H |
| 2-1771 | H | 4-αTriz | Ac | 2-Cl | H | H |
| 2-1772 | Ac | 4-αTriz | Ac | 2-Cl | H | H |
| 2-1773 | H | 4-αTriz | —CH$_2$COOH | 2-Cl | H | H |
| 2-1774 | Ac | 4-αTriz | —CH$_2$COOH | 2-Cl | H | H |
| 2-1775 | H | 4-αTriz | —(CH$_2$)$_2$COOH | 2-Cl | H | H |
| 2-1776 | Ac | 4-αTriz | —(CH$_2$)$_2$COOH | 2-Cl | H | H |
| 2-1777 | H | 4-αTriz | —(CH$_2$)$_3$COOH | 2-Cl | H | H |
| 2-1778 | Ac | 4-αTriz | —(CH$_2$)$_3$COOH | 2-Cl | H | H |
| 2-1779 | H | 4-αTriz | —(CH$_2$)$_4$COOH | 2-Cl | H | H |
| 2-1780 | Ac | 4-αTriz | —(CH$_2$)$_4$COOH | 2-Cl | H | H |
| 2-1781 | H | 4-αTriz | —CH$_2$COOMe | 2-Cl | H | H |
| 2-1782 | Ac | 4-αTriz | —CH$_2$COOMe | 2-Cl | H | H |
| 2-1783 | H | 4-αTriz | —(CH$_2$)$_2$COOMe | 2-Cl | H | H |
| 2-1784 | Ac | 4-αTriz | —(CH$_2$)$_2$COOMe | 2-Cl | H | H |

TABLE 2-continued

| | | | | | | |
|---|---|---|---|---|---|---|
| 2-1785 | H | 4-αTriz | —(CH$_2$)$_3$COOMe | 2-Cl | H | H |
| 2-1786 | Ac | 4-αTriz | —(CH$_2$)$_3$COOMe | 2-Cl | H | H |
| 2-1787 | H | 4-αTriz | —(CH$_2$)$_4$COOMe | 2-Cl | H | H |
| 2-1788 | Ac | 4-αTriz | —(CH$_2$)$_4$COOMe | 2-Cl | H | H |
| 2-1789 | H | 4-αTriz | —CH$_2$COOEt | 2-Cl | H | H |
| 2-1790 | Ac | 4-αTriz | —CH$_2$COOEt | 2-Cl | H | H |
| 2-1791 | H | 4-αTriz | —(CH$_2$)$_2$COOEt | 2-Cl | H | H |
| 2-1792 | Ac | 4-αTriz | —(CH$_2$)$_2$COOEt | 2-Cl | H | H |
| 2-1793 | H | 4-αTriz | —(CH$_2$)$_3$COOEt | 2-Cl | H | H |
| 2-1794 | Ac | 4-αTriz | —(CH$_2$)$_3$COOEt | 2-Cl | H | H |
| 2-1795 | H | 4-αTriz | —(CH$_2$)$_4$COOEt | 2-Cl | H | H |
| 2-1796 | Ac | 4-αTriz | —(CH$_2$)$_4$COOEt | 2-Cl | H | H |
| 2-1797 | H | 5-αTriz | Ac | 2-Cl | H | H |
| 2-1798 | Ac | 5-αTriz | Ac | 2-Cl | H | H |
| 2-1799 | H | 5-αTriz | —CH$_2$COOH | 2-Cl | H | H |
| 2-1800 | Ac | 5-αTriz | —CH$_2$COOH | 2-Cl | H | H |
| 2-1801 | H | 5-αTriz | —(CH$_2$)$_2$COOH | 2-Cl | H | H |
| 2-1802 | Ac | 5-αTriz | —(CH$_2$)$_2$COOH | 2-Cl | H | H |
| 2-1803 | H | 5-αTriz | —(CH$_2$)$_3$COOH | 2-Cl | H | H |
| 2-1804 | Ac | 5-αTriz | —(CH$_2$)$_3$COOH | 2-Cl | H | H |
| 2-1805 | H | 5-αTriz | —(CH$_2$)$_4$COOH | 2-Cl | H | H |
| 2-1806 | Ac | 5-αTriz | —(CH$_2$)$_4$COOH | 2-Cl | H | H |
| 2-1807 | H | 5-αTriz | —CH$_2$COOMe | 2-Cl | H | H |
| 2-1808 | Ac | 5-αTriz | —CH$_2$COOMe | 2-Cl | H | H |
| 2-1809 | H | 5-αTriz | —(CH$_2$)$_2$COOMe | 2-Cl | H | H |
| 2-1810 | Ac | 5-αTriz | —(CH$_2$)$_2$COOMe | 2-Cl | H | H |
| 2-1811 | H | 5-αTriz | —(CH$_2$)$_3$COOMe | 2-Cl | H | H |
| 2-1812 | Ac | 5-αTriz | —(CH$_2$)$_3$COOMe | 2-Cl | H | H |
| 2-1813 | H | 5-αTriz | —(CH$_2$)$_4$COOMe | 2-Cl | H | H |
| 2-1814 | Ac | 5-αTriz | —(CH$_2$)$_4$COOMe | 2-Cl | H | H |
| 2-1815 | H | 5-αTriz | —CH$_2$COOEt | 2-Cl | H | H |
| 2-1816 | Ac | 5-αTriz | —CH$_2$COOEt | 2-Cl | H | H |
| 2-1817 | H | 5-αTriz | —(CH$_2$)$_2$COOEt | 2-Cl | H | H |
| 2-1818 | Ac | 5-αTriz | —(CH$_2$)$_2$COOEt | 2-Cl | H | H |
| 2-1819 | H | 5-αTriz | —(CH$_2$)$_3$COOEt | 2-Cl | H | H |
| 2-1820 | Ac | 5-αTriz | —(CH$_2$)$_3$COOEt | 2-Cl | H | H |
| 2-1821 | H | 5-αTriz | —(CH$_2$)$_4$COOEt | 2-Cl | H | H |
| 2-1822 | Ac | 5-αTriz | —(CH$_2$)$_4$COOEt | 2-Cl | H | H |
| 2-1823 | H | Tez$_1$ | —CH$_2$COOH | 2-Cl | H | H |
| 2-1824 | Ac | Tez$_1$ | —CH$_2$COOH | 2-Cl | H | H |
| 2-1825 | H | Tez$_1$ | —(CH$_2$)$_2$COOH | 2-Cl | H | H |
| 2-1826 | Ac | Tez$_1$ | —(CH$_2$)$_2$COOH | 2-Cl | H | H |
| 2-1827 | H | Tez$_1$ | —(CH$_2$)$_3$COOH | 2-Cl | H | H |
| 2-1828 | Ac | Tez$_1$ | —(CH$_2$)$_3$COOH | 2-Cl | H | H |
| 2-1829 | H | Tez$_1$ | —(CH$_2$)$_4$COOH | 2-Cl | H | H |
| 2-1830 | Ac | Tez$_1$ | —(CH$_2$)$_4$COOH | 2-Cl | H | H |
| 2-1831 | H | Tez$_2$ | —(CH$_2$)$_4$COOH | 2-Cl | H | H |
| 2-1832 | Ac | Tez$_2$ | —(CH$_2$)$_4$COOH | 2-Cl | H | H |
| 2-1833 | H | Tez$_2$ | —(CH$_2$)$_2$COOH | 2-Cl | H | H |
| 2-1834 | Ac | Tez$_2$ | —(CH$_2$)$_2$COOH | 2-Cl | H | H |
| 2-1835 | H | Tez$_2$ | —(CH$_2$)$_3$COOH | 2-Cl | H | H |
| 2-1836 | Ac | Tez$_2$ | —(CH$_2$)$_3$COOH | 2-Cl | H | H |
| 2-1837 | H | Tez$_2$ | —(CH$_2$)$_4$COOH | 2-Cl | H | H |
| 2-1838 | Ac | Tez$_2$ | —(CH$_2$)$_4$COOH | 2-Cl | H | H |

TABLE 3

| Compd. No. | R$^1$ | R$^2$ | R$^3$ | X$^1$ | X$^2$ | X$^3$ |
|---|---|---|---|---|---|---|
| 3-1 | cPn | H | 3-Pyza | 2-F | H | H |
| 3-2 | cPn | Ac | 3-Pyza | 2-F | H | H |
| 3-3 | cPn | H | 2-Thiz | 2-F | H | H |
| 3-4 | cPn | Ac | 2-Thiz | 2-F | H | H |
| 3-5 | cHx | H | 3-Pyza | 2-F | H | H |
| 3-6 | cHx | Ac | 3-Pyza | 2-F | H | H |
| 3-7 | cHx | H | 2-Thiz | 2-F | H | H |

TABLE 3-continued

| Compd. No. | R$^1$ | R$^2$ | R$^3$ | X$^1$ | X$^2$ | X$^3$ |
|---|---|---|---|---|---|---|
| 3-8 | cHx | Ac | 2-Thiz | 2-F | H | H |
| 3-9 | OMe | H | 3-Pyza | 2-F | H | H |
| 3-10 | OMe | Ac | 3-Pyza | 2-F | H | H |
| 3-11 | OMe | H | 2-Thiz | 2-F | H | H |
| 3-12 | OMe | Ac | 2-Thiz | 2-F | H | H |
| 3-13 | OMe | H | 3-Pyza | 2-Cl | H | H |
| 3-14 | OMe | Ac | 3-Pyza | 2-Cl | H | H |

TABLE 4

| Compd. No. | R$^2$ | Htcy | R | X$^1$ | X$^2$ | X$^3$ |
|---|---|---|---|---|---|---|
| 4-1 | H | 3-Pyza | H | 2-F | H | H |
| 4-2 | Ac | 3-Pyza | H | 2-F | H | H |
| 4-3 | H | 3-Pyza | Ac | 2-F | H | H |
| 4-4 | Ac | 3-Pyza | Ac | 2-F | H | H |
| 4-5 | H | 3-Pyza | —CH$_2$COOH | 2-F | H | H |
| 4-6 | Ac | 3-Pyza | —CH$_2$COOH | 2-F | H | H |
| 4-7 | H | 3-Pyza | —(CH$_2$)$_2$COOH | 2-F | H | H |
| 4-8 | Ac | 3-Pyza | —(CH$_2$)$_2$COOH | 2-F | H | H |
| 4-9 | H | 3-Pyza | —CH$_2$COOMe | 2-F | H | H |

TABLE 4-continued

| | | | | | | |
|---|---|---|---|---|---|---|
| 4-10 | Ac | 3-Pyza | —CH₂COOMe | 2-F | H | H |
| 4-11 | H | 3-Pyza | —(CH₂)₂COOMe | 2-F | H | H |
| 4-12 | Ac | 3-Pyza | —(CH₂)₂COOMe | 2-F | H | H |
| 4-13 | H | 3-Pyza | —CH₂COOEt | 2-F | H | H |
| 4-14 | Ac | 3-Pyza | —CH₂COOEt | 2-F | H | H |
| 4-15 | H | 3-Pyza | —(CH₂)₂COOEt | 2-F | H | H |
| 4-16 | Ac | 3-Pyza | —(CH₂)₂COOEt | 2-F | H | H |
| 4-17 | H | 4-Pyza | H | 2-F | H | H |
| 4-18 | Ac | 4-Pyza | H | 2-F | H | H |
| 4-19 | H | 4-Pyza | Ac | 2-F | H | H |
| 4-20 | Ac | 4-Pyza | Ac | 2-F | H | H |
| 4-21 | H | 4-Pyza | —CH₂COOH | 2-F | H | H |
| 4-22 | Ac | 4-Pyza | —CH₂COOH | 2-F | H | H |
| 4-23 | H | 4-Pyza | —(CH₂)₂COOH | 2-F | H | H |
| 4-24 | Ac | 4-Pyza | —(CH₂)₂COOH | 2-F | H | H |
| 4-25 | H | 4-Pyza | —CH₂COOMe | 2-F | H | H |
| 4-26 | Ac | 4-Pyza | —CH₂COOMe | 2-F | H | H |
| 4-27 | H | 4-Pyza | —(CH₂)₂COOMe | 2-F | H | H |
| 4-28 | Ac | 4-Pyza | —(CH₂)₂COOMe | 2-F | H | H |
| 4-29 | H | 4-Pyza | —CH₂COOEt | 2-F | H | H |
| 4-30 | Ac | 4-Pyza | —CH₂COOEt | 2-F | H | H |
| 4-31 | H | 4-Pyza | —(CH₂)₂COOEt | 2-F | H | H |
| 4-32 | Ac | 4-Pyza | —(CH₂)₂COOEt | 2-F | H | H |
| 4-33 | H | 5-Pyza | H | 2-F | H | H |
| 4-34 | Ac | 5-Pyza | H | 2-F | H | H |
| 4-35 | H | 5-Pyza | Ac | 2-F | H | H |
| 4-36 | Ac | 5-Pyza | Ac | 2-F | H | H |
| 4-37 | H | 5-Pyza | —CH₂COOH | 2-F | H | H |
| 4-38 | Ac | 5-Pyza | —CH₂COOH | 2-F | H | H |
| 4-39 | H | 5-Pyza | —(CH₂)₂COOH | 2-F | H | H |
| 4-40 | Ac | 5-Pyza | —(CH₂)₂COOH | 2-F | H | H |
| 4-41 | H | 5-Pyza | —CH₂COOMe | 2-F | H | H |
| 4-42 | Ac | 5-Pyza | —CH₂COOMe | 2-F | H | H |
| 4-43 | H | 5-Pyza | —(CH₂)₂COOMe | 2-F | H | H |
| 4-44 | Ac | 5-Pyza | —(CH₂)₂COOMe | 2-F | H | H |
| 4-45 | H | 5-Pyza | —CH₂COOEt | 2-F | H | H |
| 4-46 | Ac | 5-Pyza | —CH₂COOEt | 2-F | H | H |
| 4-47 | H | 5-Pyza | —(CH₂)₂COOEt | 2-F | H | H |
| 4-48 | Ac | 5-Pyza | —(CH₂)₂COOEt | 2-F | H | H |
| 4-49 | H | 2-Imid | H | 2-F | H | H |
| 4-50 | Ac | 2-Imid | H | 2-F | H | H |
| 4-51 | H | 2-Imid | —CH₂COOH | 2-F | H | H |
| 4-52 | Ac | 2-Imid | —CH₂COOH | 2-F | H | H |
| 4-53 | H | 2-Imid | —(CH₂)₂COOH | 2-F | H | H |
| 4-54 | Ac | 2-Imid | —(CH₂)₂COOH | 2-F | H | H |
| 4-55 | H | 2-Imid | —CH₂COOMe | 2-F | H | H |
| 4-56 | Ac | 2-Imid | —CH₂COOMe | 2-F | H | H |
| 4-57 | H | 2-Imid | —(CH₂)₂COOMe | 2-F | H | H |
| 4-58 | Ac | 2-Imid | —(CH₂)₂COOMe | 2-F | H | H |
| 4-59 | H | 2-Imid | —CH₂COOEt | 2-F | H | H |
| 4-60 | Ac | 2-Imid | —CH₂COOEt | 2-F | H | H |
| 4-61 | H | 2-Imid | —(CH₂)₂COOEt | 2-F | H | H |
| 4-62 | Ac | 2-Imid | —(CH₂)₂COOEt | 2-F | H | H |
| 4-63 | H | 4-Imid | H | 2-F | H | H |
| 4-64 | Ac | 4-Imid | H | 2-F | H | H |
| 4-65 | H | 4-Imid | —CH₂COOH | 2-F | H | H |
| 4-66 | Ac | 4-Imid | —CH₂COOH | 2-F | H | H |
| 4-67 | H | 4-Imid | —(CH₂)₂COOH | 2-F | H | H |
| 4-68 | Ac | 4-Imid | —(CH₂)₂COOH | 2-F | H | H |
| 4-69 | H | 4-Imid | —CH₂COOMe | 2-F | H | H |
| 4-70 | Ac | 4-Imid | —CH₂COOMe | 2-F | H | H |
| 4-71 | H | 4-Imid | —(CH₂)₂COOMe | 2-F | H | H |
| 4-72 | Ac | 4-Imid | —(CH₂)₂COOMe | 2-F | H | H |
| 4-73 | H | 4-Imid | —CH₂COOEt | 2-F | H | H |
| 4-74 | Ac | 4-Imid | —CH₂COOEt | 2-F | H | H |
| 4-75 | H | 4-Imid | —(CH₂)₂COOEt | 2-F | H | H |
| 4-76 | Ac | 4-Imid | —(CH₂)₂COOEt | 2-F | H | H |
| 4-77 | H | 5-Imid | H | 2-F | H | H |
| 4-78 | Ac | 5-Imid | H | 2-F | H | H |
| 4-79 | H | 5-Imid | —CH₂COOH | 2-F | H | H |
| 4-80 | Ac | 5-Imid | —CH₂COOH | 2-F | H | H |
| 4-81 | H | 5-Imid | —(CH₂)₂COOH | 2-F | H | H |
| 4-82 | Ac | 5-Imid | —(CH₂)₂COOH | 2-F | H | H |
| 4-83 | H | 5-Imid | —CH₂COOMe | 2-F | H | H |
| 4-84 | Ac | 5-Imid | —CH₂COOMe | 2-F | H | H |
| 4-85 | H | 5-Imid | —(CH₂)₂COOMe | 2-F | H | H |
| 4-86 | Ac | 5-Imid | —(CH₂)₂COOMe | 2-F | H | H |
| 4-87 | H | 5-Imid | —CH₂COOEt | 2-F | H | H |
| 4-88 | Ac | 5-Imid | —CH₂COOEt | 2-F | H | H |
| 4-89 | H | 5-Imid | —(CH₂)₂COOEt | 2-F | H | H |
| 4-90 | Ac | 5-Imid | —(CH₂)₂COOEt | 2-F | H | H |
| 4-91 | H | 4-αTriz | H | 2-F | H | H |
| 4-92 | Ac | 4-αTriz | H | 2-F | H | H |
| 4-93 | H | 4-αTriz | H | 2-F | 4-F | H |
| 4-94 | Ac | 4-αTriz | H | 2-F | 4-F | H |
| 4-95 | H | 4-αTriz | Ac | 2-F | H | H |
| 4-96 | Ac | 4-αTriz | Ac | 2-F | H | H |
| 4-97 | H | 4-αTriz | —CH₂COOH | 2-F | H | H |
| 4-98 | Ac | 4-αTriz | —CH₂COOH | 2-F | H | H |
| 4-99 | H | 4-αTriz | —CH₂COOH | 2-F | 4-F | H |
| 4-100 | Ac | 4-αTriz | —CH₂COOH | 2-F | 4-F | H |
| 4-101 | H | 4-αTriz | —(CH₂)₂COOH | 2-F | H | H |
| 4-102 | Ac | 4-αTriz | —(CH₂)₂COOH | 2-F | H | H |
| 4-103 | H | 4-αTriz | —(CH₂)₂COOH | 2-F | 4-F | H |
| 4-104 | Ac | 4-αTriz | —(CH₂)₂COOH | 2-F | 4-F | H |
| 4-105 | H | 4-αTriz | —CH₂COOMe | 2-F | H | H |
| 4-106 | Ac | 4-αTriz | —CH₂COOMe | 2-F | H | H |
| 4-107 | H | 4-αTriz | —CH₂COOMe | 2-F | 4-F | H |
| 4-108 | Ac | 4-αTriz | —CH₂COOMe | 2-F | 4-F | H |
| 4-109 | H | 4-αTriz | —(CH₂)₂COOMe | 2-F | H | H |
| 4-110 | Ac | 4-αTriz | —(CH₂)₂COOMe | 2-F | H | H |
| 4-111 | H | 4-αTriz | —(CH₂)₂COOMe | 2-F | 4-F | H |
| 4-112 | Ac | 4-αTriz | —(CH₂)₂COOMe | 2-F | 4-F | H |
| 4-113 | H | 4-αTriz | —CH₂COOEt | 2-F | H | H |
| 4-114 | Ac | 4-αTriz | —CH₂COOEt | 2-F | H | H |
| 4-115 | H | 4-αTriz | —CH₂COOEt | 2-F | 4-F | H |
| 4-116 | Ac | 4-αTriz | —CH₂COOEt | 2-F | 4-F | H |
| 4-117 | H | 4-αTriz | —(CH₂)₂COOEt | 2-F | H | H |
| 4-118 | Ac | 4-αTriz | —(CH₂)₂COOEt | 2-F | H | H |
| 4-119 | H | 4-αTriz | —(CH₂)₂COOEt | 2-F | 4-F | H |
| 4-120 | Ac | 4-αTriz | —(CH₂)₂COOEt | 2-F | 4-F | H |
| 4-121 | H | 4-αTriz | —CH₂CONHOH | 2-F | H | H |
| 4-122 | Ac | 4-αTriz | —CH₂CONHOH | 2-F | H | H |
| 4-123 | H | 4-αTriz | —(CH₂)₂CONHOH | 2-F | H | H |
| 4-124 | Ac | 4-αTriz | —(CH₂)₂CONHOH | 2-F | H | H |
| 4-125 | H | 4-αTriz | —CH₂CONHOMe | 2-F | H | H |
| 4-126 | Ac | 4-αTriz | —CH₂CONHOMe | 2-F | H | H |
| 4-127 | H | 4-αTriz | —(CH₂)₂CONHOMe | 2-F | H | H |
| 4-128 | Ac | 4-αTriz | —(CH₂)₂CONHOMe | 2-F | H | H |
| 4-129 | H | 5-αTriz | H | 2-F | H | H |
| 4-130 | Ac | 5-αTriz | H | 2-F | H | H |
| 4-131 | H | 5-αTriz | H | 2-F | 4-F | H |
| 4-132 | Ac | 5-αTriz | H | 2-F | 4-F | H |
| 4-133 | H | 5-αTriz | Ac | 2-F | H | H |
| 4-134 | Ac | 5-αTriz | Ac | 2-F | H | H |
| 4-135 | H | 5-αTriz | —CH₂COOH | 2-F | H | H |
| 4-136 | Ac | 5-αTriz | —CH₂COOH | 2-F | H | H |
| 4-137 | H | 5-αTriz | —CH₂COOH | 2-F | 4-F | H |
| 4-138 | Ac | 5-αTriz | —CH₂COOH | 2-F | 4-F | H |
| 4-139 | H | 5-αTriz | —(CH₂)₂COOH | 2-F | H | H |
| 4-140 | Ac | 5-αTriz | —(CH₂)₂COOH | 2-F | H | H |
| 4-141 | H | 5-αTriz | —(CH₂)₂COOH | 2-F | 4-F | H |
| 4-142 | Ac | 5-αTriz | —(CH₂)₂COOH | 2-F | 4-F | H |
| 4-143 | H | 5-αTriz | —CH₂COOMe | 2-F | H | H |
| 4-144 | Ac | 5-αTriz | —CH₂COOMe | 2-F | H | H |
| 4-145 | H | 5-αTriz | —CH₂COOMe | 2-F | 4-F | H |
| 4-146 | Ac | 5-αTriz | —CH₂COOMe | 2-F | 4-F | H |
| 4-147 | H | 5-αTriz | —(CH₂)₂COOMe | 2-F | H | H |
| 4-148 | Ac | 5-αTriz | —(CH₂)₂COOMe | 2-F | H | H |
| 4-149 | H | 5-αTriz | —(CH₂)₂COOMe | 2-F | 4-F | H |
| 4-150 | Ac | 5-αTriz | —(CH₂)₂COOMe | 2-F | 4-F | H |
| 4-151 | H | 5-αTriz | —CH₂COOEt | 2-F | H | H |
| 4-152 | Ac | 5-αTriz | —CH₂COOEt | 2-F | H | H |
| 4-153 | H | 5-αTriz | —CH₂COOEt | 2-F | 4-F | H |
| 4-154 | Ac | 5-αTriz | —CH₂COOEt | 2-F | 4-F | H |
| 4-155 | H | 5-αTriz | —(CH₂)₂COOEt | 2-F | H | H |
| 4-156 | Ac | 5-αTriz | —(CH₂)₂COOEt | 2-F | H | H |
| 4-157 | H | 5-αTriz | —(CH₂)₂COOEt | 2-F | 4-F | H |
| 4-158 | Ac | 5-αTriz | —(CH₂)₂COOEt | 2-F | 4-F | H |
| 4-159 | H | 5-αTriz | —CH₂CONHOH | 2-F | H | H |
| 4-160 | Ac | 5-αTriz | —CH₂CONHOH | 2-F | H | H |
| 4-161 | H | 5-αTriz | —(CH₂)₂CONHOH | 2-F | H | H |
| 4-162 | Ac | 5-αTriz | —(CH₂)₂CONHOH | 2-F | H | H |
| 4-163 | H | 5-αTriz | —(CH₂)₂CONHOH | 2-F | H | H |
| 4-164 | Ac | 5-αTriz | —(CH₂)₃CONHOH | 2-F | H | H |
| 4-165 | H | 5-αTriz | —CH₂CONHOMe | 2-F | H | H |
| 4-166 | Ac | 5-αTriz | —CH₂CONHOMe | 2-F | H | H |
| 4-167 | H | 5-αTriz | —(CH₂)₂CONHOMe | 2-F | H | H |

TABLE 4-continued

| Compd. No. | R² | Htcy | R | X¹ | X² | X³ |
|---|---|---|---|---|---|---|
| 4-168 | Ac | 5-αTriz | —(CH₂)₂CONHOMe | 2-F | H | H |
| 4-169 | H | Tez₁ | H | 2-F | H | H |
| 4-170 | Ac | Tez₁ | H | 2-F | H | H |
| 4-171 | H | Tez₁ | —CH₂COOH | 2-F | H | H |
| 4-172 | Ac | Tez₁ | —CH₂COOH | 2-F | H | H |
| 4-173 | H | Tez₁ | —(CH₂)₂COOH | 2-F | H | H |
| 4-174 | Ac | Tez₁ | —(CH₂)₂COOH | 2-F | H | H |
| 4-175 | H | Tez₁ | —CH₂COOMe | 2-F | H | H |
| 4-176 | Ac | Tez₁ | —CH₂COOMe | 2-F | H | H |
| 4-177 | H | Tez₁ | —(CH₂)₂COOMe | 2-F | H | H |
| 4-178 | Ac | Tez₁ | —(CH₂)₂COOMe | 2-F | H | H |
| 4-179 | H | Tez₁ | —CH₂COOEt | 2-F | H | H |
| 4-180 | Ac | Tez₁ | —CH₂COOEt | 2-F | H | H |
| 4-181 | H | Tez₁ | —(CH₂)₂COOEt | 2-F | H | H |
| 4-182 | Ac | Tez₁ | —(CH₂)₂COOEt | 2-F | H | H |
| 4-183 | H | Tez₂ | H | 2-F | H | H |
| 4-184 | Ac | Tez₂ | H | 2-F | H | H |
| 4-185 | H | Tez₂ | —CH₂COOH | 2-F | H | H |
| 4-186 | Ac | Tez₂ | —CH₂COOH | 2-F | H | H |
| 4-187 | H | Tez₂ | —(CH₂)₂COOH | 2-F | H | H |
| 4-188 | Ac | Tez₂ | —(CH₂)₂COOH | 2-F | H | H |
| 4-189 | H | Tez₂ | —CH₂COOMe | 2-F | H | H |
| 4-190 | Ac | Tez₂ | —CH₂COOMe | 2-F | H | H |
| 4-191 | H | Tez₂ | —(CH₂)₂COOMe | 2-F | H | H |
| 4-192 | Ac | Tez₂ | —(CH₂)₂COOMe | 2-F | H | H |
| 4-193 | H | Tez₂ | —CH₂COOEt | 2-F | H | H |
| 4-194 | Ac | Tez₂ | —CH₂COOEt | 2-F | H | H |
| 4-195 | H | Tez₂ | —(CH₂)₂COOEt | 2-F | H | H |
| 4-196 | Ac | Tez₂ | —(CH₂)₂COOEt | 2-F | H | H |

TABLE 5

[Structural diagrams showing general formula with Htcy, R, R¹, R²S, X¹, X², X³ substituents on a piperidine-phenyl scaffold, along with heterocycle definitions: 3-Pyza, 4-Pyza, 5-Pyza (pyrazoles), 4-αTriz, 5-αTriz (triazoles), Tez₂, Tez₁ (tetrazoles)]

| Compd. No. | R² | Htcy | R | X¹ | X² | X³ | R¹ |
|---|---|---|---|---|---|---|---|
| 5-1 | H | 3-Pyza | H | 2-F | H | H | —OMe |
| 5-2 | Ac | 3-Pyza | H | 2-F | H | H | —OMe |
| 5-3 | H | 3-Pyza | Ac | 2-F | H | H | —OMe |
| 5-4 | Ac | 3-Pyza | Ac | 2-F | H | H | —OMe |
| 5-5 | H | 3-Pyza | —CH₂COOH | 2-F | H | H | —OMe |
| 5-6 | Ac | 3-Pyza | —CH₂COOH | 2-F | H | H | —OMe |
| 5-7 | H | 3-Pyza | —(CH₂)₂COOH | 2-F | H | H | —OMe |
| 5-8 | Ac | 3-Pyza | —(CH₂)₂COOH | 2-F | H | H | —OMe |
| 5-9 | H | 3-Pyza | —(CH₂)₃COOH | 2-F | H | H | —OMe |
| 5-10 | Ac | 3-Pyza | —(CH₂)₃COOH | 2-F | H | H | —OMe |
| 5-11 | H | 3-Pyza | —(CH₂)₄COOH | 2-F | H | H | —OMe |
| 5-12 | Ac | 3-Pyza | —(CH₂)₄COOH | 2-F | H | H | —OMe |
| 5-13 | H | 3-Pyza | —CH₂COOMe | 2-F | H | H | —OMe |
| 5-14 | Ac | 3-Pyza | —CH₂COOMe | 2-F | H | H | —OMe |
| 5-15 | H | 3-Pyza | —(CH₂)₂COOMe | 2-F | H | H | —OMe |
| 5-16 | Ac | 3-Pyza | —(CH₂)₂COOMe | 2-F | H | H | —OMe |
| 5-17 | H | 3-Pyza | —CH₂COOEt | 2-F | H | H | —OMe |
| 5-18 | Ac | 3-Pyza | —CH₂COOEt | 2-F | H | H | —OMe |
| 5-19 | H | 3-Pyza | —(CH₂)₂COOEt | 2-F | H | H | —OMe |
| 5-20 | Ac | 3-Pyza | —(CH₂)₂COOEt | 2-F | H | H | —OMe |
| 5-21 | H | 4-Pyza | —CH₂COOH | 2-F | H | H | —OMe |
| 5-22 | Ac | 4-Pyza | —CH₂COOH | 2-F | H | H | —OMe |
| 5-23 | H | 4-Pyza | —(CH₂)₂COOH | 2-F | H | H | —OMe |
| 5-24 | Ac | 4-Pyza | —(CH₂)₂COOH | 2-F | H | H | —OMe |
| 5-25 | H | 4-Pyza | —(CH₂)₃COOH | 2-F | H | H | —OMe |
| 5-26 | Ac | 4-Pyza | —(CH₂)₃COOH | 2-F | H | H | —OMe |
| 5-27 | H | 4-Pyza | —(CH₂)₄COOH | 2-F | H | H | —OMe |
| 5-28 | Ac | 4-Pyza | —(CH₂)₄COOH | 2-F | H | H | —OMe |
| 5-29 | H | 5-Pyza | —CH₂COOH | 2-F | H | H | —OMe |
| 5-30 | Ac | 5-Pyza | —CH₂COOH | 2-F | H | H | —OMe |
| 5-31 | H | 5-Pyza | —(CH₂)₂COOH | 2-F | H | H | —OMe |
| 5-32 | Ac | 5-Pyza | —(CH₂)₂COOH | 2-F | H | H | —OMe |
| 5-33 | H | 5-Pyza | —(CH₂)₃COOH | 2-F | H | H | —OMe |
| 5-34 | Ac | 5-Pyza | —(CH₂)₃COOH | 2-F | H | H | —OMe |
| 5-35 | H | 5-Pyza | —(CH₂)₄COOH | 2-F | H | H | —OMe |
| 5-36 | Ac | 5-Pyza | —(CH₂)₄COOH | 2-F | H | H | —OMe |
| 5-37 | H | 4-αTriz | H | 2-F | H | H | —OMe |
| 5-38 | Ac | 4-αTriz | H | 2-F | H | H | —OMe |
| 5-39 | H | 4-αTriz | Ac | 2-F | H | H | —OMe |
| 5-40 | Ac | 4-αTriz | Ac | 2-F | H | H | —OMe |
| 5-41 | H | 4-αTriz | —CH₂COOH | 2-F | H | H | —OMe |
| 5-42 | Ac | 4-αTriz | —CH₂COOH | 2-F | H | H | —OMe |
| 5-43 | H | 4-αTriz | —(CH₂)₂COOH | 2-F | H | H | —OMe |
| 5-44 | Ac | 4-αTriz | —(CH₂)₂COOH | 2-F | H | H | —OMe |
| 5-45 | H | 4-αTriz | —(CH₂)₃COOH | 2-F | H | H | —OMe |
| 5-46 | Ac | 4-αTriz | —(CH₂)₃COOH | 2-F | H | H | —OMe |
| 5-47 | H | 4-αTriz | —(CH₂)₄COOH | 2-F | H | H | —OMe |
| 5-48 | Ac | 4-αTriz | —(CH₂)₄COOH | 2-F | H | H | —OMe |
| 5-49 | H | 4-αTriz | —CH₂COOMe | 2-F | H | H | —OMe |
| 5-50 | Ac | 4-αTriz | —CH₂COOMe | 2-F | H | H | —OMe |
| 5-51 | H | 4-αTriz | —(CH₂)₂COOMe | 2-F | H | H | —OMe |
| 5-52 | Ac | 4-αTriz | —(CH₂)₂COOMe | 2-F | H | H | —OMe |
| 5-53 | H | 4-αTriz | —(CH₂)₃COOMe | 2-F | H | H | —OMe |
| 5-54 | Ac | 4-αTriz | —(CH₂)₃COOMe | 2-F | H | H | —OMe |
| 5-55 | H | 4-αTriz | —(CH₂)₄COOMe | 2-F | H | H | —OMe |
| 5-56 | Ac | 4-αTriz | —(CH₂)₄COOMe | 2-F | H | H | —OMe |
| 5-57 | H | 4-αTriz | —CH₂COOEt | 2-F | H | H | —OMe |
| 5-58 | Ac | 4-αTriz | —CH₂COOEt | 2-F | H | H | —OMe |
| 5-59 | H | 4-αTriz | —(CH₂)₂COOEt | 2-F | H | H | —OMe |
| 5-60 | Ac | 4-αTriz | —(CH₂)₂COOEt | 2-F | H | H | —OMe |
| 5-61 | H | 4-αTriz | —(CH₂)₃COOEt | 2-F | H | H | —OMe |
| 5-62 | Ac | 4-αTriz | —(CH₂)₃COOEt | 2-F | H | H | —OMe |
| 5-63 | H | 4-αTriz | —(CH₂)₄COOEt | 2-F | H | H | —OMe |
| 5-64 | Ac | 4-αTriz | —(CH₂)₄COOEt | 2-F | H | H | —OMe |
| 5-65 | H | 5-αTriz | H | 2-F | H | H | —OMe |
| 5-66 | Ac | 5-αTriz | H | 2-F | H | H | —OMe |
| 5-67 | H | 5-αTriz | Ac | 2-F | H | H | —OMe |
| 5-68 | Ac | 5-αTriz | Ac | 2-F | H | H | —OMe |
| 5-69 | H | 5-αTriz | —CH₂COOH | 2-F | H | H | —OMe |
| 5-70 | Ac | 5-αTriz | —CH₂COOH | 2-F | H | H | —OMe |
| 5-71 | H | 5-αTriz | —(CH₂)₂COOH | 2-F | H | H | —OMe |
| 5-72 | Ac | 5-αTriz | —(CH₂)₂COOH | 2-F | H | H | —OMe |
| 5-73 | H | 5-αTriz | —(CH₂)₃COOH | 2-F | H | H | —OMe |
| 5-74 | Ac | 5-αTriz | —(CH₂)₃COOH | 2-F | H | H | —OMe |
| 5-75 | H | 5-αTriz | —(CH₂)₄COOH | 2-F | H | H | —OMe |
| 5-76 | Ac | 5-αTriz | —(CH₂)₄COOH | 2-F | H | H | —OMe |
| 5-77 | H | 5-αTriz | —CH₂COOMe | 2-F | H | H | —OMe |
| 5-78 | Ac | 5-αTriz | —CH₂COOMe | 2-F | H | H | —OMe |
| 5-79 | H | 5-αTriz | —(CH₂)₂COOMe | 2-F | H | H | —OMe |
| 5-80 | Ac | 5-αTriz | —(CH₂)₂COOMe | 2-F | H | H | —OMe |
| 5-81 | H | 5-αTriz | —(CH₂)₃COOMe | 2-F | H | H | —OMe |
| 5-82 | Ac | 5-αTriz | —(CH₂)₃COOMe | 2-F | H | H | —OMe |
| 5-83 | H | 5-αTriz | —(CH₂)₄COOMe | 2-F | H | H | —OMe |
| 5-84 | Ac | 5-αTriz | —(CH₂)₄COOMe | 2-F | H | H | —OMe |
| 5-85 | H | 5-αTriz | —CH₂COOEt | 2-F | H | H | —OMe |
| 5-86 | Ac | 5-αTriz | —CH₂COOEt | 2-F | H | H | —OMe |
| 5-87 | H | 5-αTriz | —(CH₂)₂COOEt | 2-F | H | H | —OMe |
| 5-88 | Ac | 5-αTriz | —(CH₂)₂COOEt | 2-F | H | H | —OMe |

TABLE 5-continued

| | | | | | | | |
|---|---|---|---|---|---|---|---|
| 5-89 | H | 5-αTriz | —(CH$_2$)$_3$COOEt | 2-F | H | H | —OMe |
| 5-90 | Ac | 5-αTriz | —(CH$_2$)$_3$COOEt | 2-F | H | H | —OMe |
| 5-91 | H | 5-αTriz | —(CH$_2$)$_4$COOEt | 2-F | H | H | —OMe |
| 5-92 | Ac | 5-αTriz | —(CH$_2$)$_4$COOEt | 2-F | H | H | —OMe |
| 5-93 | H | Tez$_1$ | —CH$_2$COOH | 2-F | H | H | —OMe |
| 5-94 | Ac | Tez$_1$ | —CH$_2$COOH | 2-F | H | H | —OMe |
| 5-95 | H | Tez$_1$ | —(CH$_2$)$_2$COOH | 2-F | H | H | —OMe |
| 5-96 | Ac | Tez$_1$ | —(CH$_2$)$_2$COOH | 2-F | H | H | —OMe |
| 5-97 | H | Tez$_1$ | —(CH$_2$)$_3$COOH | 2-F | H | H | —OMe |
| 5-98 | Ac | Tez$_1$ | —(CH$_2$)$_3$COOH | 2-F | H | H | —OMe |
| 5-99 | H | Tez$_1$ | —(CH$_2$)$_4$COOH | 2-F | H | H | —OMe |
| 5-100 | Ac | Tez$_1$ | —(CH$_2$)$_4$COOH | 2-F | H | H | —OMe |
| 5-101 | H | Tez$_2$ | —CH$_2$COOH | 2-F | H | H | —OMe |
| 5-102 | Ac | Tez$_2$ | —CH$_2$COOH | 2-F | H | H | —OMe |
| 5-103 | H | Tez$_2$ | —(CH$_2$)$_2$COOH | 2-F | H | H | —OMe |
| 5-104 | Ac | Tez$_2$ | —(CH$_2$)$_2$COOH | 2-F | H | H | —OMe |
| 5-105 | H | Tez$_2$ | —(CH$_2$)$_3$COOH | 2-F | H | H | —OMe |
| 5-106 | Ac | Tez$_2$ | —(CH$_2$)$_3$COOH | 2-F | H | H | —OMe |
| 5-107 | H | Tez$_2$ | —(CH$_2$)$_4$COOH | 2-F | H | H | —OMe |
| 5-108 | Ac | Tez$_2$ | —(CH$_2$)$_4$COOH | 2-F | H | H | —OMe |

TABLE 6

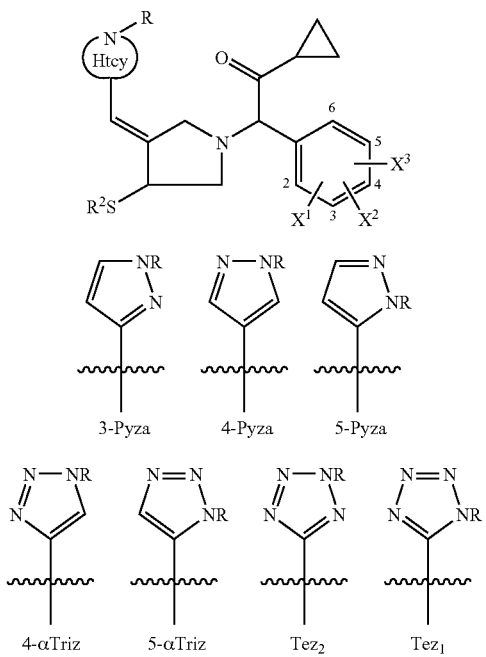

| Compd. No. | R$^2$ | Htcy | R | X$^1$ | X$^2$ | X$^3$ |
|---|---|---|---|---|---|---|
| 6-1 | H | 3-Pyza | H | 2-F | H | H |
| 6-2 | Ac | 3-Pyza | H | 2-F | H | H |
| 6-3 | H | 3-Pyza | Ac | 2-F | H | H |
| 6-4 | Ac | 3-Pyza | Ac | 2-F | H | H |
| 6-5 | H | 3-Pyza | —CH$_2$COOH | 2-F | H | H |
| 6-6 | Ac | 3-Pyza | —CH$_2$COOH | 2-F | H | H |
| 6-7 | H | 3-Pyza | —(CH$_2$)$_2$COOH | 2-F | H | H |
| 6-8 | Ac | 3-Pyza | —(CH$_2$)$_2$COOH | 2-F | H | H |
| 6-9 | H | 3-Pyza | —(CH$_2$)$_3$COOH | 2-F | H | H |
| 6-10 | Ac | 3-Pyza | —(CH$_2$)$_3$COOH | 2-F | H | H |
| 6-11 | H | 3-Pyza | —(CH$_2$)$_4$COOH | 2-F | H | H |
| 6-12 | Ac | 3-Pyza | —(CH$_2$)$_4$COOH | 2-F | H | H |
| 6-13 | H | 3-Pyza | —CH$_2$COOMe | 2-F | H | H |
| 6-14 | Ac | 3-Pyza | —CH$_2$COOMe | 2-F | H | H |
| 6-15 | H | 3-Pyza | —(CH$_2$)$_2$COOMe | 2-F | H | H |
| 6-16 | Ac | 3-Pyza | —(CH$_2$)$_2$COOMe | 2-F | H | H |
| 6-17 | H | 3-Pyza | —CH$_2$COOEt | 2-F | H | H |
| 6-18 | Ac | 3-Pyza | —CH$_2$COOEt | 2-F | H | H |
| 6-19 | H | 3-Pyza | —(CH$_2$)$_2$COOEt | 2-F | H | H |
| 6-20 | Ac | 3-Pyza | —(CH$_2$)$_2$COOEt | 2-F | H | H |
| 6-21 | H | 4-Pyza | —CH$_2$COOMe | 2-F | H | H |
| 6-22 | Ac | 4-Pyza | —CH$_2$COOMe | 2-F | H | H |
| 6-23 | H | 4-Pyza | —(CH$_2$)$_2$COOMe | 2-F | H | H |
| 6-24 | Ac | 4-Pyza | —(CH$_2$)$_2$COOMe | 2-F | H | H |
| 6-25 | H | 4-Pyza | —CH$_2$COOEt | 2-F | H | H |
| 6-26 | Ac | 4-Pyza | —CH$_2$COOEt | 2-F | H | H |
| 6-27 | H | 4-Pyza | —(CH$_2$)$_2$COOEt | 2-F | H | H |
| 6-28 | Ac | 4-Pyza | —(CH$_2$)$_2$COOEt | 2-F | H | H |
| 6-29 | H | 4-Pyza | —CH$_2$COOH | 2-F | H | H |
| 6-30 | Ac | 4-Pyza | —CH$_2$COOH | 2-F | H | H |
| 6-31 | H | 4-Pyza | —(CH$_2$)$_2$COOH | 2-F | H | H |
| 6-32 | Ac | 4-Pyza | —(CH$_2$)$_2$COOH | 2-F | H | H |
| 6-33 | H | 4-Pyza | —(CH$_2$)$_3$COOH | 2-F | H | H |
| 6-34 | Ac | 4-Pyza | —(CH$_2$)$_3$COOH | 2-F | H | H |
| 6-35 | H | 4-Pyza | —(CH$_2$)$_4$COOH | 2-F | H | H |
| 6-36 | Ac | 4-Pyza | —(CH$_2$)$_4$COOH | 2-F | H | H |
| 6-37 | H | 5-Pyza | —CH$_2$COOH | 2-F | H | H |
| 6-38 | Ac | 5-Pyza | —CH$_2$COOH | 2-F | H | H |
| 6-39 | H | 5-Pyza | —(CH$_2$)$_2$COOH | 2-F | H | H |
| 6-40 | Ac | 5-Pyza | —(CH$_2$)$_2$COOH | 2-F | H | H |
| 6-41 | H | 5-Pyza | —(CH$_2$)$_3$COOH | 2-F | H | H |
| 6-42 | Ac | 5-Pyza | —(CH$_2$)$_3$COOH | 2-F | H | H |
| 6-43 | H | 5-Pyza | —(CH$_2$)$_4$COOH | 2-F | H | H |
| 6-44 | Ac | 5-Pyza | —(CH$_2$)$_4$COOH | 2-F | H | H |
| 6-45 | H | 4-αTriz | H | 2-F | H | H |
| 6-46 | Ac | 4-αTriz | H | 2-F | H | H |
| 6-47 | H | 4-αTriz | Ac | 2-F | H | H |
| 6-48 | Ac | 4-αTriz | Ac | 2-F | H | H |
| 6-49 | H | 4-αTriz | —CH$_2$COOH | 2-F | H | H |
| 6-50 | Ac | 4-αTriz | —CH$_2$COOH | 2-F | H | H |
| 6-51 | H | 4-αTriz | —(CH$_2$)$_2$COOH | 2-F | H | H |
| 6-52 | Ac | 4-αTriz | —(CH$_2$)$_2$COOH | 2-F | H | H |
| 6-53 | H | 4-αTriz | —(CH$_2$)$_3$COOH | 2-F | H | H |
| 6-54 | Ac | 4-αTriz | —(CH$_2$)$_3$COOH | 2-F | H | H |
| 6-55 | H | 4-αTriz | —(CH$_2$)$_4$COOH | 2-F | H | H |
| 6-56 | Ac | 4-αTriz | —(CH$_2$)$_4$COOH | 2-F | H | H |
| 6-57 | H | 4-αTriz | —CH$_2$COOMe | 2-F | H | H |
| 6-58 | Ac | 4-αTriz | —CH$_2$COOMe | 2-F | H | H |
| 6-59 | H | 4-αTriz | —(CH$_2$)$_2$COOMe | 2-F | H | H |
| 6-60 | Ac | 4-αTriz | —(CH$_2$)$_2$COOMe | 2-F | H | H |
| 6-61 | H | 4-αTriz | —(CH$_2$)$_3$COOMe | 2-F | H | H |
| 6-62 | Ac | 4-αTriz | —(CH$_2$)$_3$COOMe | 2-F | H | H |
| 6-63 | H | 4-αTriz | —(CH$_2$)$_4$COOMe | 2-F | H | H |
| 6-64 | Ac | 4-αTriz | —(CH$_2$)$_4$COOMe | 2-F | H | H |
| 6-65 | H | 4-αTriz | —CH$_2$COOEt | 2-F | H | H |
| 6-66 | Ac | 4-αTriz | —CH$_2$COOEt | 2-F | H | H |
| 6-67 | H | 4-αTriz | —(CH$_2$)$_2$COOEt | 2-F | H | H |
| 6-68 | Ac | 4-αTriz | —(CH$_2$)$_2$COOEt | 2-F | H | H |
| 6-69 | H | 4-αTriz | —(CH$_2$)$_3$COOEt | 2-F | H | H |
| 6-70 | Ac | 4-αTriz | —(CH$_2$)$_3$COOEt | 2-F | H | H |
| 6-71 | H | 4-αTriz | —(CH$_2$)$_4$COOEt | 2-F | H | H |
| 6-72 | Ac | 4-αTriz | —(CH$_2$)$_4$COOEt | 2-F | H | H |
| 6-73 | H | 5-αTriz | Ac | 2-F | H | H |
| 6-74 | Ac | 5-αTriz | Ac | 2-F | H | H |
| 6-75 | H | 5-αTriz | —CH$_2$COOH | 2-F | H | H |
| 6-76 | Ac | 5-αTriz | —CH$_2$COOH | 2-F | H | H |
| 6-77 | H | 5-αTriz | —(CH$_2$)$_2$COOH | 2-F | H | H |
| 6-78 | Ac | 5-αTriz | —(CH$_2$)$_2$COOH | 2-F | H | H |
| 6-79 | H | 5-αTriz | —(CH$_2$)$_3$COOH | 2-F | H | H |
| 6-80 | Ac | 5-αTriz | —(CH$_2$)$_3$COOH | 2-F | H | H |
| 6-81 | H | 5-αTriz | —(CH$_2$)$_4$COOH | 2-F | H | H |
| 6-82 | Ac | 5-αTriz | —(CH$_2$)$_4$COOH | 2-F | H | H |
| 6-83 | H | 5-αTriz | —CH$_2$COOMe | 2-F | H | H |
| 6-84 | Ac | 5-αTriz | —CH$_2$COOMe | 2-F | H | H |
| 6-85 | H | 5-αTriz | —(CH$_2$)$_2$COOMe | 2-F | H | H |
| 6-86 | Ac | 5-αTriz | —(CH$_2$)$_2$COOMe | 2-F | H | H |
| 6-87 | H | 5-αTriz | —(CH$_2$)$_3$COOMe | 2-F | H | H |
| 6-88 | Ac | 5-αTriz | —(CH$_2$)$_3$COOMe | 2-F | H | H |
| 6-89 | H | 5-αTriz | —(CH$_2$)$_4$COOMe | 2-F | H | H |
| 6-90 | Ac | 5-αTriz | —(CH$_2$)$_4$COOMe | 2-F | H | H |
| 6-91 | H | 5-αTriz | —CH$_2$COOEt | 2-F | H | H |
| 6-92 | Ac | 5-αTriz | —CH$_2$COOEt | 2-F | H | H |
| 6-93 | H | 5-αTriz | —(CH$_2$)$_2$COOEt | 2-F | H | H |
| 6-94 | Ac | 5-αTriz | —(CH$_2$)$_2$COOEt | 2-F | H | H |
| 6-95 | H | 5-αTriz | —(CH$_2$)$_3$COOEt | 2-F | H | H |
| 6-96 | Ac | 5-αTriz | —(CH$_2$)$_3$COOEt | 2-F | H | H |
| 6-97 | H | 5-αTriz | —(CH$_2$)$_4$COOEt | 2-F | H | H |

TABLE 6-continued

| | | | | | | |
|---|---|---|---|---|---|---|
| 6-98 | Ac | 5-αTriz | —(CH$_2$)$_4$COOEt | 2-F | H | H |
| 6-99 | H | Tez$_1$ | —CH$_2$COOH | 2-F | H | H |
| 6-100 | Ac | Tez$_1$ | —CH$_2$COOH | 2-F | H | H |
| 6-101 | H | Tez$_1$ | —(CH$_2$)$_2$COOH | 2-F | H | H |
| 6-102 | Ac | Tez$_1$ | —(CH$_2$)$_2$COOH | 2-F | H | H |
| 6-103 | H | Tez$_1$ | —(CH$_2$)$_3$COOH | 2-F | H | H |
| 6-104 | Ac | Tez$_1$ | —(CH$_2$)$_3$COOH | 2-F | H | H |
| 6-105 | H | Tez$_1$ | —(CH$_2$)$_4$COOH | 2-F | H | H |
| 6-106 | Ac | Tez$_1$ | —(CH$_2$)$_4$COOH | 2-F | H | H |
| 6-107 | H | Tez$_2$ | —CH$_2$COOH | 2-F | H | H |
| 6-108 | Ac | Tez$_2$ | —CH$_2$COOH | 2-F | H | H |
| 6-109 | H | Tez$_2$ | —(CH$_2$)$_2$COOH | 2-F | H | H |
| 6-110 | Ac | Tez$_2$ | —(CH$_2$)$_2$COOH | 2-F | H | H |
| 6-111 | H | Tez$_2$ | —(CH$_2$)$_3$COOH | 2-F | H | H |
| 6-112 | Ac | Tez$_2$ | —(CH$_2$)$_3$COOH | 2-F | H | H |
| 6-113 | H | Tez$_2$ | —(CH$_2$)$_4$COOH | 2-F | H | H |
| 6-114 | Ac | Tez$_2$ | —(CH$_2$)$_4$COOH | 2-F | H | H |

Among the above compounds, preferred compounds are the compounds of Exemplification Compound Nos. 1-21, 1-22, 1-25, 1-26, 1-29, 1-30, 1-33, 1-34, 1-37, 1-38, 1-41, 1-42, 1-45, 1-46, 1-49, 1-50, 1-53, 1-54, 1-57, 1-58, 1-61, 1-62, 1-65, 1-66, 1-69, 1-70, 1-73, 1-74, 1-77, 1-78, 1-81, 1-82, 1-85, 1-86, 1-89, 1-90, 1-93, 1-94, 1-97, 1-98, 1-101, 1-102, 1-105, 1-106, 1-109, 1-110, 1-113, 1-114, 1-117, 1-118, 1-121, 1-122, 1-125, 1-126, 1-129, 1-130, 1-133, 1-134, 1-137, 1-138, 1-141, 1-142, 1-165, 1-166, 1-169, 1-170, 1-173, 1-174, 1-177, 1-178, 1-206, 1-207, 1-208, 1-209, 1-210, 1-211, 1-212, 1-213, 2-1, 2-2, 2-5, 2-6, 2-9, 2-10, 2-13, 2-14, 2-17, 2-18, 2-21, 2-22, 2-25, 2-26, 2-29, 2-30, 2-33, 2-34, 2-37, 2-38, 2-41, 2-42, 2-45, 2-46, 2-49, 2-50, 2-53, 2-54, 2-57, 2-58, 2-61, 2-62, 2-65, 2-66, 2-69, 2-70, 2-73, 2-74, 2-77, 2-78, 2-81, 2-82, 2-85, 2-86, 2-89, 2-90, 2-93, 2-94, 2-97, 2-98, 2-101, 2-102, 2-105, 2-106, 2-109, 2-110, 2-113, 2-114, 2-117, 2-118, 2-121, 2-122, 2-133, 2-134, 2-137, 2-138, 2-145, 2-146, 2-149, 2-150, 2-153, 2-154, 2-157, 2-158, 2-161, 2-162, 2-165, 2-166, 2-169, 2-170, 2-173, 2-174, 2-177, 2-178, 2-181, 2-182, 2-185, 2-186, 2-189, 2-190, 2-193, 2-194, 2-197, 2-198, 2-201, 2-202, 2-205, 2-206, 2-209, 2-210, 2-213, 2-214, 2-217, 2-218, 2-221, 2-222, 2-225, 2-226, 2-229, 2-230, 2-233, 2-234, 2-237, 2-238, 2-241, 2-242, 2-245, 2-246, 2-249, 2-250, 2-253, 2-254, 2-257, 2-258, 2-261, 2-262, 2-265, 2-266, 2-269, 2-270, 2-273, 2-274, 2-277, 2-278, 2-281, 2-282, 2-285, 2-286, 2-289, 2-290, 2-301, 2-302, 2-305, 2-306, 2-313, 2-314, 2-317, 2-318, 2-321, 2-322, 2-325, 2-326, 2-329, 2-330, 2-333, 2-334, 2-337, 2-338, 2-341, 2-342, 2-345, 2-346, 2-349, 2-350, 2-353, 2-354, 2-357, 2-358, 2-361, 2-362, 2-365, 2-366, 2-369, 2-370, 2-373, 2-374, 2-377, 2-378, 2-381, 2-382, 2-385, 2-386, 2-389, 2-390, 2-393, 2-394, 2-397, 2-398, 2-401, 2-402, 2-405, 2-406, 2-409, 2-410, 2-413, 2-414, 2-417, 2-418, 2-421, 2-422, 2-425, 2-426, 2-429, 2-430, 2-433, 2-434, 2-437, 2-438, 2-441, 2-442, 2-445, 2-446, 2-449, 2-450, 2-453, 2-454, 2-457, 2-458, 2-469, 2-470, 2-473, 2-474, 2-481, 2-482, 2-485, 2-486, 2-489, 2-490, 2-493, 2-494, 2-497, 2-498, 2-501, 2-502, 2-513, 2-514, 2-517, 2-518, 2-521, 2-522, 2-525, 2-526, 2-529, 2-530, 2-533, 2-534, 2-537, 2-538, 2-541, 2-542, 2-545, 2-546, 2-549, 2-550, 2-553, 2-554, 2-557, 2-558, 2-561, 2-562, 2-565, 2-566, 2-569, 2-570, 2-573, 2-574, 2-641, 2-642, 2-645, 2-646, 2-649, 2-650, 2-653, 2-654, 2-657, 2-658, 2-661, 2-662, 2-665, 2-666, 2-669, 2-670, 2-673, 2-674, 2-677, 2-678, 2-681, 2-682, 2-685, 2-686, 2-689, 2-690, 2-693, 2-694, 2-697, 2-698, 2-701, 2-702, 2-769, 2-770, 2-773, 2-774, 2-777, 2-778, 2-781, 2-782, 2-785, 2-786, 2-789, 2-790, 2-793, 2-794, 2-797, 2-798, 2-801, 2-802, 2-805, 2-806, 2-809, 2-810, 2-813, 2-814, 2-817, 2-818, 2-821, 2-822, 2-825, 2-826, 2-829, 2-830, 2-897, 2-898, 2-901, 2-902, 2-905, 2-906, 2-909, 2-910, 2-913, 2-914, 2-917, 2-918, 2-921, 2-922, 2-925, 2-926, 2-929, 2-930, 2-933, 2-934, 2-937, 2-938, 2-941, 2-942, 2-945, 2-946, 2-949, 2-950, 2-953, 2-954, 2-957, 2-958, 2-1025, 2-1026, 2-1029, 2-1030, 2-1033, 2-1034, 2-1037, 2-1038, 2-1041, 2-1042, 2-1045, 2-1046, 2-1049, 2-1050, 2-1053, 2-1054, 2-1057, 2-1058, 2-1061, 2-1062, 2-1065, 2-1066, 2-1069, 2-1070, 2-1073, 2-1074, 2-1077, 2-1078, 2-1081, 2-1082, 2-1085, 2-1086, 2-1145, 2-1146, 2-1149, 2-1150, 2-1153, 2-1154, 2-1157, 2-1158, 2-1161, 2-1162, 2-1165, 2-1166, 2-1169, 2-1170, 2-1173, 2-1174, 2-1177, 2-1178, 2-1181, 2-1182, 2-1185, 2-1186, 2-1189, 2-1190, 2-1193, 2-1194, 2-1197, 2-1198, 2-1201, 2-1202, 2-1205, 2-1206, 2-1209, 2-1210, 2-1213, 2-1214, 2-1217, 2-1218, 2-1221, 2-1222, 2-1225, 2-1226, 2-1229, 2-1230, 2-1233, 2-1234, 2-1237, 2-1238, 2-1241, 2-1242, 2-1245, 2-1246, 2-1249, 2-1250, 2-1253, 2-1254, 2-1257, 2-1258, 2-1261, 2-1262, 2-1265, 2-1266, 2-1269, 2-1270, 2-1273, 2-1274, 2-1277, 2-1278, 2-1281, 2-1282, 2-1285, 2-1286, 2-1289, 2-1290, 2-1293, 2-1294, 2-1297, 2-1298, 2-1301, 2-1302, 2-1305, 2-1306, 2-1309, 2-1310, 2-1313, 2-1314, 2-1317, 2-1318, 2-1321, 2-1322, 2-1325, 2-1326, 2-1329, 2-1330, 2-1333, 2-1334, 2-1337, 2-1338, 2-1341, 2-1342, 2-1345, 2-1346, 2-1349, 2-1350, 2-1353, 2-1354, 2-1357, 2-1358, 2-1361, 2-1362, 2-1365, 2-1366, 2-1369, 2-1370, 2-1373, 2-1374, 2-1377, 2-1378, 2-1381, 2-1382, 2-1385, 2-1386, 2-1389, 2-1390, 2-1393, 2-1394, 2-1397, 2-1398, 2-1401, 2-1402, 2-1405, 2-1406, 2-1409, 2-1410, 2-1413, 2-1414, 2-1417, 2-1418, 2-1421, 2-1422, 2-1425, 2-1426, 2-1429, 2-1430, 2-1433, 2-1434, 2-1437, 2-1438, 2-1441, 2-1442, 2-1445, 2-1446, 2-1449, 2-1450, 2-1453, 2-1454, 2-1457, 2-1458, 2-1461, 2-1462, 2-1465, 2-1466, 2-1469, 2-1470, 2-1473, 2-1474, 2-1477, 2-1478, 2-1481, 2-1482, 2-1485, 2-1486, 2-1489, 2-1490, 2-1493, 2-1494, 2-1497, 2-1498, 2-1501, 2-1502, 2-1505, 2-1506, 2-1509, 2-1510, 2-1513, 2-1514, 2-1517, 2-1518, 2-1521, 2-1522, 2-1525, 2-1526, 2-1529, 2-1530, 2-1533, 2-1534, 2-1537, 2-1538, 2-1541, 2-1542, 2-1545, 2-1546, 2-1549, 2-1550, 2-1553, 2-1554, 2-1557, 2-1558, 2-1561, 2-1562, 2-1565, 2-1566, 2-1569, 2-1570, 2-1573, 2-1574, 2-1577, 2-1578, 2-1581, 2-1582, 2-1585, 2-1586, 2-1589, 2-1590, 2-1593, 2-1594, 2-1597, 2-1598, 2-1601, 2-1602, 2-1605, 2-1606, 2-1609, 2-1610, 2-1613, 2-1614, 2-1617, 2-1618, 2-1621, 2-1622, 2-1625, 2-1626, 2-1629, 2-1630, 2-1633, 2-1634, 2-1637, 2-1638, 2-1641, 2-1642, 2-1645, 2-1646, 2-1649, 2-1650, 2-1653, 2-1654, 2-1665, 2-1666, 2-1669, 2-1670, 2-1673, 2-1674, 2-1681, 2-1682, 2-1685, 2-1686, 2-1689, 2-1690, 2-1693, 2-1694, 2-1709, 2-1710, 2-1713, 2-1714, 2-1717, 2-1718, 2-1721, 2-1722, 2-1729, 2-1730, 2-1731, 2-1732, 2-1733, 2-1734, 2-1745, 2-1746, 2-1747, 2-1748, 2-1749, 2-1750, 2-1761, 2-1762, 2-1763, 2-1764, 2-1765, 2-1766, 2-1773, 2-1774, 2-1775, 2-1776, 2-1777, 2-1778, 2-1791, 2-1792, 2-1793, 2-1794, 2-1799, 2-1800, 2-1801, 2-1802, 2-1803, 2-1804, 2-1823, 2-1824, 2-1825, 2-1826, 2-1827, 2-1828, 2-1831, 2-1832, 2-1833, 2-1834, 2-1835, 2-1836, 3-9, 3-10, 3-13, 3-14, 4-1, 4-2, 4-5, 4-6, 4-7, 4-8, 4-9, 4-10, 4-11, 4-12, 4-13, 4-14, 4-15, 4-16, 4-17, 4-18, 4-21, 4-22, 4-23, 4-24, 4-25, 4-26, 4-27, 4-28, 4-29, 4-30, 4-31, 4-32, 4-37, 4-38, 4-39, 4-40, 4-41, 4-42, 4-43, 4-44, 4-45, 4-46, 4-47, 4-48, 4-49, 4-50, 4-51, 4-52, 4-53, 4-54, 4-55, 4-56, 4-57, 4-58, 4-59, 4-60, 4-61, 4-62, 4-63, 4-64, 4-65, 4-66, 4-67, 4-68, 4-69, 4-70, 4-71, 4-72, 4-73, 4-74, 4-75, 4-76, 4-79, 4-80, 4-81, 4-82, 4-83, 4-84, 4-85, 4-86, 4-87, 4-88, 4-89, 4-90, 4-91, 4-92, 4-97, 4-98, 4-101, 4-102, 4-105, 4-106, 4-109, 4-110, 4-113, 4-114, 4-117, 4-118, 4-121, 4-122, 4-125, 4-126, 4-135, 4-136, 4-139, 4-140, 4-143, 4-144, 4-147, 4-148, 4-151, 4-152, 4-155, 4-156, 4-159, 4-160, 4-161, 4-162, 4-163, 4-164, 4-165, 4-166, 4-169, 4-170, 4-171, 4-172, 4-173, 4-174, 4-175, 4-176, 4-177, 4-178, 4-179, 4-180, 4-181, 4-182, 4-185, 4-186, 4-187, 4-188, 4-189, 4-190, 4-191, 4-192, 4-193, 4-194, 4-195, 4-196, 5-5, 5-6, 5-7, 5-8, 5-9, 5-10, 5-11, 5-12, 5-13, 5-14, 5-15, 5-16, 5-17, 5-18, 5-19, 5-20, 5-21, 5-22, 5-23, 5-24, 5-25, 5-26, 5-27, 5-28, 5-29, 5-30, 5-31, 5-32, 5-33, 5-34, 5-35, 5-36, 5-41, 5-42, 5-43, 5-44, 5-45, 5-46, 5-47, 5-48, 5-49, 5-50, 5-51, 5-52, 5-53, 5-54, 5-55, 5-56, 5-57, 5-58, 5-59, 5-60, 5-61, 5-62, 5-63, 5-64, 5-69, 5-70, 5-71, 5-72, 5-73, 5-74, 5-75, 5-76, 5-77, 5-78, 5-79, 5-80, 5-81, 5-82, 5-83, 5-84, 5-85, 5-86, 5-87, 5-88, 5-89, 5-90, 5-91, 5-92, 5-93, 5-94, 5-95, 5-96, 5-97, 5-98, 5-99, 5-100, 5-101, 5-102, 5-103, 5-104, 5-105, 5-106, 5-107, 5-108, 6-5, 6-5, 6-7, 6-8, 6-9, 6-10, 6-27, 6-28, 6-29, 6-30, 6-31, 6-32, 6-33, 6-34, 5-37, 6-38, 6-39, 6-40, 6-41, 6-42, 6-49, 6-50, 6-51, 6-52, 6-53, 6-54, 6-75, 6-76, 6-77, 6-78, 6-79, 6-80, 6-100, 6-101, 6-102, 6-103, 6-104, 6-107, 6-108, 6-109, 6-110, 6-111 and 6-112, more preferred compounds are the compounds of Exemplification Compound Nos. 1-21, 1-22, 1-25, 1-26, 1-45, 1-46, 1-49, 1-50, 1-53, 1-54, 1-57, 1-58, 1-125, 1-126, 1-177, 1-178, 1-206, 1-207, 1-208, 1-209, 1-210, 1-211, 2-13, 2-14, 2-17, 2-18, 2-21, 2-22, 2-25, 2-26, 2-29, 2-30, 2-33, 2-34, 2-37, 2-38, 2-41, 2-42, 2-45, 2-46, 2-49, 2-50, 2-53, 2-54, 2-57, 2-58, 2-61, 2-62, 2-65, 2-66, 2-69, 2-70, 2-73, 2-74, 2-85, 2-86, 2-89, 2-90, 2-93, 2-94, 2-181, 2-182, 2-185, 2-186, 2-189, 2-190, 2-193, 2-194, 2-197, 2-198, 2-201, 2-202, 2-205, 2-206, 2-209, 2-210, 2-213, 2-214, 2-217, 2-218, 2-221, 2-222, 2-225, 2-226, 2-229, 2-230, 2-233, 2-234, 2-237, 2-238, 2-241, 2-242, 2-253, 2-254, 2-257, 2-258, 2-261, 2-262, 2-349, 2-350, 2-353, 2-354, 2-357, 2-358, 2-365, 2-366, 2-369, 2-370, 2-373, 2-374, 2-381, 2-382, 2-385, 2-386, 2-389, 2-390, 2-769, 2-770, 2-773, 2-774, 2-777, 2-778, 2-785, 2-786, 2-789, 2-790, 2-793, 2-794, 2-801, 2-802, 2-805, 2-806, 2-809, 2-810, 2-897, 2-898, 2-901, 2-902, 2-905, 2-906, 2-913, 2-914, 2-917, 2-918, 2-921, 2-922, 2-929, 2-930, 2-933, 2-934, 2-937, 2-938, 2-1025, 2-1026, 2-1029, 2-1030, 2-1033, 2-1034, 2-1041, 2-1042, 2-1045, 2-1046, 2-1049, 2-1050, 2-1057, 2-1058, 2-1061, 2-1062, 2-1065, 2-1066, 2-1145, 2-1146, 2-1149, 2-1150, 2-1153, 2-1154, 2-1157, 2-1158, 2-1161, 2-1162, 2-1165, 2-1166, 2-1169, 2-1170, 2-1173, 2-1174, 2-1177, 2-1178, 2-1181, 2-1182, 2-1185, 2-1186, 2-1189, 2-1190, 2-1193, 2-1194, 2-1197, 2-1198, 2-1201, 2-1202, 2-1209, 2-1210, 2-1213, 2-1214, 2-1217, 2-1218, 2-1221, 2-1222, 2-1225, 2-1226, 2-1229, 2-1230, 2-1233, 2-1234, 2-1237, 2-1238, 2-1241, 2-1242, 2-1245, 2-1246, 2-1249, 2-1250, 2-1253, 2-1254, 2-1257, 2-1258, 2-1261, 2-1262, 2-1265, 2-1266, 2-1273, 2-1274, 2-1277, 2-1278, 2-1281, 2-1282, 2-1289, 2-1290, 2-1293, 2-1294, 2-1297, 2-1298, 2-1305, 2-1306, 2-1309, 2-1310, 2-1313, 2-1314, 2-1337, 2-1338, 2-1341, 2-1342, 2-1345, 2-1346, 2-1353, 2-1354, 2-1357, 2-1358, 2-1361, 2-1362, 2-1369, 2-1370, 2-1373, 2-1374, 2-1377, 2-1378, 2-1401, 2-1402, 2-1405, 2-1406, 2-1409, 2-1410, 2-1413, 2-1414, 2-1417, 2-1418, 2-1421, 2-1422, 2-1425, 2-1426, 2-1429, 2-1430, 2-1433, 2-1434, 2-1437, 2-1438, 2-1441, 2-1442, 2-1445, 2-1446, 2-1449, 2-1450, 2-1453, 2-1454, 2-1457, 2-1458, 2-1465, 2-1466, 2-1469, 2-1470, 2-1473, 2-1474, 2-1481, 2-1482, 2-1485, 2-1486, 2-1489, 2-1490, 2-1497, 2-1498, 2-1501, 2-1502, 2-1505, 2-1506, 2-1529, 2-1530, 2-1533, 2-1534, 2-1537, 2-1538, 2-1541, 2-1542, 2-1545, 2-1546, 2-1549, 2-1550, 2-1553, 2-1554, 2-1557, 2-1558, 2-1561, 2-1562, 2-1565, 2-1566, 2-1569, 2-1570, 2-1573, 2-1574, 2-1577, 2-1578, 2-1581, 2-1582, 2-1585, 2-1586, 2-1593, 2-1594, 2-1597, 2-1598, 2-1601, 2-1602, 2-1605, 2-1606, 2-1609, 2-1610, 2-1613, 2-1614, 2-1617, 2-1618, 2-1621, 2-1622, 2-1625, 2-1626, 2-1629, 2-1630, 2-1633, 2-1634, 2-1637, 2-1638, 2-1641, 2-1642, 2-1645, 2-1646, 2-1649, 2-1650, 4-1, 4-2, 4-5, 4-6, 4-7, 4-8, 4-9, 4-10, 4-11, 4-12, 4-13, 4-14, 4-15, 4-16, 4-17, 4-18, 4-21, 4-22, 4-23, 4-24, 4-25, 4-26, 4-27, 4-28, 4-29, 4-30, 4-31, 4-32, 4-91, 4-92, 4-97, 4-98, 4-101, 4-102, 4-105, 4-106, 4-109, 4-110, 4-113, 4-114, 4-117, 4-118, 4-121, 4-122, 4-125, 4-126, 4-135, 4-136, 4-139, 4-140, 4-143, 4-144, 4-147, 4-148, 4-151, 4-152, 4-155, 4-156, 4-159, 4-160, 4-161, 4-162, 4-163, 4-164, 4-165, 4-166, 4-169, 4-170, 4-171, 4-172, 4-173, 4-174, 4-175, 4-176, 4-177, 4-178, 4-179, 4-180, 4-181, 4-182, 4-185, 4-186, 4-187, 4-188, 4-189, 4-190, 4-191, 4-192, 4-193, 4-194, 4-195, 4-196, 5-5, 5-6, 5-7, 5-8, 5-9, 5-10, 5-13, 5-14, 5-15, 5-16, 5-17, 5-18, 5-19, 5-20, 5-21, 5-22, 5-23, 5-24, 5-25, 5-26, 5-29, 5-30, 5-31, 5-32, 5-33, 5-34, 5-35, 5-36, 5-41, 5-42, 5-43, 5-44, 5-45, 5-46, 5-49, 5-50, 5-51, 5-52, 5-53, 5-54, 5-57, 5-58, 5-59, 5-60, 5-61, 5-62, 5-69, 5-70, 5-71, 5-72, 5-73, 5-74, 5-77, 5-78, 5-79, 5-80, 5-81, 5-82, 5-85, 5-86, 5-87, 5-88, 5-89, 5-90, 5-93, 5-94, 5-95, 5-96, 5-97, 5-98, 5-101, 5-102, 5-103, 5-104, 5-105 and 5-106, even more preferred compounds are the compounds of Exemplification Compound Nos. 2-13, 2-17, 2-21, 2-25, 2-45, 2-49, 2-53, 2-57, 2-181, 2-185, 2-189, 2-193, 2-213, 2-217, 2-221, 2-225, 2-349, 2-353, 2-357, 2-381, 2-385, 2-389, 2-1145, 2-1149, 2-1153, 2-1157, 2-1177, 2-1181, 2-1185, 2-1189, 2-1209, 2-1213, 2-1217, 2-1221, 2-1241, 2-1245, 2-1249, 2-1253, 2-1401, 2-1405, 2-1409, 2-1414, 2-1433, 2-1437, 2-1441, 2-1529, 2-1533, 2-1537, 2-1541, 2-1561, 2-1565, 2-1569, 2-1573, 2-1593, 2-1597, 2-1601, 2-1605, 2-1625, 2-1629, 2-1633, 2-1637, 4-5, 4-7, 4-13, 4-15, 4-21, 4-23, 4-29, 4-31, 4-97, 4-101, 4-113, 4-117, 4-135, 4-139, 4-159, 4-161, 4-169, 4-171, 4-173, 4-179, 4-181, 4-185, 4-187, 4-193, 4-195, 5-7, 5-9, 5-23, 5-25, 5-31, 5-33, 5-43, 5-45, 5-71, 5-73, 5-95, 5-97, 5-103 and 5-105, and particularly preferred compounds are Exemplification Compound No. 2-13: (E)-3-{[1-(carboxymethyl)-1H-pyrazol-3-yl]methylidene}-1-[2-cyclopropyl-1-(2-fluorophenyl)-2-oxoethyl]-4-sulfanylpiperidine, Exemplification Compound No. 2-17: (E)-3-{[1-(2-carboxyethyl)-1H-pyrazol-3-yl]methylidene}-1-[2-cyclopropyl-1-(2-fluorophenyl)-2-oxoethyl]-4-sulfanylpiperidine, Exemplification Compound No. 2-21: (E)-3-{[1-(3-carboxypropyl)-1H-pyrazol-3-yl]methylidene}-1-[2-cyclopropyl-1-(2-fluorophenyl)-2-oxoethyl]-4-sulfanylpiperidine, Exemplification Compound No. 2-181: (E)-3-{[1-(carboxymethyl)-1H-pyrazol-4-yl]methylidene}-1-[2-cyclopropyl-1-(2-fluorophenyl)-2-oxoethyl]-4-sulfanylpiperidine, Exemplification Compound No. 2-185: (E)-3-{[1-(2-carboxyethyl)-1H-pyrazol-4-yl]methylidene}-1-[2-cyclopropyl-1-(2-fluorophenyl)-2-oxoethyl]-4-sulfanylpiperidine, Exemplification Compound No. 2-189: (E)-3-{[1-(3-carboxypropyl)-1H-pyrazol-4-yl]methylidene}-1-[2-cyclopropyl-1-(2-fluorophenyl)-2-oxoethyl]-4-sulfanylpiperidine, Exemplification Compound No. 2-1145: (E)-3-{[1-(carboxymethyl)-1H-1,2,3-triazol-4-yl]methylidene}-1-[2-cyclopropyl-1-(2-fluorophenyl)-2-oxoethyl]-4-sulfanylpiperidine, Exemplification Compound No. 2-1149: (E)-3-{[1-(2-carboxyethyl)-1H-1,2,3-triazol-4-yl]methylidene}-1-[2-cyclopropyl-1-(2-fluorophenyl)-2-oxoethyl]-4-sulfanylpiperidine, Exemplification Compound No. 2-1153: (E)-3-{[1-(3-carboxypropyl)-1H-1,2,3-triazol-4-yl]methylidene}-1-[2-cyclopropyl-1-(2-fluorophenyl)-2-oxoethyl]-4-sulfanylpiperidine, Exemplification Compound No. 2-1157: (E)-3-{[1-(4-carboxybutyl)-1H-1,2,3-triazol-4-yl]methylidene}-1-[2-cyclopropyl-1-(2-fluorophenyl)-2-oxoethyl]-4-sulfanylpiperidine, Exemplification Compound No. 2-1209: (E)-3-{[1-(carboxymethyl)-1H-1,2,3-triazol-5-yl]methylidene}-1-[2-cyclopropyl-1-(2-fluorophenyl)-2-oxoethyl]-4-sulfanylpiperidine, Exemplification Compound No. 2-1213: (E)-3-{[1-(2-carboxyethyl)-1H-1,2,3-triazol-5-yl]methylidene}-1-[2-cyclopropyl-1-(2-fluorophenyl)-2-oxoethyl]-4-sulfanylpiperidine, Exemplification Compound No. 2-1217: (E)-3-{[1-(3-carboxypropyl)-1H-1,2,3-triazol-5-yl]methylidene}-1-[2-cyclopropyl-1-(2-fluorophenyl)-2-oxoethyl]-4-sulfanylpiperidine, Exemplification Compound No. 2-1221: (E)-3-{[1-(4-carboxybutyl)-1H-1,2,3-triazol-5-yl]methylidene}-1-[2-cyclopropyl-1-(2-fluorophenyl)-2-oxoethyl]-4-sulfanylpiperidine, Exemplification Compound No. 2-1401: (E)-3-{[2-(carboxymethyl)-2H-1,2,3-triazol-4-yl]methylidene}-1-[2-cyclopropyl-1-(2-fluorophenyl)-2-oxoethyl]-4-sulfanylpiperidine, Exemplification Compound No. 2-1405: (E)-3-{[2-(2-carboxyethyl)-2H-1,2,3-triazol-4-yl]methylidene}-1-[2-cyclopropyl-1-(2-fluorophenyl)-2-oxoethyl]-4-sulfanylpiperidine, Exemplification Compound No. 2-1409: (E)-3-{[3-(3-carboxypropyl)-2H-1,2,3-triazol-4-yl]methylidene}-1-[2-cyclopropyl-1-(2-fluorophenyl)-2-oxoethyl]-4-sulfanylpiperidine, Exemplification Compound No. 2-1529: (E)-3-{[1-(carboxymethyl)-1H-tetrazol-5-yl]methylidene}-1-[2-cyclopropyl-1-(2-fluorophenyl)-2-oxoethyl]-4-sulfanylpiperidine, Exemplification Compound No. 2-1533: (E)-3-{[1-(2-carboxyethyl)-1H-tetrazol-5-yl]methylidene}-1-[2-cyclopropyl-1-(2-fluorophenyl)-2-oxoethyl]-4-sulfanylpiperidine, Exemplification Compound No. 2-1537: (E)-3-{[1-(3-carboxypropyl)-1H-tetrazol-5-yl]methylidene}-1-[2-cyclopropyl-1-(2-fluorophenyl)-2-oxoethyl]-4-sulfanylpiperidine, Exemplification Compound No. 2-1541: (E)-3-{[1-(4-carboxybutyl)-1H-tetrazol-5-yl]methylidene}-1-[2-cyclopropyl-1-(2-fluorophenyl)-2-oxoethyl]-4-sulfanylpiperidine, Exemplification Compound No. 2-1593: (E)-3-{[2-(carboxymethyl)-2H-tetrazol-5-yl]methylidene}-1-[2-cyclopropyl-1-(2-fluorophenyl)-2-oxoethyl]-4-sulfanylpiperidine, Exemplification Compound No. 2-1597: (E)-3-{[2-(2-carboxyethyl)-2H-tetrazol-5-yl]methylidene}-1-[2-cyclopropyl-1-(2-fluorophenyl)-2-oxoethyl]-4-sulfanylpiperidine, Exemplification Compound No. 2-1601: (E)-3-{[2-(3-carboxypropyl)-2H-tetrazol-5-yl]methylidene}-1-[2-cyclopropyl-1-(2-fluorophenyl)-2-oxoethyl]-4-sulfanylpiperidine, Exemplification Compound No. 2-1605: (E)-3-{[2-(4-carboxybutyl)-2H-tetrazol-5-yl]methylidene}-1-[2-cyclopropyl-1-(2-fluorophenyl)-2-oxoethyl]-4-sulfanylpiperidine, Exemplification Compound No. 5-7: (E)-1-[1-(2-fluorophenyl)-2-methoxy-2-oxoethyl]-3-{[1-(2-carboxyethyl)-1H-pyrazol-3-yl]methylidene}-4-sulfanylpiperidine, Exemplification Compound No. 5-9: (E)-1-[1-(2-fluorophenyl)-2-methoxy-2-oxoethyl]-3-{[1-(3-carboxypropyl)-1H-pyrazol-3-yl]methylidene}-4-sulfanylpiperidine, Exemplification Compound No. 5-23: (E)-1-[1-(2-fluorophenyl)-2-methoxy-2-oxoethyl]-3-{[1-(2-carboxyethyl)-1H-pyrazol-4-yl]methylidene}-4-sulfanylpiperidine, Exemplification Compound No. 5-25: (E)-1-[1-(2-fluorophenyl)-2-methoxy-2-oxoethyl]-3-{[1-(3-carboxypropyl)-1H-pyrazol-4-yl]methylidene}-4-sulfanylpiperidine, Exemplification Compound No. 5-31: (E)-1-[1-(2-fluorophenyl)-2-methoxy-2-oxoethyl]-3-{[1-(2-carboxyethyl)-1H-pyrazol-5-yl]methylidene}-4-sulfanylpiperidine, Exemplification Compound No. 5-33: (E)-1-[1-(2-fluorophenyl)-2-methoxy-2-oxoethyl]-3-{[1-(3-carboxypropyl)-1H-pyrazol-5-yl]methylidene}-4-sulfanylpiperidine, Exemplification Compound No. 5-43: (E)-1-[1-(2-fluorophenyl)-2-methoxy-2-oxoethyl]-3-{[1-(2-carboxyethyl)-1H-1,2,3-triazol-4-yl]methylidene}-4-sulfanylpiperidine, Exemplification Compound No. 5-45: (E)-1-[1-(2-fluorophenyl)-2-methoxy-2-oxoethyl]-3-{[1-(3-carboxypropyl)-1H-1,2,3-triazol-4-yl]methylidene}-4-sulfanylpiperidine, Exemplification Compound No. 5-71: (E)-1-[1-(2-fluorophenyl)-2-methoxy-2-oxoethyl]-3-{[1-(2-carboxyethyl)-1H-1,2,3-triazol-5-yl]methylidene}-4-sulfanylpiperidine, Exemplification Compound No. 5-73: (E)-1-[1-(2-fluorophenyl)-2-methoxy-2-oxoethyl]-3-{[1-(3-carboxypropyl)-1H-1,2,3-triazol-5-yl]methylidene}-4-sulfanylpiperidine, Exemplification Compound No. 5-95: (E)-1-[1-(2-fluorophenyl)-2-methoxy-2-oxoethyl]-3-{[1-(2-carboxyethyl)-1H-tetrazol-5-yl]methylidene}-4-sulfanylpiperidine, Exemplification Compound No. 5-97: (E)-1-[1-(2-fluorophenyl)-2-methoxy-2-oxoethyl]-3-{[1-(3-carboxypropyl)-1H-tetrazol-5-yl]methylidene}-4-sulfanylpiperidine, Exemplification Compound No. 5-103: (E)-1-[1-(2-fluorophenyl)-2-methoxy-2-oxoethyl]-3-{[2-(2-carboxyethyl)-2H-tetrazol-5-yl]methylidene}-4-sulfanylpiperidine, and Exemplification Compound No. 5-105: (E)-1-[1-(2-fluorophenyl)-2-methoxy-2-oxoethyl]-3-{[2-(3-carboxypropyl)-2H-tetrazol-5-yl]methylidene}-4-sulfanylpiperidine.

Processes and Examples

The compound (I) in the present invention can be obtained by Process A or Process B described below.

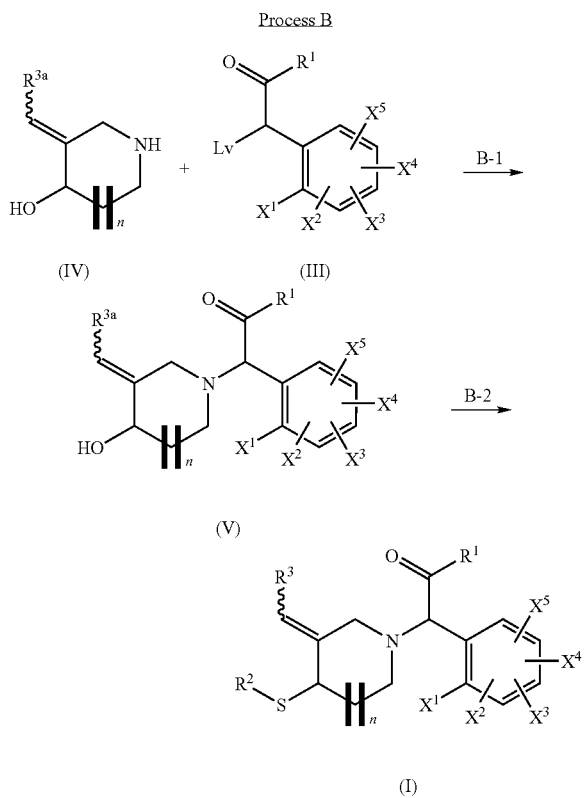

In the above, from $R^1$ to $R^3$ and from $X^1$ to $X^5$ have the same meanings as defined above; $R^{2a}$ represents $R^2$ described above or a protective group for a mercapto group; $R^{3a}$ represents $R^3$ described above or a group by which an amino group on $R^3$ may be protected, if necessary, by a protective group for an amino group; and Lv represents a leaving group.

The protective group for a mercapto group of $R^{2a}$ can be the same group as that described as the protective group for a mercapto group of the above "prodrug", and is preferably an acetyl group.

The protective group for an amino group of $R^{3a}$ is not particularly restricted provided that it can usually protect an amino group in chemical reactions, and specifically indicates a protective group that can be cleaved by a chemical process such as hydrogenolysis, hydrolysis, electrolysis and photolysis. Such protective group can be, for example, the above "aliphatic acyl group"; the above "aromatic acyl group"; the above "alkoxycarbonyl group"; the above "aralkyloxycarbonyl group"; the above "silyl group"; the above "aralkyl group"; a "substituted methylene group" that can form a Schiff base such as N,N-dimethylaminomethylene, benzylidene, 4-methoxybenzylidene, 4-nitrobenzylidene, salicylidene, 5-chlorosalicylidene, diphenylmethylene or (5-chloro-2-hydroxyphenyl)phenylmethylene group; an "aromatic sulfonyl group" consisting of: an arylsulfonyl group such as a benzenesulfonyl group, and an arylsulfonyl group substituted with lower alkyl or lower alkoxy group(s) such as a p-toluenesulfonyl, pentamethylbenzenesulfonyl, p-methoxybenzenesulfonyl, 2,4,6-trimethoxybenzenesulfonyl or 3-methoxy-4-t-butylbenzenesulfonyl group; and an "aliphatic sulfonyl group", including an alkylsulfonyl group such as a methanesulfonyl or t-butylsulfonyl group, and an alkylsulfonyl group substituted with halogen atom(s), silyl group(s), or aryl group(s) such as a trifluoromethylsulfonyl, trisilylethanesulfonyl or benzylsulfonyl group.

The leaving group of Lv is not particularly restricted provided that this group is a functional group that can achieve displacement reaction by reacting with a nucleophilic substituent, and can be, for example, the above "halogen atom" described hereinbefore; a "lower alkylsulfonyloxy group" such as a methanesulfonyloxy or ethanesulfonyloxy group; a "halogenated lower alkylsulfonyloxy group" such as trifluoromethanesulfonyloxy group; or an "aromatic sulfonyloxy group", including an arylsulfonyloxy group such as a benzenesulfonyloxy group, a lower alkylated arylsulfonyloxy group such as a p-toluenesulfonyloxy group, a halogenated arylsulfonyloxy group such as a p-chlorobenzenesulfonyloxy group and a nitrated arylsulfonyloxy group such as a p-nitrobenzenesulfonyloxy group.

Each step of Process A and Process B is hereinafter described in detail.

(Process A)

Process A is a step for the preparation of compound (I) by conducting a nucleophilic displacement reaction in the presence of a base using compound (II) obtainable by Process C and compound (III) that is well known or easily prepared from known compounds (Step A-1). Furthermore, if necessary, several reactions such as deprotection of a protective group of a mercapto group (Step A-2), introduction of a substituent onto a mercapto group (Step A-3), hydrolysis of an ester group (Step A-4), conversion of a carboxyl group into an amide group (Step A-5), conversion of a carboxyl group into an ester group (Step A-6), deprotection of a protective group for an amino group (Step A-7) and conversion of a carboxyl group into a hydroxyamino group (Step A-8) can also be carried out. The steps from A-2 to A-8 can be conducted either before or after the step A-1, and the order of these steps can easily be selected according to circumstances by a person having ordinary skill in the art.

(A-1)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; a ketone such as acetone, methyl ethyl ketone, methyl isobutyl ketone, isophorone or cyclohexanone; a nitrile such as acetonitrile, or isobutyronitrile; an amide such as formamide, N,N-dimethylformamide, N,N-dimethylacetamide, N-methyl-2-pyrrolidinone or hexamethylphosphoric triamide; or a sulfoxide such as dimethyl sulfoxide or sulfolane, and is preferably a halogenated hydrocarbon, a nitrile or an amide, and more preferably N,N-dimethylformamide, N,N-dimethylacetamide, acetonitrile or dichloromethane.

The base employed can be, for example, an inorganic base, including an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide, and an alkali metal fluoride such as sodium fluoride or potassium fluoride; an alkali metal alkoxide such as sodium methoxide, sodium ethoxide, potassium methoxide, potassium ethoxide, potassium tert-butoxide or lithium methoxide; an alkali metal mercaptan such as sodium methylmercaptan or sodium ethylmercaptan; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably an alkali metal carbonate or an organic base, and more preferably potassium carbonate or triethylamine.

The reaction temperature depends on the starting material and the reagent, and is between −50° C. and 100° C., and preferably between 0° C. and 50° C.

The reaction time depends on the reaction temperature, the starting material, the reagent and the kind of solvent employed, and is generally from 30 minutes to 48 hours, and preferably from 1 hour to 24 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(A-2)

This step is a step for the deprotection of a protective group for a mercapto group, and can easily be achieved according to procedures that are well known by a person having ordinary skill in the art (for example, the procedure described in Protective Groups in Organic Synthesis Third Edition, T. W. Green et al., John Wiley & Sons, Inc. (1999)), and is preferably carried out by a method for deprotection in the presence of an acid (Step A-2a) or a method for deprotection in the presence of a base (Step A-2b).

(A-2a)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or di(ethylene glycol)dimethyl ether; an alcohol such as methanol, ethanol, n-propanol, isopropanol, n-butanol, isobutanol, t-butanol, isoamyl alcohol, diethylene glycol, glycerol, octanol, cyclohexanol or 2-methoxyethanol; an amide such as formamide, N,N-dimethylformamide, N,N-dimethylacetamide, N-methyl-2-pyrrolidinone or hexamethylphosphoric triamide; a sulfoxide such as dimethyl sulfoxide or sulfolane; or a mixture of the above solvents, and is preferably an alcohol or a mixture of a halogenated hydrocarbon and an alcohol, and more preferably methanol, ethanol or a mixture of dichloromethane and methanol or ethanol.

The acid employed is not particularly restricted provided that it can be used in general reactions, and can be preferably an inorganic acid such as hydrochloric acid, hydrogen chloride, hydrobromic acid, sulfuric acid, perchloric acid or phosphoric acid; or an organic acid such as acetic acid, formic acid, oxalic acid, methanesulfonic acid, p-toluenesulfonic acid, camphorsulfonic acid, trifluoroacetic acid or trifluoromethane sulfonic acid, and is preferably an inorganic acid, and more preferably hydrogen chloride.

The reaction temperature depends on the starting material and the reagent, and is between −50° C. and 100° C., and preferably between 0° C. and 50° C.

The reaction time depends on the reaction temperature, the starting material, the reagent and the kind of solvent employed, and is generally from 30 minutes to 48 hours, and preferably from 1 hour to 24 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(A-2b)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, n-propanol, isopropanol, n-butanol, isobutanol, t-butanol, isoamyl alcohol, diethylene glycol, glycerol, octanol, cyclohexanol or 2-methoxyethanol; an amide such as formamide, N,N-dimethylformamide, N,N-dimethylacetamide, N-methyl-2-pyrrolidinone or hexamethylphosphoric triamide; a sulfoxide such as dimethyl sulfoxide or sulfolane; water; or a mixture of the above solvents, and is preferably an alcohol or a mixture of an alcohol and water, and more preferably methanol, ethanol, methanol containing water or ethanol containing water.

The base employed can be, for example, an inorganic base, including an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; and an alkali metal fluoride such as sodium fluoride or potassium fluoride; an alkali metal alkoxide such as sodium methoxide, sodium ethoxide, potassium methoxide, potassium ethoxide, potassium t-butoxide or lithium methoxide; an alkali metal mercaptan such as sodium methylmercaptan or sodium ethylmercaptan; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably an alkali metal carbonate or alkali metal hydroxide, and more preferably potassium carbonate or sodium hydroxide.

The reaction temperature depends on the starting material and the reagent, and is between −50° C. and 100° C., and preferably between −20° C. and 50° C.

The reaction time depends on the reaction temperature, the starting material, the reagent and the kind of solvent employed, and is generally from 1 minute to 24 hours, and preferably from 5 minutes to 5 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(A-3)

This step is a step for introducing a substituent onto a mercapto group in the presence of a base or the like. When an acid chloride, an acid anhydride, a sulfanyl halide or an active ester is employed as a reagent, this step is carried out in the presence of a base (A-3a), when a carboxylic acid is employed, this step is carried out in the presence of a condensation agent (A-3b), and when a thiol is employed, this step is carried out in the presence of iodine or a base (A-3c)

(A-3a)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or di(ethylene glycol)dimethyl ether; a ketone such as acetone, methyl ethyl ketone, methyl isobutyl ketone, isophorone or cyclohexanone; an amide such as formamide, N,N-dimethylformamide, N,N-dimethylacetamide, N-methyl-2-pyrrolidinone or hexamethylphosphoric triamide; a sulfoxide such as dimethyl sulfoxide or sulfolane, and is preferably a halogenated hydrocarbon, a ketone or an amide, and more preferably N,N-dimethylformamide, N,N-dimethylacetamide, dichloromethane or acetone.

The base employed in the above reaction can be, for example, an inorganic base, including an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; and an alkali metal fluoride such as sodium fluoride or potassium fluoride; an alkali metal alkoxide such as sodium methoxide, sodium ethoxide, potassium methoxide, potassium ethoxide, potassium t-butoxide or lithium methoxide; an alkali metal mercaptan such as sodium methylmercaptan or sodium ethylmercaptan; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably an alkali metal carbonate, an alkali metal hydride or an organic base, and more preferably sodium hydride, potassium carbonate or triethylamine.

The reaction temperature depends on the starting material and the reagent, and is between −30° C. and 100° C., and preferably between −10° C. and 50° C.

The reaction time depends on the reaction temperature, the starting material, the reagent and the kind of solvent employed, and is generally from 5 minutes to 24 hours, and preferably from 15 minutes to 10 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(A-3b)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or di(ethylene glycol)dimethyl ether; a ketone such as acetone, methyl ethyl ketone, methyl isobutyl ketone, isophorone or cyclohexanone; an amide such as formamide, N,N-dimethylformamide, N,N-dimethylacetamide, N-methyl-2-pyrrolidinone or hexamethylphosphoric triamide; a sulfoxide such as dimethyl sulfoxide or sulfolane, and is preferably a halogenated hydrocarbon or an amide, and more preferably N,N-dimethylformamide, N,N-dimethylacetamide or dichloromethane.

The "condensation agent" employed can be, (i) a combination of a phosphate ester such as diethylphosphoryl cyanide, diphenylphosphoryl azide and diethyl cyanophosphonate and a base shown below;

(ii) a carbodiimide such as 1,3-dicyclohexylcarbodiimide (DCC), 1,3-diisopropylcarbodiimide and 1-(3-dimethylaminopropyl)-3-ethylcarbodiimide (WSC); a combination of said carbodiimide and a base described below; a combination of said carbodiimide and N-hydroxyimide such as N-hydroxysuccinimide, 1-hydroxybenzotriazole and N-hydroxy-5-norbornene-2,3-dicarboxyimide; and a combination of said carbodiimide or said N-hydroxyimide and a base described below;

(iii) a combination of a disulfide such as 2,2'-dipyridyl disulfide and 2,2'-dibenzothiazolyl disulfide and a phosphine such as triphenylphosphine and tributylphosphine;

(iv) a carbonate such as N,N'-disuccinimidyl carbonate, diethyl pyrocarbonate (DEPC), di-2-pyridyl carbonate and S,S'-bis(1-phenyl-1H-tetrazol-5-yl)dithiocarbonate;

(v) a phosphinic chloride such as N,N'-bis(2-oxo-3-oxazolidinyl)phosphinic chloride;

(vi) an oxalate such as N,N'-disuccinimidyl oxalate, N,N'-diphthalimide oxalate, N,N'-bis(5-norbornene-2,3-dicarboxyimidyl)oxalate, 1,1'-bis(benzotriazolyl)oxalate, 1,1'-bis(6-chlorobenzotriazolyl)oxalate and 1,1'-bis(6-trifluoromethylbenzotriazolyl)oxalate;

(vii) a combination of said phosphine and azodicarboxylate or azodicarboxyamide such as diethyl azodicarboxylate and 1,1'-(azodicarbonyl)dipiperidine;

(viii) a N-lower alkyl-5-arylisoxazolium-3'-sulfonate such as N-ethyl-5-phenylisoxazolium-3'-sulfonate;

(ix) a di-heteroaryl diselenide such as di-2-pyridyl diselenide;

(x) an arylsulfonyl triazolide such as p-nitrobenzenesulfonyl triazolide;

(xi) a 2-halo-1-lower alkylpyridinium halide such as 2-chloro-1-methylpyridinium iodide;

(xii) an imidazole such as 1,1'-oxalydiimidazole and N,N'-carbonyldiimidazole (CDI);

(xiii) a 3-lower alkyl-2-halogen-benzothiazolium fluoroborate such as 3-ethyl-2-chloro-benzothiazolium fluoroborate;

(xiv) a 3-lower alkyl-benzothiazol-2-selone such as 3-methyl-benzothiazole-2-selone;

(xv) a phosphate such as phenyl dichlorophosphate and polyphosphate ester;

(xvi) a halogenosulfonyl isocyanate such as chlorosulfonyl isocyanate;

(xvii) a halogenosilane such as trimethylsilyl chloride and triethylsilyl chloride;

(xviii) a combination of a lower alkanesulfonyl halide such as methanesulfonyl chloride and a base described below;

(xix) a N,N,N',N'-tetra-lower alkylhalogenoformamidium chloride such as N,N,N',N'-tetramethylchloroformamidium chloride; or (xx) a combination of a pyridinium salt (Mukaiyama reagent) such as 1-methyl-2-chloropyridinium chloride and 1-ethyl-2-bromopyridinium chloride and a base described below, and is preferably a carbodiimide, and more preferably 1-(3-dimethylaminopropyl)-3-ethylcarbodiimide or 1,3-dicyclohexylcarbodiimide.

The base employed can be, for example, an organic base such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline or N,N-diethylaniline.

The reaction temperature depends on the starting material and the reagent, and is between −30° C. and 100° C., and preferably between −10° C. and 50° C.

The reaction time depends on the reaction temperature, the starting material, the reagent and the kind of solvent employed, and is generally from 5 minutes to 24 hours, and preferably from 30 minutes to 10 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(A-3c)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or di(ethylene glycol)dimethyl ether; a ketone such as acetone, methyl ethyl ketone, methyl isobutyl ketone, isophorone or cyclohexanone; an amide such as formamide, N,N-dimethylformamide, N,N-dimethylacetamide, N-methyl-2-pyrrolidinone or hexamethylphosphoric triamide; a sulfoxide such as dimethyl sulfoxide or sulfolane, and is preferably an ether, and more preferably tetrahydrofuran.

The reaction temperature depends on the starting material and the reagent, and is between −30° C. and 100° C., and preferably between −10° C. and 50° C.

The reaction time depends on the reaction temperature, the starting material, the reagent and the kind of solvent employed, and is generally from 1 minute to 5 hours, and preferably from 5 minutes to 1 hour.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(A-4)

This step is achieved by hydrolysis of an ester group (A-4).

This step is carried out in a similar manner to that indicated hereinbefore in (A-2).

(A-5)

This step is achieved by converting a carboxyl group obtained in Step A-4 into an active ester, followed by reacting said active ester with a desired amino compound.

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or di(ethylene glycol)dimethyl ether; a ketone such as acetone, methyl ethyl ketone, methyl isobutyl ketone, isophorone or cyclohexanone; an amide such as formamide, N,N-dimethylformamide, N,N-dimethylacetamide, N-methyl-2-pyrrolidinone or hexamethylphosphoric triamide; a sulfoxide such as dimethyl sulfoxide or sulfolane, and is preferably a halogenated hydrocarbon or an amide, and more preferably N,N-dimethylformamide, N,N-dimethylacetamide or dichloromethane.

The reagent employed is not particularly restricted provided that it is used for an active ester formation, and, for example, can be isobutyl chloroformate.

The base employed can be, for example, an inorganic base, including an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate;

an alkali metal hydride such as lithium hydride, sodium hydride or potassium hydride; an alkali metal hydroxide such as sodium hydroxide, potassium hydroxide or lithium hydroxide; and an alkali metal fluoride such as sodium fluoride or potassium fluoride; an alkali metal alkoxide such as sodium methoxide, sodium ethoxide, potassium methoxide, potassium ethoxide, potassium t-butoxide or lithium methoxide; an alkali metal mercaptan such as sodium methylmercaptan or sodium ethylmercaptan; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably an alkali metal carbonate or organic base, and more preferably potassium carbonate or triethylamine.

The reaction temperature depends on the starting material and the reagent, and is between −30° C. and 100° C., and preferably between −10° C. and 50° C.

The reaction time depends on the reaction temperature, the starting material, the reagent and the kind of solvent employed, and is generally from 10 minutes to 24 hours, and preferably from 30 minutes to 10 hour.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(A-6)

This step is carried out by conducting a dehydrating condensation reaction between a carboxylic acid obtained in Step A-4 and an alcohol (A-6a) or by conducting an ester interchange reaction using an ester in the presence of an acid or a base directly without performing the process of step A-4 (A-6b).

(A-6a)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, n-propanol, isopropanol, n-butanol, isobutanol, t-butanol, isoamyl alcohol, diethylene glycol, glycerol, octanol, cyclohexanol or 2-methoxyethanol; an amide such as formamide, N,N-dimethylformamide, N,N-dimethylacetamide, N-methyl-2-pyrrolidinone or hexamethylphosphoric triamide; a sulfoxide such as dimethyl sulfoxide or sulfolane; and a mixture of an alcohol and the above solvent. However, when an alcohol is used as a solvent in the above reaction, an addition of the alcohol as a reagent is not necessary.

The acid employed can be, for example, an inorganic acid such as hydrochloric acid, hydrogen chloride, hydrobromic acid, sulfuric acid, perchloric acid or phosphoric acid; or a sulfonic acid such as methanesulfonic acid, p-toluenesulfonic acid or camphorsulfonic acid, and is preferably an inorganic acid, and more preferably hydrogen chloride.

The reaction temperature depends on the starting material and the reagent, is between −30° C. and 100° C., and preferably between −10° C. and 50° C.

The reaction time depends on the reaction temperature, the starting material, the reagent and the kind of solvent employed, and is generally from 10 minutes to 24 hours, and preferably from 30 minutes to 10 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

This step is carried out in a similar manner to that indicated hereinbefore in (A-3b).

(A-6b)

In this step, an alcohol corresponding to the desired alkoxy group is used as a solvent. When an acid is used, such acid employed can be, for example, an inorganic acid such as hydrochloric acid, hydrogen chloride, hydrobromic acid, sulfuric acid, perchloric acid or phosphoric acid; and a sulfonic acid such as methanesulfonic acid, p-toluenesulfonic acid or camphorsulfonic acid, and is preferably an inorganic acid, and more preferably hydrogen chloride.

When the base is used, such base employed can be, for example, an inorganic base, including an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; and an alkali metal fluoride such as sodium fluoride or potassium fluoride, and is preferably an alkali metal carbonate, and more preferably potassium carbonate.

The reaction temperature depends on the starting material and the reagent, and is between −30° C. and 100° C., and preferably between −10° C. and 50° C.

The reaction time depends on the reaction temperature, the starting material, the reagent and the kind of solvent employed, and is generally from 10 minutes to 24 hours, and preferably from 30 minutes to 10 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(A-7)

This step is carried out in a similar manner to that indicated hereinbefore in A-2. When an acid is used, trifluoroacetic acid or hydrogen chloride gas is used as a particularly preferred reagent.

When the desired compound is obtained as its geometrical isomer, the desired compound can be obtained by conducting the photoisomerization reaction described below.

The solvent employed can be, for example, an ester such as ethyl formate, ethyl acetate, propyl acetate, butyl acetate or diethyl carbonate; an ether such as diethyl ether, diisopropyl ether, tetrahydrofuran, dioxane, dimethoxyethane or di(ethylene glycol)dimethyl ether; an alcohol such as methanol, ethanol, n-propanol, isopropanol, n-butanol, isobutanol, t-butanol, isoamyl alcohol, diethylene glycol, glycerol, octanol, cyclohexanol or methyl cellosolve; a nitrile such as acetonitrile or isobutyronitrile; an amide such as formamide, N,N-dimethylformamide, N,N-dimethylacetamide, N-methyl-2-pyrroridone, N-methylpyrrolidinone or hexamethylphosphoric triamide; a sulfoxide such as dimethyl sulfoxide or sulfolane; water; or a mixture of these solvents, and is preferably water, an alcohol, a nitrile or a mixture of these solvents.

The light source employed is a low-pressure mercury lamp (having 20 W to 100 W, preferably 32 W).

The sensitizer employed can be, for example, benzophenone, fluorenone and anthraquinone.

This reaction can also be carried out by addition of an organic sulfur compound such as dimethyl disulfide, diethyl disulfide or diphenyl disulfide in order to accelerate the reaction.

The reaction temperature depends on the starting material and the reagent, and is between −20° C. and 100° C., and preferably between 0° C. and 50° C.

The reaction time depends on the reaction temperature, the starting material, the reagent and the kind of solvent employed, and is generally from 5 minutes to 8 hours, and preferably from 10 minutes to 3 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(A-8)

This step is a step for the conversion of a carboxyl group into a hydroxylamino group, and can easily be carried out according to procedures that are well known by a person having ordinary skill in the art (for example, methods described by A. Sekar Reddy, M. Suresh Kumar and G. Rabindra Reddy: Tetrahedron Letters 41 (2000) 6285-6288).

(Process B)

Process B is steps comprising the preparation of compound (V) by conducting a nucleophilic displacement reaction in the presence of a base using the compounds (III) that are well known or easily prepared from known compounds and the compounds (IV) obtained by the method C described hereinafter (B-1) and the preparation of compound (I) by conversion of a hydroxy group of the compound (V) (B-2). Furthermore, if necessary, in process B, deprotection of the protective group for a mercapto group (B-3), introduction of a substituent onto a mercapto group (B-4), hydrolysis of an ester group (B-5), conversion of a carboxyl group into an amide group (B-6), conversion of a carboxyl group into an ester group (B-7), deprotection of the protective group for an amino group (B-8) and conversion of a carboxyl group into a hydroxyamino group (B-9) can be also carried out. The steps from B-3 to B-9 can be conducted either before or after the steps B-1 and B-2, and the order of these steps can be selected according to circumstances by a person having ordinary skill in the art.

(B-1)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or di(ethylene glycol)dimethyl ether; a ketone such as acetone, methyl ethyl ketone, methyl isobutyl ketone, isophorone or cyclohexanone; an amide such as formamide, N,N-dimethylformamide, N,N-dimethylacetamide, N-methyl-2-pyrrolidinone or hexamethylphosphoric triamide; or a sulfoxide such as dimethyl sulfoxide or sulfolane, and is preferably a halogenated hydrocarbon or an amide, and more preferably N,N-dimethylformamide, N,N-dimethylacetamide or dichloromethane.

The base employed can be, for example, an inorganic base, including an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; and an alkali metal fluoride such as sodium fluoride or potassium fluoride; an alkali metal alkoxide such as sodium methoxide, sodium ethoxide, potassium methoxide, potassium ethoxide, potassium t-butoxide or lithium methoxide; an alkali metal mercaptan such as sodium methylmercaptan or sodium ethylmercaptan; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably an alkali metal carbonate or an organic base, and more preferably potassium carbonate or triethylamine.

The reaction temperature depends on the starting material and the reagent, and is between −30° C. and 100° C., and preferably between −10° C. and 50° C.

The reaction time depends on the reaction temperature, the starting material, the reagent and the kind of solvent employed, and is generally from 10 minutes to 48 hours, and preferably from 30 minutes to 24 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(B-2)

This step is carried out by using the Mitsunobu reaction (B-2a), using an amide-acetal reagent (B-2b), or using a substitution reaction after conversion of the hydroxyl group into a leaving group (B-2c)

(B-2a)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; or an ether such as diethyl ether, diisopropyl ether, tetrahydrofuran, dioxane, dimethoxyethane or di(ethylene glycol)dimethyl ether, and is preferably a halogenated hydrocarbon or an ether, and more preferably dichloromethane and tetrahydrofuran.

The reagent employed in the Mitsunobu reaction is not particularly restricted provided that it can generally be used for the Mitsunobu reaction, and, for example, is preferably a combination of an azo compound, including a di-lower-alkyl azodicarboxylate such as diethyl azodicarboxylate or diisopropyl azodicarboxylate or a heterocyclyl azodicarbonyl such as 1,1'-(azodicarbonyl)dipiperidine, and a phosphine, including a triarylphosphine such as triphenylphosphine or a tri-lower-alkylphosphine such as tri-n-butylphosphine, and more preferably a combination of a di-lower-alkyl azodicarboxylate and a triarylphosphine, and most preferably a combination of diethyl azodicarboxylate or diisopropyl azodicarboxylate and triphenylphosphine.

The reaction temperature depends on the starting material and the reagent, and is between −50° C. and 100° C., and preferably between −10° C. and 60° C.

The reaction time depends on the reaction temperature, the starting material, the reagent and the kind of solvent employed, and is generally from 10 minutes to 48 hours, and preferably from 30 minutes to 24 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(B-2b)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; or an amide such as formamide, N,N-dimethylformamide, N,N-dimethylacetamide, N-methyl-2-pyrrolidinone or hexamethylphosphoric triamide, and is preferably an aromatic hydrocarbon, and more preferably toluene.

The amide acetal reagent employed can be, for example, a group of general formula $(CH_3)_2NCH(OR')_2$ (wherein R' represents a $C_1$-$C_6$ alkyl group or a $C_7$-$C_{15}$ aralkyl group), and is preferably N,N-dimethylformamide dineopentyl acetal.

The reaction temperature depends on the starting material and the reagent, and is between −50° C. and 150° C., and preferably between −10° C. and 120° C.

The reaction time depends on the reaction temperature, the starting material, the reagent and the kind of solvent employed, and is generally from 1 minute to 24 hours, and preferably from 5 minutes to 5 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(B-2c)

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or di(ethylene glycol)dimethyl ether; a ketone such as acetone, methyl ethyl ketone, methyl isobutyl ketone, isophorone or cyclohexanone; a nitro compound such as nitroethane or nitrobenzene; a nitrile such as acetonitrile or isobutyronitrile; an amide such as formamide, N,N-dimethylformamide, N,N-dimethylacetamide, N-methyl-2-pyrrolidinone or hexamethylphosphoric triamide; or a sulfoxide such as dimethyl sulfoxide or sulfolane, and is preferably a halogenated hydrocarbon, an amide or a sulfoxide, and more preferably N,N-dimethylformamide, N,N-dimethylacetamide, dichloromethane or dimethyl sulfoxide.

The conversion into the leaving group is achieved by addition of a halogenation agent or sulfonylation agent to the reaction solution. The halogenation agent employed can be a carbon tetrahalide such as carbon tetrabromide or carbon tetrachloride, and in these cases, a phosphine is used as a reagent. Such phosphine can be, for example, a tri-$C_1$-$C_6$ alkylphosphine such as trimethylphosphine, triethylphosphine, tripropylphosphine, tributylphosphine, tripentylphosphine or trihexylphosphine; a tri-$C_6$-$C_{10}$ arylphosphine such as triphenylphosphine, triindenylphosphine or trinaphthylphosphine; or a tri-$C_6$-$C_{10}$ arylphosphine which may have $C_1$-$C_4$ alkyl group(s) as substituent(s), such as tolyldiphenylphosphine, tritolylphosphine, trimesitylphosphine, tributylphenylphosphine or tri-6-ethyl-2-naphthylphosphine, and is preferably a tri-$C_1$-$C_6$ alkylphosphine (particularly trimethylphosphine, triethylphosphine, tripropylphosphine or tributylphosphine) or a tri-$C_6$-$C_{10}$ arylphosphine (particularly triphenylphosphine, triindenylphosphine or trinaphthylphosphine), and more preferably a tri-$C_6$-$C_{10}$ arylphosphine (particularly triphenylphosphine). The sulfonylation agent employed can be, for example, a sulfonyl halide such as methanesulfonyl chloride, ethanesulfonyl chloride or tosyl chloride, and is preferably methanesulfonyl chloride.

The base employed can be, for example, an inorganic base containing an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; and an alkali metal fluoride such as sodium fluoride or potassium fluoride; an alkali metal alkoxide such as sodium methoxide, sodium ethoxide, potassium methoxide, potassium ethoxide, potassium t-butoxide or lithium methoxide; an alkali metal mercaptan such as sodium methylmercaptan or sodium ethylmercaptan; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably an alkali metal carbonate or an organic base, and more preferably potassium carbonate or triethylamine.

The reaction temperature depends on the starting material and the reagent, and is between −50° C. and 100° C., and preferably between −20° C. and 80° C.

The reaction time depends on the reaction temperature, the starting material, the reagent and the kind of solvent employed, and is generally from 30 minutes to 24 hours, and preferably from 1 hour to 10 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

From (B-3) to (B-9)

Each of these steps is carried out in a similar manner to that indicated in (A-2) to (A-8) hereinbefore, respectively.

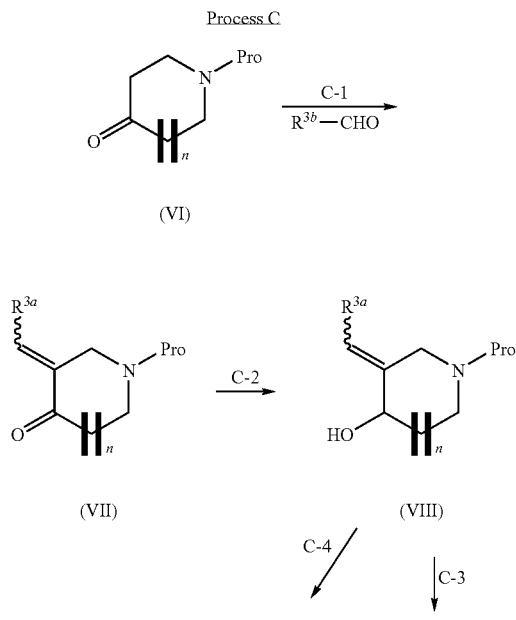

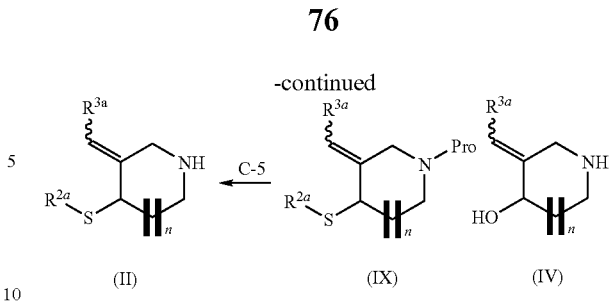

(Process C)

In the above, $R^{2a}$ and $R^{3a}$ have the same meanings as those indicated hereinbefore; $R^{3b}$ represents the same group as that indicated for $R^{3a}$ described hereinbefore; and Pro represents a protective group for an amino group.

The protective group for an amino group shown as Pro is the same as that indicated for $R^{3a}$.

Process C is hereinafter described in detail.

(C-1)

This step is a step for the preparation of compound (VII) by reacting compound (VI) that is well known or easily prepared from known compounds with a compound having of formula $R^{3b}$—CHO that is well known or can be easily prepared from known compounds, and is carried out by a route via the enamination (C-1a) or by the cross aldol reaction (C-1b).

(C-1a)

The base employed can be, for example, an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably pyrrolidine, piperidine or morpholine.

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an alcohol such as methanol, ethanol, n-propanol, isopropanol, n-butanol, isobutanol, t-butanol, isoamyl alcohol, diethylene glycol, glycerol, octanol, cyclohexanol or 2-methoxyethanol; or an ether such as diethyl ether, diisopropyl ether, tetrahydrofuran, dioxane, dimethoxyethane or di(ethylene glycol)dimethyl ether; and is preferably benzene, toluene or ethanol.

The reaction temperature depends on the starting material and the reagent, and is between 0° C. and 200° C., and preferably between 50° C. and 150° C.

The reaction time depends on the reaction temperature, the starting material, the reagent and the kind of solvent employed, and is generally from 30 minutes to 24 hours, and preferably from 1 hour to 10 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

When the compound having a hydroxyl group that is a reaction intermediate remains and the reaction is not completed, the desired product can be obtained by conducting furthermore a dehydration reaction in the presence of a base.

The solvent employed can be, for example, a halogenated hydrocarbon such as dichloromethane, chloroform, carbon tetrachloride, dichloroethane, chlorobenzene or dichlorobenzene; or an ether such as diethyl ether, diisopropyl ether, tetrahydrofuran, dioxane, dimethoxyethane or di(ethylene glycol)dimethyl ether, and is preferably a halogenated hydrocarbon, and more preferably dichloromethane.

The base employed can be an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably 1,8-diazabicyclo[5.4.0]undec-7-ene (DBU).

The reagent employed is not particularly restricted provided that it forms a leaving group by reacting with a hydroxyl group, and the conversion into the leaving group is achieved by addition of a halogenation agent or sulfonylation agent to a reaction solution. The halogenation agent employed can be, for example, a carbon tetrahalide such as carbon tetrabromide or carbon tetrachloride, and in these cases, a phosphine is used as a reagent. Such phosphine can be, for example, a tri-$C_1$-$C_6$ alkylphosphine such as trimethylphosphine, triethylphosphine, tripropylphosphine, tributylphosphine, tripentylphosphine or trihexylphosphine; a tri-$C_6$-$C_{10}$ arylphosphine such as triphenylphosphine, triindenylphosphine or trinaphthylphosphine; or tri-$C_6$-$C_{10}$ arylphosphine which may have $C_1$-$C_4$ alkyl group(s) as substituent(s), such as tolyldiphenylphosphine, tritolylphosphine, trimesitylphosphine, tributylphenylphosphine or tri-6-ethyl-2-naphthylphosphine, and is preferably a tri-$C_1$-$C_6$ alkylphosphine (particularly trimethylphosphine, triethylphosphine, tripropylphosphine or tributylphosphine) or a tri-$C_6$-$C_{10}$ arylphosphine (particularly triphenylphosphine, triindenylphosphine or trinaphthylphosphine), and more preferably a tri-$C_6$-$C_{10}$ arylphosphine (particularly triphenylphosphine). The sulfonylation agent employed can be, for example, a sulfonyl halide such as methanesulfonyl chloride, ethanesulfonyl chloride or tosyl chloride, and is preferably methanesulfonyl chloride.

The reaction temperature depends on the starting material and the reagent, and is between −50° C. and 100° C., and preferably between −20° C. and 80° C.

The reaction time depends on the reaction temperature, the starting material, the reagent and the kind of solvent employed, and is generally from 30 minutes to 24 hours, and preferably from 1 hour to 10 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(C-1b)

The base employed can be, for example, an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU); or an organometallic base such as butyllithium, lithium diisopropylamide, lithium bis(trimethylsilyl)amide, sodium bis(trimethylsilyl)amide or potassium bis(trimethylsilyl)amide, and is preferably lithium hexadisilazide, sodium hexadisilazide, potassium hexadisilazide or lithium diisopropylamide.

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an alcohol such as methanol, ethanol, n-propanol, isopropanol, n-butanol, isobutanol, t-butanol, isoamyl alcohol, diethylene glycol, glycerol, octanol, cyclohexanol or 2-methoxyethanol; or an ether such as diethyl ether, diisopropyl ether, tetrahydrofuran, dioxane, dimethoxyethane or di(ethylene glycol)dimethyl ether, and is preferably tetrahydrofuran.

The reaction temperature depends on the starting material and the reagent, and is between −100° C. and 20° C., and preferably between −78° C. and 0° C.

The reaction time depends on the reaction temperature, the starting material, the reagent and the kind of solvent employed, and is generally from 30 minutes to 24 hours, and preferably from 1 hour to 5 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

When the compound having a hydroxyl group that is a reaction intermediate is remained, a dehydration reaction can be carried out in a similar manner to that indicated in (C-1a).

(C-2)

This step is a step for the reduction of the carbonyl group of compound (VII) obtained in C-1 to a hydroxyl group.

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ether such as diethyl ether, diisopropyl ether, tetrahydrofuran, dioxane, dimethoxyethane or di(ethylene glycol)dimethyl ether; an alcohol such as methanol, ethanol, n-propanol, isopropanol, n-butanol, isobutanol, t-butanol, isoamyl alcohol, diethylene glycol, glycerol, octanol, cyclohexanol or 2-methoxyethanol; or a mixture of an alcohol and a halogenated hydrocarbon, and is preferably an alcohol, a mixture of an alcohol and a halogenated hydrocarbon, or an ether, and more preferably methanol, ethanol, tetrahydrofuran or a mixture of said alcohol and dichloromethane.

The reagent employed is not particularly restricted provided that it can be used for a reduction reaction of a carbonyl group to a hydroxyl group, and can be, for example, an aluminium hydride reagent and boron compound such as sodium borohydride or diborane, and is preferably sodium borohydride.

The reaction temperature depends on the starting material and the reagent, and is between −78° C. and 100° C., and preferably between 0° C. and 50° C.

The reaction time depends on the reaction temperature, the starting material, the reagent and the kind of solvent employed, and is generally from 10 minutes to 12 hours, and preferably from 30 minutes to 5 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

When $R^{3b}$ is different from $R^{3a}$, it can be possible to introduce a substituent onto an amino group, if necessary. In this case, after removing a protective group for the amino group in a similar manner to that described in (A-7), the introduction of the substituent can be carried out as described below.

The solvent employed can be, for example, an aromatic hydrocarbon such as benzene, toluene or xylene; a halogenated hydrocarbon such as dichloromethane, chloroform, carbon tetrachloride, dichloroethane, chlorobenzene or dichlorobenzene; an ester such as ethyl formate, ethyl acetate, propyl acetate, butyl acetate or diethyl carbonate; an ether such as diethyl ether, diisopropyl ether, tetrahydrofuran, dioxane, dimethoxyethane or di(ethylene glycol)dimethyl ether; a ketone such as acetone, methyl ethyl ketone, methyl isobutyl ketone, isophorone or cyclohexanone; an amide such as formamide, N,N-dimethylformamide, N,N-dimethylacetamide, N-methyl-2-pyrrolidinone or hexamethylphosphoric triamide; or a sulfoxide such as dimethyl sulfoxide or sulfolane, and is preferably a halogenated hydrocarbon or an amide, and more preferably N,N-dimethylformamide, N,N-dimethylacetamide or dichloromethane.

The reagent employed is not particularly restricted provided that it can be used in the displacement reaction by an amino group, and can be, for example, a reagent in which a leaving group such as a halogen atom or a sulfonyl group is bonded to a desired functional group.

The base employed can be, for example, an inorganic base, including an alkali metal carbonate such as sodium carbonate, potassium carbonate or lithium carbonate; an alkali metal hydrogencarbonate such as sodium hydrogencarbonate, potassium hydrogencarbonate or lithium hydrogencarbonate; an alkali metal hydride such as lithium hydride, sodium hydride or potassium hydride; an alkali metal hydroxide such as sodium hydroxide, potassium hydroxide or lithium hydroxide; and an alkali metal fluoride such as sodium fluoride or potassium fluoride; an alkali metal alkoxide such as sodium methoxide, sodium ethoxide, potassium methoxide, potassium ethoxide, potassium t-butoxide or lithium methoxide; an alkali metal mercaptan such as sodium methylmercaptan or sodium ethylmercaptan; or an organic base such as N-methylmorpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di-(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU), and is preferably potassium carbonate, sodium hydride or DBU.

The reaction temperature depends on the starting material and the reagent, and is between −30° C. and 150° C., and preferably between 0° C. and 100° C.

The reaction time depends on the reaction temperature, the starting material, the reagent and the kind of solvent employed, and is generally from 5 minutes to 48 hours, and preferably from 10 minutes to 15 hours.

After the reaction, the desired compound of this reaction can be obtained, for example, by concentration of the reaction mixture, addition to the mixture of an organic solvent immiscible with water such as ethyl acetate, washing the mixture with water, separation of the organic layer containing the desired compound, drying of the organic layer over anhydrous magnesium sulfate or the like, and then evaporation of the organic solvent to give the desired product.

The obtained product, if necessary, is further purified by conventional treatments, for example, by recrystallization, reprecipitation, silica gel column chromatography or the like.

(C-3)

This step is carried out in a similar manner to that indicated in A-7, and is carried out most preferably by using trifluoroacetic acid or acetic acid.

(C-4)

This step is carried out in a similar manner to that indicated in B-2.

(C-5)

This step is carried out in a similar manner to that indicated in C-3.

Compound (I) of the present invention, pharmacologically acceptable salts thereof or prodrugs thereof exert inhibiting activity in the inhibition of platelet aggregation. In addition, compound (I) of the present invention, pharmacologically acceptable salts thereof or prodrugs thereof exhibit excellent pharmacokinetics such as absorption, distribution, plasma half-life, and the like, and low toxicities in organs such as the kidney, liver and the like. Thus compound (I) of the present invention, pharmacologically acceptable salts thereof or prodrugs thereof are useful, for example as medicinal drugs, and particularly useful as therapeutic or prophylactic agents for various thrombotic diseases.

When a compound of the present invention is used as a prophylactic or therapeutic agent for diseases as described above, said compound having the general formula (I), or pharmacologically acceptable salts thereof or prodrugs thereof, can be administered alone or as a mixture with pharmaceutically acceptable excipients, diluents and the like, in various dosage forms such as tablets, capsules, granules, powders, syrups or the like for oral administration; and injections, suppositories, patches, external application or the like for parenteral administration.

Each of the above formulations can be prepared by well-known methods using additives for the formulation such as excipients (for example, organic excipients, including sugar derivatives such as lactose, sucrose, glucose, mannitol or sorbitol; starch derivatives such as corn starch, potato starch, α-starch or dextrin; cellulose derivatives such as crystalline cellulose; acacia; dextran; pullulan; and inorganic excipients including silicate derivatives such as light silicic acid anhydride, synthetic aluminium silicate, calcium silicate, or magnesium aluminate metasilicate; phosphate derivatives such as calcium hydrogenphosphate; carbonate derivatives such as calcium carbonate; or sulfate derivatives such as calcium sulfate), lubricants (for example, stearic acid; metal stearate derivatives such as calcium stearate or magnesium stearate; talc; colloidal silica; waxes such as beeswax or spermaceti; boric acid; adipic acid; sulfate derivatives such as sodium sulfate; glycol; fumaric acid; sodium benzoate; DL-leucine; lauryl sulfate derivatives such as sodium lauryl sulfate or magnesium lauryl sulfate; silicic acid derivatives such as silicic anhydride or silicic acid hydrate; or starch derivatives described above), binders (for example, hydroxypropylcellulose, hydroxypropylmethylcellulose, polyvinylpyrrolidone, macrogol or excipients as described above), disintegrants (for example, cellulose derivatives such as lower-substituted hydroxypropylcellulose, carboxymethylcellulose, calcium carboxymethylcellulose or internally cross-linked sodium carboxymethylcellulose; or chemically modified starch or cellulose derivatives such as carboxymethylstarch, sodium carboxymethylstarch, or cross-linked polyvinylpyrrolidone), emulsifiers (for example, colloidal clay such as bentonite or veegum; metal hydroxides such as magnesium hydroxide or aluminium hydroxide; anionic surfactants such as sodium lauryl sulfate or calcium stearate; cationic surfactants such as benzalkonium chloride; and non-ionic surfactants such as polyoxyethylene alkyl ethers, polyoxyethylene sorbitan fatty acid esters or sucrose esters of fatty acids), stabilizers (for example, para-hydroxybenzoic acid ester derivatives such as methylparaben or propylparaben; alcohol derivatives such as chlorobutanol, benzyl alcohol or phenylethyl alcohol; benzalkonium chloride; phenol derivatives such as phenol or cresol; thimerosal; dehydroacetic acid; or sorbic acid), corrigents (for example, sweeteners, souring agents, flavourings or the like which are conventionally used) and diluents.

The specific dose of a compound of the present invention will be varied according to the severity of the patient's symptoms, age and the like. For oral administration to a human adult the quantity of active ingredient in a unit dosage may be in the range of 1 mg (preferably 30 mg) to 2000 mg (preferably 1500 mg). A unit dose for intravenous administration may be in the range of 0.5 mg (preferably 5 mg) to 500 mg (preferably 250 mg) of a compound of the present invention. The unit dose may be administered to a human adult from 1 to 6 times per a day depending on the severity of the patient's symptoms.

For oral administration to a human adult the quantity of active ingredient in a unit dosage may be in the range of 0.016 mg/kg (preferably 0.5 mg/kg) to 33.3 mg/kg (preferably 25 mg/kg). A unit dose for intravenous administration may be in the range of 0.008 mg/kg (preferably 0.8 mg/kg) to 8.3 mg/kg (preferably 4.2 mg/kg) of a compound of the present invention. The unit dose may be administered to a human adult from 1 to 6 times per day depending on the severity of the patient's symptoms.

EXAMPLES

The present invention will be hereinafter described in more detail by way of the Examples, Test Examples and Preparation Examples below.

In the Examples, NMR spectral data of the compound with a hydrochloric salt form are presented as that of the hydrochloric salt-free derivative of the relevant compound when $CDCl_3$ is used as the solvent in the NMR measurement. The hydrochloric salt-free derivative can be prepared by treating a small amount of the compound with the hydrochloric acid salt form with aqueous sodium hydrogencarbonate solution, followed by extracting the generated salt-free derivative with ethyl acetate or dichloromethane.

Example 1

(E)-4-(Acetylsulfanyl)-3-benzylidene-1-[2-cyclopropyl-1-(2-fluorophenyl)-2-oxoethyl]piperidine (Exemplification Compound No. 1-2)

(a) (E)-3-Benzylidene-1-(triphenylmethyl)piperidin-4-one

To a solution of 1-(triphenylmethyl)piperidin-4-one (4.22 g) in benzene (50 ml) was added pyrrolidine (1.02 ml) at room temperature, and the resulting mixture was refluxed for 3 hours. After cooling to room temperature, benzaldehyde (1.26 ml) was added to the reaction mixture, and the resulting mixture was furthermore refluxed for 2 hours. After refluxing, the reaction mixture was diluted with ethyl acetate, washed with saturated aqueous sodium chloride solution and dried over anhydrous sodium sulfate. The solvent was removed in vacuo, and the residue was purified by chromatography on a silica gel column using a mixed solvent of ethyl acetate and hexane (1:3) as the eluent to afford the title compound (3.92 g, yield: 74%) as a yellow oil.
$^1$H NMR (400 MHz, $CDCl_3$) δ ppm: 2.67 (2H, bs), 2.77 (2H, t, J=6.0), 3.43 (2H, bs), 7.04-7.58 (20H, m).

(b) (E)-3-Benzylidene-1-(triphenylmethyl)piperidin-4-ol

To a solution of (E)-3-benzylidene-1-(triphenylmethyl)piperidin-4-one (3.91 g) in a mixed solvent of ethanol (30 ml) and dichloromethane (30 ml) was added sodium borohydride (0.34 g) under ice-cooling, and the resulting mixture was stirred at room temperature for 2 hours. After stirring, saturated aqueous ammonium chloride solution was added to the reaction mixture, and the resulting mixture was extracted with ethyl acetate. The extract was washed with saturated aqueous sodium chloride solution and dried over anhydrous sodium sulfate. The solvent was removed in vacuo, and the residue was purified by chromatography on a silica gel column using a mixed solvent of ethyl acetate and hexane (3:7) as the eluent to afford the title compound (2.61 g, yield: 66%) as a colourless amorphous solid.
$^1$H NMR (400 MHz, $CDCl_3$) δ ppm: 1.85-1.94 (1H, m), 1.99-2.20 (2H, m), 2.53-2.78 (2H, m), 3.39-3.57 (1H, m), 4.13-4.21 (1H, m), 6.68 (1H, s), 6.99-7.38 (20H, m).

(c) (E)-4-(Acetylsulfanyl)-3-benzylidenepiperidine hydrochloride

To a solution of triphenylphosphine (6.39 g) in tetrahydrofuran (100 ml) was added a solution of diisopropyl azodicarboxylate in toluene (13.11 ml) under ice-cooling, and the resulting mixture was stirred at the same temperature for 1 hour. Subsequently, to the reaction mixture was added dropwise a solution of (E)-3-benzylidene-1-(triphenylmethyl)piperidin-4-ol (5.26 g) and thioacetic acid (1.74 ml) in tetrahydrofuran (50 ml) at the same temperature, and the resulting mixture was furthermore stirred at room temperature for 2.5 hours. The reaction mixture was evaporated in vacuo, and the residue was purified by chromatography on a silica gel column using a mixed solvent of ethyl acetate and hexane (2:23) as the eluent to afford (E)-4-(acetylsulfanyl)-3-benzylidene-1-(triphenylmethyl)piperidine (containing impurities) as a pale yellow amorphous solid.

Subsequently, to a solution of the crude product thus obtained in dioxane (50 ml) was added a 4N solution of hydrogen chloride in dioxane (30 ml) under ice-cooling, and the resulting mixture was stirred at room temperature for 2 hours. The reaction mixture was evaporated in vacuo, and the residue was purified by chromatography on a silica gel column using a mixed solvent of methanol and dichloromethane (1:9) as the eluent to afford the title compound (1.28 g, yield: 38%) as a yellow solid.

$^1$H NMR (400 MHz, CDCl$_3$) δ ppm: 2.02-2.11 (1H, m), 2.38 (3H, s), 2.49-2.62 (1H, m), 3.07-3.19 (1H, m), 3.28-3.39 (1H, m), 3.63 (1H, d, J=14.0), 4.10 (1H, d, J=14.0), 4.60 (1H, m), 6.96 (1H, s), 7.19-7.37 (5H, m).

(d) (E)-4-(Acetylsulfanyl)-3-benzylidene-1-[2-cyclopropyl-1-(2-fluorophenyl)-2-oxoethyl]piperidine To a solution of (E)-4-(acetylsulfanyl)-3-benzylidene-piperidine hydrochloride and 2-bromo-2-(2-fluorophenyl)-1-cyclopropylethanone (713 mg) in N,N-dimethylformamide (10 ml) was added potassium carbonate (256 mg) under ice-cooling, and the resulting mixture was stirred at room temperature for 2 hours. The reaction mixture was diluted with ethyl acetate and washed with saturated aqueous sodium chloride solution. The organic layer was dried over anhydrous sodium sulfate. The solvent was removed in vacuo, and the residue was purified by chromatography on a silica gel column using a mixed solvent of ethyl acetate and hexane (3:17) as the eluent to afford the title compound (531 mg, yield: 68%) as a yellow oil.

$^1$H NMR (400 MHz, CDCl$_3$) δ ppm: 0.38-0.95 (4H, m), 1.82-1.93 (1H, m), 2.12-2.35 (2H, m), 2.33 (3H, s), 2.38-2.47 and 2.56-2.64 (total 1H, each m), 2.72-2.87 (1H, m), 2.98 and 3.08 (total 1H, each d, J=13.0), 3.57 and 3.72 (total 1H, each d, J=13.0), 4.51 (1H, m), 4.57 and 4.64 (total 1H, each s), 6.65 and 6.67 (total 1H, each s), 7.01-7.30 (8H, m), 7.33-7.43 (1H, m);

MS (FAB) m/z: 424 (M+H)$^+$.

Example 2

(E)-3-Benzylidene-1-[2-cyclopropyl-1-(2-fluorophenyl)-2-oxoethyl]-4-sulfanylpiperidine hydrogen trifluoroacetate (Exemplification Compound No. 1-1)

Into a solution of (E)-4-(acetylsulfanyl)-3-benzylidene-1-[2-cyclopropyl-1-(2-fluorophenyl)-2-oxoethyl]piperidine (126 mg) in ethanol (10 ml) was bubbled hydrogen chloride under ice-cooling, and the resulting mixture was stirred at room temperature under tightly sealed condition overnight. The reaction mixture was evaporated in vacuo, and the residue was purified using a preparative HPLC [YMC-Pack ODS-A; YMC, mobile phase: acetonitrile/0.026N aqueous trifluoroacetic acid solution (55:45, v/v)] to afford the title compound (121 mg, yield: 82%) as a colourless oil.

$^1$H NMR (400 MHz, CDCl$_3$) δ ppm: 0.42-0.95 (4H, m), 1.76-1.86 (1H, m), 2.10-2.37 (2H, m), 2.58-2.92 (2H, m), 3.36 (1H, d, J=12.5), 3.44 (1H, d, J=12.5), 3.92 and 3.96 (total 1H, each t, J=6.0), 4.61 and 4.66 (total 1H, each s), 6.62 (1H, s), 6.94-7.25 (9H, m);

MS (FAB) m/z: 382 (M+H)$^+$.

Example 3

(E)-4-(Acetylsulfanyl)-1-[2-cyclopropyl-1-(2-fluorophenyl)-2-oxoethyl]-3-[(thiophen-2-yl)methylidene]piperidine (Exemplification Compound No. 1-6)

(a) (E)-3-[(Thiophen-2-yl)methylidene]-1-(triphenylmethyl)piperidin-4-one

The title compound was synthesized in a yield of 74% as a yellow amorphous solid using thiophene-2-carbaldehyde instead of benzaldehyde by conducting the reaction similar to that mentioned in Example 1 (a).

$^1$H NMR (400 MHz, CDCl$_3$) δ ppm: 2.67 (2H, bs), 2.76 (2H, t, J=6.0), 3.52 (2H, bs), 7.06 (1H, dd, J=5.0, 3.5), 7.15-7.21 (3H, m), 7.23 (1H, d, J=3.5), 7.25-7.32 (6H, m), 7.44 (1H, d, J=5.0), 7.52-7.58 (6H, m), 7.76 (1H, s).

(b) (E)-3-[(Thiophen-2-yl)methylidene]-1-(triphenylmethyl) piperidin-4-ol

The title compound was synthesized in a yield of 84% as a colourless amorphous solid using (E)-3-[(thiophen-2-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.86-1.97 (1H, m), 2.07-2.21 (2H, m), 2.65-2.84 (2H, m), 3.53-3.76 (1H, m), 4.15-4.22 (1H, m), 6.69 (1H, s), 6.83 (1H, d, J=3.5), 6.90 (1H, dd, J=5.0, 3.5), 7.08-7.21 (10H, m), 7.39-7.45 (6H, m).

(c) (E)-4-(Acetylsulfanyl)-3-[(thiophen-2-yl)methylidene]piperidine hydrochloride The title compound was synthesized in a yield of 12% as a colourless amorphous solid using (E)-3-[(thiophen-2-yl)methylidene]-1-(triphenylmethyl)piperidin-4-ol instead of (E)-3-benzylidene-1-(triphenylmethyl)piperidin-4-ol by conducting successively reactions similar to those mentioned in Example 1 (c).

$^1$H NMR (500 MHz, CDCl$_3$) δ ppm: 2.01-2.09 (1H, m), 2.36 (3H, s), 2.53-2.63 (1H, m), 3.10-3.19 (1H, m), 3.38-3.45 (1H, m), 3.71 (1H, d, J=14.5), 4.49 (1H, d, J=14.5), 4.60 (1H, m), 6.93 (1H, s), 6.99 (1H, dd, J=5.0, 3.5), 7.06 (1H, d, J=3.5), 7.31 (1H, d, J=5.0).

(d) (E)-4-(Acetylsulfanyl)-1-[2-cyclopropyl-1-(2-fluorophenyl)-2-oxoethyl]-3-[(thiophen-2-yl)methylidene]piperidine The title compound was synthesized in a yield of 29% as a yellow oil using (E)-4-(acetylsulfanyl)-3-[(thiophen-2-yl)methylidene]piperidine hydrochloride instead of (E)-4-(acetylsulfanyl)-3-benzylidenepiperidine hydrochloride by conducting the reaction similar to that mentioned in Example 1 (d)

$^1$H NMR (500 MHz, CDCl$_3$) δ ppm: 0.63-1.02 (4H, m), 1.84-1.92 (1H, m), 2.21-2.36 (2H, m), 2.31 (3H, s), 2.43-2.49 and 2.56-2.63 (total 1H, each m), 2.75-2.81 and 2.82-2.88 (total 1H, each m), 3.04 and 3.17 (total 1H, each d, J=13.0), 3.89 and 3.97 (total 1H, each d, J=13.0), 4.52 (1H, m), 4.70 and 4.72 (total 1H, each s), 6.69 and 6.70 (total 1H, each s), 6.84-6.96 (2H, m), 7.05-7.22 (3H, m), 7.27-7.35 (1H, m), 7.39-7.44 (1H, m);

IR (Liquid film, cm$^{-1}$): 1693, 1488.

Example 4

(E)-1-[2-Cyclopropyl-1-(2-fluorophenyl)-2-oxoethyl]-4-sulfanyl-3-[(thiophen-2-yl)methylidene]piperidine hydrochloride (Exemplification Compound No. 1-6)

The title compound was synthesized in a yield of 34% as a yellow oil using (E)-4-(acetylsulfanyl)-1-[2-cyclopropyl-1-(2-fluorophenyl)-2-oxoethyl]-3-[(thiophen-2-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (500 MHz, CDCl$_3$) δ ppm: 0.63-1.08 (4H, m), 1.76-1.85 (1H, m), 2.16-2.37 (2H, m), 2.62-2.93 (2H, m), 3.46-3.75 (2H, m), 3.92-3.97 (1H, m), 4.74 and 4.76 (total 1H, each s), 6.63 and 6.64 (total 1H, each s), 6.84-6.86 (2H, m), 7.05-7.23 (3H, m), 7.25-7.34 (1H, m), 7.38-7.46 (1H, m);

IR (Thin film, cm$^{-1}$): 2559, 1713, 1670.

Example 5

(E)-4-(Acetylsulfanyl)-1-[2-cyclopropyl-1-(2-fluorophenyl)-2-oxoethyl]-3-[(thiophen-3-yl)methylidene]piperidine (Exemplification Compound No. 1-10)

(a) (E)-3-[(Thiophen-3-yl)methylidene]-1-(triphenylmethyl)piperidin-4-one

The title compound was synthesized in a yield of 90% as a yellow amorphous solid using thiophene-3-carbaldehyde instead of benzaldehyde by conducting the reaction similar to that mentioned in Example 1 (a).

$^1$H NMR (400 MHz, CDCl$_3$) δ ppm: 2.68 (2H, bs), 2.75 (2H, t, J=5.5), 3.47 (2H, bs), 6.99 (1H, d, J=5.0), 7.12-7.34 (11H, m), 7.45-7.57 (7H, m).

(b) (E)-3-[(Thiophen-3-yl)methylidene]-1-(triphenylmethyl)piperidin-4-ol

The title compound was synthesized in a yield of 76% as a colourless amorphous solid using (E)-3-[(thiophen-3-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.84-1.96 (1H, m), 2.08-2.19 (2H, m), 2.63-2.78 (2H, m), 3.41-3.66 (1H, m), 4.12-4.20 (1H, m), 6.56 (1H, s), 6.91-6.95 (2H, m), 7.06-7.21 (10H, m), 7.34-7.41 (6H, m).

(c) (E)-4-(Acetylsulfanyl)-3-[(thiophen-3-yl)methylidene]piperidine hydrochloride The title compound was synthesized in a yield of 16% as a pale yellow amorphous solid using (E)-3-[(thiophen-3-yl)methylidene]-1-(triphenylmethyl)piperidin-4-ol instead of (E)-3-benzylidene-1-(triphenylmethyl)piperidin-4-ol by conducting successively reactions similar to those mentioned in Example 1 (c).

$^1$H NMR (400 MHz, CDCl$_3$) δ ppm: 2.00-2.08 (1H, m), 2.37 (3H, s), 2.49-2.58 (1H, m), 3.08-3.19 (1H, m), 3.32-3.41 (1H, m), 3.65 (1H, d, J=14.0), 4.24 (1H, d, J=14.0), 4.57 (1H, m), 6.81 (1H, s), 7.04 (1H, d, J=5.0), 7.28-7.31 (2H, m).

(d) (E)-4-(Acetylsulfanyl)-1-[2-cyclopropyl-1-(2-fluorophenyl)-2-oxoethyl]-3-[(thiophen-3-yl)methylidene]piperidine The title compound was synthesized in a yield of 42% as a yellow oil using (E)-4-(acetylsulfanyl)-3-[(thiophen-3-yl)methylidene]piperidine hydrochloride instead of (E)-4-(acetylsulfanyl)-3-benzylidenepiperidine hydrochloride by conducting the reaction similar to that mentioned in Example 1 (d)

$^1$H NMR (400 MHz, CDCl$_3$) δ ppm: 0.55-1.02 (4H, m), 1.82-1.93 (1H, m), 2.13-2.36 (2H, m), 2.32 (3H, s), 2.40-2.49 and 2.55-2.64 (total 1H, each m), 2.72-2.80 and 2.81-2.88 (total 1H, each m), 2.99 and 3.11 (total 1H, each d, J=13.0), 3.70 and 3.80 (total 1H, each d, J=13.0), 4.49 (1H, m), 4.64 and 4.69 (total 1H, each s), 6.54 and 6.56 (total 1H, each s), 6.85-7.00 (2H, m), 7.03-7.44 (5H, m);

IR (Thin film, cm$^{-1}$): 1694, 1488.

Example 6

(E)-1-[2-Cyclopropyl-1-(2-fluorophenyl)-2-oxoethyl]-4-sulfanyl-3-[(thiophen-3-yl)methylidene]piperidine hydrochloride (Exemplification Compound No. 1-9)

The title compound was synthesized in a yield of 55% as a yellow amorphous solid using (E)-4-(acetylsulfanyl)-1-[2-cyclopropyl-1-(2-fluorophenyl)-2-oxoethyl]-3-[(thiophen-3-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (400 MHz, CDCl$_3$) δ ppm: 0.55-1.01 (4H, m), 1.74-1.85 (1H, m), 2.08-2.37 (2H, m), 2.57-2.92 (2H, m), 3.38-3.57 (2H, m), 3.85-3.97 (1H, m), 4.68 and 4.72 (total 1H, each s), 6.51 (1H, s), 6.86-7.45 (7H, m);

IR (KBr, cm$^{-1}$): 2519, 1712.

Example 7

(E)-4-(Acetylsulfanyl)-1-[2-cyclopropyl-1-(2-fluorophenyl)-2-oxoethyl]-3-[(furan-2-yl)methylidene]piperidine (Exemplification Compound No. 1-14)

(a) (E)-3-[(Furan-2-yl)methylidene]-1-(triphenylmethyl)piperidin-4-one

The title compound was synthesized in a yield of 58% as a pale yellow amorphous solid using 2-furaldehyde instead of benzaldehyde by conducting the reaction similar to that mentioned in Example 1 (a).

$^1$H NMR (400 MHz, CDCl$_3$) δ ppm: 2.65 (2H, bs), 2.74 (2H, t, J=6.0), 3.57 (2H, bs), 6.40-6.42 (2H, m), 7.14-7.22 (3H, m), 7.25-7.31 (6H, m), 7.31-7.33 (1H, m), 7.49-7.59 (7H, m).

(b) (E)-3-[(Furan-2-yl)methylidene]-1-(triphenylmethyl)piperidin-4-ol

The title compound was synthesized in a yield of 72% as a pale yellow amorphous solid using (E)-3-[(furan-2-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.82-1.94 (2H, m), 1.95-2.07 (1H, m), 2.08-2.18 (1H, m), 2.72-2.83 (2H, m), 4.05-4.12 (1H, m), 6.16 (1H, d, J=3.0), 6.29-6.32 (1H, m), 6.37 (1H, bs), 7.09-7.17 (3H, m), 7.18-7.24 (6H, m), 7.41-7.53 (7H, m).

(c) (E)-3-[(Furan-2-yl)methylidene]piperidin-4-ol hydrogen acetate

To a solution of (E)-3-[(furan-2-yl)methylidene]-1-(triphenylmethyl)piperidin-4-ol (3.70 g) in dichloromethane (75 ml) was added acetic acid (10 ml) under ice-cooling, and the resulting mixture was stirred at 60° C. for 3 hours. After stirring, acetic acid (10 ml) was added to the reaction mixture, and the resulting mixture was furthermore stirred at 60° C. for 1.5 hours. The reaction mixture was evaporated in vacuo, and the residue was purified by chromatography on a silica gel column using a mixed solvent of methanol and dichloromethane (1:19 to 1:9) as the eluent to afford the title compound (2.81 g, yield: quantitative) as a pale brown solid.

$^1$H NMR (400 MHz, CDCl$_3$) δ ppm: 1.29-1.42 (1H, m), 1.76-1.87 (1H, m), 2.48-2.62 (1H, m), 2.81-2.90 (1H, m), 3.05 (1H, d, J=13.0), 3.96-4.02 (1H, m), 4.10 (1H, d, J=13.0), 6.18 (1H, bs), 6.26-6.28 (1H, m), 6.41-6.43 (1H, m), 7.52-7.54 (1H, m).

(d) (E)-1-[2-Cyclopropyl-1-(2-fluorophenyl)-2-oxoethyl]-3-[(furan-2-yl)methylidene]piperidin-4-ol To a solution of (E)-3-[(furan-2-yl)methylidene]piperidin-4-ol hydrogen acetate (2.81 g) and 2-bromo-2-(2-fluorophenyl)-1-cyclopropylethanone (2.71 g) in N,N-dimethylformamide (60 ml) was added triethylamine (1.22 ml) under ice-cooling, and the resulting mixture was stirred at room temperature for 1 hour. After stirring, water was added to the reaction mixture, and the resulting mixture was extracted with ethyl acetate. The extract was washed with saturated aqueous sodium chloride solution, and the organic layer was dried over anhydrous sodium sulfate. The solvent was removed in vacuo, and the residue was purified by chromatography on a silica gel column using a mixed solvent of ethyl acetate and hexane (3:7 to 1:1) as the eluent to afford the title compound (2.30 g, yield: 74%) as a pale yellow amorphous solid.

$^1$H NMR (400 MHz, CDCl$_3$) δ ppm: 0.70-1.11 (4H, m), 1.61-1.86 (2H, m), 2.23-2.32 (1H, m), 2.43-2.60 (1H, m), 2.84-2.95 (1H, m), 3.20 and 3.36 (total 1H, each d, J=13.0), 3.96 and 4.01 (total 1H, each d, J=13.0), 4.19-4.25 (1H, m), 4.73 (1H, s), 6.15-6.22 (1H, m), 6.30-6.36 (2H, m), 7.03-7.19 (2H, m), 7.20-7.37 (2H, m), 7.42-7.51 (1H, m).

(e) (E)-4-(Acetylsulfanyl)-1-[2-cyclopropyl-1-(2-fluorophenyl)-2-oxoethyl]-3-[(furan-2-yl)methylidene]piperidine To a solution of (E)-1-[2-cyclopropyl-1-(2-fluorophenyl)-2-oxoethyl]-3-[(furan-2-yl)methylidene]piperidin-4-ol (2.30 g) in toluene (50 ml) were added thioacetic acid (0.92 ml) and N,N-dimethylformamide dineopentyl acetal (3.61 g) under ice-cooling, and the resulting mixture was stirred at room temperature for 1 hour. After stirring, saturated aqueous sodium hydrogencarbonate solution was added to the reaction mixture, and the resulting mixture was extracted with ethyl acetate. The extract was washed with saturated aqueous sodium chloride solution, and the organic layer was dried over anhydrous sodium sulfate. The solvent was removed in vacuo, and the residue was purified by chromatography on a silica gel column using a mixed solvent of ethyl acetate and hexane (1:19 to 1:9) as the eluent to afford the title compound (0.58 g, yield: 22%) as an orange-coloured oil.

$^1$H NMR (400 MHz, CDCl$_3$) δ ppm: 0.69-1.09 (4H, m), 1.81-1.92 (1H, m), 2.21-2.38 (2H, m), 2.31 (3H, s), 2.38-2.48 and 2.52-2.63 (total 1H, each m), 2.75-2.81 and 2.82-2.89 (total 1H, each m), 3.22 and 3.04 (total 1H, each d, J=13.0), 4.09-4.20 (1H, m), 4.46-4.51 (1H, m), 4.69 and 4.72 (total 1H, each s), 6.15 and 6.21 (total 1H, each d, J=3.0), 6.28-6.35 (1H, m), 6.35 and 6.36 (total 1H, each s), 7.04-7.19 (2H, m), 7.24-7.37 (2H, m), 7.43-7.51 (1H, m);

MS (FAB) m/z: 414 (M+H)$^+$.

Example 8

(E)-1-[2-Cyclopropyl-1-(2-fluorophenyl)-2-oxoethyl]-3-[(furan-2-yl)methylidene]-4-sulfanylpiperidine (Exemplification Compound No. 1-13)

To a solution of (E)-4-(acetylsulfanyl)-1-[2-cyclopropyl-1-(2-fluorophenyl)-2-oxoethyl]-3-[(furan-2-yl)methylidene]piperidine (100 mg) in methanol (2.5 ml) was added potassium carbonate (50 mg) under ice-cooling, and the resulting mixture was stirred at room temperature for 15 minutes. After stirring, water was added to the reaction mixture, and the resulting mixture was extracted with dichloromethane. The extract was washed with saturated aqueous sodium chloride solution, and the organic layer was dried over anhydrous sodium sulfate. The solvent was removed in vacuo, and the residue was purified using a preparative HPLC [YMC-Pack ODS-A; YMC, mobile phase: a mixture of 70% methanol/water containing acetic acid (0.20%) and triethylamine (0.45%) (70:30, v/v)]. The eluted fraction containing the reaction product was extracted with ethyl acetate, and the organic layer was dried over anhydrous sodium sulfate and evaporated in vacuo to afford the title compound (40 mg, yield: 45%) as pale brown crystals.

$^1$H NMR (400 MHz, CDCl$_3$) δ ppm: 0.68-1.08 (4H, m), 1.75-1.83 (1H, m), 2.20-2.35 (2H, m), 2.61-2.73 (1H, m), 2.74-2.91 (1H, m), 3.41-3.44 (1H, m), 3.54-3.93 (2H, m), 4.74 and 4.78 (total 1H, each s), 6.15 and 6.21 (total 1H, each d, J=3.0), 6.28-6.36 (2H m), 7.05-7.22 (2H, m), 7.25-7.36 (2H, m), 7.41-7.52 (1H, m);

MS (FAB) m/z: 372 (M+H)$^+$.

Example 9

(E)-4-(Acetylsulfanyl)-1-[2-cyclopropyl-1-(2-fluorophenyl)-2-oxoethyl]-3-[(furan-3-yl)methylidene]piperidine (Exemplification Compound No. 1-18)

(a) (E)-3-[(Furan-3-yl)methylidene]-1-(triphenylmethyl)piperidin-4-one

The title compound was synthesized in a yield of 46% as a yellow amorphous solid using 3-furaldehyde instead of benzaldehyde by conducting the reaction similar to that mentioned in Example 1 (a)

$^1$H NMR (400 MHz, CDCl$_3$) δ ppm: 2.56 (2H, bs), 2.74 (2H, t, J=5.5), 3.35 (2H, bs), 6.27 (1H, d, J=1.5), 7.15-7.22 (3H, m), 7.25-7.33 (6H, m), 7.36 (1H, t, J=1.5), 7.38 (1H, m), 7.40 (1H, s), 7.48-7.57 (6H, m).

(b) (E)-3-[(Furan-3-yl)methylidene]-1-(triphenylmethyl)piperidin-4-ol

The title compound was synthesized in a yield of 44% as a pale yellow amorphous solid using (E)-3-[(furan-3-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.82-1.94 (1H, m), 2.07-2.21 (2H, m), 2.58-2.71 (2H, m), 3.33-3.55 (1H, m), 4.15 (1H, m), 6.23 (1H, m), 6.33 (1H, s), 7.08-7.25 (10H, m), 7.30 (1H, t, J=1.5), 7.36-7.50 (6H, m).

(c) (E)-4-(Acetylsulfanyl)-3-[(furan-3-yl)methylidene]piperidine hydrochloride The title compound was synthesized in a yield of 7% as a colourless amorphous solid using (E)-3-[(furan-3-yl)methylidene]-1-(triphenylmethyl)piperidin-4-ol instead of (E)-3-benzylidene-1-(triphenylmethyl)piperidin-4-ol by conducting successively reactions similar to those mentioned in Example 1 (c).

$^1$H NMR (500 MHz, CDCl$_3$) δ ppm: 2.02-2.09 (1H, m), 2.37 (3H, s), 2.49-2.59 (1H, m), 3.15-3.23 (1H, m), 3.38-3.46 (1H, m), 3.66 (1H, d, J=14.5), 4.25 (1H, d, J=14.5), 4.57 (1H, t, J=4.0), 6.46 (1H, m), 6.63 (1H, s), 7.40 (1H, s), 7.54 (1H, s).

(d) (E)-4-(Acetylsulfanyl)-1-[2-cyclopropyl-1-(2-fluorophenyl)-2-oxoethyl]-3-[(furan-3-yl)methylidene]piperidine The title compound was synthesized in a yield of 88% as a yellow oil using (E)-4-(acetylsulfanyl)-3-[(furan-3-yl)methylidene]piperidine hydrochloride instead of (E)-4-(acetylsulfanyl)-3-benzylidenepiperidine hydrochloride by conducting the reaction similar to that mentioned in Example 1 (d)

$^1$H NMR (500 MHz, CDCl$_3$) δ ppm: 0.64-1.03 (4H, m), 1.81-1.90 (1H, m), 2.13-2.35 (2H, m), 2.30 and 2.31 (total 3H, each s), 2.40-2.48 and 2.53-2.61 (total 1H, each m), 2.70-2.77 and 2.79-2.86 (total 1H, each m), 2.93 and 3.08 (total 1H, each d, J=13.0), 3.66 and 3.73 (total 1H, each d, J=13.0), 4.48 (1H, m), 4.68 and 4.72 (total 1H, each s), 6.21 and 6.32 (total 1H, each s), 6.33 and 6.35 (total 1H, each s), 7.05-7.17 (2H, m), 7.24-7.35 (3H, m), 7.36-7.44 (1H, m);

MS (FAB) m/z: 414 (M+H)$^+$.

Example 10

(E)-1-[2-Cyclopropyl-1-(2-fluorophenyl)-2-oxoethyl]-3-[(furan-3-yl)methylidene]-4-sulfanylpiperidine hydrogen trifluoroacetate (Exemplification Compound No. 1-17)

The title compound was synthesized in a yield of 56% as a yellow oil using (E)-4-(acetylsulfanyl)-1-[2-cyclopropyl-1-(2-fluorophenyl)-2-oxoethyl]-3-[(furan-3-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (500 MHz, CDCl$_3$) δ ppm: 0.65-1.07 (4H, m), 1.72-1.82 (1H, m), 2.10-2.52 (3H, m), 2.58-2.90 (2H, m), 3.34-3.50 (1H, m), 3.90 (1H, m), 4.72 and 4.75 (total 1H, each s), 6.23 and 6.28 (total 1H, each s), 6.30 and 6.31 (total 1H, each s), 7.04-7.18 (2H, m), 7.22-7.48 (4H, m);

MS (FAB) m/z: 372 (M+H)$^+$.

Example 11

(E)-4-(Acetylsulfanyl)-1-[2-cyclopropyl-1-(2-fluorophenyl)-2-oxoethyl]-3-{[1H-pyrazol-3(5)-yl]methylidene}piperidine dihydrochloride (Exemplification Compound No. 1-22)

(a) (E)-3-{[1-(t-Butoxycarbonyl)-1H-pyrazol-3-yl]methylidene}-1-(triphenylmethyl)piperidin-4-one The title compound was synthesized in a yield of 39% as a yellow amorphous solid using 1-(t-butoxycarbonyl)-1H-pyrazole-3-carbaldehyde instead of benzaldehyde by conducting the reaction similar to that mentioned in Example 1 (a).

$^1$H NMR (500 MHz, CDCl$_3$) δ ppm: 1.60 (9H, s), 2.65 (2H, bs), 2.76 (2H, t, J=6.0), 3.70 (2H, bs), 6.28 (1H, d, J=3.0), 7.13-7.18 (3H, m), 7.22-7.28 (6H, m), 7.41 (1H, s), 7.48-7.55 (6H, m), 8.02 (1H, d, J=3.0).

(b) (E)-3-{[1-(t-Butoxycarbonyl)-1H-pyrazol-3-yl]methylidene}-1-(triphenylmethyl)piperidin-4-ol The title compound was synthesized in a yield of 99% as a colourless amorphous solid using (E)-3-{[1-(t-butoxycarbonyl)-1H-pyrazol-3-yl]methylidene}-1-(triphenylmethyl)piperidin-4-one instead of (E)-3-benzylidene-1-(triphenylmethyl)piperidin-4-one by conducting the reaction similar to that mentioned in Example 1 (b)

$^1$H NMR (500 MHz, CDCl$_3$) δ ppm: 1.59 (9H, s), 1.86-1.94 (1H, m), 2.11-2.18 (2H, m), 2.76-2.89 (2H, m), 3.25-3.36 (1H, m), 4.11-4.18 (1H, m), 6.22 (1H, d, J=3.0), 6.53 (1H, s), 7.05-7.18 (9H, m), 7.36-7.43 (6H, m), 7.99 (1H, d, J=3.0).

(c) (E)-4-(Acetylsulfanyl)-3-{[1-(t-butoxycarbonyl)-1H-pyrazol-3-yl]methylidene}piperidine hydrochloride To a solution of (E)-3-{[1-(t-butoxycarbonyl)-1H-pyrazol-3-yl]methylidene}-1-(triphenylmethyl)piperidin-4-ol (15.0 g) in dichloromethane (300 ml) were added successively methanesulfonyl chloride (2.5 ml) and triethylamine (4.5 ml) under ice-cooling, and the resulting mixture was stirred at room temperature for 1 hour and then evaporated in vacuo. Subsequently, to a solution of the residue thus obtained in dimethyl sulfoxide (200 ml) was added potassium thioacetate (16.5 g) at room temperature, and the resulting mixture was stirred at 50° C. for 30 minutes. After stirring, water was added to the reaction mixture, and the resulting mixture was extracted with ethyl acetate. The extract was washed with saturated aqueous sodium chloride solution, and the organic layer was dried over anhydrous magnesium sulfate. The solvent was removed, and the residue was purified by chromatography on a silica gel column using a mixed solvent of ethyl acetate, hexane and dichloromethane (1:8:1) as the eluent to afford (E)-4-(acetylsulfanyl)-3-{[1-(t-butoxycarbonyl)-1H-pyrazol-3-yl]methylidene}-1-(triphenylmethyl) piperidine (including impurities) as a yellow amorphous solid.

Subsequently, to a solution of the crude product thus obtained in dioxane (60 ml) was added a 4N solution of hydrogen chloride in dioxane (20 ml) under ice-cooling, and the resulting mixture was stirred at room temperature for 1 hour. The reaction mixture was evaporated in vacuo, and the residue was purified by chromatography on a silica gel column using a mixed solvent of methanol and dichloromethane (1:19) as the eluent to afford the title compound (1.2 g, yield: 11%) as a yellow solid.

$^1$H NMR (500 MHz, CDCl$_3$) δ ppm: 1.63 (9H, s), 2.07-2.14 (1H, m), 2.34 (3H, s), 2.58-2.67 (1H, m), 3.14-3.23 (1H, m), 3.48-3.55 (1H, m), 3.82 (1H, d, J=14.5), 4.59 (1H, m), 4.95 (1H, d, J=14.5), 6.40-6.41 (1H, m), 6.68 (1H, s), 7.97-7.99 (1H, m).

(d) (E)-4-(Acetylsulfanyl)-1-[2-cyclopropyl-1-(2-fluorophenyl)-2-oxoethyl]-3-{[1H-pyrazol-3(5)-yl]methylidene}piperidine dihydrochloride To a solution of (E)-4-(acetylsulfanyl)-3-{[1-(t-butoxycarbonyl)-1H-pyrazol-3-yl]methylidene}piperidine hydrochloride (1.15 g) and 2-bromo-2-(2-fluorophenyl)-1-cyclopropylethanone (0.88 g) in N,N-dimethylformamide (20 ml) was added potassium carbonate (0.24 g) under ice-cooling, and the resulting mixture was stirred at room temperature for 1 hour. The reaction mixture was diluted with ethyl acetate and washed with saturated aqueous sodium chloride solution. The organic layer was dried over anhydrous sodium sulfate. The solvent was removed in vacuo, and the residue was purified by chromatography on a silica gel column using a mixed solvent of ethyl acetate and hexane (1:3 to 1:1) as the eluent to afford (E)-4-(acetylsulfanyl)-3-{[1-(t-butoxycarbonyl)-1H-pyrazol-3-yl]methylidene}-1-[2-cyclopropyl-1-(2-fluorophenyl)-2-oxoethyl]piperidine (0.48 g, yield: 27%) as a colourless amorphous solid.

Subsequently, to the product (0.48 g) thus obtained was added a 4N solution of hydrogen chloride in dioxane (10 ml) under ice-cooling, and the resulting mixture was stirred at room temperature for 30 minutes. The reaction mixture was evaporated in vacuo, and the residue was purified by chromatography on a silica gel column using a mixed solvent of methanol and dichloromethane (1:19 to 1:4) as the eluent to afford the title compound (0.43 g, yield: 95%) as a yellow amorphous solid.

$^1$H NMR (500 MHz, CDCl$_3$) δ ppm: 0.69-0.89 (2H, m), 1.05-1.14 (2H, m), 1.83-2.04 (2H, m), 2.16-2.25 (1H, m), 2.29 and 2.33 (total 3H, each s), 2.29-2.36 and 2.63-2.70 (total 1H, each m), 2.47-2.59 (1H, m), 2.78-2.88 (1H, m), 3.26 and 3.82 (total 1H, each m), 4.39 and 4.45 (total 1H, each m), 4.81 and 4.91 (total 1H, each s), 6.13 and 6.19 (total 1H, each d, J=2.0), 6.48 (1H, s), 7.09-7.18 (2H, m), 7.22-7.39 (2H, m), 7.50 and 7.52 (total 1H, each d, J=2.0)

IR (KBr, cm$^{-1}$): 1701, 1494.

Example 12

(E)-1-[2-Cyclopropyl-1-(2-fluorophenyl)-2-oxoethyl]-3-{[1H-pyrazol-3(5)-yl]methylidene}-4-sulfanylpiperidine dihydrochloride (Exemplification Compound No. 1-21)

The title compound was synthesized in a yield of 35% as a colourless amorphous solid using (E)-4-(acetylsulfanyl)-1-[2-cyclopropyl-1-(2-fluorophenyl)-2-oxoethyl]-3-{[1H-pyrazol-3(5)-yl]methylidene}piperidine dihydrochloride instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (500 MHz, CDCl$_3$) δ ppm: 0.70-0.79 (2H, m), 0.80-0.89 (2H, m), 1.75-1.85 (1H, m), 1.91-2.02 (1H, m), 2.20-2.35 (1H, m), 2.52-2.58 and 2.60-2.67 (total 1H, each m), 2.76-2.84 (1H, m), 3.17-3.28 and 3.68-3.72 (total 1H, each m), 3.39 and 3.50 (total 1H, each d, J=11.5), 3.73-3.78 and 3.84-3.89 (total 1H, each m), 4.88 and 4.89 (total 1H, each s), 6.15 and 6.20 (total 1H, each d, J=2.0), 6.47 and 6.52 (total 1H, each s), 7.10-7.19 (2H, m), 7.24-7.38 (2H, m), 7.51 and 7.53 (total 1H, each d, J=2.0);

IR (KBr, cm$^{-1}$): 2558, 1711.

Example 13

(E)-4-(Acetylsulfanyl)-1-[2-cyclopropyl-1-(2-fluorophenyl)-2-oxoethyl]-3-[(1H-pyrazol-4-yl)methylidene]piperidine dihydrochloride (Exemplification Compound No. 1-14)

(a) (E)-3-{[1-(t-butoxycarbonyl)-1H-pyrazol-4-yl]methylidene}-1-(triphenylmethyl)piperidin-4-one To a solution of 1-(triphenylmethyl)piperidin-4-one (15.4 g) in tetrahydrofuran (250 ml) was added dropwise a 0.5N solution of potassium bis(trimethylsilyl)amide in toluene (90.4 ml) at −70° C., and the resulting mixture was stirred at the same temperature for 30 minutes. Subsequently, to the reaction mixture was added dropwise a solution of 1-(t-butoxycarbonyl)-1H-pyrazole-4-carbaldehyde (8.9 g) in tetrahydrofuran (50 ml) at −70° C., and the resulting mixture was stirred at the same temperature for 1 hour. After stirring, saturated aqueous ammonium chloride solution was added to the reaction mixture, and the resulting mixture was extracted with ethyl acetate. The extract was washed with saturated aqueous sodium chloride solution, and the organic layer was dried over anhydrous magnesium sulfate. The solvent was removed in vacuo, and the residue was purified by chromatography on a silica gel column using a mixed solvent of ethyl acetate, hexane and dichloromethane (1:5:1) as the eluent to afford the alcohol derivative (14.8 g) as a colourless amorphous solid.

Subsequently, to a solution of the alcohol derivatives (14.8 g) thus obtained in dichloromethane (150 ml) were added successively methanesulfonyl chloride (4.3 ml) and triethylamine (9.6 ml) under ice-cooling, and the resulting mixture was stirred at room temperature for 15 minutes. After cooling to 0° C., 1,8-diazabicyclo[5.4.0]undec-7-en (8.3 ml) was added to the reaction mixture with stirring, and the resulting mixture was stirred at room temperature for 15 minutes. After stirring, saturated aqueous sodium hydrogencarbonate solution was added to the reaction mixture, and the resulting mixture was extracted with ethyl acetate. The extract was washed with saturated aqueous sodium chloride solution, and the organic layer was dried over anhydrous magnesium sulfate. The solvent was removed in vacuo, and the residue was purified by chromatography on a silica gel column using a mixed solvent of ethyl acetate, hexane and dichloromethane (1:4:1) as the eluent to afford the title compound (5.86 g, yield: 31%) as a yellow amorphous solid.

$^1$H NMR (400 MHz, CDCl$_3$) δ ppm: 1.64 (9H, s), 2.70 (2H, bs), 2.75 (2H, t, J=5.5), 3.37 (2H, bs), 7.15-7.21 (3H, m), 7.25-7.32 (6H, m), 7.38 (1H, s), 7.48-7.54 (6H, m), 7.56 (1H, s), 7.97 (1H, s).

(b) (E)-4-(Acetylsulfanyl)-3-{[1-(t-butoxycarbonyl)-1H-pyrazol-4-yl]methylidene}piperidine hydrogen trifluoroacetate To a solution of (E)-3-{[1-(t-butoxycarbonyl)-1H-pyrazol-4-yl]methylidene}-1-(triphenylmethyl)piperidin-4-one (1020 mg) in methanol (40 ml) was added sodium borohydride (89 mg) under ice-cooling, and the resulting mixture was stirred at room temperature for 10 minutes. After stirring, saturated aqueous ammonium chloride solution was added to the reaction mixture, and the resulting mixture was extracted with ethyl acetate. The extract was washed with saturated aqueous sodium chloride solution, and the organic layer was dried over anhydrous magnesium sulfate. The solvent was removed in vacuo to afford the alcohol derivative (1020 mg) as a colourless amorphous solid.

Subsequently, to a solution of the alcohol derivative (1020 mg) thus obtained in dichloromethane (20 ml) were added successively methanesulfonyl chloride (0.16 ml) and triethylamine (0.33 ml) under ice-cooling, and the resulting mixture was stirred at the same temperature for 3 hours. After stirring, saturated aqueous sodium hydrogencarbonate solution was added to the reaction mixture, and the resulting mixture was extracted with ethyl acetate. The extract was washed with saturated aqueous sodium chloride solution, and the organic layer was dried over anhydrous magnesium sulfate and evaporated in vacuo. Subsequently, to a solution of the residue in dimethyl sulfoxide (20 ml) was added potassium thioacetate (1340 mg) at room temperature, and the resulting mixture was stirred at 50° C. for 1 hour. After stirring, water was added to the reaction mixture, and the resulting mixture was extracted with ethyl acetate. The extract was washed with saturated aqueous sodium chloride solution, and the organic layer was dried over anhydrous magnesium sulfate. The solvent was removed in vacuo, and the residue was purified by chromatography on a silica gel column using a mixed solvent of ethyl acetate, hexane and dichloromethane (1:6:1) as the eluent to afford the thioester derivative (420 mg, yield: 38%) as a yellow amorphous solid.

Subsequently, to a solution of the thioester derivative (420 mg) thus obtained in dichloromethane (30 ml) was added trifluoroacetic acid (0.17 ml) under ice-cooling, and the resulting mixture was stirred at room temperature for 10 minutes. After stirring, the reaction mixture was evaporated in vacuo, and the residue was purified by chromatography on a silica gel column using a mixed solvent of methanol and dichloromethane (1:19 to 1:9) as the eluent to afford the title compound (161 mg, yield: 49%) as a colourless oil.

$^1$H NMR (400 MHz, CDCl$_3$) δ ppm: 1.63 (9H, s), 2.08 (1H, m), 2.38 (3H, s), 2.48 (1H, m), 3.21 (1H, m), 3.40 (1H, m), 3.73 (1H, d, J=14.0), 4.18 (1H, d, J=14.0), 4.58 (1H, m), 6.62 (1H, s), 7.65 (1H, s), 8.01 (1H, s).

(c) (E)-4-(Acetylsulfanyl)-1-[2-cyclopropyl-1-(2-fluorophenyl)-2-oxoethyl]-3-[(1H-pyrazol-4-yl)methylidene]piperidine dihydrochloride The title compound was synthesized in a yield of 68% as a colourless amorphous solid using (E)-4-(acetylsulfanyl)-3-{[1-(t-butoxycarbonyl)-1H-pyrazol-4-yl]methylidene}piperidine hydrogen trifluoroacetate instead of (E)-4-(acetylsulfanyl)-3-{[1-(t-butoxycarbonyl)-1H-pyrazol-3-yl]methylidene}piperidine hydrochloride by conducting the reaction similar to that mentioned in Example 11 (d).

$^1$H NMR (400 MHz, CDCl$_3$) δ ppm: 0.63-0.86 (2H, m), 0.90-1.05 (2H, m), 1.81-1.92 (1H, m), 2.07-2.17 (1H, m), 2.19-2.38 (1H, m), 2.31 and 2.32 (total 3H, each s), 2.41-2.50 and 2.53-2.62 (total 1H, each m), 2.69-2.77 and 2.80-2.87 (total 1H, each m), 2.92 and 3.09 (total 1H, each d, J=12.5), 3.61-3.81 (1H, m), 4.49 (1H, t, J=4.5), 4.71 and 4.76 (total 1H, each s), 6.41 and 6.43 (total 1H, each s), 7.05-7.20 (2H, m), 7.28-7.45 (2H, m), 7.44 (1H, s), 7.52 (1H, s);
MS (FAB) m/z: 414 (M+H)$^+$.

Example 14

(E)-1-[2-Cyclopropyl-1-(2-fluorophenyl)-2-oxoethyl]-3-[(1H-pyrazol-4-yl)methylidene]-4-sulfanylpiperidine dihydrochloride (Exemplification Compound No. 1-25)

The title compound was synthesized in a yield of 20% as a colourless amorphous solid using (E)-4-(acetylsulfanyl)-1-[2-cyclopropyl-1-(2-fluorophenyl)-2-oxoethyl]-3-[(1H-pyrazol-4-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (400 MHz, CDCl$_3$) δ ppm: 0.64-0.85 (2H, m), 1.03-1.17 (2H, m), 1.74-1.83 (1H, m), 2.06-2.16 (1H, m), 2.20-2.36 (1H, m), 2.58-2.72 (1H, m), 2.73-2.90 (1H, m), 3.38 and 3.46 (total 1H, each d, J=13.0), 3.48 and 3.50 (total 1H, each d, J=13.0), 3.87-3.94 (1H, m), 4.76 and 4.78 (total 1H, each s), 6.37 and 6.38 (total 1H, each s), 7.05-7.18 (2H, m), 7.28-7.43 (2H, m), 7.45 (1H, s), 7.51 (1H, s);
IR (KBr, cm$^{-1}$): 2548, 1709.

Example 15

(E)-4-(Acetylsulfanyl)-1-[2-cyclopropyl-1-(2-fluorophenyl)-2-oxoethyl]-3-[(1,3-thiazol-2-yl)methylidene]piperidine (Exemplification Compound No. 1-30)

(a) (E)-3-[(1,3-Thiazol-2-yl)methylidene]-1-(triphenylmethyl)piperidin-4-one The title compound was synthesized in a yield of 81% as a yellow amorphous solid using 1,3-thiazole-2-carbaldehyde instead of benzaldehyde by conducting the reaction similar to that mentioned in Example 1 (a).

$^1$H NMR (500 MHz, CDCl$_3$) δ ppm: 2.69 (2H, bs), 2.80 (2H, t, J=6.0), 3.76 (2H, bs), 7.14-7.20 (3H, m), 7.24-7.31 (6H, m), 7.41 (1H, d, J=3.0), 7.51-7.56 (6H, m), 7.66 (1H, s), 7.86 (1H, d, J=3.0).

(b) (E)-3-[(1,3-Thiazol-2-yl)methylidene]-1-(triphenylmethyl)piperidin-4-ol

The title compound was synthesized in a yield of 99% as a yellow amorphous solid using (E)-3-[(1,3-thiazol-2-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (500 MHz, CDCl$_3$) δ ppm: 1.85-2.03 (1H, m), 2.10-2.22 (2H, m), 2.44-2.69 (1H, m), 2.83-2.97 (1H, m), 4.09-4.20 (1H, m), 4.24-4.48 (1H, m), 6.82 (1H, s), 7.06-7.19 (9H, m), 7.21 (1H, d, J=3.5), 7.37-7.44 (6H, m), 7.58 (1H, d, J=3.5).

(c) (E)-4-(Acetylsulfanyl)-3-[(1,3-thiazol-2-yl)methylidene]piperidine hydrochloride The title compound was synthesized in a yield of 12% as a yellow amorphous solid using (E)-3-[(1,3-thiazol-2-yl)methylidene]-1-(triphenylmethyl)piperidin-4-ol instead of (E)-3-benzylidene-1-(triphenylmethyl)piperidin-4-ol by conducting successively reactions similar to those mentioned in Example 1 (c).

$^1$H NMR (500 MHz, DMSO-d$_6$) δ ppm: 1.97-2.04 (1H, m), 2.28-2.37 (1H, m), 2.40 (3H, s), 3.07-3.17 (1H, m), 3.30-3.40 (1H, m), 4.03-4.11 (1H, m), 4.59 (1H, m), 4.99-5.06 (1H, m), 7.01 (1H, s), 7.86 (1H, d, J=3.5), 7.98 (1H, d, J=3.5).

(d) (E)-4-(Acetylsulfanyl)-1-[2-cyclopropyl-1-(2-fluorophenyl)-2-oxoethyl]-3-[(1,3-thiazol-2-yl)methylidene]piperidine The title compound was synthesized in a yield of 28% as a yellow amorphous solid using (E)-4-(acetylsulfanyl)-3-[(1,3-thiazol-2-yl)methylidene]piperidine hydrochloride instead of (E)-4-(acetylsulfanyl)-3-benzylidenepiperidine hydrochloride by conducting the reaction similar to that mentioned in Example 1 (d)

$^1$H NMR (500 MHz, CDCl$_3$) δ ppm: 0.65-0.82 (2H, m), 0.87-1.06 (2H, m), 1.91 (1H, m), 2.22-2.37 (2H, m), 2.31 and 2.32 (total 3H, each s), 2.45-2.52 and 2.61-2.68 (total 1H, each m), 2.79-2.87 (1H, m), 3.32 and 3.40 (total 1H, each d, J=13.5), 4.38-4.43 and 4.48-4.54 (total 2H, each m), 4.72 and 4.75 (total 1H, each s), 6.74 (1H, s), 7.03-7.17 (2H, m), 7.22 and 7.24 (total 1H, each d, J=3.5), 7.26-7.33 (1H, m), 7.38-7.45 (1H, m), 7.65 and 7.71 (total 1H, each d, J=3.5);
IR (Liquid film, cm$^{-1}$): 1694, 1488.

Example 16

(E)-1-[2-Cyclopropyl-1-(2-fluorophenyl)-2-oxoethyl]-4-sulfanyl-3-[(1,3-thiazol-2-yl)methylidene]piperidine hydrogen trifluoroacetate (Exemplification Compound No. 1-29)

The title compound was synthesized in a yield of 37% as a pale yellow amorphous solid using (E)-4-(acetylsulfanyl)-1-[2-cyclopropyl-1-(2-fluorophenyl)-2-oxoethyl]-3-[(1,3-thiazol-2-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.
$^1$H NMR (500 MHz, CDCl$_3$) δ ppm: 0.66-0.81 (2H, m), 0.84-1.08 (2H, m), 1.81-1.89 (1H, m), 2.18-2.26 (1H, m), 2.28-2.38 (1H, m), 2.65-2.74 (1H, m), 2.78-2.85 and 2.88-2.96 (total 1H, each m), 3.83-3.95 (2H, m), 3.97-4.08 (1H, m), 4.76 and 4.78 (total 1H, each s), 6.74 (1H, s), 7.03-7.15 (2H, m), 7.23 and 7.25 (total 1H, each d, J=3.0), 7.27-7.33 (1H, m), 7.38-7.44 (1H, m), 7.68 and 7.70 (total 1H, each d, J=3.0);
IR (KBr, cm$^{-1}$): 2553, 1713, 1672.

Example 17

(E)-4-(Acetylsulfanyl)-1-[2-cyclopropyl-1-(2-fluorophenyl)-2-oxoethyl]-3-[(1,3-thiazol-5-yl)methylidene]piperidine (Exemplification Compound No. 1-38)

(a) (E)-3-[(1,3-Thiazol-5-yl)methylidene]-1-(triphenylmethyl)piperidin-4-one

The title compound was synthesized in a yield of 55% as an orange-coloured amorphous solid using 1,3-thiazole-5-carbaldehyde instead of benzaldehyde by conducting the reaction similar to that mentioned in Example 1 (a).
$^1$H NMR (500 MHz, CDCl$_3$) δ ppm: 2.69 (2H, bs), 2.78 (2H, t, J=6.0) 3.46 (2H, bs), 7.16-7.21 (3H, m), 7.25-7.31 (6H, m), 7.50-7.56 (6H, m), 7.76 (1H, s), 7.98 (1H, s), 8.81 (1H, s).

(b) (E)-3-[(1,3-Thiazol-5-yl)methylidene]-1-(triphenylmethyl)piperidin-4-ol

The title compound was synthesized in a yield of 99% as a yellow amorphous solid using (E)-3-[(1,3-thiazol-5-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).
$^1$H NMR (500 MHz, CDCl$_3$) δ ppm: 1.88-1.97 (1H, m), 2.02-2.21 (2H, m), 2.46-2.65 (1H, m), 2.80-2.92 (1H, m), 3.59-3.80 (1H, m), 4.14-4.22 (1H, m), 6.73 (1H, s), 7.08-7.23 (9H, m), 7.37-7.46 (6H, m), 7.66 (1H, s), 8.61 (1H, s).

(c) (E)-4-(Acetylsulfanyl)-3-[(1,3-thiazol-5-yl)methylidene]piperidine hydrochloride The title compound was synthesized in a yield of 20% as a yellow amorphous solid using (E)-3-[(1,3-thiazol-5-yl)methylidene]-1-(triphenylmethyl)piperidin-4-ol instead of (E)-3-benzylidene-1-(triphenylmethyl)piperidin-4-ol by conducting successively reactions similar to those mentioned in Example 1 (c).
$^1$H NMR (500 MHz, DMSO-d$_6$) δ ppm: 1.94-2.02 (1H, m), 2.27-2.34 (1H, m), 2.40 (3H, s), 3.05-3.16 (1H, m), 3.27-3.36 (1H, m), 3.75-3.86 (1H, m), 4.06-4.15 (1H, m), 4.58 (1H, m), 7.01 (1H, s), 8.03 (1H, s), 9.17 (1H, s).

(d) (E)-4-(Acetylsulfanyl)-1-[2-cyclopropyl-1-(2-fluorophenyl)-2-oxoethyl]-3-[(1,3-thiazol-5-yl)methylidene]piperidine The title compound was synthesized in a yield of 25% as a brown oil using (E)-4-(acetylsulfanyl)-3-[(1,3-thiazol-5-yl)methylidene]piperidine hydrochloride instead of (E)-4-(acetylsulfanyl)-3-benzylidenepiperidine hydrochloride by conducting the reaction similar to that mentioned in Example 1 (d)
$^1$H NMR (500 MHz, CDCl$_3$) δ ppm: 0.67-0.87 (2H, m), 0.91-1.05 (2H, m), 1.84-1.95 (1H, m), 2.14 (1H, m), 2.21-2.36 (1H, m), 2.32 (3H, s), 2.48-2.63 (1H, m), 2.75-2.82 and 2.85-2.91 (total 1H, each m), 3.01 and 3.22 (total 1H, each d, J=12.5), 3.71-3.78 (1H, m), 4.52 (1H, m), 4.73 and 4.74 (total 1H, each s), 6.70 (1H, s), 7.05-7.19 (2H, m), 7.27-7.40 (2H, m), 7.67 and 7.70 (total 1H, each s), 8.63 and 8.67 (total 1H, each s);
IR (Thin film, cm$^{-1}$): 1695, 1488.

Example 18

(E)-1-[2-Cyclopropyl-1-(2-fluorophenyl)-2-oxoethyl]-4-sulfanyl-3-[(1,3-thiazol-5-yl)methylidene]piperidine trifluoroacetate (Exemplification Compound No. 1-37)

The title compound was synthesized in a yield of 61% as a colourless oil using (E)-4-(acetylsulfanyl)-1-[2-cyclopropyl-1-(2-fluorophenyl)-2-oxoethyl]-3-[(1,3-thiazol-5-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.
$^1$H NMR (500 MHz, CDCl$_3$) δ ppm: 0.68-0.85 (2H, m), 0.92-1.04 (2H, m), 1.77-1.88 (1H, m), 2.09-2.17 (1H, m), 2.25-2.38 (1H, m), 2.63-2.77 (1H, m), 2.81-2.92 (1H, m), 3.42-3.64 (2H, m), 3.88-3.95 (1H, m), 4.77 and 4.78 (total 1H, each s), 6.64 and 6.67 (total 1H, each s), 7.05-7.18 (2H, m), 7.27-7.42 (2H, m), 7.66 and 7.69 (total 1H, each s), 8.64 and 8.67 (total 1H, each s);
IR (KBr, cm$^{-1}$): 2546, 1712, 1674.

Example 19

(E)-4-(Acetylsulfanyl)-1-[2-cyclopropyl-1-(2-fluorophenyl)-2-oxoethyl]-3-[(1H-imidazol-2-yl)methylidene]piperidine dihydrochloride (Exemplification Compound No. 1-42)

(a) (E)-3-{[1-(t-Butoxycarbonyl)-1H-imidazol-2-yl]methylidene}-1-(triphenylmethyl)piperidin-4-one The title compound was synthesized in a yield of 12% as a yellow amorphous solid using 1-(t-butoxycarbonyl)-1H-imidazole-2-carbaldehyde instead of 1-(tert-butoxycarbonyl)-1H-pyrazole-4-carbaldehyde by conducting the reaction similar to that mentioned in Example 13 (a).

$^1$H NMR (400 MHz, CDCl$_3$) δ ppm: 1.66 (9H, s), 2.63 (2H, bs), 2.77 (2H, t, J=6.0), 3.82 (2H, bs), 6.92 (1H, d, J=1.5), 7.11-7.18 (3H, m), 7.20-7.30 (6H, m), 7.39 (1H, d, J=1.5), 7.42-7.55 (6H, m), 7.97 (1H, t, J=2.0).

(b) (E)-3-{[1-(t-Butoxycarbonyl)-1H-imidazol-2-yl]methylidene}-1-(triphenylmethyl)piperidin-4-ol The title compound was synthesized in a yield of 63% as a colourless amorphous solid using (E)-3-{[1-(t-butoxycarbonyl)-1H-imidazol-2-yl]methylidene}-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.71 (9H, s), 1.84-2.01 (3H, m), 2.10-2.18 (1H, m), 2.43 (1H, bs), 2.88 (1H, bs), 4.13 (1H, m), 6.72 (1H, d, J=1.5), 6.87 (1H, d, J=1.5), 7.05-7.20 (10H, m), 7.37 (1H, d, J=1.5), 7.35-7.40 (5H, m).

(c) (E)-4-(Acetylsulfanyl)-3-{[1-(t-butoxycarbonyl)-1H-imidazol-2-yl]methylidene}-1-(triphenylmethyl)piperidine To a solution of (E)-3-{[1-(t-butoxycarbonyl)-1H-imidazol-2-yl]methylidene}-1-(triphenylmethyl)piperidin-4-ol (2.45 g) in toluene (100 ml) were added successively thioacetic acid (0.60 ml) and N,N-dimethylformamide dineopentyl acetal (2.36 ml) under ice-cooling, and the resulting mixture was stirred at room temperature for 30 minutes. After stirring, water was added to the reaction mixture, and the resulting mixture was extracted with ethyl acetate. The extract was washed with saturated aqueous sodium chloride solution, and the organic layer was dried over anhydrous magnesium sulfate. The solvent was removed in vacuo, and the residue was purified by chromatography on a silica gel column using a mixed solvent of ethyl acetate, hexane and dichloromethane (1:5:1) as the eluent to afford the title compound (0.72 g, yield: 26%) as a colourless amorphous solid.

$^1$H NMR (400 MHz, CDCl$_3$) δ ppm: 1.72 (9H, s), 1.87-1.99 (1H, m), 2.00-2.14 (1H, m), 2.25 (3H, s), 2.31-2.48 (2H, m), 2.62-2.89 (2H, m), 4.49 (1H, m), 6.69 (1H, d, J=1.5), 6.90 (1H, s), 7.06-7.18 (10H, m), 7.33 (1H, d, J=1.5), 7.35-7.40 (3H, m), 7.47-7.53 (2H, m).

(d) (E)-4-(Acetylsulfanyl)-3-{[1-(t-butoxycarbonyl)-1H-imidazol-2-yl]methylidene}piperidine hydrogen trifluoroacetate To a solution of (E)-4-(acetylsulfanyl)-3-{[1-(t-butoxycarbonyl)-1H-imidazol-2-yl]methylidene}-1-(triphenylmethyl)piperidine (0.72 g) in dichloromethane (20 ml) was added trifluoroacetic acid (0.29 ml) under ice-cooling, and the resulting mixture was stirred at the same temperature for 15 minutes. The reaction mixture was evaporated in vacuo, and the residue was purified by chromatography on a silica gel column using a mixed solvent of methanol and dichloromethane (1:20 to 1:10) as the eluent to afford the title compound (0.58 g, yield: quantitative) as a colourless amorphous solid.

$^1$H NMR (400 MHz, CDCl$_3$) δ ppm: 1.64 (9H, s), 2.13 (1H, m), 2.37 (3H, s), 2.50 (1H, m), 3.30 (1H, m), 3.42 (1H, m), 3.90 (1H, d, J=14.5), 4.62 (1H, t, J=4.0), 4.85 (1H, d, J=14.5), 7.08 (1H, d, J=1.5), 7.21 (1H, s), 7.44 (1H, d, J=1.5).

(e) (E)-4-(Acetylsulfanyl)-1-[2-cyclopropyl-1-(2-fluorophenyl)-2-oxoethyl]-3-[(1H-imidazol-2-yl)methylidene]piperidine dihydrochloride The title compound was synthesized in a yield of 49% as a colourless amorphous solid using (E)-4-(acetylsulfanyl)-3-{[1-(t-butoxycarbonyl)-1H-imidazol-2-yl]methylidene}piperidine hydrogen trifluoroacetate instead of (E)-4-(acetylsulfanyl)-3-{[1-(t-butoxycarbonyl)-1H-pyrazol-3-yl]methylidene}piperidine hydrochloride by conducting successively reactions similar to those mentioned in Example 11 (d).

$^1$H NMR (500 MHz, CDCl$_3$) δ ppm: 0.77-0.86 (1H, m), 0.88-0.95 (1H, m), 1.05-1.17 (2H, m), 1.82-1.93 (2H, m), 2.12-2.19 and 2.24-2.31 (total 1H, each m), 2.28 and 2.32 (total 3H, each s), 2.50-2.83 (2H, m), 2.88 and 3.36 (total 1H, each d, J=12.5), 3.42 and 3.77 (total 1H, each d, J=12.5), 4.28 and 4.41 (total 1H, each t, J=5.0), 4.90 and 4.97 (total 1H, each s), 6.54 (1H, s), 7.07-7.13 (1H, m), 7.10 (1H, s), 7.14-7.23 (2H, m), 7.14 (1H, s), 7.34-7.42 (1H, m);

IR (KBr, cm$^{-1}$): 1704, 1493.

Example 20

(E)-1-[2-Cyclopropyl-1-(2-fluorophenyl)-2-oxoethyl]-3-[(1H-imidazol-2-yl)methylidene]-4-sulfanylpiperidine dihydrochloride (Exemplification Compound No. 1-41)

The title compound was synthesized in a yield of 71% as a colourless amorphous solid using (E)-4-(acetylsulfanyl)-1-[2-cyclopropyl-1-(2-fluorophenyl)-2-oxoethyl]-3-[(1H-imidazol-2-yl)methylidene]piperidine dihydrochloride instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (500 MHz, CDCl$_3$) δ ppm: 0.78-0.86 (1H, m), 0.89-0.96 (1H, m), 1.05-1.17 (2H, m), 1.72-1.91 (2H, m), 2.18 and 2.26 (total 1H, each m), 2.47 and 2.58 (total 1H, each m), 2.70-2.80 (total 1H, each m), 3.07 and 3.35 (total 1H, each d, J=12.5), 3.45 and 3.74 (total 1H, each d, J=12.5), 3.70 and 3.86 (total 1H, each m), 4.95 and 4.97 (total 1H, each s), 6.55 and 6.61 (total 1H, each s), 7.07-7.13 (1H, m), 7.11 (1H, s), 7.14-7.26 (3H, m), 7.34-7.42 (1H, m);

IR (KBr, cm$^{-1}$): 2562, 1709.

Example 21

(E)-4-(Acetylsulfanyl)-1-[2-cyclopropyl-1-(2-fluorophenyl)-2-oxoethyl]-3-{[1H-imidazol-4(5)-yl]methylidene}piperidine dihydrochloride (Exemplification Compound No. 1-46)

(a) (E)-3-{[1-(t-Butoxycarbonyl)-1H-imidazol-5-yl]methylidene}-1-(triphenylmethyl)piperidin-4-one The title compound was synthesized in a yield of 50% as a yellow amorphous solid using 1-(t-butoxycarbonyl)-1H-imidazole-5-carbaldehyde instead of benzaldehyde by conducting the reaction similar to that mentioned in Example 1 (a).

$^1$H NMR (500 MHz, CDCl$_3$) δ ppm: 1.60 (9H, s), 2.66 (2H, bs), 2.75 (2H, t, J=6.0), 3.63 (2H, bs), 7.14-7.20 (3H, m), 7.23-7.30 (7H, m), 7.38 (1H, s), 7.49-7.57 (6H, m), 7.95 (1H, s).

(b) (E)-3-{[1-(t-Butoxycarbonyl)-1H-imidazol-5-yl]methylidene}-1-(triphenylmethyl)piperidin-4-ol The title compound was synthesized in a yield of 99% as a yellow amorphous solid using (E)-3-{[1-(t-butoxycarbonyl)-1H-imidazol-5-yl]methylidene}-1-(triphenylmethyl)piperidin-4-one instead of (E)-3-benzylidene-1-(triphenylmethyl)piperidin-4-one by conducting the reaction similar to that mentioned in Example 1 (b)

$^1$H NMR (500 MHz, CDCl$_3$) δ ppm: 1.60 (9H, s), 1.84-1.94 (1H, m), 2.01-2.19 (2H, m), 2.65-2.85 (2H, m), 3.72-3.93 (1H, m), 4.10-4.19 (1H, m), 6.44 (1H, s), 7.02 (1H, s), 7.05-7.23 (9H, m), 7.34-7.49 (6H, m), 7.90 (1H, s).

(c) (E)-4-(Acetylsulfanyl)-3-{[1-(t-butoxycarbonyl)-1H-imidazol-5-yl]methylidene}piperidine hydrogen trifluoroacetate To a solution of (E)-3-{[1-(t-butoxycarbonyl)-1H-imidazol-5-yl]methylidene}-1-(triphenylmethyl)piperidin-4-ol (6.00 g) in toluene (100 ml) were added successively thioacetic acid (1.64 ml) and N,N-dimethylformamide dineopentyl acetal (6.40 ml) under ice-cooling, and the resulting mixture was stirred at room temperature for 1 hour. After stirring, water was added to the reaction mixture, and the resulting mixture was extracted with ethyl acetate. The extract was washed with saturated aqueous sodium chloride solution, and the organic layer was dried over anhydrous magnesium sulfate. The solvent was removed in vacuo, and the residue was purified by chromatography on a silica gel column using a mixed solvent of ethyl acetate, hexane and dichloromethane (1:3:1) as the eluent to afford (E)-4-(acetylsulfanyl)-3-{[1-(t-butoxycarbonyl)-1H-imidazol-5-yl]methylidene}-1-(triphenylmethyl)piperidine (including impurities) as a yellow amorphous solid.

Subsequently, to a solution of the crude product thus obtained in dichloromethane (100 ml) was added trifluoroacetic acid (0.83 ml) under ice-cooling, and the resulting mixture was stirred at the same temperature for 45 minutes. The reaction mixture was evaporated in vacuo, and the residue was purified by chromatography on a silica gel column using a mixed solvent of methanol and dichloromethane (1:19) as the eluent to afford the title compound (0.59 g, yield: 32%) as a yellow amorphous solid.

$^1$H NMR (500 MHz, CDCl$_3$) δ ppm: 1.61 (9H, s), 2.03-2.10 (1H, m), 2.36 (3H, s), 2.47-2.56 (1H, m), 3.14-3.26 (1H, m), 3.37-3.45 (1H, m), 3.79-3.88 (1H, m), 4.56 (1H, m), 5.48-5.56 (1H, m), 6.54 (1H, s), 7.31 (1H, s), 8.04 (1H, s).

(d) (E)-4-(Acetylsulfanyl)-1-[2-cyclopropyl-1-(2-fluorophenyl)-2-oxoethyl]-3-{[1H-imidazol-4(5)-yl]methylidene}piperidine dihydrochloride The title compound was synthesized in a yield of 48% as a yellow amorphous solid using (E)-4-(acetylsulfanyl)-3-{[1-(t-butoxycarbonyl)-1H-imidazol-5-yl]methylidene}piperidine hydrogen trifluoroacetate instead of (E)-4-(acetylsulfanyl)-3-{[1-(t-butoxycarbonyl)-1H-pyrazol-3-yl]methylidene}piperidine hydrochloride by conducting successively reactions similar to those mentioned in Example 11 (d).

$^1$H NMR (500 MHz, CDCl$_3$) δ ppm: 0.65-1.22 (4H, m), 1.78-1.93 (2H, m), 2.08-2.37 and 2.74-2.83 (total 2H, each m), 2.28 and 2.34 (total 3H, each s), 2.44-2.61 (1H, m), 2.68 and 3.20 (total 1H, each d, J=12.0), 3.29 and 3.66 (total 1H, each d, J=12.0), 4.30 and 4.41 (total 1H, each m), 4.88 and 4.99 (total 1H, each s), 6.45 (1H, s), 6.96 and 6.99 (total 1H, each s), 7.12-7.24 (2H, m), 7.25-7.47 (2H, m), 7.68 (1H, s); IR (KBr, cm$^{-1}$): 1702, 1494.

Example 22

(E)-1-[2-Cyclopropyl-1-(2-fluorophenyl)-2-oxoethyl]-3-{[1H-imidazol-4(5)-yl]methylidene}-4-sulfanylpiperidine dihydrochloride (Exemplification Compound No. 1-45)

The title compound was synthesized in a yield of 69% as a pale yellow amorphous solid using (E)-4-(acetylsulfanyl)-1-[2-cyclopropyl-1-(2-fluorophenyl)-2-oxoethyl]-3-{[1H-imidazol-4(5)-yl]methylidene}piperidine dihydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (500 MHz, CDCl$_3$) δ ppm: 0.76-0.85 (2H, m), 0.87-0.95 (2H, m), 1.71-1.83 (1H, m), 1.87-1.96 (1H, m), 2.15-2.32 (1H, m), 2.45-2.52 and 2.55-2.62 (total 1H, each m), 2.70-2.82 (1H, m), 3.01-3.14 (1H, m), 3.32 and 3.42 (total 1H, each d, J=12.0), 3.63-3.74 and 3.80-3.87 (total 1H, each m), 4.93 (1H, s), 6.46 and 6.52 (total 1H, each s), 7.00 and 7.03 (total 1H, each s), 7.13-7.22 (2H, m), 7.23-7.29 (1H, m), 7.33-7.41 (1H, m), 7.69 and 7.70 (total 1H, each s); IR (KBr, cm$^{-1}$): 2597, 1710.

Example 23

(E)-4-(Acetylsulfanyl)-1-[2-cyclopropyl-1-(2-fluorophenyl)-2-oxoethyl]-3-[(1,2,4-triazol-3-yl)methylidene]piperidine dihydrochloride (Exemplification Compound No. 1-54)

(a) (E)-3-{[1-(t-Butoxycarbonyl)-1,2,4-triazol-3-yl]methylidene}-1-(triphenylmethyl)piperidin-4-one The title compound was synthesized in a yield of 31% as a yellow amorphous solid using 1-(t-butoxycarbonyl)-1,2,4-triazole-3-carbaldehyde instead of benzaldehyde by conducting the reaction similar to that mentioned in Example 1 (a).

$^1$H NMR (500 MHz, CDCl$_3$) δ ppm: 1.62 (9H, s), 2.65 (2H, bs), 2.78 (2H, t, J=6.5), 3.87 (2H, bs), 7.12-7.19 (3H, m), 7.21-7.28 (6H, m), 7.40 (1H, s), 7.48-7.55 (6H, m), 8.62 (1H, s).

(b) (E)-3-{[1-(t-Butoxycarbonyl)-1,2,4-triazol-3-yl]methylidene}-1-(triphenylmethyl)piperidin-4-ol The title compound was synthesized in a yield of 91% as a pale yellow amorphous solid using (E)-3-{[1-(t-butoxycarbonyl)-1,2,4-triazol-3-yl]methylidene}-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.63 (9H, s), 1.86-1.99 (1H, m), 2.06-2.25 (2H, m), 2.76-3.06 (2H, m), 3.23-3.39 (1H, m), 4.07-4.18 (1H, m), 6.62 (1H, s), 7.05-7.22 (9H, m), 7.36-7.45 (6H, m), 8.57 (1H, s).

(c) (E)-4-(Acetylsulfanyl)-3-{[1-(t-butoxycarbonyl)-1,2,4-triazol-3-yl]methylidene}piperidine hydrogen trifluoroacetate The title compound was synthesized in a yield of 20% as a yellow amorphous solid using (E)-3-{[1-(t-butoxycarbonyl)-1,2,4-triazol-3-yl]methylidene}-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c).
$^1$H NMR (500 MHz, CDCl$_3$) δ ppm: 1.66 (9H, s), 2.08-2.16 (1H, m), 2.37 (3H, s), 2.46-2.56 (1H, m), 3.21-3.31 (1H, m), 3.37-3.46 (1H, m), 4.06 (1H, d, J=14.0), 4.61 (1H, m), 5.32 (1H, d, J=14.0), 6.84 (1H, s), 8.68 (1H, s).

(d) (E)-4-(Acetylsulfanyl)-1-[2-cyclopropyl-1-(2-fluorophenyl)-2-oxoethyl]-3-[(1,2,4-triazol-3-yl)methylidene]piperidine dihydrochloride The title compound was synthesized in a yield of 47% as a yellow amorphous solid using (E)-4-(acetylsulfanyl)-3-{[1-(t-butoxycarbonyl)-1,2,4-triazol-3-yl]methylidene}piperidine trifluoroacetate instead of (E)-4-(acetylsulfanyl)-3-{[1-(t-butoxycarbonyl)-1H-pyrazol-3-yl]methylidene}piperidine hydrochloride by conducting successively reactions similar to those mentioned in Example 11 (d).
$^1$H NMR (400 MHz, CDCl$_3$) δ ppm: 0.74-0.97 (2H, m), 1.08-1.23 (2H, m), 1.76-1.96 (2H, m), 2.13-2.39 (2H, m), 2.29 and 2.33 (total 3H, each s), 2.49-2.68 (1H, m), 2.71-2.99 (1H, m), 3.46-3.91 (1H, m), 4.27 and 4.44 (total 1H, each m), 4.94 and 4.98 (total 1H, each s), 6.57 (1H, s), 7.12-7.30 (3H, m), 7.34-7.44 (1H, m), 7.97 and 7.99 (total 1H, each s);
IR (KBr, cm$^{-1}$): 1704, 1494.

Example 24

(E)-1-[2-Cyclopropyl-1-(2-fluorophenyl)-2-oxoethyl]-4-sulfanyl-3-[(1,2,4-triazol-3-yl)methylidene]piperidine dihydrochloride (Exemplification Compound No. 1-53)

The title compound was synthesized in a yield of 98% as a pale yellow amorphous solid using (E)-4-(acetylsulfanyl)-1-[2-cyclopropyl-1-(2-fluorophenyl)-2-oxoethyl]-3-[(1,2,4-triazol-3-yl)methylidene]piperidine dihydrochloride instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.
$^1$H NMR (500 MHz, CDCl$_3$) δ ppm: 0.74-0.98 (2H, m), 1.08-1.23 (2H, m), 1.68-1.88 (2H, m), 2.21-2.37 (1H, m), 2.48-2.57 and 2.58-2.65 (total 1H, each m), 2.73-2.88 (1H, m), 2.89-3.07 (1H, m), 3.35-3.56 (1H, m), 3.60-3.73 and 3.82-3.90 (total 1H, each m), 4.98 (1H, s), 6.58 and 6.68 (total 1H, each s), 7.13-7.25 (3H, m), 7.34-7.42 (1H, m), 7.99 and 8.00 (total 1H, each s);
IR (KBr, cm$^{-1}$): 2564, 1710.

Example 25

(E)-4-(Acetylsulfanyl)-1-[2-cyclopropyl-1-(2-fluorophenyl)-2-oxoethyl]-3-[(pyridin-2-yl)methylidene]piperidine (Exemplification Compound No. 1-62)

(a) (E)-3-[(Pyridin-2-yl)methylidene]-1-(triphenylmethyl)piperidin-4-one

The title compound was synthesized in a yield of 66% as a pale yellow amorphous solid using pyridine-2-carbaldehyde instead of benzaldehyde by conducting the reaction similar to that mentioned in Example 1 (a).
$^1$H NMR (400 MHz, CDCl$_3$) δ ppm: 2.60-2.70 (2H, m), 2.78 (2H, t, J=6.0), 3.89 (2H, bs), 7.06-7.17 (4H, m), 7.19-7.33 (7H, m), 7.40 (1H, t, J=2.0), 7.47-7.54 (6H, m), 7.64 (1H, dt, J=7.5, 2.0), 8.40-8.44 (1H, m).

(b) (E)-3-[(Pyridin-2-yl)methylidene]-1-(triphenylmethyl)piperidin-4-ol

The title compound was synthesized in a yield of 91% as a colourless amorphous solid using (E)-3-[(pyridin-2-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).
$^1$H NMR (400 MHz, CDCl$_3$) δ ppm: 1.85-2.04 (2H, m), 2.12-2.22 (2H, m), 2.47-2.91 (2H, m), 4.15 (1H, m), 6.71 (1H, s), 6.97-7.18 (11H, m), 7.29-7.42 (6H, m), 7.64 (1H, dt, J=7.5, 2.0), 8.31-8.36 (1H, m).

(c) (E)-4-(Acetylsulfanyl)-3-[(pyridin-2-yl)methylidene]piperidine dihydrochloride The title compound was synthesized in a yield of 18% as a yellow oil using (E)-3-[(pyridin-2-yl)methylidene]-1-(triphenylmethyl)piperidin-4-ol instead of (E)-3-{[1-(t-butoxycarbonyl)-1H-pyrazol-3-yl]methylidene}-1-(triphenylmethyl)piperidin-4-ol by conducting successively reactions similar to those mentioned in Example 11 (c).
$^1$H NMR (500 MHz, CDCl$_3$) δ ppm: 2.15-2.23 (1H, m), 2.42 (3H, s), 2.64-2.75 (1H, m), 3.24-3.36 (1H, m), 3.51-3.59 (1H, m), 3.92-4.02 (1H, m), 4.19 (1H, d, J=14.5), 4.64 (1H, t, J=4.5), 7.02 (1H, s), 7.83 (1H, d, J=8.0), 7.94 (1H, t, J=6.0), 8.44 (1H, t, J=8.0), 8.94 (1H, d, J=6.0).

(d) (E)-4-(Acetylsulfanyl)-1-[2-cyclopropyl-1-(2-fluorophenyl)-2-oxoethyl]-3-[(pyridin-2-yl)methylidene]piperidine The title compound was synthesized in a yield of 18% as a yellow oil using (E)-4-(acetylsulfanyl)-3-[(pyridin-2-yl)methylidene]piperidine dihydrochloride instead of (E)-4-(acetylsulfanyl)-3-benzylidenepiperidine hydrochloride by conducting the reaction similar to that mentioned in Example 1 (d)
$^1$H NMR (500 MHz, CDCl$_3$) δ ppm: 0.50-0.75 (2H, m), 0.78-0.87 (1H, m), 0.89-0.97 (1H, m), 1.85-1.95 (1H, m), 2.21-2.40 (2H, m), 2.31 (3H, s), 2.45-2.52 and 2.57-2.64 (total 1H, each m), 2.75-2.81 and 2.83-2.89 (total 1H, each m), 3.13 and 3.31 (total 1H, each d, J=13.5), 4.42 (1H, d, J=13.5), 4.53 (1H, m), 4.64 and 4.68 (total 1H, each s), 6.62 and 6.64 (total 1H, each s), 7.00-7.16 (4H, m), 7.22-7.31 (1H, m), 7.36-7.46 (1H, m), 7.52-7.60 (1H, m), 8.35 and 8.47 (total 1H, each d, J=4.0);
MS (FAB) m/z: 425 (M+H)$^+$.

Example 26

(E)-1-[2-Cyclopropyl-1-(2-fluorophenyl)-2-oxoethyl]-3-[(pyridin-2-yl)methylidene]-4-sulfanylpiperidine bis(hydrogen trifluoroacetate) (Exemplification Compound No. 1-61)

The title compound was synthesized in a yield of 88% as a brown oil using (E)-4-(acetylsulfanyl)-1-[2-cyclopropyl-1-

(2-fluorophenyl)-2-oxoethyl]-3-[(pyridin-2-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (400 MHz, CDCl$_3$) δ ppm: 0.52-0.96 (4H, m), 1.79-1.89 (1H, m), 2.20-2.40 (2H, m), 2.61-2.74 (1H, m), 2.78-2.95 (1H, m), 3.69 and 3.82 (total 1H, each d, J=13.0), 3.88-4.02 (2H, m), 4.68 and 4.71 (total 1H, each s), 6.61 and 6.63 (total 1H, each s), 6.99-7.17 (4H, m), 7.23-7.31 (1H, m), 7.37-7.46 (1H, m), 7.52-7.61 (1H, m), 8.39-8.42 and 8.45-8.48 (total 1H, each m);

MS (FAB) m/z: 383 (M+H)$^+$.

Example 27

(E)-4-(Acetylsulfanyl)-1-[2-cyclopropyl-1-(2-fluorophenyl)-2-oxoethyl]-3-[(pyridin-3-yl)methylidene]piperidine (Exemplification Compound No. 1-70)

(a) (E)-3-[(Pyridin-3-yl)methylidene]-1-(triphenylmethyl)piperidin-4-one

The title compound was synthesized in a yield of 51% as a pale yellow amorphous solid using nicotinaldehyde instead of benzaldehyde by conducting the reaction similar to that mentioned in Example 1 (a).

$^1$H NMR (400 MHz, CDCl$_3$) δ ppm: 2.69 (2H, bs), 2.70 (2H, t, J=6.0), 3.42 (2H, bs), 7.11-7.18 (3H, m), 7.19-7.32 (7H, m), 7.41-7.48 (6H, m), 7.49-7.57 (2H, m), 8.43-8.51 (2H, m).

(b) (E)-3-[(Pyridin-3-yl)methylidene]-1-(triphenylmethyl)piperidin-4-ol

The title compound was synthesized in a yield of 92% as a colourless amorphous solid using (E)-3-[(pyridin-3-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.78-1.97 (2H, m), 1.98-2.22 (2H, m), 2.73-2.91 (1H, m), 3.43-3.68 (1H, m), 4.12-4.23 (1H, m), 6.66 (1H, s), 6.98-7.19 (10H, m), 7.22-7.38 (6H, m), 7.43 (1H, d, J=8.0), 8.36-8.42 (2H, m).

(c) (E)-4-(Acetylsulfanyl)-3-[(pyridin-3-yl)methylidene]-1-(triphenylmethyl)piperidine To a solution of (E)-3-[(pyridin-3-yl)methylidene]-1-(triphenylmethyl)piperidin-4-ol (5.40 g) in dichloromethane (85 ml) were added successively methanesulfonyl chloride (1.93 ml) and triethylamine (3.49 ml) under ice-cooling, and the resulting mixture was stirred at room temperature for 3 hours. The reaction mixture was evaporated in vacuo, and the residue was diluted with ethyl acetate and washed with saturated aqueous sodium chloride solution. The organic layer was dried over anhydrous sodium sulfate, and the solvent was evaporated in vacuo. Subsequently, to a solution of the residue thus obtained in dimethyl sulfoxide (75 ml) was added potassium thioacetate (7.10 g) at room temperature, and the resulting mixture was stirred at 40° C. for 1 hour. The reaction mixture was diluted with ethyl acetate and washed with saturated aqueous sodium chloride solution. The organic layer was dried over anhydrous sodium sulfate. The solvent was removed, and the residue was purified by chromatography on a silica gel column using a mixed solvent of ethyl acetate and hexane (1:9) as the eluent to afford the title compound (2.68 g, yield: 42%) as a pale brown amorphous solid.

$^1$H NMR (400 MHz, CDCl$_3$) δ ppm: 1.88-1.98 (1H, m), 2.20-2.46 (2H, m), 2.40 (3H, s), 2.56-2.87 (2H, m), 3.27-3.49 (1H, m), 4.42-4.53 (1H, m), 6.65 (1H, s), 6.99-7.16 (9H, m), 7.17-7.24 (1H, m), 7.25-7.35 (6H, m), 7.36-7.45 (1H, m), 8.34-8.41 (2H, m).

(d) (E)-4-(Acetylsulfanyl)-3-[(pyridin-3-yl)methylidene]piperidine bis(hydrogen trifluoroacetate)

The title compound was synthesized in a yield of 99% as a pale brown amorphous solid using (E)-4-(acetylsulfanyl)-3-[(pyridin-3-yl)methylidene]-1-(triphenylmethyl)piperidine instead of (E)-4-(acetylsulfanyl)-3-{[1-(t-butoxycarbonyl)-1H-imidazol-2-yl]methylidene}-1-(triphenylmethyl)piperidine by conducting the reaction similar to that mentioned in Example 19 (d).

$^1$H NMR (400 MHz, d-MeOH) δ ppm: 2.11-2.19 (1H, m), 2.38-2.46 (1H, m), 2.40 (3H, s), 3.18-3.27 (1H, m), 3.39-3.47 (1H, m), 3.75 (1H, d, J=14.5), 4.09 (1H, d, J=14.5), 4.66-4.72 (1H, m), 7.04 (1H, s), 7.54-7.61 (1H, m), 7.81-7.87 (1H, m), 8.48-8.57 (2H, m).

(e) (E)-4-(Acetylsulfanyl)-1-[2-cyclopropyl-1-(2-fluorophenyl)-2-oxoethyl]-3-[(pyridin-3-yl)methylidene]piperidine The title compound was synthesized in a yield of 63% as a yellow oil using (E)-4-(acetylsulfanyl)-3-[(pyridin-3-yl)methylidene]piperidine bis(hydrogen trifluoroacetate) instead of (E)-4-(acetylsulfanyl)-3-benzylidenepiperidine hydrochloride by conducting the reaction similar to that mentioned in Example 1 (d).

$^1$H NMR (400 MHz, CDCl$_3$) δ ppm: 0.66-0.99 (4H, m), 1.83-1.96 (1H, m), 2.06-2.23 (2H, m), 2.34 (3H, s), 2.40-2.53 and 2.57-2.71 (total 1H, each m), 2.73-2.89 (1H, m), 2.98 and 3.12 (total 1H, each d, J=12.5), 3.44 and 3.56 (total 1H, each d, J=12.5), 4.46-4.55 (1H, m), 4.63 and 4.67 (total 1H, each s), 6.60 and 6.61 (total 1H, each s), 7.00-7.17 (2H, m), 7.17-7.49 (4H, m), 8.33-3.51 (2H, m);

MS (FAB) m/z: 425 (M+H)$^+$.

Example 28

(E)-1-[2-Cyclopropyl-1-(2-fluorophenyl)-2-oxoethyl]-3-[(pyridin-3-yl)methylidene]-4-sulfanylpiperidine dihydrochloride (Exemplification Compound No. 1-69)

The title compound was synthesized in a yield of 8% as colourless powdery crystals using (E)-4-(acetylsulfanyl)-1-[2-cyclopropyl-1-(2-fluorophenyl)-2-oxoethyl]-3-[(pyridin-3-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (400 MHz, CDCl$_3$) δ ppm: 0.60-0.98 (4H, m), 1.76-1.91 (1H, m), 2.02-2.16 (1H, m), 2.23-2.39 (1H, m), 2.59-2.73 (1H, m), 2.75-2.93 (1H, m), 3.21-3.33 (1H, m), 3.41 and 3.49 (total 1H, each d, J=12.5), 3.86-3.96 (1H, m), 4.69 and 4.66 (total 1H, each s), 6.58 (1H, s), 6.98-7.12 (2H, m), 7.13-7.21 (1H, m), 7.22-7.38 (2H, m), 7.38-7.50 (1H, m), 8.34-3.48 (2H, m);

MS (FAB) m/z: 383 (M+H)$^+$.

Example 29

(E)-4-(Acetylsulfanyl)-1-[2-cyclopropyl-1-(2-fluorophenyl)-2-oxoethyl]-3-[(pyridin-4-yl)methylidene]piperidine (Exemplification Compound No. 1-74)

(a) (E)-3-[(Pyridin-4-yl)methylidene]-1-(triphenylmethyl)piperidin-4-one

The title compound was synthesized in a yield of 71% as a pale yellow amorphous solid using isonicotinaldehyde instead of benzaldehyde by conducting the reaction similar to that mentioned in Example 1 (a).
$^1$H NMR (500 MHz, CDCl$_3$) δ ppm: 2.68 (2H, bs), 2.79 (2H, t, J=6.0), 3.38 (2H, bs), 7.04 (2H, d, J=6.0), 7.13-7.18 (3H, m), 7.22-7.28 (6H, m), 7.40-7.48 (7H, m), 8.53 (2H, d, J=6.0).

(b) (E)-3-[(Pyridin-4-yl)methylidene]-1-(triphenylmethyl)piperidin-4-ol

The title compound was synthesized in a yield of 79% as colourless powdery crystals using (E)-3-[(pyridin-4-yl)methylidene]-1-(triphenylmethyl)piperidin-4-one instead of (E)-3-benzylidene-1-(triphenylmethyl)piperidin-4-one by conducting the reaction similar to that mentioned in Example 1 (b)
$^1$H NMR (500 MHz, CDCl$_3$) δ ppm: 1.85-2.04 (2H, m), 2.11-2.31 (1H, m), 2.49 (1H, m), 2.86 (1H, m), 3.58-3.85 (1H, m), 4.14 (1H, m), 6.64 (1H, s), 7.04 (2H, d, J=6.0), 7.05-7.17 (9H, m), 7.25-7.38 (6H, m), 8.44 (2H, d, J=6.0).

(c) (E)-4-(Acetylsulfanyl)-3-[(pyridin-4-yl)methylidene]-1-(triphenylmethyl)piperidine The title compound was synthesized in a yield of 33% as a yellow amorphous solid using (E)-3-[(pyridin-4-yl)methylidene]-1-(triphenylmethyl)piperidin-4-ol instead of (E)-3-[(pyridin-3-yl)methylidene]-1-(triphenylmethyl)piperidin-4-ol by conducting the reaction similar to that mentioned in Example 27 (c).
$^1$H NMR (400 MHz, CDCl$_3$) δ ppm: 1.88-1.98 (1H, m), 2.01-2.21 (1H, m), 2.28 (3H, s), 2.33-2.45 (1H, m), 2.54-2.82 (2H, m), 3.33-3.60 (1H, m), 4.45 (1H, m), 6.61 (1H, s), 6.99 (2H, d, J=6.0), 7.03-7.37 (15H, m), 8.43 (2H, d, J=6.0).

(d) (E)-4-(Acetylsulfanyl)-3-[(pyridin-4-yl)methylidene]piperidine bis(hydrogen trifluoroacetate)

The title compound was synthesized in a yield of 54% as a yellow amorphous solid using (E)-4-(acetylsulfanyl)-3-[(pyridin-4-yl)methylidene]-1-(triphenylmethyl)piperidine instead of (E)-4-(acetylsulfanyl)-3-{[1-(t-butoxycarbonyl)-1H-imidazol-2-yl]methylidene}-1-(triphenylmethyl)piperidine by conducting the reaction similar to that mentioned in Example 19 (d).
$^1$H NMR (500 MHz, CDCl$_3$) δ ppm: 2.09-2.17 (1H, m), 2.41 (3H, s), 2.48-2.58 (1H, m), 3.15-3.24 (1H, m), 3.32-3.40 (1H, m), 3.76 (1H, d, J=14.5), 4.04 (1H, d, J=14.5), 4.61 (1H, t, J=4.0), 6.96 (1H, s), 7.47 (2H, d, J=6.0), 8.64 (2H, d, J=6.0).

(e) (E)-4-(Acetylsulfanyl)-1-[2-cyclopropyl-1-(2-fluorophenyl)-2-oxoethyl]-3-[(pyridin-4-yl)methylidene]piperidine The title compound was synthesized in a yield of 46% as a yellow oil using (E)-4-(acetylsulfanyl)-3-[(pyridin-4-yl)methylidene]piperidine bis(hydrogen trifluoroacetate) instead of (E)-4-(acetylsulfanyl)-3-benzylidenepiperidine hydrochloride by conducting the reaction similar to that mentioned in Example 1 (d).
$^1$H NMR (400 MHz, CDCl$_3$) δ ppm: 0.52-0.99 (4H, m), 1.83-1.95 (1H, m), 2.01-2.38 (2H, m), 2.34 (3H, s), 2.44-2.68 (1H, m), 2.72-2.93 (1H, m), 2.94 and 3.18 (total 1H, each d, J=12.5), 3.51 and 3.54 (total 1H, each d, J=12.5), 4.48 (1H, t, J=4.5), 4.66 and 4.67 (total 1H, each s), 6.56 and 6.57 (total 1H, each s), 6.98 and 7.02 (total 2H, each d, J=6.0), 7.04-7.16 (2H, m), 7.26-7.41 (2H, m), 8.42 and 8.48 (total 2H, each d, J=6.0);
MS (FAB) m/z: 425 (M+H)$^+$.

Example 30

(E)-1-[2-Cyclopropyl-1-(2-fluorophenyl)-2-oxoethyl]-3-[(pyridin-4-yl)methylidene]-4-sulfanylpiperidine dihydrochloride (Exemplification Compound No. 1-73)

The title compound was synthesized in a yield of 98% as a colourless solid using (E)-4-(acetylsulfanyl)-1-[2-cyclopropyl-1-(2-fluorophenyl)-2-oxoethyl]-3-[(pyridin-4-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.
$^1$H NMR (400 MHz, CDCl$_3$) δ ppm: 0.56-0.78 (2H, m), 0.82-0.99 (2H, m), 1.83-1.91 (1H, m), 2.03-2.11 (1H, m), 2.23-2.38 (1H, m), 2.58-2.76 (1H, m), 2.80-2.91 (1H, m), 3.25 and 3.29 (total 1H, each d, J=12.5), 3.39 and 3.54 (total 1H, each d, J=12.5), 3.88 (1H, m), 4.67 and 4.70 (total 1H, each s), 6.54 and 6.55 (total 1H, each s), 6.99 and 7.03 (total 2H, each d, J=6.0), 7.02-7.13 (2H, m), 7.24-7.38 (2H, m), 8.44 and 8.47 (total 2H, each d, J=6.0);
MS (FAB) m/z: 383 (M+H)$^+$.

Example 31

(E)-4-(Acetylsulfanyl)-1-[2-cyclopropyl-1-(2-fluorophenyl)-2-oxoethyl]-3-[(pyrazin-2-yl)methylidene]piperidine hydrochloride (Exemplification Compound No. 1-102)

(a) (E)-3-[(Pyrazin-2-yl)methylidene]-1-(triphenylmethyl)piperidin-4-one

The title compound was synthesized in a yield of 26% as a yellow amorphous solid using pyrazine-2-carbaldehyde instead of 1-(t-butoxycarbonyl)-1H-pyrazole-4-carbaldehyde by conducting successively reactions similar to those mentioned in Example 13 (a)
$^1$H NMR (400 MHz, CDCl$_3$) δ ppm: 2.67 (2H, bs), 2.81 (2H, t, J=6.0), 3.87 (2H, bs), 7.12-7.18 (3H, m), 7.21-7.28 (5H, m), 7.40 (1H, t, J=2.0), 7.46-7.53 (7H, m), 8.35 (1H, d, J=3.0), 8.38 (1H, dd, J=3.0, 1.5), 8.59 (1H, d, J=1.5).

(b) (E)-3-[(Pyrazin-2-yl)methylidene]-1-(triphenylmethyl)piperidin-4-ol

The title compound was synthesized in a yield of 99% as a colourless amorphous solid using (E)-3-[(pyrazin-2-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).
$^1$H NMR (400 MHz, CDCl$_3$) δ ppm: 1.85-2.03 (2H, m), 2.18 (1H, m), 2.47 (1H, bs), 2.93 (1H, bs), 4.17 (1H, bs), 4.37

(1H, bs), 6.73 (1H, s), 7.04-7.17 (10H, m), 7.33-7.40 (5H, m), 8.23 (1H, dd, J=3.0, 1.5), 8.30 (1H, d, J=3.0), 8.48 (1H, d, J=1.5).

(c) (E)-4-(Acetylsulfanyl)-3-[(pyrazin-2-yl)methylidene]piperidine hydrogen trifluoroacetate The title compound was synthesized in a yield of 20% as a colourless amorphous solid using (E)-3-[(pyrazin-2-yl)methylidene]-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c).

$^1$H NMR (400 MHz, CDCl$_3$) δ ppm: 2.18 (1H, m), 2.41 (3H, s), 2.53 (1H, m), 3.32 (1H, m), 3.53 (1H, d, J=14.0), 4.03 (1H, dd, J=12.5, 9.0), 4.66 (1H, t, J=4.0), 5.50 (1H, d, J=14.0), 6.92 (1H, s), 8.20 (1H, bs), 8.40-8.91 (2H, m).

(d) (E)-4-(Acetylsulfanyl)-1-[2-cyclopropyl-1-(2-fluorophenyl)-2-oxoethyl]-3-[(pyrazin-2-yl)methylidene]piperidine hydrochloride The title compound was synthesized in a yield of 41% as a pale yellow amorphous solid using (E)-4-(acetylsulfanyl)-3-[(pyrazin-2-yl)methylidene]piperidine hydrogen trifluoroacetate instead of (E)-4-(acetylsulfanyl)-3-benzylidenepiperidine hydrochloride by conducting the reaction similar to that mentioned in Example 1 (d).

$^1$H NMR (400 MHz, CDCl$_3$) δ ppm: 0.58-0.81 (2H, m), 0.84-1.01 (2H, m), 1.86-1.97 (1H, m), 2.15-2.27 (1H, m), 2.27-2.41 (1H, m), 2.32 (3H, s), 2.47-2.56 and 2.56-2.65 (total 1H, each m), 2.80 and 2.88 (total 1H, each m), 3.18 and 3.38 (total 1H, each d, J=14.0), 4.45 (1H, d, J=14.0), 4.53 (1H, t, J=4.0), 4.69 and 4.70 (total 1H, each s), 6.59 and 6.60 (total 1H, each s), 6.97-7.12 (2H, m), 7.21-7.32 (1H, m), 7.32-7.41 (1H, m), 8.24 and 8.35 (total 1H, each dd, J=3.0, 1.5), 8.26 and 8.29 (total 1H, each d, J=3.0), 8.38 and 8.40 (total 1H, each d, J=1.5);

IR (KBr, cm$^{-1}$): 1699, 1493.

Example 32

(E)-4-(Acetylsulfanyl)-1-[2-cyclopropyl-1-(2-fluorophenyl)-2-oxoethyl]-3-[(1,3-oxazol-2-yl)methylidene]piperidine (Exemplification Compound No. 1-78)

(a) (E)-3-[(1,3-Oxazol-2-yl)methylidene]-1-(triphenylmethyl)piperidin-4-one The title compound was synthesized in a yield of 66% as a pale yellow amorphous solid using 1,3-oxazole-2-carbaldehyde instead of benzaldehyde by conducting the reaction similar to that mentioned in Example 1 (a).

$^1$H NMR (400 MHz, CDCl$_3$) δ ppm: 2.66 (2H, bs), 2.79 (2H, t, J=6.0), 3.82 (2H, bs), 7.14-7.32 (11H, m), 7.49-7.57 (6H, m), 7.59 (1H, s).

(b) (E)-3-[(1,3-Oxazol-2-yl)methylidene]-1-(triphenylmethyl)piperidin-4-ol

The title compound was synthesized in a yield of 97% as a colourless amorphous solid using (E)-3-[(1,3-oxazol-2-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.83-1.98 (2H, m), 2.11-2.22 (1H, m), 2.36-2.56 (1H, m), 2.88-3.01 (1H, m), 4.05-4.15 (1H, m), 4.34-4.60 (1H, m), 6.55 (1H, s), 7.04 (1H, s), 7.09-7.24 (9H, m), 7.39-7.49 (7H, m).

(c) (E)-4-(Acetylsulfanyl)-3-[(1,3-oxazol-2-yl)methylidene]-1-(triphenylmethyl)piperidine The title compound was synthesized in a yield of 47% as a brown oil using (E)-3-[(1,3-oxazol-2-yl)methylidene]-1-(triphenylmethyl)piperidin-4-ol instead of (E)-3-[(pyridin-3-yl)methylidene]-1-(triphenylmethyl)piperidin-4-ol by conducting the reaction similar to that mentioned in Example 27 (c).

$^1$H NMR (400 MHz, CDCl$_3$) δ ppm: 1.90-1.99 (1H, m), 2.08-2.22 (1H, m), 2.26 (3H, s), 2.33-2.44 (1H, m), 2.56-2.73 (1H, m), 2.90-3.12 (1H, m), 3.91-4.12 (1H, m), 4.43 (1H, t, J=4.5), 6.49 (1H, s), 7.01 (1H, s), 7.09-7.25 (9H, m), 7.36-7.50 (7H, m).

(d) (E)-4-(Acetylsulfanyl)-3-[(1,3-oxazol-2-yl)methylidene]piperidine hydrogen trifluoroacetate The title compound was synthesized in a yield of 86% as a brown solid using (E)-4-(acetylsulfanyl)-3-[(1,3-oxazol-2-yl)methylidene]-1-(triphenylmethyl)piperidine instead of (E)-4-(acetylsulfanyl)-3-{[1-(t-butoxycarbonyl)-1H-imidazol-2-yl]methylidene}-1-(triphenylmethyl)piperidine by conducting the reaction similar to that mentioned in Example 19 (d).

$^1$H NMR (400 MHz, DMSO-d$_6$) δ ppm: 1.93-2.03 (1H, m), 2.21-2.33 (1H, m), 2.39 (3H, m), 3.10-3.33 (2H, m), 4.14 (1H, d, J=14.5), 4.60 (1H, t, J=4.5), 4.84 (1H, d, J=14.5), 6.68 (1H, s), 7.40 (1H, s), 8.18 (1H, s).

(e) (E)-4-(Acetylsulfanyl)-1-[2-cyclopropyl-1-(2-fluorophenyl)-2-oxoethyl]-3-[(1,3-oxazol-2-yl)methylidene]piperidine The title compound was synthesized in a yield of 85% as a pale brown oil using (E)-4-(acetylsulfanyl)-3-[(1,3-oxazol-2-yl)methylidene]piperidine hydrogen trifluoroacetate instead of (E)-4-(acetylsulfanyl)-3-benzylidenepiperidine hydrochloride by conducting the reaction similar to that mentioned in Example 1 (d).

$^1$H NMR (400 MHz, CDCl$_3$) δ ppm: 0.69-0.85 (2H, m), 0.90-1.09 (2H, m), 1.84-1.94 (1H, m), 2.20-2.29 (2H, m), 2.31 and 2.32 (total 3H, each s), 2.42-2.71 (1H, m), 2.75-2.86 (1H, m), 3.38-3.46 (1H, m), 4.30 and 4.42 (total 1H, each d, J=13.0), 4.45-4.51 (1H, m), 4.74 and 4.77 (total 1H, each s), 6.45 (1H, s), 7.03-7.17 (3H, m), 7.27-7.35 (1H, m), 7.37-7.52 (2H, m);

IR (liquid film, cm$^{-1}$): 1696, 1488.

Example 33

(E)-1-[2-Cyclopropyl-1-(2-fluorophenyl)-2-oxoethyl]-3-[(1,3-oxazol-2-yl)methylidene]-4-sulfanylpiperidine (Exemplification Compound No. 1-77)

The title compound was synthesized in a yield of 84% as a colourless oil using (E)-4-(acetylsulfanyl)-1-[2-cyclopropyl-1-(2-fluorophenyl)-2-oxoethyl]-3-[(1,3-oxazol-2-yl)methylidene]piperidine instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

¹H NMR (400 MHz, CDCl₃) δ ppm: 0.72-0.82 (2H, m), 0.91-1.08 (2H, m), 1.78-1.89 (1H, m), 2.21-2.37 (2H, m), 2.62-2.97 (2H, m), 3.83-4.06 (3H, m), 4.77 and 4.79 (total 1H, each s), 6.45 and 6.46 (total 1H, each s), 7.05-7.18 (3H, m), 7.27-7.34 (1H, m), 7.39-7.46 (1H, m), 7.47 and 7.51 (total 1H, each s);
IR (liquid film, cm⁻¹): 2563, 1699, 1488.

Example 34

(E)-4-(Acetylsulfanyl)-1-[2-cyclopropyl-1-(2-fluorophenyl)-2-oxoethyl]-3-[(1,3-oxazol-4-yl)methylidene]piperidine (Exemplification Compound No. 1-82)

(a) (E)-3-[(1,3-Oxazol-4-yl)methylidene]-1-(triphenylmethyl)piperidin-4-one

The title compound was synthesized in a yield of 19% as a yellow oil using 1,3-oxazole-4-carbaldehyde instead of benzaldehyde by conducting the reaction similar to that mentioned in Example 1 (a)
¹H NMR (400 MHz, CDCl₃) δ ppm: 2.66 (2H, bs), 2.76 (2H, t, J=6.0), 3.61 (2H, bs), 7.15-7.34 (9H, m), 7.35 (1H, s), 7.51-7.57 (6H, m), 7.59 (1H, s), 7.76 (1H, s).

(b) (E)-3-[(1,3-Oxazol-4-yl)methylidene]-1-(triphenylmethyl)piperidin-4-ol

The title compound was synthesized in a yield of 57% as a pale brown oil using (E)-3-[(1,3-oxazol-4-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).
¹H NMR (400 MHz, CDCl₃) δ ppm: 1.82-1.95 (1H, m), 2.09-2.19 (1H, m), 2.42-2.86 (3H, m), 3.77-4.18 (2H, m), 6.42 (1H, s), 7.08-7.23 (9H, m), 7.36-7.48 (7H, m), 7.69 (1H, s).

(c) (E)-4-(Acetylsulfanyl)-3-[(1,3-oxazol-4-yl)methylidene]-1-(triphenylmethyl)piperidine The title compound was synthesized in a yield of 57% as a yellow oil using (E)-3-[(1,3-oxazol-4-yl)methylidene]-1-(triphenylmethyl)piperidin-4-ol instead of (E)-3-[(pyridin-3-yl)methylidene]-1-(triphenylmethyl)piperidin-4-ol by conducting the reaction similar to that mentioned in Example 27 (c).
¹H NMR (400 MHz, CDCl₃) δ ppm: 1.88-2.20 (3H, m), 2.26 (3H, s), 2.33-2.44 (1H, m), 2.65 (1H, bs), 3.83 (1H, bs), 4.46 (1H, t, J=4.5), 6.41 (1H, s), 7.08-7.24 (9H, m), 7.34-7.52 (7H, m), 7.66 (1H, s).

(d) (E)-4-(Acetylsulfanyl)-3-[(1,3-oxazol-4-yl)methylidene]piperidine hydrogen trifluoroacetate The title compound was synthesized in a yield of 88% as a brown solid using (E)-4-(acetylsulfanyl)-3-[(1,3-oxazol-4-yl)methylidene]-1-(triphenylmethyl)piperidine instead of (E)-4-(acetylsulfanyl)-3-{[1-(t-butoxycarbonyl)-1H-imidazol-2-yl]methylidene}-1-(triphenylmethyl)piperidine by conducting the reaction similar to that mentioned in Example 19 (d).
¹H NMR (500 MHz, CDCl₃) δ ppm: 2.03-2.11 (1H, m), 2.36 (3H, s), 2.46-2.57 (1H, m), 3.12-3.25 (1H, m), 3.35-3.44 (1H, m), 3.84 (1H, d, J=14.0), 4.57 (1H, t, J=3.5), 5.40 (1H, d, J=14.0), 6.59 (1H, s), 7.68 (1H, s), 7.84 (1H, s).

(e) (E)-4-(Acetylsulfanyl)-1-[2-cyclopropyl-1-(2-fluorophenyl)-2-oxoethyl]-3-[(1,3-oxazol-4-yl)methylidene]piperidine The title compound was synthesized in a yield of 76% as a yellow oil using (E)-4-(acetylsulfanyl)-3-[(1,3-oxazol-4-yl)methylidene]piperidine hydrogen trifluoroacetate instead of (E)-4-(acetylsulfanyl)-3-benzylidenepiperidine hydrochloride by conducting the reaction similar to that mentioned in Example 1 (d)
¹H NMR (400 MHz, CDCl₃) δ ppm: 0.69-0.85 (2H, m), 0.91-1.07 (2H, m), 1.83-1.91 (1H, m), 2.17-2.35 (2H, m), 2.30 (3H, s), 2.41-2.66 (1H, m), 2.75-2.85 (1H, m), 3.15 and 3.24 (total 1H, each d, J=13.0), 4.13 and 4.22 (total 1H, each d, J=13.0), 4.47 (1H, t, J=4.5), 4.73 and 4.76 (total 1H, each s), 6.38 (1H, s), 7.04-7.18 (2H, m), 7.28-7.45 (2H, m), 7.54 and 7.59 (total 1H, each s), 7.71 and 7.76 (total 1H, each s);
IR (liquid film, cm⁻¹): 1694, 1488.

Example 35

(E)-1-[2-Cyclopropyl-1-(2-fluorophenyl)-2-oxoethyl]-3-[(1,3-oxazol-4-yl)methylidene]-4-sulfanylpiperidine (Exemplification Compound No. 1-81)

The title compound was synthesized in a yield of 92% as a yellow oil using (E)-4-(acetylsulfanyl)-1-[2-cyclopropyl-1-(2-fluorophenyl)-2-oxoethyl]-3-[(1,3-oxazol-4-yl)methylidene]piperidine instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.
¹H NMR (400 MHz, CDCl₃) δ ppm: 0.70-0.82 (2H, m), 0.91-1.06 (2H, m), 1.75-1.84 (1H, m), 2.14-2.34 (2H, m), 2.60-2.69 (1H, m), 2.74-2.92 (1H, m), 3.63-3.80 (2H, m), 3.85-3.91 (1H, m), 4.76 and 4.78 (total 1H, each s), 6.36 (1H, s), 7.05-7.18 (2H, m), 7.27-7.45 (2H, m), 7.55 and 7.60 (total 1H, each s), 7.74 and 7.77 (total 1H, each s);
IR (KBr, cm¹): 2569, 1694, 1487.

Example 36

(E)-4-(Acetylsulfanyl)-1-[2-cyclopropyl-1-(2-fluorophenyl)-2-oxoethyl]-3-[(1,3-oxazol-5-yl)methylidene]piperidine hydrochloride (Exemplification Compound No. 1-86)

(a) (E)-4-(t-Butyldimethylsilyloxy)-3-[(ethoxycarbonyl)methylidene]-1-(triphenylmethyl)piperidine To a solution of (E)-3-[(ethoxycarbonyl)methylidene]-1-(triphenylmethyl)piperidin-4-ol (14.97 g) in N,N-dimethylformamide (130 ml) were added successively t-butyldimethylsilyl chloride (6.86 g), 1H-imidazole (3.34 g) and 4-dimethylaminopyridine (0.43 g) under ice-cooling, and the resulting mixture was stirred at room temperature overnight. The reaction mixture was diluted with ethyl acetate and washed with saturated aqueous sodium chloride solution. The organic layer was dried over anhydrous sodium sulfate. The solvent was removed, and the residue was purified by chromatography on a silica gel column using a mixed solvent of ethyl acetate and hexane (1:19) as the eluent to afford the title compound (16.38 g, yield: 86%) as a colourless amorphous solid.
¹H NMR (400 MHz, CDCl₃) δ ppm: 0.01 (3H, s), 0.02 (3H, s), 0.90 (9H, s), 1.12 (3H, t, J=7.0), 1.59-1.74 (1H, m), 1.83-2.01 (3H, m), 3.00-3.12 (1H, m), 3.90 (1H, t, J=9.0), 3.96-

4.15 (2H, m), 4.73 (1H, m), 6.06 (1H, s), 7.11-7.18 (3H, m), 7.20-7.28 (6H, m), 7.36-7.54 (6H, m).

(b) (E)-4-(t-Butyldimethylsilyloxy)-3-(2-hydroxyethylidene]-1-(triphenylmethyl)piperidine To a solution of (E)-4-(t-butyldimethylsilyloxy)-3-[(ethoxycarbonyl)methylidene]-1-(triphenylmethyl)piperidine (15.14 g) in dichloromethane (110 ml) was added dropwise a 1.01N solution of diisobutyl aluminium hydride in toluene (66.40 ml) at −70° C., and the resulting mixture was stirred at the same temperature for 3 hours. After stirring, saturated aqueous ammonium chloride solution was added to the reaction mixture, and the resulting mixture was extracted with ethyl acetate. The extract was washed with saturated aqueous sodium chloride solution, and the organic layer was dried over anhydrous sodium sulfate. The solvent was removed in vacuo, and the residue was purified by chromatography on a silica gel column using a mixed solvent of ethyl acetate and hexane (1:3) as the eluent to afford the title compound (13.22 g, yield: 95%) as a colourless amorphous solid.

$^1$H NMR (400 MHz, CDCl$_3$) δ ppm: 0.01 (6H, s), 0.88 (9H, s), 1.62-2.00 (4H, m), 2.88-3.05 (1H, m), 3.51-3.71 (1H, m), 3.86 (1H, m), 4.07-4.24 (2H, m), 5.79 (1H, t, J=7.0), 7.11-7.33 (9H, m), 7.36-7.58 (6H, m).

(c) (E)-4-(t-Butyldimethylsilyloxy)-3-(formylmethylidene)-1-(triphenylmethyl)piperidine To a solution of (E)-4-(t-butyldimethylsilyloxy)-3-(2-hydroxyethylidene)-1-(triphenylmethyl)piperidine (8.50 g) in dichloromethane (120 ml) was added manganese dioxide (8.87 g) at room temperature, and the resulting mixture was stirred at room temperature for 45 hours. After stirring, the insoluble materials were filtered off. The filtrate was evaporated in vacuo, and the residue was purified by chromatography on a silica gel column using a mixed solvent of ethyl acetate and hexane (3:17) as the eluent to afford the title compound (7.54 g, yield: 89%) as a colourless amorphous solid.

$^1$H NMR (400 MHz, CDCl$_3$) δ ppm: 0.01 (3H, s), 0.02 (3H, s), 0.89 (9H, s), 1.59-1.88 (1H, m), 1.96-2.07 (3H, m), 3.08-3.18 (1H, m), 3.95 (1H, t, J=9.0), 4.37 (1H, m), 6.24 (1H, d, J=9.0), 7.14-7.22 (3H, m), 7.24-7.33 (6H, m), 7.39-7.55 (6H, m), 9.85 (1H, d, J=9.0)

(d) (E)-4-(t-Butyldimethylsilyloxy)-3-[(1,3-oxazol-5-yl)methylidene]-1-(triphenylmethyl)piperidine To a solution of (E)-4-(t-butyldimethylsilyloxy)-3-(formylmethylidene)-1-(triphenylmethyl)piperidine (112 mg) in methanol (2.5 ml) were added successively p-toluenesulfonylmethyl isocyanide (45 mg) and potassium carbonate (32 mg), and the resulting mixture was refluxed for 3.5 hours. After refluxing, water was added to the reaction mixture, and the resulting mixture was extracted with ethyl acetate. The extract was washed with saturated aqueous sodium chloride solution, and the organic layer was dried over anhydrous sodium sulfate. The solvent was removed in vacuo, and the residue was purified by chromatography on a silica gel column using a mixed solvent of ethyl acetate and hexane (1:19 to 1:3) as the eluent to afford the title compound (40 mg, yield: 32%) as a yellow oil.

$^1$H NMR (400 MHz, CDCl$_3$) δ ppm: 0.02 (3H, s), 0.04 (3H, s), 0.91 (9H, s), 1.64-2.11 (4H, m), 3.00-3.10 (1H, m), 3.98 (1H, t, J=7.0), 4.26-4.38 (1H, m), 6.46 (1H, s), 6.86 (1H, s), 7.09-7.33 (9H, m), 7.37-7.51 (6H, m), 7.56 (1H, s).

(e) (E)-3-[(1,3-Oxazol-5-yl)methylidene]-1-(triphenylmethyl)piperidin-4-ol

To a solution of (E)-4-(t-butyldimethylsilyloxy)-3-[(1,3-oxazol-5-yl)methylidene]-1-(triphenylmethyl)piperidine (499 mg) in tetrahydrofuran (8 ml) was added tetrabutylammonium fluoride (483 mg) under ice-cooling, and the resulting mixture was stirred at room temperature for 22 hours. The reaction mixture was diluted with ethyl acetate and washed with water and saturated aqueous sodium chloride solution, and the organic layer was dried over anhydrous sodium sulfate. The solvent was removed in vacuo, and the residue was purified by chromatography on a silica gel column using a mixed solvent of ethyl acetate and hexane (3:7) as the eluent to afford the title compound (254 mg, yield: 65%) as a yellow oil.

$^1$H NMR (500 MHz, CDCl$_3$) δ ppm: 1.85-1.99 (2H, m), 2.11-2.19 (1H, m), 2.36-2.54 (1H, m), 2.85-2.98 (1H, m), 3.93-4.14 (2H, m), 6.45 (1H, s), 6.88 (1H, s), 7.11-7.24 (9H, m), 7.41-7.51 (6H, m), 7.58 (1H, s).

(f) (E)-4-(Acetylsulfanyl)-3-[(1,3-oxazol-5-yl)methylidene]-1-(triphenylmethyl)piperidine The title compound was synthesized in a yield of 45% as a yellow solid using (E)-3-[(1,3-oxazol-5-yl)methylidene]-1-(triphenylmethyl)piperidin-4-ol instead of (E)-3-[(pyridin-3-yl)methylidene]-1-(triphenylmethyl)piperidin-4-ol by conducting the reaction similar to that mentioned in Example 27 (c).

$^1$H NMR (400 MHz, CDCl$_3$) δ ppm: 1.89-2.29 (3H, m), 2.27 (3H, s), 2.35-2.45 (1H, m), 2.64-2.79 (1H, m), 3.69-3.85 (1H, m), 4.42-4.48 (1H, m), 6.42 (1H, s), 6.86 (1H, s), 7.12-7.28 (9H, m), 7.41-7.49 (6H, m), 7.56 (1H, s).

(g) (E)-4-(Acetylsulfanyl)-3-[(1,3-oxazol-5-yl)methylidene]piperidine hydrogen trifluoroacetate The title compound was synthesized in a yield of 94% as a brown amorphous solid using (E)-4-(acetylsulfanyl)-3-[(1,3-oxazol-5-yl)methylidene]-1-(triphenylmethyl)piperidine instead of (E)-4-(acetylsulfanyl)-3-{[1-(t-butoxycarbonyl)-1H-imidazol-2-yl]methylidene}-1-(triphenylmethyl)piperidine by conducting the reaction similar to that mentioned in Example 19 (d).

$^1$H NMR (500 MHz, CDCl$_3$+DMSO-d$_6$) δ ppm: 2.01-2.09 (1H, m), 2.37-2.43 (1H, m), 2.38 (3H, s), 3.14-3.42 (2H, m), 3.90 (1H, d, J=14.5), 4.47-4.59 (2H, m), 6.68 (1H, s), 7.92-7.97 (1H, m), 8.17-8.21 (1H, m).

(h) (E)-4-(Acetylsulfanyl)-1-[2-cyclopropyl-1-(2-fluorophenyl)-2-oxoethyl]-3-[(1,3-oxazol-5-yl)methylidene]piperidine hydrochloride The title compound was synthesized in a yield of 81% as a pale brown solid using (E)-4-(acetylsulfanyl)-3-[(1,3-oxazol-5-yl)methylidene]piperidine hydrogen trifluoroacetate instead of (E)-4-(acetylsulfanyl)-3-benzylidenepiperidine hydrochloride by conducting the reaction similar to that mentioned in Example 1 (d)

$^1$H NMR (400 MHz, CDCl$_3$) δ ppm: 0.72-0.87 (2H, m), 0.93-1.09 (2H, m), 1.83-1.94 (1H, m), 2.15-2.36 (2H, m), 2.32 (3H, s), 2.48-2.62 (1H, m), 2.76-2.92 (1H, m), 3.07 and 3.30 (total 1H, each d, J=13.0), 3.90 (1H, d, J=13.0), 4.45-4.50 (1H, m), 4.75 (1H, s), 6.38 and 6.40 (total 1H, each s), 6.86 and 6.93 (total 1H, each s), 7.05-7.19 (2H, m), 7.29-7.45 (2H, m), 7.64 and 7.71 (total 1H, each s);
IR (KBr, cm$^{-1}$): 1698, 1494.

Example 37

(E)-1-[2-Cyclopropyl-1-(2-fluorophenyl)-2-oxoethyl]-3-[(1,3-oxazol-5-yl)methylidene]-4-sulfanylpiperidine hydrochloride (Exemplification Compound No. 1-85)

The title compound was synthesized in a quantitative yield as a pale yellow solid using (E)-4-(acetylsulfanyl)-1-[2-cyclopropyl-1-(2-fluorophenyl)-2-oxoethyl]-3-[(1,3-oxazol-5-yl)methylidene]piperidine hydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (400 MHz, CDCl$_3$) δ ppm: 0.73-0.86 (2H, m), 0.93-1.07 (2H, m), 1.77-1.87 (1H, m), 2.13-2.36 (2H, m), 2.61-2.75 (1H, m), 2.81-2.91 (1H, m), 3.51-3.78 (2H, m), 3.81-3.91 (1H, m), 4.77 and 4.78 (total 1H, each s), 6.36 and 6.39 (total 1H, each s), 6.86 and 6.92 (total 1H, each s), 7.06-7.19 (2H, m), 7.29-7.46 (2H, m), 7.66 and 7.70 (total 1H, each s);

IR (KBr, cm$^{-1}$): 1712, 1494.

Example 38

(E)-4-(Acetylsulfanyl)-1-[2-cyclopropyl-1-(2-fluorophenyl)-2-oxoethyl]-3-[(isoxazol-3-yl)methylidene]piperidine hydrochloride (Exemplification Compound No. 1-90)

(a) (E)-3-[(Isoxazol-3-yl)methylidene]-1-(triphenylmethyl)piperidin-4-one

The title compound was synthesized in a yield of 82% as a pale yellow oil using isoxazole-3-carbaldehyde instead of benzaldehyde by conducting the reaction similar to that mentioned in Example 1 (a).

$^1$H NMR (400 MHz, CDCl$_3$) δ ppm: 2.68 (2H, bs), 2.79 (2H, t, J=6.0), 3.60 (2H, bs), 6.25 (1H, s), 7.14-7.22 (3H, m), 7.23-7.38 (7H, m), 7.48-7.56 (6H, m), 8.35 (1H, s).

(b) (E)-3-[(Isoxazol-3-yl)methylidene]-1-(triphenylmethyl)piperidin-4-ol

The title compound was synthesized in a yield of 69% as a colourless solid using (E)-3-[(isoxazol-3-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.86-1.98 (2H, m), 2.10-2.20 (1H, m), 2.31-2.50 (1H, m), 2.83-2.97 (1H, m), 3.84-4.17 (2H, m), 6.19 (1H, d, J=1.5), 6.53 (1H, s), 7.07-7.21 (9H, m), 7.32-7.45 (6H, m), 8.29 (1H, d, J=1.5).

(c) (E)-4-(Acetylsulfanyl)-3-[(isoxazol-3-yl)methylidene]-1-(triphenylmethyl)piperidine The title compound was synthesized in a yield of 75% as a yellow amorphous solid using (E)-3-[(isoxazol-3-yl)methylidene]-1-(triphenylmethyl)piperidin-4-ol instead of (E)-3-[(pyridin-3-yl)methylidene]-1-(triphenylmethyl)piperidin-4-ol by conducting the reaction similar to that mentioned in Example 27 (c).

$^1$H NMR (500 MHz, CDCl$_3$) δ ppm: 1.91-1.99 (1H, m), 2.12-2.22 (1H, m), 2.27 (3H, s), 2.34-2.44 (1H, m), 2.58-2.96 (2H, m), 3.51-3.69 (1H, m), 4.46 (1H, m), 6.13 (1H, s), 6.51 (1H, s), 7.08-7.31 (9H, m), 7.34-7.47 (6H, m), 8.25 (1H, s).

(d) (E)-4-(Acetylsulfanyl)-3-[(isoxazol-3-yl)methylidene]piperidine hydrogen trifluoroacetate The title compound was synthesized in a yield of 68% as a white solid using (E)-4-(acetylsulfanyl)-3-[(isoxazol-3-yl)methylidene]-1-(triphenylmethyl)piperidine instead of (E)-4-(acetylsulfanyl)-3-{[1-(t-butoxycarbonyl)-1H-imidazol-2-yl]methylidene}-1-(triphenylmethyl)piperidine by conducting the reaction similar to that mentioned in Example 19 (d).

$^1$H NMR (400 MHz, CDCl$_3$) δ ppm: 2.08-2.16 (1H, m), 2.38 (3H, s), 2.49-2.62 (1H, m), 3.15-3.25 (1H, m), 3.38-3.46 (1H, m), 3.83 (1H, d, J=14.5), 4.62 (1H, t, J=4.5), 4.80 (1H, d, J=14.5), 6.32 (1H, s), 6.63 (1H, s), 8.37 (1H, s).

(e) (E)-4-(Acetylsulfanyl)-1-[2-cyclopropyl-1-(2-fluorophenyl)-2-oxoethyl]-3-[(isoxazol-3-yl)methylidene]piperidine hydrochloride The title compound was synthesized in a yield of 69% as a pale yellow solid using (E)-4-(acetylsulfanyl)-3-[(isoxazol-3-yl)methylidene]piperidine hydrogen trifluoroacetate instead of (E)-4-(acetylsulfanyl)-3-benzylidenepiperidine hydrochloride by conducting the reaction similar to that mentioned in Example 1 (d)

$^1$H NMR (400 MHz, CDCl$_3$) δ ppm: 0.69-0.85 (2H, m), 0.91-1.05 (2H, m), 1.85-1.94 (1H, m), 2.12-2.35 (2H, m), 2.32 (3H, s), 2.45-2.68 (1H, m), 2.75-2.83 (1H, m), 3.18 and 3.26 (total 1H, each d, J=13.5), 3.86 and 3.93 (total 1H, each d, J=13.5), 4.50 (1H, t, J=4.5), 4.71 and 4.76 (total 1H, each s), 6.27 and 6.31 (total 1H, each d, J=2.0), 6.48 (1H, s), 7.06-7.18 (2H, m), 7.28-7.42 (2H, m), 8.30 and 8.33 (total 1H, each d, J=2.0);

IR (KBr, cm$^{-1}$): 1698, 1495.

Example 39

(E)-1-[2-Cyclopropyl-1-(2-fluorophenyl)-2-oxoethyl]-3-[(isoxazol-3-yl)methylidene]-4-sulfanylpiperidine hydrochloride (Exemplification Compound No. 1-89)

The title compound was synthesized in a yield of 84% as a colourless solid using (E)-4-(acetylsulfanyl)-1-[2-cyclopropyl-1-(2-fluorophenyl)-2-oxoethyl]-3-[(isoxazol-3-yl)methylidene]piperidine hydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (400 MHz, CDCl$_3$) δ ppm: 0.69-0.82 (2H, m), 0.91-1.04 (2H, m), 1.79-1.87 (1H, m), 2.09-2.18 (1H, m), 2.23-2.36 (1H, m), 2.60-2.69 (1H, m), 2.75-2.93 (1H, m), 3.54 and 3.57 (total 1H, each d, J=12.5), 3.65 and 3.70 (total 1H, each d, J=12.5), 3.85-3.92 (1H, m), 4.75 and 4.77 (total 1H, each s), 6.29 and 6.34 (total 1H, each d, J=1.5), 6.49 and 6.50 (total 1H, each s), 7.06-7.17 (2H, m), 7.28-7.41 (2H, m), 8.31 and 8.33 (total 1H, each d, J=1.5);

IR (KBr, cm$^{-1}$): 1713, 1495.

Example 40

(E)-4-(Acetylsulfanyl)-1-[2-cyclopropyl-1-(2-fluorophenyl)-2-oxoethyl]-3-[(isoxazol-5-yl)methylidene]piperidine (Exemplification Compound No. 1-98)

(a) (E)-3-[(Isoxazol-5-yl)methylidene]-1-(triphenylmethyl)piperidin-4-one

The title compound was synthesized in a yield of 70% as a yellow amorphous solid using isoxazole-5-carbaldehyde instead of benzaldehyde by conducting the reaction similar to that mentioned in Example 1 (a).

$^1$H NMR (400 MHz, CDCl$_3$) δ ppm: 2.69 (2H, bs), 2.80 (2H, t, J=6.0), 3.63 (2H, bs), 6.21 (1H, s), 7.16-7.21 (3H, m), 7.24-7.32 (6H, m), 7.36 (1H, s), 7.48-7.55 (6H, m), 8.19 (1H, s).

(b) (E)-3-[(Isoxazol-5-yl)methylidene]-1-(triphenylmethyl)piperidin-4-ol

The title compound was synthesized in a yield of 69% as a colourless solid using (E)-3-[(isoxazol-5-yl)methylidene]-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.85-1.98 (2H, m), 2.11-2.21 (1H, m), 2.30-2.47 (1H, m), 2.89-3.02 (1H, m), 4.02-4.16 (2H, m), 5.98 (1H, s), 6.60 (1H, s), 7.09-7.25 (9H, m), 7.37-7.49 (6H, m), 8.11 (1H, s).

(c) (E)-4-(Acetylsulfanyl)-3-[(isoxazol-5-yl)methylidene]-1-(triphenylmethyl)piperidine The title compound was synthesized in a yield of 68% as a brown amorphous solid using (E)-3-[(isoxazol-5-yl)methylidene]-1-(triphenylmethyl)piperidin-4-ol instead of (E)-3-[(pyridin-3-yl)methylidene]-1-(triphenylmethyl)piperidin-4-ol by conducting the reaction similar to that mentioned in Example 27 (c).

$^1$H NMR (400 MHz, CDCl$_3$) δ ppm: 1.92-2.00 (1H, m), 2.08-2.24 (1H, m), 2.28 (3H, s), 2.34-2.46 (1H, m), 2.58-2.72 (1H, m), 2.78-2.96 (1H, m), 3.61-3.78 (1H, m), 4.46 (1H, t, J=5.0), 5.95 (1H, s), 6.54 (1H, s), 7.12-7.25 (9H, m), 7.39-7.47 (6H, m), 8.08 (1H, s).

(d) (E)-4-(Acetylsulfanyl)-3-[(isoxazol-5-yl)methylidene]piperidine hydrogen trifluoroacetate The title compound was synthesized in a yield of 90% as a pale brown solid using (E)-4-(acetylsulfanyl)-3-[(isoxazol-5-yl)methylidene]-1-(triphenylmethyl)piperidine instead of (E)-4-(acetylsulfanyl)-3-{[1-(t-butoxycarbonyl)-1H-imidazol-2-yl]methylidene}-1-(triphenylmethyl)piperidine by conducting the reaction similar to that mentioned in Example 19 (d).

$^1$H NMR (400 MHz, CDCl$_3$) δ ppm: 2.08-2.16 (1H, m), 2.38 (3H, s), 2.51-2.64 (1H, m), 3.14-3.25 (1H, m), 3.42-3.51 (1H, m), 3.91 (1H, d, J=14.5), 4.59 (1H, t, J=4.0), 4.84 (1H, d, J=14.5), 6.28 (1H, s), 6.70 (1H, s), 8.20 (1H, s).

(e) (E)-4-(Acetylsulfanyl)-1-[2-cyclopropyl-1-(2-fluorophenyl)-2-oxoethyl]-3-[(isoxazol-5-yl)methylidene]piperidine The title compound was synthesized in a yield of 89% as a yellow oil using (E)-4-(acetylsulfanyl)-3-[(isoxazol-5-yl)methylidene]piperidine hydrogen trifluoroacetate instead of (E)-4-(acetylsulfanyl)-3-benzylidenepiperidine hydrochloride by conducting the reaction similar to that mentioned in Example 1 (d)

$^1$H NMR (400 MHz, CDCl$_3$) δ ppm: 0.75-0.87 (2H, m), 0.95-1.09 (2H, m), 1.86-1.95 (1H, m), 2.12-2.35 (2H, m), 2.32 (3H, s), 2.43-2.67 (1H, m), 2.77-2.85 (1H, m), 3.20 and 3.32 (total 1H, each d, J=14.0), 3.93 and 3.96 (total 1H, each d, J=14.0), 4.47 (1H, t, J=4.5), 4.76 and 4.78 (total 1H, each s), 6.09 and 6.14 (total 1H, each s), 6.50 (1H, s), 7.07-7.20 (2H, m), 7.29-7.42 (2H, m), 8.13 and 8.15 (total 1H, each s);

IR (liquid film, cm$^{-1}$): 1695, 1488.

Example 41

(E)-1-[2-Cyclopropyl-1-(2-fluorophenyl)-2-oxoethyl]-3-[(isoxazol-5-yl)methylidene]-4-sulfanylpiperidine hydrochloride (Exemplification Compound No. 1-97)

The title compound was synthesized in a quantitative yield as a colourless amorphous solid using (E)-4-(acetylsulfanyl)-1-[2-cyclopropyl-1-(2-fluorophenyl)-2-oxoethyl]-3-[(isoxazol-5-yl)methylidene]piperidine instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (400 MHz, CDCl$_3$) δ ppm: 0.74-0.86 (2H, m), 0.94-1.08 (2H, m), 1.80-1.88 (1H, m), 2.11-2.18 (1H, m), 2.25-2.36 (1H, m), 2.62-2.70 (1H, m), 2.76-2.93 (1H, m), 3.59 and 3.60 (total 1H, each d, J=13.0), 3.68 and 3.77 (total 1H, each d, J=13.0), 3.82-3.88 (1H, m), 4.79 and 4.80 (total 1H, each s), 6.10 and 6.15 (total 1H, each s), 6.51 (1H, s), 7.07-7.20 (2H, m), 7.29-7.42 (2H, m), 8.14 and 8.16 (total 1H, each s);

IR (KBr, cm$^{-1}$): 1712, 1494.

Example 42

(E)-4-(Acetylsulfanyl)-1-[2-cyclopropyl-1-(2-fluorophenyl)-2-oxoethyl]-3-[(1,2,3-thiadiazol-4-yl)methylidene]piperidine hydrochloride (Exemplification Compound No. 1-126)

(a) (E)-3-[(1,2,3-Thiadiazol-4-yl)methylidene]-1-(triphenylmethyl)piperidin-4-one The title compound was synthesized in a yield of 36% as an orange-coloured amorphous solid using 1,2,3-thiadiazole-4-carbaldehyde instead of benzaldehyde by conducting the reaction similar to that mentioned in Example 1(a)

$^1$H NMR (500 MHz, CDCl$_3$) δ ppm: 2.71 (2H, bs), 2.83 (2H, t, J=6.5), 3.82 (2H, bs), 7.13-7.19 (3H, m), 7.22-7.30 (6H, m), 7.49-7.56 (6H, m), 7.74 (1H, s), 8.41 (1H, s).

(b) (E)-3-[(1,2,3-Thiadiazol-4-yl)methylidene]-1-(triphenylmethyl)piperidin-4-ol The title compound was synthesized in a yield of 95% as an orange-coloured amorphous solid using (E)-3-[(1,2,3-thiadiazol-4-yl)methylidene]-1-(triphenylmethyl)piperidin-4-one instead of (E)-3-benzylidene-1-(triphenylmethyl)piperidin-4-one by conducting the reaction similar to that mentioned in Example 1 (b)

$^1$H NMR (500 MHz, CDCl$_3$) δ ppm: 1.90-2.02 (2H, m), 2.14-2.25 (1H, m), 2.40-2.63 (1H, m), 2.85-2.99 (1H, m), 3.97-4.13 (1H, m), 4.18-4.27 (1H, m), 6.97 (1H, s), 7.03-7.20 (9H, m), 7.31-7.42 (6H, m), 8.14 (1H, s).

(c) (E)-4-(Acetylsulfanyl)-3-[(1,2,3-thiadiazol-4-yl)methylidene]piperidine hydrogen trifluoroacetate The title compound was synthesized in a yield of 19% as a pale yellow amorphous solid using (E)-3-[(1,2,3-thiadiazol-4-yl)methylidene]-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21(c).

$^1$H NMR (500 MHz, CDCl$_3$) δ ppm: 2.11-2.21 (1H, m), 2.39 (3H, s), 2.54-2.67 (1H, m), 3.17-3.29 (1H, m), 3.44-3.54 (1H, m), 3.90-4.02 (1H, m), 4.68 (1H, m), 5.29-5.36 (1H, m), 6.97 (1H, s), 8.44 (1H, s).

(d) (E)-4-(Acetylsulfanyl)-1-[2-cyclopropyl-1-(2-fluorophenyl)-2-oxoethyl]-3-[(1,2,3-thiadiazol-4-yl)methylidene]piperidine hydrochloride The title compound was synthesized in a yield of 54% as an orange-coloured amorphous solid using (E)-4-(acetylsulfanyl)-3-[(1,2,3-thiadiazol-4-yl)methylidene]piperidine hydrogen trifluoroacetate instead of (E)-4-(acetylsulfanyl)-3-benzylidenepiperidine hydrochloride by conducting the reaction similar to that mentioned in Example 1(d).

$^1$H NMR (500 MHz, CDCl$_3$) δ ppm: 0.64-0.84 (2H, m), 0.90-1.05 (2H, m), 1.88-1.98 (1H, m), 2.05-2.13 (1H, m), 2.27-2.39 (1H, m), 2.33 and 2.34 (total 3H, each s), 2.52 and 2.65 (total 1H, each m), 2.76-2.88 (1H, m), 3.22 and 3.36 (total 1H, each d, J=12.0), 4.12-4.12 (1H, m), 4.53-4.59 (1H, m), 4.76 and 4.79 (total 1H, each s), 6.91 (1H, s), 7.03-7.17 (2H, m), 7.27-7.40 (2H, m), 8.42 and 8.44 (total 1H, each s);
IR (KBr, cm$^{-1}$): 1698, 1495.

Example 43

(E)-1-[2-Cyclopropyl-1-(2-fluorophenyl)-2-oxoethyl]-4-sulfanyl-3-[(1,2,3-thiadiazol-4-yl)methylidene]piperidine hydrochloride (Exemplification Compound No. 1-125)

The title compound was synthesized in a yield of 89% as a yellow amorphous solid using (E)-4-(acetylsulfanyl)-1-[2-cyclopropyl-1-(2-fluorophenyl)-2-oxoethyl]-3-[(1,2,3-thiadiazol-4-yl)methylidene]piperidine hydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (500 MHz, CDCl$_3$) δ ppm: 0.65-0.85 (2H, m), 0.89-1.04 (2H, m), 1.82-1.91 (1H, m), 2.01-2.12 (1H, m), 2.28-2.40 (1H, m), 2.60-2.73 (1H, m), 2.80-2.94 (1H, m), 3.59-3.73 and 3.76-3.83 (total 2H, each m), 3.91-3.98 (1H, m), 4.79 and 4.81 (total 1H, each s), 6.95 and 6.96 (total 1H, each s), 7.03-7.18 (2H, m), 7.27-7.40 (2H, m), 8.47 and 8.49 (total 1H, each s);
IR (KBr, cm$^{-1}$): 2449, 1712.

Example 44

(E)-4-(Acetylsulfanyl)-1-[2-cyclopropyl-1-(2-fluorophenyl)-2-oxoethyl]-3-[(1,2,5-thiadiazol-3-yl)methylidene]piperidine hydrochloride (Exemplification Compound No. 1-142)

(a) (E)-3-[(1,2,5-Thiadiazol-3-yl)methylidene]-1-(triphenylmethyl)piperidin-4-one The title compound was synthesized in a yield of 49% as a brown oil using 1,2,5-thiadiazole-3-carbaldehyde instead of benzaldehyde by conducting the reaction similar to that mentioned in Example 1(a)

$^1$H NMR (400 MHz, CDCl$_3$) δ ppm: 2.68 (2H, bs), 2.81 (2H, t, J=6.0), 3.85 (2H, bs), 7.14-7.20 (3H, m), 7.22-7.30 (6H, m), 7.49-7.59 (7H, m), 8.56 (1H, s).

(b) (E)-3-[(1,2,5-Thiadiazol-3-yl)methylidene]-1-(triphenylmethyl)piperidin-4-ol The title compound was synthesized in a yield of 63% as a colourless oil using (E)-3-[(1,2,5-thiadiazol-3-yl)methylidene]-1-(triphenylmethyl)piperidin-4-one instead of (E)-3-benzylidene-1-(triphenylmethyl)piperidin-4-one by conducting the reaction similar to that mentioned in Example 1(b).

$^1$H NMR (500 MHz, CDCl$_3$) δ ppm: 1.88-1.99 (2H, m), 2.15-2.22 (1H, m), 2.35-2.53 (1H, m), 2.91-3.03 (1H, m), 4.15-4.21 (1H, m), 4.25-4.43 (1H, m), 6.82 (1H, s), 7.07-7.19 (9H, m), 7.32-7.53 (7H, m), 8.43 (1H, s).

(c) (E)-4-(Acetylsulfanyl)-3-[(1,2,5-thiadiazol-3-yl)methylidene]-1-(triphenylmethyl)piperidine The title compound was synthesized in a yield of 46% as a brown oil using (E)-3-[(1,2,5-thiadiazol-3-yl)methylidene]-1-(triphenylmethyl)piperidin-4-ol instead of (E)-3-[(pyridin-3-yl)methylidene]-1-(triphenylmethyl)piperidin-4-ol by conducting the reaction similar to that mentioned in Example 27(c).

$^1$H NMR (400 MHz, CDCl$_3$) δ ppm: 1.93-2.02 (1H, m), 2.09-2.24 (1H, m), 2.28 (3H, s), 2.38-2.49 (1H, m), 2.63-2.76 (1H, m), 2.80-3.01 (1H, m), 3.90-4.08 (1H, m), 4.50 (1H, t, J=4.5), 6.78 (1H, s), 7.08-7.19 (9H, m), 7.34-7.41 (6H, m), 8.39 (1H, s).

(d) (E)-4-(Acetylsulfanyl)-3-[(1,2,5-thiadiazol-3-yl)methylidene]piperidine hydrogen trifluoroacetate The title compound was synthesized in a yield of 31% as a colourless solid using (E)-4-(acetylsulfanyl)-3-[(1,2,5-thiadiazol-3-yl)methylidene]-1-(triphenylmethyl)piperidine instead of (E)-4-(acetylsulfanyl)-3-{[1-(t-butoxycarbonyl)-1H-imidazol-2-yl]methylidene}-1-(triphenylmethyl)piperidine by conducting the reaction similar to that mentioned in Example 19(d).

$^1$H NMR (400 MHz, CDCl$_3$) δ ppm: 2.08-2.18 (1H, m), 2.39 (3H, s), 2.50-2.63 (1H, m), 3.13-3.24 (1H, m), 3.33-3.43 (1H, m), 3.92 (1H, d, J=14.5), 4.64 (1H, t, J=4.5), 5.25 (1H, d, J=14.5), 6.99 (1H, s), 8.49 (1H, s).

(e) (E)-4-(Acetylsulfanyl)-1-[2-cyclopropyl-1-(2-fluorophenyl)-2-oxoethyl]-3-[(1,2,5-thiadiazol-3-yl)methylidene]piperidine hydrochloride The title compound was synthesized in a yield of 69% as a pale brown solid using (E)-4-(acetylsulfanyl)-3-[(1,2,5-thiadiazol-3-yl)methylidene]piperidine hydrogen trifluoroacetate instead of (E)-4-(acetylsulfanyl)-3-benzylidenepiperidine hydrochloride by conducting the reaction similar to that mentioned in Example 1(d)

$^1$H NMR (400 MHz, CDCl$_3$) δ ppm: 0.65-1.07 (4H, m), 1.87-1.98 (1H, m), 2.13-2.39 (2H, m), 2.33 (3H, s), 2.47-2.68 (1H, m), 2.80-2.90 (1H, m), 3.27 and 3.43 (total 1H, each d, J=13.5), 4.31 and 4.35 (total 1H, each d, J=13.5), 4.50-4.56 (1H, m), 4.75 and 4.76 (total 1H, each s), 6.75 and 6.76 (total 1H, each s), 7.02-7.17 (2H, m), 7.27-7.42 (2H, m), 8.40 and 8.42 (total 1H, each s);
IR (KBr, cm$^{-1}$): 1698, 1494.

Example 45

(E)-1-[2-Cyclopropyl-1-(2-fluorophenyl)-2-oxoethyl]-4-sulfanyl-3-[(1,2,5-thiadiazol-3-yl)methylidene]piperidine hydrochloride (Exemplification Compound No. 1-141)

The title compound was synthesized in a yield of 71% as a colourless solid using (E)-4-(acetylsulfanyl)-1-[2-cyclopropyl-1-(2-fluorophenyl)-2-oxoethyl]-3-[(1,2,5-thiadiazol-3-yl)methylidene]piperidine hydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (400 MHz, CDCl$_3$) δ ppm: 0.66-0.82 (2H, m), 0.90-1.05 (2H, m), 1.80-1.92 (1H, m), 2.11-2.20 (1H, m), 2.28-2.39 (1H, m), 2.65-2.74 (1H, m), 2.82-2.96 (1H, m), 3.81-3.98 (3H, m), 4.76 and 4.78 (total 1H, each s), 6.75 (1H, s), 7.03-7.16 (2H, m), 7.28-7.41 (2H, m), 8.42 and 8.43 (total 1H, each s);

IR (KBr, cm$^{-1}$): 2599, 1713, 1494.

Example 46

(E)-4-(Acetylsulfanyl)-1-[2-cyclopropyl-1-(2-fluorophenyl)-2-oxoethyl]-3-[(indol-3-yl)methylidene]piperidine (Exemplification Compound No. 1-166)

(a) (E)-3-{[1-(t-Butoxycarbonyl)indol-3-yl]methylidene}-1-(triphenylmethyl)piperidin-4-one The title compound was synthesized in a yield of 62% as a yellow crystal using 1-(t-butoxycarbonyl)indole-3-carbaldehyde instead of benzaldehyde by conducting the reaction similar to that mentioned in Example 1(a).

$^1$H NMR (400 MHz, CDCl$_3$) δ ppm: 1.62 (9H, s), 2.49-2.60 (1H, m), 2.64-2.74 (1H, m), 2.76-2.83 (1H, m), 3.24-3.37 (2H, m), 3.49 (1H, bs), 7.14-7.23 (3H, m), 7.24-7.44 (7H, m), 7.48-7.63 (9H, m), 7.75-7.85 (1H, m), 8.12-8.18 (1H, m).

(b) (E)-3-{[1-(t-Butoxycarbonyl)indol-3-yl]methylidene}-1-(triphenylmethyl)piperidin-4-ol The title compound was synthesized in a yield of 32% as a pale yellow amorphous solid using (E)-3-{[1-(t-butoxycarbonyl)indol-3-yl]methylidene}-1-(triphenylmethyl)piperidin-4-one instead of (E)-3-benzylidene-1-(triphenylmethyl)piperidin-4-one by conducting the reaction similar to that mentioned in Example 1(b)

$^1$H NMR (400 MHz, CDCl$_3$) δ ppm: 1.62 (9H, s), 1.65-1.74 (1H, m), 1.86-1.99 (2H, m), 2.03-2.27 (2H, m), 2.65-2.83 (1H, m), 4.28 (1H, bs), 6.62 (1H, s), 6.93-7.13 (9H, m), 7.15 (1H, s), 7.23-7.39 (8H, m), 7.63 (1H, d, J=7.5), 8.08-8.20 (1H, m).

(c) (E)-3-{[1-(t-Butoxycarbonyl)indol-3-yl]methylidene}piperidin-4-ol hydrogen acetate The title compound was synthesized in a yield of 99% as a colourless crystal using (E)-3-{[1-(t-butoxycarbonyl)indol-3-yl]methylidene}-1-(triphenylmethyl)piperidin-4-ol instead of (E)-3-[1-(furan-2-yl)methylidene]-1-(triphenylmethyl)piperidin-4-ol by conducting the reaction similar to that mentioned in Example 7 (c)

$^1$H NMR (400 MHz, CDCl$_3$) δ ppm: 1.45-1.57 (1H, m), 1.64 (9H, s), 1.88-1.98 (1H, m), 2.62-2.74 (1H, m), 2.92-3.03 (1H, m), 3.11 (1H, d, J=13.5), 3.77 (1H, d, J=13.5), 4.14-4.23 (1H, m), 6.47 (1H, s), 7.28 (1H, t, J=7.5), 7.36 (1H, t, J=7.5), 7.51 (1H, s), 7.59 (1H, d, J=7.5), 8.05 (1H, d, J=7.5).

(d) (E)-3-{[1-(t-Butoxycarbonyl)indol-3-yl]methylidene}-1-[2-cyclopropyl-1-(2-fluorophenyl)-2-oxoethyl]piperidin-4-ol The title compound was synthesized in a yield of 76% as a pale yellow amorphous solid using (E)-3-{[1-(t-butoxycarbonyl)indol-3-yl]methylidene}piperidin-4-ol hydrogen acetate instead of (E)-3-[(furan-2-yl)methylidene]piperidin-4-ol hydrogen acetate by conducting the reaction similar to that mentioned in Example 7 (d).

$^1$H NMR (400 MHz, CDCl$_3$) δ ppm: 0.50-0.71 (2H, m), 0.78-0.96 (2H, m), 1.69 (9H, s), 1.80-1.93 (1H, m), 2.03-2.17 (2H, m), 2.41-2.51 and 2.56-2.66 (total 1H, each m), 2.79-2.88 and 2.89-2.97 (total 1H, each m), 3.15 and 3.25 (total 1H, each d, J=13.0), 3.60 and 3.74 (total 1H, each d, J=13.0), 4.30-4.39 (1H, m), 4.69 and 4.71 (total 1H, each s), 6.59 and 6.61 (total 1H, each s), 6.93-7.09 (2H, m), 7.19-7.28 (2H, m), 7.29-7.37 (2H, m), 7.45 (1H, s), 7.53-7.58 (1H, m), 8.15 (1H, d, J=7.5).

(e) (E)-4-(Acetylsulfanyl)-1-[2-cyclopropyl-1-(2-fluorophenyl)-2-oxoethyl]-3-[(indol-3-yl)methylidene]piperidine To a solution of (E)-3-{[1-(t-butoxycarbonyl)indol-3-yl]methylidene}-1-[2-cyclopropyl-1-(2-fluorophenyl)-2-oxoethyl]piperidin-4-ol (1.58 g) in toluene (32 ml) were added thioacetic acid (0.45 ml) and N,N-dimethylformamide dineopentyl acetal (1.75 ml) under ice-cooling, and the resulting mixture was stirred at room temperature for 1 hour. After stirring, to the reaction mixture was added saturated aqueous sodium hydrogencarbonate solution, and the resulting mixture was extracted with ethyl acetate. The extract was washed with saturated aqueous sodium chloride solution, and the organic layer was dried over anhydrous sodium sulfate. The solvent was evaporated in vacuo, and the residue was purified by chromatography on a silica gel column using a mixed solvent of ethyl acetate and hexane (1:9) as the eluent to afford (E)-4-(acetylsulfanyl)-3-{[1-(t-butoxycarbonyl)indol-3-yl]methylidene}-1-[2-cyclopropyl-1-(2-fluorophenyl)-2-oxoethyl]piperidine (0.66 g, yield: 38%) as a pale yellow amorphous solid.

To a solution of the compound obtained as above, a 4N solution of hydrogen chloride in dioxane (14.60 ml) was added under ice-cooling, and the resulting mixture was stirred at room temperature for 7 hours. The reaction mixture was evaporated in vacuo, and the residue was diluted with ethyl acetate. The resulting mixture was washed with saturated aqueous sodium hydrogencarbonate solution and saturated aqueous sodium chloride solution. The organic layer was dried over anhydrous sodium sulfate. The solvent was evaporated in vacuo, and the residue was purified by chromatography on a silica gel column using a mixed solvent of ethyl acetate and hexane (1:4) as the eluent to afford the title compound (0.32 g, yield: 59%) as a pale yellow amorphous solid.

$^1$H NMR (500 MHz, CDCl$_3$) δ ppm: 0.41-0.94 (4H, m), 1.85-1.93 (1H, m), 2.07-2.23 (2H, m), 2.33 (3H, s), 2.39-2.48 and 2.62-2.70 (total 1H, each m), 2.73-2.84 (1H, m), 3.09 (1H, d, J=13.0), 3.75 and 3.89 (total 1H, each d, J=13.0), 4.58-4.66 (1H, m), 4.64 and 4.74 (total 1H, each s), 6.76 and 6.77 (total 1H, each s), 6.99-7.30 (5H, m), 7.31-7.44 (2H, m), 7.59-7.65 (1H, m), 8.25-8.31 (1H, m);

MS (FAB) m/z: 463 (M+H)$^+$.

Example 47

(E)-1-[2-Cyclopropyl-1-(2-fluorophenyl)-2-oxoethyl]-3-[(indol-3-yl)methylidene]-4-sulfanylpiperidine dihydrochloride (Exemplification Compound No. 1-165)

The title compound was synthesized in a yield of 43% as an orange-coloured crystal using (E)-4-(acetylsulfanyl)-1-[2-cyclopropyl-1-(2-fluorophenyl)-2-oxoethyl]-3-[(indol-3-yl)methylidene]piperidine instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (500 MHz, CDCl$_3$) δ ppm: 0.37-0.93 (4H, m), 1.67-1.75 (1H, m), 1.76-1.85 (1H, m), 2.01-2.16 (1H, m), 2.24-2.37 (1H, m), 2.61-2.69 (1H, m), 2.70-2.78 and 2.86-2.97 (total 1H, each m), 3.48 and 3.68 (total 1H, each d, J=12.5), 4.00-4.15 (1H, m), 4.69 and 4.76 (total 1H, each s), 6.69 and 6.72 (total 1H, each s), 6.97-7.29 (5H, m), 7.31-7.42 (2H, m), 7.61 (1H, d, J=7.5)), 8.20-8.34 (1H, m);

MS (FAB) m/z: 421 (M+H)$^+$.

Example 48

(E)-4-(Acetylsulfanyl)-1-[2-cyclopropyl-1-(2-fluorophenyl)-2-oxoethyl]-3-[(quinolin-3-yl)methylidene]piperidine (Exemplification Compound No. 1-170)

(a) (E)-3-[Quinolin-3-yl]methylidene]-1-(triphenylmethyl)piperidin-4-one

The title compound was synthesized in a yield of 48% as a yellow oil using quinoline-3-carbaldehyde instead of benzaldehyde by conducting the reaction similar to that mentioned in Example 1(a)

$^1$H NMR (400 MHz, CDCl$_3$) δ ppm: 2.69-2.78 (2H, m), 2.80-2.86 (2H, m), 3.54 (2H, bs), 7.08-7.16 (3H, m), 7.18-7.31 (7H, m), 7.43-7.53 (6H, m), 7.56 (1H, t, J=8.0), 7.90 (1H, t, J=8.0), 7.93-8.08 (2H, m), 8.21 (1H, d, J=8.0), 8.65 (1H, s).

(b) (E)-3-[(Quinolin-3-yl)methylidene]-1-(triphenylmethyl)piperidin-4-ol

The title compound was synthesized in a yield of 55% as a pale yellow amorphous solid using (E)-3-[(quinolin-3-yl)methylidene]-1-(triphenylmethyl)piperidin-4-one instead of (E)-3-benzylidene-1-(triphenylmethyl)piperidin-4-one by conducting the reaction similar to that mentioned in Example 1(b).

$^1$H NMR (400 MHz, CDCl$_3$) δ ppm: 1.89-2.08 (2H, m), 2.13-2.25 (1H, m), 2.35-2.60 (1H, m), 2.84 (1H, bs), 3.66 (1H, bs), 4.18-4.28 (1H, m), 6.83 (1H, s), 6.84-7.07 (9H, m), 7.19-7.35 (6H, m), 7.52 (1H, t, J=8.0), 7.65-7.72 (2H, m), 7.89 (1H, s), 8.04 (1H, d, J=8.0), 8.70 (1H, s).

(c) (E)-3-[(Quinolin-3-yl)methylidene]piperidin-4-ol bis(hydrogen acetate)

The title compound was synthesized in a yield of 94% as a pale yellow crystal using (E)-3-[(quinolin-3-yl)methylidene]-1-(triphenylmethyl)piperidin-4-ol instead of (E)-3-[(furan-2-yl)methylidene]-1-(triphenylmethyl)piperidin-4-ol by conducting the reaction similar to that mentioned in Example 7(c).

$^1$H NMR (400 MHz, CDCl$_3$) δ ppm: 1.46-1.59 (1H, m), 1.92-2.01 (1H, m), 2.62-2.72 (1H, m), 2.93-3.03 (1H, m), 3.11 (1H, d, J=13.5), 3.80 (1H, d, J=13.5), 4.15-4.24 (1H, m), 6.66 (1H, s), 7.60 (1H, t, J=8.0) 7.72 (1H, t, J=8.0), 7.93-8.04 (2H, m), 8.15 (1H, s), 8.78 (1H, s).

(d) (E)-1-[2-Cyclopropyl-1-(2-fluorophenyl)-2-oxoethyl]-3-[(quinolin-3-yl)methylidene]piperidin-4-ol The title compound was synthesized in a yield of 94% as a brown oil using (E)-3-[(quinolin-3-yl)methylidene]piperidin-4-ol bis(hydrogen acetate) instead of (E)-3-[(furan-2-yl)methylidene]piperidin-4-ol acetate by conducting the reaction similar to that mentioned in Example 7(d).

$^1$H NMR (500 MHz, CDCl$_3$) δ ppm: 0.42-0.92 (4H, m), 1.80-1.94 (2H, m), 1.99-2.07 (1H, m), 2.09-2.18 (1H, m), 2.45-2.53 and 2.56-2.63 (total 1H, each m), 3.03 and 3.10 (total 1H, each d, J=12.5), 3.64-3.76 (1H, m), 4.29-4.37 (1H, m), 4.70 and 4.73 (total 1H, each s), 6.76 and 6.78 (total 1H, each s), 6.91-7.04 (2H, m), 7.11-7.19 (1H, m), 7.23-7.36 (1H, m), 7.55 (1H, t, J=8.0), 7.69 (1H, t, J=8.0), 7.82 (1H, t, J=8.0), 8.04-8.10 (2H, m), 8.74 and 8.75 (total 1H, each s).

(e) (E)-4-(Acetylsulfanyl)-1-[2-cyclopropyl-1-(2-fluorophenyl)-2-oxoethyl]-3-[(quinolin-3-yl)methylidene]piperidine The title compound was synthesized in a yield of 13% as a pale brown oil using (E)-1-[2-cyclopropyl-1-(2-fluorophenyl)-2-oxoethyl]-3-[(quinolin-3-yl)methylidene]piperidin-4-ol instead of (E)-3-[(pyridin-3-yl)methylidene]-1-(triphenylmethyl)piperidin-4-ol by conducting the reaction similar to that mentioned in Example 27(c).

$^1$H NMR (500 MHz, CDCl$_3$) δ ppm: 0.38-0.94 (4H, m), 1.87-2.09 (2H, m), 2.29-2.40 (1H, m), 2.38 (3H, s), 2.46-2.55 and 2.61-2.70 (total 1H, each m), 2.77-2.87 (1H, m), 3.08 and 3.18 (total 1H, each d, J=12.5), 3.57 and 3.68 (total 1H, each d, J=12.5), 4.52-4.60 (1H, m), 4.67 and 4.71 (total 1H, each s), 6.77 and 6.79 (total 1H, each s), 6.90-7.07 (2H, m), 7.10-7.36 (2H, m), 7.49-7.58 (1H, m), 7.65-7.85 (2H, m), 7.95-8.10 (2H, m), 8.69 and 8.72 (total 1H, each s);

MS (FAB) m/z: 475 (M+H)$^+$.

Example 49

(E)-1-[2-Cyclopropyl-1-(2-fluorophenyl)-2-oxoethyl]-3-[(quinolin-3-yl)methylidene]-4-sulfanylpiperidine dihydrochloride (Exemplification Compound No. 1-169)

The title compound was synthesized in a yield of 65% as a yellow powdery crystal using (E)-4-(acetylsulfanyl)-1-[2-cyclopropyl-1-(2-fluorophenyl)-2-oxoethyl]-3-[(quinolin-3-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (500 MHz, CDCl$_3$) δ ppm: 0.38-0.94 (4H, m), 1.80-1.92 (1H, m), 1.98-2.07 (1H, m), 2.28-2.39 (1H, m), 2.61-2.72 (1H, m), 2.78-2.87 and 2.88-2.95 (total 1H, each m), 3.33 and 3.42 (total 1H, each d, J=12.5), 3.51 and 3.57 (total 1H, each d, J=12.5), 3.90-4.03 (1H, m), 4.70 and 4.72 (total 1H, each s), 6.75 and 6.78 (total 1H, each s), 6.91-7.02

(2H, m), 7.08-7.18 (1H, m), 7.21-7.34 (1H, m), 7.50-7.59 (1H, m), 7.65-7.72 (1H, m), 7.75-7.85 (1H, m), 7.96-8.10 (2H, m), 8.67-8.75 (1H, m);
MS (FAB) m/z: 433 (M+H)$^+$.

Example 50

(E)-4-(Acetylsulfanyl)-1-[2-cyclopropyl-1-(2-fluorophenyl)-2-oxoethyl]-3-[(6-methylpyridin-2-yl)methylidene]piperidine (Exemplification Compound No. 1-66)

(a) (E)-3-[(6-Methylpyridin-2-yl)methylidene]-1-(triphenylmethyl)piperidin-4-one The title compound was synthesized in a yield of 56% as a pale yellow crystal using 6-methylpyridine-2-carbaldehyde instead of benzaldehyde by conducting the reaction similar to that mentioned in Example 1(a).
$^1$H NMR (500 MHz, CDCl$_3$) δ ppm: 2.24 (3H, s), 2.60-2.71 (2H, m), 2.73-2.81 (2H, m), 4.01 (2H, bs), 6.94 (1H, d, J=7.5), 7.11-7.18 (4H, m), 7.19-7.27 (6H, m), 7.36 (1H, s), 7.46-7.56 (7H, m).

(b) (E)-3-[(6-Methylpyridin-2-yl)methylidene]-1-(triphenylmethyl)piperidin-4-ol

The title compound was synthesized in a yield of 99% as a pale yellow amorphous solid using (E)-3-[(6-methylpyridin-2-yl)methylidene]-1-(triphenylmethyl)piperidin-4-one instead of (E)-3-benzylidene-1-(triphenylmethyl)piperidin-4-one by conducting the reaction similar to that mentioned in Example 1(b).
$^1$H NMR (400 MHz, CDCl$_3$) δ ppm: 1.75-1.83 (1H, m), 1.87-2.07 (2H, m), 2.11-2.22 (1H, m), 2.19 (3H, s), 2.55-2.89 (2H, m), 4.08-4.20 (1H, m), 6.66 (1H, s), 6.90 (1H, d, J=7.5), 6.97 (1H, d, J=7.5), 7.00-7.15 (9H, m), 7.29-7.40 (6H, m), 7.47 (1H, t, J=7.5).

(c) (E)-3-[(6-Methylpyridin-2-yl)methylidene]piperidin-4-ol bis(hydrogen acetate)

The title compound was synthesized in a yield of 65% as a yellowish green crystal using (E)-3-[(6-methylpyridin-2-yl)methylidene]-1-(triphenylmethyl)piperidin-4-ol instead of (E)-3-[(furan-2-yl)methylidene]-1-(triphenylmethyl)piperidin-4-ol by conducting the reaction similar to that mentioned in Example 7(c).
$^1$H NMR (400 MHz, CDCl$_3$) δ ppm: 1.42-1.54 (1H, m), 1.88-1.97 (1H, m), 2.44 (3H, s), 2.58-2.70 (1H, m), 2.90-3.00 (1H, m), 3.12-3.21 (1H, m), 4.05-4.13 (1H, m), 4.52 (1H, d, J=14.0), 6.45 (1H, s), 7.01-7.07 (2H, m), 7.61 (1H, t, J=7.5).

(d) (E)-1-[2-Cyclopropyl-1-(2-fluorophenyl)-2-oxoethyl]-3-[(6-methylpyridin-2-yl)methylidene]piperidin-4-ol The title compound was synthesized in a yield of 99% as a reddish brown oil using (E)-3-[(6-methylpyridin-2-yl)methylidene]piperidin-4-ol bis(hydrogen acetate) instead of (E)-3-[(furan-2-yl)methylidene]piperidin-4-ol acetate by conducting the reaction similar to that mentioned in Example 7 (d)
$^1$H NMR (500 MHz, CDCl$_3$) δ ppm: 0.52-0.94 (4H, m), 1.81-1.92 (1H, m), 1.96-2.13 (2H, m), 2.18-2.25 (1H, m), 2.38-2.58 (1H, m), 2.42 (3H, s), 2.84-2.98 (1H, m), 3.25 and 3.38 (total 1H, each d, J=13.0), 4.23-4.31 (1H, m), 4.68 (1H, s), 6.61 (1H, s), 6.91-7.11 (4H, m), 7.21-7.29 (1H, m), 7.33-7.41 (1H, m), 7.44-7.50 (1H, m).

(e) (E)-4-(Acetylsulfanyl)-1-[2-cyclopropyl-1-(2-fluorophenyl)-2-oxoethyl]-3-[(6-methylpyridin-2-yl)methylidene]piperidine The title compound was synthesized in a yield of 28% as a pale yellow oil using (E)-1-[2-cyclopropyl-1-(2-fluorophenyl)-2-oxoethyl]-3-[(6-methylpyridin-2-yl)methylidene]piperidin-4-ol instead of (E)-1-[2-cyclopropyl-1-(2-fluorophenyl)-2-oxoethyl]-3-[(furan-2-yl)methylidene]piperidin-4-ol by conducting the reaction similar to that mentioned in Example 7(e).
$^1$H NMR (500 MHz, CDCl$_3$) δ ppm: 0.45-0.99 (4H, m), 1.84-1.95 (1H, m), 2.17-2.38 (2H, m), 2.31 (3H, s), 2.43 (3H, s), 2.57-2.65 (1H, m), 2.73-2.87 (1H, m), 3.16 and 3.29 (total 1H, each d, J=13.0), 4.42 (1H, d, J=13.0), 4.49-4.55 (1H, m), 4.67 and 4.68 (total 1H, each s), 6.60 and 6.62 (total 1H, each s), 6.87-6.97 (2H, m), 6.99-7.13 (2H, m), 7.22-7.30 (1H, m), 7.31-7.50 (2H, m);
MS (FAB) m/z: 439 (M+H)$^+$.

Example 51

(E)-1-[2-Cyclopropyl-1-(2-fluorophenyl)-2-oxoethyl]-3-[(6-methylpyridin-2-yl)methylidene]-4-sulfanylpiperidine dihydrochloride (Exemplification Compound No. 1-65)

The title compound was synthesized in a yield of 69% as a colourless amorphous solid using (E)-4-(acetylsulfanyl)-1-[2-cyclopropyl-1-(2-fluorophenyl)-2-oxoethyl]-3-[(6-methylpyridin-2-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.
$^1$H NMR (400 MHz, CDCl$_3$) δ ppm: 0.47-0.95 (4H, m), 1.77-1.90 (1H, m), 2.17-2.38 (2H, m), 2.44 (3H, s), 2.59-2.73 (1H, m), 2.76-2.93 (1H, m), 3.67 and 3.76 (total 1H, each d, J=13.0), 3.88-3.98 (2H, m), 4.68 and 4.71 (total 1H, each s), 6.60 and 6.61 (total 1H, each s), 6.89-7.11 (4H, m), 7.21-7.30 (1H, m), 7.33-7.51 (2H, m);
MS (FAB) m/z: 397 (M+H)$^+$.

Example 52

(E)-4-(Acetylsulfanyl)-1-[2-cyclopropyl-1-(2-fluorophenyl)-2-oxoethyl]-3-[(1-methyl-1H-imidazol-2-yl)methylidene]piperidine (Exemplification Compound No. 2-762)

(a) (E)-3-[(1-Methyl-1H-imidazol-2-yl)methylidene]-1-(triphenylmethyl)piperidin-4-one The title compound was synthesized in a yield of 51% as a pale yellow amorphous solid using 1-methyl-1H-imidazole-2-carbaldehyde instead of benzaldehyde by conducting the reaction similar to that mentioned in Example 1(a).
H NMR (500 MHz, CDCl$_3$) δ ppm: 2.63 (2H, bs), 2.76 (2H, t, J=6.0), 3.73 (3H, s), 3.93 (2H, bs), 6.87 (1H, s), 7.02 (1H, s), 7.12-7.17 (3H, m), 7.22-7.28 (6H, m), 7.30 (1H, s), 7.50-7.57 (6H, m).

(b) (E)-3-[(1-Methyl-1H-imidazol-2-yl)methylidene]-1-(triphenylmethyl)piperidin-4-ol The title compound was synthesized in a yield of 78% as a pale yellow amorphous solid using (E)-3-[(1-methyl-1H-imidazol-2-yl)methylidene]-1-(triphenylmethyl)piperidin-4-one instead of (E)-3-benzylidene-1-(triphenylmethyl)piperidin-4-one by conducting the reaction similar to that mentioned in Example 1 (b)

$^1$H NMR (500 MHz, CDCl$_3$) δ ppm: 1.83-1.94 (1H, m), 2.07-2.24 (3H, m), 2.87-2.98 (1H, m), 3.68 (3H, s), 4.00-4.06 (1H, m), 4.13-4.25 (1H, m), 6.34 (1H, s), 6.80 (1H, s), 6.82 (1H, s), 7.02-7.16 (9H, m), 7.29-7.39 (6H, m).

(c) (E)-4-(Acetylsulfanyl)-3-[(1-methyl-1H-imidazol-2-yl)methylidene]piperidine hydrogen trifluoroacetate To a solution of (E)-3-[(1-methyl-1H-imidazol-2-yl)methylidene]-1-(triphenylmethyl)piperidin-4-ol (4.50 g) in dichloromethane (100 ml) were added methanesulfonyl chloride (0.90 ml) and triethylamine (1.60 ml) under ice-cooling, the resulting mixture was stirred at room temperature for 1 hour. The reaction mixture was evaporated in vacuo. To a solution of the residue in dimethyl sulfoxide (100 ml) was added potassium thioacetate (5.90 g) at room temperature, and the resulting mixture was stirred at 50° C. for 30 minutes. After stirring, water was added to the reaction mixture, and the resulting mixture was extracted with ethyl acetate. The extract was washed with saturated aqueous sodium chloride solution, and the organic layer was dried over anhydrous sodium sulfate. The solvent was evaporated in vacuo, and the residue was purified by chromatography on a silica gel column using a mixed solvent of methanol and dichloromethane (1:19) as the eluent to afford (E)-4-(acetylsulfanyl)-3-[(1-methyl-1H-imidazol-2-yl)methylidene]-1-(triphenylmethyl)piperidine (1.00 g, yield: 19%) as a reddish brown amorphous solid.

To a solution of the compound obtained as above (1.00 g) in dichloromethane (20 ml) was added trifluoroacetic acid (0.31 ml) under ice-cooling, and the resulting mixture was stirred at the same temperature for 1.5 hours. The reaction mixture was evaporated in vacuo, and the residue was purified by chromatography on a silica gel column using a mixed solvent of methanol and dichloromethane (1:19 to 1:4) as the eluent to afford the title compound (0.44 g, yield: 45%) as a colourless amorphous solid.

$^1$H NMR (500 MHz, CDCl$_3$) δ ppm: 2.10-2.17 (1H, m), 2.38 (3H, s), 2.55-2.64 (1H, m), 3.17-3.25 (1H, m), 3.38-3.47 (1H, m), 3.74 (3H, s), 4.00 (1H, d, J=14.5), 4.20 (1H, d, J=14.5), 4.60 (1H, m), 6.59 (1H, s), 7.14 (1H, s), 7.40 (1H, s).

(d) (E)-4-(Acetylsulfanyl)-1-[2-cyclopropyl-1-(2-fluorophenyl)-2-oxoethyl]-3-[(1-methyl-1H-imidazol-2-yl)methylidene]piperidine The title compound was synthesized in a yield of 12% as a pale orange-coloured amorphous solid using (E)-4-(acetylsulfanyl)-3-[(1-methyl-1H-imidazol-2-yl)methylidene]piperidine hydrogen trifluoroacetate instead of (E)-4-(acetylsulfanyl)-3-benzylidenepiperidine hydrochloride by conducting the reaction similar to that mentioned in Example 1(d).

$^1$H NMR (500 MHz, CDCl$_3$) δ ppm: 0.67-0.82 (2H, m), 0.86-1.05 (2H, m), 1.83-1.91 (1H, m), 2.16-2.26 (2H, m), 2.28 and 2.30 (total 3H, each s), 2.31-2.36 and 2.65-2.72 (total 1H, each m), 2.76-2.82 and 2.84-2.90 (total 1H, each m), 3.20 and 3.37 (total 1H, each d, J=13.5), 3.60 and 3.61 (total 3H, each s), 4.47-4.55 (2H, m), 4.71 and 4.75 (total 1H, each s), 6.35 and 6.36 (total 1H, each s), 6.76 and 6.78 (total 1H, each s), 6.90 and 6.97 (total 1H, each s), 7.01-7.15 (2H, m), 7.24-7.31 (1H, m), 7.37-7.49 (1H, m).

Example 53

(E)-1-[2-Cyclopropyl-1-(2-fluorophenyl)-2-oxoethyl]-3-[(1-methyl-1H-imidazol-2-yl)methylidene]-4-sulfanylpiperidine hydrogen trifluoroacetate (Exemplification Compound No. 2-761)

The title compound was synthesized in a yield of 9% as a pale yellow amorphous solid using (E)-4-(acetylsulfanyl)-1-[2-cyclopropyl-1-(2-fluorophenyl)-2-oxoethyl]-3-[(1-methyl-1H-imidazol-2-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (500 MHz, CDCl$_3$) δ ppm: 0.66-0.80 (2H, m), 0.87-1.02 (2H, m), 1.76-1.87 (1H, m), 2.15-2.22 (1H, m), 2.24-2.34 (1H, m), 2.52-2.59 and 2.95-3.02 (total 1H, each m), 2.68-2.80 (1H, m), 3.61 (3H, s), 3.76 and 3.86 (total 1H, each d, J=13.5), 3.80-3.85 and 3.91-3.95 (total 1H, each m), 4.10 and 4.15 (total 1H, each d, J=13.5), 4.74 and 4.76 (total 1H, each s), 6.33 and 6.42 (total 1H, each s), 6.77 and 6.78 (total 1H, each s), 6.92 and 6.94 (total 1H, each s), 7.02-7.08 (1H, m), 7.09-7.15 (1H, m), 7.25-7.31 (1H, m), 7.38-7.45 (1H, m);

IR (Liquid film, cm$^{-1}$): 2532, 1712, 1672.

Example 54

(E)-4-(Acetylsulfanyl)-1-[2-cyclopropyl-1-(2-fluorophenyl)-2-oxoethyl]-3-[(1-methyl-1H-pyrazol-5-yl)methylidene]piperidine hydrochloride (Exemplification Compound No. 2-338)

(a) (E)-3-[(1-Methyl-1H-pyrazol-5-yl)methylidene]-1-(triphenylmethyl)piperidin-4-one The title compound was synthesized in a yield of 76% as a pale yellow amorphous solid using 1-methyl-1H-pyrazole-5-carbaldehyde instead of benzaldehyde by conducting the reaction similar to that mentioned in Example 1(a).

$^1$H NMR (500 MHz, CDCl$_3$) δ ppm: 2.69 (2H, bs), 2.78 (2H, t, J=6.0), 3.39 (2H, bs), 3.96 (3H, s), 5.93 (1H, s), 7.15-7.21 (3H, m), 7.24-7.31 (6H, m), 7.39 (1H, s), 7.45 (1H, s), 7.48-7.54 (6H, m).

(b) (E)-3-[(1-Methyl-1H-pyrazol-5-yl)methylidene]-1-(triphenylmethyl)piperidin-4-ol The title compound was synthesized in a yield of 99% as a pale yellow amorphous solid using (E)-3-[(1-methyl-1H-pyrazol-5-yl)methylidene]-1-(triphenylmethyl)piperidin-4-one instead of (E)-3-benzylidene-1-(triphenylmethyl)piperidin-4-one by conducting the reaction similar to that mentioned in Example 1(b)

$^1$H NMR (500 MHz, CDCl$_3$) δ ppm: 1.87-2.01 (2H, m), 2.12-2.19 (1H, m), 2.28-2.40 (1H, m), 2.85-2.93 (1H, m), 3.67-3.77 (1H, m), 3.91 (3H, s), 4.12-4.19 (1H, m), 5.86 (1H, s), 6.43 (1H, s), 7.07-7.21 (10H, m), 7.31-7.40 (6H, m).

(c) (E)-4-(Acetylsulfanyl)-3-[(1-methyl-1H-pyrazol-5-yl)methylidene]piperidine hydrogen trifluoroacetate The title compound was synthesized in a yield of 64% as a purple amorphous solid using (E)-3-[(1-methyl-1H-pyrazol-5-yl)methylidene]-1-(triphenylmethyl)piperidin-4-ol instead of (E)-3-[(1-methyl-1H-imidazol-2-yl)methylidene]-1-(triphenylmethyl)piperidin-4-ol by conducting successively reactions similar to those mentioned in Example 52(c).

$^1$H NMR (500 MHz, CDCl$_3$) δ ppm: 2.04-2.12 (1H, m), 2.39 (3H, s), 2.44-2.54 (1H, m), 3.07-3.16 (1H, m), 3.21-3.28 (1H, m), 3.68 (1H, d, J=14.5), 3.80 (3H, s), 4.18 (1H, d, J=14.5), 4.62 (1H, m), 6.10 (1H, s), 6.68 (1H, s), 7.40 (1H, s).

(d) (E)-4-(Acetylsulfanyl)-1-[2-cyclopropyl-1-(2-fluorophenyl)-2-oxoethyl]-3-[(1-methyl-1H-pyrazol-5-yl)methylidene]piperidine hydrochloride The title compound was synthesized in a yield of 39% as a pale yellow amorphous solid using (E)-4-(acetylsulfanyl)-3-[(1-methyl-1H-pyrazol-5-yl)methylidene]piperidine hydrogen trifluoroacetate instead of (E)-4-(acetylsulfanyl)-3-benzylidenepiperidine hydrochloride by conducting the reaction similar to that mentioned in Example 1(d).

$^1$H NMR (400 MHz, CDCl$_3$) δ ppm: 0.65-0.85 (2H, m), 0.90-1.04 (2H, m), 1.83-1.95 (1H, m), 2.06-2.14 (1H, m), 2.23-2.37 (1H, m), 2.32 (3H, s), 2.41-2.50 and 2.55-2.64 (total 1H, each m), 2.76-2.89 (1H, m), 3.00 and 3.11 (total 1H, each d, J=13.0), 3.62 and 3.72 (total 1H, each d, J=13.0), 3.78 and 3.80 (total 3H, each s), 4.47-4.54 (1H, m), 4.71 and 4.72 (total 1H, each s), 5.94 and 6.04 (total 1H, each d, J=2.0), 6.39 and 6.40 (total 1H, each s), 7.05-7.18 (2H, m), 7.28-7.38 (3H, m);

IR (KBr, cm$^{-1}$): 1700, 1494.

Example 55

(E)-1-[2-Cyclopropyl-1-(2-fluorophenyl)-2-oxoethyl]-3-[(1-methyl-1H-pyrazol-5-yl)methylidene]-4-sulfanylpiperidine hydrochloride (Exemplification Compound No. 2-337)

The title compound was synthesized in a yield of 21% as a colourless amorphous solid using (E)-4-(acetylsulfanyl)-1-[2-cyclopropyl-1-(2-fluorophenyl)-2-oxoethyl]-3-[(1-methyl-1H-pyrazol-5-yl)methylidene]piperidine hydrochloride instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (500 MHz, CDCl$_3$) δ ppm: 0.66-0.85 (2H, m), 0.89-1.04 (2H, m), 1.78-1.87 (1H, m), 2.04-2.12 (1H, m), 2.25-2.35 (1H, m), 2.62-2.73 (1H, m), 2.77-2.86 and 2.87-2.95 (total 1H, each m), 3.30-3.42 (1H, m), 3.47-3.58 (1H, m), 3.80 and 3.81 (total 3H, each s), 3.84-3.93 (1H, m), 4.73 and 4.75 (total 1H, each s), 5.96 and 6.03 (total 1H, each s), 6.37 and 6.39 (total 1H, each s), 7.04-7.18 (2H, m), 7.28-7.39 (3H, m);

IR (KBr, cm$^{-1}$): 2536, 1710.

Example 56

(E)-4-(Acetylsulfanyl)-1-[2-cyclopropyl-1-(2-fluorophenyl)-2-oxoethyl]-3-[(1,3-dimethyl-1H-pyrazol-5-yl)methylidene]piperidine hydrochloride (Exemplification Compound No. 1-178)

(a) (E)-3-[(1,3-Dimethyl-1H-pyrazol-5-yl)methylidene]-1-(triphenylmethyl)piperidin-4-one The title compound was synthesized in a yield of 78% as a yellow amorphous solid using 1,3-dimethyl-1H-pyrazole-5-carbaldehyde instead of benzaldehyde by conducting the reaction similar to that mentioned in Example 1(a).

$^1$H NMR (500 MHz, CDCl$_3$) δ ppm: 2.17 (3H, s), 2.68 (2H, bs), 2.76 (2H, t, J=6.0), 3.35 (2H, bs), 3.88 (3H, s), 5.68 (1H, s), 7.16-7.22 (3H, m), 7.25-7.32 (6H, m), 7.38 (1H, s), 7.47-7.55 (6H, m).

(b) (E)-3-[(1,3-Dimethyl-1H-pyrazol-5-yl)methylidene]-1-(triphenylmethyl)piperidin-4-ol The title compound was synthesized in a yield of 99% as a yellow amorphous solid using (E)-3-[(1,3-dimethyl-1H-pyrazol-5-yl)methylidene]-1-(triphenylmethyl)piperidin-4-one instead of (E)-3-benzylidene-1-(triphenylmethyl)piperidin-4-one by conducting the reaction similar to that mentioned in Example 1(b)

$^1$H NMR (400 MHz, CDCl$_3$) δ ppm: 1.85-1.97 (2H, m), 2.10 (3H, s), 2.10-2.18 (1H, m), 2.28-2.40 (1H, m), 2.82-2.93 (1H, m), 3.66-3.79 (1H, m), 3.82 (3H, s), 4.08-4.16 (1H, m), 5.64 (1H, s), 6.38 (1H, s), 7.09-7.24 (9H, m), 7.33-7.44 (6H, m).

(c) (E)-4-(Acetylsulfanyl)-3-[(1,3-dimethyl-1H-pyrazol-5-yl)methylidene]piperidine hydrogen trifluoroacetate The title compound was synthesized in a yield of 44% as a brown amorphous solid using (E)-3-[(1,3-dimethyl-1H-pyrazol-5-yl)methylidene]-1-(triphenylmethyl)piperidin-4-ol instead of (E)-3-[(1-methyl-1H-imidazol-2-yl)methylidene]-1-(triphenylmethyl)piperidin-4-ol by conducting successively reactions similar to those mentioned in Example 52(c).

$^1$H NMR (500 MHz, CDCl$_3$) δ ppm: 2.02-2.11 (1H, m), 2.20 (3H, s), 2.38 (3H, s), 2.44-2.54 (1H, m), 3.07-3.16 (1H, m), 3.20-3.27 (1H, m), 3.68 (1H, d, J=14.0), 3.72 (3H, s), 4.20 (1H, d, J=14.0), 4.61 (1H, m), 5.88 (1H, s), 6.64 (1H, s).

(d) (E)-4-(Acetylsulfanyl)-1-[2-cyclopropyl-1-(2-fluorophenyl)-2-oxoethyl]-3-[(1,3-dimethyl-1H-pyrazol-5-yl)methylidene]piperidine hydrochloride The title compound was synthesized in a yield of 28% as a yellow amorphous solid using (E)-4-(acetylsulfanyl)-3-[(1,3-dimethyl-1H-pyrazol-5-yl)methylidene]piperidine hydrogen trifluoroacetate instead of (E)-4-(acetylsulfanyl)-3-benzylidenepiperidine hydrochloride by conducting the reaction similar to that mentioned in Example 1(d).

$^1$H NMR (500 MHz, CDCl$_3$) δ ppm: 0.66-0.86 (2H, m), 0.90-1.04 (2H, m), 1.83-1.94 (1H, m), 2.11-2.18 (1H, m), 2.13 and 2.18 (total 3H, each s), 2.24-2.34 (1H, m), 2.32 (3H, s), 2.45-2.53 and 2.54-2.60 (total 1H, each m), 2.77-2.83 and 2.85-2.91 (total 1H, each m), 2.97 and 3.13 (total 1H, each d, J=13.0), 3.60 and 3.70 (total 1H, each d, J=13.0), 3.69 and 3.72 (total 3H, each s), 4.46-4.52 (1H, m), 4.70 (1H, s), 5.61 and 5.75 (total 1H, each s), 6.34 and 6.35 (total 1H, each s), 7.05-7.18 (2H, m), 7.28-7.41 (2H, m);

IR (KBr, cm$^{-1}$): 1701, 1494.

Example 57

(E)-1-[2-Cyclopropyl-1-(2-fluorophenyl)-2-oxoethyl]-3-[(1,3-dimethyl-1H-pyrazol-5-yl)methylidene]-4-sulfanylpiperidine hydrochloride (Exemplification Compound No. 1-177)

The title compound was synthesized in a yield of 50% as a pale green amorphous solid using (E)-4-(acetylsulfanyl)-1-

[2-cyclopropyl-1-(2-fluorophenyl)-2-oxoethyl]-3-[(1,3-dimethyl-1H-pyrazol-5-yl)methylidene]piperidine hydrochloride instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (500 MHz, CDCl$_3$) δ ppm: 0.66-0.86 (2H, m), 0.89-1.03 (2H, m), 1.76-1.87 (1H, m), 2.08-2.20 (1H, m), 2.15 and 2.17 (total 3H, each s), 2.25-2.35 (1H, m), 2.61-2.73 (1H, m), 2.81-2.92 (1H, m), 3.32 and 3.37 (total 1H, each d, J=13.0), 3.47 and 3.54 (total 1H, each d, J=13.0), 3.71 and 3.72 (total 3H, each s), 3.84-3.92 (1H, m), 4.71 and 4.72 (total 1H, each s), 5.65 and 5.73 (total 1H, each s), 6.32 (1H, s), 7.04-7.18 (2H, m), 7.27-7.42 (2H, m);

IR (KBr, cm$^{-1}$): 2541, 1710.

Example 58

(E)-4-(Acetylsulfanyl)-1-[1-(2-fluorophenyl)-2-methoxy-2-oxoethyl]-3-{[1H-pyrazol-3(5)-yl]methylidene}piperidine dihydrochloride (Exemplification Compound No. 3-10)

The title compound was synthesized in a yield of 82% as a pale brown amorphous solid using methyl bromo(2-fluorophenyl)acetate instead of 2-bromo-2-(2-fluorophenyl)-1-cyclopropylethanone by conducting successively reactions similar to those mentioned in Example 11(d).

$^1$H NMR (400 MHz, CDCl$_3$) δ ppm: 1.83-1.91 (1H, m), 2.16-2.28 (1H, m), 2.30 and 2.33 (total 3H, each s), 2.53-3.02 (3H, m), 3.35 and 3.95 (total 1H, each d, J=13.0), 3.73 (3H, s), 4.40 and 4.46 (total 1H, each t, J=4.5), 4.64 and 4.72 (total 1H, each s), 6.13 and 6.15 (total 1H, each s), 6.48 (1H, s), 7.04-7.18 (2H, m), 7.28-7.52 (3H, m);

IR (KBr, cm$^{-1}$): 1697, 1495.

Example 59

(E)-1-[1-(2-Fluorophenyl)-2-methoxy-2-oxoethyl]-3-{[1H-pyrazol-3(5)-yl]methylidene}-4-sulfanylpiperidine bis(hydrogen trifluoroacetate) (Exemplification Compound No. 3-9)

The title compound was synthesized in a yield of 59% as a colourless oil using (E)-4-(acetylsulfanyl)-1-[1-(2-fluorophenyl)-2-methoxy-2-oxoethyl]-3-{[1H-pyrazol-3(5)-yl]methylidene}piperidine dihydrochloride instead of (E)-4-(acetylsulfanyl)-1-[2-cyclopropyl-1-(2-fluorophenyl)-2-oxoethyl]-3-[(furan-2-yl)methylidene}piperidine by conducting the reaction similar to that mentioned in Example 8.

$^1$H NMR (400 MHz, CDCl$_3$) δ ppm: 1.75-1.85 (1H, m), 2.19-2.34 (1H, m), 2.57-2.69 (1H, m), 2.81-2.91 (1H, m), 3.30 and 3.49 (total 1H, each d, J=12.5), 3.59-3.90 (2H, m), 3.72 and 3.73 (total 3H, each s), 4.70 (1H, s), 6.13 and 6.17 (total 1H, each d, J=2.0), 6.47 and 6.52 (total 1H, each s), 7.05-7.45 (4H, m), 7.50 and 7.52 (total 1H, each d, J=2.0);

IR (thin film, cm$^{-1}$): 2560, 1670, 1496.

Example 60

(E)-4-(Acetylsulfanyl)-1-[1-(2-chlorophenyl)-2-methoxy-2-oxoethyl]-3-{[1H-pyrazol-3(5)-yl]methyliden}piperidine dihydrochloride (Exemplification Compound No. 3-14)

The title compound was synthesized in a yield of 18% as a yellow amorphous solid using methyl bromo(2-chlorophenyl)acetate instead of 2-bromo-2-(2-fluorophenyl)-1-cyclopropylethanone by conducting successively reactions similar to those mentioned in Example 11(d).

$^1$H NMR (500 MHz, CDCl$_3$) δ ppm: 1.83-1.90 (1H, m), 2.17-2.32 (1H, m), 2.32 and 2.34 (total 3H, each s), 2.54-2.74 (1H, m), 2.82-2.90 and 3.18-3.30 (total 1H, each m), 3.62-3.68 (1H, m), 3.69 and 3.71 (total 3H, each s), 3.87-3.94 (1H, m), 4.44-4.49 (1H, m), 4.79 (1H, s), 6.04 and 6.14 (total 1H, each s), 6.50 (1H, s), 7.23-7.29 (2H, m), 7.36-7.43 (1H, m), 7.46 and 7.49 (total 1H, each s), 7.52-7.62 (1H, m);

IR (KBr, cm$^{-1}$): 1751, 1437.

Example 61

(E)-1-[1-(2-Chlorophenyl)-2-methoxy-2-oxoethyl]-3-{[1H-pyrazol-3(5)-yl]methylidene}-4-sulfanylpiperidine dihydrochloride (Exemplification Compound No. 3-13)

Into a solution of (E)-4-(acetylsulfanyl)-1-[1-(2-chlorophenyl)-2-methoxy-2-oxoethyl]-3-{[1H-pyrazol-3(5)-yl]methylidene}piperidine dihydrochloride (50 mg) in methanol (10 ml) was bubbled hydrogen chloride under ice-cooling, and the resulting mixture was stirred under tightly sealed condition at room temperature for 2.5 hours. The reaction mixture was evaporated in vacuo, and the residue was purified by a preparative HPLC (YMC-Pack ODS-A; YMC, mobile phase: 30% acetonitrile/water (0.2% trifluoroacetic acid) to afford the title compound (45 mg, yield: 62%) as a pale yellow amorphous solid.

$^1$H NMR (500 MHz, CDCl$_3$) δ ppm: 1.72-1.83 (1H, m), 2.18-2.32 (1H, m), 2.54-2.61 and 2.63-2.71 (total 1H, each m), 2.81-2.91 (1H, m), 3.40-3.58 (1H, m), 3.63-3.69 (1H, m), 3.70 and 3.71 (total 3H, each s), 3.81-3.90 (1H, m), 4.86 and 4.87 (total 1H, each s), 6.08 and 6.13 (total 1H, each s), 6.47 and 6.51 (total 1H, each s), 7.23-7.28 (2H, m), 7.37-7.43 (1H, m), 7.48 and 7.49 (total 1H, each s), 7.54-7.59 (1H, m);

IR (Thin film, cm$^{-1}$): 2567, 1753.

Example 62

(E)-4-(Acetylsulfanyl)-1-[1-(2-fluorophenyl)-2-methoxy-2-oxoethyl]-3-[(1,3-thiazol-2-yl)methylidene]piperidine (Exemplification Compound No. 3-12)

The title compound was synthesized in a yield of 48% as a colourless oil using methyl bromo (2-fluorophenyl)acetate instead of 2-bromo-2-(2-fluorophenyl)-1-cyclopropylethanone by conducting the reaction similar to that mentioned in Example 15 (d).

$^1$H NMR (400 MHz, CDCl$_3$) δ ppm: 1.85-1.94 (1H, m), 2.26-2.35 (1H, m), 2.32 (3H, s), 2.52-2.91 (2H, m), 3.43-3.49 (1H, m), 3.68 and 3.71 (total 3H, each s), 4.46-4.61 (2H, m), 4.68 and 4.69 (total 1H, each s), 6.73 (1H, s), 7.00-7.16 (2H, m), 7.20-7.34 (2H, m), 7.47-7.55 (1H, m), 7.66 and 7.69 (total 1H, each d, J=3.5);

IR (liquid film, cm$^{-1}$): 1693, 1489.

Example 63

(E)-1-[1-(2-Fluorophenyl)-2-methoxy-2-oxoethyl]-4-sulfanyl-3-[(1,3-thiazol-2-yl)methylidene]piperidine (Exemplification Compound No. 3-11)

The title compound was synthesized in a yield of 32% as a colourless oil using (E)-4-(acetylsulfanyl)-1-[1-(2-fluorophenyl)-2-methoxy-2-oxoethyl]-3-[(1,3-thiazol-2-yl)methylidene]piperidine instead of (E)-4-(acetylsulfanyl)-1-[2- cyclopropyl-1-(2-fluorophenyl)-2-oxoethyl]-3-[(furan-2-yl) methylidene]piperidine by conducting the reaction similar to that mentioned in Example 8.

$^1$H NMR (400 MHz, CDCl$_3$) δ ppm: 1.79-1.88 (1H, m), 2.26-2.36 (1H, m), 2.66-2.79 (1H, m), 2.83-3.03 (1H, m), 3.69 and 3.70 (total 3H, each s), 3.86-3.93 (1H, m), 3.99 (1H, d, J=13.0), 4.08 (1H, d, J=13.0), 4.70 (1H, s), 6.72 and 6.73 (total 1H, each s), 7.00-7.15 (2H, m), 7.20-7.33 (2H, m), 7.48-7.55 (1H, m), 7.67 and 7.69 (total 1H, each d, J=3.5);

IR (KBr, cm$^{-1}$): 2539, 1675, 1495.

Example 64

(E)-1-[2-Cyclopropyl-1-(2-fluorophenyl)-2-oxoethyl]-4-(isobutyrylsulfanyl)-3-[(1,2,3-thiazol-4-yl) methylidene]piperidine hydrochloride (Exemplification Compound No. 1-187)

To a solution of (E)-1-[2-cyclopropyl-1-(2-fluorophenyl)-2-oxoethyl]-4-sulfanyl-3-[(1,2,3-thiazol-4-yl)methyliden]piperidine hydrochloride (110 mg) in dichloromethane (3 ml) were added isobutyryl chloride (0.03 ml) and triethylamine (0.08 ml) under ice-cooling, and the resulting mixture was stirred at room temperature for 15 minutes. After stirring, to the reaction mixture was added water, the resulting reaction mixture was extracted with dichloromethane. The extract was washed with saturated aqueous sodium chloride solution, and the organic layer was dried over anhydrous magnesium sulfate. The solvent was evaporated in vacuo, and a 4N solution of hydrogen chloride in dioxane (0.03 ml) was added to a solution of the residue in dichloromethane (3 ml). The reaction mixture was concentrated to afford the title compound (120 mg, yield: 93%) as a colourless amorphous solid.

$^1$H NMR (500 MHz, CDCl$_3$) δ ppm: 0.65-0.72 (2H, m), 0.90-1.03 (2H, m), 1.16-1.21 (6H, m), 1.87-1.96 (1H, m), 2.06-2.13 (1H, m), 2.26-2.38 (1H, m), 2.51-2.57 and 2.63-2.75 (total 2H, each m), 2.76-2.87 (1H, m), 3.23 and 3.36 (total 1H, each d, J=13.0), 4.05 and 4.09 (total 1H, each d, J=13.0), 4.51-4.55 (1H, m), 4.76 and 4.79 (total 1H, each s), 6.91 (1H, s), 7.04-7.17 (2H, m), 7.28-7.40 (2H, m), 8.41 and 8.45 (total 1H, each s);

IR (KBr, cm$^{-1}$): 1713, 1495.

Example 65

(E)-1-[2-Cyclopropyl-1-(2-fluorophenyl)-2-oxoethyl]-4-(methoxyacetylsulfanyl)-3-[(1,2,3-thiadiazol-4-yl)methylidene]piperidine hydrochloride (Exemplification Compound No. 1-188)

The title compound was synthesized in a yield of 93% as a colourless amorphous solid using methoxyacetyl chloride instead of isobutyryl chloride by conducting the reaction similar to that mentioned in Example 64.

$^1$H NMR (400 MHz, CDCl$_3$) δ ppm: 0.65-0.85 (2H, m), 0.90-1.04 (2H, m), 1.88-1.99 (1H, m), 2.04-2.12 (1H, m), 2.29-2.44 (1H, m), 2.50-2.58 and 2.64-2.72 (total 1H, each m), 2.78-2.91 (1H, m), 3.21 and 3.36 (total 1H, each d, J=13.0), 4.07 and 4.12 (total 1H, each d, J=13.0), 3.48 (3H, s), 4.09 (2H, s), 4.59-4.64 (1H, m), 4.77 and 4.81 (total 1H, each s), 6.94 (1H, s), 7.04-7.19 (2H, m), 7.28-7.41 (2H, m), 8.45 and 8.47 (total 1H, each s);

IR (KBr, cm$^{-1}$): 1709, 1495.

Example 66

(E)-4-(Aminoacetylsulfanyl)-1-[2-cyclopropyl-1-(2-fluorophenyl)-2-oxoethyl]-3-[(1,2,3-thiadiazol-4-yl) methylidene]piperidine dihydrochloride (Exemplification Compound No. 1-189)

To a solution of (E)-1-[2-cyclopropyl-1-(2-fluorophenyl)-2-oxoethyl]-4-sulfanyl-3-[(1,2,3-thiadiazol-4-yl)methylidene]piperidine hydrochloride (100 mg) and N-(t-butoxycarbonyl) glycine (50 mg) in N,N-dimethylformamide (5 ml) were added 1-hydroxybenzotriazole (70 mg) and 1-(3-dimethylaminopropyl)-3-ethylcarbodiimide hydrochloride (100 mg) at room temperature with stirring, and the resulting mixture was stirred at room temperature for 30 minutes. After stirring, triethylamine (0.11 ml) was added to the reaction mixture, and the resulting mixture was furthermore stirred at room temperature for 50 minutes. After stirring, water was added to the reaction mixture, and the resulting mixture was extracted with ethyl acetate. The extract was washed with water and saturated aqueous sodium chloride solution and dried over anhydrous magnesium sulfate. The solvent was removed in vacuo to afford an intermediate (140 mg) as a yellow oil.

A 4N solution of hydrogen chloride in dioxane (5 ml) was added to the above product (140 mg) under ice-cooling, and the reaction mixture was stirred at room temperature for 30 minutes. After stirring, reaction mixture was evaporated in vacuo, and the residue was purified by chromatography on a silica gel column using methanol and dichloromethane (1:19 to 1:1) as the eluent to afford the title compound (120 mg, yield: 89%) as a yellow amorphous solid.

$^1$H NMR (500 MHz, CDCl$_3$) δ ppm: 0.65-0.85 (2H, m), 0.91-1.03 (2H, m), 1.88-1.98 (1H, m), 2.04-2.11 (1H, m), 2.29-2.42 (1H, m), 2.49-2.56 and 2.63-2.70 (total 1H, each m), 2.78-2.89 (1H, m), 3.20 and 3.35 (total 1H, each d, J=13.0), 4.07 and 4.12 (total 1H, each d, J=13.0), 3.60 (2H, s), 4.58-4.63 (1H, m), 4.77 and 4.81 (total 1H, each s), 6.92 and 6.93 (total 1H, each s), 7.04-7.17 (2H, m), 7.28-7.39 (2H, m), 8.45 and 8.46 (total 1H, each s);

IR (KBr, cm$^{-1}$): 1705, 1494.

Example 67

(E)-1-[2-Cyclopropyl-1-(2-fluorophenyl)-2-oxoethyl]-4-(N,N-dimethylamino)acetylsulfanyl-3-[(1,2,3-thiadiazol-4-yl)methylidene]piperidine dihydrochloride (Exemplification Compound No. 1-190)

The title compound was synthesized in a yield of 78% as a yellow amorphous solid using N,N-dimethylaminoacetylchloride hydrochloride instead of isobutyryl chloride by conducting the reaction similar to that mentioned in Example 64.

$^1$H NMR (400 MHz, CDCl$_3$) δ ppm: 0.64-0.85 (2H, m), 0.89-1.04 (2H, m), 1.86-1.97 (1H, m), 2.04-2.13 (1H, m), 2.28-2.42 (1H, m), 2.35 (3H, s), 2.36 (3H, s), 2.49-2.58 and 2.63-2.71 (total 1H, each m), 2.76-2.89 (1H, m), 3.20 and 3.35 (total 1H, each d, J=13.0), 3.23 (2H, s), 4.06 and 4.11 (total 1H, each d, J=13.0), 4.52-4.57 (1H, m), 4.76 and 4.80 (total 1H, each s), 6.93 (1H, s), 7.03-7.17 (2H, m), 7.28-7.40 (2H, m), 8.44 and 8.46 (total 1H, each s);

IR (KBr, cm$^{-1}$): 1702, 1494.

Example 68

(E)-4-[(R)-2-Acetylamino-2-carboxyethyldisulfanyl]-1-[2-cyclopropyl-1-(2-fluorophenyl)-2-oxoethyl]-3-[(1,2,3-thiadiazol-4-yl)methylidene]piperidine hydrochloride (Exemplification Compound No. 1-191)

To a solution of (E)-1-[2-cyclopropyl-1-(2-fluorophenyl)-2-oxoethyl]-4-sulfanyl-3-[(1,2,3-thiadiazol-4-yl)methylidene]piperidine hydrochloride (100 mg) and N-acetyl-L-cysteine (840 mg) in tetrahydrofuran (10 ml) was stirred dropwise iodide in tetrahydrofuran under ice-cooling until colour of iodide remained in the reaction mixture, the resulting mixture was stirred at room temperature for 5 minutes. After stirring, the excess iodide was removed by chromatography on a silica gel column using tetrahydrofuran as the eluent. The solvent was removed in vacuo, and the residue was purified using a preparative HPLC [YMC-Pack ODS-A; YMC, mobile phase: 30% acetonitrile/water (0.2% aqueous hydrochloric acid solution)] to afford the title compound (30 mg, yield: 19%) as a yellow amorphous solid.

$^1$H NMR (500 MHz, DMSO-d$_6$) δ ppm: 0.80-1.20 (4H, m), 1.78-2.29 (3H, m), 1.85 (3H, s), 2.44-3.17 (4H, m), 3.28-3.81 (3H, m), 4.10-4.21 (1H, m), 4.49 and 4.50 (total 1H, each s), 7.03 and 7.08 (total 1H, each s), 7.29-7.73 (4H, m), 8.37 (1H, s);

IR (KBr, cm$^{-1}$): 1713, 1494.

Example 69

(E)-4-[(3-Carboxypropanoyl)sulfanyl]-1-[2-cyclopropyl-1-(2-fluorophenyl)-2-oxoethyl]-3-[(1,2,3-thiadiazol-4-yl)methylidene]piperidine hydrochloride (Exemplification Compound No. 1-192)

To a solution of (E)-1-[2-cyclopropyl-1-(2-fluorophenyl)-2-oxoethyl]-4-sulfanyl-3-[(1,2,3-thiadiazol-4-yl)methylidene]piperidine hydrochloride (100 mg) in acetone (10 ml) were added anhydrous succinic acid (26 mg) and potassium iodide (45 mg) with stirring at room temperature, and the resulting mixture was stirred at room temperature for 2 hours. After stirring, anhydrous succinic acid (130 mg) and potassium iodide (180 mg) were further added, and the resulting mixture was furthermore stirred at room temperature for 1.5 hours. After the reaction mixture was evaporated in vacuo, the residue was purified by chromatography on a silica gel column using methanol and dichloromethane (1:50) as the eluent. The amorphous solid obtained was dissolved in a 4N solution of hydrogen chloride in dioxane (2 ml), and the resulting mixture was evaporated in vacuo to afford the title compound (40 mg, yield: 29%) as a colourless amorphous solid.

$^1$H NMR (500 MHz, CDCl$_3$) δ ppm: 0.66-0.84 (2H, m), 0.91-1.04 (2H, m), 1.89-1.98 (1H, m), 2.04-2.10 (1H, m), 2.27-2.39 (1H, m), 2.51-2.58 and 2.77-2.86 (total 1H, each m), 2.62-2.73 (4H, m), 2.87-2.92 (1H, m), 3.25 and 3.40 (total 1H, each d, J=13.5), 4.03 and 4.04 (total 1H, each d, J=13.5), 4.56-4.61 (1H, m), 4.78 and 4.81 (total 1H, each s), 6.91 (1H, s), 7.04-7.16 (2H, m), 7.28-7.39 (2H, m), 8.45 and 8.47 (total 1H, each s);

IR (KBr, cm$^{-1}$): 1709, 1494.

Example 70

(E)-1-[2-Cyclopropyl-1-(2-fluorophenyl)-2-oxoethyl]-3-[(1,2,3-thiadiazol-4-yl)methylidene]-4-(tosylsulfanyl)piperidine hydrochloride (Exemplification Compound No. 1-193)

The title compound was synthesized in a yield of 33% as a colourless amorphous solid using p-toluenesulfonyl bromide instead of isobutyryl chloride by conducting the reaction similar to that mentioned in Example 64.

$^1$H NMR (400 MHz, CDCl$_3$) δ ppm: 0.63-0.83 (2H, m), 0.87-1.01 (2H, m), 1.97-2.13 (2H, m), 2.27-2.41 (1H, m), 2.23 (3H, s), 2.43-2.52 and 2.59-2.67 (total 1H, each m), 2.70-2.81 (1H, m), 3.07 and 3.21 (total 1H, each d, J=13.5), 3.94 and 4.00 (total 1H, each d, J=13.5), 4.35-4.42 (1H, m), 4.70 and 4.77 (total 1H, each s), 6.58 and 6.59 (total 1H, each s), 7.02-7.16 (2H, m), 7.20 (2H, d, J=8.0), 7.22-7.37 (2H, m), 7.76 (2H, d, J=8.0), 8.30 and 8.33 (total 1H, each s);

IR (KBr, cm$^{-1}$): 1712, 1494.

Example 71

(E)-4-(Acetylsulfanyl)-1-[2-cyclopropyl-1-(2-fluorophenyl)-2-oxoethyl]-3-[(1-methyl-1H-pyrazol-3-yl)methylidene]piperidine (Exemplification Compound No. 2-2)

(a) (E)-3-[(1-Methyl-1H-pyrazol-3-yl)methylidene]-1-(triphenylmethyl)piperidin-4-one The title compound was synthesized in a yield of 22% as a pale yellow amorphous solid using 1-methyl-1H-pyrazole-3-carbaldehyde instead of benzaldehyde by conducting the reaction similar to that mentioned in Example 1 (a).

$^1$H NMR (500 MHz, CDCl$_3$) δ ppm: 2.66 (2H, bs), 2.74 (2H, t, J=6.0), 3.60 (2H, bs), 3.80 (3H, s), 6.12 (1H, d, J=2.0), 7.14-7.19 (3H, m), 7.23-7.29 (7H, m), 7.45 (1H, s), 7.50-7.55 (6H, m).

(b) (E)-3-[(1-Methyl-1H-pyrazol-3-yl)methylidene]-1-triphenylmethyl)piperidin-4-ol The title compound was synthesized in a yield of 99% as a colourless amorphous solid using (E)-3-[(1-methyl-1H-pyrazol-3-yl)methylidene]-1-(triphenylmethyl)piperidin-4-one instead of (E)-3-benzylidene-1-(triphenylmethyl)piperidin-4-one by conducting the reaction similar to that mentioned in Example 1 (b)

$^1$H NMR (500 MHz, CDCl$_3$) δ ppm: 1.83-1.94 (2H, m), 2.01-2.18 (2H, m), 2.61-2.80 (1H, m), 3.69 (3H, s), 3.71-3.98 (1H, m), 4.12-4.19 (1H, m), 6.04 (1H, d, J=2.0), 6.48 (1H, s), 7.05-7.21 (9H, m), 7.21 (1H, d, J=2.0), 7.35-7.49 (6H, m).

(c) (E)-4-(Acetylsulfanyl)-3-[(1-methyl-1H-pyrazol-3-yl)methylidene]piperidine hydrogen trifluoroacetate The title compound was synthesized in a yield of 29% as a colourless amorphous solid using (E)-3-[(1-methyl-1H-pyrazol-3-yl)methylidene]-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c).

$^1$H NMR (500 MHz, CDCl$_3$) δ ppm: 2.01-2.09 (1H, m), 2.35 (3H, s), 2.41-2.51 (1H, m), 3.14-3.23 (1H, m), 3.32-3.39 (1H, m), 3.79 (1H, d, J=14.5), 3.85 (3H, s), 4.59 (1H, m), 5.14 (1H, d, J=14.5), 6.19 (1H, d, J=2.0), 6.62 (1H, s), 7.27 (1H, m).

(d) (E)-4-(Acetylsulfanyl)-1-[2-cyclopropyl-1-(2-fluorophenyl)-2-oxoethyl]-3-[(1-methyl-1H-pyrazol-3-yl)methylidene]piperidine The title compound was synthesized in a yield of 32% as a yellow amorphous solid using (E)-4-(acetylsulfanyl)-3-[(1-methyl-1H-pyrazol-3-yl)methylidene]piperidine hydrogen trifluoroacetate instead of (E)-4-(acetylsulfanyl)-3-benzylidenepiperidine hydrochloride by conducting the reaction similar to that mentioned in Example 1 (d).

¹H NMR (500 MHz, CDCl₃) δ ppm: 0.60-0.81 (2H, m), 0.84-1.02 (2H, m), 1.82-1.92 (1H, m), 2.21-2.36 (2H, m), 2.30 (3H, s), 2.43-2.50 and 2.56-2.62 (total 1H, each m), 2.71-2.78 and 2.80-2.86 (total 1H, each m), 3.07 and 3.23 (total 1H, each d, J=13.0), 3.76 and 3.83 (total 3H, each s), 4.15 and 4.17 (total 1H, each d, J=13.0), 4.50 (1H, m), 4.67 and 4.69 (total 1H, each s), 6.04 and 6.13 (total 1H, each d, J=2.0), 6.47 and 6.49 (total 1H, each s), 7.03-7.15 (2H, m), 7.17-7.32 (2H, m), 7.40-7.47 (1H, m).

Example 72

(E)-1-[2-Cyclopropyl-1-(2-fluorophenyl)-2-oxoethyl]-3-[(1-methyl-1H-pyrazol-3-yl)methylidene]-4-sulfanylpiperidine hydrochloride (Exemplification Compound No. 2-1)

The title compound was synthesized in a yield of 12% as a colourless amorphous solid using (E)-4-(acetylsulfanyl)-1-[2-cyclopropyl-1-(2-fluorophenyl)-2-oxoethyl]-3-[(1-methyl-1H-pyrazol-3-yl)methylidene]piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

¹H NMR (500 MHz, CDCl₃) δ ppm: 0.61-0.80 (2H, m), 0.85-1.02 (2H, m), 1.75-1.84 (1H, m), 2.22-2.36 (2H, m), 2.59-2.72 (1H, m), 2.73-2.80 and 2.83-2.91 (total 1H, each m), 3.55 and 3.67 (total 1H, each d, J=13.0), 3.80 and 3.85 (total 1H, each d, J=13.0), 3.78 and 3.83 (total 3H, each s), 3.92-3.97 (1H, m), 4.71 and 4.74 (total 1H, each s), 6.04 and 6.13 (total 1H, each d, J=2.0), 6.44 and 6.46 (total 1H, each s), 7.03-7.15 (2H, m), 7.21 and 7.24 (total 1H, each m), 7.26-7.32 (1H, m), 7.40-7.47 (1H, m);

IR (KBr, cm⁻¹): 2486, 1710.

Example 73

(E)-4-(Acetylsulfanyl)-1-[2-cyclopropyl-1-(2-fluorophenyl)-2-oxoethyl]-3-{[1-(2-methoxyethyl)-1H-pyrazol-3-yl]methylidene}piperidine (Exemplification Compound No. 2-166)

(a) (E)-3-{[1H-Pyrazol-3(5)-yl]methylidene}-1-(triphenylmethyl)piperidin-4-one

To a solution of (E)-3-{[1-(t-butoxycarbonyl)-1H-pyrazol-3-yl]methylidene}-1-(triphenylmethyl)piperidin-4-one (690 mg) in a mixed solvent of methanol (4 ml) and dichloromethane (1 ml) was added potassium carbonate (551 mg) at room temperature, and the resulting mixture was stirred at room temperature for 1.5 hours. After stirring, the reaction mixture was diluted with ethyl acetate and washed with saturated aqueous sodium chloride solution. Then the organic layer was dried over anhydrous sodium sulfate. The solvent was removed in vacuo to afford the title compound (568 mg, yield: quantitative) as a pale yellow amorphous solid.

¹H NMR (500 MHz, CDCl₃) δ ppm: 2.68 (2H, bs), 2.77 (2H, t, J=6.0), 3.56 (2H, bs), 6.15 (1H, d, J=2.0), 7.14-7.21 (3H, m), 7.23-7.32 (6H, m), 7.47-7.57 (8H, m).

(b) (E)-3-{[1H-Pyrazol-3(5)-yl]methylidene}-1-(triphenylmethyl)piperidin-4-ol

The title compound was synthesized in a quantitative yield as a colourless amorphous solid using (E)-3-{[1H-pyrazol-3(5)-yl]methylidene}-1-(triphenylmethyl)piperidin-4-one instead of (E)-3-benzylidene-1-(triphenylmethyl)piperidin-4-one by conducting the reaction similar to that mentioned in Example 1 (b)

¹H NMR (500 MHz, CDCl₃) δ ppm: 1.86-2.08 (2H, m), 2.11-2.19 (1H, m), 2.47-2.66 (1H, m), 2.75-2.90 (1H, m), 3.72-3.92 (1H, m), 4.09-4.18 (1H, m), 6.06 (1H, d, J=2.0), 6.55 (1H, s), 7.05-7.23 (9H, m), 7.34-7.48 (7H, m).

(c) (E)-3-{[1-(2-Methoxyethyl)-1H-pyrazol-3-yl]methylidene}-1-(triphenylmethyl)piperidin-4-ol To a solution of (E)-3-{[1H-pyrazol-3(5)-yl]methylidene}-1-(triphenylmethyl)piperidin-4-ol (1.00 g) and 2-methoxyethyl bromide (1.12 ml) in N,N-dimethylformamide (15 ml) were added potassium carbonate (0.83 g) and potassium iodide (2.00 g) with stirring at room temperature and the resulting mixture was stirred at 80° C. for 1.5 hours. 2-Methoxyethyl bromide (1.12 ml), potassium carbonate (0.83 g) and potassium iodide (2.00 g) were further added to the reaction mixture and the resulting mixture was stirred at 80° C. for 5.5 hours. After stirring, water was added to the reaction mixture, and the resulting reaction mixture was extracted with ethyl acetate. The extract was washed with water and saturated aqueous sodium chloride solution, and the organic layer was dried over anhydrous sodium sulfate. The solvent was removed in vacuo, and the residue was purified by chromatography on a silica gel column using methanol and dichloromethane (1:19) as the eluent to afford the title compound (0.57 g, yield: 50%) as a brown amorphous solid.

¹H NMR (500 MHz, CDCl₃) δ ppm: 1.85-1.94 (1H, m), 2.11-2.20 (2H, m), 2.64-3.02 (2H, m), 3.32 (3H, s), 3.56-3.61 (2H, m), 3.65-3.87 (1H, m), 4.06-4.11 (2H, m), 4.13-4.20 (1H, m), 6.04 (1H, d, J=2.5), 6.50 (1H, s), 7.06-7.22 (9H, m), 7.32 (1H, d, J=2.5), 7.38-7.45 (6H, m).

(d) (E)-4-(Acetylsulfanyl)-3-{[1-(2-methoxyethyl)-1H-pyrazol-3-yl]methylidene}-1-piperidine hydrogen trifluoroacetate The title compound was synthesized in a yield of 11% as a colourless oil using (E)-3-{[1-(2-methoxyethyl)-1H-pyrazol-3-yl]methylidene}-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c).

¹H NMR (500 MHz, CDCl₃) δ ppm: 2.01-2.10 (1H, m), 2.35 (3H, s), 2.41-2.51 (1H, m), 3.13-3.24 (1H, m), 3.31 (3H, s), 3.32-3.39 (1H, m), 3.70 (2H, t, J=5.5), 3.79 (1H, d, J=14.0), 4.22 (2H, t, J=5.5), 4.59 (1H, m), 5.12 (1H, d, J=14.0), 6.19 (1H, d, J=2.5), 6.64 (1H, s), 7.39 (1H, d, J=2.5).

(e) (E)-4-(Acetylsulfanyl)-1-[2-cyclopropyl-1-(2-fluorophenyl)-2-oxoethyl]-3-{[1-(2-methoxyethyl)-1H-pyrazol-3-yl]methylidene}piperidine The title compound was synthesized in a yield of 62% as a colourless oil using (E)-4-(acetylsulfanyl)-3-{[1-(2-methoxyethyl)-1H-pyrazol-3-yl]methylidene}piperidine hydrogen trifluoroacetate instead of (E)-4-(acetylsulfanyl)-3-benzylidenepiperidine hydrochloride by conducting the reaction similar to that mentioned in Example 1 (d).

¹H NMR (500 MHz, CDCl₃) δ ppm: 0.62-0.81 (2H, m), 0.83-1.01 (2H, m), 1.84-1.92 (1H, m), 2.21-2.35 (2H, m), 2.30 (3H, s), 2.43-2.50 and 2.57-2.64 (total 1H, each m), 2.72-2.78 and 2.79-2.85 (total 1H, each m), 3.10 and 3.23 (total 1H, each d, J=13.5), 3.31 and 3.32 (total 3H, each s), 3.64 and 3.70 (total 2H, each t, J=5.0), 4.11-4.18 (1H, m), 4.13 and 4.20 (total 2H, each t, J=5.0), 4.51 (1H, m), 4.68 and 4.70 (total 1H, each s), 6.04 and 6.13 (total 1H, each d, J=2.5), 6.49 and 6.50 (total 1H, each s), 7.03-7.16 (2H, m), 7.25-7.32 (1H, m), 7.31 and 7.36 (total 1H, each d, J=2.5), 7.40-7.46 (1H, m).

Example 74

(E)-1-[2-Cyclopropyl-1-(2-fluorophenyl)-2-oxoethyl]-3-{[1-(2-methoxyethyl)-1H-pyrazol-3-yl]methylidene}-4-sulfanylpiperidine hydrochloride (Exemplification Compound No. 2-165)

The title compound was synthesized in a yield of 48% as a colourless amorphous solid using (E)-4-(acetylsulfanyl)-1-[2-cyclopropyl-1-(2-fluorophenyl)-2-oxoethyl]-3-{[1-(2-methoxyethyl)-1H-pyrazol-3-yl]methylidene}piperidine instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (500 MHz, CDCl$_3$) δ ppm: 0.63-0.81 (2H, m), 0.84-1.02 (2H, m), 1.75-1.84 (1H, m), 2.21-2.36 (2H, m), 2.60-2.79 and 2.83-2.91 (total 2H, each m), 3.32 and 3.33 (total 3H, each s), 3.55 and 3.65 (total 1H, each d, J=13.0), 3.67 and 3.71 (total 2H, each t, J=5.5), 3.80-3.88 (1H, m), 3.91-3.97 (1H, m), 4.16 and 4.20 (total 2H, each t, J=5.5), 4.72 and 4.75 (total 1H, each s), 6.04 and 6.13 (total 1H, each d, J=2.5), 6.45 and 6.47 (total 1H, each s), 7.04-7.16 (2H, m), 7.25-7.32 (1H, m), 7.33 and 7.37 (total 1H, each d, J=2.5), 7.40-7.46 (1H, m);

IR (KBr, cm$^{-1}$): 2524, 1710.

Example 75

(E)-4-(Acetylsulfanyl)-3-{[1-(t-butoxycarbonylmethyl)-1H-pyrazol-3-yl]methylidene}-1-[2-cyclopropyl-1-(2-fluorophenyl)-2-oxoethyl]piperidine (Exemplification Compound No. 2-78)

(a) (E)-3-{[1-(t-Butoxycarbonylmethyl)-1H-pyrazol-3-yl]methylidene}-1-(triphenylmethyl)piperidin-4-one To a solution of (E)-3-{[1H-pyrazol-3(5)-yl]methylidene}-1-(triphenylmethyl)piperidin-4-one (3.2 g) and t-butyl bromoacetate (5.7 ml) in N,N-dimethylformamide (30 ml) were added potassium carbonate (2.7 g) and potassium iodide (6.4 g) at room temperature, and the resulting mixture was stirred at 80° C. for 1 hour. After stirring, water was added to the reaction mixture, and the resulting mixture was extracted with ethyl acetate. The extract was washed with water and saturated aqueous sodium chloride solution, and the organic layer was dried over anhydrous magnesium sulfate. The solvent was removed in vacuo, and the residue was purified by chromatography on a silica gel column using ethyl acetate, hexane, and dichloromethane (1:4:1) as the eluent to afford the title compound (4.1 g, yield: 90%) as a yellow amorphous solid.

$^1$H NMR (500 MHz, CDCl$_3$) δ ppm: 1.45 (9H, s), 2.65 (2H, bs), 2.74 (2H, t, J=6.0), 3.59 (2H, bs), 4.68 (2H, s), 6.19 (1H, d, J=2.5), 7.13-7.19 (3H, m), 7.23-7.29 (6H, m), 7.37 (1H, d, J=2.5), 7.45 (1H, s), 7.49-7.54 (6H, m).

(b) (E)-3-{[1-(t-Butoxycarbonylmethyl)-1H-pyrazol-3-yl]methylidene}-1-(triphenylmethyl)piperidin-4-ol The title compound was synthesized in a yield of 80% as a yellow amorphous solid using (E)-3-{[1-(t-butoxycarbonylmethyl)-1H-pyrazol-3-yl]methylidene}-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (500 MHz, CDCl$_3$) δ ppm: 1.48 (9H, s), 1.84-1.93 (1H, m), 2.06-2.18 (2H, m), 2.64-2.94 (2H, m), 3.71-3.89 (1H, m), 4.11-4.18 (1H, m), 4.59 (2H, s), 6.11 (1H, d, J=2.0), 6.50 (1H, s), 7.07-7.22 (9H, m), 7.33 (1H, d, J=2.0), 7.39-7.45 (6H, m).

(c) (E)-4-(Acetylsulfanyl)-3-{[1-(t-butoxycarbonylmethyl)-1H-pyrazol-3-yl]methylidene}piperidine hydrogen trifluoroacetate The title compound was synthesized in a yield of 30% as a colourless amorphous solid using (E)-3-{[1-(t-butoxycarbonylmethyl)-1H-pyrazol-3-yl]methylidene}-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c)

$^1$H NMR (500 MHz, CDCl$_3$) δ ppm: 1.47 (9H, s), 2.01-2.09 (1H, m), 2.35 (3H, s), 2.41-2.51 (1H, m), 3.14-3.22 (1H, m), 3.31-3.38 (1H, m), 3.78 (1H, d, J=14.5), 4.58 (1H, m), 4.71-4.82 (2H, m), 5.04 (1H, d, J=14.5), 6.27 (1H, d, J=2.0), 6.63 (1H, s), 7.39 (1H, d, J=2.0).

(d) (E)-4-(Acetylsulfanyl)-3-{[1-(t-butoxycarbonylmethyl)-1H-pyrazol-3-yl]methylidene}-1-[2-cyclopropyl-1-(2-fluorophenyl)-2-oxoethyl]piperidine The title compound was synthesized in a yield of 60% as a pale yellow amorphous solid using (E)-4-(acetylsulfanyl)-3-{[1-(t-butoxycarbonylmethyl)-1H-pyrazol-3-yl]methylidene hydrogen trifluoroacetate instead of (E)-4-(acetylsulfanyl)-3-benzylidenepiperidine hydrochloride by conducting the reaction similar to that mentioned in Example 1 (d).

$^1$H NMR (500 MHz, CDCl$_3$) δ ppm: 0.64-0.81 (2H, m), 0.86-1.02 (2H, m), 1.48 (9H, s), 1.83-1.92 (1H, m), 2.21-2.35 (2H, m), 2.29 (3H, s), 2.42-2.49 and 2.55-2.63 (total 1H, each m), 2.71-2.78 and 2.79-2.86 (total 1H, each m), 3.07 and 3.22 (total 1H, each d, J=13.5), 4.09-4.16 (1H, m), 4.50 (1H, m), 4.65 and 4.73 (total 2H, each s), 4.66 and 4.68 (total 1H, each s), 6.13 and 6.22 (total 1H, each d, J=2.0), 6.47 and 6.49 (total 1H, each s), 7.04-7.16 (2H, m), 7.25-7.32 (1H, m) 7.32 and 7.37 (total 1H, each d, J=2.0), 7.41-7.47 (1H, m).

Example 76

(E)-4-(Acetylsulfanyl)-3-{[1-(carboxymethyl)-1H-pyrazol-3-yl]methylidene}-1-[2-cyclopropyl-1-(2-fluorophenyl)-2-oxoethyl]piperidine hydrochloride (Exemplification Compound No. 2-14)

To a solution of (E)-4-(acetylsulfanyl)-3-{[1-(t-butoxycarbonylmethyl)-1H-pyrazol-3-yl]methylidene}-1-[2-cyclopropyl-1-(2-fluorophenyl)-2-oxoethyl]piperidine (770 mg) in dichloromethane (10 ml) was added trifluoroacetic acid (10 ml) under ice-cooling, and the resulting mixture was stirred at room temperature for 2 hours. The reaction mixture was concentrated in vacuo, and the residue was diluted with ethyl acetate and washed saturated aqueous sodium hydrogencarbonate solution. The organic layer was neutralized with 1N hydrochloric acid and dried over anhydrous magnesium sulfate. The solvent was removed in vacuo, and the residue was dissolved in dichloromethane (10 ml) and a 4N solution of hydrogen chloride in dioxane (1.1 ml) was added to the resulting mixture. The reaction mixture was removed in vacuo, and the residue was purified by chromatography on a silica gel column using methanol and dichloromethane (1:40) as the eluent to afford the title compound (640 mg, yield: 80%) as a pale yellow amorphous solid.

$^1$H NMR (500 MHz, CDCl$_3$) δ ppm: 0.68-1.08 (4H, m), 1.85-2.02 (1H, m), 2.17-3.04 (4H, m), 2.30 (3H, s), 3.32-3.69 (1H, m), 4.08-4.17 (1H, m), 4.41-4.52 (1H, m), 4.63-4.83 (3H, m), 6.05-6.22 (1H, m), 6.48-6.59 (1H, m), 7.05-7.49 (5H, m);

IR (KBr, cm$^{-1}$): 1699, 1495.

Example 77

(E)-3-{[1-(Carboxymethyl)-1H-pyrazol-3-yl]methylidene}-1-[2-cyclopropyl-1-(2-fluorophenyl)-2-oxoethyl]-4-sulfanylpiperidine hydrochloride (Exemplification Compound No. 2-13)

The title compound was synthesized in a yield of 44% as a colourless amorphous solid using (E)-4-(acetylsulfanyl)-3-{[1-(carboxymethyl)-1H-pyrazol-3-yl]methylidene}-1-[2-cyclopropyl-1-(2-fluorophenyl)-2-oxoethyl]piperidine hydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (400 MHz, DMSO-d$_6$) δ ppm: 0.81-1.16 (4H, m), 1.82-1.99 (1H, m), 2.12-3.11 (4H, m), 3.22-4.09 (3H, m), 4.62 (1H, m), 4.96 (2H, m), 6.24 (1H, m), 6.63 (1H, m), 7.35-7.83 (5H, m);

IR (KBr, cm$^{-1}$): 2561, 1741, 1711.

Example 78

(E)-1-[2-Cyclopropyl-1-(2-fluorophenyl)-2-oxoethyl]-3-{[1-(ethoxycarbonylmethyl)-1H-pyrazol-3-yl]methylidene}-4-sulfanylpiperidine hydrochloride (Exemplification Compound No. 2-45)

To a solution of (E)-4-(acetylsulfanyl)-3-{[1-(carboxymethyl)-1H-pyrazol-3-yl]methylidene}-1-[2-cyclopropyl-1-(2-fluorophenyl)-2-oxoethyl]piperidine hydrochloride (600 mg) in ethanol (15 ml) was bubbled hydrogen chloride under ice-cooling, and the resulting mixture was stirred at room temperature under tightly sealed condition for 4 hours. After stirring, the reaction mixture was evaporated in vacuo, and the residue was purified by a preparative HPLC [YMC-Pack ODS-A; YMC, mobile phase: 40% acetonitrile/water (0.2% hydrochloric acid solution)] to afford the title compound (250 mg, yield: 37%) as a colourless amorphous solid.

$^1$H NMR (500 MHz, CDCl$_3$) δ ppm: 0.65-0.81 (2H, m), 0.86-1.01 (2H, m), 1.29 (3H, t, J=7.0), 1.75-1.84 (1H, m), 2.22-2.35 (2H, m), 2.60-2.66 and 2.67-2.72 (total 1H, each m), 2.73-2.79 and 2.83-2.89 (total 1H, each m), 3.53 and 3.66 (total 1H, each d, J=12.5), 3.81 and 3.83 (total 1H, each d, J=12.5), 3.90-3.96 (1H, m), 4.24 (2H, q, J=7.0), 4.70 and 4.73 (total 1H, each s), 4.77 and 4.82 (total 2H, each s), 6.13 and 6.23 (total 1H, each d, J=2.0), 6.44 and 6.47 (total 1H, each s), 7.03-7.17 (2H, m), 7.24-7.32 (1H, m), 7.34 and 7.38 (total 1H, each d, J=2.0), 7.41-7.46 (1H, m);

IR (KBr, cm$^{-1}$): 2486, 1749, 1712.

Example 79

(E)-4-(Acetylsulfanyl)-1-[2-cyclopropyl-1-(2-fluorophenyl)-2-oxoethyl]-3-{[1-(ethoxycarbonylmethyl)-1H-pyrazol-3-yl]methylidene}piperidine hydrochloride (Exemplification Compound No. 2-46)

To a solution of (E)-1-[2-cyclopropyl-1-(2-fluorophenyl)-2-oxoethyl]-3-{[1-(ethoxycarbonylmethyl)-1H-pyrazol-3-yl]methylidene}-4-sulfanylpiperidine hydrochloride (140 mg) in dichloromethane (5 ml) were added acetyl chloride (0.02 ml) and triethylamine (0.12 ml), and the resulting mixture was stirred at room temperature for 40 minutes. To the resulting reaction mixture were added acetyl chloride (0.02 ml) and triethylamine (0.4 ml), and the resulting mixture was stirred at room temperature for 80 minutes. The reaction mixture was concentrated in vacuo, and the residue was purified by chromatography on a silica gel column using methanol and dichloromethane (1:19) as the eluent. The yellow oily product obtained was dissolved in dichloromethane (3 ml) and a 4N solution of hydrogen chloride in dioxane (0.11 ml) was added to the resulting solution. After evaporation of the solvent of the reaction mixture under reduced pressure, the title compound (70 mg, yield: 46%) was afforded as a pale yellow amorphous solid.

$^1$H NMR (500 MHz, CDCl$_3$) δ ppm: 0.64-0.82 (2H, m), 0.86-1.02 (2H, m), 1.29 (3H, t, J=7.0), 1.83-1.92 (1H, m), 2.21-2.33 (2H, m), 2.30 (3H, s), 2.43-2.50 and 2.55-2.62 (total 1H, each m), 2.71-2.78 and 2.80-2.85 (total 1H, each m), 3.06 and 3.23 (total 1H, each d, J=13.0), 4.11 and 4.12 (total 1H, each d, J=13.0), 4.24 (2H, q, J=7.0), 4.50 (1H, m), 4.67 and 4.69 (total 1H, each s), 4.78 and 4.82 (total 2H, each s), 6.14 and 6.22 (total 1H, each d, J=3.0), 6.47 and 6.50 (total 1H, each s), 7.04-7.16 (2H, m), 7.25-7.31 (1H, m), 7.33 and 7.38 (total 1H, each d, J=3.0), 7.41-7.47 (1H, m);

IR (KBr, cm$^{-1}$): 1697, 1495.

Another Synthesis Method (a) (E)-3-{[1-(Ethoxycarbonylmethyl)-1H-pyrazol-3-yl]methylidene}-1-(triphenylmethyl)piperidin-4-ol (Compound A), and (E)-3-{[1-(2-Hydroxyethyl)-1H-pyrazol-3-yl]methylidene}-1-(triphenylmethyl)piperidin-4-ol (Compound B)

To a solution of (E)-3-{([1H-pyrazol-3(5)-yl]methylidene}-1-(triphenylmethyl)piperidin-4-one (40.6 g) and ethyl bromoacetate (53.9 ml) in N,N-dimethylformamide (420 ml) were added potassium carbonate (33.4 g) and potassium iodide (80.3 g) under ice-cooling, and the resulting mixture was stirred at room temperature for 30 minutes and subsequently furthermore stirred at 80° C. for 30 minutes. After stirring, water was added to the reaction mixture, and the resulting mixture was extracted with ethyl acetate. The organic layer was washed with water and saturated aqueous sodium chloride solution and dried over anhydrous magnesium sulfate. The solvent was removed in vacuo, and the residue was purified by chromatography on a silica gel column using a mixed solvent of ethyl acetate, hexane, and dichloromethane (1:2:1) as the eluent to afford (E)-3-{[1-(ethoxycarbonylmethyl)-1H-pyrazol-3-yl]methylidene}-1-(triphenylmethyl)piperidin-4-one (including impurities) as a yellow solid.

To a solution of the mixture mentioned above in a mixed solvent of ethanol (500 ml) and dichloromethane (200 ml) was added sodium borohydride (1.9 g) under ice-cooling, and the resulting mixture was stirred at room temperature for 1 hour. After stirring, water was added to the reaction mixture, and the resulting mixture was extracted with ethyl acetate. The organic layer was washed with saturated aqueous sodium chloride solution and dried over anhydrous magnesium sulfate. The solvent was removed in vacuo, and the residue was purified by chromatography on a silica gel column using a mixed solvent of ethyl acetate and dichloromethane (1:4 to 1:1) as the eluent to afford the title compounds, Compound A (27.0 g, yield: 54%), Compound B (10.0 g, yield: 22%), and a mixed compounds (1.5 g) of (E)-3-{[1-(ethoxycarbonylmethyl)-1H-pyrazol-5-yl]methylidene}-1-(triphenylmethyl) piperidin-4-ol and (E)-3-({1-[1,2-bis(ethoxycarbonyl)ethyl]-1H-pyrazol-3-yl}methylidene)-1-(triphenylmethyl) piperidin-4-ol as a yellow oil, respectively.

(Compound A)

$^1$H NMR (400 MHz, CDCl$_3$) δ ppm: 1.29 (3H, t, J=7.0), 1.83-1.95 (1H, m), 2.08-2.20 (2H, m), 2.64-2.78 (2H, m), 3.39-3.59 (1H, m), 4.10-4.18 (1H, m), 4.12 (2H, q, J=7.0), 4.68 (2H, s), 6.13 (1H, d, J=2.0), 6.50 (1H, s), 7.07-7.21 (9H, m), 7.35 (1H, d, J=2.0), 7.39-7.46 (6H, m).

(Compound B)

$^1$H NMR (500 MHz, CDCl$_3$) δ ppm: 1.86-1.94 (1H, m), 2.11-2.18 (2H, m), 2.67-2.87 (2H, m), 3.46-3.52 (1H, m), 3.63-3.76 (2H, m), 3.95-4.08 (2H, m), 4.12-4.20 (1H, m), 6.12 (1H, d, J=2.0), 6.48 (1H, s), 7.05-7.21 (9H, m), 7.29 (1H, d, J=2.0), 7.37-7.46 (6H, m).

(b) (E)-4-(Acetylsulfanyl)-3-{[1-(ethoxycarbonylmethyl)-1H-pyrazol-3-yl]methylidene}piperidine hydrogen trifluoroacetate The title compound was synthesized in a yield of 16% as a white solid using (E)-3-{[1-(ethoxycarbonylmethyl)-1H-pyrazol-3-yl]methylidene}-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c).

$^1$H NMR (500 MHz, CDCl$_3$) δ ppm: 1.28 (3H, t, J=7.0), 2.03-2.11 (1H, m), 2.36 (3H, s), 2.40-2.49 (1H, m), 3.16-3.24 (1H, m), 3.33-3.40 (1H, m), 3.79 (1H, d, J=14.5), 4.23 (2H, q, J=7.0), 4.58 (1H, m), 4.86 and 4.87 (total 2H, each s), 5.04 (1H, d, J=14.5), 6.28 (1H, d, J=2.5), 6.64 (1H, s), 7.40 (1H, d, J=2.5).

(c) (E)-4-(Acetylsulfanyl)-1-[2-cyclopropyl-1-(2-fluorophenyl)-2-oxoethyl]-3-{[1-(ethoxycarbonylmethyl)-1H-pyrazol-3-yl]methylidene}piperidine hydrochloride The title compound was synthesized in a yield of 59% as a pale yellow amorphous solid using (E)-4-(acetylsulfanyl)-3-{[1-(ethoxycarbonylmethyl)-1H-pyrazol-3-yl]methylidene}piperidine hydrogen trifluoroacetate instead of (E)-4-(acetylsulfanyl)-3-benzylidenepiperidine hydrochloride by conducting the reaction similar to that mentioned in Example 1 (d).

Example 80

(E)-1-[2-Cyclopropyl-1-(2-fluorophenyl)-2-oxoethyl]-3-{[1-(methoxycarbonylmethyl)-1H-pyrazol-3-yl]methylidene}-4-sulfanylpiperidine hydrochloride (Exemplification Compound No. 2-29)

To a solution of (E)-4-(acetylsulfanyl)-3-{[1-(t-butoxycarbonylmethyl)-1H-pyrazol-3-yl]methylidene}-1-[2-cyclopropyl-1-(2-fluorophenyl)-2-oxoethyl]piperidine (120 mg) in methanol (20 ml) was bubbled hydrogen chloride under ice-cooling, and the resulting reaction mixture was stirred at room temperature under tightly sealed condition for 2.5 hours. The reaction mixture was concentrated in vacuo, and the residue was purified by a preparative HPLC [YMC-Pack ODS-A; YMC, mobile phase: 33% acetonitrile/water (0.2% hydrochloric acid solution)] to afford the title compound (100 mg, yield: 85%) as a colourless amorphous solid.

$^1$H NMR (500 MHz, CDCl$_3$) δ ppm: 0.64-0.82 (2H, m), 0.86-1.02 (2H, m), 1.75-1.84 (1H, m), 2.21-2.36 (2H, m), 2.60-2.66 and 2.67-2.72 (total 1H, each m), 2.73-2.80 and 2.82-2.89 (total 1H, each m), 3.53 and 3.67 (total 1H, each d, J=13.0), 3.77 and 3.84 (total 1H, each d, J=13.0), 3.77 and 3.78 (total 3H, each s), 3.90-3.96 (1H, m), 4.71 and 4.73 (total 1H, each s), 4.83 (2H, s), 6.14 and 6.23 (total 1H, each d, J=2.5), 6.44 and 6.47 (total 1H, each s), 7.04-7.15 (2H, m), 7.25-7.32 (1H, m), 7.34 and 7.38 (total 1H, each d, J=2.5), 7.40-7.46 (1H, m);

IR (KBr, cm$^-$): 2492, 1750, 1711.

Example 81

(E)-4-(Acetylsulfanyl)-1-[2-cyclopropyl-1-(2-fluorophenyl)-2-oxoethyl]-3-{[1-(methoxycarbonylmethyl)-1H-pyrazol-3-yl]methylidene}piperidine hydrochloride (Exemplification Compound No. 2-30)

The title compound was synthesized in a yield of 69% as a pale yellow amorphous solid using (E)-1-[2-cyclopropyl-1-(2-fluorophenyl)-2-oxoethyl]-3-{[1-(methoxycarbonylmethyl)-1H-pyrazol-3-yl]methylidene}-4-sulfanylpiperidine hydrochloride instead of (E)-1-[2-cyclopropyl-1-(2-fluorophenyl)-2-oxoethyl]-3-{[1-(ethoxycarbonylmethyl)-1H-pyrazol-3-yl]methylidene}-4-sulfanylpiperidine hydrochloride by conducting the reaction similar to that mentioned in Example 79.

$^1$H NMR (500 MHz, CDCl$_3$) δ ppm: 0.63-0.82 (2H, m), 0.86-1.02 (2H, m), 1.83-1.92 (1H, m), 2.21-2.35 (2H, m), 2.30 (3H, s), 2.43-2.50 and 2.55-2.62 (total 1H, each m), 2.71-2.77 and 2.80-2.86 (total 1H, each m), 3.06 and 3.24 (total 1H, each d, J=12.5), 4.10 and 4.12 (total 1H, each d, J=12.5), 3.77 (3H, s), 4.50 (1H, m), 4.67 and 4.69 (total 1H, each s), 4.76 and 4.84 (total 2H, each s), 6.14 and 6.22 (total 1H, each d, J=2.5), 6.47 and 6.49 (total 1H, each s), 7.03-7.16 (2H, m), 7.26-7.31 (1H, m), 7.33 and 7.37 (total 1H, each d, J=2.5), 7.40-7.46 (1H, m);

IR (KBr, cm$^{-1}$): 1696, 1495.

Example 82

(E)-1-[2-Cyclopropyl-1-(2-fluorophenyl)-2-oxoethyl]-3-{[1-(propoxycarbonylmethyl)-1H-pyrazol-3-yl]methylidene}-4-sulfanylpiperidine hydrochloride (Exemplification Compound No. 2-61)

The title compound was synthesized in a yield of 64% as a colourless amorphous solid using n-propanol instead of methanol by conducting the reaction similar to that mentioned in Example 80.

¹H NMR (500 MHz, CDCl₃) δ ppm: 0.64-0.82 (2H, m), 0.86-1.02 (2H, m), 0.93 (3H, t, J=8.0), 1.63-1.71 (2H, m), 1.75-1.84 (1H, m), 2.22-2.36 (2H, m), 2.59-2.80 and 2.82-2.89 (total 2H, each m), 3.53 and 3.67 (total 1H, each d, J=13.5), 3.80 and 3.83 (total 1H, each d, J=13.5), 3.90-3.96 (1H, m), 4.11-4.16 (2H, m), 4.70 and 4.73 (total 1H, each s), 4.78 and 4.83 (total 2H, each s), 6.13 and 6.23 (total 1H, each d, J=2.5), 6.44 and 6.47 (total 1H, each s), 7.04-7.16 (2H, m), 7.25-7.32 (1H, m), 7.34 and 7.39 (total 1H, each d, J=2.5), 7.41-7.47 (1H, m);

IR (KBr, cm⁻¹): 2520, 1749, 1713.

Example 83

(E)-3-{[1-(Butoxycarbonylmethyl)-1H-pyrazol-3-yl]methylidene}-1-[2-cyclopropyl-1-(2-fluorophenyl)-2-oxoethyl]-4-sulfanylpiperidine hydrochloride (Exemplification Compound No. 2-69)

The title compound was synthesized in a yield of 55% as a colourless amorphous solid using n-butanol instead of methanol by conducting the reaction similar to that mentioned in Example 80.

¹H NMR (500 MHz, CDCl₃) δ ppm: 0.66-0.80 (2H, m), 0.86-1.02 (2H, m), 0.93 (3H, t, J=7.5), 1.32-1.41 (2H, m), 1.58-1.66 (2H, m), 1.76-1.84 (1H, m), 2.22-2.35 (2H, m), 2.60-2.79 and 2.82-2.89 (total 2H, each m), 3.52 and 3.66 (total 1H, each d, J=13.0), 3.81 and 3.84 (total 1H, each d, J=13.0), 3.91-3.96 (1H, m), 4.15-4.20 (2H, m), 4.70 and 4.73 (total 1H, each s), 4.77 and 4.82 (total 2H, each s), 6.13 and 6.23 (total 1H, each d, J=2.5), 6.44 and 6.47 (total 1H, each s), 7.04-7.15 (2H, m), 7.26-7.32 (1H, m), 7.34 and 7.38 (total 1H, each d, J=2.5), 7.41-7.47 (1H, m);

IR (KBr, cm⁻¹): 2518, 1749, 1713.

Example 84

(E)-4-(Acetylsulfanyl)-3-{[1-(carbamoylmethyl)-1H-pyrazol-3-yl]methylidene}-1-[2-cyclopropyl-1-(2-fluorophenyl)-2-oxoethyl]piperidine (Exemplification Compound No. 2-102)

To a solution of (E)-4-(acetylsulfanyl)-3-{[1-(carboxymethyl)-1H-pyrazol-3-yl]methylidene}-1-[2-cyclopropyl-1-(2-fluorophenyl)-2-oxoethyl]piperidine hydrochloride (190 mg) in dichloromethane (15 ml) were added isobutyl chloroformate (0.06 ml) and triethylamine (0.18 ml) under ice-cooling, and the resulting mixture was stirred at the same temperature for 30 minutes. To this reaction mixture was added 28% aqueous ammonia solution (0.03 ml), and the resulting mixture was stirred at room temperature for 45 minutes. After stirring, saturated aqueous sodium hydrogencarbonate solution was added to the reaction mixture and extracted with dichloromethane. The extract was dried over anhydrous magnesium sulfate. The solvent was removed in vacuo, and the residue was purified by chromatography on a silica gel column using a mixed solvent of methanol and dichloromethane (1:19) as the eluent to afford the title compound (80 mg, yield: 42%) as a yellow oil.

¹H NMR (500 MHz, CDCl₃) δ ppm: 0.68-1.01 (4H, m), 1.86-1.96 (1H, m), 2.07-2.13 (1H, m), 2.21-2.30 (1H, m), 2.30 and 2.31 (total 3H, each s), 2.43-2.52 and 2.54-2.62 (total 1H, each m), 2.68-2.75 and 2.81-2.88 (total 1H, each m), 3.05 and 3.25 (total 1H, each d, J=12.5), 4.21-4.31 (1H, m), 4.47-4.52 (1H, m), 4.63-4.73 (2H, m), 4.75 and 4.76 (total 1H, each s), 6.17 and 6.23 (total 1H, each d, J=2.0), 6.46 and 6.47 (total 1H, each s), 7.06-7.17 (2H, m), 7.25-7.41 (3H, m); MS (FAB) m/z: 471 (M+H)⁺.

Example 85

(E)-3-{[1-(Carbamoylmethyl)-1H-pyrazol-3-yl]methylidene}-1-[2-cyclopropyl-1-(2-fluorophenyl)-2-oxoethyl]-4-sulfanylpiperidine hydrochloride (Exemplification Compound No. 2-101)

The title compound was synthesized in a yield of 19% as a colourless amorphous solid using (E)-4-(acetylsulfanyl)-3-{[1-(carbamoylmethyl)-1H-pyrazol-3-yl]methylidene}-1-[2-cyclopropyl-1-(2-fluorophenyl)-2-oxoethyl]piperidine instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

¹H NMR (500 MHz, CDCl₃) δ ppm: 0.69-0.86 (2H, m), 0.88-1.00 (2H, m), 1.76-1.84 (1H, m), 2.05-2.12 (1H, m), 2.22-2.38 (1H, m), 2.56-2.63 and 2.66-2.73 (total 1H, each m), 2.74-2.81 and 2.82-2.89 (total 1H, each m), 3.56 and 3.71 (total 1H, each d, J=12.5), 3.87-3.97 (2H, m), 4.66-4.73 (3H, m), 6.17 and 6.23 (total 1H, each d, J=2.0), 6.42 and 6.44 (total 1H, each s), 7.07-7.17 (2H, m), 7.29-7.40 (2H, m), 7.35 and 7.38 (total 1H, each d, J=2.0);

IR (KBr, cm⁻¹): 2531, 1708.

Example 86

(E)-3-{(1-Acetyl-1H-pyrazol-3-yl)methylidene}-1-[2-cyclopropyl-1-(2-fluorophenyl)-2-oxoethyl]-4-sulfanylpiperidine hydrogen trifluoroacetate (Exemplification Compound No. 2-9)

The title compound was synthesized in a yield of 25% as a colourless amorphous solid using (E)-1-[2-cyclopropyl-1-(2-fluorophenyl)-2-oxoethyl]-3-{[1H-pyrazol-3(5)-yl]methylidene}-4-sulfanylpiperidine bis(hydrogen trifluoroacetate) instead of (E)-1-[2-cyclopropyl-1-(2-fluorophenyl)-2-oxoethyl]-3-{[1-(ethoxycarbonylmethyl)-1H-pyrazol-3-yl]methylidene}-4-sulfanylpiperidine hydrochloride by conducting the reaction similar to that mentioned in Example 79.

¹H NMR (500 MHz, CDCl₃) δ ppm: 0.65-0.81 (2H, m), 0.85-0.99 (2H, m), 1.79-1.89 (1H, m), 2.12-2.19 (1H, m), 2.27-2.38 (1H, m), 2.52 and 2.58 (total 3H, each s), 2.64-2.75 (1H, m), 2.82-2.93 (1H, m), 3.66 and 3.79 (total 1H, each d, J=13.5), 3.82 and 3.88 (total 1H, each d, J=13.5), 3.90-3.95 (1H, m), 4.78 and 4.79 (total 1H, each s), 6.30 and 6.35 (total 1H, each d, J=3.0), 6.44 and 6.45 (total 1H, each s), 7.02-7.13 (2H, m), 7.26-7.32 (1H, m), 7.34-7.39 (1H, m), 8.12 and 8.15 (total 1H, each d, J=3.0);

IR (Thin film, cm⁻¹): 2564, 1713, 1672.

Example 87

(E)-4-(Acetylsulfanyl)-1-[2-cyclopropyl-1-(2-fluorophenyl)-2-oxoethyl]-3-{[1-(ethoxycarbonylmethyl)pyrrol-2-yl)methylidene]piperidine (Exemplification Compound No. 2-546)

(a) (E)-3-[(Pyrrol-2-yl)methylidene]-1-(triphenylmethyl)piperidin-4-one

To a solution of 1-(triphenylmethyl)piperidin-4-one (17.00 g) in tetrahydrofuran (400 ml) was added dropwise a 0.5N solution of potassium bis(trimethylsilyl)amide in toluene (100 ml) at −70° C., and the resulting mixture was stirred at the same temperature for 20 minutes. Subsequently, to the reaction mixture was added dropwise a solution of 1-(t-butoxycarbonyl)pyrrole-2-carbaldehyde (11.00 g) in tetrahydrofuran (100 ml) at −70° C., and the resulting mixture was stirred at the same temperature for 1 hour. After saturated aqueous ammonium chloride solution was added, the resulting reaction mixture was extracted with ethyl acetate. The extract was washed with saturated aqueous sodium chloride solution and the organic layer was dried over anhydrous magnesium sulfate. The solvent was removed in vacuo, and the residue was purified by chromatography on a silica gel column using a mixed solvent of ethyl acetate, hexane, and dichloromethane (1:3:1) as the eluent to afford the title compound (7.26 g, yield: 35%) as a yellow amorphous solid.

$^1$H NMR (400 MHz, CDCl$_3$) δ ppm: 2.67 (2H, bs), 2.74 (2H, t, J=5.5), 3.41 (2H, bs), 6.11 (1H, bs), 6.25 (1H, m), 6.94 (1H, m), 7.15-7.21 (3H, m), 7.25-7.32 (5H, m), 7.49 (1H, bs), 7.51-7.58 (7H, m).

(b) (E)-3-{[1-(Ethoxycarbonylmethyl)pyrrol-2yl]methylidene]-1-(triphenylmethyl)piperidin-4-one To a solution of (E)-3-[(pyrrol-2-yl)methylidene]-1-(triphenylmethyl)piperidin-4-one (7.16 g) and ethyl bromoacetate (8.60 g) in N,N-dimethylformamide (80 ml) were added potassium carbonate (7.10 g) and potassium iodide (8.50 g) with stirring at room temperature, and the resulting mixture was stirred at 80° C. for 4 hours. After filtration, the reaction mixture was diluted with dichloromethane, subsequently washed with saturated aqueous sodium chloride solution, and the organic layer was dried over anhydrous magnesium sulfate. The solvent was removed in vacuo, and the residue was purified by chromatography on a silica gel column using a mixed solvent of ethyl acetate, hexane, and dichloromethane (1:2:1) as the eluent to afford the title compound (7.13 g, yield: 83%) as a yellow amorphous solid.

$^1$H NMR (400 MHz, CDCl$_3$) δ ppm: 1.29 (3H, t, J=7.5), 2.66 (2H, bs), 2.72 (2H, t, J=5.0), 3.40 (2H, bs), 4.23 (2H, q, J=7.5), 4.76 (2H, s), 6.05 (1H, d, J=4.0), 6.20 (1H, t, J=3.0), 6.80 (1H, bs), 7.13-7.20 (3H, m), 7.24-7.32 (5H, m), 7.36 (1H, bs), 7.49-7.58 (7H, m).

(c) (E)-3-{[1-(Ethoxycarbonylmethyl)pyrrol-2-yl]methylidene}-1-(triphenylmethyl)piperidin-4-ol The title compound was synthesized in a yield of 83% as a yellow amorphous solid using (E)-3-{[1-(ethoxycarbonylmethyl)pyrrol-2-yl]methylidene}-1-(triphenylmethyl)piperidin-4-one instead of (E)-3-benzylidene-1-(triphenylmethyl)piperidin-4-one by conducting the reaction similar to that mentioned in Example 1 (b)

$^1$H NMR (400 MHz, CDCl$_3$) δ ppm: 1.30 (3H, t, J=7.5), 1.86 (1H, m), 2.03-2.16 (2H, m), 2.61-2.79 (2H, m), 3.64 (1H, bs), 4.15 (1H, m), 4.25 (2H, q, J=7.5), 4.68 (2H, s), 5.83 (1H, d, J=3.0), 6.01 (1H, t, J=3.0), 6.27 (1H, s), 6.64 (1H, t, J=2.0), 7.07-7.24 (9H, m), 7.35-7.43 (6H, m).

(d) (E)-4-(Acetylsulfanyl)-1-[2-cyclopropyl-1-(2-fluorophenyl)-2-oxoethyl]-3-{[1-(ethoxycarbonylmethyl)pyrrol-2-yl]methylidene}piperidine To a solution of (E)-3-{[1-(ethoxycarbonylmethyl)pyrrol-2-yl]methylidene}-1-(triphenylmethyl)piperidin-4-ol (5.64 g) in toluene (100 ml) were added thioacetic acid (1.64 ml) and N,N-dimethylformamide dineopentyl acetal (6.2 ml) at room temperature, and the resulting mixture was stirred at the same temperature for 15 minutes. After water was added to the reaction mixture, the resulting mixture was extracted with ethyl acetate. The extract was washed with saturated aqueous sodium chloride solution and the organic layer was dried over anhydrous magnesium sulfate. The solvent was removed in vacuo, and the residue was purified by chromatography on a silica gel column using a mixed solvent of ethyl acetate and hexane (1:3) as the eluent to afford the thioester derivative (including impurities) as a yellow amorphous solid.

Subsequently, to a solution of the mixture mentioned above in dichloromethane (200 ml) was added trifluoroacetic acid (2.0 ml) under ice-cooling, and the resulting mixture was stirred at the same temperature for 15 minutes. After sodium hydrogencarbonate was added to the reaction mixture, the insoluble products were filtrated off. The solvent was removed in vacuo, and the residue was purified by chromatography on a silica gel column using a mixed solvent of methanol and dichloromethane (1:5) as the eluent to afford the detriphenylmethyl derivative (including impurities).

Subsequently, to a solution of the mixture mentioned above and 2-bromo-2-(2-fluorophenyl)-1-cyclopropylethanone (3.26 g) in N,N-dimethylformamide (50 ml) was added triethylamine (1.8 ml) under ice-cooling, and the resulting mixture was stirred at room temperature for 2 hours. After water was added to the reaction mixture, the resulting mixture was extracted with ethyl acetate. The extract was washed with saturated aqueous sodium chloride solution and the organic layer was dried over anhydrous magnesium sulfate. The solvent was removed in vacuo, and the residue was purified by chromatography on a silica gel column using a mixed solvent of ethyl acetate, hexane, and dichloromethane (1:3:1) as the eluent. The yellow amorphous solid thus obtained was dissolved in methanol (30 ml), and the resulting mixture was stirred at 50° C. for 1 day. The reaction mixture was concentrated in vacuo to afford the title compound (1.41 g, yield: quantitative) as a yellow amorphous solid.

$^1$H NMR (400 MHz, CDCl$_3$) δ ppm: 0.65-0.83 (2H, m), 0.87-1.04 (2H, m), 1.27 and 1.29 (total 3H, each t, J=7.5), 1.80-1.90 (1H, m), 2.18-2.27 (2H, m), 2.28 (3H, s), 2.38 and 2.61 (total 1H, each dt, J=11.0, 2.0), 2.75-2.83 (1H, m), 3.04 and 3.06 (total 1H, each d, J=13.0), 3.72 and 3.93 (total 1H, each d, J=13.0), 4.20 and 4.22 (total 2H, each q, J=7.5), 4.45 and 4.49 (total 1H, each t, J=4.0), 4.56 and 4.58 (total 2H, each s), 4.65 and 4.69 (total 1H, each s), 5.91 and 6.02 (total 1H, each d, J=3.5), 6.06 and 6.13 (total 1H, each t, J=3.5), 6.26 and 6.27 (total 1H, each s), 6.59 and 6.62 (total 1H, each t, J=1.5), 7.04-7.19 (2H, m), 7.26-7.42 (2H, m);

IR (Thin film, cm$^{-1}$): 1753, 1692, 1487, 1476.

Example 88

(E)-1-[2-Cyclopropyl-1-(2-fluorophenyl)-2-oxoethyl]-3-{[1-(ethoxycarbonylmethyl)pyrrol-2-yl]methylidene}-4-sulfanylpiperidine (Exemplification Compound No. 2-545)

To a solution of (E)-4-(acetylsulfanyl)-1-[2-cyclopropyl-1-(2-fluorophenyl)-2-oxoethyl]-3-{[1-(ethoxycarbonylmethyl)pyrrol-2-yl]methylidene}piperidine (1.41 g) in ethanol (30 ml) was added potassium carbonate (4.00 g) under ice-cooling, and the resulting mixture was stirred at room temperature for 2 hours. After filtration, water was added to the filtrate, and the resulting mixture was extracted with ethyl acetate. The extract was washed with saturated aqueous sodium chloride solution, and the organic layer was dried over anhydrous magnesium sulfate. The solvent was removed in vacuo, and the residue was purified by a preparative HPLC (YMC-Pack ODS-A; YMC, mobile phase: 80% acetonitrile/water) to afford the title compound (0.49 g, yield: 38%) as a colourless amorphous solid.

$^1$H NMR (400 MHz, CDCl$_3$) δ ppm: 0.65-0.83 (2H, m), 0.85-1.03 (2H, m), 1.27 and 1.28 (total 3H, each t, J=7.5), 1.73-1.82 (1H, m), 2.12-2.21 (1H, m), 2.21-2.35 (1H, m), 2.63-2.82 (1H, m), 2.75 and 2.97 (total 1H, each m), 3.53 and 3.55 (total 1H, each d, J=13.0), 3.62 and 3.68 (total 1H, each d, J=13.0), 3.88 and 3.93 (total 1H, each m), 4.21 and 4.22 (total 2H, each q, J=7.5), 4.58 and 4.59 (total 2H, each s), 4.75 and 4.79 (total 1H, each s), 5.94 and 6.00 (total 1H, each d, J=3.5), 6.09 and 6.12 (total 1H, each t, J=3.5), 6.24 and 6.27 (total 1H, each s), 6.59-6.64 (1H, m), 7.04-7.18 (2H, m), 7.27-7.34 (1H, m), 7.37-7.44 (1H, m);

IR (Thin film, cm$^{-1}$): 1752, 1700.

Example 89

(E)-4-(Acetylsulfanyl)-1-[2-cyclopropyl-1-(2-fluorophenyl)-2-oxoethyl]-3-{[1-(ethoxycarbonylmethyl)pyrrol-3-yl]methylidene}piperidine (Exemplification Compound No. 2-674)

(a) (E)-3-{[1-(Ethoxycarbonylmethyl)pyrrol-3-yl]methylidene}-1-(triphenylmethyl)piperidin-4-one The title compound was synthesized in a yield of 26% as a yellow amorphous solid using 1-(ethoxycarbonylmethyl)pyrrole-3-carbaldehyde instead of benzaldehyde by conducting the reaction similar to that mentioned in Example 1 (a).

$^1$H NMR (400 MHz, CDCl$_3$) δ ppm: 1.26 (3H, t, J=7.5), 2.64 (2H, bs), 2.71 (2H, t, J=5.0), 3.39 (2H, bs), 4.20 (2H, q, J=7.5), 4.54 (2H, s), 6.04 (1H, t, J=2.5), 6.57 (1H, t, J=2.5), 6.73 (1H, t, J=1.5), 7.13-7.20 (3H, m), 7.24-7.31 (5H, m), 7.48 (1H, t, J=1.5), 7.51-7.56 (7H, m).

(b) (E)-3-{[1-(Ethoxycarbonylmethyl)pyrrol-3-yl]methylidene}-1-(triphenylmethyl)piperidin-4-ol The title compound was synthesized in a quantitative yield as a pale yellow amorphous solid using (E)-3-{[1-(ethoxycarbonylmethyl)pyrrol-3-yl]methylidene}-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (400 MHz, CDCl$_3$) δ ppm: 1.28 (3H, t, J=7.5), 2.07-2.18 (1H, m), 2.26 (1H, m), 2.54 (1H, m), 3.02 (1H, m), 3.29 (1H, m), 4.16 (1H, m), 4.22 (2H, q, J=7.5), 4.46 (2H, s), 6.02 (1H, dd, J=3.0, 2.0), 6.35 (1H, bs), 6.45 (1H, t, J=2.0), 6.51 (1H, t, J=3.0), 7.08-7.32 (7H, m), 7.42-7.56 (8H, m).

(c) (E)-4-(Acetylsulfanyl)-1-[2-cyclopropyl-1-(2-fluorophenyl)-2-oxoethyl]-3-{[1-(ethoxycarbonylmethyl)pyrrol-3-yl]methylidene}piperidine The title compound was synthesized in a yield of 38% as a pale yellow amorphous solid using (E)-3-{[1-(ethoxycarbonylmethyl)pyrrol-3-yl]methylidene}-1-(triphenylmethyl)piperidin-4-ol instead of (E)-3-{[1-(ethoxycarbonylmethyl)pyrrol-2-yl]methylidene)-1-(triphenylmethyl)piperidin-4-ol by conducting successively reactions similar to those mentioned in Example 87 (d).

$^1$H NMR (500 MHz, CDCl$_3$) δ ppm: 0.65-0.84 (2H, m), 0.87-1.04 (2H, m), 1.29 (3H, t, J=7.5), 1.81-1.92 (1H, m), 2.19-2.33 (2H, m), 2.29 (3H, s), 2.43 and 2.61 (total 1H, each m), 2.76 and 2.86 (total 1H, each m), 2.98 and 3.06 (total 1H, each d, J=13.0), 3.84 and 3.95 (total 1H, each d, J=13.0), 4.22 (2H, q, J=7.5), 4.49 and 4.54 (total 2H, each s), 4.51 and 4.54 (total 1H, each m), 4.68 and 4.75 (total 1H, each s), 5.98 and 6.10 (total 1H, each s), 6.40 and 6.42 (total 1H, each s), 6.46 and 6.51 (total 1H, each s), 6.56 and 6.57 (total 1H, each s), 7.04-7.19 (2H, m), 7.27-7.35 (1H, m), 7.45-7.51 (1H, m);

IR (Liquid film, cm$^-$): 1754, 1692, 1488.

Example 90

(E)-1-[2-Cyclopropyl-1-(2-fluorophenyl)-2-oxoethyl]-3-{[1-(methoxycarbonylmethyl)pyrrol-3-yl]methylidene}-4-sulfanylpiperidine (Exemplification Compound No. 2-657)

The title compound was synthesized in a yield of 69% as a pale yellow amorphous solid using (E)-4-(acetylsulfanyl)-1-[2-cyclopropyl-1-(2-fluorophenyl)-2-oxoethyl]-3-{[1-(ethoxycarbonylmethyl)pyrrol-3-yl]methylidene}piperidine instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (500 MHz, CDCl$_3$) δ ppm: 0.64-0.83 (2H, m), 0.86-1.03 (2H, m), 1.71-1.80 (1H, m), 2.18-2.33 (2H, m), 2.58-2.76 (1H, m), 2.70 and 2.84 (total 1H, each m), 3.39 and 3.45 (total 1H, each d, J=13.0), 3.58 and 3.70 (total 1H, each d, J=13.0), 3.76 (3H, s), 3.91-3.98 (1H, m), 4.51 and 4.56 (total 2H, each s), 4.62 and 4.72 (total 1H, each s), 5.99 and 6.09 (total 1H, each s), 6.31 and 6.34 (total 1H, each s), 6.44 and 6.51 (total 1H, each s), 6.56 (1H, s), 7.04-7.17 (2H, m), 7.26-7.33 (1H, m), 7.43-7.50 (1H, m);

IR (Liquid film, cm$^-$): 1756, 1698, 1488.

Example 91

(E)-4-(Acetylsulfanyl)-1-[2-cyclopropyl-1-(2-fluorophenyl)-2-oxoethyl]-3-{[1-(ethoxycarbonylmethyl)-1H-imidazol-4-yl]methylidene}piperidine (Exemplification Compound No. 2-930)

(a) (E)-3-{[1-(Ethoxycarbonylmethyl)-1H-imidazol-4-yl]methylidene}-1-(triphenylmethyl)piperidin-4-one The title compound was synthesized in a yield of 35% as a yellow amorphous solid using 1-(ethoxycarbonylmethyl)-1H-imidazole-4-carbaldehyde instead of benzaldehyde by conducting the reaction similar to that mentioned in Example 1 (a).

$^1$H NMR (400 MHz, CDCl$_3$) δ ppm: 1.27 (3H, t, J=7.0), 2.64 (2H, bs), 2.73 (2H, t, J=5.0), 3.64 (2H, bs), 4.23 (2H, q, J=7.0), 4.61 (2H, s), 6.90 (1H, s), 7.13-7.29 (9H, m), 7.39 (1H, s), 7.43 (1H, s), 7.51-7.56 (6H, m).

(b) (E)-3-{[1-(Ethoxycarbonylmethyl)-1H-imidazol-4-yl]methylidene}-1-(triphenylmethyl)piperidin-4-ol The title compound was synthesized in a yield of 93% as a yellow amorphous solid using (E)-3-{[1-(ethoxycarbonylmethyl)-1H-imidazol-4-yl]methylidene}-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (500 MHz, CDCl$_3$) δ ppm: 1.31 (3H, t, J=7.0), 1.84-1.92 (1H, m), 2.08-2.21 (2H, m), 2.59-2.70 (1H, m), 2.78-3.02 (1H, m), 3.58-3.81 (1H, m), 4.13-4.18 (1H, m), 4.25 (2H, q, J=7.0), 4.53 (2H, s), 6.46 (1H, s), 6.64 (1H, s), 7.08-7.20 (9H, m), 7.34 (1H, s), 7.40-7.48 (6H, m).

(c) (E)-4-(Acetylsulfanyl)-3-{[1-(ethoxycarbonylmethyl)-1H-imidazol-4-yl]methylidene}piperidine hydrogen trifluoroacetate The title compound was synthesized in a yield of 17% as a white solid using (E)-3-{[1-(ethoxycarbonylmethyl)-1H-imidazol-4-yl]methylidene}-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c).

$^1$H NMR (400 MHz, CDCl$_3$) δ ppm: 1.31 (3H, t, J=7.5), 2.10-2.19 (1H, m), 2.39 (3H, s), 2.44-2.54 (1H, m), 3.25-3.36 (1H, m), 3.44-3.53 (1H, m), 3.82-3.91 (1H, m), 4.05-4.13 (1H, m), 4.28 (2H, q, J=7.5), 4.57 (1H, t, J=4.0), 4.95 (2H, s), 6.69 (1H, s), 7.28 (1H, s), 8.75 (1H, s).

(d) (E)-4-(Acetylsulfanyl)-1-[2-cyclopropyl-1-(2-fluorophenyl)-2-oxoethyl]-3-{[1-(ethoxycarbonylmethyl)-1H-imidazol-4-yl]methylidene}piperidine The title compound was synthesized in a yield of 59% as a pale yellow oil using (E)-4-(acetylsulfanyl)-3-{[1-(ethoxycarbonylmethyl)-1H-imidazol-4-yl]methylidene}piperidine hydrogen trifluoroacetate instead of (E)-4-(acetylsulfanyl)-3-benzylidenepiperidine by conducting the reaction similar to that mentioned in Example 1 (d).

$^1$H NMR (500 MHz, CDCl$_3$) δ ppm: 0.66-0.82 (2H, m), 0.87-1.05 (2H, m), 1.30 (3H, t, J=7.0), 1.82-1.90 (1H, m), 2.22-2.35 (2H, m), 2.29 (3H, s), 2.39-2.67 (1H, m), 2.73-2.82 (1H, m), 3.18 (1H, d, J=12.5), 4.23 and 4.39 (total 1H, each d, J=12.5), 4.25 (2H, q, J=7.0), 4.47-4.51 (1H, m), 4.58 and 4.61 (total 2H, each s), 4.68 and 4.74 (total 1H, each s), 6.43 (1H, s), 6.74 and 6.83 (total 1H, each s), 7.03-7.16 (2H, m), 7.26-7.31 (1H, m), 7.34 and 7.39 (total 1H, each s), 7.43-7.50 (1H, m);

MS (FAB) m/z: 500 (M+H)$^+$.

Example 92

(E)-1-[2-Cyclopropyl-1-(2-fluorophenyl)-2-oxoethyl]-3-{[1-(ethoxycarbonylmethyl)-1H-imidazol-4-yl]methylidene}-4-sulfanylpiperidine hydrochloride (Exemplification Compound No. 2-929)

The title compound was synthesized in a yield of 84% as a pale yellow solid using (E)-4-(acetylsulfanyl)-1-[2-cyclopropyl-1-(2-fluorophenyl)-2-oxoethyl]-3-{[1-(ethoxycarbonylmethyl)-1H-imidazol-4-yl]methylidene}piperidine instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (400 MHz, CDCl$_3$) δ ppm: 0.65-0.82 (2H, m), 0.84-1.03 (2H, m), 1.30 (3H, t, J=7.0), 1.71-1.82 (1H, m), 2.19-2.34 (2H, m), 2.58-2.92 (2H, m), 3.61-3.67 (1H, m), 3.77-3.98 (2H, m), 4.25 (2H, q, J=7.0), 4.58 and 4.62 (total 2H, each s), 4.73 and 4.76 (total 1H, each s), 6.40 and 6.41 (total 1H, each s), 6.72 and 6.84 (total 1H, each s), 7.03-7.16 (2H, m), 7.27-7.33 (1H, m), 7.37 and 7.40 (total 1H, each s), 7.43-7.49 (1H, m).

Example 93

(E)-3-{[1-(Carboxymethyl)-1H-imidazol-4-yl]methylidene}-1-[2-cyclopropyl-1-(2-fluorophenyl)-2-oxoethyl]-4-sulfanylpiperidine hydrochloride (Exemplification Compound No. 2-897)

To a solution of (E)-1-[2-cyclopropyl-1-(2-fluorophenyl)-2-oxoethyl]-3-{[1-(ethoxycarbonylmethyl)-1H-imidazol-4-yl]methylidene}-4-sulfanylpiperidine hydrochloride (72.6 mg) in a mixed solvent of tetrahydrofuran (2 ml) and water (1 ml) was added 1N aqueous sodium hydroxide solution (0.55 ml) with stirring under ice-cooling, and the resulting mixture was stirred at the same temperature for 3 minutes. To the reaction mixture was added 1N hydrochloric acid solution (1.00 ml). The reaction mixture was concentrated in vacuo, and the residue was purified by chromatography on a silica gel column using a mixed solvent of methanol and dichloromethane (1:4) as the eluent to afford the title compound (55.4 mg, yield: 80%) as a pale yellow solid.

$^1$H NMR (400 MHz, DMSO-d$_6$) δ ppm: 0.81-1.11 (4H, m), 1.82-1.98 (3H, m), 2.27-2.57 (2H, m), 4.02-4.47 (3H, m), 4.93-5.13 (3H, m), 5.77-6.01 (1H, m), 6.63 and 6.66 (total 1H, each s), 7.31-7.66 (5H, m);

IR (KBr, cm$^-$): 2601, 1711, 1494.

Example 94

(E)-4-(Acetylsulfanyl)-1-[2-cyclopropyl-1-(2,4-difluorophenyl)-2-oxoethyl]-3-{[1H-imidazol-4(5)-yl]methylidene}piperidine dihydrochloride (Exemplification Compound No. 1-48)

(a) 2-(2,4-Difluorophenyl)-1-cyclopropylethanone

Magnesium (142 mg) was suspended in diethyl ether (10 ml) under an atmosphere of nitrogen and to the suspension was added dropwise a solution of 4-difluorobenzyl bromide (1000 mg) in diethyl ether (10 ml) with stirring at room temperature. The resulting mixture was stirred at the same temperature for 1 hour. To a solution of cyclopropyl cyanide (0.36 ml) in diethyl ether (10 ml) was added dropwise the diethyl ether solution obtained before, and the resulting mixture was stirred at room temperature overnight. To the reaction mixture was added aqueous ammonium chloride solution, the resulting mixture was extracted with ethyl acetate. The extract was washed with saturated aqueous sodium chloride solution, and the organic layer was dried over anhydrous sodium sulfate. The solvent was removed in vacuo, and the residue was purified by chromatography on a silica gel column using a mixed solvent of ethyl acetate and hexane (1:25) as the eluent to afford the title compound (357 mg, yield: 38%) as a colourless oil.

$^1$H NMR (400 MHz, CDCl$_3$) δ ppm: 0.87-0.93 (2H, m), 1.03-1.10 (2H, m), 1.94-2.02 (1H, m), 3.84 (2H, s), 6.80-6.89 (2H, m), 7.13-7.20 (1H, m).

(b) 2-Bromo-2-(2,4-difluorophenyl)-1-cyclopropylethanone

To a solution of 2-(2,4-difluorophenyl)-1-cyclopropylethanone (329 mg) in carbon tetrachloride (10 ml) was added N-bromosuccinimide (360 mg) and 75% benzoyl peroxide with stirring at room temperature, and the resulting mixture was refluxed for 3.5 hours. After the reaction mixture was filtered, 1N aqueous sodium hydroxide solution was added to the filtrate. The resulting mixture was extracted with ethyl acetate, and the extract was washed with saturated sodium chloride solution. The organic layer was dried over anhydrous sodium sulfate, and the solvent was removed in vacuo to afford the title compound (390 mg, yield: 84%) as a yellow oil.

$^1$H NMR (400 MHz, CDCl$_3$) δ ppm: 0.93-1.29 (4H, m), 2.12-2.20 (1H, m), 5.89 (1H, s), 6.80-6.97 (2H, m), 7.47-7.56 (1H, m).

(c) (E)-4-(Acetylsulfanyl)-1-[2-cyclopropyl-1-(2,4-difluorophenyl)-2-oxoethyl]-3-{[1H-imidazol-4(5)-yl]methylidene}piperidine dihydrochloride The title compound was synthesized in a yield of 83% as a pale yellow solid using 2-bromo-2-(2,4-difluorophenyl)-1-cyclopropylethanone instead of 2-bromo-2-(2-fluorophenyl)-1-cyclopropylethanone by conducting successively reactions similar to those mentioned in Example 21 (d).

$^1$H NMR (400 MHz, CDCl$_3$) δ ppm: 0.75-0.95 (2H, m), 1.01-1.12 (2H, m), 1.80-2.34 (4H, m), 2.29 and 2.33 (total 3H, each s), 2.40-2.84 (2H, m), 2.77 and 3.15 (total 1H, each d, J=12.5), 4.33-4.46 (1H, m), 4.77 and 4.88 (total 1H, each s), 6.46 (1H, s), 6.85-7.03 (3H, m), 7.19-7.37 (1H, m), 7.65 (1H, s);

IR (KBr, cm$^{-1}$): 1703, 1506.

Example 95

(E)-1-[2-Cyclopropyl-1-(2,4-difluorophenyl)-2-oxoethyl]-3-{[1H-imidazol-4(5)-yl]methylidene}-4-sulfanylpiperidine dihydrochloride (Exemplification Compound No. 1-47)

The title compound was synthesized in a yield of 81% as a pale yellow solid using (E)-4-(acetylsulfanyl)-1-[2-cyclopropyl-1-(2,4-difluorophenyl)-2-oxoethyl]-3-{[1H-imidazol-4(5)-yl]methylidene}piperidine dihydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (400 MHz, CDCl$_3$) δ ppm: 0.77-0.96 (2H, m), 1.02-1.14 (2H, m), 1.71-1.83 (1H, m), 1.88-2.01 (1H, m), 2.14-2.32 (1H, m), 2.44-2.62 (1H, m), 2.70-2.80 (1H, m), 3.17-3.70 (2H, m), 3.73-3.89 (1H, m), 4.85 and 4.86 (total 1H, each s), 6.47 and 6.49 (total 1H, each s), 6.87-7.09 (3H, m), 7.23-7.33 (1H, m), 7.64-7.73 (1H, s);

IR (KBr, cm$^{-1}$): 2599, 1709, 1506.

Example 96

(E)-4-(Acetylsulfanyl)-1-[2-cyclopropyl-1-(2,5-difluorophenyl)-2-oxoethyl]-3-{[1H-imidazol-4(5)-yl]methylidene}piperidine dihydrochloride (Exemplification Compound No. 1-182)

(a) 2-(2,5-Difluorophenyl)-1-cyclopropylethanone

The title compound was synthesized in a yield of 35% as a pale yellow oil using 2,5-difluorobenzyl bromide instead of 2,4-difluorobenzyl bromide by conducting successively reactions similar to those mentioned in Example 94 (a).

$^1$H NMR (400 MHz, CDCl$_3$) δ ppm: 0.88-0.95 (2H, m), 1.06-1.12 (2H, m), 1.96-2.03 (1H, m), 3.86 (2H, s), 6.89-7.06 (3H, m).

(b) 2-Bromo-2-(2,5-difluorophenyl)-1-cyclopropylethanone

The title compound was synthesized in a yield of 85% as a yellow oil using 2-(2,5-difluorophenyl)-1-cyclopropylethanone instead of 2-(2,4-difluorophenyl)-1-cyclopropylethanone by conducting the reaction similar to that mentioned in Example 94 (b).

$^1$H NMR (400 MHz, CDCl$_3$) δ ppm: 0.95-1.25 (4H, m), 2.14-2.21 (1H, m), 5.87 (1H, s), 7.01-7.08 (2H, m), 7.22-7.28 (1H, m).

(c) (E)-4-(Acetylsulfanyl)-1-[2-cyclopropyl-1-(2,5-difluorophenyl)-2-oxoethyl]-3-{[1H-imidazol-4(5)-yl]methylidene}piperidine dihydrochloride The title compound was synthesized in a yield of 74% as a pale yellow solid using 2-bromo-2-(2,5-difluorophenyl)-1-cyclopropylethanone instead of 2-bromo-2-(2-fluorophenyl)-1-cyclopropylethanone by conducting successively reactions similar to those mentioned in Example 21 (d).

$^1$H NMR (400 MHz, CDCl$_3$) δ ppm: 0.77-0.96 (2H, m), 1.02-1.13 (2H, m), 1.82-1.91 (1H, m), 1.95-2.08 (1H, m), 2.14-2.28 (1H, m), 2.30 and 2.33 (total 3H, each s), 2.40-2.58 (1H, m), 2.59-2.81 (1H, m), 2.89 and 3.15 (total 1H, each d, J=12.5), 3.65-3.92 (1H, m), 4.40 and 4.43 (total 1H, each t, J=4.5), 4.76 and 4.84 (total 1H, each s), 6.47 (1H, s), 6.96-7.16 (4H, m), 7.62-7.69 (1H, m);

IR (KBr, cm$^{-1}$): 1701, 1499.

Example 97

(E)-1-[2-Cyclopropyl-1-(2,5-difluorophenyl)-2-oxoethyl]-3-{[1H-imidazol-4(5)-yl]methylidene}-4-sulfanylpiperidine dihydrochloride (Exemplification Compound No. 1-181)

The title compound was synthesized in a yield of 70% as a colourless solid using (E)-4-(acetylsulfanyl)-1-[2-cyclopropyl-1-(2,5-difluorophenyl)-2-oxoethyl]-3-{[1H-imidazol-4(5)-yl]methylidene}piperidine dihydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (400 MHz, CDCl$_3$) δ ppm: 0.78-0.96 (2H, m), 1.04-1.11 (2H, m), 1.72-1.83 (1H, m), 1.94-2.06 (1H, m), 2.16-2.32 (1H, m), 2.47-2.62 (1H, m), 2.71-2.82 (1H, m), 3.23-3.67 (2H, m), 3.77-3.88 (1H, m), 4.84 (1H, s), 6.48 (1H, s), 6.97-7.20 (4H, m), 7.66 (1H, s);

IR (KBr, cm$^{-1}$): 2598, 1711, 1499.

Example 98

(E)-4-(Acetylsulfanyl)-1-[2-cyclopropyl-1-(2-fluorophenyl)-2-oxoethyl]-3-{[1-(methoxycarbonylmethyl)-1H-pyrazol-4-yl]methylidene}piperidine hydrochloride (Exemplification Compound No. 2-198)

(a) (E)-3-[(1H-Pyrazol-4-yl)methylidene]-1-(triphenylmethyl)piperidin-4-one

The title compound was synthesized in a quantitative yield as a yellow amorphous solid using (E)-3-{[1-(t-butoxycarbonyl)-1H-pyrazol-4-yl]methylidene}-1-(triphenylmethyl)piperidin-4-one instead of (E)-3-{[1-(t-butoxycarbonyl)-1H- pyrazol-3-yl]methylidene}-1-(triphenylmethyl)piperidin-4-one by conducting the reaction similar to that mentioned in Example 73 (a).

$^1$H NMR (400 MHz, CDCl$_3$) δ ppm: 2.69 (2H, bs), 2.75 (2H, t, J=6.0), 3.38 (2H, bs), 7.08-7.58 (18H, m).

(b) (E)-3-[(1H-Pyrazol-4-yl)methylidene}-1-(triphenylmethyl)piperidin-4-ol

The title compound was synthesized in a quantitative yield as a pale yellow amorphous solid using (E)-3-[(1H-pyrazol-4-yl)methylidene]-1-(triphenylmethyl)piperidin-4-one instead of (E)-3-benzylidene-1-(triphenylmethyl)piperidin-4-one by conducting the reaction similar to that mentioned in Example 1 (b)

$^1$H NMR (400 MHz, CDCl$_3$) δ ppm: 1.83-1.95 (1H, m), 2.08-2.21 (2H, m), 2.69 (2H, bs), 3.43 (1H, bs), 4.16 (1H, t, J=6.0), 6.41 (1H, s), 7.05-7.49 (17H, m).

(c) (E)-3-{[1-(Methoxycarbonylmethyl)-1H-pyrazol-4-yl]methylidene}-1-(triphenylmethyl)piperidin-4-ol To a solution of (E)-3-[(1H-pyrazol-4-yl)methylidene]-1-(triphenylmethyl)piperidin-4-ol (10.31 g) and methyl bromoacetate (7.0 ml) in N,N-dimethylformamide (150 ml) were added potassium carbonate (10.20 g) and potassium iodide (12.30 g) with stirring at room temperature, and the resulting mixture was refluxed for 1 hour. After water was added, the reaction mixture was extracted with ethyl acetate. The extract was washed with saturated aqueous sodium chloride solution, and the organic layer was dried over anhydrous magnesium sulfate. The solvent was removed in vacuo, and the residue was purified by chromatography on a silica gel column using a mixed solvent of ethyl acetate, hexane, and dichloromethane (2:1:1) as the eluent to afford the title compound (4.74 g, yield: 39%) as a pale yellow amorphous solid.

$^1$H NMR (400 MHz, CDCl$_3$) δ ppm: 1.62-1.94 (1H, m), 2.08-2.19 (2H, m), 2.61-2.78 (2H, bs), 3.41 (1H, bs), 3.77 (3H, s), 4.16 (1H, m), 4.76 (2H, d, J=4.0), 6.35 (1H, s), 7.08-7.51 (17H, m).

(d) (E)-4-(Acetylsulfanyl)-3-{[1-(methoxycarbonylmethyl)-1H-pyrazol-4-yl]methylidene}piperidine hydrogen trifluoroacetate The title compound was synthesized in a yield of 18% as a pale yellow amorphous solid using (E)-3-{[1-(methoxycarbonylmethyl)-1H-pyrazol-4-yl]methylidene}-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c)

$^1$H NMR (400 MHz, CDCl$_3$) δ ppm: 2.06 (1H, m), 2.37 (3H, s), 2.39-2.47 (1H, m), 3.21 (1H, bs), 3.38 (1H, d, J=13.5), 3.65-3.77 (1H, m), 4.25 (1H, d, J=13.5), 4.57 (1H, t, J=3.5), 4.90 (2H, s), 6.64 (1H, s), 7.50 (1H, s), 7.55 (1H, s).

(e) (E)-4-(Acetylsulfanyl)-1-[2-cyclopropyl-1-(2-fluorophenyl)-2-oxoethyl]-3-{[1-(methoxycarbonylmethyl)-1H-pyrazol-4-yl]methylidene}piperidine hydrochloride The title compound was synthesized in a yield of 43% as a pale yellow amorphous solid using (E)-4-(acetylsulfanyl)-3-{[1-(methoxycarbonylmethyl)-1H-pyrazol-4-yl]methylidene}piperidine hydrogen trifluoroacetate instead of (E)-4-(acetylsulfanyl)-3-benzylidenepiperidine hydrochloride by conducting the reaction similar to that mentioned in Example 1 (d).

$^1$H NMR (400 MHz, CDCl$_3$) δ ppm: 0.66-0.86 (2H, m), 0.89-1.05 (2H, m), 1.80-1.92 (1H, m), 2.12-2.35 (2H, m), 2.31 (3H, s), 2.46 and 2.55 (total 1H, each dd, J=11.0, 3.0), 2.72 and 2.85 (total 1H, each m), 2.92 and 3.08 (total 1H, each d, J=13.0), 3.64 and 3.70 (total 1H, each d, J=13.0), 3.78 (3H, s), 4.48 (1H, t, J=4.5), 4.70 and 4.72 (total 1H, each s), 4.81 and 4.86 (total 2H, each s), 6.35 and 6.38 (total 1H, each s), 7.05-7.19 (2H, m), 7.27 and 7.32 (total 1H, each s), 7.27-7.37 (1H, m), 7.40 and 7.42 (total 1H, each s), 7.41-7.45 (1H, m);

IR (KBr, cm$^{-1}$): 1753, 1695, 1493.

Example 99

(E)-1-[2-Cyclopropyl-1-(2-fluorophenyl)-2-oxoethyl]-3-{[1-(methoxycarbonylmethyl)-1H-pyrazol-4-yl]methylidene}-4-sulfanylpiperidine hydrochloride (Exemplification Compound No. 2-197)

The title compound was synthesized in a yield of 48% as a pale yellow amorphous solid using (E)-4-(acetylsulfanyl)-1-[2-cyclopropyl-1-(2-fluorophenyl)-2-oxoethyl]-3-{[1-(methoxycarbonylmethyl)-1H-pyrazol-4-yl]methylidene}piperidine hydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (500 MHz, CDCl$_3$) δ ppm: 0.66-0.86 (2H, m), 0.90-1.04 (2H, m), 1.73-1.82 (1H, m), 2.09-2.19 (1H, m), 2.19-2.34 (1H, m), 2.61 and 2.70 (total 1H, each m), 2.74-2.87 (1H, m), 3.36 and 3.42 (total 1H, each d, J=12.5), 3.44 and 3.48 (total 1H, each d, J=12.5), 3.78 (3H, s), 3.87-3.93 (1H, m), 4.74 and 4.76 (total 1H, each s), 4.82 and 4.86 (total 2H, each s), 6.31 and 6.33 (total 1H, each s), 7.05-7.19 (2H, m), 7.26 and 7.29 (total 1H, each s), 7.28-7.37 (1H, m), 7.39 and 7.42 (total 1H, each s), 7.38-7.46 (1H, m);

IR (KBr, cm$^{-1}$): 2524, 1748, 1710, 1493.

Example 100

(E)-3-{[1-(t-Butoxycarbonylmethyl)-1H-pyrazol-3-yl]methylidene}-1-[2-cyclopropyl-1-(2-fluorophenyl)-2-oxoethyl]-4-sulfanylpiperidine hydrochloride (Exemplification Compound No. 2-77)

The title compound was synthesized in a yield of 32% as a pale yellow amorphous solid using (E)-4-(acetylsulfanyl)-3-{[1-(t-butoxycarbonylmethyl)-1H-pyrazol-3-yl]methylidene}-1-[2-cyclopropyl-1-(2-fluorophenyl)-2-oxoethyl]piperidine instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (500 MHz, CDCl$_3$) δ ppm: 0.65-0.81 (2H, m), 0.86-1.02 (2H, m), 1.48 (9H, s), 1.75-1.83 (1H, m), 2.22-2.35 (2H, m), 2.60-2.79 and 2.83-2.89 (total 2H, each m), 3.54 and 3.66 (total 1H, each d, J=12.5), 3.83 (1H, m), 3.90-3.96 (1H, m), 4.68 and 4.72 (total 2H, each s), 4.70 and 4.72 (total 1H, each s), 6.13 and 6.22 (total 1H, each d, J=2.0), 6.45 and 6.47

(total 1H, each s), 7.04-7.15 (2H, m), 7.26-7.32 (1H, m), 7.33 and 7.37 (total 1H, each d, J=2.0), 7.41-7.47 (1H, m);
IR (KBr, cm$^{-1}$): 2474, 1745, 1714.

Example 101

(E)-4-(Acetylsulfanyl)-1-[2-cyclopropyl-1-(2-fluorophenyl)-2-oxoethyl]-3-{[1-(2-oxobutyl)-1H-pyrazol-3-yl]methylidene}piperidine hydrochloride (Exemplification Compound No. 2-134)

(a) (E)-3-{[1-(2-Oxobutyl)-1H-pyrazol-3-yl]methylidene}-1-(triphenylmethyl)piperidin-4-ol The title compound was synthesized in a yield of 76% as a brown amorphous solid using 1-bromo-2-butanone instead of 2-methoxyethyl bromide by conducting the reaction similar to that mentioned in Example 73 (c).
$^1$H NMR (500 MHz, CDCl$_3$) δ ppm: 1.03 (3H, t, J=7.0), 1.86-1.94 (1H, m), 2.11-2.18 (2H, m), 2.25-2.31 (2H, m), 2.67-2.70 (2H, m), 3.68-3.92 (1H, m), 4.11-4.19 (1H, m), 4.66 (2H, s), 6.15 (1H, d, J=2.0), 6.49 (1H, s), 7.06-7.22 (9H, m), 7.30 (1H, d, J=2.0), 7.37-7.46 (6H, m).

(b) (E)-4-(Acetylsulfanyl)-3-{[1-(2-oxobutyl)-1H-pyrazol-3-yl]methylidene}piperidine hydrogen trifluoroacetate The title compound was synthesized in a yield of 15% as a pale yellow solid using (E)-3-{[1-(2-oxobutyl)-1H-pyrazol-3-yl]methylidene}-1-(triphenylmethyl)piperidin-4-ol instead of (E)-3-{[1-(tert-butoxycarbonyl)-1H-imidazol-5-yl]methylidene}-1-(triphenylmethyl)piperidin-4-ol by conducting successively reactions similar to those mentioned in Example 21 (c).
$^1$H NMR (500 MHz, CDCl$_3$) δ ppm: 1.07 (3H, t, J=7.0), 2.03-2.11 (1H, m), 2.36 (3H, s), 2.43 (2H, q, J=7.0), 2.44-2.50 (1H, m), 3.15-3.24 (1H, m), 3.33-3.40 (1H, m), 3.78 (1H, d, J=14.5), 4.58 (1H, m), 4.89 and 4.90 (total 2H, each s), 5.04 (1H, d, J=14.5), 6.29 (1H, d, J=2.0), 6.64 (1H, s), 7.35 (1H, d, J=2.0).

(c) (E)-4-(Acetylsulfanyl)-1-[2-cyclopropyl-1-(2-fluorophenyl)-2-oxoethyl]-3-{[1-(2-oxobutyl)-1H-pyrazol-3-yl]methylidene}piperidine hydrochloride The title compound was synthesized in a yield of 62% as a yellow amorphous solid using (E)-4-(acetylsulfanyl)-3-{[1-(2-oxobutyl)-1H-pyrazol-3-yl]methylidene}piperidine hydrogen trifluoroacetate instead of (E)-4-(acetylsulfanyl)-3-benzylidenepiperidine hydrochloride by conducting the reaction similar to that mentioned in Example 1 (d).
$^1$H NMR (500 MHz, CDCl$_3$) δ ppm: 0.66-0.83 (2H, m), 0.87-1.01 (2H, m), 1.04 and 1.06 (total 3H, each t, J=7.0), 1.84-1.93 (1H, m), 2.19-2.27 (2H, m), 2.28-2.41 (2H, m), 2.30 (3H, s), 2.43-2.50 and 2.55-2.62 (total 1H, each m), 2.72-2.77 and 2.81-2.86 (total 1H, each m), 3.07 and 3.23 (total 1H, each d, J=13.0), 4.13 and 4.14 (total 1H, each d, J=13.0), 4.50 (1H, m), 4.69 and 4.70 (total 1H, each s), 4.73 and 4.81 (total 2H, each s), 6.15 and 6.24 (total 1H, each d, J=2.5), 6.47 and 6.49 (total 1H, each s), 7.05-7.16 (2H, m), 7.27-7.31 (1H, m), 7.28 and 7.32 (total 1H, each d, J=2.5), 7.40-7.44 (1H, m);
IR (KBr, cm$^{-1}$): 2514, 1708.

Example 102

(E)-1-[2-Cyclopropyl-1-(2-fluorophenyl)-2-oxoethyl]-3-{[1-(2-oxobutyl)-1H-pyrazol-3-yl]methylidene}-4-sulfanylpiperidine hydrochloride (Exemplification Compound No. 2-133)

The title compound was synthesized in a yield of 93% as a yellow amorphous solid using (E)-4-(acetylsulfanyl)-1-[2-cyclopropyl-1-(2-fluorophenyl)-2-oxoethyl]-3-{[1-(2-oxobutyl)-1H-pyrazol-3-yl]methylidene}piperidine hydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.
$^1$H NMR (500 MHz, CDCl$_3$) δ ppm: 0.66-0.82 (2H, m), 0.87-1.01 (2H, m), 1.05 and 1.06 (total 3H, each t, J=7.5), 1.76-1.84 (1H, m), 2.18-2.32 (2H, m), 2.35 and 2.38 (total 2H, each q, J=7.5), 2.60-2.66 and 2.67-2.73 (total 1H, each m), 2.73-2.80 and 2.83-2.89 (total 1H, each m), 3.54 and 3.66 (total 1H, each d, J=13.0), 3.83 and 3.84 (total 1H, each d, J=13.0), 3.91-3.96 (1H, m), 4.72 and 4.74 (total 1H, each s), 4.76 and 4.81 (total 2H, each s), 6.15 and 6.24 (total 1H, each d, J=2.0), 6.44 and 6.46 (total 1H, each s), 7.05-7.15 (2H, m), 7.26-7.32 (1H, m), 7.29 and 7.33 (total 1H, each d, J=2.0), 7.39-7.45 (1H, m);
IR (KBr, cm$^{-1}$): 2500, 1733, 1712.

Example 103

(E)-4-(Acetylsulfanyl)-1-[2-cyclopropyl-1-(2-fluorophenyl)-2-oxoethyl]-3-{[1-(N-methylcarbamoylmethyl)-1H-pyrazol-3-yl]methylidene}piperidine hydrochloride (Exemplification Compound No. 2-110)

The title compound was synthesized in a yield of 80% as a pale yellow amorphous solid using 40% aqueous methylamine solution instead of 28% aqueous ammonia solution by conducting the reaction similar to that mentioned in Example 84.
$^1$H NMR (500 MHz, CDCl$_3$) δ ppm: 0.68-0.99 (4H, m), 1.83-1.92 (1H, m), 2.06-2.14 (1H, m), 2.22-2.38 (1H, m), 2.31 and 2.32 (total 3H, each s), 2.42-2.49 and 2.55-2.62 (total 1H, each m), 2.68-2.74 and 2.81-2.88 (total 1H, each m), 2.78, 2.79, 2.80 and 2.81 (total 3H, each s), 3.11 and 3.22 (total 1H, each d, J=13.5), 4.23 and 4.32 (total 1H, each d, J=13.5), 4.50 (1H, m), 4.70 and 4.72 (total 1H, each s), 4.73 and 4.76 (total 2H, each s), 6.16 and 6.22 (total 1H, each d, J=2.0), 6.46 and 6.47 (total 1H, each s), 7.04-7.16 (2H, m), 7.24-7.41 (2H, m), 7.30 and 7.34 (total 1H, each d, J=2.0);
IR (KBr, cm$^{-1}$): 2548, 1691.

Example 104

(E)-1-[2-Cyclopropyl-1-(2-fluorophenyl)-2-oxoethyl]-3-{[1-(N-methylcarbamoylmethyl)-1H-pyrazol-3-yl]methylidene}-4-sulfanylpiperidine hydrochloride (Exemplification Compound No. 2-109)

The title compound was synthesized in a yield of 70% as a colourless amorphous solid using (E)-4-(acetylsulfanyl)-1-[2-cyclopropyl-1-(2-fluorophenyl)-2-oxoethyl]-3-{[1-(N-methylcarbamoylmethyl)-1H-pyrazol-3-yl]methylidene}piperidine hydrochloride instead of (E)-4-(acetylsulfanyl)-1-[2-cyclopropyl-1-(2-fluorophenyl)-2- oxoethyl]-3-[(furan-2-yl)methylidene]piperidine by conducting the reaction similar to that mentioned in Example 8.

¹H NMR (500 MHz, CDCl₃) δ ppm: 0.69-1.00 (4H, m), 1.77-1.84 (1H, m), 2.05-2.13 (1H, m), 2.23-2.37 (1H, m), 2.57-2.63 and 2.66-2.73 (total 1H, each m), 2.74-2.81 and 2.83-2.90 (total 1H, each m), 2.79, 2.80, 2.81 and 2.82 (total 3H, each s), 3.62 and 3.67 (total 1H, each d, J=13.0), 3.92 and 3.99 (total 1H, each d, J=13.0), 3.93 (1H, m), 4.71 and 4.72 (total 1H, each s), 4.79 and 4.85 (total 2H, each s), 6.16 and 6.22 (total 1H, each d, J=2.5), 6.43 and 6.44 (total 1H, each s), 7.05-7.16 (2H, m), 7.28-7.36 (1H, m), 7.32 and 7.35 (total 1H, each d, J=2.5), 7.36-7.41 (1H, m);

IR (KBr, cm⁻¹): 2539, 1711, 1675.

Example 105

(E)-4-(Acetylsulfanyl)-1-[2-cyclopropyl-1-(2-fluorophenyl)-2-oxoethyl]-3-{[1-(N,N-dimethylcarbamoylmethyl)-1H-pyrazol-3-yl]methylidene}piperidine hydrochloride (Exemplification Compound No. 2-118)

The title compound was synthesized in a yield of 78% as a pale yellow amorphous solid using 50% aqueous dimethylamine solution instead of 28% aqueous ammonia solution by conducting the reaction similar to that mentioned in Example 84.

¹H NMR (500 MHz, CDCl₃) δ ppm: 0.64-1.01 (4H, m), 1.83-1.91 (1H, m), 2.22-2.35 (2H, m), 2.30 (3H, s), 2.41-2.48 and 2.56-2.64 (total 1H, each m), 2.71-2.85 (1H, m), 2.97 and 2.98 (total 3H, each s), 3.04 and 3.08 (total 3H, each s), 3.10 and 3.20 (total 1H, each d, J=13.0), 4.12 and 4.16 (total 1H, each d, J=13.0), 4.48-4.52 (1H, m), 4.66 and 4.70 (total 1H, each s), 4.83 and 4.90 (total 2H, each s), 6.12 and 6.21 (total 1H, each d, J=2.0), 6.48 and 6.49 (total 1H, each s), 7.04-7.16 (2H, m), 7.24-7.32 (1H, m), 7.39 and 7.44 (total 1H, each d, J=2.0), 7.41-7.46 (1H, m);

IR (KBr, cm⁻¹): 2483, 1694, 1666.

Example 106

(E)-1-[2-Cyclopropyl-1-(2-fluorophenyl)-2-oxoethyl]-3-{[1-(N,N-dimethylcarbamoylmethyl)-1H-pyrazol-3-yl]methylidene}-4-sulfanylpiperidine hydrochloride (Exemplification Compound No. 2-117)

The title compound was synthesized in a yield of 70% as a colourless amorphous solid using (E)-4-(acetylsulfanyl)-1-[2-cyclopropyl-1-(2-fluorophenyl)-2-oxoethyl]-3-{[1-(N,N-dimethylcarbamoylmethyl)-1H-pyrazol-3-yl] methylidene}piperidine hydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

¹H NMR (500 MHz, CDCl₃) δ ppm: 0.65-1.00 (4H, m), 1.75-1.83 (1H, m), 2.21-2.35 (2H, m), 2.60-2.70 (1H, m), 2.71-2.78 and 2.83-2.90 (total 1H, each m), 2.98 and 2.99 (total 3H, each s), 3.05 and 3.08 (total 3H, each s), 3.55 and 3.63 (total 1H, each d, J=13.0), 3.83 and 3.87 (total 1H, each d, J=13.0), 3.94 (1H, m), 4.71 and 4.73 (total 1H, each s), 4.85 and 4.90 (total 2H, each s), 6.12 and 6.21 (total 1H, each d, J=2.5), 6.44 and 6.45 (total 1H, each s), 7.04-7.15 (2H, m), 7.24-7.32 (1H, m), 7.40 and 7.44 (total 1H, each d, J=2.5), 7.41-7.46 (1H, m);

IR (KBr, cm⁻¹): 2447, 1713, 1663.

Example 107

(E)-1-[2-Cyclopropyl-1-(2-fluorophenyl)-2-oxoethyl]-3-{[1-(ethoxycarbonylmethyl)-1H-pyrazol-5-yl] methylidene]-4-sulfanylpiperidine hydrochloride (Exemplification Compound No. 2-381)

(a) (E)-4-(Acetylsulfanyl)-3-{[1-(ethoxycarbonylmethyl)-1H-pyrazol-5-yl]methylidene}piperidine hydrogen trifluoroacetate (Compound A), and (E)-4-(Acetylsulfanyl)-3-({1-[1,2-bis(ethoxycarbonyl) ethyl]-1H-pyrazol-3-yl}methylidene)piperidine hydrogen trifluoroacetate (Compound B)

The title Compound A (yield: 14%) and Compound B (yield: 13%) were obtained as a colourless amorphous solid, respectively, using a mixture of (E)-3-{[1-(ethoxycarbonylmethyl)-1H-pyrazol-5-yl]methylidene}-1-(triphenylmethyl) piperidin-4-ol and (E)-3-({1-[1,2-bis(ethoxycarbonyl)ethyl]-1H-pyrazol-3-yl}methylidene)-1-(triphenylmethyl) piperidin-4-ol that were obtained in Example 79<Another Synthesis Method> (a), instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c).

Compound A

¹H NMR (500 MHz, CDCl₃) δ ppm: 1.29 (3H, t, J=7.0), 2.04-2.11 (1H, m), 2.38 (3H, s), 2.41-2.51 (1H, m), 3.11-3.20 (1H, m), 3.28-3.35 (1H, m), 3.70 (1H, d, J=14.5), 4.14 (1H, d, J=14.5), 4.22 (2H, q, J=7.0), 4.57 (1H, m), 4.85 (2H, s), 6.19 (1H, d, J=1.5), 6.62 (1H, s), 7.49 (1H, d, J=1.5).

Compound B

¹H NMR (500 MHz, CDCl₃) δ ppm: 1.17-1.26 (6H, m), 2.05-2.13 (1H, m), 2.36 (3H, s), 2.40-2.46 (1H, m), 3.12-3.30 (3H, m), 3.38-3.46 (1H, m), 3.76-3.85 (1H, m), 4.06-4.25 (4H, m), 4.58 (1H, m), 4.97-5.07 (1H, m), 5.26-5.34 (1H, m), 6.24 (1H, d, J=2.0), 6.63 (1H, s), 7.48 (1H, d, J=2.0).

(b) (E)-1-[2-Cyclopropyl-1-(2-fluorophenyl)-2-oxoethyl]-3-{[1-(ethoxycarbonylmethyl)-1H-pyrazol-5-yl]methylidene}-4-sulfanylpiperidine hydrochloride A mixture of the title compound and (E)-4-(acetylsulfanyl)-1-[2-cyclopropyl-1-(2-fluorophenyl)-2-oxoethyl]-3-{[1-(ethoxycarbonylmethyl)-1H-pyrazol-5-yl] methylidene}piperidine were obtained as a colourless amorphous solid using (E)-4-(acetylsulfanyl)-3-{[1-(ethoxycarbonylmethyl)-1H-pyrazol-5-yl]methylidene}piperidine hydrogen trifluoroacetate instead of (E)-4-(acetylsulfanyl)-3-benzylidenepiperidine hydrochloride by conducting the reaction similar to that mentioned in Example 1 (d)

The title compound was synthesized in a yield of 30% as a colourless amorphous solid using a mixture of compounds mentioned above instead of (E)-4-(acetylsulfanyl)-3-benzylidene-1-[2-cyclopropyl-1-(2-fluorophenyl)-2-oxoethyl] piperidine by conducting the reaction similar to that mentioned in Example 2.

¹H NMR (500 MHz, CDCl₃) δ ppm: 0.67-0.83 (2H, m), 0.89-1.01 (2H, m), 1.27 and 1.28 (total 3H, each t, J=7.0), 1.76-1.84 (1H, m), 2.06-2.13 (1H, m), 2.22-2.32 (1H, m), 2.60-2.68 (1H, m), 2.76-2.82 and 2.85-2.92 (total 1H, each m), 3.28 and 3.34 (total 1H, each d, J=13.0), 3.48 and 3.52 (total 1H, each d, J=13.0), 3.79-3.88 (1H, m), 4.22 and 4.23 (total 2H, each q, J=7.0), 4.71 and 4.72 (total 1H, each s), 4.85 and 4.87 (total 2H, each s), 6.04 and 6.09 (total 1H, each d, J=1.5), 6.28 and 6.29 (total 1H, each s), 7.04-7.16 (2H, m), 7.26-7.37 (2H, m), 7.41 and 7.43 (total 1H, each d, J=1.5);
IR (KBr, cm$^{-1}$): 2448, 1747, 1713.

Example 108

(E)-3-{[1-(Carboxymethyl)-1H-pyrazol-5-yl]methylidene}-1-[2-cyclopropyl-1-(2-fluorophenyl)-2-oxoethyl]-4-sulfanylpiperidine hydrochloride (Exemplification Compound No. 2-349)

To a solution of (E)-1-[2-cyclopropyl-1-(2-fluorophenyl)-2-oxoethyl]-3-{[1-(ethoxycarbonylmethyl)-1H-pyrazol-5-yl]methylidene}-4-sulfanylpiperidine hydrochloride (70 mg) in 3N aqueous hydrochloric acid solution (15 ml), and the resulting mixture was stirred at 50° C. for 2.5 hours. The reaction mixture was concentrated in vacuo, and the residue was purified by a preparative HPLC [YMC-Pack ODS-A; YMC, mobile phase: 25 to 27% acetonitrile/water (0.02% aqueous hydrochloric acid solution)] to afford the title compound (50 mg, yield: 75%) as a pale yellow amorphous solid.
$^1$H NMR (400 MHz, pyridine-d$_5$) δ ppm: 0.67-0.80 (2H, m), 0.93-1.12 (2H, m), 1.77-1.90 (1H, m), 2.20-2.34 (1H, m), 2.39-2.48 (1H, m), 2.63-2.78 (1H, m), 2.84-2.93 and 2.94-3.04 (total 1H, each m), 3.66-3.74 and 3.79-3.90 (total 2H, each m), 3.95-4.07 (1H, m), 4.95 and 4.96 (total 1H, each s), 5.37 and 5.38 (total 2H, each s), 6.38 and 6.44 (total 1H, each d, J=1.5), 6.86 and 6.90 (total 1H, each s), 7.14-7.25 (2H, m), 7.28-7.36 (1H, m), 7.60-7.70 (1H, m), 7.72 and 7.74 (total 1H, each d, J=1.5);
IR (KBr, cm$^{-1}$): 2559, 1739, 1711.

Example 109

(E)-4-(Acetylsulfanyl)-1-[2-cyclopropyl-1-(2-fluorophenyl)-2-oxoethyl]-3-({1-[1,2-bis(ethoxycarbonyl)ethyl]-1H-pyrazol-3-yl}methylidene)piperidine hydrochloride (Exemplification Compound No. 2-142)

The title compound was synthesized in a yield of 33% as a pale yellow amorphous solid using (E)-4-(acetylsulfanyl)-3-({1-[1,2-bis(ethoxycarbonyl)ethyl]-1H-pyrazol-3-yl}methylidene)piperidine hydrogen trifluoroacetate obtained in Example 107 (a) instead of (E)-4-(acetylsulfanyl)-3-benzylidenepiperidine hydrochloride by conducting the reaction similar to that mentioned in Example 1 (d)
$^1$H NMR (500 MHz, CDCl$_3$) δ ppm: 0.65-0.82 (2H, m), 0.85-1.03 (2H, m), 1.21-1.27 (6H, m), 1.83-1.92 (1H, m), 2.20-2.28 (2H, m), 2.30 (3H, s), 2.39-2.50 and 2.56-2.64 (total 1H, each m), 2.72-2.84 (1H, m), 3.00-3.33 (3H, m), 4.00-4.26 (5H, m), 4.47-4.52 (1H, m), 4.68-4.72 (1H, m), 5.19-5.24 and 5.26-5.31 (total 1H, each m), 6.08 and 6.16 (total 1H, each d, J=2.5), 6.46 and 6.48 (total 1H, each s), 7.04-7.17 (2H, m), 7.26-7.33 (1H, m), 7.37-7.45 (2H, m);
IR (KBr, cm$^{-1}$): 2505, 1737, 1696.

Example 110

(E)-1-[2-Cyclopropyl-1-(2-fluorophenyl)-2-oxoethyl]-3-({1-[1,2-bis(ethoxycarbonyl)ethyl]-1H-pyrazol-3-yl}methylidene)-4-sulfanylpiperidine hydrochloride (Exemplification Compound No. 2-141)

The title compound was synthesized in a yield of 56% as a colourless amorphous solid using (E)-4-(acetylsulfanyl)-1-[2-cyclopropyl-1-(2-fluorophenyl)-2-oxoethyl]-3-({1-[1,2-bis(ethoxycarbonyl)ethyl]-1H-pyrazol-3-yl}methylidene)piperidine hydrochloride instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.
$^1$H NMR (500 MHz, CDCl$_3$) δ ppm: 0.65-0.82 (2H, m), 0.86-1.04 (2H, m), 1.22-1.28 (6H, m), 1.75-1.84 (1H, m), 2.17-2.35 (2H, m), 2.61-2.77 and 2.83-2.89 (total 2H, each m), 3.00-3.32 (2H, m), 3.45-3.66 (1H, m), 3.72-3.98 (2H, m), 4.09-4.27 (4H, m), 4.72-4.77 (1H, m), 5.21-5.31 (1H, m), 6.08 and 6.18 (total 1H, each m), 6.41-6.47 (1H, m), 7.04-7.17 (2H, m), 7.24-7.34 (1H, m), 7.38-7.46 (2H, m);
IR (KBr, cm$^{-1}$): 2446, 1737.

Example 111

(E)-4-(Acetylsulfanyl)-1-[2-cyclopropyl-1-(2-fluorophenyl)-2-oxoethyl]-3-({1-[2-(ethoxycarbonyl)ethyl]-1H-pyrazol-3-yl}methylidene)piperidine hydrochloride (Exemplification Compound No. 2-50)

(a) (E)-3-({1-[2-(Ethoxycarbonyl)ethyl]-1H-pyrazol-3-yl}methylidene)-1-(triphenylmethyl)piperidin-4-one To a solution of (E)-3-{[1H-pyrazol-3(5)-yl]methylidene}-1-(triphenylmethyl)piperidin-4-one (2.68 g) in benzene (30 ml) was added dropwise a solution of tetrabutylammonium sulfate (1.64 g) in 50% aqueous sodium hydroxide solution (30 ml) at 4° C. with stirring. To the resulting mixture was further added dropwise ethyl 3-bromopropionate (3.30 ml) at the same temperature, and the resulting mixture was stirred for 10 minutes. After water was added to the reaction mixture, the resulting mixture was extracted with a mixed solvent of ethyl acetate and benzene. The extract was washed with saturated aqueous sodium chloride solution, and the organic layer was dried over anhydrous sodium sulfate. The solvent was removed in vacuo, and the residue was purified by chromatography on a silica gel column using a mixed solvent of hexane and ethyl acetate (17:3 to 7:3) as the eluent to afford the title compound (2.61 g, yield: 79%) as a colourless amorphous solid.
$^1$H NMR (400 MHz, CDCl$_3$) δ ppm: 1.24 (3H, t, J=7.5), 2.61-2.78 (6H, m), 3.64 (2H, bs), 4.13 (2H, q, J=7.5), 4.27 (2H, t, J=7.0), 6.15 (1H, s), 7.13-7.19 (3H, m), 7.23-7.34 (7H, m), 7.42 (1H, s), 7.49-7.56 (6H, m).

(b) (E)-3-({1-[2-(Ethoxycarbonyl)ethyl]-1H-pyrazol-3-yl}methylidene)-1-(triphenylmethyl)piperidin-4-ol The title compound was synthesized in a yield of 91% as a colourless amorphous solid using (E)-3-({1-[2-(ethoxycarbonyl)ethyl]-1H-pyrazol-3-yl}methylidene)-1-(triphenylmethyl)piperidin-4-one instead of (E)-3-benzylidene-1-(triphenylmethyl)piperidin-4-one by conducting the reaction similar to that mentioned in Example 1 (b).
$^1$H NMR (400 MHz, CDCl$_3$) δ ppm: 1.26 (3H, t, J=7.0), 1.86-1.94 (1H, m), 2.09-2.19 (1H, m), 2.55-2.73 (4H, m), 4.09-4.22 (7H, m), 6.04 (1H, d, J=2.5), 6.48 (1H, s), 7.06-7.30 (10H, m), 7.37-7.45 (6H, m).

(c) (E)-4-(Acetylsulfanyl)-3-({1-[2-(ethoxycarbonyl)ethyl]-1H-pyrazol-3-yl}methylidene)piperidine hydrogen trifluoroacetate The title compound was synthesized in a yield of 19% as a colourless oil using (E)-3-({1-[2-(ethoxycarbonyl)ethyl]-1H-pyrazol-3-yl}methylidene)-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c).

$^1$H NMR (500 MHz, CDCl$_3$) δ ppm: 1.22 (3H, t, J=7.0), 2.12-2.20 (1H, m), 2.38 (3H, s), 2.41-2.50 (1H, m), 2.86 (2H, t, J=7.0), 3.29-3.40 (1H, m), 3.50 (1H, d, J=14.0), 3.83-3.92 (1H, m), 4.13 (2H, q, J=7.0), 4.43 (2H, t, J=7.0), 4.59 (1H, t, J=4.0), 4.94 (1H, d, J=14.0), 6.21 (1H, s), 6.68 (1H, s), 7.47 (1H, s).

(d) (E)-4-(Acetylsulfanyl)-1-[2-cyclopropyl-1-(2-fluorophenyl)-2-oxoethyl]-3-({1-[2-(ethoxycarbonyl)ethyl]-1H-pyrazol-3-yl}methylidene)piperidine hydrochloride The title compound was synthesized in a yield of 71% as a colourless amorphous solid using (E)-4-(acetylsulfanyl)-3-({1-[2-(ethoxycarbonyl)ethyl]-1H-pyrazol-3-yl}methylidene)piperidine hydrogen trifluoroacetate instead of (E)-4-(acetylsulfanyl)-3-benzylidenepiperidine hydrochloride by conducting the reaction similar to that mentioned in Example 1 (d).

$^1$H NMR (500 MHz, CDCl$_3$) δ ppm: 0.66-0.82 (2H, m), 0.87-1.05 (2H, m), 1.30 (3H, t, J=7.0), 1.82-1.90 (1H, m), 2.22-2.35 (2H, m), 2.29 (3H, s), 2.39-2.67 (1H, m), 2.71-2.87 (3H, m), 3.18 (1H, d, J=12.5), 4.23 and 4.39 (total 1H, each d, J=12.5), 4.25 (2H, q, J=7.0), 4.47-4.51 (1H, m), 4.58 and 4.61 (total 2H, each s), 4.68 and 4.74 (total 1H, each s), 6.43 (1H, s), 6.74 and 6.83 (total 1H, each s), 7.03-7.16 (2H, m), 7.26-7.31 (1H, m), 7.34 and 7.39 (total 1H, each s), 7.43-7.50 (1H, m);

IR (KBr, cm$^{-1}$): 1695, 1495.

Example 112

(E)-1-[2-Cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride (Exemplification Compound No. 2-49)

The title compound was synthesized in a yield of 98% as a colourless amorphous solid using (E)-4-(acetylsulfanyl)-1-[2-cyclopropyl-1-(2-fluorophenyl)-2-oxoethyl]-3-({1-[2-(ethoxycarbonyl)ethyl]-1H-pyrazol-3-yl}methylidene)piperidine hydrochloride instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (400 MHz, CDCl$_3$) δ ppm: 0.62-1.02 (4H, m), 1.25 (3H, t, J=7.0), 1.74-1.84 (1H, m), 2.19-2.36 (2H, m), 2.59-2.90 (4H, m), 3.53 and 3.66 (total 1H, each d, J=13.5), 3.81-3.88 (1H, m), 3.90-3.96 (1H, m), 4.14 (2H, q, J=7.0), 4.28 and 4.32 (total 2H, each t, J=7.0), 4.72 and 4.73 (total 1H, each s), 6.01 and 6.10 (total 1H, each d, J=2.5), 6.42 and 6.44 (total 1H, each s), 7.03-7.16 (2H, m), 7.25-7.34 (2H, m), 7.39-7.47 (1H, m);

IR (KBr, cm$^{-1}$): 2612, 1716, 1494.

Example 113

(E)-3-{[1-(2-Carboxyethyl)-1H-pyrazol-3-yl]methylidene}-1-[2-cyclopropyl-1-(2-fluorophenyl)-2-oxoethyl]-4-sulfanylpiperidine hydrochloride (Exemplification Compound No. 2-17)

The title compound was synthesized in a yield of 95% as a colourless amorphous solid using (E)-1-[2-cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride instead of (E)-1-[2-cyclopropyl-1-(2-fluorophenyl)-2-oxoethyl]-3-{[1-(ethoxycarbonylmethyl)-1H-pyrazol-5-yl]methylidene}-4-sulfanylpiperidine hydrochloride by conducting the reaction similar to that mentioned in Example 108.

$^1$H NMR (400 MHz, pyridine-d5) δ ppm: 0.61-0.76 (2H, m), 0.93-1.01 (1H, m), 1.07-1.15 (1H, m), 2.26-2.88 (4H, m), 2.91-3.04 (1H, m), 3.08 and 3.14 (total 2H, each t, J=7.0), 3.83-4.10 (2H, m), 4.30 and 4.41 (total 1H, each d, J=13.0), 4.50 and 4.56 (total 2H, each d, J=7.0), 4.98 (1H, m), 6.24 and 6.31 (total 1H, each d, J=2.0), 6.69 and 6.74 (total 1H, each s), 7.15-7.39 (3H, m), 7.67-7.77 (2H, m);

IR (KBr, cm$^{-1}$): 2618, 1712, 1494.

Example 114

(E)-4-(Acetylsulfanyl)-3-{[1-(2-carboxyethyl)-1H-pyrazol-3-yl]methylidene}-1-[2-cyclopropyl-1-(2-fluorophenyl)-2-oxoethyl]piperidine hydrochloride (Exemplification Compound No. 2-18)

To a solution of (E)-3-{[1-(2-carboxyethyl)-1H-pyrazol-3-yl]methylidene}-1-[2-cyclopropyl-1-(2-fluorophenyl)-2-oxoethyl]-4-sulfanylpiperidine hydrochloride (90 mg) in dichloromethane (4 ml) were added acetic anhydride (0.09 ml) and triethylamine (0.13 ml) under ice-cooling, and the resulting mixture was stirred at room temperature for 3.5 hours. Subsequently, water (0.40 ml) was added to the reaction mixture. The resulting mixture was concentrated in vacuo, and the residue was purified by chromatography on a silica gel column using a mixed solvent of methanol and dichloromethane (3:200) as the eluent. To a solution of a colourless amorphous solid obtained in acetonitrile (3 ml) was added a 4N solution of hydrogen chloride in dioxane (0.07 ml) with stirring. The reaction mixture was concentrated in vacuo to afford the title compound (45 mg, yield: 43%) as a colourless amorphous solid.

$^1$H NMR (400 MHz, CDCl$_3$) δ ppm: 0.66-1.04 (4H, m), 1.83-1.94 (1H, m), 2.06-2.19 (1H, m), 2.25-2.36 (4H, m), 2.42-2.95 (4H, m), 3.20 and 3.22 (total 1H, each d, J=13.5), 4.08-4.36 (3H, m), 4.45-4.52 (1H, m), 4.82 and 4.93 (total 1H, each s), 6.07 and 6.14 (total 1H, each d, J=2.5), 6.46 and 6.48 (total 1H, each s), 7.07-7.37 (4H, m), 7.40-7.47 (1H, m);

IR (KBr, cm$^-$): 1710, 1494.

Example 115

(E)-4-(Acetylsulfanyl)-1-[2-cyclopropyl-1-(2-fluorophenyl)-2-oxoethyl]-3-({1-[3-(ethoxycarbonyl)propyl]-1H-pyrazol-3-yl}methylidene)piperidine hydrochloride (Exemplification Compound No. 2-54)

(a) (E)-3-({1-[3-(Ethoxycarbonyl)propyl]-1H-pyrazol-3-yl}methylidene)-1-(triphenylmethyl)piperidin-4-one The title compound was synthesized in a yield of 72% as a colourless amorphous solid using ethyl 4-bromobutyrate instead of t-butyl bromoacetate by conducting the reaction similar to that mentioned in Example 75 (a).

$^1$H NMR (500 MHz, CDCl$_3$) δ ppm: 1.26 (3H, t, J=7.5), 2.00 (2H, t, J=7.0), 2.12 (2H, t, J=7.0), 2.60-2.79 (4H, m), 3.34-3.71 (2H, m), 4.06 (2H, t, J=7.0), 4.13 (2H, q, J=7.5), 6.18 (1H, s), 7.13-7.30 (10H, m), 7.44 (1H, s), 7.48-7.55 (6H, m).

(b) (E)-3-({1-[3-(Ethoxycarbonyl)propyl]-1H-pyrazol-3-yl}methylidene)-1-(triphenylmethyl)piperidin-4-ol The title compound was synthesized in a yield of 99% as a colourless amorphous solid using (E)-3-({1-[3-(ethoxycarbonyl)propyl]-1H-pyrazol-3-yl}methylidene)-1-(triphenylmethyl)piperidin-4-one instead of (E)-3-benzylidene-1-(triphenylmethyl)piperidin-4-one by conducting the reaction similar to that mentioned in Example 1 (b).

$^1$H NMR (500 MHz, CDCl$_3$) δ ppm: 1.27 (3H, t, J=7.0)', 1.85-2.26 (6H, m), 2.64-2.93 (1H, m), 3.40-3.83 (1H, m), 3.98 (2H, t, J=7.0), 4.09-4.20 (5H, m), 6.05 (1H, s), 6.49 (1H, s), 7.07-7.28 (10H, m), 7.33-7.45 (6H, m).

(c) (E)-4-(Acetylsulfanyl)-3-({1-[3-(ethoxycarbonyl)propyl]-1H-pyrazol-3-yl}methylidene)piperidine hydrogen trifluoroacetate The title compound was synthesized in a yield of 19% as a brown oil using (E)-3-({1-[3-(ethoxycarbonyl)propyl]-1H-pyrazol-3-yl}methylidene)-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c).

$^1$H NMR (500 MHz, CDCl$_3$) δ ppm: 1.24 (3H, t, J=7.0), 2.04-2.19 (3H, m), 2.27 (2H, t, J=7.0), 2.36 (3H, s), 2.40-2.50 (1H, m), 3.18-3.27 (1H, m), 3.35-3.42 (1H, m), 3.81 (1H, d, J=14.5), 4.07-4.17 (4H, m), 4.59 (1H, bs), 5.11 (1H, d, J=14.5), 6.19 (1H, s), 6.63 (1H, s), 7.31 (1H, s).

(d) (E)-4-(Acetylsulfanyl)-1-[2-cyclopropyl-1-(2-fluorophenyl)-2-oxoethyl]-3-({1-[3-(ethoxycarbonyl)propyl]-1H-pyrazol-3-yl}methylidene)piperidine hydrochloride The title compound was synthesized in a quantitative yield as a colourless amorphous solid using (E)-4-(acetylsulfanyl)-3-({1-[3-(ethoxycarbonyl)propyl]-1H-pyrazol-3-yl}methylidene)piperidine hydrogen trifluoroacetate instead of (E)-4-(acetylsulfanyl)-3-benzylidenepiperidine hydrochloride by conducting the reaction similar to that mentioned in Example 1 (d).

$^1$H NMR (400 MHz, CDCl$_3$) δ ppm: 0.63-1.02 (4H, m), 1.26 (3H, t, J=7.0), 1.82-1.93 (1H, m), 2.03-2.35 (7H, m), 2.28 (3H, s), 2.43-2.65 (1H, m), 2.72-2.85 (1H, m), 3.10 and 3.22 (total 1H, each d, J=13.0), 4.01-4.16 (4H, m), 4.50 (1H, t, J=4.5), 4.69 and 4.70 (total 1H, each s), 6.03 and 6.12 (total 1H, each d, J=2.5), 6.48 and 6.49 (total 1H, each s), 7.04-7.16 (2H, m), 7.21-7.33 (2H, m),

Example 116

(E)-1-[2-Cyclopropyl-1-(2-fluorophenyl)-2-oxoethyl]-3-({1-[3-(ethoxycarbonyl)propyl]-1H-pyrazol-3-yl}methylidene)-4-sulfanylpiperidine hydrochloride (Exemplification Compound No. 2-53)

The title compound was synthesized in a yield of 90% as a pale yellow amorphous solid using (E)-4-(acetylsulfanyl)-1-[2-cyclopropyl-1-(2-fluorophenyl)-2-oxoethyl]-3-({1-[3-(ethoxycarbonyl)propyl]-1H-pyrazol-3-yl}methylidene)piperidine hydrochloride instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

$^1$H NMR (500 MHz, CDCl$_3$) δ ppm: 0.64-0.80 (2H, m), 0.85-1.02 (2H, m), 1.26 (3H, t, J=7.0), 1.75-1.84 (1H, m), 2.06-2.18 (2H, m), 2.21-2.34 (4H, m), 2.60-2.92 (2H, m), 3.54 and 3.64 (total 1H, each d, J=13.0), 3.79-3.86 (1H, m), 3.90-3.96 (1H, m), 4.03-4.17 (4H, m), 4.72 and 4.74 (total 1H, each s), 6.03 and 6.13 (total 1H, each s), 6.44 and 6.46 (total 1H, each s), 7.04-7.15 (2H, m), 7.21-7.31 (2H, m), 7.39-7.46 (1H, m);

IR (KBr, cm$^{-1}$): 2611, 1728, 1494.

Example 117

(E)-3-{[1-(3-Carboxypropyl)-1H-pyrazol-3-yl]methylidene}-1-[2-cyclopropyl-1-(2-fluorophenyl)-2-oxoethyl]-4-sulfanylpiperidine hydrochloride (Exemplification Compound No. 2-21)

The title compound was synthesized in a yield of 87% as a colourless amorphous solid using (E)-1-[2-cyclopropyl-1-(2-fluorophenyl)-2-oxoethyl]-3-({1-[3-(ethoxycarbonyl)propyl]-1H-pyrazol-3-yl}methylidene)-4-sulfanylpiperidine hydrochloride instead of (E)-1-[2-cyclopropyl-1-(2-fluorophenyl)-2-oxoethyl]-3-{[1-(ethoxycarbonylmethyl)-1H-pyrazol-5-yl]methylidene}-4-sulfanylpiperidine hydrochloride by conducting the reaction similar to that mentioned in Example 108.

$^1$H NMR (500 MHz, CDCl$_3$) δ ppm: 0.66-1.04 (4H, m), 2.04-2.37 (5H, m), 2.55-2.76 (2H, m), 2.91-2.99 (1H, m), 3.49-3.66 (2H, m), 3.80-3.99 (2H, m), 4.09-4.22 (2H, m), 4.82 and 4.84 (total 1H, each s), 6.07 and 6.14 (total 1H, each s), 6.45 and 6.50 (total 1H, each s), 7.05-7.41 (5H, m);

IR (KBr, cm$^{-1}$): 2622, 1711, 1494.

Example 118

(E)-4-(Acetylsulfanyl)-3-{[1-(3-carboxypropyl)-1H-pyrazol-3-yl]methylidene}-1-[2-cyclopropyl-1-(2-fluorophenyl)-2-oxoethyl]piperidine hydrochloride (Exemplification Compound No. 2-22)

The title compound was synthesized in a yield of 59% as a pale yellow amorphous solid using (E)-3-{[1-(3-carboxypropyl)-1H-pyrazol-3-yl]methylidene}-1-[2-cyclopropyl-1-(2-fluorophenyl)-2-oxoethyl]-4-sulfanylpiperidine hydrochloride instead of (E)-3-{[1-(2-carboxyethyl)-1H-pyrazol-3-yl]methylidene}-1-[2-cyclopropyl-1-(2-fluorophenyl)-2-oxoethyl]-4-sulfanylpiperidine hydrochloride by conducting the reaction similar to that mentioned in Example 114.

¹H NMR (500 MHz, CDCl₃) δ ppm: 0.66-1.03 (4H, m), 1.83-1.93 (1H, m), 2.04-2.20 (3H, m), 2.25-2.35 (4H, m), 2.38-2.93 (4H, m), 3.15 and 3.25 (total 1H, each d, J=13.0), 3.94-4.23 (3H, m), 4.45 and 4.50 (total 1H, each t, J=4.5), 4.81 and 4.86 (total 1H, each s), 6.07 and 6.15 (total 1H, each d, J=2.0), 6.49 and 6.51 (total 1H, each s), 7.08-7.19 (2H, m), 7.24-7.42 (3H, m);

IR (KBr, cm⁻¹): 1709, 1494.

Example 119

(E)-4-(Acetylsulfanyl)-1-[2-cyclopropyl-1-(2-fluorophenyl)-2-oxoethyl]-3-({1-[4-(ethoxycarbonyl)butyl]-1H-pyrazol-3-yl}methylidene)piperidine hydrochloride (Exemplification Compound No. 2-58)

(a) (E)-3-({1-[4-(Ethoxycarbonyl)butyl]-1H-pyrazol-3-yl}methylidene)-1-(triphenylmethyl)piperidin-4-one The title compound was synthesized in a yield of 65% as a white solid using ethyl 5-bromovalerate instead of t-butyl bromoacetate by conducting the reaction similar to that mentioned in Example 75 (a).

¹H NMR (400 MHz, CDCl₃) δ ppm: 1.26 (3H, t, J=7.0), 1.45-1.78 (4H, m), 2.24 (2H, t, J=7.5), 2.60-2.79 (4H, m), 3.58-3.70 (2H, m), 4.00 (2H, t, J=7.0), 4.13 (2H, q, J=7.0), 6.17 (1H, s), 7.12-7.30 (10H, m), 7.43-7.56 (7H, m).

(b) (E)-3-({1-[4-(Ethoxycarbonyl)butyl]-1H-pyrazol-3-yl}methylidene)-1-(triphenylmethyl)piperidin-4-ol The title compound was synthesized in a quantitative yield as a colourless amorphous solid using (E)-3-({1-[4-(ethoxycarbonyl)butyl]-1H-pyrazol-3-yl}methylidene)-1-(triphenylmethyl)piperidin-4-one instead of (E)-3-benzylidene-1-(triphenylmethyl)piperidin-4-one by conducting the reaction similar to that mentioned in Example 1 (b).

¹H NMR (500 MHz, CDCl₃) δ ppm: 1.25 (3H, t, J=7.0), 1.67-1.77 (2H, m), 1.83-1.97 (2H, m), 2.09-2.20 (2H, m), 2.29 (2H, t, J=8.0), 2.60-2.97 (2H, m), 3.92 (2H, t, J=7.0), 4.08-4.22 (5H, m), 6.04 (1H, s), 6.49 (1H, s), 7.06-7.24 (10H, m), 7.32-7.45 (6H, m).

(c) (E)-4-(Acetylsulfanyl)-3-({1-[4-(ethoxycarbonyl)butyl]-1H-pyrazol-3-yl}methylidene)piperidine hydrogen trifluoroacetate The title compound was synthesized in a yield of 20% as a brown oil using (E)-3-({1-[4-(ethoxycarbonyl)butyl]-1H-pyrazol-3-yl}methylidene)-1-(triphenylmethyl)piperidin-4-ol instead of (E)-3-{[1-(t-butoxycarbonyl)-1H-imidazol-5-yl]methylidene}-1-(triphenylmethyl)piperidin-4-ol by conducting successively reactions similar to those mentioned in Example 21 (c).

¹H NMR (500 MHz, CDCl₃) ppm: 1.24 (3H, t, J=7.0), 1.43-1.54 (2H, m), 1.82-1.92 (2H, m), 2.05-2.13 (1H, m), 2.28-2.34 (2H, m), 2.36 (3H, s), 2.39-2.49 (1H, m), 3.19-3.28 (1H, m), 3.36-3.44 (1H, m), 3.81 (1H, d, J=14.5), 4.04-4.15 (4H, m), 4.59 (1H, bs), 5.10 (1H, d, J=14.5), 6.19 (1H, s), 6.64 (1H, s), 7.31 (1H, s).

(d) (E)-4-(Acetylsulfanyl)-1-[2-cyclopropyl-1-(2-fluorophenyl)-2-oxoethyl]-3-({1-[4-(ethoxycarbonyl)butyl]-1H-pyrazol-3-yl}methylidene)piperidine hydrochloride The title compound was synthesized in a quantitative yield as a colourless amorphous solid using (E)-4-(acetylsulfanyl)-3-({1-[4-(ethoxycarbonyl)butyl]-1H-pyrazol-3-yl}methylidene)piperidine hydrogen trifluoroacetate instead of (E)-4-(acetylsulfanyl)-3-benzylidenepiperidine hydrochloride by conducting the reaction similar to that mentioned in Example 1 (d).

¹H NMR (500 MHz, CDCl₃) δ ppm: 0.63-1.02 (4H, m), 1.25 (3H, t, J=7.0), 1.52-1.66 (2H, m), 1.76-1.93 (3H, m), 2.22-2.35 (7H, m), 2.43-2.65 (1H, m), 2.71-2.85 (1H, m), 3.10 and 3.22 (total 1H, each d, J=12.5), 3.98 and 4.05 (total 2H, each t, J=7.0), 4.07-4.16 (3H, m), 4.50 (1H, t, J=5.0), 4.69 and 4.70 (total 1H, each s), 6.03 and 6.12 (total 1H, each s), 6.48 and 6.50 (total 1H, each s), 7.03-7.16 (2H, m), 7.20-7.32 (2H, m), 7.40-7.45 (1H, m);

IR (KBr, cm⁻¹): 1710, 1495.

Example 120

(E)-1-[2-Cyclopropyl-1-(2-fluorophenyl)-2-oxoethyl]-3-({1-[4-(ethoxycarbonyl)butyl]-1H-pyrazol-3-yl}methylidene)-4-sulfanylpiperidine hydrochloride (Exemplification Compound No. 2-57)

The title compound was synthesized in a yield of 64% as a colourless amorphous solid using (E)-4-(acetylsulfanyl)-1-[2-cyclopropyl-1-(2-fluorophenyl)-2-oxoethyl]-3-({1-[4-(ethoxycarbonyl)butyl]-1H-pyrazol-3-yl}methylidene)piperidine hydrochloride instead of (E)-4-(acetylsulfanyl)-3-benzylidene-1-[2-cyclopropyl-1-(2-fluorophenyl)-2-oxoethyl]piperidine by conducting the reaction similar to that mentioned in Example 2.

¹H NMR (500 MHz, CDCl₃) δ ppm: 0.63-0.81 (2H, m), 0.84-1.02 (2H, m), 1.25 (3H, t, J=7.0), 1.55-1.92 (5H, m), 2.21-2.36 (4H, m), 2.59-2.92 (2H, m), 3.55 and 3.64 (total 1H, each d, J=12.5), 3.77-3.89 (2H, m), 4.01 and 4.05 (total 2H, each t, J=7.0), 4.13 (2H, q, J=7.0), 4.73 and 4.74 (total 1H, each s), 6.03 and 6.12 (total 1H, each d, J=2.0), 6.45 and 6.47 (total 1H, each s), 7.03-7.15 (2H, m), 7.21-7.33 (2H, m), 7.40-7.47 (1H, m);

IR (KBr, cm⁻¹): 1716, 1495.

Example 121

(E)-3-{[1-(4-Carboxybutyl)-1H-pyrazol-3-yl]methylidene}-1-[2-cyclopropyl-1-(2-fluorophenyl)-2-oxoethyl]-4-sulfanylpiperidine hydrochloride (Exemplification Compound No. 2-25)

The title compound was synthesized in a yield of 74% as a colourless amorphous solid using (E)-1-[2-cyclopropyl-1-(2-fluorophenyl)-2-oxoethyl]-3-({1-[4-(ethoxycarbonyl)butyl]-1H-pyrazol-3-yl}methylidene)-4-sulfanylpiperidine hydrochloride instead of (E)-1-[2-cyclopropyl-1-(2-fluorophenyl)-2-oxoethyl]-3-{[1-(ethoxycarbonylmethyl)-1H-pyrazol-5-yl]methylidene}-4-sulfanylpiperidine hydrochloride by conducting the reaction similar to that mentioned in Example 108.

¹H NMR (500 MHz, CDCl₃) δ ppm: 0.65-0.82 (2H, m), 0.84-1.03 (2H, m), 1.56-1.92 (5H, m), 2.14-2.37 (4H, m), 2.61-2.94 (2H, m), 3.55-4.14 (5H, m), 4.78 and 4.80 (total 1H, each s), 6.04 and 6.13 (total 1H, each d, J=2.0), 6.44 and 6.46 (total 1H, each s), 7.06-7.16 (2H, m), 7.21-7.33 (2H, m), 7.38-7.43 (1H, m);

IR (KBr, cm$^{-1}$): 2614, 1711, 1495.

Example 122

(E)-4-(Acetylsulfanyl)-3-{[1-(4-carboxybutyl)-1H-pyrazol-3-yl]methylidene}-1-[2-cyclopropyl-1-(2-fluorophenyl)-2-oxoethyl]piperidine hydrochloride (Exemplification Compound No. 2-26)

The title compound was synthesized in a yield of 37% as a pale yellow solid using (E)-3-{[1-(4-carboxybutyl)-1H-pyrazol-3-yl]methylidene}-1-[2-cyclopropyl-1-(2-fluorophenyl)-2-oxoethyl]-4-sulfanylpiperidine hydrochloride instead of (E)-3-{[1-(2-carboxyethyl)-1H-pyrazol-3-yl]methylidene}-1-[2-cyclopropyl-1-(2-fluorophenyl)-2-oxoethyl]-4-sulfanylpiperidine hydrochloride by conducting the reaction similar to that mentioned in Example 114.

$^1$H NMR (400 MHz, CDCl$_3$) δ ppm: 0.63-1.04 (4H, m), 1.54-1.70 (2H, m), 1.80-2.36 (9H, m), 2.37-2.47 and 2.60-2.69 (total 1H, each m), 2.74-2.87 (1H, m), 3.13-3.21 (1H, m), 3.98-4.26 (4H, m), 4.46-4.53 (1H, m), 4.75 and 4.79 (total 1H, each s), 6.05 and 6.13 (total 1H, each d, J=2.5), 6.48 and 6.49 (total 1H, each s), 7.06-7.45 (5H, m);

IR (KBr, cm$^{-1}$): 1709, 1494.

Example 123

(E)-4-(Acetylsulfanyl)-1-[2-cyclopropyl-1-(2-fluorophenyl)-2-oxoethyl]-3-{[1-(N-hydroxycarbamoylmethyl)-1H-pyrazol-3-yl]methylidene}piperidine (Exemplification Compound No. 2-86)

To a solution of (E)-4-(acetylsulfanyl)-3-{[1-(carboxymethyl)-1H-pyrazol-3-yl]methylidene}-1-[2-cyclopropyl-1-(2-fluorophenyl)-2-oxoethyl]piperidine (300 mg) in diethyl ether (5 ml) was added dropwise ethyl chloroformate (0.073 ml) and N-methylmorpholine (0.091 ml) under ice-cooling, and the resulting mixture was stirred at the same temperature for 15 minutes. Subsequently, to the reaction mixture was added a solution of hydroxylamine derived from hydroxylamine hydrochloride (67 mg) and potassium hydroxide (54 mg) in methanol (5 ml). The resulting mixture was stirred at room temperature for 30 minutes. The reaction mixture was concentrated in vacuo, and the residue was purified by chromatography on a silica gel column using a mixed solvent of ethyl acetate and dichloromethane (5:1) as the eluent to afford the title compound (160 mg, yield: 51%) as a colourless amorphous solid.

$^1$H NMR (500 MHz, CDCl$_3$) δ ppm: 0.71-1.01 (4H, m), 1.84-1.91 (1H, m), 2.00-2.09 (1H, m), 2.21-2.40 (1H, m), 2.30 and 2.32 (total 3H, each s), 2.39-2.47 and 2.52-2.60 (total 1H, each m), 2.65-2.73 and 2.81-2.88 (total 1H, each m), 3.08 and 3.20 (total 1H, each d, J=13.5), 4.32 and 4.37 (total 1H, each d, J=13.5), 4.48 (1H, m), 4.72 and 4.77 (total 2H, each s), 4.78 and 4.81 (total 1H, each s), 6.16 and 6.22 (total 1H, each d, J=2.0), 6.44 and 6.45 (total 1H, each s), 7.07-7.18 (2H, m), 7.28-7.40 (2H, m), 7.34 and 7.38 (total 1H, each d, J=2.0)

Example 124

(E)-1-[2-Cyclopropyl-1-(2-fluorophenyl)-2-oxoethyl]-3-{[1-(N-hydroxycarbamoylmethyl)-1H-pyrazol-3-yl]methylidene}-4-sulfanylpiperidine hydrochloride (Exemplification Compound No. 2-85)

The title compound was synthesized in a yield of 20% as a colourless amorphous solid using (E)-4-(acetylsulfanyl)-1-[2-cyclopropyl-1-(2-fluorophenyl)-2-oxoethyl]-3-{[1-(N-hydroxycarbamoylmethyl)-1H-pyrazol-3-yl]methylidene}piperidine instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (500 MHz, CDCl$_3$) δ ppm: 0.70-1.03 (4H, m), 1.76-1.85 (1H, m), 2.00-2.08 (1H, m), 2.22-2.40 (1H, m), 2.54-2.61 and 2.64-2.71 (total 1H, each m), 2.72-2.79 and 2.81-2.88 (total 1H, each m), 3.63 and 3.69 (total 1H, each d, J=12.5), 3.91 (1H, m), 3.96 and 4.00 (total 1H, each d, J=12.5), 4.73 (1H, s), 4.77, 4.78, 4.82, and 4.83 (total 2H, each s), 6.16 and 6.21 (total 1H, each d, J=2.0), 6.41 and 6.42 (total 1H, each s), 7.08-7.17 (2H, m), 7.28-7.41 (2H, m), 7.36 and 7.39 (total 1H, each d, J=2.0);

IR (KBr, cm$^{-1}$): 2555, 1708.

Example 125

(E)-3-{[1-(Carboxymethyl)-1H-pyrazol-4-yl]methylidene}-1-[2-cyclopropyl-1-(2-fluorophenyl)-2-oxoethyl]-4-sulfanylpiperidine hydrochloride (Exemplification Compound No. 2-181)

The title compound was synthesized in a yield of 38% as a pale yellow amorphous solid using (E)-1-[2-cyclopropyl-1-(2-fluorophenyl)-2-oxoethyl]-3-{[1-(methoxycarbonylmethyl)-1H-pyrazol-4-yl]methylidene}-4-sulfanylpiperidine instead of (E)-1-[2-cyclopropyl-1-(2-fluorophenyl)-2-oxoethyl]-3-{[1-(ethoxycarbonylmethyl)-1H-pyrazol-5-yl]methylidene}-4-sulfanylpiperidine hydrochloride by conducting the reaction similar to that mentioned in Example 108.

$^1$H NMR (400 MHz, pyridine-d$_5$) δ ppm: 0.69-0.76 (2H, m), 0.96-1.12 (2H, m), 1.85-1.87 (1H, m), 2.27-2.44 (2H, m), 2.58 and 2.71 (total 1H, each m), 2.89-3.01 (1H, m), 3.59-3.87 (2H, m), 4.03 (1H, bs), 4.94 and 4.95 (total 1H, each s), 5.29 and 5.32 (total 2H, each s), 6.55 and 6.56 (total 1H, each s), 7.17-7.22 (2H, m), 7.23-7.35 (1H, m), 7.65-7.80 (1H, m), 7.74 and 7.79 (total 1H, each s), 7.82 and 7.91 (total 1H, each s);

IR (KBr, cm$^{-1}$): 2520, 1742, 1710.

Example 126

(E)-4-(Acetylsulfanyl)-3-{[1-(carboxymethyl)-1H-pyrazol-4-yl]methylidene}-1-[2-cyclopropyl-1-(2-fluorophenyl)-2-oxoethyl]piperidine hydrochloride (Exemplification Compound No. 2-182)

The title compound was synthesized in a yield of 60% as a pale yellow amorphous solid using (E)-3-{[1-(carboxymethyl)-1H-pyrazol-4-yl]methylidene}-1-[2-cyclopropyl-1-(2-fluorophenyl)-2-oxoethyl]-4-sulfanylpiperidine hydrochloride instead of (E)-3-{[1-(2-carboxyethyl)-1H-pyrazol-3-yl]methylidene}-1-[2-cyclopropyl-1-(2-fluorophenyl)-2-oxoethyl]-4-sulfanylpiperidine hydrochloride by conducting the reaction similar to that mentioned in Example 114.

¹H NMR (400 MHz, CDCl₃) δ ppm: 0.67-0.91 (2H, m), 0.95-1.07 (2H, m), 1.72-1.96 (2H, m), 2.27 and 2.31 (total 3H, each s), 2.27-2.46 (2H, m), 2.82-2.90 and 2.93-2.99 (total 1H, each m), 3.07 and 3.31 (total 1H, each d, J=13.0), 3.69 and 3.93 (total 1H, each d, J=13.0), 4.35-4.41 and 4.46-4.50 (total 1H, each m), 4.74-4.85 (2H, m), 5.11 and 5.29 (total 1H, each s), 6.41 and 6.46 (total 1H, each s), 7.11-7.31 (2H, m), 7.34-7.46 (3H, m), 7.51 and 7.63 (total 1H, each s);

IR (KBr, cm⁻¹): 1741, 1705.

Example 127

(E)-4-(Acetylsulfanyl)-1-[2-cyclopropyl-1-(2-fluorophenyl)-2-oxoethyl]-3-{[1-(methoxycarbonylmethyl)pyrrol-3-yl]methylidene}piperidine hydrochloride (Exemplification Compound No. 2-658)

(a) (E)-3-{[1-(Methoxycarbonylmethyl)pyrrol-3-yl]methylidene}-1-(triphenylmethyl)piperidin-4-ol To a solution of (E)-3-{[1-(ethoxycarbonylmethyl)pyrrol-3-yl]methylidene}-1-(triphenylmethyl)piperidin-4-one (19.4 g) in ethanol (100 ml) was added sodium borohydride (3.0 g) under ice-cooling, and the resulting mixture was stirred at room temperature for 2 hours. To the reaction mixture was added aqueous ammonium chloride solution, the resulting mixture was extracted with ethyl acetate. The extract was washed with saturated aqueous sodium chloride solution. The organic layer was dried over anhydrous sodium sulfate, and the solvent was removed in vacuo. To a solution of the residue in methanol (100 ml) was added potassium carbonate (10.6 g), and the resulting mixture was stirred at room temperature for 15 minutes. To the reaction mixture was added water, and the resulting mixture was extracted with ethyl acetate. The extract was washed with saturated aqueous sodium chloride solution, and the organic layer was dried over anhydrous sodium sulfate. The solvent was removed in vacuo to afford the title compound (12.1 g, yield: 64%) as a pale yellow amorphous solid.

¹H NMR (400 MHz, CDCl₃) δ ppm: 1.82-1.92 (1H, m), 2.12 (1H, m), 2.23 (1H, m), 2.54 (1H, m), 3.03 (1H, m), 3.30 (1H, m), 3.76 (3H, s), 4.16 (1H, m), 4.48 (2H, s), 6.02 (1H, dd, J=3.0, 2.0), 6.35 (1H, bs), 6.44 (1H, t, J=2.0), 6.51 (1H, t, J=3.0), 7.08-7.30 (7H, m), 7.43-7.51 (8H, m).

(b) (E)-4-(Acetylsulfanyl)-3-{[1-(methoxycarbonylmethyl)pyrrol-3-yl]methylidene}-1-(triphenylmethyl)piperidine To a solution of (E)-3-{[1-(methoxycarbonylmethyl)pyrrol-3-yl]methylidene}-1-(triphenylmethyl)piperidin-4-ol (12.1 g) in toluene (100 ml) were added thioacetic acid (3.5 ml) and N,N-dimethylformamide dineopentyl acetal (13.7 ml) under ice-cooling, and the resulting mixture was stirred at room temperature for 30 minutes. To the reaction mixture was added water, and the resulting mixture was extracted with ethyl acetate. The extract was washed with saturated aqueous sodium chloride solution, and the organic layer was dried over anhydrous magnesium sulfate. The solvent was removed in vacuo, and the residue was purified by chromatography on a silica gel column using a mixed solvent of ethyl acetate and hexane (1:3) as the eluent. The amorphous solid obtained was dissolved in methanol (100 ml), and the resulting mixture was stirred at 50° C. for 2 days. The reaction mixture was concentrated in vacuo to afford the title compound (12.8 g, yield: 95%) as a pale yellow amorphous solid.

¹H NMR (400 MHz, CDCl₃) δ ppm: 1.83-1.95 (1H, m), 1.98-2.12 (1H, m), 2.24 (3H, s), 2.32-2.43 (1H, m), 2.50-2.74 (2H, m), 3.65-3.80 (1H, m), 3.74 (3H, s), 4.46 (2H, s), 4.47-4.54 (1H, m), 5.98 (1H, bs), 6.40 (1H, bs), 6.41 (1H, bs), 6.48 (1H, t, J=3.0), 7.07-7.33 (7H, m), 7.41-7.51 (8H, m).

(c) (E)-4-(Acetylsulfanyl)-1-[2-cyclopropyl-1-(2-fluorophenyl)-2-oxoethyl]-3-{[1-(methoxycarbonylmethyl)pyrrol-3-yl]methylidene}piperidine hydrochloride To a solution of (E)-4-(acetylsulfanyl)-3-{[1-(methoxycarbonylmethyl)pyrrol-3-yl]methylidene}-1-(triphenylmethyl) piperidine (3.47 g) in dichloromethane (100 ml) was added trifluoroacetic acid (1.2 ml) under ice-cooling, and the resulting mixture was stirred at the same temperature for 5 minutes. The reaction mixture was concentrated in vacuo, and the residue was purified by chromatography on a silica gel column using a mixed solvent of methanol and dichloromethane (20:1 to 1:4) to afford the detriphenylmethyl derivative.

To a solution of the compound mentioned above and 2-bromo-2-(2-fluorophenyl)-1-cyclopropylethanone (3.24 g) in N,N-dimethylformamide (50 ml) was added triethylamine (1.8 ml) under ice-cooling, and the resulting mixture was stirred at room temperature for 1 hour. After stirring, water was added to the reaction mixture, and the resulting mixture was extracted with ethyl acetate. The extract was washed with saturated aqueous sodium chloride solution, and the organic layer was dried over anhydrous magnesium sulfate. The solvent was removed in vacuo, and the residue was purified by chromatography on a silica gel column using a mixed solvent of ethyl acetate, hexane and dichloromethane (1:3:1) as the eluent to afford the title compound (1.48 g, yield: 45%) as a pale yellow amorphous solid.

¹H NMR (400 MHz, CDCl₃) δ ppm: 0.64-0.84 (2H, m), 0.86-1.04 (2H, m), 1.79-1.91 (1H, m), 2.16-2.35 (2H, m), 2.29 (3H, s), 2.35-2.44 and 2.51-2.60 (total 1H, each m), 2.69-2.77 and 2.80-2.87 (total 1H, each m), 2.94 and 3.03 (total 1H, each d, J=13.0), 3.76 (3H, s), 3.78 and 3.93 (total 1H, each d, J=13.0), 4.50 (1H, m), 4.51 and 4.56 (total 2H, each s), 4.65 and 4.68 (total 1H, each s), 5.97 and 6.11 (total 1H, each dd, J=3.0, 2.0), 6.38 and 6.41 (total 1H, each s), 6.43 and 6.50 (total 1H, each t, J=2.0), 6.54-6.58 (1H, m), 7.04-7.17 (2H, m), 7.26-7.34 (1H, m), 7.44-7.50 (1H, m);

IR (KBr, cm⁻¹): 1752, 1708, 1693.

Example 128

(E)-4-(Acetylsulfanyl)-1-[2-cyclopropyl-1-(2,4,5-trifluorophenyl)-2-oxoethyl]-3-{[1H-imidazol-4(5)-yl]methylidene}piperidine dihydrochloride (Exemplification Compound No. 1-184)

(a) 2-(2,4,5-Trifluorophenyl)-1-cyclopropylethanone

The title compound was synthesized in a yield of 70% as a pale yellow oil using 2,4,5-trifluorobenzyl bromide instead of 2,4-difluorobenzyl bromide by conducting successively reactions similar to those mentioned in Example 94 (a).

¹H NMR (400 MHz, CDCl₃) δ ppm: 0.90-0.97 (2H, m), 1.06-1.12 (2H, m), 1.95-2.03 (1H, m), 3.83 (2H, s), 6.88-6.97 (1H, m), 6.99-7.17 (1H, m).

(b) 2-Bromo-2-(2,4,5-trifluorophenyl)-1-cyclopropylethanone

The title compound was synthesized in a yield of 50% as a colourless needle crystal using 2-(2,4,5-trifluorophenyl)-1-cyclopropylethanone instead of 2-(2,4-difluorophenyl)-1-cyclopropylethanone by conducting the reaction similar to that mentioned in Example 94 (b).

$^1$H NMR (400 MHz, CDCl$_3$) δ ppm: 0.98-1.24 (4H, m), 2.15-2.22 (1H, m), 5.83 (1H, s), 6.92-6.99 (1H, m), 7.37-7.45 (1H, m).

(c) (E)-4-(Acetylsulfanyl)-1-[2-cyclopropyl-1-(2,4,5-trifluorophenyl)-2-oxoethyl]-3-{[1H-imidazol-4(5)-yl]methylidene}piperidine dihydrochloride The title compound was synthesized in a yield of 51% as a pale yellow solid using 2-bromo-2-(2,4,5-trifluorophenyl)-1-cyclopropylethanone instead of 2-bromo-2-(2-fluorophenyl)-1-cyclopropylethanone by conducting the reaction similar to that mentioned in Example 21 (d).

$^1$H NMR (400 MHz, CD$_3$OD) δ ppm: 0.96-1.30 (4H, m), 1.89-2.01 (1H, m), 2.11-2.24 (1H, m), 2.37 and 2.38 (total 3H, each s), 2.44-2.66 (1H, m), 3.21-3.55 (2H, m), 3.92-4.39 (2H, m), 4.58 and 4.63 (total 1H, each t, J=5.0), 4.85 (1H, s), 6.00 and 6.06 (total 1H, each s), 6.81 and 6.83 (total 1H, each s), 7.53 (1H, m), 7.61-7.76 (1H, m), 7.78 and 7.85 (total 1H, each s);

IR (KBr, cm$^{-1}$): 2596, 1702, 1520.

Example 129

(E)-1-[2-Cyclopropyl-1-(2,4,5-trifluorophenyl)-2-oxoethyl]-3-{[1H-imidazol-4(5)-yl]methylidene}-4-sulfanylpiperidine dihydrochloride (Exemplification Compound No. 1-183)

The title compound was synthesized in a yield of 86% as a colourless solid using (E)-4-(acetylsulfanyl)-1-[2-cyclopropyl-1-(2,4,5-trifluorophenyl)-2-oxoethyl]-3-{[1H-imidazol-4(5)-yl]methylidene}piperidine dihydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (400 MHz, CDCl$_3$) δ ppm: 0.79-0.96 (2H, m), 1.01-1.11 (2H, m), 1.73-1.82 (1H, m), 1.98-2.11 (1H, m), 2.16-2.32 (1H, m), 2.45-2.62 (1H, m), 2.70-2.82 (1H, m), 3.41-3.66 (1H, m), 3.46 and 3.64 (total 1H, each d, J=12.5), 3.82-3.88 (1H, m), 4.77 (1H, s), 6.46 and 6.48 (total 1H, each s), 6.95-7.05 (1H, m), 6.98 and 7.00 (total 1H, each s), 7.16-7.27 (1H, m), 7.64 and 7.65 (total 1H, each s);

IR (KBr, cm$^{-1}$): 2599, 1710, 1520.

Example 130

(E)-4-(Acetylsulfanyl)-1-[2-cyclopropyl-1-(2,3,4-trifluorophenyl)-2-oxoethyl]-3-{[1H-imidazol-4(5)-yl]methylidene}piperidine dihydrochloride (Exemplification Compound No. 1-186)

(a) 2-(2,3,4-Trifluorophenyl)-1-cyclopropylethanone

The title compound was synthesized in a yield of 66% as a white solid using 2,3,4-trifluorobenzyl bromide instead of 2,4-difluorobenzyl bromide by conducting successively reactions similar to those mentioned in Example 94 (a).

$^1$H NMR (400 MHz, CDCl$_3$) δ ppm: 0.91-0.97 (2H, m), 1.06-1.12 (2H, m), 1.96-2.04 (1H, m), 3.88 (2H, s), 6.86-6.96 (2H, m).

(b) 2-Bromo-2-(2,3,4-trifluorophenyl)-1-cyclopropylethanone

The title compound was synthesized in a yield of 52% as a yellow oil using 2-(2,3,4-trifluorophenyl)-1-cyclopropylethanone instead of 2-(2,4-difluorophenyl)-1-cyclopropylethanone by conducting the reaction similar to that mentioned in Example 94 (b).

$^1$H NMR (400 MHz, CDCl$_3$) δ ppm: 0.96-1.24 (4H, m), 2.15-2.24 (1H, m), 5.85 (1H, s), 6.98-7.07 (1H, m), 7.22-7.31 (1H, m).

(c) (E)-4-(Acetylsulfanyl)-1-[2-cyclopropyl-1-(2,3,4-trifluorophenyl)-2-oxoethyl]-3-{[1H-imidazol-4(5)-yl]methylidene}piperidine dihydrochloride The title compound was synthesized in a yield of 33% as a pale yellow solid using 2-bromo-2-(2,3,4-trifluorophenyl)-1-cyclopropylethanone instead of 2-bromo-2-(2-fluorophenyl)-1-cyclopropylethanone by conducting successively reactions similar to those mentioned in Example 21 (d).

$^1$H NMR (400 MHz, CD$_3$OD) δ ppm: 0.95-1.30 (4H, m), 1.90-1.99 (1H, m), 2.12-2.24 (1H, m), 2.37 (3H, s), 2.42-2.62 (1H, m), 3.18-3.36 (2H, m), 3.88-4.35 (2H, m), 4.57 and 4.62 (total 1H, each t, J=5.0), 4.86 (1H, s), 6.03 and 6.09 (total 1H, each s), 6.80 and 6.83 (total 1H, each s), 7.33-7.61 (2H, m), 7.76 and 7.84 (total 1H, each s);

IR (KBr, cm$^{-1}$): 2596, 1701, 1490.

Example 131

(E)-1-[2-Cyclopropyl-1-(2,3,4-trifluorophenyl)-2-oxoethyl]-3-{[1H-imidazol-4(5)-yl]methylidene}-4-sulfanylpiperidine dihydrochloride (Exemplification Compound No. 1-185)

The title compound was synthesized in a yield of 97% as a colourless solid using (E)-4-(acetylsulfanyl)-1-[2-cyclopropyl-1-(2,3,4-trifluorophenyl)-2-oxoethyl]-3-{[1H-imidazol-4(5)-yl]methylidene}piperidine dihydrochloride instead of (E)-4-(acetylsulfanyl)-1-[2-cyclopropyl-1-(2-fluorophenyl)-2-oxoethyl]-3-[(furan-2-yl)methylidene]piperidine by conducting the reaction similar to that mentioned in Example 8.

$^1$H NMR (400 MHz, CDCl$_3$) δ ppm: 0.78-0.96 (2H, m), 1.11-1.21 (2H, m), 1.72-1.83 (1H, m), 1.94-2.08 (1H, m), 2.16-2.31 (1H, m), 2.45-2.54 and 2.55-2.64 (total 1H, each m), 2.71-2.82 (1H, m), 3.32-3.58 (1H, m), 3.41 and 3.64 (total 1H, each d, J=12.5), 3.77-3.88 (1H, m), 4.81 and 4.82 (total 1H, each s), 6.45 (1H, s), 6.93-7.18 (2H, m), 6.96 and 6.97 (total 1H, each s); 7.61 (1H, s);

IR (KBr, cm$^{-1}$): 2599, 1711, 1490.

Example 132

(E)-4-(Acetylsulfanyl)-1-[2-cyclopropyl-1-(2-fluorophenyl)-2-oxoethyl]-3-({1-[2-(methoxycarbonyl)ethyl]-1H-1,2,3-triazol-5-yl}methylidene)piperidine hydrochloride (Exemplification Compound No. 2-1230)

(a) Methyl 3-[5-(hydroxymethyl)-1H-1,2,3-triazol-1-yl]propanoate and methyl 3-[4-(hydroxymethyl)-1H-1,2,3-triazol-1-yl]propanoate To a solution of methyl 3-azidopropanoate (41.9 g) in toluene (800 ml) was added propargyl alcohol (25.0 g), and the resulting mixture was stirred at 110° C. for 20 hours. After the mixture was cooled to room temperature, it was concentrated under reduced pressure to afford a crude isomeric mixture of the two title compounds (51.52 g, gross yield: 86%, isomeric ratio: approximately 1:1) as an oil.

$^1$H NMR (400 MHz, CDCl$_3$) δ ppm: 2.94 and 3.07 (total 2H, each t, J=7.0), 3.65 and 3.67 (total 3H, each s), 4.57-4.64 (2H, m), 4.72 and 4.76 (total 2H, each s), 7.51 and 7.62 (total 1H, each s).

This product was used for the next step without further purification.

(b) Methyl 3-(5-formyl-1H-1,2,3-triazol-1-yl)propanoate and methyl 3-(4-formyl-1H-1,2,3-triazol-1-yl)propanoate To a stirred solution of the crude product obtained in the process mentioned above (51.52 g) in dichloromethane (800 ml) were added molecular sieves 4A (100 g) and pyridinium dichromate (160 g), and the resulting mixture was stirred at room temperature for 30 minutes. After filtration of the reaction mixture, the filtrate was washed with 1 N aqueous hydrochloric acid solution, and the organic layer was washed with a saturated aqueous sodium chloride solution and dried over anhydrous magnesium sulfate. After evaporation of the solvent under reduced pressure, the residue was purified by silica gel chromatography using dichloromethane and methanol (20:1) as the eluent to afford a mixture of the two title isomers (17.14 g, yield: 34%, isomeric ratio: approximately 1:1) as an oil.

$^1$H NMR (400 MHz, CDCl$_3$) δ ppm: 2.98 and 3.00 (total 2H, each t, J=7.0), 3.66 and 3.68 (total 3H, each s), 4.71 and 4.96 (total 2H, each t, J=7.0), 8.82 and 8.83 (total 1H, each s), 10.00 and 10.01 (total 1H, each s).

(c) (E)-3-({1-[2-(Methoxycarbonyl)ethyl]-1H-1,2,3-triazol-5-yl}methylidene)-1-(triphenylmethyl)piperidin-4-one and (E)-3-({1-[2-(methoxycarbonyl)ethyl]-1H-1,2,3-triazol-4-yl}methylidene)-1-(triphenylmethyl)piperidin-4-one To a solution of 1-(triphenylmethyl)piperidin-4-one (32.0 g) in benzene (500 ml) was added pyrrolidine (7.8 ml), and the resulting mixture was heated under reflux for 3 hours removing water under a Dean-Staak apparatus. After cooling to room temperature, a mixture (17.14 g) of methyl 3-(5-formyl-1H-1,2,3-triazol-1-yl)propanoate and methyl 3-(4-formyl-1H-1,2,3-triazol-1-yl)propanoate which was obtained as described above was added. The resulting mixture was heated under reflux for additional 3 hours. After the mixture was cooled to room temperature and diluted with water, products were extracted with ethyl acetate. The organic layer was washed with a saturated aqueous sodium chloride solution and dried over anhydrous magnesium sulfate. After evaporation of the solvent under reduced pressure, the residue was purified by silica gel chromatography using hexane, ethyl acetate, and dichloromethane (1:1:1) as the eluent to afford a mixture of two title isomers (32.89 g, yield: 69%, isomeric ratio: approximately 1:1) as an oil.

$^1$H NMR (400 MHz, CDCl$_3$) δ ppm: 2.62-2.83 (total 4H, m), 2.89 and 3.02 (total 2H, each t, J=6.5), 3.37 and 3.57 (total 2H, each bs), 3.62 and 3.69 (total 3H, s), 4.59 and 4.65 (total 2H, each t, J=6.5), 7.11-7.58 (17H, m).

The mixture was further purified by silica gel chromatography using hexane and ethyl acetate (1:1) as the eluent to afford the less polar isomer (E)-3-({1-[2-(methoxycarbonyl)ethyl]-1H-1,2,3-triazol-5-yl}methylidene)-1-(triphenylmethyl)piperidin-4-one (12.87 g), the more polar isomer (E)-3-({1-[2-(methoxycarbonyl)ethyl]-1H-1,2,3-triazol-4-yl}methylidene)-1-(triphenylmethyl)piperidin-4-one (13.36 g), and a mixture (5.21 g) of these two isomers, all as pale yellow amorphous solids.

(d) (E)-3-({1-[2-(Methoxycarbonyl)ethyl]-1H-1,2,3-triazol-5-yl}methylidene)-1-(triphenylmethyl)piperidin-4-ol (E)-3-({1-[2-(Methoxycarbonyl)ethyl]-1H-1,2,3-triazol-5-yl}methylidene)-1-(triphenylmethyl)piperidin-4-one (12.87 g) was dissolved in a mixed solvent of dichloromethane (100 ml) and methanol (100 ml). While the solution was being stirred at 0° C., sodium borohydride (480 mg) was added thereto. The resulting mixture was stirred at 0° C. for 30 minutes, and the reaction was stopped by addition of a saturated aqueous ammonium chloride solution. The product was extracted with dichloromethane. The organic layer was washed with a saturated sodium chloride solution and dried over anhydrous magnesium sulfate. The solvent was removed under reduced pressure to afford the crude title compound (13.22 g) as a pale yellow amorphous solid. This product was used in the next process without further purification.

$^1$H NMR (400 MHz, CDCl$_3$) δ ppm: 1.85-1.95 (2H, m), 2.11-2.17 (1H, m), 2.18-2.24 (2H, m), 2.90-2.98 (1H, m), 3.05 (2H, t, J=7.0), 3.68 (3H, s), 4.13 (1H, bs), 4.56 (2H, dt, J=7.0, 2.5), 6.45 (1H, s), 7.07-7.18 (10H, m), 7.30-7.35 (6H, m).

(e) (E)-4-(Acetylsulfanyl)-3-({1-[2-(methoxycarbonyl)ethyl]-1H-1,2,3-triazol-5-yl}methylidene)-1-(triphenylmethyl)piperidine, and 5-((acetylsulfanyl){1-[2-(methoxycarbonyl)ethyl]-1H-1,2,3-triazol-5-yl}methyl)-1-(triphenylmethyl)-1,2,3,6-tetrahydropyridine To a solution of (E)-3-({1-[2-(methoxycarbonyl)ethyl]-1H-1,2,3-triazol-5-yl}methylidene)-1-(triphenylmethyl)piperidin-4-ol (13.22 g) in toluene (200 ml) were added thioacetic acid (3.7 ml) and N,N-dimethylformamide dineopentyl acetal (14.5 ml) with stirring at room temperature, and the resulting mixture was stirred at the same temperature for 2 hours. After addition of aqueous sodium chloride solution, products were extracted with ethyl acetate. The extract was washed with a saturated aqueous sodium chloride solution and the organic layer was dried over anhydrous magnesium sulfate. After evaporation of the solvent under reduced pressure, the residue was purified by silica gel chromatography using a mixed solvent of ethyl acetate and hexane (2:1) as the eluent to afford 5-((acetylsulfanyl){1-[2-(methoxycarbonyl)ethyl]-1H-1,2,3-triazol-5-yl}methyl)-1-(triphenylmethyl)-1,2,3,6-tetrahydropyridine (8.17 mg, yield: 55%) as a pale yellow amorphous solid.

$^1$H NMR (400 MHz, CDCl$_3$) δ ppm: 2.13-2.33 (2H, m), 2.29 (3H, s), 2.34-2.48 (1H, m), 2.71 (1H, d, J=15.0), 2.86-3.11 (4H, m), 3.65 (3H, s), 4.43-4.50 (2H, m), 5.12 (1H, s), 5.59 (1H, bs), 7.08-7.50 (15H, m), 7.55 (1H, s).

Further elution with a mixed solvent of ethyl acetate and hexane (1:1) afforded (E)-4-(acetylsulfanyl)-3-({1-[2-(methoxycarbonyl)ethyl]-1H-1,2,3-triazol-5-yl}methylidene)-1-(triphenylmethyl)piperidine (4.27 g, yield: 29%) as a pale yellow amorphous solid.

$^1$H NMR (400 MHz, CDCl$_3$) δ ppm: 1.91-2.02 (1H, m), 2.08-2.25 (1H, m), 2.28 (3H, s), 2.34-2.47 (1H, m), 2.59-2.78 (2H, m), 3.03 (2H, t, J=7.0), 3.27-3.45 (1H, m), 3.72 (3H, s), 4.46-4.53 (1H, m), 4.57 (2H, t, J=7.0), 6.43 (1H, s), 7.08-7.51 (16H, m).

(f) (E)-4-(Acetylsulfanyl)-3-({1-[2-(methoxycarbonyl)ethyl]-1H-1,2,3-triazol-5-yl}methylidene)piperidine hydrogen trifluoroacetate To a solution of (E)-4-(acetylsulfanyl)-3-({1-[2-(methoxycarbonyl)ethyl]-1H-1,2,3-triazol-5-yl}methylidene)-1-(triphenylmethyl)piperidine (4.27 g) in dichloromethane (100 ml) was added trifluoroacetic acid (1.2 ml) with stirring at 0° C. The resulting mixture was stirred at 0° C. for 15 minutes and the solvent was evaporated under reduced pressure, and the residue was purified by silica gel chromatography using dichloromethane and methanol (10:1) as the eluent to afford the title compound (2.0 mg, yield: 61%) as a yellow amorphous solid.

$^1$H NMR (400 MHz, CDCl$_3$) δ ppm: 2.09-2.21 (1H, m), 2.38 (3H, s), 2.46-2.58 (1H, m), 3.04 (2H, t, J=6.0), 3.21-3.36 (1H, m), 3.51 (1H, d, J=13.5), 3.64 (3H, s), 3.83-3.94 (1H, m), 4.10 (1H, d, J=13.5), 4.52 (2H, t, J=6.0), 4.60-4.65 (1H, m), 6.82 (1H, s), 7.92 (1H, s).

(g) (E)-4-(Acetylsulfanyl)-1-[2-cyclopropyl-1-(2-fluorophenyl)-2-oxoethyl]-3-({1-[2-(methoxycarbonyl)ethyl]-1H-1,2,3-triazol-5-yl}methylidene)piperidine hydrochloride To a solution of (E)-4-(acetylsulfanyl)-3-({1-[2-(methoxycarbonyl)ethyl]-1H-1,2,3-triazol-5-yl}methylidene)piperidine hydrogen trifluoroacetate (3.5 g) in acetonitrile (100 ml) were added 2-bromo-2-(2-fluorophenyl)-1-cyclopropylethanone (4.1 g) and triethylamine (3.3 ml), and the resulting mixture was stirred at room temperature for 15 minutes. After addition of aqueous sodium chloride solution, products was extracted with ethyl acetate. The extract was washed with a saturated aqueous sodium chloride solution and the organic layer was dried over anhydrous magnesium sulfate. After evaporation of the solvent under reduced pressure, the residue was purified by silica gel chromatography using hexane, ethyl acetate, and dichloromethane (1:2:1) as the eluent to afford a free base of the title compound (1.97 g) as a pale yellow amorphous solid.

The free base obtained was treated with hydrogen chloride (4 N dioxane solution, 4 ml). The solvent and the excess hydrogen chloride were removed under reduced pressure to afford the title compound (2.2 g, yield: 51%) as a pale yellow amorphous solid.

$^1$H NMR (400 MHz, CDCl$_3$) δ ppm: 0.64-0.87 (2H, m), 0.91-1.05 (2H, m), 1.79-1.94 (1H, m), 1.95-2.04 (1H, m), 2.20-2.40 (1H, m), 2.31 and 2.32 (total 3H, each s), 2.43-2.62 (1H, m), 2.72-2.89 (1H, m), 2.90-3.21 (3H, m), 3.43-3.54 (1H, m), 3.68 and 3.70 (total 3H, each s), 4.40-4.54 (3H, m), 4.73 and 4.74 (total 1H, each s), 6.40 (1H, s), 7.05-7.18 (2H, m), 7.21-7.38 (2H, m), 7.39 and 7.45 (total 1H, each s);

IR (KBr, cm$^{-1}$): 2471, 1737, 1699.

Example 133

(E)-1-[2-Cyclopropyl-1-(2-fluorophenyl)-2-oxoethyl]-3-({1-[2-(ethoxycarbonyl)ethyl]-1H-1,2,3-triazol-5-yl}methylidene)-4-sulfanylpiperidine hydrochloride (Exemplification Compound No. 2-1245)

Hydrogen chloride was passed through a solution of (E)-4-(acetylsulfanyl)-1-[2-cyclopropyl-1-(2-fluorophenyl)-2-oxoethyl]-3-({1-[2-(methoxycarbonyl)ethyl]-1H-1,2,3-triazol-5-yl}methylidene)piperidine hydrochloride (2.0 g) in ethanol (5.0 ml) with stirring at 0° C. for one hour, and the resulting mixture was stirred at room temperature under tightly sealed condition for 4 hours. After the reaction mixture was concentrated under reduced pressure, the residue was purified using preparative HPLC [YMC-Pack ODS-A; YMC, eluent: acetonitrile/0.024 N aqueous hydrochloric acid solution (33:67, v/v)]. The eluate was treated with hydrogen chloride (4 N dioxane solution, 2 ml). The solvent and excess hydrogen chloride were removed under reduced pressure to afford the title compound (1.29 g, yield: 68%) as a colourless amorphous solid.

$^1$H NMR (400 MHz, CDCl$_3$) δ ppm: 0.66-0.83 (2H, m), 0.92-1.02 (2H, m), 1.19-1.27 (3H, m), 1.78-1.86 (1H, m), 1.95-2.02 (1H, m), 2.24-2.34 (1H, m), 2.62-2.70 (1H, m), 2.80-2.91 (1H, m), 2.92-3.01 (2H, m), 3.18 and 3.54 (total 1H, each d, J=13.0), 3.25 and 3.40 (total 1H, each d, J=13.0), 3.83-3.89 (1H, m), 4.08-4.17 (2H, m), 4.46-4.53 (2H, m), 4.74 and 4.75 (total 1H, each s), 6.40 and 6.41 (total 1H, each s), 7.05-7.17 (2H, m), 7.24-7.35 (2H, m), 7.38 and 7.44 (total 1H, each s);

IR (KBr, cm$^{-1}$): 2452, 1731, 1715.

Example 134

(E)-3-{[1-(2-Carboxyethyl)-1H-1,2,3-triazol-5-yl]methylidene}-1-[2-cyclopropyl-1-(2-fluorophenyl)-2-oxoethyl]-4-sulfanylpiperidine hydrochloride (Exemplification Compound No. 2-1213)

To (E)-1-[2-cyclopropyl-1-(2-fluorophenyl)-2-oxoethyl]-3-({1-[2-(ethoxycarbonyl)ethyl]-1H-1,2,3-triazol-5-yl}methylidene)-4-sulfanylpiperidine hydrochloride (500 mg) was added 3 N aqueous hydrochloric acid solution (20 ml) and the resulting mixture was stirred at 50° C. for 3 hours. After the reaction mixture was concentrated under reduced pressure, the residue was purified using preparative HPLC [YMC-Pack ODS-A; YMC, eluent: acetonitrile/0.024 N aqueous hydrochloric acid solution (25:75, v/v)] to afford the title compound (410 mg, yield: 87%) as a pale colourless amorphous solid.

$^1$H NMR (400 MHz, pyridine-d$_5$) δ ppm: 0.56-0.78 (2H, m), 0.86-1.08 (2H, m), 1.76-1.92 (1H, m), 2.19-2.36 (1H, m), 2.60-2.77 (1H, m), 2.82-3.04 (2H, m), 3.20-3.33 (2H, m), 3.55 and 3.79 (total 1H, each d, J=12.5), 3.57-3.73 (total 1H, each d, J=12.5), 4.00-4.07 (1H, m), 4.75-4.82 (2H, m), 4.94 and 4.95 (total 1H, each s), 6.81 and 6.83 (total 1H, each s), 7.13-7.21 (2H, m), 7.24-7.32 (1H, m), 7.55-7.62 (1H, m), 7.87 and 7.92 (total 1H, each s);

IR (KBr, cm$^{-1}$): 3403, 2552, 1712.

Example 135

(E)-4-(Acetylsulfanyl)-1-[2-cyclopropyl-1-(2-fluorophenyl)-2-oxoethyl]-3-({1-[2-(methoxycarbonyl)ethyl]-1H-1,2,3-triazol-4-yl}methylidene)piperidine (Exemplification Compound No. 2-1166)

(a) (E)-3-({1-[2-(Methoxycarbonyl)ethyl]-1H-1,2,3-triazol-4-yl}methylidene)-1-(triphenylmethyl)piperidin-4-ol Using (E)-3-({1-[2-(methoxycarbonyl)ethyl]-1H-1,2,3-triazol-4-yl}methylidene)-1-(triphenylmethyl)piperidin-4-one (13.36 g) which was obtained in Example 132 (c), a reaction similar to that described in Example 132 (d) afforded crude title compound (13.15 g; gross yield: 100%) as a pale yellow amorphous solid.

$^1$H NMR (400 MHz, CDCl$_3$) δ ppm: 1.84-1.95 (1H, m), 1.97-2.11 (2H, m), 2.11-2.21 (1H, m), 2.58 (1H, bs), 2.78 (1H, bs), 2.83-2.93 (2H, m), 3.70 (3H, s), 4.16 (1H, bs), 4.49 (2H, t, J=7.0), 6.61 (1H, s), 7.05-7.20 (10H, m), 7.35-7.45 (6H, m).

This product was used in the next process without further purification.

(b) (E)-4-(Acetylsulfanyl)-3-({1-[2-(methoxycarbonyl)ethyl]-1H-1,2,3-triazol-4-yl}methylidene)piperidine hydrogen trifluoroacetate To a solution of (E)-3-({1-[2-(methoxycarbonyl)ethyl]-1H-1,2,3-triazol-4-yl}methylidene)-1-(triphenylmethyl)piperidin-4-ol (13.15 g) in toluene (200 ml) were added thioacetic acid (3.7 ml) and N,N-dimethylformamide dineopentyl acetal (14.5 ml) at room temperature and the resulting mixture was stirred at the same temperature for 30 minutes. After aqueous sodium chloride solution was added, products were extracted with ethyl acetate and the extract was washed with a saturated aqueous sodium chloride solution. The organic layer was dried over anhydrous magnesium sulfate. After evaporation of the solvent under reduced pressure, the residue was purified by silica gel chromatography using ethyl acetate and hexane (1:1) as the eluent to afford a mixture (12.92 g) of (E)-4-(acetylsulfanyl)-3-({1-[2-(methoxycarbonyl)ethyl]-1H-1,2,3-triazol-4-yl}methylidene)-1-(triphenylmethyl)piperidine and 5-((acetylsulfanyl){1-[2-(methoxycarbonyl)ethyl]-1H-1,2,3-triazol-4-yl}methyl)-1-(triphenylmethyl)-1,2,3,6-tetrahydropyridine.

To a solution of this mixture in dimethyl sulfoxide (180 ml) was added potassium thioacetate (326.0 g) and the resulting mixture was stirred at 80° C. for 4 hours. After the mixture was cooled to room temperature, water was added and products were extracted with ethyl acetate. The extract was washed with a saturated aqueous sodium chloride solution and the organic layer was dried over anhydrous magnesium sulfate. The solvent was removed under reduced pressure to afford an approximately 3:1 mixture of (E)-4-(acetylsulfanyl)-3-({1-[2-(methoxycarbonyl)ethyl]-1H-1,2,3-triazol-4-yl}methylidene)-1-(triphenylmethyl)piperidine and its (Z)-isomer (12.92 g, containing a small amount of 5-((acetylsulfanyl){1-[2-(methoxycarbonyl)ethyl]-1H-1,2,3-triazol-4-yl}methyl)-1-(triphenylmethyl)-1,2,3,6-tetrahydropyridine).

To a solution of this mixture in dichloromethane (400 ml) was added trifluoroacetic acid (4.2 ml) and the resulting mixture was stirred at room temperature for 15 minutes. After evaporation of the solvent under reduced pressure, the residue was purified by silica gel chromatography using a mixed solvent of dichloromethane and methanol (10:1) as the eluent to afford the title compound (3.62 g, yield: 38%) as a yellow amorphous solid.

$^1$H NMR (400 MHz, CDCl$_3$) δ ppm: 2.05-2.13 (1H, m), 2.33 (3H, s), 2.44-2.56 (1H, m), 2.91 (2H, t, J=6.5), 3.15-3.25 (1H, m), 3.43-3.48 (1H, m), 3.66 (3H, s), 3.87 (1H, d, J=14.0), 4.53-4.61 (3H, m), 5.17 (1H, d, J=14.0), 6.60 (1H, s), 7.62 (1H, s).

Further elution with the same solvent afforded a mixture (2.22 g) of (Z)-4-(acetylsulfanyl)-3-({1-[2-(methoxycarbonyl)ethyl]-1H-1,2,3-triazol-4-yl}methylidene)piperidine hydrogen trifluoroacetate and 5-((acetylsulfanyl){1-[2-(methoxycarbonyl)ethyl]-1H-1,2,3-triazol-4-yl}methyl)-1,2,3,6-tetrahydropyridine hydrogen trifluoroacetate as a colourless amorphous solid.

(c) (E)-4-(Acetylsulfanyl)-1-[2-cyclopropyl-1-(2-fluorophenyl)-2-oxoethyl]-3-({1-[2-(methoxycarbonyl)ethyl]-1H-1,2,3-triazol-4-yl}methylidene]piperidine Using (E)-4-(acetylsulfanyl)-3-({1-[2-(methoxycarbonyl)ethyl]-1H-1,2,3-triazol-5-yl}methylidene)piperidine hydrogen trifluoroacetate (3.62 g), a similar reaction to that mentioned in Example 132 (g) gave the title compound (2.72 g, yield: 66%) as a pale yellow amorphous solid.

$^1$H NMR (400 MHz, CDCl$_3$) δ ppm: 0.62-1.05 (4H, m), 1.75-1.91 (1H, m), 2.06-2.18 (1H, m), 2.16-2.30 (1H, m), 2.28 (3H, s), 2.38-2.49 and 2.54-2.66 (total 1H, each m), 2.69-2.81 (1H, m), 2.92 and 2.94 (total 2H, each t, J=7.0), 3.14 and 3.21 (total 1H, each d, J=13.0), 3.69 (3H, s), 3.87 and 3.99 (total 1H, each d, J=13.0), 4.42-4.48 (1H, m), 4.56 and 4.59 (total 2H, each t, J=7.0), 4.72 and 4.75 (total 1H, each s), 6.51 and 6.52 (total 1H, each s), 7.03-7.16 (2H, m), 7.26-7.40 (2H, m), 7.52 and 7.59 (total 1H, each s).

Example 136

(E)-1-[2-Cyclopropyl-1-(2-fluorophenyl)-2-oxoethyl]-3-({1-[2-(ethoxycarbonyl)ethyl]-1H-1,2,3-triazol-4-yl}methylidene)-4-sulfanylpiperidine hydrochloride (Exemplification Compound No. 2-1181)

Using (E)-4-(acetylsulfanyl)-1-[2-cyclopropyl-1-(2-fluorophenyl)-2-oxoethyl]-3-({1-[2-(methoxycarbonyl)ethyl]-1H-1,2,3-triazol-4-yl}methylidene)piperidine (3.13 g), a similar reaction to that mentioned in Example 133 gave the title compound (2.42 g, yield: 82%) as a colourless amorphous solid.

$^1$H NMR (400 MHz, CDCl$_3$) δ ppm: 0.63-0.86 (2H, m), 0.89-1.06 (2H, m), 1.19-1.30 (3H, m), 1.71-1.84 (1H, m), 2.05-2.16 (1H, m), 2.18-2.34 (1H, m), 2.54-2.68 (1H, m), 2.71-2.91 (1H, m), 2.93 (2H, q, J=7.0), 3.50-3.67 (2H, m), 3.85-3.92 (1H, m), 4.10-4.15 (total 2H, q, J=7.0), 4.53-4.63 (2H, m), 4.77 and 4.78 (total 1H, each s), 6.53 and 6.54 (total 1H, each s), 7.03-7.18 (2H, m), 7.26-7.42 (2H, m), 7.54 and 7.62 (total 1H, each s);

IR (KBr, cm$^{-1}$): 2916, 2516, 2452, 1731, 1716.

Example 137

(E)-3-{[1-(2-Carboxyethyl)-1H-1,2,3-triazol-4-yl]methylidene}-1-[2-cyclopropyl-1-(2-fluorophenyl)-2-oxoethyl]-4-sulfanylpiperidine hydrochloride (Exemplification Compound No. 2-1149)

Using (E)-1-[2-cyclopropyl-1-(2-fluorophenyl)-2-oxoethyl]-3-({1-[2-(ethoxycarbonyl)ethyl]-1H-1,2,3-triazol-4-yl}methylidene)-4-sulfanylpiperidine hydrochloride (600 mg), a similar reaction to that mentioned in Example 134 gave the title compound (470 mg, yield: 83%) as a colourless amorphous solid.

$^1$H NMR (500 MHz, pyridine-$d_5$) δ ppm: 0.62-0.75 (2H, m), 0.90-1.03 (1H, m), 1.04-1.20 (1H, m), 1.76-1.92 (1H, m), 2.22-2.35 (1H, m), 2.35-2.45 (1H, m), 2.65-2.77 (1H, m), 2.85-2.92 and 2.96-3.03 (total 1H, each m), 3.19 (2H, q, J=7.0), 3.95-4.31 (3H, m), 4.81 (2H, q, J=7.0), 4.96 and 4.97 (total 1H, each s), 6.74 and 6.97 (total 1H, each s), 7.12-7.22 (2H, m), 7.26-7.34 (1H, m), 7.61-7.70 (1H, m), 7.99 and 8.07 (total 1H, each s);

IR (KBr, cm$^{-1}$): 2927, 2560, 1712.

Example 138

(E)-4-(Acetylsulfanyl)-1-[2-cyclopropyl-1-(2-fluorophenyl)-2-oxoethyl]-3-({1-[3-(ethoxycarbonyl)propyl]-1H-1,2,3-triazol-5-yl}methylidene)piperidine hydrochloride (Exemplification Compound No. 2-1250)

(a) Ethyl 4-(5-formyl-1H-1,2,3-triazol-1-yl)butanoate and ethyl 4-(4-formyl-1H-1,2,3-triazol-1-yl)butanoate To a solution of ethyl 4-azidobutanoate (60 g) in toluene (500 ml) was added propargyl alcohol (31 ml). The resulting mixture was stirred at 110° C. for 18 hours. After cooling to room temperature, the reaction mixture was concentrated under reduced pressure to afford a crude product of a mixture of ethyl 4-[5-(hydroxymethyl)-1H-1,2,3-triazol-1-yl]butanoate and ethyl 3-[4-(hydroxymethyl)-1H-1,2,3-triazol-1-yl]butanoate (82 g, gross yield: quantitative, isomeric ratio: approximately 1:1) as an oil. The crude product, without further purification, was dissolved in dichloromethane (700 ml), and molecular sieves 4A (100 g) was added thereto with stirring. Then pyridinium dichromate (145 g) was carefully added to the reaction mixture with cooling using a water-bath. After the mixture was stirred at room temperature for one hour, it was filtrated with celite, and the filtrate was concentrated under reduced pressure. The residue was purified by silica gel chromatography using dichloromethane and methanol (19:1) as the eluent to afford a mixture of two title isomers (31 g, yield: 38%, isomeric ratio: approximately 1:1) as a yellow oil.

$^1$H NMR (500 MHz, CDCl$_3$) δ ppm: 1.26 (3H, t, J=7.0), 1.27 (3H, t, J=7.0), 2.23 (2H, t, J=7.0), 2.28 (2H, t, J=7.0), 2.34-2.40 (4H, m), 4.13 (2H, q, J=7.0), 4.16 (2H, q, J=7.0), 4.54 (2H, t, J=7.0), 4.79 (2H, t, J=7.0), 8.13 (1H, s), 8.26 (1H, s), 10.01 (1H, s), 10.15 (1H, s).

(b) (E)-3-({1-[3-(Ethoxycarbonyl)propyl]-1H-1,2,3-triazol-5-yl}methylidene)-1-(triphenylmethyl)piperidin-4-one and (E)-3-({1-[3-(ethoxycarbonyl)propyl]-1H-1,2,3-triazol-4-yl}methylidene)-1-(triphenylmethyl)piperidin-4-one To a solution of 1-(triphenylmethyl)piperidin-4-one (24.3 g) in benzene (200 ml) was added pyrrolidine (6.46 ml) and the resulting mixture was heated under reflux for 3.5 hours removing water using a Dean-Staak apparatus. The reaction mixture was cooled with ice and the above obtained mixture (15.0 g) of ethyl 4-(5-formyl-1H-1,2,3-triazol-1-yl)butanoate and ethyl 4-(4-formyl-1H-1,2,3-triazol-1-yl)butanoate was added thereto. The resulting mixture was heated under reflux for further 5.5 hours, cooled to room temperature, and diluted with water. The product was extracted with ethyl acetate. After the organic layer was washed with a saturated aqueous sodium chloride solution, it was dried over anhydrous magnesium sulfate. After evaporation of the solvent under reduced pressure, the residue was repeatedly purified by silica gel chromatography for 4 times using hexane and ethyl acetate (1:1) as the eluent to afford the less polar isomer (E)-3-({1-[3-(ethoxycarbonyl)propyl]-1H-1,2,3-triazol-5-yl}methylidene}-1-(triphenylmethyl)piperidin-4-one (14.48 g, yield: 38%) as a pale yellow crystalline solid and the more polar isomer, (E)-3-({1-[3-(ethoxycarbonyl)propyl]-1H-1,2,3-triazol-4-yl}methylidene}-1-(triphenylmethyl)piperidin-4-one (13.08 g, yield: 34%) as a yellow crystalline solid, respectively.

The less polar isomer, (E)-3-({1-[3-(ethoxycarbonyl)propyl]-1H-1,2,3-triazol-5-yl}methylidene)-1-(triphenylmethyl)piperidin-4-one: $^1$H NMR (500 MHz, CDCl$_3$) δ ppm: 1.27 (3H, t, J=7.0), 2.21 (2H, t, J=7.0), 2.33 (2H, t, J=7.0), 2.73 (2H, bs), 2.80 (2H, t, J=6.0), 3.38 (2H, bs), 4.16 (2H, q, J=7.0), 4.51 (2H, t, J=7.0), 7.16-7.53 (17H, m).

The more polar isomer, (E)-3-({1-[3-(ethoxycarbonyl)propyl]-1H-1,2,3-triazol-4-yl}methylidene)-1-(triphenylmethyl)piperidin-4-one: $^1$H NMR (500 MHz, CDCl$_3$) δ ppm: 1.26 (3H, t, J=7.0), 2.13-2.19 (2H, m), 2.25 (2H, t, J=7.0), 2.67 (2H, bs), 2.77 (2H, t, J=6.0), 3.63 (2H, bs), 4.14 (2H, q, J=7.0), 4.39 (2H, t, J=7.0), 7.16 (3H, t, J=7.0), 7.23-7.56 (14H, m).

(c) (E)-3-({1-[3-(Ethoxycarbonyl)propyl]-1H-1,2,3-triazol-5-yl}methylidene)-1-(triphenylmethyl)piperidin-4-ol To a solution of (E)-3-({1-[3-(ethoxycarbonyl)propyl]-1H-1,2,3-triazol-5-yl}methylidene)-1-(triphenylmethyl)piperidin-4-one (14.48 g) in a mixed solvent of dichloromethane (50 ml) and ethanol (200 ml) was added sodium borohydride (1.13 g) with stirring under ice-cooling. After the resulting mixture was stirred at room temperature for 30 minutes, the reaction was stopped by addition of an aqueous ammonium chloride solution. The product was extracted with ethyl acetate. After the organic layer was washed with a saturated aqueous sodium chloride solution, it was dried over anhydrous magnesium sulfate. Solvents were removed under reduced pressure to afford the title compound (14.63 g, yield: quantitative) as a colourless crystalline solid.

$^1$H NMR (400 MHz, CDCl$_3$) δ ppm: 1.28 (3H, t, J=7.0), 1.84-1.97 (2H, m), 2.11-2.33 (4H, m), 2.34-2.51 (2H, m), 2.99 (1H, bs), 3.75 (1H, bs), 4.07-4.22 (3H, m), 4.35-4.51 (2H, m), 6.45 (1H, s), 7.07-7.42 (16H, m).

(d) (E)-4-(Acetylsulfanyl)-3-({1-[3-(ethoxycarbonyl)propyl]-1H-1,2,3-triazol-5-yl}methylidene)-1-(triphenylmethyl)piperidine To a solution of (E)-3-({1-[3-(ethoxycarbonyl)propyl]-1H-1,2,3-triazol-5-yl}methylidene)-1-(triphenylmethyl)piperidin-4-ol (14.34 g) in N,N-dimethylformamide (100 ml) was added N,N-dimethylformamide dineopentyl acetal (14.90 ml). Then thioacetic acid (3.58 ml) was added to the reaction mixture under ice-cooling. The resulting mixture was stirred at room temperature for 30 minutes and then N,N-dimethylformamide dineopentyl acetal (14.90 ml) and additional thioacetic acid (3.58 ml) were supplemented, and the resulting mixture was stirred for one hour. Further N,N-dimethylformamide dineopentyl acetal (14.90 ml) and thioacetic acid (3.58 ml) were added, and the resulting mixture was stirred for 30 minutes. Still further N,N-dimethylformamide dineopentyl acetal (14.90 ml) and thioacetic acid (3.58 ml) were added, and the resulting mixture was stirred for 30 minutes. Then aqueous sodium chloride solution was added to the reaction mixture, and the product was extracted with ethyl acetate. The extract was washed with a saturated aqueous sodium chloride solution and the organic layer was dried over anhydrous magnesium sulfate. After evaporation of the solvent under reduced pressure, the residue was repeatedly purified for three times by silica gel chromatography using ethyl acetate and hexane (1:1 or 2:1) as the eluent to afford the less polar isomer title compound (7.45 g, yield: 47%), as a yellow foam and the more polar isomer 5-((acetylsulfanyl){1-[3-(ethoxycarbonyl)propyl]-1H-1,2,3-triazol-5-yl}methyl)-1-(triphenylmethyl)-1,2,3,6-tetrahydropyridine (5.58 g, yield: 35%) as an orange-coloured foam, respectively.

The less polar isomer title compound (E)-4-(acetylsulfanyl)-3-({1-[3-(ethoxycarbonyl)propyl]-1H-1,2,3-triazol-5-yl}methylidene)-1-(triphenylmethyl)piperidine: $^1$H NMR (400 MHz, CDCl$_3$) δ ppm: 1.26 (3H, t, J=7.0), 1.92-2.01 (1H, m), 2.06-2.27 (2H, m), 2.29 (3H, s), 2.35-2.46 (3H, m), 2.70 (2H, bs), 3.30 (1H, d, J=5.0), 3.41 (1H, bs), 4.17 (2H, q, J=7.0), 4.40 (2H, t, J=7.0), 4.48-4.53 (1H, m), 6.38 (1H, s), 7.11-7.43 (16H, m).

The more polar isomer 5-((acetylsulfanyl){1-[3-(ethoxycarbonyl)propyl]-1H-1,2,3-triazol-5-yl}methyl)-1-(triphenylmethyl)-1,2,3,6-tetrahydropyridine: $^1$H NMR (400 MHz, CDCl$_3$) δ ppm: 1.21-1.30 (3H, m), 2.09-2.50 (7H, m), 2.59-2.75 (1H, m), 2.86-3.10 (2H, m), 3.17-3.24 (1H, m), 3.28-3.34 (2H, m), 4.05-4.18 (2H, m), 4.21-4.36 (2H, m), 5.07 (1H, bs), 5.58 (1H, bs), 7.12-7.57 (16H, m).

(e) (E)-4-(Acetylsulfanyl)-3-({1-[3-(ethoxycarbonyl)propyl]-1H-1,2,3-triazol-5-yl}methylidene)piperidine hydrogen trifluoroacetate To a solution of (E)-4-(acetylsulfanyl)-3-({1-[3-(ethoxycarbonyl)propyl]-1H-1,2,3-triazol-5-yl}methylidene)-1-(triphenylmethyl)piperidine (7.45 g) in dichloromethane (80 ml) was added trifluoroacetic acid (2.86 ml) with stirring at room temperature. After the resulting mixture was stirred at room temperature for one hour, solvents were removed under reduced pressure. The residue was purified by silica gel chromatography using dichloromethane and methanol (10:1) as the eluent to afford the title compound (5.39 g, including impurities) as an orange-coloured oil.

$^1$H NMR (500 MHz, CDCl$_3$, selected signals) δ ppm: 1.22-1.28 (3H, m), 1.79-1.93 (1H, m), 2.09-2.19 (3H, m), 2.33-2.38 (2H, m), 2.40 (3H, s), 2.47-2.57 (1H, m), 3.14-3.22 (1H, m), 3.36-3.43 (1H, m), 3.76 (1H, d, J=14.0), 4.08-4.15 (2H, m), 4.30-4.39 (2H, m), 4.61-4.65 (1H, m), 6.67 (1H, s), 7.60-7.64 (1H, m).

This product was used in the next process without further purification.

(f) (E)-4-(Acetylsulfanyl)-1-[2-cyclopropyl-1-(2-fluorophenyl)-2-oxoethyl]-3-({1-[3-(ethoxycarbonyl)propyl]-1H-1,2,3-triazol-5-yl}methylidene)piperidine hydrochloride To 2-bromo-2-(2-fluorophenyl)-1-cyclopropylethanone (4.46 g) was added a solution of the crude product of (E)-4-(acetylsulfanyl)-3-({1-[3-(ethoxycarbonyl)propyl]-1H-1,2,3-triazol-5-yl}methylidene)piperidine hydrogen trifluoroacetate (5.39 g), obtained as described above, in acetonitrile (100 ml) with stirring, and then triethylamine (4.05 ml) was added thereto. The resulting mixture was stirred at room temperature for 2.5 hours, and diluted with water. The product was extracted with ethyl acetate and the extract was washed with a saturated aqueous sodium chloride solution. The organic layer was dried over anhydrous magnesium sulfate. After evaporation of the solvent under reduced pressure, the residue was purified by silica gel chromatography using hexane and ethyl acetate (1:2) as the eluent to afford the free base of the title compound (3.24 g, yield: 53%) as a yellow oil.

To a solution of the resulting free base obtained in dichloromethane (30 ml) was added hydrogen chloride (4 N dioxane solution, 4.60 ml). The solvent and excess hydrogen chloride were removed under reduced pressure to afford the title compound (4.22 g, yield from the free base: quantitative) as a pale yellow foam.

$^1$H NMR (500 MHz, pyridine-d$_5$) δ ppm: 0.64-0.78 (2H, m), 0.96-1.09 (2H, m), 1.09-1.15 (3H, m), 1.89-1.98 (1H, m), 2.18-2.30 (3H, m), 2.34 (3H, d, J=11.0), 2.39-2.45 (2H, m), 2.57-2.64 and 2.65-2.72 (total 1H, each m), 2.81-2.88 and 2.91-2.99 (total 1H, each m), 3.24 and 3.43 (total 1H, each d, J=13.0), 3.89 (1H, q, J=7.0), 4.06-4.13 (2H, m), 4.50 (2H, t, J=7.0), 4.70 (1H, bs), 5.00 (1H, d, J=8.0), 6.70 (1H, bs), 7.20-7.28 (2H, m), 7.33-7.39 (1H, m), 7.58-7.65 (1H, m), 7.95 and 7.98 (total 1H, each s);

MS (FAB) m/z: 529 (M+H)$^+$;

IR (KBr, cm$^{-1}$): 1709, 1493.

Example 139

(E)-1-[2-Cyclopropyl-1-(2-fluorophenyl)-2-oxoethyl]-3-({1-[3-(ethoxycarbonyl)propyl]-1H-1,2,3-triazol-5-yl}methylidene)-4-sulfanylpiperidine hydrochloride (Exemplification Compound No. 2-1249)

Hydrogen chloride was passed through a solution of (E)-4-(acetylsulfanyl)-1-[2-cyclopropyl-1-(2-fluorophenyl)-2-oxoethyl]-3-({1-[3-(ethoxycarbonyl)propyl]-1H-1,2,3-triazol-5-yl}methylidene)piperidine hydrochloride (4.15 g) in ethanol (50 ml) with stirring under ice-cooling for one hour and the resulting mixture was stirred at room temperature overnight under a tightly sealed condition. After concentration of the reaction mixture under reduced pressure, ethyl acetate and an aqueous sodium hydrogencarbonate solution were added to the residue. The organic layer was collected, washed with a saturated aqueous sodium chloride solution, and dried over anhydrous magnesium sulfate. After evaporation of the solvent under reduced pressure, the residue was purified by silica gel chromatography using hexane and ethyl acetate (1:3) as the eluent, and the crude fraction thus obtained was further purified by preparative HPLC (YMC-Pack ODS-A; YMC, eluent: acetonitrile/0.024 N aqueous hydrochloric acid solution, 40:60, v/v). The fraction obtained was neutralized with an aqueous sodium hydrogencarbonate solution. The resulting free base was extracted with ethyl acetate, and the organic layer was washed with a saturated aqueous sodium chloride solution and dried over anhydrous magnesium sulfate. The solvent was removed under reduced pressure to afford the free base of the title compound (1.93 g, yield: 54%) as a pale yellow oil.

To a solution of the free base thus obtained (1.93 g) in dichloromethane (20 ml) was added hydrogen chloride (4 N dioxane solution, 2.97 ml). After 10 minutes, the solvent and excess hydrogen chloride were removed under reduced pressure to afford the title compound (2.37 g, yield from the free base: quantitative) as a pale yellow foam.

$^1$H NMR (500 MHz, pyridine-$d_5$) δ ppm: 0.63-0.77 (2H, m), 0.94-1.00 (1H, m), 1.01-1.07 (1H, m), 1.12 (3H, t, J=7.0), 1.85-1.94 (1H, m), 2.21-2.38 (4H, m), 2.40-2.45 (2H, m), 2.67-2.79 (1H, m), 2.92-3.04 (1H, m), 3.54-3.61 (1H, m), 3.75 and 3.83 (total 1H, each d, J=12.0), 4.06-4.13 (3H, m), 4.50 (2H, t, J=7.0), 4.98 (1H, bs), 6.69 (1H, bs), 7.19-7.25 (2H, m), 7.30-7.37 (1H, m) 7.59-7.65 (1H, m), 7.90 and 7.95 (total 1H, each s);

MS (FAB) m/z: 487 (M+H)$^+$;

IR (KBr, cm$^{-1}$): 1716, 1493.

Example 140

(E)-3-{[1-(3-Carboxypropyl)-1H-1,2,3-triazol-5-yl] methylidene}-1-[2-cyclopropyl-1-(2-fluorophenyl)-2-oxoethyl]-4-sulfanylpiperidine hydrochloride (Exemplification Compound No. 2-1217)

Using (E)-1-[2-cyclopropyl-1-(2-fluorophenyl)-2-oxoethyl]-3-{[1-[3-(ethoxycarbonyl)propyl]-1H-1,2,3-triazol-5-yl}methylidene)-4-sulfanylpiperidine hydrochloride (1.58 g), a similar reaction to that mentioned in Example 134 gave the title compound (696 mg, yield: 47%) as a pale yellow foam.

$^1$H NMR (500 MHz, pyridine-$d_5$) δ ppm: 0.64-0.78 (2H, m), 0.93-1.00 (1H, m), 1.01-1.08 (1H, m), 1.85-1.94 (1H, m), 2.28-2.39 (3H, m), 2.55-2.61 (2H, m), 2.68-2.77 (1H, m), 2.91-3.03 (2H, m), 3.61 (1H, d, J=13.0), 3.77 and 3.85 (total 1H, each d, J=13.0), 4.11 (1H, bs), 4.60 (2H, t, J=7.0), 4.99 (1H, s), 6.77 (1H, d, J=4.0), 7.18-7.25 (2H, m), 7.28-7.36 (1H, m) 7.59-7.68 (1H, m), 7.91 and 7.97 (total 1H, each s);

MS (FAB) m/z: 259 (M+H)$^+$;

IR (KBr, cm$^{-1}$): 1711, 1493.

Example 141

(E)-4-(Acetylsulfanyl)-1-[2-cyclopropyl-1-(2-fluorophenyl)-2-oxoethyl]-3-({-[3-(ethoxycarbonyl)propyl]-1H-1,2,3-triazol-4-yl}methylidene)piperidine hydrochloride (Exemplification Compound No. 2-1186)

(a) (E)-3-({1-[3-(Ethoxycarbonyl)propyl]-1H-1,2,3-triazol-4-yl}methylidene)-1-(triphenylmethyl)piperidin-4-ol Using (E)-3-({1-[3-(ethoxycarbonyl)propyl]-1H-1,2,3-triazol-4-yl}methylidene)-1-(triphenylmethyl)piperidin-4-one (13.08 g), which was obtained as described in Example 138 (b), a similar reaction to that mentioned in Example 138 (c) gave the title compound (13.69 g, yield: quantitative) as a pale yellow foam.

$^1$H NMR (400 MHz, CDCl$_3$) δ ppm: 1.23-1.29 (3H, m), 1.75 (1H, bs), 1.85-1.96 (1H, m), 2.05-2.21 (3H, m), 2.27 (2H, t, J=7.0), 2.49-2.68 (1H, m), 2.70-2.85 (1H, m), 3.75 (1H, bs), 4.08-4.19 (3H, m), 4.22-4.31 (2H, m), 6.64 (1H, s), 7.03-7.22 (10H, m), 7.33-7.46 (6H, m).

(b) (E)-4-(Acetylsulfanyl)-3-({1-[3-(ethoxycarbonyl) propyl]-1H-1,2,3-triazol-4-yl}methylidene)piperidine hydrogen trifluoroacetate To a solution of (E)-3-({1-[3-(ethoxycarbonyl)propyl]-1H-1,2,3-triazol-4-yl}methylidene)-1-(triphenylmethyl)piperidin-4-ol (13.7 g) in N,N-dimethylformamide (50 ml) were added N,N-dimethylformamide dineopentyl acetal (14.2 ml) and thioacetic acid (3.4 ml) with stirring at room temperature. The resulting mixture was stirred at room temperature for 0.5 hours and then water and ethyl acetate were added to separate the layers. After the organic layer was washed with a saturated aqueous sodium chloride solution, it was dried over anhydrous magnesium sulfate. After evaporation of the under reduced pressure, the residue was purified by silica gel chromatography using ethyl acetate, hexane, and dichloromethane (2:1:1 to 1:1:1) as the eluent to afford an approximately 1:2 mixture (12.8 g) of (E)-4-(acetylsulfanyl)-3-({1-[3-(ethoxycarbonyl)propyl]-1H-1,2,3-triazol-4-yl}methylidene)-1-(triphenylmethyl)piperidine and 5-((acetylsulfanyl){1-[3-(ethoxycarbonyl)propyl]-1H-1,2,3-triazol-4-yl}methyl)-1-(triphenylmethyl)-1,2,3-tetrahydropyridine. Furthermore, this mixture contained a small amount of (Z)-4-(acetylsulfanyl)-3-({1-[3-(ethoxycarbonyl)propyl]-1H-1,2,3-triazol-4-yl}methylidene)-1-(triphenylmethyl)piperidine.

To a solution of the mixture (12.8 g) obtained in the process mentioned above in dichloromethane (100 ml) was added trifluoroacetic acid (4.91 ml) at room temperature. After the mixture was stirred at room temperature for one hour, solvents were removed under reduced pressure, and the residue was purified twice repeatedly by silica gel chromatography using dichloromethane and methanol (10:1) as the eluent to afford the least polar isomer (Z)-4-(acetylsulfanyl)-3-({1-[3-(ethoxycarbonyl)propyl]-1H-1,2,3-triazol-4-yl}methylidene)piperidine hydrogen trifluoroacetate (0.46 mg, total yield from process (a): 3.9%) as a pale yellow oil, the more polar isomer title compound (2.37 g, total yield from process (a): 21%) as a colourless crystalline solid, and the most polar isomer 5-((acetylsulfanyl){1-[3-(ethoxycarbonyl) propyl]-1H-1,2,3-triazol-4-yl}methyl)-1,2,3,6-tetrahydropyridine hydrogen trifluoroacetate (6.49 g, total yield from process (a): 55%) as a yellow oil, respectively.

The title compound (E)-4-(acetylsulfanyl)-3-({1-[3-(ethoxycarbonyl)propyl]-1H-1,2,3-triazol-4-yl}methylidene)piperidine hydrogen trifluoroacetate:

$^1$H NMR (500 MHz, CDCl$_3$) δ ppm: 1.26 (3H, t, J=7.0), 1.84 (1H, bs), 2.07-2.14 (1H, m), 2.14-2.22 (2H, m), 2.33 (2H, t, J=7.0), 2.37 (3H, s), 2.49-2.59 (1H, m), 3.22 (1H, t, J=12.0), 3.45-3.52 (1H, m), 3.89 (1H, d, J=14.0), 4.14 (2H, q, J=7.0), 4.40 (2H, t, J=7.0), 4.57-4.61 (1H, m), 5.22 (1H, d, J=14.0), 6.66 (1H, s), 7.55 (1H, s).

(c) (E)-4-(Acetylsulfanyl)-1-[2-cyclopropyl-1-(2-fluorophenyl)-2-oxoethyl]-3-({1-[3-(ethoxycarbonyl) propyl]-1H-1,2,3-triazol-4-yl}methylidene)piperidine hydrochloride To 2-bromo-2-(2-fluorophenyl)-1-cyclopropylethanone (1.96 g) was added a solution of (E)-4-(acetylsulfanyl)-3-({1-[3-(ethoxycarbonyl)propyl]-1H-1,2,3-triazol-4-yl}methylidene)piperidine hydrogen trifluoroacetate (2.37 g) in acetonitrile (40 ml) with stirring, and triethylamine (1.78 ml) was further added. After the mixture was stirred at room temperature for 2.5 hours, water was added, the product was extracted with ethyl acetate, the extract was washed with a saturated aqueous sodium chloride solution, and the organic layer was dried over anhydrous magnesium sulfate. After evaporation of the solvent under reduced pressure, the residue was purified by chromatography on silica gel column using hexane and ethyl acetate (1:2) as the eluent to afford the free base of the title compound (2.07 g, yield: 77%) as a yellow oil.

To a solution of the thus obtained free base in dichloromethane (20 ml) was added hydrogen chloride (4 N dioxane solution, 2.94 ml). The solvent and excess hydrogen chloride were removed under reduced pressure to afford the title compound (2.42 g, yield from the free base: quantitative) as a pale yellow foam.

$^1$H NMR (500 MHz, pyridine-$d_5$) δ ppm: 0.68-0.79 (2H, m), 0.99-1.05 (1H, m), 1.10-1.20 (4H, m), 1.91-2.00 (1H, m), 2.18-2.26 (2H, m), 2.27 (3H, s), 2.32-2.46 (5H, m), 2.55-2.61 and 2.72-2.79 (total 1H, each m), 2.89-2.96 (11H, m), 3.51-3.59 (1H, m), 4.06-4.13 (2H, m), 4.44-4.51 (2H, m), 4.72-4.77 (1H, m), 5.02 (1H, d, J=11.0), 6.90 (1H, d, J=9.0), 7.20-7.27 (2H, m), 7.32-7.40 (1H, m), 7.64-7.72 (1H, m), 7.91 and 8.00 (total 1H, each s);

MS (FAB) m/z: 529 (M+H)$^+$;

IR (KBr, cm$^{-1}$): 1710, 1494.

Example 142

(E)-1-[2-Cyclopropyl-1-(2-fluorophenyl)-2-oxoethyl]-3-({1-[3-(ethoxycarbonyl)propyl]-1H-1,2,3-triazol-4-yl}methylidene)-4-sulfanylpiperidine hydrochloride (Exemplification Compound No. 2-1185)

The title compound (1.32 g) was synthesized in a yield of 62% as a pale yellow foam using (E)-4-(acetylsulfanyl)-1-[2-cyclopropyl-1-(2-fluorophenyl)-2-oxoethyl]-3-({1-[3-(ethoxycarbonyl)propyl]-1H-1,2,3-triazol-4-yl}methylidene)piperidine hydrochloride (2.33 g) by conducting a similar reaction to that mentioned in Example 139.

$^1$H NMR (500 MHz, pyridine-$d_5$) δ ppm: 0.67-0.78 (2H, m), 0.97-1.03 (1H, m), 1.10-1.17 (4H, m), 1.84-1.94 (1H, m), 2.21-2.29 (2H, m), 2.29-2.38 (1H, m), 2.38-2.44 (4H, m), 2.72-2.79 (1H, m), 2.90-2.96 and 3.00-3.07 total 1H, m), 4.00-4.26 (4H, m), 4.45-4.52 (2H, m), 5.02 (1H, d, J=5.0), 6.83 and 6.86 (total 1H, each s), 7.19-7.25 (2H, m), 7.32-7.37 (1H, m), 7.65-7.73 (1H, m), 7.90 and 7.99 (total 1H, each s);

MS (FAB) m/z: 487 (M+H)$^+$;

IR (KBr, cm$^{-1}$): 1727, 1493.

Example 143

(E)-3-{[1-(3-Carboxypropyl)-1H-1,2,3-triazol-4-yl]methylidene}-1-[2-cyclopropyl-1-(2-fluorophenyl)-2-oxoethyl]-4-sulfanylpiperidine hydrochloride (Exemplification Compound No. 2-1153)

The title compound (444 mg, yield: 72%) was obtained as a colourless foam using (E)-1-[2-cyclopropyl-1-(2-fluorophenyl)-2-oxoethyl]-3-({1-[3-(ethoxycarbonyl)propyl]-1H-1,2,3-triazol-4-yl}methylidene)-4-sulfanylpiperidine hydrochloride (648 mg) as the starting material by conducting a reaction similar to that mentioned in Example 140.

$^1$H NMR (500 MHz, pyridine-$d_5$) δ ppm: 0.66-0.77 (2H, m), 0.97-1.04 (1H, m), 1.11-1.18 (1H, m), 1.84-1.94 (1H, m), 2.28-2.38 (3H, m), 2.38-2.45 (1H, m), 2.54-2.60 (2H, m), 2.66-2.72 (1H, m), 2.72-2.80 (1H, m), 2.91-2.98 and 3.00-3.07 (total 1H, m), 4.02-4.10 and 4.20-4.27 (total 3H, m), 4.52-4.59 (2H, m), 5.02 (1H, d, J=3.0), 6.83 and 6.86 (total 1H, each s), 7.18-7.25 (2H, m), 7.31-7.39 (1H, m), 7.66-7.73 (1H, m), 7.87 and 7.97 (total 1H, each s);

MS (FAB) m/z: 459 (M+H)$^+$;

IR (KBr, cm$^{-1}$): 1711, 1493.

Example 144

(E)-3-[(1-Acetyl-5-methyl-1H-pyrazol-3-yl)methylidene]-1-[2-cyclopropyl-1-(2-fluorophenyl)-2-oxoethyl]-4-sulfanylpiperidine hydrogen trifluoroacetate (E)-4-(Acetylsulfanyl)-1-[2-cyclopropyl-1-(2-fluorophenyl)-2-oxoethyl]-3-{[1-(t-butoxycarbonyl)-5-methyl-1H-pyrazol-3-yl]methylidene}piperidine (389.6 mg), obtained by conducting the similar reactions to those mentioned in Example 11 using 1-(t-butoxycarbonyl)-5-methyl-1H-pyrazole-3-carbaldehyde as the starting material, was treated with 4N hydrogen chloride dioxane solution (8 ml) at room temperature for 2 hours. The reaction mixture was concentrated under reduced pressure and the resulting residue was purified by preparative HPLC (YMC-Pack ODS-A; YMC, eluent: acetonitrile/0.026 N aqueous trifluoroacetic acid solution, 45/55, v/v) to afford the title compound (140.0 mg, yield: 35%) as a colourless amorphous solid.

$^1$H NMR (400 MHz, CDCl$_3$) δ ppm: 0.74-1.17 (4H, m), 1.88-2.21 (3H, m), 2.11 (3H, s), 2.43 and 2.54 (total 3H, each s), 3.47-3.94 (3H, m), 3.76 and 4.00 (total 1H, each d, J=14.5), 5.03 and 5.11 (total 1H, each s), 5.06 and 5.26 (total 1H, each d, J=14.5), 6.07 and 6.18 (total 1H, each s), 6.51 and 6.68 (total 1H, each s), 6.96-7.53 (4H, m);

IR (CHCl$_3$ solution, cm$^{-1}$): 1701, 1636.

Example 145

(E)-1-[2-Cyclopropyl-1-(2-fluorophenyl)-2-oxoethyl]-3-[(pyrazin-2-yl)methylidene]-4-sulfanylpiperidine hydrochloride (Exemplification Compound No. 1-101)

(E)-4-(Acetylsulfanyl)-1-[2-cyclopropyl-1-(2-fluorophenyl)-2-oxoethyl]-3-[(pyrazin-2-yl)methylidene]piperidine (Example 31, free base, 540 mg) was treated with hydrogen chloride in ethanol in a similar manner to that described in Example 133, and the crude product was purified by preparative HPLC (YMC-Pack ODS-A; YMC, eluent: acetonitrile/0.024 N hydrochloric acid, 25/75, v/v) to afford the title compound (295 mg, yield: 60%) as a colourless amorphous solid.

$^1$H NMR (400 MHz, CD$_3$OD) δ ppm: 0.84-1.34 (4H, m), 1.73-1.92 (1H, m), 1.96-2.18 (1H, m), 2.21-3.09 (3H, m), 3.45-3.56 (1H, m), 3.58-3.67 (1H, m), 4.22 (1H, bs), 5.94 and 5.96 (total 1H, each s), 7.29-7.55 (3H, m), 7.59-7.74 (1H, m), 8.15-8.29 (3H, m);

IR (KBr, cm$^{-1}$): 3408, 2928, 2543, 1710.

Example 146

(E)-4-(Acetylsulfanyl)-1-[2-cyclopropyl-1-(2-fluorophenyl)-2-oxoethyl]-3-({1-[(1,3-thiazol-4-yl)methyl]-1H-pyrazol-3-yl}methylidene)piperidine hydrochloride (Exemplification Compound No. 2-146)

(a) (E)-3-({1-[(1,3-Thiazol-4-yl)methyl]-1H-pyrazol-3-yl}methylidene)-1-(triphenylmethyl)piperidin-4-one To a solution of (E)-3-([1H-pyrazol-3(5)-yl]methylidene)-1-(triphenylmethyl)piperidin-4-one (Example 73-(a), 5.0 g)

in acetonitrile (50 ml) were added 4-(chloromethyl)-1,3-thiazole hydrochloride (4.0 g) and 1,8-diazabicyclo[5.4.0]undec-7-ene (DBU) (7.0 ml). The mixture was stirred at 50° C. for 1.5 hour. After cooling, water and ethyl acetate were added to separate the layers. The organic layer was collected, washed with a saturated aqueous sodium chloride solution and dried over anhydrous magnesium sulfate. The solvent was removed by evaporation under reduced pressure, and the residue was purified by silica gel chromatography (hexane:ethyl acetate:dichloromethane=4:3:3, then 1:1:1) and then 1:2:2) to afford the title compound (1.96 g, yield: 37%) as a pale yellow amorphous solid.

$^1$H NMR (500 MHz, CDCl$_3$) δ ppm: 2.65 (2H, bs), 2.75 (2H, t, J=5.0), 3.64 (2H, bs), 5.37 (2H, s), 6.24 (1H, d, J=2.5), 6.75 (1H, bs), 7.13-7.30 (9H, m), 7.44 (1H, d, J=2.5), 7.45 (1H, bs), 7.47-7.55 (6H, m) 8.75 (1H, d, J=2.0).

(b) (E)-4-(Acetylsulfanyl)-3-({1-[(1,3-thiazol-4-yl)methyl]-1H-pyrazol-3-yl}methylidene)piperidine bis(hydrogen trifluoroacetate)

To a solution of (E)-3-({1-[(1,3-thiazol-4-yl)methyl]-1H-pyrazol-3-yl}methylidene)-1-(triphenylmethyl)piperidin-4-one (2.48 g) in methanol (25 ml) was added sodium borohydride (0.09 g) at room temperature. After being stirred at the same temperature for 0.5 hour, water and ethyl acetate were added and the product was extracted. The separated organic layer was washed with a saturated aqueous sodium chloride solution and dried over anhydrous magnesium sulfate. Evaporation of the solvent under reduced pressure gave (E)-3-({1-[(1,3-thiazol-4-yl)methyl]-1H-pyrazol-3-yl}methylidene)-1-(triphenylmethyl)piperidin-4-ol (ca. 2.5 g) as a crude pale yellow amorphous solid.

$^1$H NMR (500 MHz, CDCl$_3$) δ ppm: 1.84-1.95 (1H, m), 2.08-2.19 (2H, m), 2.66-2.79 (2H, m), 3.44-3.58 (1H, m), 4.13-4.19 (1H, m), 5.29 (1H, d, J=16.0), 5.33 (1H, d, J=16.0), 6.13 (1H, d, J=2.5), 6.51 (1H, bs), 6.69 (1H, bs), 7.05-7.20 (9H, m), 7.38 (1H, d, J=2.0), 7.39-7.45 (6H, m), 8.77 (1H, d, J=2.0).

The above-mentioned product, without further purification, was dissolved in toluene (25 ml), and N,N-dimethylformamide dineopentyl acetal (2.7 ml) and thioacetic acid (0.65 ml) were added thereto at room temperature. After the mixture was stirred at the same temperature for 0.5 hour, water and ethyl acetate were added, and the product was extracted. The separated organic layer was washed successively with water and a saturated aqueous sodium chloride solution and dried over anhydrous magnesium sulfate. Evaporation of the solvent under reduced pressure gave crude (E)-4-(acetylsulfanyl)-3-({1-[(1,3-thiazol-4-yl)methyl]-1H-pyrazol-3-yl}methylidene)-1-(triphenylmethyl)piperidine (ca. 2.9 g) as a yellow amorphous solid.

The above-mentioned product, without further purification, was dissolved in dichloromethane (25 ml), and trifluoroacetic acid (1.1 ml) was added thereto. After being stirred at room temperature for 0.5 hour, the mixture was concentrated under reduced pressure. The residue was purified by silica gel chromatography using dichloromethane and methanol (19:1) as eluents to afford the title compound (400 mg, yield: 14%) as a yellow amorphous solid.

$^1$H NMR (400 MHz, CDCl$_3$) δ ppm: 2.02-2.12 (1H, m), 2.36 (3H, s), 2.37-2.49 (1H, m), 3.13-3.24 (1H, m), 3.31-3.40 (1H, m), 3.78 (1H, d, J=14.5), 4.58 (1H, m), 5.11 (1H, d, J=14.5), 5.43 (2H, s), 6.24 (1H, d, J=2.5), 6.63 (1H, bs), 7.21 (1H, bs), 7.46 (1H, d, J=2.0), 8.78 (1H, d, J=2.0).

(c) (E)-4-(Acetylsulfanyl)-1-[2-cyclopropyl-1-(2-fluorophenyl)-2-oxoethyl]-3-({1-[(1,3-thiazol-4-yl)methyl]-1H-pyrazol-3-yl}methylidene)piperidine hydrochloride To a solution of (E)-4-(acetylsulfanyl)-3-({1-[(1,3-thiazol-4-yl)methyl]-1H-pyrazol-3-yl}methylidene)piperidine bis(hydrogen trifluoroacetate) (400 mg) in N,N-dimethylformamide (10 ml) was added 2-bromo-2-(2-fluorophenyl)-1-cyclopropylethanone (370 mg) and triethylamine (400 µl). After being stirred at room temperature for 0.5 hour, the mixture was partitioned between water and ethyl acetate. The organic layer was separated, washed with a saturated aqueous sodium chloride solution and dried over anhydrous magnesium sulfate. The solvent was evaporated under reduced pressure, and the residue thus obtained was treated with a 4N hydrogen chloride dioxane solution (1.8 ml) and purified by silica gel chromatography using dichloromethane, ethyl acetate and methanol (5:5:1), then dichloromethane and methanol (1:1) as eluents. After the fractions containing the objective compound were concentrated, ether was added, and insoluble materials were collected by filtration to afford the title compound (450 mg, containing moisture due to hygroscopicity) as a pale yellow amorphous solid.

$^1$H NMR (500 MHz, CDCl$_3$) δ ppm: 0.60-1.00 (4H, m), 1.83-1.92 (1H, m), 2.19-2.36 (2H, m), 2.30 (3H, s), 2.43-2.50 and 2.56-2.63 (total 1H, each m), 2.71-2.77 and 2.79-2.85 (total 1H, each m), 3.09 and 3.23 (total 1H, each d, J=13.0), 4.09-4.17 (1H, m), 4.50 (1H, m), 4.68 and 4.70 (total 1H, each s), 5.35 and 5.42 (total 2H, each s), 6.10 and 6.18 (total 1H, each d, J=2.0), 6.49 and 6.51 (total 1H, each bs), 7.03-7.17 (3H, m), 7.24-7.31 (1H, m), 7.37-7.45 (2H, m), 8.78 (1H, bs);

IR (KBr, cm$^{-1}$): 1695.

Example 147

(E)-1-[2-Cyclopropyl-1-(2-fluorophenyl)-2-oxoethyl]-3-({1-[(1,3-thiazol-4-yl)methyl]-1H-pyrazol-3-yl}methylidene)-4-sulfanylpiperidine dihydrochloride (Exemplification Compound No. 2-145)

Dichloromethane and an aqueous sodium hydrogen carbonate solution were added to (E)-4-(acetylsulfanyl)-1-[2-cyclopropyl-1-(2-fluorophenyl)-2-oxoethyl]-3-({1-[(1,3-thiazol-4-yl)methyl]-1H-pyrazol-3-yl}methylidene)piperidine hydrochloride (ca. 200 mg, containing moisture) obtained in Example 146. The organic layer was separated, dried over anhydrous magnesium sulfate and concentrated to afford the free base (160 mg) as a pale yellow amorphous solid. To a solution of the solid obtained above in methanol (4 ml) was added potassium carbonate (44 mg) at room temperature. After the mixture being stirred at the same temperature for 0.5 hour, 1N hydrochloric acid (3.1 ml) was added, and insoluble materials were filtered off using a membrane filter. The filtrate was concentrated and the residue was purified by preparative HPLC (YMC-Pack ODS-A; YMC, eluent: acetonitrile/0.024 N hydrochloric acid, 30/70, v/v) to afford the title compound (90 mg, yield: 53%) as a colourless amorphous solid.

$^1$H NMR (500 MHz, CDCl$_3$) δ ppm: 0.61-1.00 (4H, m), 1.75-1.85 (1H, m), 2.16-2.37 (2H, m), 2.59-2.80 and 2.83-2.92 (total 2H, each m), 3.54 and 3.65 (total 1H, each d, J=12.5), 3.84 (1H, d, J=12.5), 3.94 (1H, m), 4.72 and 4.74 (total 1H, each s), 5.38 and 5.42 (total 2H, each s), 6.10 and 6.19 (total 1H, each d, J=2.5), 6.46 and 6.48 (total 1H, each bs), 7.03-7.18 (3H, m), 7.24-7.31 (1H, m), 7.38-7.48 (2H, m), 8.79 (1H, d, J=2.0);

IR (KBr, cm$^{-1}$): 2532, 1711.

Example 148

(E)-4-(Acetylsulfanyl)-1-[2-cyclopropyl-1-(2-fluorophenyl)-2-oxoethyl]-3-{[1-(2-hydroxyethyl)-1H-pyrazol-3-yl]methylidene}piperidine hydrochloride (Exemplification Compound No. 2-158)

(a) (E)-4-(Acetylsulfanyl)-3-{[1-(2-hydroxyethyl)-1H-pyrazol-3-yl]methylidene}piperidine bis(hydrogen trifluoroacetate)

(E)-3-([1H-Pyrazol-3(5)-yl]methylidene)-1-(triphenylmethyl)piperidin-4-one (Example 73-(a), 40.6 g) was portioned between two flasks for the reaction. To solutions of the compound in N,N-dimethylformamide (420 ml, total amount of the two flasks) were added ethyl bromoacetate (53.9 ml, total amount of the two flasks), potassium carbonate (33.4 g, total amount of the two flasks) and potassium iodide (80.3 g, total amount of the two flasks) under ice-cooling. The mixtures were stirred at room temperature for 0.5 hour and then at 80° C. for 0.5 hour. Water and ethyl acetate were added to reaction mixtures, which was then combined, and the layers were separated. The organic layer was washed successively with water and a saturated aqueous sodium chloride solution and dried over anhydrous magnesium sulfate. The solvent was removed under reduced pressure and the residue was purified by silica gel chromatography (eluent: hexane/ethyl acetate/dichloromethane=2/2/1) to afford (E)-3-{[1-(ethoxycarbonyl)-1H-pyrazol-3-yl]methylidene}-1-(triphenylmethyl)piperidin-4-one (49 g, containing a small amount of the regioisomer regarding the position on the pyrazole ring) as a yellow solid. This product, without further purification, was dissolved in ethanol (500 ml), and sodium borohydride (1.9 g) was added thereto at 0° C. After the mixture was stirred at room temperature for 1 hour, dichloromethane (200 ml) was added to dilute the reaction solution. Then water and ethyl acetate were added, and the mixture was concentrated under reduced pressure to remove most of dichloromethane and ethanol. Products were extracted with ethyl acetate, and the organic layer was washed successively with water and a saturated aqueous sodium chloride solution. The extract was dried over anhydrous magnesium sulfate, and the solvent was evaporated under reduced pressure. The residue was purified by silica gel chromatography using dichloromethane and ethyl acetate (4:1 to 1:1), then dichloromethane and methanol (9:1 to 4:1) as eluents to afford (E)-3-{[1-(2-hydroxyethyl)-1H-pyrazol-3-yl]methylidene}-1-(triphenylmethyl)piperidin-4-ol (10 g, yield: 22%).

Using a portion (7.0 g) of this product as the starting material, the title compound (400 mg, yield: 28%) was obtained as a colourless amorphous solid following a procedure similar to that mentioned in Example 132-(e)~(f) by conducting the reaction with thioacetic acid and N,N-dimethylformamide dineopentyl acetal followed by treatment with trifluoroacetic acid and purification with silica gel chromatography.

$^1$H NMR (500 MHz, CDCl$_3$) δ ppm: 2.03-2.11 (1H, m), 2.36 (3H, s), 2.40-2.50 (1H, m), 3.16-3.25 (1H, m), 3.32-3.40 (1H, m), 3.77 (1H, d, J=14.0), 3.83-3.90 (1H, m), 3.96-4.04 (1H, m), 4.12 (2H, m), 4.56 (1H, m), 5.21 (1H, d, J=14.0), 6.19 (1H, d, J=2.0), 6.62 (1H, bs), 7.34 (1H, d, J=2.0).

(b) (E)-4-(Acetylsulfanyl)-1-[2-cyclopropyl-1-(2-fluorophenyl)-2-oxoethyl]-3-{[1-(2-hydroxyethyl)-1H-pyrazol-3-yl]methylidene}piperidine hydrochloride To a solution of (E)-4-(acetylsulfanyl)-3-{[1-(2-hydroxyethyl)-1H-pyrazol-3-yl]methylidene}piperidine bis(hydrogen trifluoroacetate) (400 mg) in N,N-dimethylformamide (10 ml) was added 2-bromo-2-(2-fluorophenyl)-1-cyclopropylethanone (410 mg) and triethylamine (440 µl). The mixture was stirred at room temperature for 0.5 hour, and then partitioned between water and ethyl acetate. The organic layer was washed with a saturated aqueous sodium chloride solution and dried over anhydrous magnesium sulfate. The solvent was removed under reduced pressure and the residue was purified by silica gel column chromatography (eluent: dichloromethane/ethyl acetate/methanol=10/10/1) to afford the free base of the title compound (630 mg, yield: 96%) as a yellow oil.

The above-mentioned free base (320 mg) was treated with a 4N hydrogen chloride dioxane solution (2.8 ml). The solvent and excess hydrogen chloride were removed under reduced pressure, and the residue was purified by silica gel chromatography using dichloromethane, ethyl acetate, and methanol (10:10:1) as an eluent to afford the title compound as a colourless amorphous solid.

$^1$H NMR (500 MHz, CDCl$_3$) δ ppm: 0.65-1.03 (4H, m), 1.83-1.91 (1H, m), 2.10-2.38 (2H, m), 2.29 and 2.31 (total 3H, each s), 2.40-2.48 and 2.56-2.64 (total 1H, each m), 2.70-2.84 (1H, m), 3.07 and 3.24 (total 1H, each d, J=12.5), 3.87-4.02 (2H, m), 4.09-4.25 (3H, m), 4.50 (1H, m), 4.74 and 4.78 (total 1H, each s), 6.10 and 6.17 (total 1H, each d, J=2.5), 6.49 (1H, bs), 7.04-7.17 (2H, m), 7.28-7.41 (3H, m);

IR (KBr, cm$^{-1}$): 1696.

Example 149

(E)-1-[2-Cyclopropyl-1-(2-fluorophenyl)-2-oxoethyl]-3-{[1-(2-hydroxyethyl)-1H-pyrazol-3-yl]methylidene}-4-sulfanylpiperidine hydrochloride (Exemplification Compound No. 2-157)

(E)-4-(Acetylsulfanyl)-1-[2-cyclopropyl-1-(2-fluorophenyl)-2-oxoethyl]-3-{[1-(2-hydroxyethyl)-1H-pyrazol-3-yl]methylidene}piperidine (free base, 310 mg) obtained in Example 148 was treated with potassium carbonate in methanol in a similar manner to that described in Example 147. The product thus obtained was purified by preparative HPLC (YMC-Pack ODS-A; YMC, eluent: acetonitrile/0.024 N hydrochloric acid, 25/75, v/v) to afford the title compound (100 mg, yield: 32%) as a colourless highly hygroscopic amorphous solid.

$^1$H NMR (500 MHz, CDCl$_3$) δ ppm: 0.64-1.02 (4H, m), 1.75-1.84 (1H, m), 2.08-2.38 (2H, m), 2.58-2.78 and 2.83-2.91 (total 2H, each m), 3.55 and 3.69 (total 1H, each d, J=12.5), 3.82-4.02 (4H, m), 4.13-4.20 (2H, m), 4.78 and 4.80 (total 1H, each s), 6.09 and 6.17 (total 1H, each d, J=2.5), 6.45 and 6.47 (total 1H, each bs), 7.05-7.17 (2H, m), 7.28-7.41 (3H, m);

IR (KBr, cm$^{-1}$): 2524, 1709.

Example 150

(E)-4-(Acetylsulfanyl)-1-[2-cyclopropyl-1-(2-fluorophenyl)-2-oxoethyl]-3-{[2-(methoxycarbonylmethyl)-2H-tetrazol-5-yl]methylidene}piperidine hydrochloride (Exemplification Compound No. 2-1610)

(a) Methyl [5-(hydroxymethyl)-2H-tetrazol-2-yl]acetate and methyl [5-(hydroxymethyl)-1H-tetrazol-1-yl]acetate To a solution of [1(2)H-tetrazol-5-yl]methanol (7.08 g) in acetonitrile (400 ml) were added methyl bromoacetate (26.8 ml) and triethylamine (40 ml). After being stirred at room temperature for 1 day, the mixture was concentrated under reduced pressure. The residue was purified by silica gel chromatography using ethyl acetate and methanol (19:1) as an eluent to afford an isomeric mixture of two title compounds (10.82 g, yield: 89%) as a colourless oil.

$^1$H NMR (400 MHz, CDCl$_3$) δ ppm: 3.79 (3H, s), 4.92 and 4.97 (total 2H, each s), 5.34 and 5.41 (total 2H, each s).

(b) Methyl(5-formyl-2H-tetrazol-2-yl)acetate and methyl(5-formyl-1H-tetrazol-1-yl)acetate To a solution of a mixture of methyl [5-(hydroxymethyl)-2H-tetrazol-2-yl]acetate and methyl [5-(hydroxymethyl)-1H-tetrazol-1-yl]acetate (10.82 g) obtained as above in dichloromethane (250 ml) were added molecular sieves 4A (47.5 g) and pyridinium dichromate (47.5 g). After being stirred at room temperature for 1 hour, the mixture was filtered. The filtrate was concentrated under reduced pressure and the residue was purified by column chromatography on silica gel using ethyl acetate and methanol (10:1) as an eluent to afford an isomeric mixture of two title compounds (5.76 g, yield: 54%) as a colourless oil.

$^1$H NMR (400 MHz, CDCl$_3$) δ ppm: 3.78 and 3.80 (total 3H, each s), 5.46 and 5.53 (total 2H, each s), 10.20 and 10.22 (total 1H, each s).

(c) (E)-3-{[2-(Methoxycarbonylmethyl)-2H-tetrazol-5-yl]methylidene}-1-(triphenylmethyl)piperidin-4-one and (E)-3-{[1-(Methoxycarbonylmethyl)-1H-tetrazol-5-yl]methylidene}-1-(triphenylmethyl)piperidin-4-one To a solution of 1-(triphenylmethyl)piperidin-4-one (11.6 g) in benzene (300 ml) was added pyrrolidine (2.8 ml). The mixture was heated under reflux under a Dean-Staak apparatus for 3 hours with water being removed. After the mixture was cooled to room temperature, a solution of the mixture of methyl(5-formyl-2H-tetrazol-2-yl)acetate and methyl(5-formyl-1H-tetrazol-1-yl)acetate obtained above in dichloromethane was added thereto. After the mixture was heated for 5 further hours under reflux, it was cooled, and the reaction was quenched by addition of water. Products were extracted with ethyl acetate, and the organic layer was washed with a saturated aqueous sodium chloride solution and dried over anhydrous magnesium sulfate. The solvent was removed under reduced pressure, and the residue was purified by silica gel chromatography using hexane, ethyl acetate and dichloromethane (2:1:1) as an eluent to afford the two title compounds.

The less polar isomer (E)-3-{[2-(methoxycarbonylmethyl)-2H-tetrazol-5-yl]methylidene}-1-(triphenylmethyl)piperidin-4-one; amount: 5.39 g, yield: 32%, a yellow amorphous solid. $^1$H NMR (400 MHz, CDCl$_3$) δ ppm: 2.68 (2H, bs), 2.81 (2H, t, J=6.0), 3.77 (3H, s), 3.79-3.85 (2H, m), 5.30 (2H, s), 7.11-7.32 (10H, m), 7.47-7.54 (6H, m).

The more polar isomer (E)-3-{[1-(methoxycarbonylmethyl)-1H-tetrazol-5-yl]methylidene}-1-(triphenylmethyl)piperidin-4-one; amount: 2.24 g, yield: 13%, a yellow amorphous solid. $^1$H NMR (400 MHz, CDCl$_3$) δ ppm: 2.70 (2H, bs), 2.83 (2H, t, J=6.0), 3.84 (3H, s), 3.94 (2H, bs), 5.20 (2H, s), 7.04-7.29 (10H, m), 7.47-7.54 (6H, m).

(d) (E)-3-{[2-(Methoxycarbonylmethyl)-2H-tetrazol-5-yl]methylidene}-1-(triphenylmethyl)piperidin-4-ol Sodium borohydride (400 mg) was added to a solution of (E)-3-{[2-(methoxycarbonylmethyl)-2H-tetrazol-5-yl]methylidene}-1-(triphenylmethyl)piperidin-4-one (5.18 g) in tetrahydrofuran (100 ml) at 0° C. After the mixture was stirred at the same temperature for 2 hours, the reaction was quenched by addition of a saturated aqueous ammonium chloride solution. The mixture was extracted with ethyl acetate, and the extract was washed with a saturated aqueous sodium chloride solution and dried over anhydrous magnesium sulfate. The extract was concentrated under reduced pressure, and the objective material that emerged was collected by filtration. The mother liquor was concentrated and the residue was purified by silica gel chromatography using hexane, ethyl acetate, and dichloromethane (1:1:1) as an eluent to afford an additional amount of the title compound as a colourless amorphous solid. Total amount: 1.5 g, total yield: 29%.

$^1$H NMR (400 MHz, DMSO-d$_6$) δ ppm: 1.67-1.83 (2H, m), 1.99-2.06 (1H, m), 2.82 (1H, bs), 3.73 (3H, s), 3.95 (1H, bs), 4.40 (1H, bs), 5.32 (1H, d, J=4.5), 5.49 (1H, d, J=17.0), 5.73 (1H, d, J=17.0), 6.61 (1H, s), 7.07-7.34 (15H, m).

(e) (E)-4-(Acetylsulfanyl)-3-{[2-(methoxycarbonylmethyl)-2H-tetrazol-5-yl]methylidene}piperidine hydrogen trifluoroacetate To a solution of (E)-3-{[2-(methoxycarbonylmethyl)-2H-tetrazol-5-yl]methylidene}-1-(triphenylmethyl)piperidin-4-ol (1.5 g) in a mixed solvent of dichloromethane (30 ml) and toluene (30 ml) was added thioacetic acid (2.2 ml) and N,N-dimethylformamide dineopentyl acetal (8.5 ml). After the mixture was stirred at 50° C. for 2 hours, it was cooled, water and dichloromethane were added and the layers were separated. The organic layer was washed with a saturated aqueous sodium chloride solution and dried over anhydrous magnesium sulfate. The extract was concentrated under reduced pressure and the residue was purified by silica gel column chromatography using hexane, ethyl acetate, and dichloromethane (2:1:1) as an eluent to afford (E)-4-(acetylsulfanyl)-3-{[2-(methoxycarbonylmethyl)-2H-tetrazol-5-yl]methylidene}-1-(triphenylmethyl)piperidine (containing impurity, gross amount: 880 mg, gross yield: 58.4%).

The compound described above was dissolved in dichloromethane (40 ml) and treated with trifluoroacetic acid (350 μl). After 15 minutes, the mixture was concentrated under reduced pressure and the residue was purified by silica gel column chromatography using dichloromethane and methanol (20:1) as an eluent to afford the title compound (450 mg, yield: 67%) as a yellow amorphous solid.

$^1$H NMR (400 MHz, CDCl$_3$) δ ppm: 2.06-2.19 (1H, m), 2.37 (3H, s), 2.44-2.60 (1H, m), 3.16-3.29 (1H, m), 3.39-3.49 (1H, m), 3.79 (3H, s), 4.01 (1H, d, J=14.5), 4.63 (1H, m), 5.14 (1H, d, J=14.5), 5.38 (2H, s), 6.90 (1H, s).

(f) (E)-4-(Acetylsulfanyl)-1-[2-cyclopropyl-1-(2-fluorophenyl)-2-oxoethyl]-3-{[2-(methoxycarbonylmethyl)-2H-tetrazol-5-yl]methylidene}piperidine hydrochloride Following a procedure similar to that described in Example 132-(g), (E)-4-(acetylsulfanyl)-3-{[2-(methoxycarbonylmethyl)-2H-tetrazol-5-yl]methylidene}piperidine hydrogen trifluoroacetate (450 mg) was subjected to the reaction with 2-bromo-2-(2-fluorophenyl)-1-cyclopropylethanone and triethylamine, and the product was purified by silica gel chromatography to afford the free base of the title compound (347 mg, yield: 67%), which was similarly treated with a 4N hydrogen chloride dioxane solution to yield the title compound (404 mg) as a pale yellow amorphous solid.

$^1$H NMR (400 MHz, CDCl$_3$) δ ppm: 0.65-0.83 (2H, m), 0.86-1.05 (2H, m), 1.85-1.97 (1H, m), 2.15-2.38 (2H, m), 2.30 and 2.31 (total 3H, each s), 2.46-2.55 and 2.60-2.69 (total 1H, each m), 2.75-2.85 (1H, m), 3.39 and 3.49 (total 1H, each d, J=14.0), 3.79 (3H, s), 4.25 and 4.30 (total 1H, each d, J=14.0), 4.48-4.54 (1H, m), 4.73 (1H, s), 5.26 and 5.31 (total 2H, each d, J=4.5), 6.66 and 6.67 (total 1H, each s), 7.02-7.15 (2H, m), 7.23-7.32 (1H, m), 7.35-7.42 (1H, m);

IR (KBr, cm$^{-1}$): 1775, 1755, 1699.

Example 151

(E)-1-[2-Cyclopropyl-1-(2-fluorophenyl)-2-oxoethyl]-3-{[2-(methoxycarbonylmethyl)-2H-tetrazol-5-yl]methylidene}-4-sulfanylpiperidine hydrochloride (Exemplification Compound No. 2-1609)

Potassium carbonate (275 mg) was added to a solution of (E)-4-(acetylsulfanyl)-1-[2-cyclopropyl-1-(2-fluorophenyl)-2-oxoethyl]-3-{[2-(methoxycarbonylmethyl)-2H-tetrazol-5-yl]methylidene}piperidine hydrochloride (347 mg) in methanol (10 ml). After being stirred at room temperature for 15 minutes, the mixture was diluted with ethyl acetate, and the reaction was quenched by addition of water. The organic layer was separated, washed with a saturated aqueous sodium chloride solution and dried over anhydrous magnesium sulfate. Removal of the solvent under reduced pressure followed by purification of the residue by preparative HPLC (YMC-Pack ODS-A; YMC, eluent: acetonitrile/0.024 N hydrochloric acid, 35/65, v/v) to afford the title compound (185 mg, yield: 58%) as a colourless amorphous solid.

$^1$H NMR (400 MHz, pyridine-d$_5$) ppm: 0.64-0.79 (2H, m), 0.92-1.04 (1H, m), 1.09-1.20 (1H, m), 1.81-1.97 (1H, m), 2.26-2.39 (1H, m), 2.39-2.52 (1H, m), 2.68-2.86 (1H, m), 2.88-3.08 (1H, m), 3.64 (3H, s), 3.98-4.06 (1H, m), 4.15-4.34 (2H, m), 4.96 and 4.98 (total 1H, each s), 5.90-5.98 (2H, m), 6.92 (1H, s), 7.13-7.22 (2H, m), 7.26-7.34 (1H, m), 7.61-7.70 (1H, m);

IR (KBr, cm$^{-1}$): 2443, 1756, 1712.

Example 152

(E)-3-{[2-(Carboxymethyl)-2H-tetrazol-5-yl]methylidene}-1-[2-cyclopropyl-1-(2-fluorophenyl)-2-oxoethyl]-4-sulfanylpiperidine hydrochloride (Exemplification Compound No. 2-1593)

(E)-1-[2-cyclopropyl-1-(2-fluorophenyl)-2-oxoethyl]-3-{[2-(methoxycarbonylmethyl)-2H-tetrazol-5-yl]methylidene}-4-sulfanylpiperidine hydrochloride (135 mg) was subjected to the procedure similar to that described in Example 134. After purification by preparative HPLC (YMC-Pack ODS-A; YMC, eluent: acetonitrile/0.024 N hydrochloric acid, 25/75, v/v), the title compound (91.6 mg, yield: 70%) was obtained as a colourless amorphous solid.

$^1$H NMR (400 MHz, pyridine-d$_5$) δ ppm: 0.65-0.78 (2H, m), 0.91-0.99 (1H, m), 1.07-1.19 (1H, m), 1.81-1.95 (1H, m), 2.26-2.36 (1H, m), 2.41-2.50 (1H, m), 2.68-2.81 (1H, m), 2.89-3.03 (1H, m), 4.01 (1H, bs), 4.14-4.39 (2H, m), 4.95 and 4.96 (total 1H, each s), 5.84-5.96 (2H, m), 6.94 and 6.96 (total 1H, each s), 7.12-7.23 (2H, m), 7.26-7.34 (1H, m), 7.63-7.71 (1H, m);

IR (KBr, cm$^{-1}$): 2927, 1746, 1712.

Example 153

(Z)-4-(Acetylsulfanyl)-1-[2-cyclopropyl-1-(2-fluorophenyl)-2-oxoethyl]-3-{[1-(ethoxycarbonylmethyl)-1H-pyrazol-3-yl]methylidene}piperidine hydrochloride (Exemplification Compound No. 4-14)

(a) (E)- and (Z)-4-(Acetylsulfanyl)-3-{[1-(ethoxycarbonylmethyl)-1H-pyrazol-3-yl]methylidene}piperidine hydrogen trifluoroacetate Following a procedure similar to that described in Example 75-(a) and (b), the use of ethyl bromoacetate, instead of t-butyl bromoacetate, afforded (E)-4-(acetylsulfanyl)-3-{[1-(ethoxycarbonylmethyl)-1H-pyrazol-3-yl]methylidene}-1-(triphenylmethyl)piperidine. To a solution of this compound (18.02 g) in dimethyl sulfoxide (150 ml) was added potassium thioacetate (36.4 g). After the mixture was stirred at 80° C. for 5 hours, it was cooled, and products were extracted by ethyl acetate. After the organic layer was washed with an aqueous sodium chloride solution and dried over anhydrous magnesium sulfate, it was concentrated under reduced pressure. The residue was purified by silica gel column chromatography using hexane and ethyl acetate (3:2) as an eluent to afford 4-(acetylsulfanyl)-3-{[1-(ethoxycarbonylmethyl)-1H-pyrazol-3-yl]methylidene}-1-(triphenylmethyl)piperidine (11.7 g, yield: 65%) as a mixture of geometric isomers as a brown oil.

The above obtained mixture (11 g) was dissolved in dichloromethane (100 ml) and trifluoroacetic acid (4.43 ml) was added thereto. After the mixture was stirred at room temperature for 1 hour, solvents were evaporated under reduced pressure. The residue was subjected to silica gel chromatography (dichloromethane/methanol=10/1) to afford the less polar isomer, (E)-4-(acetylsulfanyl)-3-{[1-(ethoxycarbonylmethyl)-1H-pyrazol-3-yl]methylidene}piperidine hydrogen trifluoroacetate (3.24 g, yield: 38%), as a pale orange-coloured crystalline solid. Further elution with a mixed solvent of dichloromethane and methanol (4:1) afforded the more polar isomer, (Z)-4-(acetylsulfanyl)-3-{[1-(ethoxycarbonylmethyl)-1H-pyrazol-3-yl]methylidene}piperidine hydrogen trifluoroacetate (3.57 g, yield: 42%), as a pale yellow crystalline solid.

The more polar isomer, (Z)-4-(acetylsulfanyl)-3-{[1-(ethoxycarbonylmethyl)-1H-pyrazol-3-yl]methylidene}piperidine hydrogen trifluoroacetate: $^1$H NMR (400 MHz, CDCl$_3$) δ ppm: 1.27 (3H, t, J=7.0), 2.01-2.03 (1H, m), 2.35-2.38 (4H, m), 3.22-3.33 (1H, m), 3.35-3.45 (1H, m), 3.56-3.69 (1H, m), 3.78-3.87 (1H, m), 4.21 (2H, q, J=7.0), 4.84 (2H, s), 5.60-5.65 (1H, m), 6.30 (1H, s,), 6.39 (1H, bs), 7.41 (1H, s).

(b) (Z)-4-(Acetylsulfanyl)-1-[2-cyclopropyl-1-(2-fluorophenyl)-2-oxoethyl]-3-{[1-(ethoxycarbonylmethyl)-1H-pyrazol-3-yl]methylidene}piperidine hydrochloride Following a procedure similar to that described in Example 132-(g), (Z)-4-(acetylsulfanyl)-3-{[1-(ethoxycarbonylmethyl)-1H-pyrazol-3-yl]methylidene}piperidine hydrogen trifluoroacetate (1.5 g) was subjected to the reaction with 2-bromo-2-(2-fluorophenyl)-1-cyclopropylethanone and triethylamine. The product thus obtained was purified by silica gel chromatography to afford the free base of the title compound (0.66 g) as a yellow foam, which was treated with a 4N hydrogen chloride dioxane solution to afford the title compound (0.83 g, yield: 45%) as a yellow foam.

$^1$H NMR (500 MHz, pyridine-$d_5$) δ ppm: 0.75-0.87 (2H, m), 1.04 (3H, t, J=7.0), 1.09-1.17 (2H, m), 1.88-2.01 (1H, m), 2.20-2.39 (3H, m), 2.51-2.58 and 2.70-2.78 (total 2H, each m), 2.91-3.01 (1H, m), 3.05-3.18 (1H, m), 3.48-3.71 (2H, m), 4.07 (2H, q, J=7.0), 4.90 (1H, d, J=11.0), 5.22 (2H, d, J=6.5), 5.97-6.03 (1H, m), 6.50-6.63 (2H, m), 7.20-7.27 (2H, m), 7.29-7.37 (1H, m), 7.67-7.76 (1H, m), 7.80-7.85 (1H, m);
MS (FAB) m/z: 500 (M+H)$^+$;
IR (KBr, cm$^{-1}$): 1695, 1493.

Example 154

(Z)-1-[2-Cyclopropyl-1-(2-fluorophenyl)-2-oxoethyl]-3-{[1-(ethoxycarbonylmethyl)-1H-pyrazol-3-yl]methylidene}-4-sulfanylpiperidine hydrochloride (Exemplification Compound No. 4-15)

(Z)-4-(Acetylsulfanyl)-1-[2-cyclopropyl-1-(2-fluorophenyl)-2-oxoethyl]-3-{[1-(ethoxycarbonylmethyl)-1H-pyrazol-3-yl]methylidene}piperidine hydrochloride (0.80 g) was treated with hydrogen chloride in a similar manner to that described in Example 133, and the product was purified by preparative HPLC to afford the free base of the title compound (0.31 g) as a pale yellow foam, which was treated with 4N hydrogen chloride dioxane solution to afford the title compound (0.38 g, yield: 51%) as a pale yellow foam.

$^1$H NMR (500 MHz, pyridine-$d_5$) δ ppm: 0.79-0.83 (2H, m), 0.99-1.08 (4H, m), 1.09-1.15 (1H, m), 1.73 and 1.80 (total 1H, each d, J=14), 2.18-2.27 and 2.27-2.36 (total 1H, each m), 2.52-2.59 (1H, m), 2.65-3.04 (2H, m), 3.37 and 3.67 (total 1H, each d, J=12.5), 3.52 (1H, t, J=14.0), 4.06-4.12 (2H, m), 4.92 (1H, d, J=8.0), 5.27 (2H, d, J=7.0), 5.47-5.51 (1H, m), 6.27 and 6.38 (total 1H, each s), 6.53 and 6.59 (total 1H, each s), 7.19-7.25 (2H, m), 7.28-7.34 (1H, m), 7.71-7.77 (1H, m), 7.85 and 7.87 (total 1H, each d, J=2.0);
MS (FAB) m/z: 458 (M+H)$^+$;
IR (KBr, cm$^{-1}$): 2523, 1712, 1493.

Example 155

(Z)-3-{[1-(Carboxymethyl)-1H-pyrazol-3-yl]methylidene}-1-[2-cyclopropyl-1-(2-fluorophenyl)-2-oxoethyl]-4-sulfanylpiperidine hydrochloride (Exemplification Compound No. 4-5)

To a solution of (Z)-1-[2-cyclopropyl-1-(2-fluorophenyl)-2-oxoethyl]-3-{[1-(ethoxycarbonylmethyl)-1H-pyrazol-3-yl]methylidene}-4-sulfanylpiperidine hydrochloride (309 mg) was added 3N hydrochloric acid (10 ml), and the mixture was stirred at 60° C. for 1 hour. After the mixture was concentrated under reduced pressure, the residue was purified by preparative HPLC (YMC-Pack ODS-A; YMC, eluent: acetonitrile/0.024 N hydrochloric acid, 40/60, v/v) to afford the title compound (227 mg, yield: 67%) as a colourless crystalline solid.

$^1$H NMR (500 MHz, pyridine-$d_5$) δ ppm: 0.77-0.84 (2H, m), 0.98-1.04 (1H, m), 1.09-1.15 (1H, m), 1.73 and 1.80 (total 1H, each d, J=14), 2.18-2.27 and 2.27-2.36 (total 1H, each m), 2.53-2.61 (1H, m), 2.65-3.04 (3H, m), 3.38 and 3.67 (total 1H, each d, J=12.0), 3.49-3.57 (1H, m), 4.92 (1H, d, J=9.0), 5.36 (2H, d, J=9.0), 5.48-5.56 (1H, m), 6.30 and 6.42 (total 1H, each s), 6.57 and 6.62 (total 1H, each s), 7.14-7.35 (3H, m), 7.72-7.77 (1H, m), 7.90-7.95 (1H, m);
MS (FAB) m/z: 430 (M+H)$^+$;
IR (KBr, cm$^{-1}$): 2550, 1711, 1493.

Example 156

(E)-4-(Acetylsulfanyl)-1-[2-cyclopropyl-1-(2-fluorophenyl)-2-oxoethyl]-3-{[1(2)H-tetrazol-5-yl]methylidene}piperidine hydrogen trifluoroacetate (Exemplification Compound No. 1-58)

(a) [2-(4-Methoxybenzyl)-2H-tetrazol-5-yl]methanol and [1-(4-Methoxybenzyl)-1H-tetrazol-5-yl]methanol To a solution of [1(2)-tetrazol-5-yl]methanol (5 g) in acetonitrile (60 ml) was added triethylamine (8.3 ml) and 4-methoxybenzyl chloride (8.1 ml). After the mixture was stirred at room temperature for 1 hour and 15 minutes, and then at 75° C. for 45 minutes, it was cooled. The residue which was obtained by extraction in an usual manner was purified by silica gel chromatography using hexane, ethyl acetate, and dichloromethane (1:1:1), then hexane and ethyl acetate (1:3) as eluents to afford a mixture of the two title isomers (3.17 g, yield: 29%) as a colourless oil.

$^1$H NMR (400 MHz, CDCl$_3$) δ ppm: 3.79 (3H, s), 4.83 and 4.93 (total 2H, each s), 5.57 and 5.66 (total 2H, each s), 6.86 and 6.87 (total 2H, each d, J=9.0), 7.24 and 7.31 (total 2H, each d, J=9.0).

(b) 2-(4-Methoxybenzyl)-2H-tetrazol-5-carbaldehyde and 1-(4-Methoxybenzyl)-1H-tetrazol-5-carbaldehyde Following a procedure similar to that described in Example 132-(b), a mixture (27.82 g) of [2-(4-methoxybenzyl)-2H-tetrazol-5-yl]methanol and [1-(4-methoxybenzyl)-1H-tetrazol-5-yl]methanol was oxidized in dichloromethane (400 ml) with pyridinium dichromate (95.0 g) in the presence of molecular sieves 4A (95 g). After the mixture was filtered and concentrated, the residue was purified by silica gel chromatography using ethyl acetate as an eluent to afford a mixture of the two title isomers (12.89 g, yield: 47%) as a yellow oil.

$^1$H NMR (400 MHz, CDCl$_3$) δ ppm: 3.79 and 3.81 (total 3H, each s), 5.80 and 5.81 (total 2H, each s), 6.87 and 6.91 (total 2H, each d, J=8.5), 7.36 and 7.81 (total 2H, each d, J=8.0), 10.20 and 10.26 (total 1H, each s).

(c) (E)-3-{[2-(4-Methoxybenzyl)-2H-tetrazol-5-yl]methylidene}-1-(triphenylmethyl)piperidin-4-one and (E)-3-{[1-(4-Methoxybenzyl)-1H-tetrazol-5-yl]methylidene}-1-(triphenylmethyl)piperidin-4-one Following a procedure similar to that described in Example 132-(c), the mixture obtained in Example 156-(b) (11.89 g) was subjected to the reaction with 1-(triphenylmethyl)piperidin-4-one (18.6 g) and pyrrolidine (4.5 ml) and the product was purified by silica gel chromatography using hexane and ethyl acetate (3:1) as an eluent to afford a mixture of the two title isomers (16.88 g, yield: 57%) as a yellow amorphous solid.

$^1$H NMR (400 MHz, CDCl$_3$) δ ppm: 2.60-2.70 (2H, bs), 2.78 (2H, dd, J=13.5, 6.0), 3.81 (3H, s), 3.82-3.87 (2H, m), 5.53 (2H, s), 6.82-6.88 (2H, m), 7.11-7.17 (4H, m), 7.19-7.29 (7H, m), 7.45-7.48 (7H, m).

(d) (E)-3-{[2-(4-Methoxybenzyl)-2H-tetrazol-5-yl]methylidene}-1-(triphenylmethyl)piperidin-4-ol and (E)-3-{[1-(4-Methoxybenzyl)-1H-tetrazol-5-yl]methylidene}-1-(triphenylmethyl)piperidin-4-ol Following a procedure similar to that described in Example 132-(d), a mixture (17.88 g) of (E)-3-{[2-(4-methoxybenzyl)-2H-tetrazol-5-yl]methylidene}-1-(triphenylmethyl)piperidin-4-one and (E)-3-{[1-(4-methoxybenzyl)-1H-tetrazol-5-yl]methylidene}-1-(triphenylmethyl)piperidin-4-one was reduced with sodium borohydride (1.25 g) in a mixed solvent of dichloromethane (100 ml) and methanol (100 ml). The products were extracted in a usual manner and purified by silica gel chromatography using hexane and ethyl acetate (2:1) as an eluent to afford the less polar isomer of the title compound (9.33 g, yield: 52%) as a colourless amorphous solid.

$^1$H NMR (400 MHz, CDCl$_3$) δ ppm: 1.84-1.87 (4H, m), 2.14-2.19 (1H, m), 2.89-2.99 (1H, m), 3.61 (3H, s), 5.38 (1H, d, J=14.5), 5.54 (1H, d, J=14.5), 6.69 (1H, s), 6.88 (2H, d, J=8.0), 7.12-7.17 (11H, m), 7.89-7.90 (7H, m).

Further elution with hexane/ethyl acetate (1/2) afforded the more polar isomer of the title compound (4.55 g, yield: 25.4%), as a colourless amorphous solid.

(e) (E)-4-(Acetylsulfanyl)-3-{[2-(4-methoxybenzyl)-2H-tetrazol-5-yl]methylidene}piperidine hydrogen trifluoroacetate or (E)-4-(Acetylsulfanyl)-3-{[1-(4-methoxybenzyl)-1H-tetrazol-5-yl]methylidene}piperidine hydrogen trifluoroacetate Following a procedure similar to that described in Example 132-(e), the less polar isomer (9.33 g) obtained in Example 156-(d) was subjected to the reaction with thioacetic acid (11.3 ml) and N,N-dimethylformamide dineopentyl acetal (48.0 ml) in toluene (100 ml). After usual extraction, the product was purified by silica gel chromatography using hexane and ethyl acetate (3:1) as an eluent to afford the thioacetate (6.7 g, containing impurities) as a brown oil. This compound was treated with trifluoroacetic acid (2.2 ml) in dichloromethane (100 ml) in a similar manner to that described in Example 132-(f), and the product was purified by silica gel chromatography using dichloromethane and methanol (20:1 to 5:1) to afford either (corresponding to the raw material) isomer of the title compounds (3.11 g, yield: 38%) as a brown amorphous solid.

$^1$H NMR (400 MHz, CDCl$_3$) δ ppm: 2.07-2.14 (1H, m), 2.37 (3H, s), 2.45-2.53 (1H, m), 3.19-3.25 (2H, m), 3.42-3.47 (1H, m), 3.79 (3H, s), 3.99 (1H, d, J=15.0), 4.59-4.61 (1H, m), 5.19 (1H, d, J=14.0), 5.63 (2H, s), 6.86-6.88 (3H, s), 7.29 (2H, d, J=9.0)

(f) (E)-4-(Acetylsulfanyl)-1-[2-cyclopropyl-1-(2-fluorophenyl)-2-oxoethyl]-3-{[2-(4-methoxybenzyl)-2H-tetrazol-5-yl]methylidene}piperidine or (E)-4-(Acetylsulfanyl)-1-[2-cyclopropyl-1-(2-fluorophenyl)-2-oxoethyl]-3-{[1-(4-methoxybenzyl)-1H-tetrazol-5-yl]methylidene}piperidine Following a procedure similar to that described in Example 132-(g), the compound (3.11 g) obtained in Example 156-(e) was subjected to the reaction with 2-bromo-2-(2-fluorophenyl)-1-cyclopropylethanone (2.03 g) and triethylamine (2.2 ml) in acetonitrile (50 ml). The crude product, that was obtained by usual extraction, was purified by silica gel chromatography using hexane and ethyl acetate (2:1) as an eluent to afford either (corresponding to the raw material) isomer of the title compounds (2.08 g, yield: 59%) as a brownish amorphous solid.

$^1$H NMR (400 MHz, CDCl$_3$) δ ppm: 0.66-0.99 (4H, m), 1.86-1.93 (1H, m), 2.18-2.25 (2H, m), 2.30 (3H, s), 2.46-2.61 (1H, m), 2.76-2.83 (1H, m), 3.42-3.47 (1H, m), 3.80 (3H, s), 4.22 (1H, d, J=13.5), 4.48-4.52 (1H, m), 4.74 (1H, d, J=3.0), 5.51-5.64 (2H, m), 6.64 (1H, s), 6.87-6.90 (2H, m), 7.04-7.14 (2H, m), 7.29-7.40 (4H, m).

(g) (E)-4-(Acetylsulfanyl)-1-[2-cyclopropyl-1-(2-fluorophenyl)-2-oxoethyl]-3-{[1(2)H-tetrazol-5-yl]methylidene}piperidine hydrogen trifluoroacetate A solution of the compound (2.08 g) obtained in Example 156-(f) in trifluoroacetic acid (20 ml) was stirred at 60° C. for 14.5 hours. After cooling, the mixture was concentrated under reduced pressure and the residue was purified by column chromatography on silica gel using dichloromethane and methanol (20:1) as an eluent to afford the title compound (2.65 g, yield: 100%) as a brown oil.

$^1$H NMR (400 MHz, CDCl$_3$) δ ppm: 0.86-0.94 (1H, m), 0.99-1.06 (1H, m), 1.15-1.22 (2H, m), 1.66-1.75 (1H, m), 2.12-2.18 (1H, m), 2.35 (3H, s), 2.56-2.68 (1H, m), 3.08-3.14 (1H, m), 3.32-3.38 (1H, m), 3.60 (1H, s), 4.47-4.49 (1H, m), 4.55-4.61 (2H, m), 5.62 (1H, s), 6.89 (1H, d, J=10.0), 7.29-7.45 (3H, m), 7.57-7.62 (1H, m).

Example 157

(E)-1-[2-Cyclopropyl-1-(2-fluorophenyl)-2-oxoethyl]-4-sulfanyl-3-{[1(2)H-tetrazol-5-yl]methylidene}piperidine hydrochloride (Exemplification Compound No. 1-57)

Following a procedure similar to that described in Example 133, (E)-4-(acetylsulfanyl)-1-[2-cyclopropyl-1-(2-fluorophenyl)-2-oxoethyl]-3-{[1(2)H-tetrazol-5-yl]methylidene}piperidine hydrogen trifluoroacetate (500 mg) was treated with hydrogen chloride, and the product was purified by preparative HPLC (YMC-Pack ODS-A; YMC, eluent: acetonitrile/0.024 N hydrochloric acid, 30/70, v/v) to afford the title compound (310 mg, yield: 80%) as a colourless amorphous solid.

$^1$H NMR (500 MHz, pyridine-d$_5$) δ ppm: 0.64-0.75 (2H, m), 0.91-1.01 (1H, m), 1.06-1.21 (1H, m), 1.81-1.96 (1H, m), 2.23-2.35 (1H, m), 2.36-2.44 (1H, m), 2.61-2.69 and 2.73-2.82 (total 1H, each m), 2.84-2.93 and 3.00-3.10 (total 1H, each m), 3.99 and 4.05 (total 1H, each t, J=5.5), 4.22 and 4.50 (total 1H, each d, J=13.0), 4.33 and 4.46 (total 1H, each d, J=13.0), 5.01 and 5.02 (total 1H, each s), 7.01 and 7.06 (total 1H, each s), 7.12-7.19 (2H, m), 7.24-7.30 (1H, m), 7.59-7.66 (1H, m)

IR (KBr, cm$^{-1}$): 2939, 1710. .

Example 158

(E)-4-(Acetylsulfanyl)-1-[2-cyclopropyl-1-(2-fluorophenyl)-2-oxoethyl]-3-{[1-(methoxycarbonylmethyl)-1H-tetrazol-5-yl]methylidene}piperidine hydrochloride (Exemplification Compound No. 2-1546)

(a) (E)-3-{[1-(Methoxycarbonylmethyl)-1H-tetrazol-5-yl]methylidene}-1-(triphenylmethyl)piperidin-4-ol Following a procedure similar to that described in Example 150-(d), (E)-3-{[1-(methoxycarbonylmethyl)-1H-tetrazol-5-yl]methylidene}-1-(triphenylmethyl)piperidin-4-one (Example 150-(c), 2.2 g) was reduced with sodium borohydride. Purification gave the title compound (1.5 g, yield: 68%) as a pale yellow amorphous solid.

$^1$H NMR (400 MHz, DMSO-$d_6$) δ ppm: 1.65-1.80 (2H, m), 1.98-2.05 (1H, m), 2.80-3.10 (2H, m), 3.29-3.31 (1H, m), 3.79 (3H, s), 3.99 (1H, bs), 5.75 (2H, s), 6.47 (1H, s), 7.06-7.41 (15H, m).

(b) (E)-4-(Acetylsulfanyl)-3-{[1-(methoxycarbonylmethyl)-1H-tetrazol-5-yl]methylidene}piperidine hydrogen trifluoroacetate Following a procedure similar to that described in Example 150-(e), (E)-3-{[1-(methoxycarbonylmethyl)-1H-tetrazol-5-yl]methylidene}-1-(triphenylmethyl)piperidin-4-ol (1.5 g) was subjected to the reaction with thioacetic acid and N,N-dimethylformamide dineopentyl acetal. The product was purified by silica gel chromatography to afford (E)-4-(acetylsulfanyl)-3-{([1-(methoxycarbonylmethyl)-1H-tetrazol-5-yl]methylidene}-1-(triphenylmethyl)piperidine (980 mg). This product was similarly treated with trifluoroacetic acid in dichloromethane, and the resulting product was purified by silica gel chromatography using dichloromethane and methanol (20:1) as an eluent to afford the title compound (342 mg, overall yield: 27%) as a yellow amorphous solid.

$^1$H NMR (400 MHz, CDCl$_3$) δ ppm: 2.07-2.18 (1H, m), 2.36 (3H, s), 2.52-2.65 (1H, m), 3.12-3.26 (1H, m), 3.44-3.55 (1H, m), 3.82 (3H, s), 3.91 (1H, d, J=15.0), 4.60 (1H, t, J=4.0), 5.08 (1H, d, J=15.0), 5.10 (1H, d, J=17.5), 5.23 (1H, d, J=17.5), 6.57 (1H, s).

(c) (E)-4-(Acetylsulfanyl)-1-[2-cyclopropyl-1-(2-fluorophenyl)-2-oxoethyl]-3-{[1-(methoxycarbonylmethyl)-1H-tetrazol-5-yl]methylidene}piperidine hydrochloride To a solution of (E)-4-(acetylsulfanyl)-3-{[1-(methoxycarbonylmethyl)-1H-tetrazol-5-yl]methylidene}piperidine hydrogen trifluoroacetate (342 mg) in acetonitrile (10 ml) was added 2-bromo-2-(2-fluorophenyl)-1-cyclopropylethanone (414 mg) and triethylamine (340 µl). After being stirred at room temperature for 3 hours, the mixture was partitioned between water and ethyl acetate. The organic layer was separated, washed with a saturated aqueous sodium chloride solution and dried over anhydrous magnesium sulfate. Removal of the solvent by evaporation under reduced pressure followed by purification of the residue by column chromatography on silica gel using hexane, ethyl acetate, and dichloromethane (2:1:1) as an eluent afforded the free base of the title compound, which was further purified by preparative HPLC (YMC-Pack ODS-A; YMC, eluent: acetonitrile/0.024 N hydrochloric acid, 30/70, v/v) to afford the title compound (176 mg, yield: 42%) as a colourless amorphous solid.

$^1$H NMR (400 MHz, pyridine-$d_5$) δ ppm: 0.67-0.78 (2H, m), 0.94-1.21 (2H, m), 1.81-1.91 (1H, m), 2.19 (3H, s), 2.22-2.33 (1H, m), 2.33-2.47 (1H, m), 2.43-2.52 and 2.69-2.78 (total 1H, each m), 2.81-2.97 (1H, m), 3.58 and 3.65 (total 1H, each d, J=14.0), 3.59 (3H, s), 4.59-4.67 (1H, m), 4.77 and 4.92 (total 1H, each d, J=14.0), 4.99 and 5.03 (total 1H, each s), 5.85 (2H, s), 6.90 and 6.92 (total 1H, each s), 7.12-7.35 (3H, m), 7.57-7.63 (1H, m);

IR (KBr, cm$^{-1}$): 2504, 1753, 1706.

Example 159

(E)-3-{[1-(Carboxylmethyl)-1H-tetrazol-5-yl]methylidene}-1-[2-cyclopropyl-1-(2-fluorophenyl)-2-oxoethyl]-4-sulfanylpiperidine hydrochloride (Exemplification Compound No. 2-1529)

Potassium carbonate (74 mg) was added to a solution of (E)-4-(acetylsulfanyl)-1-[2-cyclopropyl-1-(2-fluorophenyl)-2-oxoethyl]-3-{[1-(methoxycarbonylmethyl)-1H-tetrazol-5-yl]methylidene}piperidine hydrochloride (128 mg) in methanol (5 ml). After being stirred at room temperature for 15 minutes, the mixture was partitioned between water and ethyl acetate. The organic layer was separated, washed with a saturated aqueous sodium chloride solution and dried over anhydrous sodium sulfate. Concentration under reduced pressure gave a residue, which was purified by preparative HPLC (YMC-Pack ODS-A; YMC, eluent: acetonitrile/0.024N hydrochloric acid, 30/70, v/v) to give (E)-1-[2-cyclopropyl-1-(2-fluorophenyl)-2-oxoethyl]-3-{[1-(methoxycarbonylmethyl)-1H-tetrazol-5-yl]methylidene}-4-sulfanylpiperidine hydrochloride (57 mg, gross yield: 49%, a part of this product had been hydrolyzed at the methyl ester moiety). This product (40 mg) was treated with hydrochloric acid in a similar manner to that described in Example 134, and the resulting product was purified by preparative HPLC (YMC-Pack ODS-A; YMC, eluent: acetonitrile/0.024 N hydrochloric acid, 25/75, v/v) to afford the title compound (13 mg, yield: 34%) as a colourless amorphous solid.

$^1$H NMR (500 MHz, pyridine-$d_5$) δ ppm: 0.67-0.77 (2H, m), 0.94-1.02 (1H, m), 1.07-1.18 (1H, m), 1.77-1.89 (1H, m), 2.21-2.32 (1H, m), 2.37-2.47 (1H, m), 2.60-2.67 and 2.72-2.80 (total 1H, each m), 2.82-2.89 and 2.99-3.07 (total 1H, each m), 3.94-4.07 (1H, m), 4.23 and 4.51 (total 1H, each d, J=13.0), 4.27 and 4.37 (total 1H, each d, J=13.0), 4.99 and 5.01 (total 1H, each s), 5.77 (2H, s), 7.00 and 7.03 (total 1H, each s), 7.10-7.49 (3H, m), 7.58-7.65 (1H, m);

FAB-MS [M+H]$^+$: 432.

Example 160

(E)-4-(Acetylsulfanyl)-1-[2-cyclopropyl-1-(2-fluorophenyl)-2-oxoethyl]-3-{[1-(methoxycarbonylmethyl)-1H-1,2,3-triazol-5-yl]methylidene}piperidine hydrochloride (Exemplification Compound No. 2-1226)

(a) Methyl [5-(hydroxymethyl)-1H-1,2,3-triazol-1-yl]acetate and methyl [4-(hydroxymethyl)-1H-1,2,3-triazol-1-yl]acetate To a solution of methyl azidoacetate (24.41 g) in toluene (400 ml) was added propargyl alcohol (11.9 g), and the mixture was heated under reflux for 8 hours. After cooling, the solvent and the unchanged starting materials were removed by evaporation under reduced pressure to afford a mixture of the two title isomers (31.74 g, yield: 87%, isomeric ratio: ca. 1:1) as a yellow oil.

$^1$H NMR (400 MHz, CDCl$_3$) δ ppm: 3.78 and 3.79 (total 3H, s), 4.72 and 4.76 (total 2H, each s), 5.15 and 5.26 (total 2H, each s), 7.54 and 7.64 (total 1H, s).

(b) Methyl(5-formyl-1H-1,2,3-triazol-1-yl)acetate and methyl (4-formyl-1H-1,2,3-triazol-1-yl)acetate Active manganese dioxide (30.5 g) was added to a solution of a mixture of methyl [5-(hydroxymethyl)-1H-1,2,3-triazol-1-yl]acetate and methyl [4-(hydroxymethyl)-1H-1,2,3-triazol-1-yl]acetate (6.0 g) obtained above in dichloromethane (100 ml). After being stirred at room temperature for 3 hours, the mixture was filtered and the filtrate was concentrated under reduced pressure. The residue was purified by silica gel chromatography using dichloromethane and methanol (20:1) as an eluent to afford a mixture of the two title isomers (1.93 g, yield: 33%, isomeric ratio: ca. 1:4) as a yellow oil.

$^1$H NMR (400 MHz, CDCl$_3$) δ ppm: 3.79 and 3.84 (total 3H, each s), 5.25 and 5.29 (total 2H, each s), 8.25 and 8.28 (total 1H, each s), 10.20 and 10.22 (total 1H, each s).

(c) (E)-3-{[1-(Methoxycarbonylmethyl)-1H-1,2,3-triazol-5-yl]methylidene}-1-(triphenylmethyl)piperidin-4-one and (E)-3-{[1-(Methoxycarbonylmethyl)-1H-1,2,3-triazol-4-yl]methylidene}-1-(triphenylmethyl)piperidin-4-one Following a procedure similar to that described in Example 132-(c), a mixture (13.0 g) of methyl(5-formyl-1H-1,2,3-triazol-1-yl)acetate and methyl(4-formyl-1H-1,2,3-triazol-1-yl)acetate obtained above was subjected to the reaction with 1-(triphenylmethyl)piperidin-4-one (13.0 g). The crude products obtained by extraction was separated and purified by silica gel chromatography using hexane, ethyl acetate, and dichloromethane (2:1:1) as an eluent to afford respectively the two title isomers.

The less polar isomer (E)-3-{[1-(methoxycarbonylmethyl)-1H-1,2,3-triazol-5-yl]methylidene}-1-(triphenylmethyl)piperidin-4-one; amount: 3.74 g, yield: 15%, a yellow amorphous solid. $^1$H NMR (400 MHz, CDCl$_3$) δ ppm: 2.64 (2H, bs), 2.71 (2H, t, J=6.0), 3.32 (2H, bs), 3.73 (3H, s), 5.14 (2H, s), 7.05-7.50 (17H, m).

The more polar isomer (E)-3-{[1-(methoxycarbonylmethyl)-1H-1,2,3-triazol-4-yl]methylidene}-1-(triphenylmethyl)piperidin-4-one; amount: 10.53 g, yield: 41%, a yellow amorphous solid. $^1$H NMR (400 MHz, CDCl$_3$) δ ppm: 2.67 (2H, bs), 2.76 (2H, t, J=6.0), 3.67 (2H, bs), 3.78 (3H, s), 5.09 (2H, s), 7.10-7.27 (10H, m), 7.44-7.56 (7H, m).

(d) (E)-3-{[1-(Methoxycarbonylmethyl)-1H-1,2,3-triazol-5-yl]methylidene}-1-(triphenylmethyl)piperidin-4-ol Sodium borohydride (830 mg) was added to a solution of (E)-3-{[1-(methoxycarbonylmethyl)-1H-1,2,3-triazol-5-yl]methylidene}-1-(triphenylmethyl)piperidin-4-one (21.46 g) in tetrahydrofuran (500 ml) at 0° C. After the mixture was stirred at 0° C. for 4 hours, it was filtered, and the filtrate was diluted with ethyl acetate. Then the reaction was quenched by addition of a saturated aqueous ammonium chloride solution. The mixture was extracted with ethyl acetate, and the separated organic layer was washed with a saturated aqueous sodium chloride solution and dried over anhydrous magnesium sulfate. The extract was concentrated under reduced pressure and the residue was purified by silica gel chromatography using hexane, ethyl acetate, and dichloromethane (1:2:1) as an eluent to afford the title compound (6.27 g, yield: 29%) as a pale yellow amorphous solid.

$^1$H NMR (400 MHz, DMSO-d$_6$) δ ppm: 1.63-1.81 (2H, m), 2.14 (1H, bs), 2.72 (1H, bs), 3.60 (1H, bs), 3.74 (3H, s), 3.92 (1H, bs), 5.22 (1H, bs), 5.39 (1H, d, J=17.5), 5.46 (1H, d, J=17.5), 6.31 (1H, s), 7.01-7.49 (16H, m).

(e) (E)-4-(Acetylsulfanyl)-3-{[1-(methoxycarbonylmethyl)-1H-1,2,3-triazol-5-yl]methylidene}piperidine hydrogen trifluoroacetate To a solution of (E)-3-{[1-(methoxycarbonylmethyl)-1H-1,2,3-triazol-5-yl]methylidene}-1-(triphenylmethyl)piperidin-4-ol (6.27 g) in a mixed solvent of dichloromethane (100 ml) and toluene (100 ml) were added thioacetic acid (3.62 ml) and N,N-dimethylformamide dineopentyl acetal (14.0 ml). After the mixture was stirred at room temperature for 1 hour, water was added thereto and products were extracted with ethyl acetate. The organic layer was washed with a saturated aqueous sodium chloride solution and dried over anhydrous magnesium sulfate. Concentration under reduced pressure followed by purification of the residue by silica gel chromatography using hexane, ethyl acetate, and dichloromethane (2:1:1) as an eluent afforded crude (E)-4-(acetylsulfanyl)-3-{[1-(methoxycarbonylmethyl)-1H-1,2,3-triazol-5-yl]methylidene}-1-(triphenylmethyl)piperidine (4.0 g).

The product obtained above was dissolved in dichloromethane (200 ml) and trifluoroacetic acid (1.11 ml) was added thereto. The mixture was stirred at room temperature for 15 minutes, and then concentrated under reduced pressure. The residue was purified by preparative HPLC (YMC-Pack ODS-A; YMC, eluent: acetonitrile/0.026 N aqueous trifluoroacetic acid solution, 15/85, v/v) to afford the title compound (1.06 g, yield: 20%) as a yellow amorphous solid.

$^1$H NMR (400 MHz, CDCl$_3$) δ ppm: 2.08-2.17 (1H, m), 2.37 (3H, s), 2.43-2.55 (1H, m), 3.25 (1H, bs), 3.49 (1H, d, J=13.5), 3.79 (3H, s), 3.79-3.88 (1H, m), 4.09 (1H, d, J=13.5), 4.56 (1H, t, J=4.0), 5.09 (1H, d, J=17.5), 5.15 (1H, d, J=17.5), 6.58 (1H, s), 7.83 (1H, s).

(f) (E)-4-(Acetylsulfanyl)-1-[2-cyclopropyl-1-(2-fluorophenyl)-2-oxoethyl]-3-{[1-(methoxycarbonylmethyl)-1H-1,2,3-triazol-5-yl]methylidene}piperidine hydrochloride Following a procedure similar to that described in Example 150-(g), (E)-4-(acetylsulfanyl)-3-{[1-(methoxycarbonylmethyl)-1H-1,2,3-triazol-5-yl]methylidene}piperidine hydrogen trifluoroacetate (1.06 g) was subjected to the reaction with 2-bromo-2-(2-fluorophenyl)-1-cyclopropylethanone and triethylamine and the free base that was obtained by silica gel chromatography was similarly treated with hydrogen chloride to yield the title compound (650 mg, yield: 50%) as a pale yellow amorphous solid.

$^1$H NMR (400 MHz, CDCl$_3$) δ ppm: 0.67-0.83 (2H, m), 0.89-1.02 (2H, m), 1.80-1.90 (1H, m), 1.94-2.01 (1H, m), 2.16-2.28 (1H, m), 2.28 and 2.29 (total 3H, each s), 2.41-2.57 (1H, m), 2.72-2.77 and 2.80-2.87 (total 1H, each m), 2.88 and 3.12 (total 1H, each d, J=13.0), 3.44 and 3.47 (total 1H, each d, J=13.0), 3.74 and 3.76 (total 3H, each s), 4.38-4.43 (1H, m), 4.70 and 4.72 (total 1H, each s), 5.02-5.10 (2H, m), 6.21 (1H, s), 7.04-7.18 (2H, m), 7.23-7.36 (2H, m), 7.43 and 7.48 (total 1H, each s);

IR (KBr, cm$^{-1}$): 2470, 1753, 1699.

Example 161

(E)-1-[2-Cyclopropyl-1-(2-fluorophenyl)-2-oxoethyl]-3-{[1-(methoxycarbonylmethyl)-1H-1,2,3-triazol-5-yl]methylidene}-4-sulfanylpiperidine hydrochloride (Exemplification Compound No. 2-1225)

Following a procedure similar to that described in Example 151, (E)-4-(acetylsulfanyl)-1-[2-cyclopropyl-1-(2-fluorophenyl)-2-oxoethyl]-3-{[1-(methoxycarbonylmethyl)-1H-1,2,3-triazol-5-yl]methylidene}piperidine hydrochloride (560 mg) was treated with potassium carbonate in methanol and the concentrated extract was purified by preparative HPLC (YMC-Pack ODS-A; YMC, eluent: acetonitrile/0.024 N hydrochloric acid, 30/70, v/v) to afford the title compound (370 mg, yield: 72%) as a yellow amorphous solid.

$^1$H NMR (400 MHz, CDCl$_3$) δ ppm: 0.65-0.85 (2H, m), 0.89-1.02 (2H, m), 1.73-1.84 (1H, m), 1.91-2.02 (1H, m), 2.18-2.32 (1H, m), 2.56-2.70 (1H, m), 2.77-2.91 (1H, m), 3.13 and 3.20 (total 1H, each d, J=12.5), 3.38 and 3.53 (total 1H, each d, J=12.5), 3.71-3.84 (1H, m), 3.76 (3H, s), 4.73 and 4.74 (total 1H, each s), 5.09 (2H, s), 6.22 and 6.23 (total 1H, each s), 7.05-7.17 (2H, m), 7.23-7.36 (2H, m), 7.43 and 7.48 (total 1H, each s);
IR (KBr, cm$^{-1}$): 2449, 1752, 1711.

Example 162

(E)-3-{[1-(Carboxymethyl)-1H-1,2,3-triazol-5-yl]methylidene}-1-[2-cyclopropyl-1-(2-fluorophenyl)-2-oxoethyl]-4-sulfanylpiperidine hydrochloride (Exemplification Compound No. 2-1209)

Following a procedure similar to that described in Example 134, (E)-1-[2-cyclopropyl-1-(2-fluorophenyl)-2-oxoethyl]-3-{[1-(methoxycarbonylmethyl)-1H-1,2,3-triazol-5-yl]methylidene}-4-sulfanylpiperidine hydrochloride (200 mg) was treated with hydrochloric acid and the residue obtained by concentration was purified by preparative HPLC (YMC-Pack ODS-A; YMC, eluent: acetonitrile/0.024 N hydrochloric acid, 25/75, v/v) to afford the title compound (174 mg, yield: 90%) as a colourless amorphous solid.

$^1$H NMR (400 MHz, pyridine-d$_5$) δ ppm: 0.61-0.77 (2H, m), 0.90-1.08 (2H, m), 1.74-1.86 (1H, m), 2.16-2.36 (2H, m), 2.58-2.82 (1H, m), 2.82-3.00 (1H, m), 3.60 and 3.62 (total 1H, each d, J=13.0), 3.75 and 3.82 (total 1H, each d, J=13.0), 3.93-4.01 (1H, m), 4.94 and 4.95 (total 1H, each s), 5.65 (2H, s), 6.83 and 6.85 (total 1H, each s), 7.12-7.23 (2H, m), 7.24-7.34 (1H, m), 7.52-7.63 (1H, m), 7.96 and 8.03 (total 1H, each s);
IR (KBr, cm$^{-1}$): 2923, 2519, 1740, 1710.

Example 163

(E)-4-(Acetylsulfanyl)-1-[2-cyclopropyl-1-(2-fluorophenyl)-2-oxoethyl]-3-{[1-(methoxycarbonylmethyl)-1H-1,2,3-triazol-5-yl]methylidene}piperidin-4-ol hydrochloride (Exemplification Compound No. 2-1162)

(a) (E)-3-{[1-(Methoxycarbonylmethyl)-1H-1,2,3-triazol-4-yl]methylidene}-1-(triphenylmethyl)piperidin-4-ol Sodium borohydride (508 mg) was added to a solution of (E)-3-{[1-(methoxycarbonylmethyl)-1H-1,2,3-triazol-4-yl]methylidene}-1-(triphenylmethyl)piperidin-4-one (6.61 g) obtained in Example 160-(c) in tetrahydrofuran (150 ml) at 0° C. After being stirred at 0° C. for 6 hours, the mixture was filtered and the filtrate was diluted with ethyl acetate, then the reaction was quenched by addition of a saturated aqueous ammonium chloride solution. Products were extracted with ethyl acetate, and the separated organic layer was washed with a saturated aqueous sodium chloride solution. Concentration under reduced pressure gave a solid, which was collected by filtration and washed with a mixed solvent of hexane-ethyl acetate-dichloromethane (1:1:1) to afford the title compound (4.7 g, yield: 71%) as a pale yellow amorphous solid.

$^1$H NMR (400 MHz, DMSO-d$_6$) ppm: 1.67-1.82 (2H, m), 1.91-2.03 (1H, m), 2.62-2.76 (1H, m), 3.36-3.47 (1H, m), 3.72 (3H, s), 3.91 (1H, bs), 5.08 (1H, bs), 5.21 (1H, d, J=17.5), 5.32 (1H, d, J=17.5), 6.48 (1H, s), 7.00-7.53 (15H, m), 7.85 (1H, s).

(b) (E)-4-(Acetylsulfanyl)-3-{[1-(methoxycarbonylmethyl)-1H-1,2,3-triazol-4-yl]methylidene}piperidine hydrogen trifluoroacetate Following a procedure similar to that described in Example 160-(e), (E)-3-{[1-(methoxycarbonylmethyl)-1H-1,2,3-triazol-4-yl]methylidene}-1-(triphenylmethyl)piperidin-4-ol (4.7 g) was treated with thioacetic acid and N,N-dimethylformamide dineopentyl acetal. After extraction, the obtained substance was purified by silica gel chromatography to afford (E)-4-(acetylsulfanyl)-3-{[1-(methoxycarbonylmethyl)-1H-1,2,3-triazol-4-yl]methylidene}-1-(triphenylmethyl)piperidine (2.6 g). This compound was similarly treated with trifluoroacetic acid in dichloromethane and the residue obtained by concentration of the reaction mixture was purified by preparative HPLC (YMC-Pack ODS-A; YMC, eluent: acetonitrile/0.026 N aqueous trifluoroacetic acid solution, 18/82, v/v) to afford the title compound (550 mg, yield: 14%) as a yellow amorphous solid.

$^1$H NMR (400 MHz, CDCl$_3$) δ ppm: 2.09-2.16 (1H, m), 2.37 (3H, s), 2.42-2.56 (1H, m), 3.23-3.36 (1H, m), 3.51 (1H, d, J=12.0), 3.79 (3H, s), 3.90-4.00 (1H, m), 4.58 (1H, t, J=4.0), 5.04 (1H, d, J=14.0), 5.14 (2H, d, J=5.0), 6.70 (1H, s), 7.72 (1H, s).

(c) (E)-4-(Acetylsulfanyl)-1-[2-cyclopropyl-1-(2-fluorophenyl)-2-oxoethyl]-3-{[1-(methoxycarbonylmethyl)-1H-1,2,3-triazol-4-yl]methylidene}piperidine hydrochloride Following a procedure similar to that described in Example 150-(g), (E)-4-(acetylsulfanyl)-3-{[1-(methoxycarbonylmethyl)-1H-1,2,3-triazol-4-yl]methylidene}piperidine hydrogen trifluoroacetate (550 mg) was subjected to the reaction with 2-bromo-2-(2-fluorophenyl)-1-cyclopropylethanone and triethylamine, and the free base that was obtained by chromatographic purification on silica gel was treated with hydrogen chloride to yield the title compound (380 mg, yield: 56%) as a pale yellow amorphous solid.

$^1$H NMR (500 MHz, CDCl$_3$) δ ppm: 0.64-0.83 (2H, m), 0.86-1.00 (2H, m), 1.80-1.89 (1H, m), 2.07-2.15 (1H, m), 2.19-2.30 (1H, m), 2.27 (3H, s), 2.37-2.46 and 2.55-2.64 (total 1H, each m), 2.68-2.79 (1H, m), 3.15 and 3.19 (total 1H, each d, J=12.5), 3.77 (3H, s), 3.90 and 4.02 (total 1H, each d, J=12.5), 4.45 (1H, t, J=5.0), 4.70 and 4.74 (total 1H, each s), 5.06-5.13 (2H, m), 6.54 (1H, s), 7.02-7.14 (2H, m), 7.25-7.30 (1H, m), 7.32-7.39 (1H, m), 7.55 and 7.63 (total 1H, each s);
IR (KBr, cm$^{-1}$): 2505, 1753, 1697.

Example 164

(E)-1-[2-Cyclopropyl-1-(2-fluorophenyl)-2-oxoethyl]-3-{[1-(methoxycarbonylmethyl)-1H-1,2,3-triazol-4-yl]methylidene}-4-sulfanylpiperidine hydrochloride (Exemplification Compound No. 2-1161)

Following a procedure similar to that described in Example 151, (E)-4-(acetylsulfanyl)-1-[2-cyclopropyl-1-(2-fluorophenyl)-2-oxoethyl]-3-{[1-(methoxycarbonylmethyl)-1H-1,2,3-triazol-4-yl]methylidene}piperidine hydrochloride (300 mg) was treated with potassium carbonate in methanol and the concentrated extract was purified by preparative HPLC (YMC-Pack ODS-A; YMC, eluent: acetonitrile/0.024 N hydrochloric acid, 25/75, v/v) to afford the title compound (130 mg, yield: 47%) as a yellow amorphous solid.

1H NMR (400 MHz, CDCl$_3$) δ ppm: 0.64-1.06 (4H, m), 1.72-1.85 (1H, m), 2.02-2.15 (1H, m), 2.18-2.35 (1H, m), 2.54-2.68 (1H, m), 2.69-2.92 (1H, m), 3.52-3.65 (2H, m), 3.81 (3H, s), 3.86-3.93 (1H, m), 4.78 and 4.80 (total 1H, each s), 5.08-5.15 (2H, m), 6.56 and 6.58 (total 1H, each s), 7.05-7.16 (2H, m), 7.26-7.42 (2H, m), 7.60 and 7.69 (total 1H, each s);

IR (KBr, cm$^{-1}$): 2515, 2463, 1753, 1712.

Example 165

(E)-3-{[1-(Carboxymethyl)-1H-1,2,3-triazol-4-yl]methylidene}-1-[2-cyclopropyl-1-(2-fluorophenyl)-2-oxoethyl]-4-sulfanylpiperidine hydrochloride (Exemplification Compound No. 2-1145)

Following a procedure similar to that described in Example 134, (E)-1-[2-cyclopropyl-1-(2-fluorophenyl)-2-oxoethyl]-3-{[1-(methoxycarbonylmethyl)-1H-1,2,3-triazol-4-yl]methylidene}-4-sulfanylpiperidine hydrochloride (82.8 mg) was treated with hydrochloric acid and the residue obtained by concentration of the reaction mixture was purified by preparative HPLC (YMC-Pack ODS-A; YMC, eluent: acetonitrile/0.024 N hydrochloric acid, 25/75, v/v) to afford the title compound (76.0 mg, yield: 95%) as a colourless amorphous solid.

$^1$H NMR (400 MHz, pyridine-d$_5$) δ ppm: 0.61-0.79 (2H, m), 0.91-1.03 (1H, m), 1.05-1.21 (1H, m), 1.76-1.93 (1H, m), 2.22-2.36 (1H, m), 2.38-2.47 (1H, m), 2.65-2.77 (1H, m), 2.82-2.93 and 2.94-3.06 (total 1H, each m), 3.92-4.41 (3H, m), 4.95 and 4.97 (total 1H, each s), 5.55-5.65 (2H, m), 6.84 (1H, s), 7.11-7.22 (2H, m), 7.24-7.32 (1H, m), 7.60-7.72 (1H, m), 8.13 and 8.20 (total 1H, each s).

IR (KBr, cm$^{-1}$): 2913, 1743, 1710.

Example 166

(E)-4-(Acetylsulfanyl)-1-[2-cyclopropyl-1-(2-fluorophenyl)-2-oxoethyl]-3-{[1-(methoxycarbonylmethyl)-1H-1,2,4-triazol-3-yl]methylidene}piperidine hydrochloride (Exemplification Compound No. 2-1290)

(a) (E)-3-[(1,2,4-Triazol-3-yl)methylidene]-1-(triphenylmethyl)piperidin-4-one

Di(t-butyl) dicarbonate (50.0 g) and potassium carbonate (41.0 g) were added to a solution of 1,2,4-triazole-3-carbaldehyde hydrochloride (19.8 g) in a mixed solvent of 2-propanol (300 ml) and water (300 ml). After the mixture was stirred at room temperature for 2 hours, the product was extracted with ethyl acetate. The organic layer was washed with a saturated aqueous sodium chloride solution and dried over anhydrous magnesium sulfate. The extract was concentrated under reduced pressure and the residue was purified by silica gel chromatography using hexane and ethyl acetate (1:1) as an eluent to give 1-(t-butoxycarbonyl)-1H-1,2,4-triazole-3-carbaldehyde (10.26 g).

Pyrrolidine (4.3 ml) was added to a solution of 1-(triphenylmethyl)piperidin-4-one (17.7 g) in benzene (500 ml). The mixture was heated under reflux for 3 hours removing water using a Dean-Staak apparatus. The mixture was cooled to room temperature, and 1-(t-butoxycarbonyl)-1H-1,2,4-triazole-3-carbaldehyde (10.2 g) was added. After the mixture was heated for 3 further hours under reflux, it was cooled, then water was added, and products were extracted with ethyl acetate. The organic layer was washed with a saturated aqueous sodium chloride solution and dried over anhydrous magnesium sulfate. After concentration under reduced pressure, the residue was treated with methanol (200 ml) at room temperature for 30 minutes. The solution was partitioned between water and ethyl acetate, and the organic layer was washed with a saturated aqueous sodium chloride solution and then dried over anhydrous magnesium sulfate. Concentration under reduced pressure gave a residue, which was purified by silica gel chromatography using hexane, ethyl acetate, and dichloromethane (1:2:1) as an eluent to give the title compound (2.92 g, yield: 13%) as a yellow amorphous solid.

$^1$H NMR (400 MHz, CDCl$_3$) δ ppm: 2.66 (2H, bs), 2.79 (2H, t, J=6.0), 3.88 (2H, bs), 7.10-7.55 (16H, m), 8.04 (1H, s).

(b) (E)-3-{[1-(Methoxycarbonylmethyl)-1H-1,2,4-triazol-5-yl]methylidene}-1-(triphenylmethyl)piperidin-4-ol and (E)-3-{[1-(methoxycarbonylmethyl)-1H-1,2,4-triazol-3-yl]methylidene}-1-(triphenylmethyl)piperidin-4-ol Sodium borohydride (131 mg) was added to a solution of (E)-3-[(1,2,4-triazol-3-yl)methylidene]-1-(triphenylmethyl)piperidin-4-one (2.92 g) in a mixed solvent of dichloromethane (60 ml) and methanol (60 ml) at 0° C. After the mixture was stirred at room temperature for 30 minutes, the reaction was quenched by addition of a saturated aqueous ammonium chloride solution. Products were extracted with ethyl acetate, and the extract was washed with a saturated aqueous sodium chloride solution and dried over anhydrous magnesium sulfate. Solvents were removed under reduced pressure to afford crude (E)-3-[(1,2,4-triazol-3-yl)methylidene]-1-(triphenylmethyl)piperidin-4-ol. The crude product was dissolved in acetonitrile (60 ml) and methyl bromoacetate (920 μl) was added. After DBU (1.25 ml) was added thereto under cooling at 0° C., the mixture was stirred at 0° C. for 15 minutes. Water and ethyl acetate were added to the mixture and the layers were separated. The organic layer was washed with a saturated aqueous sodium chloride solution and dried over anhydrous magnesium sulfate. Removal of the solvent by evaporation under reduced pressure gave an approximately 1:3 mixture of the two title isomers (2.98 g, yield: 87%) as a pale yellow amorphous solid.

The less polar isomer (E)-3-{[1-(methoxycarbonylmethyl)-1H-1,2,4-triazol-5-yl]methylidene}-1-(triphenylmethyl)piperidin-4-ol: $^1$H NMR (500 MHz, CDCl$_3$, selected signals) δ ppm: 1.69-1.79 (1H, m), 1.85-1.95 (1H, m), 2.08-2.17 (1H, m), 3.01 (1H, bs), 3.82 (3H, s), 4.03-4.15 (1H, m), 4.61 (1H, bs), 5.03 (2H, s), 6.36 (1H, s), 7.04-7.21 (8H, m), 7.29-7.42 (7H, m), 7.65 (1H, s).

The more polar isomer (E)-3-{[1-(methoxycarbonylmethyl)-1H-1,2,4-triazol-3-yl]methylidene}-1-(triphenylmethyl)piperidin-4-ol: $^1$H NMR (500 MHz, CDCl$_3$, selected signals) δ ppm: 1.82 (1H, bs), 1.86-1.93 (2H, m), 2.10-2.18 (2H, m), 2.83 (1H, bs), 3.80 (3H, s), 4.08-4.15 (1H, m), 4.30 (1H, bs), 4.72 (2H, d, J=17.5), 6.55 (1H, s), 7.03-7.19 (8H, m), 7.36-7.45 (7H, m), 8.00 (1H, s).

(c) (E)-4-(Acetylsulfanyl)-3-{[1-(methoxycarbonylmethyl)-1H-1,2,4-triazol-5-yl]methylidene}-1-(triphenylmethyl)piperidine and (E)-4-(acetylsulfanyl)-3-{[1-(methoxycarbonylmethyl)-1H-1,2,4-triazol-3-yl]methylidene}-1-(triphenylmethyl)piperidine The mixture (2.98 g) of (E)-3-{[1-(methoxycarbonylmethyl)-1H-1,2,4-triazol-5-yl]methylidene}-1-(triphenylmethyl)piperidin-4-ol and (E)-3-{[1-(methoxycarbonylmethyl)-1H-1,2,4-triazol-3-yl]methylidene}-1-(triphenylmethyl)piperidin-4-ol obtained in Example 166-(b) was dissolved in a mixed solvent of dichloromethane (40 ml) and toluene (40 ml), and thioacetic acid (1.3 ml) and N,N-dimethylformamide dineopentyl acetal (5.0 ml) were added thereto. After the mixture was stirred at room temperature for 2 hours, it was partitioned between water and ethyl acetate. The organic layer was washed with a saturated aqueous sodium chloride solution and dried over anhydrous sodium sulfate. The solvent was evaporated under reduced pressure gave a residue, which was purified by silica gel chromatography using hexane, ethyl acetate, and dichloromethane (1:1:1) to afford (E)-4-(acetylsulfanyl)-3-{[1-(methoxycarbonylmethyl)-1H-1,2,4-triazol-5-yl]methylidene}-1-(triphenylmethyl)piperidine (containing impurities, 1.52 g, gross yield: 46%) as the less polar isomer, and (E)-4-(acetylsulfanyl)-3-{[1-(methoxycarbonylmethyl)-1H-1,2,4-triazol-3-yl]methylidene}-1-(triphenylmethyl)piperidine (2.08 g, yield: 62%) as the polar isomer, respectively.

(d) (E)-4-(Acetylsulfanyl)-3-{[1-(methoxycarbonylmethyl)-1H-1,2,4-triazol-3-yl]methylidene}piperidine hydrogen trifluoroacetate Following a procedure similar to that described in Example 132-(f), (E)-4-(acetylsulfanyl)-3-{[1-(methoxycarbonylmethyl)-1H-1,2,4-triazol-3-yl]methylidene}-1-(triphenylmethyl)piperidine obtained in Example 166-(c) was treated with trifluoroacetic acid in dichloromethane and the crude product was purified by silica gel chromatography using dichloromethane and methanol (20:1 to 10:1) as an eluent to afford the title compound (860 mg, yield: 54%) as a yellow amorphous solid.

$^1$H NMR (400 MHz, CDCl$_3$) δ ppm: 2.02-2.14 (1H, m), 2.34 (3H, s), 2.38-2.51 (1H, m), 3.14-3.29 (1H, m), 3.32-3.43 (1H, m), 3.74 (3H, s), 3.95 (1H, d, J=14.0), 4.56 (1H, m), 4.90 (2H, s), 5.28 (1H, d, J=14.0), 6.73 (1H, s), 8.12 (1H, s).

(e) (E)-4-(Acetylsulfanyl)-1-[2-cyclopropyl-1-(2-fluorophenyl)-2-oxoethyl]-3-{[1-(methoxycarbonylmethyl)-1H-1,2,4-triazol-3-yl]methylidene}piperidine hydrochloride Following a procedure similar to that described in Example 132-(g), (E)-4-(acetylsulfanyl)-3-{[1-(methoxycarbonylmethyl)-1H-1,2,4-triazol-3-yl]methylidene}piperidine hydrogen trifluoroacetate (860 mg) was subjected to the reaction with 2-bromo-2-(2-fluorophenyl)-1-cyclopropylethanone and, after purification by silica gel chromatography, the product was similarly treated with hydrogen chloride to yield the title compound (916 mg, yield: 86%) as a pale yellow amorphous solid.

$^1$H NMR (400 MHz, CDCl$_3$) δ ppm: 0.61-1.08 (4H, m), 1.77-1.96 (1H, m), 2.20-2.36 (2H, m), 2.30 (3H, s), 2.42-2.54 and 2.59-2.71 (total 1H, each m), 2.72-2.86 (1H, m), 3.38 and 3.45 (total 1H, each d, J=13.5), 3.80 (3H, s), 4.38-4.53 (2H, m), 4.71 and 4.73 (total 1H, each s), 4.83 and 4.89 (total 2H, each s), 6.53 and 6.54 (total 1H, each s), 7.03-7.17 (2H, m), 7.24-7.33 (1H, m), 7.40-7.48 (1H, m), 8.01 and 8.05 (total 1H, each s);

IR (KBr, cm$^{-1}$): 2507, 1754, 1699.

Example 167

(E)-1-[2-Cyclopropyl-1-(2-fluorophenyl)-2-oxoethyl]-3-{[1-(methoxycarbonylmethyl)-1H-1,2,4-triazol-3-yl]methylidene}-4-sulfanylpiperidine hydrochloride (Exemplification Compound No. 2-1289)

Following a procedure similar to that described in Example 151, (E)-4-(acetylsulfanyl)-1-[2-cyclopropyl-1-(2-fluorophenyl)-2-oxoethyl]-3-{[1-(methoxycarbonylmethyl)-1H-1,2,4-triazol-3-yl]methylidene}piperidine hydrochloride (820 mg) was treated with potassium carbonate and the crude product was purified by preparative HPLC (YMC-Pack ODS-A; YMC, eluent: acetonitrile/0.024N hydrochloric acid, 30/70, v/v) to afford the title compound (560 mg, yield: 74%) as a colourless amorphous solid.

$^1$H NMR (400 MHz, CDCl$_3$) δ ppm: 0.64-0.88 (2H, m), 0.84-1.06 (2H, m), 1.74-1.87 (1H, m), 2.22-2.37 (2H, m), 2.58-2.72 (1H, m), 2.72-2.82 and 2.86-2.95 (total 1H, each m), 3.79 (3H, s), 3.80-3.94 (2H, m), 4.17 and 4.20 (total 1H, each d, J=13.0), 4.74 and 4.75 (total 1H, each s), 4.83 and 4.87 (total 2H, each s), 6.49 and 6.50 (total 1H, each s), 7.01-7.14 (2H, m), 7.23-7.31 (1H, m), 7.39-7.47 (1H, m), 8.01 and 8.03 (total 1H, each s);

IR (KBr, cm$^{-1}$): 2480, 1753, 1711.

Example 168

(E)-4-(Acetylsulfanyl)-1-[2-cyclopropyl-1-(2-fluorophenyl)-2-oxoethyl]-3-{[1-(ethoxycarbonylmethyl)-1H-imidazol-5-yl]methylidene}piperidine (Exemplification Compound No. 2-1058)

(a) Ethyl(5-formyl-1H-imidazol-1-yl)acetate

To a solution of 1H-imidazole-4(5)-carbaldehyde (5.5 g) in acetonitrile (100 ml) were added ethyl bromoacetate (7.65 ml), potassium carbonate (15.8 g) and potassium iodide (11.4 g) with stirring. The mixture was stirred at 50° C. for 3.5 hours, and after cooling, precipitates were removed by filtration, and the filtrate was concentrated under reduced pressure. The residue thus obtained was purified successively by silica gel chromatography using dichloromethane and methanol (10:1) as an eluent and by preparative HPLC (YMC-Pack ODS-A; YMC, eluent: acetonitrile/water, 15/85, v/v) to afford ethyl(4-formyl-1H-imidazol-1-yl)acetate (4.60 g, yield: 44%) as the more mobile isomer, and the title compound (1.95 g, yield: 19%) as the less mobile isomer, both as yellow oils respectively. The less mobile, title isomer: $^1$H NMR (500 MHz, CDCl$_3$) δ ppm: 1.30 (3H, t, J=7.0), 4.26 (2H, q, J=7.0), 5.05 (2H, s), 7.68 (1H, s), 7.84 (1H, s), 9.75 (1H, s).

(b) (E)-3-{[1-(ethoxycarbonylmethyl)-1H-imidazol-5-yl]methylidene}-1-(triphenylmethyl)piperidin-4-one To a solution of 1-(triphenylmethyl)piperidin-4-one (3.66 g) in benzene (40 ml) was added pyrrolidine (0.97 ml), and the mixture was heated under reflux for 3.5 hours. To this mixture was added a solution of ethyl(5-formyl-1H-imidazol-1-yl)acetate (1.95 g) in benzene (10 ml) under cooling using an ice bath. Then, the whole was heated further under reflux for 8.5 hours. After cooling, the mixture was partitioned between water and ethyl acetate. The organic layer was washed with a saturated aqueous sodium chloride solution and dried over anhydrous magnesium sulfate. The extract was concentrated under reduced pressure and the residue was purified by silica gel chromatography using hexane and ethyl acetate (1:3) as an eluent to afford the title compound (1.0 g, yield: 19%) as a yellow oil.

$^1$H NMR (500 MHz, CDCl$_3$) δ ppm: 1.30 (3H, t, J=7.0), 2.62-2.78 (4H, m), 3.38 (2H, bs), 4.26 (2H, q, J=7.0), 4.75 (2H, s), 7.14-7.58 (18H, m).

(c) (E)-3-{[1-(Ethoxycarbonylmethyl)-1H-imidazol-5-yl]methylidene}-1-(triphenylmethyl)piperidin-4-ol Sodium borohydride (0.06 g) was added to a solution of (E)-3-{[1-(ethoxycarbonylmethyl)-1H-imidazol-5-yl]methylidene}-1-(triphenylmethyl)piperidin-4-one (1.5 g) in a mixed solvent of dichloromethane (10 ml) and ethanol (10 ml) at 0° C. After the mixture was stirred at 0° C. for 0.5 hour and then at room temperature for 1.5 hour, it was partitioned between water and ethyl acetate. The organic layer was separated, washed with a saturated aqueous sodium chloride solution and dried over anhydrous magnesium sulfate. Removal of the solvent under reduced pressure followed by purification of the residue by silica gel chromatography using dichloromethane and methanol (19:1) as an eluent to give the title compound (560 mg, yield: 37%) as a yellow amorphous solid.

$^1$H NMR (500 MHz, CDCl$_3$) δ ppm: 1.26 (3H, t, J=7.0), 1.84-1.93 (1H, m), 1.95-2.16 (2H, m), 2.33-2.52 (1H, m), 2.79-2.92 (1H, m), 3.65-3.79 (1H, m), 4.11-4.19 (1H, m), 4.29 (2H, q, J=7.0), 4.71 (2H, s), 6.21 (1H, s), 6.69 (1H, s), 7.08-7.23 (9H, m), 7.33-7.42 (6H, m) 7.48 (1H, s).

(d) (E)-4-(Acetylsulfanyl)-3-{[1-(ethoxycarbonylmethyl)-1H-imidazol-5-yl]methylidene}piperidine hydrogen trifluoroacetate To a solution of (E)-3-{[1-(ethoxycarbonylmethyl)-1H-imidazol-5-yl]methylidene}-1-(triphenylmethyl)piperidin-4-ol (560 mg) in N,N-dimethylformamide (5 ml) were added N,N-dimethylformamide dineopentyl acetal (2.5 ml) and thioacetic acid (0.6 ml) at room temperature. After being stirred at the same temperature for 1.5 hour, the mixture was partitioned between ethyl acetate and water. The organic layer was separated, washed with a saturated aqueous sodium chloride solution and dried over anhydrous magnesium sulfate. Solvents were removed under reduced pressure, and residue was purified by silica gel chromatography using hexane, ethyl acetate, and dichloromethane (1:2:2) as an eluent. In a separate run, further starting material (E)-3-{[1-(ethoxycarbonylmethyl)-1H-imidazol-5-yl]methylidene}-1-(triphenylmethyl)piperidin-4-ol (1.0 g) was subjected to the similar reaction/purification procedure. Both products were combined to afford an approximately 5:2 mixture of (E)-4-(acetylsulfanyl)-3-{[1-(ethoxycarbonylmethyl)-1H-imidazol-5-yl]methylidene}-1-(triphenylmethyl)piperidine and 5-{(acetylsulfanyl)[1-(ethoxycarbonylmethyl)-1H-imidazol-5-yl]methyl}-1-(triphenylmethyl)-1,2,3,6-tetrahydropyridine (500 mg, gross yield: 29%), as a yellow amorphous solid.

Trifluoroacetic acid (1 ml) was added dropwise to a solution of the above mixture (500 mg) in dichloromethane (10 ml) at room temperature over a period of 2.5 hours with stirring. The mixture was concentrated under reduced pressure and the residue was purified by silica gel chromatography using dichloromethane and methanol (19:1 to 2:1) as eluents to afford a mixture (370 mg, gross yield: 76%) of the title compound and 5-{(acetylsulfanyl)[1-(ethoxycarbonylmethyl)-1H-imidazol-5-yl]methyl}-1,2,3,6-tetrahydropyridine hydrogen trifluoroacetate as a yellow amorphous solid.

$^1$H NMR (500 MHz, CDCl$_3$, selected signals) δ ppm: 1.33 (3H, t, J=7.0), 2.06-2.09 (1H, m), 2.38 (3H, s), 2.48-2.62 (1H, m), 3.12-3.33 (1H, m), 3.38-3.46 (1H, m), 3.76 (1H, d, J=15.0), 4.22-4.34 (2H, m), 4.23 (1H, d, J=15.0), 4.58 (1H, m), 4.76-4.96 (2H, m), 6.42 (1H, s), 7.26 (1H, s), 8.73 (1H, s).

(e) (E)-4-(Acetylsulfanyl)-1-[2-cyclopropyl-1-(2-fluorophenyl)-2-oxoethyl]-3-{[1-(ethoxycarbonylmethyl)-1H-imidazol-5-yl]methylidene}piperidine To a solution of the mixture (370 mg) obtained in Example 168-(d) in acetonitrile (10 ml) was added 2-bromo-2-(2-fluorophenyl)-1-cyclopropylethanone (270 mg) and triethylamine (290 µl). After being stirred at room temperature for 0.5 hour, the mixture was concentrated under reduced pressure and the residue was purified by silica gel chromatography using dichloromethane and methanol (19:1) as an eluent to afford the title compound (240 mg, containing impurities, gross yield: 56%) as a yellow oil.

$^1$H NMR (500 MHz, CDCl$_3$, selected signals) δ ppm: 0.68-0.87 (2H, m), 0.92-1.05 (2H, m), 1.28 (3H, t, J=7.0), 1.81-1.91 (1H, m), 2.07-2.29 (2H, m), 2.30 (3H, s), 2.40-2.48 (1H, m), 2.57-2.69 (1H, m), 3.01 and 3.11 (total 1H, each d, J=13.0), 3.61 and 3.70 (total 1H, each d, J=13.0), 4.23 (2H, q, J=7.0), 4.43-4.49 (1H, m), 4.59 and 4.62 (total 2H, each s), 4.70 and 4.72 (total 1H, each s), 6.17 and 6.18 (total 1H, bs), 6.75 and 6.85 (total 1H, each bs), 7.06-7.19 (2H, m), 7.28-7.38 (2H, m), 7.44 and 7.47 (total 1H, each bs).

Example 169

(E)-3-{[1-(carboxylmethyl)-1H-imidazol-5-yl]methylidene}-1-[2-cyclopropyl-1-(2-fluorophenyl)-2-oxoethyl]-4-sulfanylpiperidine hydrochloride (Exemplification Compound No. 2-1025)

(E)-4-(acetylsulfanyl)-1-[2-cyclopropyl-1-(2-fluorophenyl)-2-oxoethyl]-3-{[1-(ethoxycarbonylmethyl)-1H-imidazol-5-yl]methylidene}piperidine (240 mg, containing impurities) obtained in Example 168 was dissolved in methanol (5 ml), and potassium carbonate (67 mg) was added thereto at room temperature. After being stirred at the same temperature for 0.5 hour, the mixture was partitioned between water and ethyl acetate. The organic layer was separated, washed with a saturated aqueous sodium chloride solution and dried over anhydrous magnesium sulfate. Removal of the solvent by evaporation under reduced pressure gave crude (E)-1-[2-cyclopropyl-1-(2-fluorophenyl)-2-oxoethyl]-3-{[1-(ethoxycarbonylmethyl)-1H-imidazol-5-yl]methylidene}-4-sulfanylpiperidine (160 mg). This product was treated with 3N hydrochloric acid in a similar manner to that described in Example 134, and the residue obtained by concentration of the reaction mixture was purified by preparative HPLC (YMC-Pack ODS-A; YMC, eluent: acetonitrile/0.024 N hydrochloric acid, 10/90, v/v) to afford the title compound (90 mg, yield: 40%) as a colourless amorphous solid.

$^1$H NMR (500 MHz, pyridine-$d_5$) δ ppm: 0.70-0.79 (2H, m), 0.93-1.02 (1H, m), 1.04-1.12 (1H, m), 1.76-1.88 (1H, m), 2.20-2.32 (1H, m), 2.38-2.46 (1H, m), 2.61-2.75 (1H, m), 2.83-2.92 and 2.95-3.04 (total 1H, each m), 3.75 and 3.82 (total 1H, each d, J=12.5), 3.87 and 3.92 (total 1H, each d, J=12.5), 3.99 and 4.05 (total 1H, each m), 4.93 and 4.95 (total 1H, each s), 5.16 (2H, bs), 6.73 and 6.77 (total 1H, each bs), 7.15-7.24 (2H, m), 7.27-7.34 (1H, m), 7.36 and 7.42 (total 1H, each bs), 7.60-7.66 (1H, m), 8.15 and 8.16 (total 1H, each bs).

IR (KBr, cm$^{-1}$): 2601, 1739, 1710.

Example 170

(Z)-4-(Acetylsulfanyl)-1-[2-cyclopropyl-1-(2-fluorophenyl)-2-oxoethyl]-3-({1-[2-(ethoxycarbonyl)ethyl]-1H-pyrazol-3-yl}methylidene)piperidine (Exemplification Compound No. 4-16)

(a) 5-((Acetylsulfanyl){1-[2-(ethoxycarbonyl)ethyl]-1H-pyrazol-3-yl}methyl)-1-(triphenylmethyl)-1,2,3,6-tetrahydropyridine To a solution of (E)-3-{1-[2-(ethoxycarbonyl)ethyl]-1H-pyrazol-3-yl}methylidene)-1-(triphenylmethyl)piperidin-4-ol (Example 111-(b), 70.74 g) in toluene (400 ml) were added thioacetic acid (20 ml) and N,N-dimethylformamide dineopentyl acetal (76 ml) at 0° C. After being stirred at the same temperature for 0.5 hour, the mixture was diluted with ethyl acetate, and washed successively with water and a saturated aqueous sodium chloride solution. After the extract was dried over anhydrous sodium sulfate, it was concentrated under reduced pressure, and the colourless precipitates were collected by filtration to afford the title compound (35.26 g, yield: 45%) as a colourless solid.

$^1$H NMR (400 MHz, CDCl$_3$) δ ppm: 1.26 (3H, t, J=7.5), 2.16-2.37 (5H, m), 2.71-2.91 (4H, m), 4.08-4.18 (4H, m), 4.31 (2H, t, J=6.5), 5.21 (1H, s), 5.76 (1H, bs), 6.07 (1H, d, J=2.5), 7.08-7.52 (16H, m).

(b) (Z)-4-(Acetylsulfanyl)-3-{1-[2-(ethoxycarbonyl)ethyl]-1H-pyrazol-3-yl}methylidene)piperidine hydrogen trifluoroacetate Potassium thioacetate (5.91 g) was added to a solution of 5-((acetylsulfanyl){1-[2-(ethoxycarbonyl)ethyl]-1H-pyrazol-3-yl}methyl)-1-(triphenylmethyl)-1,2,3,6-tetrahydropyridine (3.00 g), in dimethyl sulfoxide (30 ml). The mixture was stirred at 80° C. for 4 hours. After cooling to room temperature, the mixture was diluted with ethyl acetate, and washed successively with water and a saturated aqueous sodium chloride solution. After the extract was dried over anhydrous sodium sulfate, it was concentrated under reduced pressure, and the residue was purified by silica gel chromatography using ethyl acetate and hexane (1:9 to 2:3) as eluents to afford a crude product of 4-(acetylsulfanyl)-3-({1-[2-(ethoxycarbonyl)ethyl]-1H-pyrazol-3-yl}methylidene)-1-(triphenylmethyl)piperidine (2.93 g) as a mixture of geometric isomers.

Trifluoroacetic acid (1.2 ml) was added to a solution of the crude product obtained above in dichloromethane (25 ml). After being stirred at room temperature for 1 hour, the mixture was concentrated under reduced pressure and the residue was purified by silica gel chromatography using dichloromethane and ethanol (99:1 to 4:1) as eluents. First, as the less polar eluate, (E)-4-(acetylsulfanyl)-3-({1-[2-(ethoxycarbonyl)ethyl]-1H-pyrazol-3-yl}methylidene)piperidine hydrogen trifluoroacetate (1.15 g, yield: 40%), which corresponds to the (E)-isomer of the title compound, was afforded as a brown oil. Further elution afforded the (Z)-isomer title compound (822.2 mg, yield: 28%) as a dark brown solid. The latter product contained regioisomer 5-((acetylsulfanyl){1-[2-(ethoxycarbonyl)ethyl]-1H-pyrazol-3-yl}methyl)-1,2,3,6-tetrahydropyridine hydrogen trifluoroacetate (the ratio of the title compound and its regioisomer was ca. 3:1).

$^1$H NMR (500 MHz, CDCl$_3$, selected signals) δ ppm: 1.24 (3H, t, J=7.0), 1.99-2.07 (1H, m), 2.31-2.46 (1H, m), 2.40 (3H, s), 2.90 (2H, t, J=6.5), 3.28-3.44 (2H, m), 3.64-3.82 (2H, m), 4.13 (2H, q, J=7.0), 4.37 (2H, t, J=6.5), 5.79 (1H, bs), 6.21 (1H, d, J=2.0), 6.39 (1H, s), 7.40 (1H, d, J=2.0).

(c) (Z)-4-(Acetylsulfanyl)-1-[2-cyclopropyl-1-(2-fluorophenyl)-2-oxoethyl]-3-({1-[2-(ethoxycarbonyl)ethyl]-1H-pyrazol-3-yl}methylidene)piperidine Following a procedure similar to that described in Example 132-(g), the mixture (822 mg) obtained in Example 170-(b) was subjected to the reaction with 2-bromo-2-(2-fluorophenyl)-1-cyclopropylethanone and triethylamine, and the crude product was purified by silica gel chromatography (eluent: ethyl acetate/hexane=1/3~1/1) to afford the title compound (224.7 mg, yield: 30%) as a pale yellow oil.

$^1$H NMR (400 MHz, CDCl$_3$) δ ppm: 0.79-0.91 (2H, m), 0.94-1.09 (2H, m), 1.23 and 1.24 (total 3H, each t, J=7.5), 1.72-1.85 (1H, m), 2.12-2.40 (2H, m), 2.33 and 2.34 (total 3H, each s), 2.54-2.99 (5H, m), 3.24 and 3.43 (total 1H, each d, J=12.5), 4.08-4.17 (2H, m), 4.32-4.41 (2H, m), 4.62 and 4.66 (total 1H, each s), 5.44 (1H, bs), 6.15-6.30 (2H, m), 7.06-7.21 (2H, m), 7.25-7.40 (2H, m), 7.42-7.52 (1H, m).

Example 171

(Z)-1-[2-Cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride (Exemplification Compound No. 4-15)

Hydrogen chloride was passed through a solution of (Z)-4-(acetylsulfanyl)-1-[2-cyclopropyl-1-(2-fluorophenyl)-2-oxoethyl]-3-({1-[2-(ethoxycarbonyl)ethyl]-1H-pyrazol-3-yl}methylidene)piperidine (514 mg) in ethanol (10 ml) at 0° C. for 10 minutes and the sealed mixture was stirred at room temperature for 6 hours. The mixture was concentrated under reduced pressure and the residue was purified by preparative HPLC (YMC-Pack ODS-A; YMC, eluent: acetonitrile/0.026 N aqueous trifluoroacetic acid solution, 33/67, v/v) to afford the trifluoroacetic acid salt of the title compound, which was treated with an aqueous sodium hydrogen carbonate solution. The liberated free base was extracted with ethyl acetate. The extract was dried over anhydrous sodium sulfate and concentrated under reduced pressure to afford the free base of the title compound (218 mg, yield: 46%) as a colourless oil.

A portion (59.3 mg) of the free base obtained above was dissolved in acetonitrile (2 ml) and treated with a 4N hydrogen chloride dioxane solution (100 μl). The solvent and excess hydrogen chloride was removed by evaporation under reduced pressure. Further, acetonitrile was used to remove azeotropically the solvent and excess hydrogen chloride under reduced pressure to afford the title compound (59.2 mg, yield: 92%) as a pale yellow amorphous solid.

$^1$H NMR (400 MHz, CDCl$_3$) δ ppm: 0.78-1.10 (4H, m), 1.24 (3H, t, J=7.0), 1.67-1.80 (1H, m), 2.14-2.35 (2H, m), 2.45-2.94 (4H, m), 3.11 and 3.26 (total 1H, each d, J=12.5), 3.30 and 3.44 (total 1H, each d, J=12.5), 4.14 (2H, q, J=7.0), 4.39 and 4.40 (total 2H, each t, J=6.5), 4.69 and 4.72 (total 1H, each s), 5.01 (1H, bs), 5.97 and 6.08 (total 1H, each s), 6.23 and 6.25 (total 1H, each d, J=2.5), 7.06-7.22 (2H, m), 7.25-7.40 (2H, m), 7.42-7.53 (1H, m);

IR (KBr, cm$^{-1}$): 2615, 1716, 1494.

Example 172

(E)-4-(Acetylsulfanyl)-1-[2-cyclopropyl-1-(2-fluorophenyl)-2-oxoethyl]-3-{[1-(methoxycarbonylmethyl)-1H-1,2,4-triazol-5-yl]methylidene}piperidine hydrochloride (Exemplification Compound No. 2-1354)

(a) (E)-4-(Acetylsulfanyl)-3-{[1-(methoxycarbonylmethyl)-1H-1,2,4-triazol-5-yl] methylidene}piperidine hydrogen trifluoroacetate Following a procedure similar to that described in Example 132-(f), the crude (E)-4-(acetylsulfanyl)-3-{[1-(methoxycarbonylmethyl)-1H-1,2,4-triazol-5-yl]methylidene}-1-(triphenylmethyl)piperidine (1.57 g) obtained in Example 166-(c) was treated with trifluoroacetic acid in dichloromethane and the product was purified by silica gel chromatography using dichloromethane and methanol (20:1 to 10:1) as eluents to afford the title compound (330 mg, yield: 29%) as a yellow amorphous solid.

$^1$H NMR (400 MHz, CDCl$_3$) δ ppm: 2.12-2.22 (1H, m), 2.38 (3H, s), 2.47-2.57 (1H, m), 3.25-3.37 (1H, m), 3.53 (1H, d, J=13.0), 3.82 (3H, s), 3.97 (1H, d, J=13.0), 4.44 (1H, d, J=14.5 Hz), 4.56 (1H, t, J=3.5), 4.97 (2H, s), 6.66 (1H, s), 8.13 (1H, s).

(b) (E)-4-(Acetylsulfanyl)-1-[2-cyclopropyl-1-(2-fluorophenyl)-2-oxoethyl]-3-{[1-(methoxycarbonylmethyl)-1H-1,2,4-triazol-5-yl] methylidene}piperidine hydrochloride Following a procedure similar to that described in Example 132-(g), (E)-4-(acetylsulfanyl)-3-{[1-(methoxycarbonylmethyl)-1H-1,2,4-triazol-5-yl]methylidene}piperidine hydrogen trifluoroacetate (330 mg) was subjected to the reaction with 2-bromo-2-(2-fluorophenyl)-1-cyclopropylethanone and the product was purified by silica gel chromatography to afford the free base of the title compound, which was treated with hydrogen chloride to yield the title compound (184 mg, yield: 45%) as a pale yellow amorphous solid.

$^1$H NMR (400 MHz, CDCl$_3$) δ ppm: 0.66-0.86 (2H, m), 0.87-1.07 (2H, m), 1.81-1.95 (1H, m), 2.12-2.24 (1H, m), 2.25-2.35 (1H, m), 2.29 and 2.30 (total 3H, each s), 2.36-2.44 and 2.59-2.70 (total 1H, each m), 2.74-2.92 (1H, m), 3.27 and 3.30 (total 1H, each d, J=13.5), 3.79 (3H, s), 4.31-4.53 (2H, m), 4.71 and 4.75 (total 1H, each s), 4.92 and 4.93 (total 2H, each s), 6.28 and 6.29 (total 1H, each s), 7.01-7.15 (2H, m), 7.24-7.40 (2H, m), 7.73 and 7.79 (total 1H, each s);

IR (KBr, cm$^{-1}$): 2545, 2507, 1752, 1699.

Example 173

(E)-1-[2-Cyclopropyl-1-(2-fluorophenyl)-2-oxoethyl]-3-{[1-(methoxycarbonylmethyl)-1H-1,2,4-triazol-5-yl]methylidene}-4-sulfanylpiperidine hydrochloride (Exemplification Compound No. 2-1353)

Following a procedure similar to that described in Example 151, (E)-4-(acetylsulfanyl)-1-[2-cyclopropyl-1-(2-fluorophenyl)-2-oxoethyl]-3-{[1-(methoxycarbonylmethyl)-1H-1,2,4-triazol-5-yl]methylidene}piperidine hydrochloride (140 mg) was treated with potassium carbonate and the crude product was purified by preparative HPLC (YMC-Pack ODS-A; YMC, eluent: acetonitrile/0.024 N hydrochloric acid, 30/70, v/v) to afford the title compound (82.7 mg, yield: 64%) as a colourless amorphous solid.

$^1$H NMR (400 MHz, CDCl$_3$) δ ppm: 0.65-0.80 (2H, m), 0.85-1.03 (2H, m), 1.74-1.88 (1H, m), 2.09-2.19 (1H, m), 2.21-2.35 (1H, m), 2.53-2.62 and 2.66-2.74 (total 1H, each m), 2.78-2.86 and 2.92-3.00 (total 1H, each m), 3.63-3.88 (2H, m), 3.78 (3H, s), 3.98 and 4.07 (total 1H, d, J=13.5), 4.74 and 4.75 (total 1H, each s), 4.94 (2H, s), 6.32 and 6.37 (total 1H, each s), 7.01-7.14 (2H, m), 7.24-7.38 (2H, m), 7.77 and 7.78 (total 1H, each s);

IR (KBr, cm$^{-1}$): 2954, 2449, 1752, 1712.

Example 174

(E)-4-(Acetylsulfanyl)-1-[2-cyclopropyl-1-(2-fluorophenyl)-2-oxoethyl]-3-({1-[(2-pyridyl)methyl]-1H-pyrazol-3-yl}methylidene)piperidine (Exemplification Compound No. 2-1678)

(a) (E)-3-({1-[(2-pyridyl)methyl]-1H-pyrazol-3-yl}methylidene)-1-(triphenylmethyl)piperidin-4-one To a solution of (E)-3-{[1H-pyrazol-3(5)-yl]methylidene}-1-(triphenylmethyl)piperidin-4-one (Example 73-(a), 5.0 g) in acetonitrile (100 ml) were added 2-(bromomethyl)pyridine hydrobromide (2.9 g), DBU (3.4 ml) and potassium iodide (1.9 g) at room temperature. After the mixture was stirred at 50° C. for 2 hours, further 2-(bromomethyl)pyridine hydrobromide (2.9 g), DBU (3.4 ml) and potassium iodide (1.9 g) were added, and the whole was stirred at 50° C. for 1.5 hour. After being cooled, the mixture was partitioned between water and ethyl acetate. The organic layer was separated, washed successively with water and a saturated aqueous sodium chloride solution, and dried over anhydrous magnesium sulfate. The solvent was removed by evaporation under reduced pressure and the residue was purified by silica gel chromatography using hexane, ethyl acetate, and dichloromethane (3:3:4), then ethyl acetate and dichloromethane (1:1) as eluents to afford the title compound (780 mg, yield: 15%) as a pale yellow amorphous solid.

$^1$H NMR (500 MHz, CDCl$_3$) δ ppm: 2.65 (2H, bs), 2.74 (2H, t, J=5.5), 3.62 (2H, bs), 5.31 (2H, s), 6.25 (1H, d, J=2.5), 6.78-6.81 (1H, m), 7.12-7.29 (9H, m), 7.43-7.55 (10H, m), 8.54-8.57 (1H, m).

(b) (E)-4-(Acetylsulfanyl)-3-({1-[(2-pyridyl)methyl]-1H-pyrazol-3-yl}methylidene)piperidine bis (hydrogen trifluoroacetate)

Following a procedure similar to that described in Example 146-(b), (E)-3-({1-[(2-pyridyl)methyl]-1H-pyrazol-3-yl}methylidene)-1-(triphenylmethyl)piperidin-4-one (1.8 g) was treated with sodium borohydride to afford (E)-3-({1-[(2-pyridyl)methyl]-1H-pyrazol-3-yl}methylidene)-1-(triphenylmethyl)piperidin-4-ol as a yellow amorphous solid in a quantitative yield.

$^1$H NMR (500 MHz, CDCl$_3$) δ ppm: 1.85-1.95 (1H, m), 2.06-2.20 (2H, m), 2.63-2.83 (2H, m), 3.46-3.53 (1H, m), 4.13-4.20 (1H, m), 5.23 (1H, d, J=16.0), 5.27 (1H, d, J=16.0), 6.12 (1H, d, J=2.5), 6.53 (1H, bs), 6.81-6.84 (1H, m), 7.06-7.31 (10H, m), 7.37-7.46 (7H, m), 7.56-7.62 (1H, m), 8.55-8.58 (1H, m).

This compound was subjected to the reaction with N,N-dimethylformamide dineopentyl acetal and thioacetic acid to afford the crude product, (E)-4-(acetylsulfanyl)-3-({1-[(2-pyridyl)methyl]-1H-pyrazol-3-yl}methylidene)-1-(triphenylmethyl)piperidine, which was subsequently treated with trifluoroacetic acid and the product was purified twice by silica gel chromatography using dichloromethane and methanol (19:1) as an eluent to afford the title compound (190 mg, yield: 9%) as a pale yellow amorphous solid.

$^1$H NMR (400 MHz, CDCl$_3$) δ ppm: 2.00-2.11 (1H, m), 2.35 (3H, s), 2.36-2.49 (1H, m), 3.09-3.24 (1H, m), 3.28-3.38 (1H, m), 3.75 (1H, d, J=14.0), 4.56 (1H, m), 5.07 (1H, d, J=14.0), 5.38 (2H, s), 6.24 (1H, d, J=2.5), 6.61 (1H, bs), 7.05-7.11 (1H, m), 7.19-7.28 (1H, m), 7.44 (1H, d, J=2.5), 7.66-7.74 (1H, m), 8.52-8.57 (1H, m).

(c) (E)-4-(Acetylsulfanyl)-1-[2-cyclopropyl-1-(2-fluorophenyl)-2-oxoethyl]-3-({1-[(2-pyridyl)methyl]-1H-pyrazol-3-yl}methylidene)piperidine To a solution of (E)-4-(acetylsulfanyl)-3-({1-[(2-pyridyl)methyl]-1H-pyrazol-3-yl}methylidene)piperidine bis(hydrogen trifluoroacetate) (190 mg) in acetonitrile (5 ml) were added 2-bromo-2-(2-fluorophenyl)-1-cyclopropylethanone (180 mg) and triethylamine (190 µl). After being stirred at room temperature for 0.5 hour, the mixture was partitioned between water and ethyl acetate. The organic layer was separated, washed successively with water and a saturated aqueous sodium chloride solution and dried over anhydrous magnesium sulfate. The solvent was evaporated under reduced pressure and the residue was purified by silica gel chromatography using dichloromethane and ethyl acetate (1:1) as an eluent to afford the title compound (140 mg, yield: 81%) as a pale yellow amorphous solid.

$^1$H NMR (500 MHz, CDCl$_3$) δ ppm: 0.59-0.99 (4H, m), 1.82-1.92 (1H, m), 2.18-2.38 (2H, m), 2.30 (3H, s), 2.43-2.51 and 2.55-2.64 (total 1H, each m), 2.71-2.79 and 2.80-2.87 (total 1H, each m), 3.08 and 3.25 (total 1H, each d, J=13.0), 4.09-4.20 (1H, m), 4.51 (1H, m), 4.68 and 4.69 (total 1H, each s), 5.29 and 5.36 (total 2H, each s), 6.12 and 6.20 (total 1H, each d, J=2.0), 6.50 and 6.52 (total 1H, each bs), 6.89-6.92 and 6.98-7.13 (total 3H, each m), 7.18-7.31 (2H, m), 7.35-7.44 (2H, m), 7.61-7.67 (1H, m), 8.55-8.59 (1H, m).

Example 175

(E)-1-[2-Cyclopropyl-1-(2-fluorophenyl)-2-oxoethyl]-3-({1-[(2-pyridyl)methyl]-1H-pyrazol-3-yl}methylidene)-4-sulfanylpiperidine dihydrochloride (Exemplification Compound No. 2-1677)

Potassium carbonate (39 mg) was added to a solution of (E)-4-(acetylsulfanyl)-1-[2-cyclopropyl-1-(2-fluorophenyl)-2-oxoethyl]-3-({1-[(2-pyridyl)methyl]-1H-pyrazol-3-yl}methylidene)piperidine (140 mg) in methanol (5 ml). After stirring for 0.5 hour, 1N hydrochloric acid (3 ml) was added to the mixture. The mixture was filtered using a membrane filter. The filtrate was concentrated under reduced pressure and the residue was purified by preparative HPLC (YMC-Pack ODS-A; YMC, eluent: acetonitrile/0.024 N hydrochloric acid, 25/75, v/v) to afford the title compound (120 mg, yield: 80%) as a yellow amorphous solid.

$^1$H NMR (500 MHz, CDCl$_3$) δ ppm: 0.61-0.98 (4H, m), 1.76-1.84 (1H, m), 2.17-2.36 (2H, m), 2.60-2.90 (2H, m), 3.53 and 3.67 (total 1H, each d, J=13.0), 3.84 and 3.87 (total 1H, each d, J=13.0), 3.94 (1H, m), 4.72 and 4.74 (total 1H, each s), 5.32 and 5.36 (total 2H, each s), 6.12 and 6.21 (total 1H, each d, J=2.5), 6.46 and 6.49 (total 1H, each bs), 6.94 and 7.00 (total 1H, each d, J=8.0), 7.03-7.12 (2H, m), 7.19-7.29 (2H, m), 7.37-7.44 (2H, m), 7.62-7.67 (1H, m), 8.55-8.58 (1H, m);

IR (KBr, cm$^{-1}$): 2555, 1710.

Example 176

(E)-4-(Acetylsulfanyl)-1-[2-cyclopropyl-1-(2-fluorophenyl)-2-oxoethyl]-3-{[5(3)-(ethoxycarbonylmethyl)-1H-pyrazol-3(5)-yl]methylidene}piperidine hydrogen trifluoroacetate (Exemplification Compound No. 1-209)

(a) Ethyl {5(3)-[(t-Butyldimethylsilyloxy)methyl]-1H-pyrazol-3(5)-yl}acetate

Anhydrous hydrazine (4.25 ml) was added to a solution of ethyl 6-(t-butyldimethylsilyloxy)-3,5-dioxohexanoate (36.3 g) in ethanol (500 ml) at 0° C. After the mixture was heated under reflux for 30 minutes, solvents were removed under reduced pressure. The residue was dissolved in ethyl acetate and washed successively with water and a saturated aqueous sodium chloride solution. The extract was dried over anhydrous magnesium sulfate and concentrated under reduced pressure. The residue was purified by silica gel chromatography using hexane and ethyl acetate (2:1) as an eluent to afford the title compound (27.3 g, yield: 76%), as a colourless oil.

$^1$H NMR (400 MHz, CDCl$_3$) δ ppm: 0.08 (6H, s), 0.90 (9H, s), 1.25 (3H, t, J=7.0), 3.68 (2H, s), 4.16 (2H, q, J=7.0), 4.73 (2H, s), 6.10 (1H, s).

(b) Ethyl {1-(t-butoxycarbonyl)-3-[(t-butyldimethylsilyloxy)methyl]-1H-pyrazol-5-yl}acetate and ethyl {1-(t-butoxycarbonyl)-5-[(t-butyldimethylsilyloxy)methyl]-1H-pyrazol-3-yl}acetate Di(t-butyl)dicarbonate (40.0 g) and tetramethylammonium hydroxide (33.2 g) were added to a solution of ethyl {5(3)-[(t-butyldimethylsilyloxy)methyl]-1H-pyrazol-3(5)-yl}acetate (27.3 g) in acetonitrile (1000 ml). After the mixture was stirred at room temperature for 1 hour, the reaction was quenched by addition of water and the product was extracted with ethyl acetate. The extract was washed with a saturated aqueous sodium chloride solution and dried over anhydrous magnesium sulfate. The solvent was removed under reduced pressure and the residue was purified by silica gel chromatography using hexane and ethyl acetate (4:1) as an eluent to afford an approximately 1:1 mixture of the two title compounds (34.04 g, yield: 93%) as a colourless oil.

$^1$H NMR (500 MHz, CDCl$_3$) δ ppm: 0.07 and 0.09 (total 6H, each s), 0.89 and 0.92 (total 9H, each s), 1.20-1.28 (3H, m), 1.60 and 1.61 (total 9H, each s), 3.69 and 3.94 (total 2H, each s), 4.12-4.19 (2H, m), 4.72 and 4.91 (total 2H, each s), 6.31 and 6.41 (total 1H, each s).

(c) Ethyl [1-(t-butoxycarbonyl)-3-formyl-1H-pyrazol-5-yl]acetate

A 1N tetrabutylammonium fluoride tetrahydrofuran solution (90 ml) was added to a solution of the mixture (34.04 g) obtained in Example 176-(b) in tetrahydrofuran (500 ml). After the mixture was stirred at room temperature for 30 minutes, the reaction was quenched by addition of water. The product was extracted with dichloromethane. Removal of the solvent under reduced pressure gave crude ethyl [1-(t-butoxycarbonyl)-3-(hydroxymethyl)-1H-pyrazol-5-yl]acetate.

To a solution of the product thus obtained in dichloromethane (800 ml) was added molecular sieves 4A (50.0 g) and pyridinium dichromate (50.0 g). After being stirred at room temperature for 1 hour, the mixture was filtered. The filtrate was concentrated under reduced pressure and the residue was purified by column chromatography using hexane and ethyl acetate (1:1) as an eluent to afford the title compound (7.84 g, yield: 26%) as a colourless oil.

$^1$H NMR (400 MHz, CDCl$_3$) δ ppm: 1.25 (3H, t, J=7.0), 1.65 (9H, s), 4.00 (2H, s), 4.17 (2H, q, J=7.0), 6.72 (1H, s), 10.03 (1H, s).

(d) (E)-3-{[1-(t-butoxycarbonyl)-5-(ethoxycarbonylmethyl)-1H-pyrazol-3-yl]methylidene}-1-(triphenylmethyl)piperidin-4-one Following a procedure similar to that described in Example 132-(c), ethyl [1-(t-butoxycarbonyl)-3-formyl-1H-pyrazol-5-yl]acetate (7.84 g) was subjected to the reaction with 1-(triphenylmethyl)piperidin-4-one in benzene using pyrrolidine. The crude product thus obtained was purified by silica gel chromatography using hexane, ethyl acetate, and dichloromethane (3:1:1) as an eluent to afford the title compound (9.64 g, yield: 57%) as a yellow amorphous solid.

$^1$H NMR (400 MHz, CDCl$_3$) δ ppm: 1.24 (3H, t, J=7.5), 1.55 (9H, s), 2.62 (2H, bs), 2.76 (2H, t, J=6.0), 3.72 (2H, bs), 3.92 (2H, s), 4.16 (2H, q, J=7.5), 6.21 (1H, s), 7.10-7.36 (10H, m), 7.47-7.56 (6H, m).

(e) (E)-3-{[1-(tert-Butoxycarbonyl)-5-(ethoxycarbonylmethyl)-1H-pyrazol-3-yl]methylidene}-1-(triphenylmethyl)piperidin-4-ol Sodium borohydride (300 mg) was added to a solution of (E)-3-{[1-(t-butoxycarbonyl)-5-(ethoxycarbonylmethyl)-1H-pyrazol-3-yl]methylidene}-1-(triphenylmethyl)piperidin-4-one (9.64 g) in ethanol (100 ml) at 0° C. After the mixture was stirred at the same temperature for 1.5 hours, the reaction was quenched by addition of a saturated aqueous ammonium chloride solution. The product was extracted with ethyl acetate. The organic layer was washed with a saturated aqueous sodium chloride solution and dried over anhydrous magnesium sulfate. Evaporation of the solvent under reduced pressure followed by purification of the residue by silica gel chromatography using hexane, ethyl acetate, and dichloromethane (1:1:1) as eluent gave the title compound (7.7 g, yield: 80%) as a pale yellow amorphous solid.

$^1$H NMR (400 MHz, CDCl$_3$) δ ppm: 1.26 (3H, t, J=7.0), 1.54 (9H, s), 1.76-2.19 (3H, m), 2.40-3.00 (3H, m), 3.89 (2H, d, J=2.0), 4.08-4.22 (3H, m), 6.10 (1H, s), 6.48 (1H, s), 7.00-7.47 (15H, m).

(f) (E)-4-(Acetylsulfanyl)-3-{[1-(t-butoxycarbonyl)-5-(ethoxycarbonylmethyl)-1H-pyrazol-3-yl]methylidene}piperidine hydrogen trifluoroacetate Following a procedure similar to that described in Example 132-(e), (E)-3-{[1-(t-butoxycarbonyl)-5-(ethoxycarbonylmethyl)-1H-pyrazol-3-yl]methylidene}-1-(triphenylmethyl)piperidin-4-ol (7.7 g) was subjected to the reaction with thioacetic acid and N,N-dimethylformamide dineopentyl acetal, and the crude product thus obtained was purified by silica gel chromatography (eluent: hexane/ethyl acetate/dichloromethane=4/1/1) to afford an approximately 1:1 mixture of (E)-4-(acetylsulfanyl)-3-{[1-(t-butoxycarbonyl)-5-(ethoxycarbonylmethyl)-1H-pyrazol-3-yl]methylidene}-1-(triphenylmethyl)piperidine and 5-{(acetylsulfanyl)[1-(t-butoxycarbonyl)-5-(ethoxycarbonylmethyl)-1H-pyrazol-3-yl]methyl}-1-(triphenylmethyl)-1,2,3,6-tetrahydropyridine (6.34 g, yield: 75%).

Treatment of the mixture (6.2 g) obtained above with trifluoroacetic acid in dichloromethane in a similar manner to that described in Example 132-(f) and purification of the crude product by silica gel chromatography using dichloromethane and methanol (15:1) as an eluent gave the title compound (1.23 g, yield: 25%) as a yellow amorphous solid.

$^1$H NMR (400 MHz, CDCl$_3$) δ ppm: 1.23 (3H, t, J=7.0), 1.57 (9H, s), 1.98-2.10 (1H, m), 2.33 (3H, s), 2.40-2.55 (1H, m), 3.10-3.25 (1H, m), 3.36 (1H, d, J=13.5), 3.82 (1H, d, J=15.0), 3.90 (2H, s), 4.15 (2H, q, J=7.0), 4.51-4.60 (1H, m), 4.92 (1H, d, J=15.0), 6.23 (1H, s), 6.60 (1H, s).

(g) (E)-4-(Acetylsulfanyl)-3-{[1-(t-butoxycarbonyl)-5-(ethoxycarbonylmethyl)-1H-pyrazol-3-yl]methylidene}-1-[2-cyclopropyl-1-(2-fluorophenyl)-2-oxoethyl]piperidine Following a procedure similar to that described in Example 132-(g), (E)-4-(acetylsulfanyl)-3-{[1-(t-butoxycarbonyl)-5-(ethoxycarbonylmethyl)-1H-pyrazol-3-yl]methylidene}piperidine hydrogen trifluoroacetate (1.23 g) was subjected to the reaction with 2-bromo-2-(2-fluorophenyl)-1-cyclopropylethanone. The product was purified by silica gel chromatography to afford the title compound (1.11 g, yield: 81%) as a pale yellow amorphous solid.

$^1$H NMR (400 MHz, CDCl$_3$) δ ppm: 0.58-1.06 (4H, m), 1.19-1.28 (3H, m), 1.60 (9H, s), 1.81-1.91 (1H, m), 2.20-2.32 (2H, m), 2.28 (3H, s), 2.40-2.50 and 2.55-2.63 (total 1H, each m), 2.71-2.83 (1H, m), 3.17 and 3.22 (total 1H, each d, J=13.5), 3.83-4.21 (5H, m), 4.42-4.50 (1H, m), 4.67 and 4.73 (total 1H, each s), 6.06 and 6.16 (total 1H, each s), 6.47 and 6.48 (total 1H, each s), 7.01-7.17 (2H, m), 7.23-7.44 (2H, m).

(h) (E)-4-(Acetylsulfanyl)-1-[2-cyclopropyl-1-(2-fluorophenyl)-2-oxoethyl]-3-{[5(3)-(ethoxycarbonylmethyl)-1H-pyrazol-3(5)-yl]methylidene}piperidine hydrogen trifluoroacetate Trifluoroacetic acid (20 ml) was added to (E)-4-(acetylsulfanyl)-3-{[1-(t-butoxycarbonyl)-5-(ethoxycarbonylmethyl)-1H-pyrazol-3-yl]methylidene}-1-[2-cyclopropyl-1-(2-fluorophenyl)-2-oxoethyl]piperidine (1.11 g) at 0° C., and after the mixture was stirred at 0° C. for 20 minutes, it was concentrated under reduced pressure. The resulting residue was purified by silica gel chromatography to afford the title compound (1.00 g, yield: 88%) as a pale yellow amorphous solid.

$^1$H NMR (400 MHz, CDCl$_3$) δ ppm: 0.71-1.00 (2H, m), 1.00-1.20 (2H, m), 1.19-1.32 (3H, m), 1.62-1.77 (1H, m), 1.92-2.07 (1H, m), 2.29 and 2.30 (3H, s), 2.42-2.54 (1H, m), 2.92-3.42 (2H, m), 3.61 and 3.81 (total 1H, each d, J=13.5), 3.69 and 3.71 (total 2H, each s), 4.18 (2H, q, J=7.0), 4.22 and 4.60 (total 1H, each d, J=13.5), 4.37-4.43 and 4.46-4.52 (total 1H, each m), 5.50 and 5.55 (total 1H, each s), 6.13 and 6.17 (total 1H, each s), 6.60 and 6.68 (total 1H, each s), 7.14-7.31 (2H, m), 7.37-7.53 (2H, m);

IR (KBr, cm$^{-1}$): 1736, 1694.

Example 177

(E)-1-[2-Cyclopropyl-1-(2-fluorophenyl)-2-oxoethyl]-3-{[5(3)-(ethoxycarbonylmethyl)-1H-pyrazol-3(5)-yl]methylidene}-4-sulfanylpiperidine hydrochloride (Exemplification Compound No. 1-208)

Hydrogen chloride was blown into a solution of (E)-4-(acetylsulfanyl)-1-[2-cyclopropyl-1-(2-fluorophenyl)-2-oxoethyl]-3-{[5(3)-(ethoxycarbonylmethyl)-1H-pyrazol-3(5)-yl]methylidene}piperidine hydrogen trifluoroacetate (810 mg) in ethanol (80 ml) at 0° C. for 1 hour. After the sealed mixture was stirred for 1 hour, the solvent and excess hydrogen chloride were removed by evaporation under reduced pressure. The residue was purified by preparative HPLC (YMC-Pack ODS-A; YMC, eluent: acetonitrile/0.024 N hydrochloric acid, 35/65, v/v) to afford the crude objective compound, which was treated with a saturated aqueous sodium hydrogen carbonate solution. The resulting free base was extracted with ethyl acetate. The organic layer was washed with a saturated aqueous sodium chloride solution and dried over anhydrous magnesium sulfate. Concentrated under reduced pressure gave a residue, which was treated with a 4N hydrogen chloride dioxane solution. The solvent and excess hydrogen chloride were removed by evaporation under reduced pressure to afford the title compound (645.2 mg, yield: 99%) as a colourless amorphous solid.

$^1$H NMR (400 MHz, CDCl$_3$) δ ppm: 0.65-0.91 (2H, m), 1.02-1.14 (2H, m), 1.17-1.32 (3H, m), 1.70-1.83 (1H, m), 1.83-1.95 (1H, m), 2.17-2.36 (1H, m), 2.52-2.74 (1H, m), 2.75-2.90 (1H, m), 3.15 and 3.35 (total 1H, each d, J=12.0), 3.54-3.90 (2H, m), 3.68 and 3.69 (total 2H, each s), 4.17 (2H, q, J=7.0), 4.95 and 4.97 (total 1H, each s), 6.06 and 6.11 (total 1H, each s), 6.40 and 6.49 (total 1H, each s), 7.08-7.20 (2H, m), 7.26-7.39 (2H, m);

IR (KBr, cm$^{-1}$): 2629, 2559, 1736, 1712.

Example 178

(E)-3-{[5(3)-(Carboxymethyl)-1H-pyrazol-3(5)-yl]methylidene}-1-[2-cyclopropyl-1-(2-fluorophenyl)-2-oxoethyl]-4-sulfanylpiperidine dihydrochloride (Exemplification Compound No. 1-206)

Following a procedure similar to that described in Example 134, (E)-1-[2-cyclopropyl-1-(2-fluorophenyl)-2-oxoethyl]-3-{[5(3)-(ethoxycarbonylmethyl)-1H-pyrazol-3(5)-yl]methylidene}-4-sulfanylpiperidine hydrochloride (570 mg) was treated with 3N hydrochloric acid and the crude product thus obtained was purified by preparative HPLC (YMC-Pack ODS-A; YMC, eluent: acetonitrile/0.024 N hydrochloric acid, 25/75, v/v) to afford the title compound (498 mg, yield: 86%) as a colourless amorphous solid.

$^1$H NMR (400 MHz, pyridine-d$_5$) δ ppm: 0.63-0.79 (2H, m), 0.88-1.01 (1H, m), 1.06-1.19 (1H, m), 1.77-1.92 (1H, m), 2.33-0.236 (1H, m), 2.37-2.49 (1H, m), 2.62-2.80 (1H, m), 2.84-3.04 (1H, m), 3.87-4.22 (3H, m), 4.06 and 4.08 (total 2H, each s), 4.92 and 4.94 (total 1H, each s), 6.40 and 6.49 (total 1H, each s), 6.83 and 6.85 (total 1H, each s), 7.12-7.24 (2H, m), 7.25-7.33 (1H, m), 7.62-7.73 (1H, m);

IR (KBr, cm$^{-1}$): 2924, 2660, 1710.

Example 179

(Z)-3-{[1-(2-Carboxyethyl)-1H-pyrazol-3-yl]methylidene}-1-[2-cyclopropyl-1-(2-fluorophenyl)-2-oxoethyl]-4-sulfanylpiperidine hydrochloride (Exemplification Compound No. 4-7)

(Z)-1-[2-Cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine (the free base described in Example 171, 158 mg) was treated with 3N hydrochloric acid (5 ml) at 50° C. for 2 hours. The mixture was concentrated under reduced pressure and the residue was purified by preparative HPLC (YMC-Pack ODS-A; YMC, eluent: acetonitrile/0.024 N hydrochloric acid, 35/65, v/v) to afford the title compound (156.6 mg, yield: 97%) as a colourless amorphous solid.

$^1$H NMR (400 MHz, pyridine-d$_5$) δ ppm: 0.77-0.86 (2H, m), 0.98-1.14 (2H, m), 2.23-2.38 (1H, m), 2.50-2.59 (1H, m), 2.65-3.08 (3H, m), 3.13-3.22 (2H, m), 3.38 and 3.52 (total 1H, each d, J=12.0), 3.56 and 3.68 (total 1H, each d, J=12.0), 4.61 and 4.63 (total 2H, each t, J=6.0), 4.93 and 4.95 (total 1H, each s), 5.49 and 5.51 (total 1H, each bs), 6.26 and 6.38 (total 1H, each s), 6.43 and 6.48 (total 1H, each d, J=2.0), 7.17-7.36 (3H, m), 7.72-7.80 (2H, m);

IR (KBr, cm$^{-1}$): 2629, 1712, 1495.

Example 180

(4R)-(E)-4-(Acetylsulfanyl)-1-[(1RS)-2-cyclopropyl-1-(2-fluorophenyl)-2-oxoethyl]-3-({1-[2-(ethoxycarbonyl)ethyl]-1H-pyrazol-3-yl}methylidene)piperidine hydrochloride (Exemplification Compound No. 2-50)

(a) (4S)- and (4R)-(E)-4-(Acetylsulfanyl)-3-{1-[2-(ethoxycarbonyl)ethyl]-1H-pyrazol-3-yl}methylidene)piperidine hydrogen trifluoroacetate Triethylamine (16.2 ml) and chlorotriphenylmethane (10.91 g) were added to a solution of the racemic (E)-4-(acetylsulfanyl)-3-({1-[2-(ethoxycarbonyl)ethyl]-1H-pyrazol-3-yl}methylidene)piperidine hydrogen trifluoroacetate (Example 111-(c), 22.09 g) in N,N-dimethylformamide (150 ml) at 0° C. After the mixture was stirred at room temperature for 2 hours, it was diluted with a mixed solvent of ethyl acetate and diethyl ether (2:1), and the solution was washed successively with water and a saturated aqueous sodium chloride solution. The extract was dried over anhydrous sodium sulfate and concentrated under reduced pressure. The residue was purified by silica gel chromatography (eluent: hexane/ethyl acetate=95/5~30/70) to give racemic (E)-4-(acetylsulfanyl)-3-({1-[2-(ethoxycarbonyl)ethyl]-1H-pyrazol-3-yl}methylidene)-1-(triphenylmethyl)piperidine (19.40 g, yield: 86%).

Optical resolution of the racemate obtained above was performed by HPLC using a chiral column (Chiralcel OD-H, 0.46φ×250 mm, Daicel Chemical Industries Co., Ltd., eluent: 2-propanol/hexane=1.5/98.5, 1.0 ml/minute) to afford each enantiomer as shown below.

221

The more mobile enantiomer (4S)-(E)-4-(acetylsulfanyl)-3-({1-[2-(ethoxycarbonyl)ethyl]-1H-pyrazol-3-yl}methylidene)-1-(triphenylmethyl)piperidine, retention time=14.2 minutes.

The less mobile enantiomer (4R)-(E)-4-(acetylsulfanyl)-3-({1-[2-(ethoxycarbonyl)ethyl]-1H-pyrazol-3-yl}methylidene)-1-(triphenylmethyl)piperidine, retention time=18.4 minutes.

(4S)-(E)-4-(Acetylsulfanyl)-3-({1-[2-(ethoxycarbonyl)ethyl]-1H-pyrazol-3-yl}methylidene)-1-(triphenylmethyl)piperidine (1.00 g) was subjected to the detritylation reaction in a similar manner to that described in Example 132-(f) to afford (4S)-(E)-4-(acetylsulfanyl)-3-({1-[2-(ethoxycarbonyl)ethyl]-1H-pyrazol-3-yl}methylidene)piperidine hydrogen trifluoroacetate (842 mg, yield: 87%) as a colourless oil.

$^1$H-NMR Spectrum: identical with that of the racemate.

$[\alpha]_D$ −141.1° (c=1.63, CHCl$_3$).

(4R)-(E)-4-(Acetylsulfanyl)-3-({1-[2-(ethoxycarbonyl)ethyl]-1H-pyrazol-3-yl}methylidene)-1-(triphenyl methyl)piperidine (1.00 g) was detritylated in a similar manner to that described in Example 132-(f) to afford (4R)-(E)-4-(acetylsulfanyl)-3-({1-[2-(ethoxycarbonyl)ethyl]-1H-pyrazol-3-yl}methylidene)piperidine hydrogen trifluoroacetate (863 mg, yield: 89%) as a colourless oil.

$^1$H-NMR Spectrum: identical with that of the racemate.

$[\alpha]_D$ +150.3° (c=1.28, CHCl$_3$).

(b) (4R)-(E)-4-(Acetylsulfanyl)-1-[(1RS)-2-cyclopropyl-1-(2-fluorophenyl)-2-oxoethyl]-3-({1-[2-(ethoxycarbonyl)ethyl]-1H-pyrazol-3-yl}methylidene)piperidine hydrochloride (4R)-(E)-4-(Acetylsulfanyl)-3-({1-[2-(ethoxycarbonyl)ethyl]-1H-pyrazol-3-yl}methylidene)piperidine hydrogen trifluoroacetate (863.1 mg) obtained in Example 180-(a) was subjected to the reaction similar to that described in Example 132-(g). After extraction, the product was purified by silica gel chromatography using ethyl acetate and hexane (1:4 to 1:1) as eluents to afford the free base of the title compound (757 mg, yield: 96%) as a pale yellow oil, a portion (104.7 mg) of which was treated with a 4N hydrogen chloride dioxane solution to afford the title compound (108.5 mg, yield: 97%) as a pale yellow amorphous solid.

$^1$H-NMR and IR Spectra: identical with those of the racemate described in Example 111-(d).

Example 181

(4R)-(E)-1-[(1RS)-2-Cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride (Exemplification Compound No. 2-49)

(4R)-(E)-4-(Acetylsulfanyl)-1-[(1RS)-2-cyclopropyl-1-(2-fluorophenyl)-2-oxoethyl]-3-({1-[2-(ethoxycarbonyl)ethyl]-1H-pyrazol-3-yl}methylidene)piperidine (the free base described in Example 180-(b), 652.3 mg) was subjected to the reaction similar to that described in Example 133. The mixture was concentrated and the resulting residue was purified by silica gel chromatography using dichloromethane and ethanol (99:1 to 9:1) as an eluent to afford the title compound (568.4 mg, yield: 88%) as a pale yellow amorphous solid.

$^1$H-NMR and IR Spectra: identical with those of the racemate described in Example 112.

Example 182

(4R)-(E)-3-{[1-(2-Carboxyethyl)-1H-pyrazol-3-yl]methylidene}-1-[(1RS)-2-cyclopropyl-1-(2-fluorophenyl)-2-oxoethyl]-4-sulfanylpiperidine hydrochloride (Exemplification Compound No. 2-17)

(4R)-(E)-1-[(1RS)-2-Cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride (424.2 mg) was subjected to the reaction similar to that described in Example 134 and the crude product thus obtained was purified by preparative HPLC (YMC-Pack ODS-A; YMC, eluent: acetonitrile/0.024 N hydrochloric acid, 30/70, v/v) to afford the title compound (369 mg, yield: 92%) as a colourless amorphous solid.

$^1$H-NMR and IR Spectra: identical with those of the racemate described in Example 113.

Example 183

(4R)-(E)-4-(Acetylsulfanyl)-3-{[1-(2-carboxyethyl)-1H-pyrazol-3-yl]methylidene}-1-[(1RS)-2-cyclopropyl-1-(2-fluorophenyl)-2-oxoethyl]piperidine hydrochloride (Exemplification Compound No. 2-18)

To a solution of (4R)-(E)-3-{[1-(2-carboxyethyl)-1H-pyrazol-3-yl]methylidene}-1-[(1RS)-2-cyclopropyl-1-(2-fluorophenyl)-2-oxoethyl]-4-sulfanylpiperidine hydrochloride (249.4 mg) in dichloromethane (12 ml) were added pyridine (0.24 ml) and acetic anhydride (0.24 ml) at 0° C. After the mixture was stirred at room temperature for 2.5 hours, solvents were removed under reduced pressure and the residue was purified by silica gel chromatography using dichloromethane and methanol (99:1 to 93:7) as eluents to afford the free base of the title compound (75.5 mg), which was treated in acetonitrile (2 ml) with a 4N hydrogen chloride dioxane solution (120 µl). The solvent and excess hydrogen chloride were removed under reduced pressure to afford the title compound (79.4 mg, yield: 29%) as a pale yellow amorphous solid.

$^1$H-NMR and IR Spectra: identical with those of the racemate described in Example 114.

Example 184

(4S)-(E)-4-(Acetylsulfanyl)-1-[(1RS)-2-cyclopropyl-1-(2-fluorophenyl)-2-oxoethyl]-3-({1-[2-(ethoxycarbonyl)ethyl]-1H-pyrazol-3-yl}methylidene)piperidine hydrochloride (Exemplification Compound No. 2-50)

(4S)-(E)-4-(Acetylsulfanyl)-3-({1-[2-(ethoxycarbonyl)ethyl]1H-pyrazol-3-yl}methylidene)piperidine hydrogen trifluoroacetate obtained in Example 180-(a) was subjected to the reaction similar to that described in Example 180-(b) to afford the title compound as a pale yellow amorphous solid in a quantitative yield.

$^1$H-NMR and IR Spectra: identical with those of the racemate described in Example 111-(d).

Example 185

(4S)-(E)-1-[(1RS)-2-Cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride (Exemplification Compound No. 2-49)

(4S)-(E)-4-(Acetylsulfanyl)-1-[(1RS)-2-cyclopropyl-1-(2-fluorophenyl)-2-oxoethyl]-3-({1-[2-(ethoxycarbonyl)ethyl]-1H-pyrazol-3-yl}methylidene)piperidine was subjected to the reaction similar to that described in Example 181 to afford the title compound as a pale yellow amorphous solid in 81% yield.

$^1$H-NMR and IR Spectra: identical with those of the racemate described in Example 112.

Example 186

(4S)-(E)-3-{[1-(2-Carboxyethyl)-1H-pyrazol-3-yl]methylidene}-1-[(1RS)-2-cyclopropyl-1-(2-fluorophenyl)-2-oxoethyl]-4-sulfanylpiperidine hydrochloride (Exemplification Compound No. 2-17)

(4S)-(E)-1-[(1RS)-2-Cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride was subjected to the reaction similar to that described in Example 182 to afford the title compound as a colourless amorphous solid in 92% yield.

$^1$H-NMR and IR Spectra: identical with those of the racemate described in Example 113.

Example 187

(4S)-(E)-4-(Acetylsulfanyl)-3-{[1-(2-carboxyethyl)-1H-pyrazol-3-yl]methylidene}-1-[(1RS)-2-cyclopropyl-1-(2-fluorophenyl)-2-oxoethyl]piperidine hydrochloride (Exemplification Compound No. 2-18)

To a solution of (4S)-(E)-3-{[1-(2-carboxyethyl)-1H-pyrazol-3-yl]methylidene}-1-[(1RS)-2-cyclopropyl-1-(2-fluorophenyl)-2-oxoethyl]-4-sulfanylpiperidine was subjected to the reaction similar to that described in Example 183 to afford the title compound as a pale yellow amorphous solid in 75% yield.

$^1$H-NMR and IR Spectra: identical with those of the racemate described in Example 114.

Example 188

(E)-4-(Acetylsulfanyl)-1-[2-cyclopropyl-1-(2-fluorophenyl)-2-oxoethyl]-3-[(1-{[1(2)H-tetrazol-5-yl]methyl}-1H-pyrazol-3-yl)methylidene]piperidine hydrogen trifluoroacetate (Exemplification Compound No. 2-1674)

(a) (E)-3-[(1-{[1-(4-Methoxybenzyl)-1H-tetrazol-5-yl]methyl}-1H-pyrazol-3-yl)methylidene]-1-(triphenylmethyl)piperidin-4-one and (E)-3-[(1-{[2-(4-methoxybenzyl)-2H-tetrazol-5-yl]methyl}-1H-pyrazol-3-yl)methylidene]-1-(triphenylmethyl)piperidin-4-one To a solution of [1(2)H-tetrazol-5-yl]methanol (9.26 g) in acetonitrile (200 ml) were added 4-methoxybenzyl chloride (42 ml) and triethylamine (50 ml). After the mixture was stirred at room temperature overnight, it was partitioned between water and dichloromethane. The organic layer was dried over anhydrous magnesium sulfate and concentrated under reduced pressure. The residue was purified by silica gel chromatography using hexane, ethyl acetate, and dichloromethane (1:1:2) as an eluent to afford a mixture of [1-(4-methoxybenzyl)-1H-tetrazol-5-yl]methanol and [2-(4-methoxybenzyl)-2H-tetrazol-5-yl]methanol (12 g, yield: quantitative, ingredient ratio: the less polar isomer/the more polar isomer=1/3~1/4) as a colourless solid.

(E)-3-{[1H-pyrazol-3(5)-yl]methylidene}-1-(triphenylmethyl)piperidin-4-one (Example 73-(b), 9.0 g) was dissolved in dichloromethane (100 ml), and a mixture of [1-(4-methoxybenzyl)-1H-tetrazol-5-yl]methanol and [2-(4-methoxybenzyl)-2H-tetrazol-5-yl]methanol obtained above (5.7 g) and triphenylphoshine (6.8 g) were added. Diethyl azodicarboxylate was added dropwise thereto, with stirring at 0° C. After the mixture was stirred at room temperature overnight, it was concentrated under reduced pressure. The residue was purified by silica gel chromatography (eluent: dichloromethane/methanol=9/1, then 8/1) to afford a mixture of the two title isomers (8.2 g, yield: 61%) as a yellow amorphous solid. Further elution gave the pure polar isomer (2.0 g, yield: 15%) as a colourless amorphous solid.

The more polar isomer: $^1$H NMR (400 MHz, CDCl$_3$) δ ppm: 2.65 (2H, bs), 2.76 (2H, t, J=5.5), 3.56 (2H, bs), 3.78 (3H, s), 5.25 (2H, s), 5.35 (2H, s), 6.19 (1H, d, J=2.5), 6.81 (2H, d, J=9.0), 7.03 (2H, d, J=9.0), 7.10-7.17 (3H, m), 7.20-7.26 (6H, m), 7.33 (1H, d, J=2.5), 7.40 (1H, m), 7.43-7.50 (6H, m).

(b) (E)-4-(Acetylsulfanyl)-3-[(1-{[1-(4-methoxybenzyl)-1H-tetrazol-5-yl]methyl}-1H-pyrazol-3-yl)methylidene]piperidine hydrogen trifluoroacetate or (E)-4-(acetylsulfanyl)-3-[(1-{[2-(4-methoxybenzyl)-2H-tetrazol-5-yl]methyl}-1H-pyrazol-3-yl)methylidene]piperidine hydrogen trifluoroacetate The mixture of the two isomers (8.2 g) obtained in Example 188-(a) was subjected to the reaction similar to that described in Example 132-(d)~(f) to afford a mixture of the two title isomers, which was further separated by silica gel chromatography to afford the more polar isomer (690 mg, yield: 9.4%) as a pale yellow amorphous solid.

$^1$H NMR (400 MHz, CDCl$_3$) δ ppm: 2.01-2.11 (1H, m), 2.34 (3H, s), 2.39-2.53 (1H, m), 3.15-3.28 (1H, m), 3.34-3.42 (1H, m), 3.72-3.82 (1H, m), 3.79 (3H, s), 4.57 (1H, m), 5.06 (1H, d, J=15.0), 5.45 (1H, d, J=15.5), 5.49 (1H, d, J=15.5), 5.65 (2H, s), 6.22 (1H, d, J=2.5), 6.61 (1H, bs), 6.88 (2H, d, J=8.5), 7.32 (2H, d, J=8.5), 7.45 (1H, d, J=2.5).

(c) (E)-4-(Acetylsulfanyl)-1-[2-cyclopropyl-1-(2-fluorophenyl)-2-oxoethyl]-3-[(1-{[1-(4-methoxybenzyl)-1H-tetrazol-5-yl]methyl}-1H-pyrazol-3-yl)methylidene]piperidine or (E)-4-(Acetylsulfanyl)-1-[2-cyclopropyl-1-(2-fluorophenyl)-2-oxoethyl]-3-[(1-{[2-(4-methoxybenzyl)-2H-tetrazol-5-yl]methyl}-1H-pyrazol-3-yl)methylidene]piperidine The isomer obtained in Example 188-(b) (690 mg) was subjected to the reaction with 2-bromo-2-(2-fluorophenyl)-1-cyclopropylethanone (480 mg) and triethylamine (430 μl) in acetonitrile (20 ml) in a similar manner to that described in Example 132-(g). Purification of the crude product by silica gel chromatography gave either isomer of the two title compounds (470 mg, yield: 61%) as a pale yellow amorphous solid.

¹H NMR (400 MHz, CDCl₃) δ ppm: 0.58-1.03 (4H, m), 1.80-1.92 (1H, m), 2.13-2.34 (2H, m), 2.29 (3H, s), 2.42-2.51 and 2.54-2.63 (total 1H, each m), 2.71-2.86 (1H, m), 3.04 and 3.23 (total 1H, each d, J=13.5), 3.80 (3H, s), 4.03-4.10 (1H, m), 4.48 (1H, m), 4.66 and 4.68 (total 1H, each s), 5.40 and 5.47 (total 2H, each s), 5.67 (2H, s), 6.10 and 6.18 (total 1H, each d, J=2.5), 6.47 and 6.49 (total 1H, each bs), 6.89 (2H, d, J=8.5), 7.01-7.15 (2H, m), 7.23-7.31 (1H, m), 7.34 (2H, d, J=8.5), 7.37-7.44 (1H, m), 7.39 and 7.43 (total 1H, each d, J=2.5).

(d) (E)-4-(Acetylsulfanyl)-1-[2-cyclopropyl-1-(2-fluorophenyl)-2-oxoethyl]-3-[(1-{[1(2)H-tetrazol-5-yl]methyl}-1H-pyrazol-3-yl)methylidene]piperidine hydrogen trifluoroacetate To a solution of the compound (470 mg) obtained in Example 188-(c) was added trifluoroacetic acid (10 ml), and the mixture was stirred at 60° C. for 4 hours. After cooling, the mixture was concentrated under reduced pressure and the residue was purified by silica gel chromatography using dichloromethane and methanol (9:1) as an eluent to afford the title compound (450 mg, yield: 96%) as a pale yellow amorphous solid.

¹H NMR (500 MHz, pyridine-d₅) δ ppm: 0.57-0.75 (2H, m), 0.89-1.11 (2H, m), 1.88-2.00 (1H, m), 2.27 and 2.28 (total 3H, each s), 2.29-2.43 (2H, m), 2.56-2.71 (1H, m), 2.82-2.89 and 2.92-2.99 (total 1H, each m), 3.25 and 3.48 (total 1H, each d, J=13.0), 4.46 and 4.47 (total 1H, each d, J=13.0), 4.70 (1H, m), 4.91 and 4.93 (total 1H, each s), 5.91-6.06 (2H, m), 6.27 and 6.33 (total 1H, each d, J=2.5), 6.70 and 6.73 (total 1H, each bs), 7.13-7.23 (2H, m), 7.27-7.33 (1H, m), 7.60-7.67 (1H, m), 7.82 and 7.85 (total 1H, each d, J=2.5);

IR (KBr, cm⁻¹): 1698, 1671.

Example 189

(E)-1-[2-Cyclopropyl-1-(2-fluorophenyl)-2-oxoethyl]-4-sulfanyl-3-[(1-{[1(2)H-tetrazol-5-yl]methyl}-1H-pyrazol-3-yl)methylidene]piperidine hydrochloride (Exemplification Compound No. 2-1673)

Hydrogen chloride was passed through a solution of (E)-4-(acetylsulfanyl)-1-[2-cyclopropyl-1-(2-fluorophenyl)-2-oxoethyl]-3-[(1-{[1(2)H-tetrazol-5-yl]methyl}-1H-pyrazol-3-yl)methylidene]piperidine hydrogen trifluoroacetate (200 mg) in ethanol (15 ml) at 0° C. for 1 hour and the sealed mixture was allowed to stand at room temperature overnight. The mixture was concentrated under reduced pressure and the residue was purified by preparative HPLC (YMC-Pack ODS-A; YMC, eluent: acetonitrile/0.024N hydrochloric acid, 25/75, v/v) to afford the title compound (80 mg, yield: 49%) as a colourless amorphous solid.

¹H NMR (500 MHz, pyridine-d₅) δ ppm: 0.57-0.74 (2H, m), 0.89-0.96 (1H, m), 1.02-1.10 (1H, m), 1.80-1.93 (1H, m), 2.24-2.43 (2H, m), 2.68-2.75 and 2.76-2.83 (total 1H, each m), 2.89-3.02 (1H, m), 3.76 and 3.94 (total 1H, each d, J=12.5), 4.00 (1H, m), 4.10 and 4.15 (total 1H, each d, J=12.5), 4.93 and 4.94 (total 1H, each s), 5.94-6.06 (2H, m), 6.26 and 6.33 (total 1H, each d, J=2.0), 6.61 and 6.63 (total 1H, each bs), 7.12-7.21 (2H, m), 7.26-7.32 (1H, m), 7.61-7.69 (1H, m), 7.87 and 7.89 (total 1H, each d, J=2.0).

IR (KBr, cm⁻¹): 2562, 1710.

Example 190

(4R)-(E)-1-[(1S)-2-Cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride and (4R)-(E)-1-[(1R)-2-Cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride (Exemplification Compound No. 2-49)

(4R)-(E)-1-[(1RS)-2-Cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride (Example 181, 61.9 mg) was treated with an aqueous sodium hydrogen carbonate solution. The resulting free base was extracted with dichloromethane and divided into three portions, each of which was subjected to preparative HPLC using a chiral column (Chiralcel OD-H, 20 id×250 mm, Daicel Chemical Industries Co., Ltd.) to separate two isomers.

The more mobile isomer thus obtained was dissolved in acetonitrile and treated with a 4N hydrogen chloride dioxane solution. The solvent and excess hydrogen chloride were removed under reduced pressure to afford (4R)-(E)-1-[(1S)-2-cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride (18.7 mg) as a colourless amorphous solid.

¹H NMR (400 MHz, CDCl₃) δ ppm: 0.61-0.81 (2H, m), 0.86-1.01 (2H, m), 1.25 (3H, t, J=7.0), 1.73-1.84 (1H, m), 2.20-2.30 (2H, m), 2.57-2.88 (4H, m), 3.66 (1H, d, J=12.0), 3.81-3.96 (2H, m), 4.15 (2H, q, J=7.0), 4.33 (2H, t, J=6.5), 4.72 (1H, s), 6.10 (1H, d, J=2.5), 6.45 (1H, s), 7.03-7.17 (2H, m), 7.22-7.36 (2H, m), 7.39-7.48 (1H, m);

[α]_D=+74.2° (c=0.50, CHCl₃)

The less mobile isomer was treated with hydrogen chloride in a similar manner to that described above to afford (4R)-(E)-1-[(1R)-2-cyclopropyl-1-(2-fluorophenyl)-2-oxoethyl]-3-({1-[2-(ethoxycarbonyl)ethyl]-1H-pyrazol-3-yl}methylidene)-4-sulfanylpiperidine hydrochloride (28.2 mg) as a colourless amorphous solid.

¹H NMR (400 MHz, CDCl₃) δ ppm: 0.69-0.75 (2H, m), 0.82-0.91 (1H, m), 0.94-1.02 (1H, m), 1.25 (3H, t, J=7.0), 1.76-1.85 (1H, m), 2.20-2.36 (2H, m), 2.65-2.91 (4H, m), 3.53 (1H, d, J=13.0), 3.83-3.97 (2H, m), 4.14 (2H, q, J=7.0), 4.28 (2H, t, J=6.5), 4.73 (1H, s), 6.01 (1H, d, J=2.0), 6.42 (1H, s), 7.05-7.16 (2H, m), 7.22-7.33 (2H, m), 7.39-7.47 (1H, m);

[α]_D=-124.3° (c=0.53, CHCl₃).

Example 191

(E)-4-(Acetylsulfanyl)-1-[2-cyclopropyl-1-(2-fluorophenyl)-2-oxoethyl]-3-{[1-(N-methoxycarbamoylmethyl)-1H-pyrazol-3-yl]methylidene}piperidine hydrochloride (Exemplification Compound No. 2-1667)

Isobutyl chloroformate (74 µl) and triethylamine (78 µl) were added to a solution of (E)-4-(acetylsulfanyl)-3-{[1-(carboxymethyl)-1H-pyrazol-3-yl]methylidene}-1-[2-cyclopropyl-1-(2-fluorophenyl)-2-oxoethyl]piperidine (the free base described in Example 76, 240 mg) in dichloromethane (3 ml) and the mixture was stirred at room temperature for 30 minutes. To this was added a solution of O-methylhydroxylamine in methanol (the solution was prepared by addition of potassium hydroxide (60 mg) to a solution of O-methylhydroxylamine hydrochloride (70 mg) in methanol (3 ml) followed by removal of the resulting precipitates by filtration). After being stirred at room temperature for 1 hour, the mixture was purified by silica gel chromatography using dichloromethane and methanol (19:1) as eluent. The free base thus obtained was treated with a 4N hydrogen chloride dioxane solution (70 μl). The solvent and excess hydrogen chloride were removed by under reduced pressure to afford the title compound (60 mg, yield: 22%) as a yellow amorphous solid.

$^1$H NMR (500 MHz, pyridine-$d_5$) δ ppm: 0.65-0.83 (2H, m), 0.91-1.03 (1H, m), 1.05-1.17 (1H, m), 1.88-2.03 (1H, m), 2.23-2.53 (2H, m), 2.28 (3H, s), 2.54-2.62 and 2.64-2.73 (total 1H, each m), 2.83-3.01 (1H, m), 3.31 and 3.50 (total 1H, each d, J=12.5), 3.83 (3H, s), 4.50-4.61 (1H, m), 4.69-4.77 (1H, m), 4.92 and 4.93 (total 1H, each s), 5.07 and 5.12 (total 2H, each s), 6.31 and 6.38 (total 1H, bs), 6.78 and 6.81 (total 1H, each bs), 7.18-7.28 (2H, m), 7.31-7.41 (1H, m), 7.62-7.73 (1H, m), 7.85 and 7.89 (total 1H, each d, J=2.0);

IR (KBr, cm$^{-1}$): 1698.

Example 192

(E)-1-[2-Cyclopropyl-1-(2-fluorophenyl)-2-oxoethyl]-3-{[1-(N-methoxycarbamoylmethyl)-1H-pyrazol-3-yl]methylidene}-4-sulfanylpiperidine hydrochloride (Exemplification Compound No. 2-1666)

Following a procedure similar to that described in Example 151, (E)-4-(acetylsulfanyl)-1-[2-cyclopropyl-1-(2-fluorophenyl)-2-oxoethyl]-3-{[1-(N-methoxycarbamoylmethyl)-1H-pyrazol-3-yl]methylidene}piperidine (the free base described in Example 191, 130 mg) was treated with potassium carbonate in methanol and the crude product obtained by extraction was purified by silica gel chromatography (eluent: dichloromethane/methanol=19/1). The free base thus obtained was treated with a 4N hydrogen chloride dioxane solution (400 μl) in dichloromethane. The solvent and excess hydrogen chloride were removed by evaporation under reduced pressure to afford the title compound (60 mg, yield: 50%) as a colourless amorphous solid.

$^1$H NMR (500 MHz, pyridine-$d_5$) δ ppm: 0.64-0.80 (2H, m), 0.89-1.00 (1H, m), 1.04-1.16 (1H, m), 1.81-1.95 (1H, m), 2.26-2.54 (2H, m), 2.68-2.85 (1H, m), 2.87-3.03 (1H, m), 3.75-3.88 and 3.92-3.99 (total 1H, each m), 3.84 (3H, s), 4.00-4.08 (1H, m), 4.17-4.27 (1H, m), 4.93 and 4.94 (total 1H, each s), 5.09 and 5.13 (total 2H, each s), 6.29 and 6.37 (total 1H, bs), 6.69 and 6.71 (total 1H, each bs), 7.16-7.26 (2H, m), 7.31-7.39 (1H, m), 7.64-7.73 (1H, m), 7.87 and 7.90 (total 1H, each d, J=2.0);

IR (KBr, cm$^{-1}$): 2486, 1708.

Example 193

(E)-4-(Acetylsulfanyl)-3-[(2-amino-1,3-thiazol-4-yl)methylidene]-1-[2-cyclopropyl-1-(2-fluorophenyl)-2-oxoethyl]piperidine dihydrochloride (Exemplification Compound No. 1-199)

(a) 2-(t-Butoxycarbonylamino)-1,3-thiazole-4-carbaldehyde

A 1.0M diisobutylaluminium hydride toluene solution (142 ml) was added dropwise to a stirred solution of ethyl 2-(t-butoxycarbonylamino)-1,3-thiazole-4-carboxylate (14.9 g) in dichloromethane (250 ml) under cooling at −70° C. After the mixture was stirred successively at −78° C. for 2 hours and at 0° C. for 1 hour, an aqueous potassium sodium tartrate solution was added carefully to the mixture, and the whole was further stirred for 2 hours. The mixture was filtered using dichloromethane, and the filtrate was partitioned between dichloromethane and water. The organic layer was separated and dried over anhydrous magnesium sulfate. Concentration under reduced pressure afforded a crude product of [2-(t-butoxycarbonylamino)-1,3-thiazol-4-yl]methanol (9.2 g). The product thus obtained was treated with manganese dioxide (70 g) in dichloromethane (300 ml) with stirring at room temperature.

The mixture was filtered through Celite using dichloromethane, and the filtrate was concentrated under reduced pressure to afford the title compound (6.4 g, yield based on the ester: 51%) as a yellow solid.

$^1$H NMR (500 MHz, CDCl$_3$) δ ppm: 1.55 (9H, s), 7.81 (1H, s), 9.90 (1H, s).

(b) (E)-3-{[2-(t-Butoxycarbonylamino)-1,3-thiazol-4-yl]methylidene}-1-(triphenylmethyl)piperidin-4-one Following a procedure similar to that described in Example 132-(c), 2-(t-butoxycarbonylamino)-1,3-thiazole-4-carbaldehyde (3.2 g) was subjected to the reaction with 1-(triphenylmethyl)piperidin-4-one (4.8 g) and pyrrolidine (0.24 ml), and the crude product was purified by silica gel chromatography using hexane, ethyl acetate, and dichloromethane (1:3:1 to 1:5:1) as eluents to afford the title compound (2.8 g, yield: 36%) as an oil.

$^1$H NMR (400 MHz, CDCl$_3$) δ ppm: 1.55 (9H, s), 2.58 (2H, bs), 2.73 (2H, t, J=6.0), 3.83 (2H, bs), 6.91 (1H, s), 7.13-7.28 (10H, m), 7.48-7.54 (6H, m).

(c) (E)-3-{[2-(t-Butoxycarbonylamino)-1,3-thiazol-4-yl]methylidene}-1-(triphenylmethyl)piperidin-4-ol Sodium borohydride (0.27 g) was added to a solution of (E)-3-{[2-(t-butoxycarbonylamino)-1,3-thiazol-4-yl]methylidene}-1-(triphenylmethyl)piperidin-4-one (3.1 g) in a mixed solvent of dichloromethane (15 ml) and ethanol (15 ml), while stirring at 0° C. After being stirred at room temperature for 1.5 hours, the mixture was partitioned between water and ethyl acetate. The organic layer was separated, washed with a saturated aqueous sodium chloride solution and dried over anhydrous magnesium sulfate. The extract was concentrated under reduced pressure to afford the title compound as a yellow amorphous solid in a quantitative yield.

$^1$H NMR (400 MHz, CDCl$_3$) δ ppm: 1.57 (9H, s), 1.81-2.06 (2H, m), 2.07-2.18 (2H, m), 2.66-2.84 (2H, m), 4.00-4.14 (1H, m), 6.42 (1H, s), 6.65 (1H, s), 7.04-7.34 (9H, m), 7.39-7.54 (6H, m).

(d) (E)-4-(Acetylsulfanyl)-3-{[2-(t-butoxycarbonylamino)-1,3-thiazol-4-yl]methylidene}piperidine hydrogen trifluoroacetate (E)-3-{[2-(t-butoxycarbonylamino)-1,3-thiazol-4-yl]methylidene}-1-(triphenylmethyl)piperidin-4-ol (the whole amount obtained in Example 193-(c)) was subjected to the similar reactions to those described in Example 132-(e)~(f). The product was purified by silica gel chromatography using dichloromethane and methanol (19:1) as an eluent to afford the title compound (420 mg, yield: 15%) as a yellow amorphous solid.

$^1$H NMR (500 MHz, CDCl$_3$) δ ppm: 1.41 (9H, s), 2.04-2.12 (1H, m), 2.37 (3H, s), 2.49-2.59 (1H, m), 3.13-3.24 (1H, m), 3.28-3.36 (1H, m), 3.63-3.73 (1H, m), 4.61 (1H, m), 5.39-5.48 (1H, m), 6.62 (1H, s), 6.89 (1H, s).

(e) (E)-4-(Acetylsulfanyl)-3-{[2-amino-1,3-thiazol-4-yl]methylidene}-1-[2-cyclopropyl-1-(2-fluorophenyl)-2-oxoethyl]piperidine dihydrochloride Following a procedure similar to that described in Example 132-(g), (E)-4-(acetylsulfanyl)-3-{[2-(t-butoxycarbonylamino)-1,3-thiazol-4-yl]methylidene}piperidine hydrogen trifluoroacetate (420 mg) was subjected to the reaction with 2-bromo-2-(2-fluorophenyl)-1-cyclopropylethanone (340 mg) and triethylamine (310 µl) in acetonitrile (5 ml). The product obtained by usual extraction was purified by silica gel chromatography (eluent: hexane/ethylacetate=2/1~2/3) to afford (E)-4-(acetylsulfanyl)-3-{[2-(t-butoxycarbonylamino)-1,3-thiazol-4-yl]methylidene}-1-[2-cyclopropyl-1-(2-fluorophenyl)-2-oxoethyl]piperidine (230 mg) as a pale yellow amorphous solid.

A portion (110 mg) of the compound obtained above was dissolved in dichloromethane (5 ml) and trifluoroacetic acid (1 ml) was added. The mixture was stirred at 50° C. for 1.5 hours. After cooling, the mixture was treated with an aqueous sodium hydrogen carbonate solution and the resulting free base was extracted with ethyl acetate. The extract was washed with a saturated aqueous sodium chloride solution and dried over anhydrous magnesium sulfate. Solvents were removed under reduced pressure, and the residue was purified by silica gel chromatography using hexane, ethyl acetate, and dichloromethane (1:2:1) as an eluent to afford the free base of the title compound (55 mg), all amount of which was treated with a 4N hydrogen chloride dioxane solution. The solvent and excess hydrogen chloride were evaporated under reduced pressure to afford the title dihydrochloride (60 mg, overall yield: 29%) as a yellow amorphous solid.

$^1$H NMR (400 MHz, pyridine-$d_5$) δ ppm: 0.67-0.83 (2H, m), 0.93-1.01 and 1.05-1.17 and 1.23-1.32 (total 2H, each m), 1.88-2.01 (1H, m), 2.23 and 2.24 (total 3H, each s), 2.32-2.46 (1H, m), 2.47-2.61 and 2.69-2.79 (total 2H, each m), 2.92-3.02 (1H, m), 3.48 and 3.52 (total 1H, each d, J=13.0), 4.70 (1H, m), 4.96 and 5.00 (total 1H, each s), 5.23 and 5.34 (total 1H, each d, J=13.0), 6.59 and 6.61 (total 1H, s), 6.64 and 6.66 (total 1H, each s), 7.12-7.23 (2H, m), 7.25-7.33 (1H, m), 7.67-7.74 (1H, m).

IR (KBr, cm$^{-1}$): 1702, 1626.

Example 194

(E)-3-[(2-Amino-1,3-thiazol-4-yl)methylidene]-1-[2-cyclopropyl-1-(2-fluorophenyl)-2-oxoethyl]-4-sulfanylpiperidine dihydrochloride (Exemplification Compound No. 1-198)

Removal of the Boc group was performed by treatment of (E)-4-(acetylsulfanyl)-3-{[2-(t-butoxycarbonylamino)-1,3-thiazol-4-yl]methylidene}-1-[2-cyclopropyl-1-(2-fluorophenyl)-2-oxoethyl]piperidine (described in Example 193-(e), the compound before the removal of the Boc group, 40 mg) with trifluoroacetic acid in a similar manner to that described in Example 193-(e). The crude (E)-4-(acetylsulfanyl)-3-[(2-Amino-1,3-thiazol-4-yl)methylidene]-1-[2-cyclopropyl-1-(2-fluorophenyl)-2-oxoethyl]piperidine bis(hydrogen trifluoroacetate), thus obtained was dissolved in ethanol (5 ml), and hydrogen chloride was passed therethrough under ice-cooling for 45 minutes. After the sealed mixture was stirred at room temperature for 4 hours, the solvent and excess hydrogen chloride were removed under reduced pressure and the residue was treated with an aqueous sodium hydrogen carbonate solution. The liberated base was extracted with ethyl acetate. The extract was washed with a saturated aqueous sodium chloride solution and dried over anhydrous magnesium sulfate. The free base of the title compound (20 mg), obtained after concentration, was treated in dichloromethane with a 4N hydrogen chloride dioxane solution), and the solvent and excess hydrogen chloride were removed by evaporation under reduced pressure to afford the title compound (20 mg, overall yield: 57%) as an orange-coloured amorphous solid.

$^1$H NMR (500 MHz, pyridine-$d_5$) δ ppm: 0.63-1.39 (4H, m), 1.79-1.93 (1H, m), 2.29-2.41 (1H, m), 2.47-2.65 (1H, m), 2.74-2.84 (1H, m), 2.86-2.97 and 3.02-3.10 (total 1H, each m), 4.01 and 4.05 (total 1H, each m), 4.12 and 4.13 (total 1H, each d, J=13.0), 4.79 and 4.89 (total 1H, each d, J=13.0), 4.97 and 5.02 (total 1H, each s), 6.54-6.61 (2H, m), 7.10-7.39 (3H, m), 7.74 (1H, m).

IR (KBr, cm$^{-1}$): 2565, 1711, 1626.

Example 195

(E)-4-(Acetylsulfanyl)-1-[2-cyclopropyl-1-(2-fluorophenyl)-2-oxoethyl]-3-{[1-(ethoxycarbonylmethyl)-1H-imidazol-2-yl]methylidene}piperidine hydrochloride (Exemplification Compound No. 2-802)

(a) Ethyl(2-formyl-1H-imidazol-1-yl)acetate

To a solution of 1H-imidazole-2-carbaldehyde (4.47 g) in acetonitrile (80 ml) were added potassium carbonate (12.93 g), ethyl bromoacetate (6.2 ml) and potassium iodide (7.78 g) at room temperature. The mixture was stirred at 50° C. for 1 hour. After cooling to room temperature, the mixture was filtered to remove the precipitates. The filtrate was concentrated under reduced pressure and the residue was purified by silica gel chromatography using dichloromethane and methanol (99:1 to 96:4) as eluents to afford the title compound (5.23 g, yield: 62%) as a brown oil.

$^1$H NMR (400 MHz, CDCl$_3$) δ ppm: 1.30 (3H, t, J=7.0), 4.26 (2H, q, J=7.0), 5.14 (2H, s), 7.16 (1H, s), 7.34 (1H, s), 9.80 (1H, s).

(b) (E)-3-{[1-(Ethoxycarbonylmethyl)-1H-imidazol-2-yl]methylidene}-1-(triphenylmethyl)piperidin-4-one Ethyl(2-formyl-1H-imidazol-1-yl)acetate (5.94 g) was subjected to the reaction with 1-(triphenylmethyl)piperidin-4-one (11.10 g) and pyrrolidine (2.7 ml) in benzene (250 ml) in a similar manner to that described in Example 132-(c). The crude product obtained by extraction in a usual manner was purified by silica gel chromatography using hexane and ethyl acetate (9:1 to 4:6) as eluents to afford the title compound (11.32 g, yield: 69%) as a yellow amorphous solid.

$^1$H NMR (500 MHz, CDCl$_3$) δ ppm: 1.30 (3H, t, J=7.5), 2.58-2.78 (4H, m), 3.86-3.99 (2H, m), 4.25 (2H, q, J=7.5), 4.78 (2H, s), 6.93 (1H, s), 7.07 (1H, s), 7.11-7.30 (10H, m), 7.47-7.57 (6H, m).

(c) (E)-3-{[1-(Ethoxycarbonylmethyl)-1H-imidazol-2-yl]methylidene}-1-(triphenylmethyl)piperidin-4-ol (E)-3-{[1-(Ethoxycarbonylmethyl)-1H-imidazol-2-yl]methylidene}-1-(triphenylmethyl)piperidin-4-one (11.32 g) was reduced with sodium borohydride (941 mg) in a mixed solvent of ethanol (120 ml) and dichloromethane (40 ml) in a similar manner to that described in Example 138-(c). The crude product obtained by usual extraction was purified by silica gel chromatography using ethyl acetate and hexane (3:7 to 10:0) as an eluent to afford the title compound (10.11 g, yield: 89%) as a pale yellow amorphous solid.

$^1$H NMR (500 MHz, CDCl$_3$) δ ppm: 1.31 (3H, t, J=7.0), 1.66-1.92 (2H, m), 2.02-2.30 (2H, m), 2.82-2.98 (1H, m), 3.32-3.56 (1H, m), 3.96-4.06 (1H, m), 4.26 (2H, q, J=7.0), 4.72 (2H, s), 6.21 (1H, s), 6.84 (1H, s), 6.88 (1H, s), 7.00-7.39 (15H, m).

(d) (E)-4-(Acetylsulfanyl)-3-{[1-(ethoxycarbonylmethyl)-1H-imidazol-2-yl]methylidene}piperidine bis(hydrogen trifluoroacetate)

To a solution of (E)-3-{[1-(ethoxycarbonylmethyl)-1H-imidazol-2-yl]methylidene}-1-(triphenylmethyl)piperidin-4-ol (4.52 g) in toluene (80 ml) were added N,N-dimethylformamide dineopentyl acetal (5.0 ml) and thioacetic acid (1.3 ml) at 0° C. After the mixture was stirred at room temperature, the reaction was quenched by addition of water. The product was extracted with ethyl acetate. The organic layer was washed with a saturated aqueous sodium chloride solution and dried over anhydrous sodium sulfate. Removal of the solvent under reduced pressure followed by purification of the residue by silica gel chromatography using ethyl acetate and hexane (25:75 to 70:30) gave 5-{(acetylsulfanyl)[1-(ethoxycarbonylmethyl)-1H-imidazol-2-yl]methyl}-1-(triphenylmethyl)-1,2,3,6-tetrahydropyridine (3.92 g, yield: 78%) as a pale yellow amorphous solid.

All of the above obtained solid was dissolved in dimethyl sulfoxide (60 ml) and potassium thioacetate (7.94 g) was added. The mixture was stirred at 80° C. for 5 hours. After cooling, the mixture was diluted with ethyl acetate, washed successively with water and a saturated aqueous sodium chloride solution and dried over anhydrous sodium sulfate. Removal of the solvent by evaporation under reduced pressure followed by purification of the residue by silica gel chromatography (eluent: ethyl acetate/hexane=3/7~6/4) gave three fractions shown below.

The less polar isomer (E)-4-(acetylsulfanyl)-3-{[1-(ethoxycarbonylmethyl)-1H-imidazol-2-yl]methylidene}-1-(triphenylmethyl)piperidine: 0.57 g, yield from the tetrahydropyridine derivative: 15%, brown oil.

The more polar isomer (Z)-4-(acetylsulfanyl)-3-{[1-(ethoxycarbonylmethyl)-1H-imidazol-2-yl]methylidene}-1-(triphenylmethyl)piperidine: 0.29 g, yield from the tetrahydropyridine derivative: 7%, brown oil.

A mixture of the above two components: 2.00 g, yield from the tetrahydropyridine derivative: 51%.

Trifluoroacetic acid (230 µl) was added dropwise to a solution of the above-mentioned less polar isomer (0.57 g) in dichloromethane (10 ml) at 0° C. The mixture was stirred at room temperature for 20 minutes and then solvents were removed under reduced pressure. The residue was purified by silica gel chromatography (eluent: methanol/dichloromethane=3/97~20/80) to afford the title compound (396.8 mg, yield of the de-triphenylmethylation step: 71%) as a brown oil.

$^1$H NMR (400 MHz, CDCl$_3$) δ ppm: 1.33 (3H, t, J=7.0), 2.07-2.16 (1H, m), 2.37 (3H, s), 2.49-2.62 (1H, m), 3.18-3.29 (1H, m), 3.38-3.45 (1H, m), 3.95 (1H, d, J=15.0), 4.22-4.36 (3H, m), 4.55 (1H, t, J=4.0), 4.72 (1H, d, J=17.5), 4.79 (1H, d, J=17.5), 6.52 (1H, s), 7.14 (1H, s), 7.29 (1H, s).

(e) (E)-4-(Acetylsulfanyl)-1-[2-cyclopropyl-1-(2-fluorophenyl)-2-oxoethyl]-3-{[1-(ethoxycarbonylmethyl)-1H-imidazol-2-yl]methylidene}piperidine hydrochloride Following a procedure similar to that described in Example 132-(g), (E)-4-(acetylsulfanyl)-3-{[1-(ethoxycarbonylmethyl)-1H-imidazol-2-yl]methylidene}piperidine bis(hydrogen trifluoroacetate) (396.8 mg) was subjected to the reaction with 2-bromo-2-(2-fluorophenyl)-1-cyclopropylethanone (229.3 mg) and triethylamine (400 µl) in acetonitrile (7 ml). The product was purified by silica gel chromatography (eluent: ethyl acetate/hexane=1/4~1/0) to afford the free base of the title compound (225.8 mg) as a brown oil, which was treated with a 4N hydrogen chloride dioxane solution (0.34 ml) in acetonitrile (5 ml) and the solvent and excess hydrogen chloride were removed under reduced pressure to afford the title compound (243.7 mg, yield: 63%) as a pale yellow amorphous solid.

$^1$H NMR (400 MHz, CDCl$_3$) δ ppm: 0.67-1.04 (4H, m), 1.29 and 1.30 (total 3H, each t, J=7.0), 1.81-1.91 (1H, m), 2.20-2.88 (7H, m), 3.21 and 3.33 (total 1H, each d, J=13.5), 4.24 and 4.25 (total 2H, each q, J=7.0), 4.40 and 4.62 (total 1H, each d, J=13.5), 4.46 and 4.49 (total 1H, each t, J=4.5), 4.64-4.67 (2H, m), 4.67 and 4.74 (total 1H, each s), 6.25 and 6.26 (total 1H, each s), 6.83 and 6.86 (total 1H, each s), 6.95 and 7.02 (total 1H, each s), 7.03-7.16 (2H, m), 7.24-7.45 (2H, m);

IR (KBr, cm$^{-1}$): 1705, 1494.

Example 196

(E)-1-[2-Cyclopropyl-1-(2-fluorophenyl)-2-oxoethyl]-3-{[1-(ethoxycarbonylmethyl)-1H-imidazol-2-yl]methylidene}-4-sulfanylpiperidine hydrochloride (Exemplification Compound No. 2-801)

Hydrogen chloride was passed through a solution of (E)-4-(acetylsulfanyl)-1-[2-cyclopropyl-1-(2-fluorophenyl)-2-oxoethyl]-3-{[1-(ethoxycarbonylmethyl)-1H-imidazol-2-yl]methylidene}piperidine hydrochloride (169.4 mg) in ethanol (4 ml) at 0° C. and the sealed mixture was stirred at room temperature for 6.5 hours. The mixture was concentrated under reduced pressure and the residue was purified by preparative HPLC (YMC-Pack ODS-A; YMC, eluent: acetonitrile/0.026 N aqueous trifluoroacetic acid solution, 25/75, v/v). The thus obtained trifluoroacetic acid salt of the title compound was neutralized with an aqueous sodium hydrogen carbonate solution, and the liberated free base was extracted twice with dichloromethane. The extract was dried over anhydrous sodium sulfate and solvents were removed under reduced pressure to afford the free base of the title compound (67.7 mg, yield: 47%) as a colourless oil. The oil thus obtained was treated with a 4N hydrogen chloride dioxane solution (120 µl) in acetonitrile (3 ml). The solvent and excess hydrogen chloride were removed by evaporation under reduced pressure to afford the title compound (88.9 mg) as a pale yellow amorphous solid.

$^1$H NMR (400 MHz, CDCl$_3$) δ ppm: 0.65-0.79 (2H, m), 0.84-1.02 (2H, m), 1.30 (3H, t, J=7.5), 1.72-1.89 (1H, m), 2.15-2.32 (2H, m), 2.49-3.02 (2H, m), 3.63-4.13 (3H, m), 4.25 (2H, q, J=7.5), 4.67 (2H, s), 4.71 and 4.73 (total 1H, each s), 6.26 and 6.33 (total 1H, each s), 6.86 and 6.87 (total 1H, each s), 6.96-7.16 (3H, m), 7.22-7.45 (2H, m);

IR (KBr, cm$^{-1}$): 2659, 1711, 1494.

Example 197

(E)-3-{[1-(Carboxymethyl)-1H-imidazol-2-yl]methylidene}-1-[2-cyclopropyl-1-(2-fluorophenyl)-2-oxoethyl]-4-sulfanylpiperidine hydrochloride (Exemplification Compound No. 2-769)

Following a procedure similar to that described in Example 134, (E)-1-[2-cyclopropyl-1-(2-fluorophenyl)-2-oxoethyl]-3-{[1-(ethoxycarbonylmethyl)-1H-imidazol-2-yl]methylidene}-4-sulfanylpiperidine hydrochloride (155.6 mg) was treated with 3N hydrochloric acid (5 ml) at 50° C. for 2.5 hours. After the reaction solution of was concentrated under reduced pressure, the residue was purified by preparative HPLC (YMC-Pack ODS-A; YMC, eluent: acetonitrile/0.024 N hydrochloric acid, 15/85, v/v) to afford the title compound (149.0 mg, yield: quantitative) as a colourless amorphous solid.

$^1$H NMR (400 MHz, pyridine-d$_5$) δ ppm: 0.68-0.81 (2H, m), 0.96-1.22 (2H, m), 1.76-1.90 (1H, m), 2.24-2.35 (1H, m), 2.50-3.10 (4H, m), 3.96 and 4.05 (total 1H, each t, J=4.5), 4.20 and 4.46 (total 1H, each d, J=13.0), 4.62 and 4.99 (total 1H, each d, J=13.0), 4.98 and 5.02 (total 1H, each s), 5.16 and 5.17 (total 2H, each s), 6.83 and 6.88 (total 1H, each s), 7.11-7.36 (4H, m), 7.68-7.76 (1H, m);

IR (KBr, cm$^{-1}$): 2717, 1711, 1494.

Example 198

(E)-4-(Acetylsulfanyl)-3-{[1-(carboxymethyl)-1H-imidazol-2-yl]methylidene}-1-[2-cyclopropyl-1-(2-fluorophenyl)-2-oxoethyl]piperidine hydrochloride (Exemplification Compound No. 2-770)

To a solution of (E)-3-{[1-(carboxymethyl)-1H-imidazol-2-yl]methylidene}-1-[2-cyclopropyl-1-(2-fluorophenyl)-2-oxoethyl]-4-sulfanylpiperidine hydrochloride (85.6 mg) in dichloromethane (4 ml) were added triethylamine (120 µl) and acetic anhydride (80 µl) at 0° C. After the mixture was stirred at room temperature for 3 hours, solvents were removed under reduced pressure and the residue was purified by silica gel chromatography using methanol and dichloromethane (5:95 to 25:75) as eluents to afford the free base of the title compound (57.7 mg, yield: 71%) as a colourless oil.

The compound thus obtained (59.7 mg) was treated with a 4N hydrogen chloride dioxane solution (150 µl) in acetonitrile (3 ml). The solvent and excess hydrogen chloride were removed under reduced pressure to afford the title compound (58.2 mg, overall yield: 64%) as a pale yellow amorphous solid.

$^1$H NMR (400 MHz, CDCl$_3$) δ ppm: 0.69-1.02 (4H, m), 1.80-2.08 (2H, m), 2.29 (3H, s), 2.20-2.33 (1H, m), 2.42-2.89 (2H, m), 3.25 and 3.33 (total 1H, each d, J=13.0), 3.72-3.87 (1H, m), 4.42 (1H, t, J=4.5), 4.64 (2H, s), 4.83 and 4.89 (total 1H, each s), 6.39 (1H, s), 7.05-7.40 (6H, m);

IR (KBr, cm$^{-1}$): 1707, 1494.

Example 199

(Z)-4-(Acetylsulfanyl)-1-[2-cyclopropyl-1-(2-fluorophenyl)-2-oxoethyl]-3-{[1-(ethoxycarbonylmethyl)-1H-imidazol-2-yl]methylidene}piperidine hydrochloride (Exemplification Compound No. 4-60)

(a) (Z)-4-(Acetylsulfanyl)-3-{[1-(ethoxycarbonylmethyl)-1H-imidazol-2-yl]methylidene}piperidine bis(hydrogen trifluoroacetate)

Trifluoroacetic acid (120 µl) was added to a solution of (Z)-4-(acetylsulfanyl)-3-{[1-(ethoxycarbonylmethyl)-1H-imidazol-2-yl]methylidene}-1-(triphenylmethyl)piperidine (described in Example 195-(d), 0.29 g) in dichloromethane (5 ml) at 0° C. After the mixture was stirred at room temperature for 2 hours, solvents were removed under reduced pressure and the residue was purified by silica gel chromatography using methanol and dichloromethane (5:95 to 20:80) as eluents to afford the title compound (185.2 mg, yield: 65%) as a brown oil.

$^1$H NMR (500 MHz, CDCl$_3$) δ ppm: 1.32 (3H, t, J=7.0), 2.00-2.10 (1H, m), 2.29 (3H, s), 2.75-2.86 (1H, m), 3.18-3.29 (1H, m), 3.39-3.47 (1H, m), 3.97 (1H, d, J=13.5), 4.05 (1H, d, J=13.5), 4.28 (2H, q, J=7.0), 4.73 (1H, d, J=17.5), 4.78 (1H, d, J=17.5), 4.83 (1H, bs), 6.41 (1H, s), 7.24 (1H, s), 7.41 (1H, s).

(b) (Z)-4-(Acetylsulfanyl)-1-[2-cyclopropyl-1-(2-fluorophenyl)-2-oxoethyl]-3-{[1-(ethoxycarbonylmethyl)-1H-imidazol-2-yl]methylidene}piperidine hydrochloride Following a procedure similar to that described in Example 132-(g), (Z)-4-(acetylsulfanyl)-3-{[1-(ethoxycarbonylmethyl)-1H-imidazol-2-yl]methylidene}piperidine bis(hydrogen trifluoroacetate) (185.2 mg) was subjected to the reaction with 2-bromo-2-(2-fluorophenyl)-1-cyclopropylethanone (99.3 mg) and triethylamine (190 µl) in acetonitrile (4 ml). The product was purified by silica gel chromatography (eluent: ethyl acetate/hexane=1/9~1/0) to afford the free base of the title compound (113.5 mg) as a pale yellow oil, which was dissolved in acetonitrile (3 ml) and a 4N hydrogen chloride dioxane solution (170 µl) was added. The solvent and excess hydrogen chloride were removed under reduced pressure to afford the title compound (119.6 mg, yield: 64%) as a pale yellow amorphous solid.

$^1$H NMR (400 MHz, CDCl$_3$) δ ppm: 0.78-1.09 (4H, m), 1.29 (3H, t, J=7.0), 1.81-1.95 (1H, m), 2.18-2.36 (5H, m), 2.37-2.68 (1H, m), 2.75-3.10 (2H, m), 3.26 and 3.38 (total 1H, each d, J=12.0), 4.18-4.27 (2H, m), 4.55-4.79 (3H, m), 5.87-6.02 (2H, m), 6.88 (1H, d, J=3.5), 7.07-7.46 (5H, m);

IR (KBr, cm$^{-1}$): 1708, 1495.

Example 200

(Z)-1-[2-Cyclopropyl-1-(2-fluorophenyl)-2-oxoethyl]-3-{[1-(ethoxycarbonylmethyl)-1H-imidazol-2-yl]methylidene}-4-sulfanylpiperidine hydrochloride (Exemplification Compound No. 4-59)

To a solution of the mixture of (Z)-4-(acetylsulfanyl)-3-{[1-(ethoxycarbonylmethyl)-1H-imidazol-2-yl]methylidene}-1-(triphenylmethyl)piperidine and its (E)-isomer (2.00 g) obtained in Example 195-(d) in dichloromethane (30 ml) was added trifluoroacetic acid (810 μl) at 0° C. After the mixture was stirred at room temperature for 1 hour, solvents were removed under reduced pressure. The residue was purified by silica gel column chromatography using methanol and dichloromethane (5:95 to 20:80) as eluents. The crude product thus was further purified by preparative HPLC (YMC-Pack ODS-A; YMC, eluent: acetonitrile/0.026 N aqueous trifluoroacetic acid, 15/85, v/v) to afford a mixture of (Z)-4-(acetylsulfanyl)-3-{[1-(ethoxycarbonylmethyl)-1H-imidazol-2-yl]methylidene}piperidine bis(hydrogen trifluoroacetate) and its (E) isomer (1.55 g, yield: 80%).

A portion (1.00 g) of this mixture was treated with 2-bromo-2-(2-fluorophenyl)-1-cyclopropylethanone (557.5 mg) and triethylamine (1.0 ml) in acetonitrile (15 ml) in a similar manner to that described in Example 132-(g) and the product was purified by silica gel chromatography (eluent: ethyl acetate/hexane=2/8~1/0) to afford a mixture of (Z)-4-(acetylsulfanyl)-1-[2-cyclopropyl-1-(2-fluorophenyl)-2-oxoethyl]-3-{[1-(ethoxycarbonylmethyl)-1H-imidazol-2-yl]methylidene}piperidine and its (E)-isomer (609.9 mg, yield: 67%) as a pale brown amorphous solid.

Hydrogen chloride was passed through a solution of the whole amount of the above-mentioned mixture in ethanol (10 ml) at 0° C. and the sealed mixture was stirred at room temperature for 7 hours. The mixture was concentrated under reduced pressure and the residue was purified by preparative HPLC (YMC-Pack ODS-A; YMC, eluent: acetonitrile/0.026 N aqueous trifluoroacetic acid solution, 25/75, v/v) to afford the title compound (115.8 mg, yield: 19%) as a colourless amorphous solid. Further elution gave the (E)-isomer (127.6 mg, yield: 21%).

Spectral data for the (Z)-isomer was as follows:

$^1$H NMR (400 MHz, CDCl$_3$) δ ppm: 0.77-0.92 (2H, m), 0.97-1.10 (2H, m), 1.31 (3H, t, J=7.0), 1.72-1.85 (1H, m), 2.13-2.35 (2H, m), 2.44-2.92 (2H, m), 3.18 and 3.30 (total 1H, each d. J=12.5), 3.34 and 3.52 (total 1H, each d, J=12.5), 4.26 (2H, q, J=7.0), 4.57-4.72 (2H, m), 4.79 and 4.81 (total 1H, each s), 5.30-5.42 (1H, m), 5.72 and 5.80 (total 1H, each s), 6.87 and 6.89 (total 1H, each s), 7.08-7.23 (3H, m), 7.29-7.46 (2H, m);

IR (KBr, cm$^-$): 2646, 1712, 1494.

Example 201

(Z)-3-{[1-(Carboxymethyl)-1H-imidazol-2-yl]methylidene}-1-[2-cyclopropyl-1-(2-fluorophenyl)-2-oxoethyl]-4-sulfanylpiperidine hydrochloride (Exemplification Compound No. 4-51)

Following a procedure similar to that described in Example 134, (Z-1-[2-cyclopropyl-1-(2-fluorophenyl)-2-oxoethyl]-3-{[1-(ethoxycarbonylmethyl)-1H-imidazol-2-yl]methylidene}-4-sulfanylpiperidine hydrochloride (73.5 mg) was treated with 3N hydrochloric acid (3 ml) at 50° C. for 2 hours. The reaction solution was concentrated under reduced pressure and the residue was purified by preparative HPLC (YMC-Pack ODS-A; YMC, eluent: acetonitrile/0.024 N hydrochloric acid, 10/90, v/v) to afford the title compound (52.3 mg, yield: 95%) as a colourless amorphous solid.

$^1$H NMR (400 MHz, pyridine-d$_5$) δ ppm: 0.68-0.86 (2H, m), 0.94-1.10 (2H, m), 1.79-1.90 (1H, m), 2.29-3.03 (4H, m), 3.43 and 3.53 (total 1H, each d, J=12.5), 3.63 and 3.74 (total 1H, each d, J=12.5), 4.88 and 4.94 (total 1H, each s), 5.10-5.28 (2H, m), 6.10-6.16 (1H, m), 6.43 and 6.47 (total 1H, each s), 7.04-7.43 (5H, m), 7.58-7.64 (1H, m);

IR (KBr, cm$^{-1}$): 2712, 1712, 1494.

Example 202

(4R)-(E)-4-(Acetylsulfanyl)-1-[(1RS)-1-(2-fluorophenyl)-2-methoxy-2-oxoethyl]-3-({1-[2-(ethoxycarbonyl)ethyl]-1H-pyrazol-3-yl}methylidene)piperidine (Exemplification Compound No. 5-16)

To a solution of (4R)-(E)-4-(acetylsulfanyl)-3-{1-[2-(ethoxycarbonyl)ethyl]-1H-pyrazol-3-yl}methylidene)piperidine hydrogen trifluoroacetate (Example 180-(a), 766.6 mg) in acetonitrile (10 ml) were added methyl bromo (2-fluorophenyl)acetate (406.1 mg) and triethylamine (570 μl) at 0° C. After being stirred at room temperature for 1 hour, the mixture was diluted with ethyl acetate. The solution was washed successively with water and a saturated aqueous sodium chloride solution and dried over anhydrous sodium sulfate. The solvent was evaporated under reduced pressure and the residue was purified by silica gel chromatography using ethyl acetate and hexane (3:7 to 6:4) as eluents to afford the title compound (530.2 mg, yield: 77%) as a pale yellow oil.

$^1$H NMR (400 MHz, CDCl$_3$) δ ppm: 1.26 (3H, t, J=7.0), 1.81-1.92 (1H, m), 2.19-2.34 (4H, m), 2.51-2.71 (1H, m), 2.73-2.88 (3H, m), 3.17 and 3.28 (total 1H, each d, J=13.5), 3.67 and 3.70 (total 3H, each s), 4.07-4.34 (5H, m), 4.44-4.53 (1H, m), 4.62 (1H, s), 6.00 and 6.04 (total 1H, each s), 6.45 (1H, d, J=4.5), 7.00-7.15 (2H, m), 7.23-7.34 (2H, m), 7.49-7.58 (1H, m);

IR (KBr, cm$^{-1}$): 1732, 1496.

Example 203

(4R)-(E)-1-[(1RS)-1-(2-Fluorophenyl)-2-methoxy-2-oxoethyl]-3-({1-[2-(ethoxycarbonyl)ethyl]-1H-pyrazol-3-yl}methylidene) 4-sulfanylpiperidine hydrochloride (Exemplification Compound No. 5-11)

Hydrogen chloride was passed through a solution of (4R)-(E)-4-(acetylsulfanyl)-1-[(1RS)-1-(2-fluorophenyl)-2-methoxy-2-oxoethyl]-3-({1-[2-(ethoxycarbonyl)ethyl]-1H-pyrazol-3-yl}methylidene)piperidine (223.8 mg) in methanol (6 ml) while stirring at 0° C. and the sealed mixture was stirred at room temperature for 7 hours. The solvent and excess hydrogen chloride were evaporated under reduced pressure and the residue was purified by silica gel chromatography using methanol and dichloromethane (3:97 to 15:85, v/v) as eluents to afford the title compound (213.9 mg, yield: 99%) as a colourless amorphous solid.

$^1$H NMR (400 MHz, CDCl$_3$) δ ppm: 1.72-1.84 (1H, m), 2.19-2.34 (1H, m), 2.63-2.98 (4H, m), 3.59-3.72 (7H, m), 3.85-3.96 (2H, m), 4.25-4.35 (2H, m), 4.65 (1H, s), 5.99 and 6.06 (total 1H, each d, J=2.5), 6.41 and 6.43 (total 1H, each s), 7.00-7.15 (2H, m), 7.25-7.33 (2H, m), 7.50-7.58 (1H, m);

IR (KBr, cm$^{-1}$): 2607, 1750, 1496.

Example 204

(4R)-(E)-1-[(1S)-1-(2-Fluorophenyl)-2-methoxy-2-oxoethyl]-3-({1-[2-(ethoxycarbonyl)ethyl]-1H-pyrazol-3-yl}methylidene)-4-sulfanylpiperidine hydrochloride and (4R)-(E)-1-[(1R)-1-(2-Fluorophenyl)-2-methoxy-2-oxoethyl]-3-({1-[2-(ethoxycarbonyl)ethyl]-1H-pyrazol-3-yl}methylidene)-4-sulfanylpiperidine hydrochloride (Exemplification Compound No. 5-11)

(4R)-(E)-1-[(1RS)-1-(2-Fluorophenyl)-2-methoxy-2-oxoethyl]-3-({1-[2-(ethoxycarbonyl)ethyl]-1H-pyrazol-3-yl}methylidene)-4-sulfanylpiperidine hydrochloride was treated with an aqueous sodium hydrogen carbonate solution. The liberated base was extracted with dichloromethane. The free base thus obtained (ca. 200 mg) was divided into five portions and subjected to preparative HPLC (Chiralcel OD-H, 20φ×250 mm, Daicel Chemical Industries Co., Ltd., eluent: 2-propanol/hexane=1/2, 4 ml/minute) to afford the more mobile isomer, (4R)-(E)-1-[(1S)-1-(2-fluorophenyl)-2-methoxy-2-oxoethyl]-3-({1-[2-(ethoxycarbonyl)ethyl]-1H-pyrazol-3-yl}methylidene)-4-sulfanylpiperidine (103.9 mg), and the less mobile isomer, (4R)-(E)-1-[(1R)-1-(2-fluorophenyl)-2-methoxy-2-oxoethyl]-3-({1-[2-(ethoxycarbonyl)ethyl]-1H-pyrazol-3-yl}methylidene)-4-sulfanylpiperidine (100.3 mg), both as colourless oils.

Both isomers were treated with a 4N hydrogen chloride dioxane solution in acetonitrile. The solvent and excess hydrogen chloride were removed under reduced pressure to respectively afford the two title hydrochloric salts, both as colourless amorphous solids.

(4R)-(E)-1-[(1S)-1-(2-Fluorophenyl)-2-methoxy-2-oxoethyl]-3-({1-[2-(ethoxycarbonyl)ethyl]-1H-pyrazol-3-yl}methylidene)-4-sulfanylpiperidine hydrochloride $^1$H NMR (500 MHz, CDCl$_3$) δ ppm: 1.73-1.84 (1H, m), 2.19-2.29 (1H, m), 2.64-2.73 (1H, m), 2.80-2.90 (3H, m), 3.65-3.72 (7H, m), 3.87-3.95 (2H, m), 4.29-4.35 (2H, m), 4.65 (1H, s), 6.06 (1H, d, J=2.5), 6.43 (1H, s), 7.01-7.15 (2H, m), 7.24-7.34 (2H, m), 7.52-7.58 (1H, m);
[α]$_D$=+14.7° (c=0.54, CHCl$_3$).

(4R)-(E)-1-[(1R)-1-(2-Fluorophenyl)-2-methoxy-2-oxoethyl]-3-({1-[2-(ethoxycarbonyl)ethyl]-1H-pyrazol-3-yl}methylidene)-4-sulfanylpiperidine hydrochloride $^1$H NMR (500 MHz, CDCl$_3$) δ ppm: 1.74-1.84 (1H, m), 2.22-2.34 (1H, m), 2.66-2.74 (1H, m), 2.82 (2H, t, J=7.0), 2.88-2.96 (1H, m), 3.60-3.72 (7H, m), 3.86-3.97 (2H, m), 4.28 (2H, t, J=7.0), 4.65 (1H, s), 5.99 (1H, d, J=2.5), 6.41 (1H, s), 7.03-7.16 (2H, m), 7.24-7.33 (2H, m), 7.51-7.58 (1H, m);
[α]$_D$=−78.3° (c=0.51, CHCl$_3$).

Example 205

(Z)-4-(Acetylsulfanyl)-1-[2-cyclopropyl-1-(2-fluorophenyl)-2-oxoethyl]-3-{[1-(ethoxycarbonylmethyl)-1H-imidazol-5-yl]methylidene}piperidine hydrochloride (Exemplification Compound No. 4-88)

(a) (Z)-4-(Acetylsulfanyl)-3-{[1-(ethoxycarbonylmethyl)-1H-imidazol-5-yl]methylidene}piperidine bis(hydrogen trifluoroacetate)

To a solution of (E)-3-{[1-(ethoxycarbonylmethyl)-1H-imidazol-5-yl]methylidene}-1-(triphenylmethyl)piperidin-4-ol (3.15 g) in toluene (50 ml) were added N,N-dimethylformamide dineopentyl acetal (3.5 ml) and thioacetic acid (0.89 ml) at room temperature. After being stirred at room temperature for 1 hour, the mixture was diluted with ethyl acetate, washed successively with water and a saturated aqueous sodium chloride solution and dried over anhydrous sodium sulfate. Removal of the solvent under reduced pressure followed by purification of the residue by silica gel chromatography using ethyl acetate and hexane (1:4 to 1:0) as eluents gave crude (E)-4-(acetylsulfanyl)-3-{[1-(ethoxycarbonylmethyl)-1H-imidazol-5-yl]methylidene}-1-(triphenylmethyl)piperidine (3.29 g) as a yellow amorphous solid.

The product thus obtained was dissolved in dimethyl sulfoxide (50 ml) and potassium thioacetate (6.56 g) was added. The mixture was stirred at 80° C. for 4 hours. After cooling, the mixture was partitioned between water and ethyl acetate. The organic layer was separated, washed with a saturated aqueous sodium chloride solution and dried over anhydrous sodium sulfate. Removal of the solvent under reduced pressure followed by purification of the residue by silica gel chromatography (eluent: ethyl acetate/hexane=1/1~1/0) gave an approximately 1:1 mixture of (Z)-4-(acetylsulfanyl)-3-{[1-(ethoxycarbonylmethyl)-1H-imidazol-5-yl]methylidene}-1-(triphenylmethyl)piperidine and its (E)-isomer (2.73 g).

Trifluoroacetic acid (1.1 ml) was added to a solution of the mixture obtained above in dichloromethane (40 ml) at 0° C. After being stirred at room temperature for 15 minutes, the mixture was concentrated under reduced pressure and the residue was purified by silica gel chromatography (eluent: methanol/dichloromethane=5/95~25/75) to afford the title compound (1.44 g, overall yield: 54%) as a pale yellow oil.

$^1$H NMR (400 MHz, CDCl$_3$) δ ppm: 1.32 (3H, t, J=7.5), 2.04-2.32 (2H, m), 2.42 (3H, s), 3.28-3.63 (2H, m), 3.88 (1H, d, J=12.0), 4.00 (1H, d, J=12.0), 4.28 (2H, q, J=7.5), 4.80-4.99 (3H, m), 6.26 (1H, s), 7.47 (1H, s), 8.98 (1H, s).

(b) (Z)-4-(Acetylsulfanyl)-1-[2-cyclopropyl-1-(2-fluorophenyl)-2-oxoethyl]-3-{[1-(ethoxycarbonylmethyl)-1H-imidazol-5-yl]methylidene}piperidine hydrochloride Following a procedure similar to that described in Example 132-(g), (Z)-4-(acetylsulfanyl)-3-{[1-(ethoxycarbonylmethyl)-1H-imidazol-5-yl]methylidene}piperidine bis(hydrogen trifluoroacetate) (784.7 mg) was subjected to the reaction with 2-bromo-2-(2-fluorophenyl)-1-cyclopropylethanone (442.9 mg) and triethylamine (790 μl) in acetonitrile (10 ml). The product obtained by usual workup was purified by silica gel chromatography using ethyl acetate and hexane (3:7 to 7:3), then methanol and dichloromethane (1:19) as eluents to afford the free base of the title compound (608.8 mg, yield: 86%) as a yellow oil.

A portion (73.7 mg) of the free base obtained above was treated with a 4N hydrogen chloride dioxane solution (4 ml) in dichloromethane (4 ml). The solvent and excess hydrogen chloride were removed under reduced pressure to afford the title compound (74.7 mg, overall yield: 81%) as a pale brown amorphous solid.

$^1$H NMR (400 MHz, CDCl$_3$) δ ppm: 0.77-0.92 (2H, m), 0.98-1.09 (2H, m), 1.28 and 1.30 (total 3H, each t, J=7.0), 1.72-1.86 (1H, m), 2.07-2.67 (3H, m), 2.32 and 2.33 (total 3H, each s), 2.76-3.01 (2H, m), 3.31 and 3.41 (total 1H, each d, J=13.0), 4.26 (2H, q, J=7.0), 4.61 and 4.65 (total 2H, each s), 4.74 and 4.78 (total 1H, each s), 4.93 (1H, bs), 5.86 and 5.94 (total 1H, each s), 7.01 and 7.02 (total 1H, each s), 7.08-7.23 (2H, m), 7.31-7.42 (2H, m), 7.49 and 7.50 (total 1H, each s);

IR (KBr, cm$^{-1}$): 1701, 1494.

Example 206

(Z)-4-(Acetylsulfanyl)-1-[2-cyclopropyl-1-(2-fluorophenyl)-2-oxoethyl]-3-{[1H-imidazol-4(5)-yl]methylidene}piperidine hydrochloride (Exemplification Compound No. 4-64)

(a) (Z)-4-(Acetylsulfanyl)-3-{[1H-imidazol-4(5)-yl]methylidene}piperidine bis(hydrogen trifluoroacetate)

To a solution of crude (E)-4-(acetylsulfanyl)-3-{[1-(t-butoxycarbonyl)-1H-imidazol-5-yl]methylidene}-1-(triphenylmethyl)piperidine (4.00 g) obtained in accordance with the method mentioned in Example 21(c) in dimethyl sulfoxide (50 ml) was added potassium thioacetate (7.90 g). The resulting mixture was stirred at 80° C. for 2.5 hours, cooled, and partitioned between ethyl acetate and water. The separated organic layer was washed with a saturated aqueous sodium chloride solution and dried over anhydrous sodium sulfate. The solvent was removed in vacuo, and the residue was purified by chromatography on silica gel using a mixture of ethyl acetate and hexane (3:7 to 7:3), then a mixture of methanol and dichloromethane (1:9) as eluents to afford a mixture of (Z)-4-(acetylsulfanyl)-3-{[1H-imidazol-4(5)-yl]methylidene}-1-(triphenylmethyl)piperidine and its (E)-isomer as a brown amorphous solid (2.35 g).

To a portion (2.09 g) of the above compound in a mixed solvent of dichloromethane (38 ml) and methanol (2 ml), was added trifluoroacetic acid (1.0 ml) at 0° C. The resulting mixture was stirred at 0° C. for one hour, concentrated in vacuo, and the residue was purified by chromatography on silica gel using a mixture of methanol and dichloromethane (5:95 to 40:60) as the eluent to afford a mixture of the title compound and its (E)-isomer (1.37 g). The product was purified further by preparative HPLC (YMC-Pack ODS-A; YMC, eluent: acetonitrile/0.026 N aqueous trifluoroacetic acid, 11/89, v/v) to afford the title compound as a yellow solid (749 mg, overall yield: 26%).

$^1$H NMR (400 MHz, DMSO-d$_6$) δ ppm: 1.86-1.97 (1H, m), 2.16-2.32 (1H, m), 2.37 (3H, s), 3.02-3.17 (1H, m), 3.28-4.02 (3H, m), 4.97 (1H, bs), 6.47 (1H, s), 7.54 (1H, s), 8.91-9.07 (1H, s).

(b) (Z)-4-(Acetylsulfanyl)-1-[2-cyclopropyl-1-(2-fluorophenyl)-2-oxoethyl]-3-{[1H-imidazol-4(5)-yl]methylidene}piperidine hydrochloride (Z)-4-(Acetylsulfanyl)-3-{[1H-imidazol-4(5)-yl]methylidene}piperidine bis(hydrogen trifluoroacetate) (749 mg) was treated with 2-bromo-2-(2-fluorophenyl)-1-cyclopropylethanone (374 mg) and triethylamine (670 μl) in acetonitrile (15 ml) in a similar manner to that described in Example 132(g), and the crude residue obtained by conventional extraction procedures was purified by chromatography on silica gel using a mixture of methanol and dichloromethane (1:99 to 15:85) as the eluent to afford the free base of the title compound as a yellow oil (506 mg). To a portion of the free base (93.6 mg) in acetonitrile (4 ml), was added 4 N solution of hydrogen chloride in dioxane (230 μl). The solvent and excess hydrogen chloride were removed in vacuo to afford the title hydrochloride as a pale yellow amorphous solid (93.9 mg, overall yield: 70%).

$^1$H NMR (400 MHz, CDCl$_3$) δ ppm: 0.78-0.93 (2H, m), 0.97-1.08 (2H, m), 1.74-1.86 (1H, m), 2.12-2.58 (3H, m), 2.38 (3H, m), 2.81-3.06 (2H, m), 3.26 and 3.42 (total 1H, each d, J=12.5), 4.71 and 4.75 (total 1H, each s), 5.02 (1H, bs), 6.15 and 6.24 (total 1H, each s), 7.03 and 7.05 (total 1H, each s), 7.08-7.23 (2H, m), 7.30-7.43 (2H, m), 7.76 (1H, s);

IR (KBr, cm$^{-1}$): 1700, 1494.

Example 207

(Z)-1-[2-Cyclopropyl-1-(2-fluorophenyl)-2-oxoethyl]-3-{[1H-imidazol-4(5)-yl]methylidene}-4-sulfanylpiperidine hydrochloride (Exemplification Compound No. 4-63)

(Z)-4-(Acetylsulfanyl)-1-[2-cyclopropyl-1-(2-fluorophenyl)-2-oxoethyl]-3-{[1H-imidazol-4(5)-yl]methylidene}piperidine (258 mg) was allowed to react with hydrogen chloride in ethanol (8 ml) using a manner similar to that described in Example 133. The reaction mixture was concentrated in vacuo, and the residue was purified by preparative HPLC (YMC-Pack ODS-A; YMC, eluent: acetonitrile/0.024 N aqueous HCl, 15/85, v/v) to afford the title compound as a colourless amorphous solid (226 mg, yield: 89%).

$^1$H NMR (400 MHz, CDCl$_3$) δ ppm: 0.82-1.20 (4H, m), 1.80-1.99 (2H, m), 2.59-2.77 (1H, m), 3.07-3.45 (2H, m), 3.71-3.84 (1H, m), 3.92-4.04 (1H, m), 4.45-4.58 (1H, m), 5.57 and 5.61 (total 1H, each s), 6.43 and 6.46 (total 1H, each s), 7.19-7.37 (2H, m), 7.44-7.77 (3H, m), 8.90 and 8.96 (total 1H, each s);

IR (KBr, cm$^{-1}$): 2652, 1710, 1494.

Example 208

(Z)-4-(Acetylsulfanyl)-1-[2-cyclopropyl-1-(2-fluorophenyl)-2-oxoethyl]-3-{[1H-pyrazol-3(5)-yl]methylidene}piperidine hydrochloride (Exemplification Compound No. 4-2)

(a) (Z)-4-(Acetylsulfanyl)-3-{[1H-pyrazol-3(5)-yl]methylidene}piperidine bis(hydrogen trifluoroacetate)

To a solution of crude (E)-4-(acetylsulfanyl)-3-{[1-(t-butoxycarbonyl)-1H-pyrazol-3-yl]methylidene}-1-(triphenylmethyl)piperidine (7.67 g) obtained in accordance with the methods mentioned in Example 11(c) in dimethyl sulfoxide (80 ml) was added potassium thioacetate (14.92 g). The resulting mixture was stirred at 80° C. for 4 hours, cooled, and partitioned between ethyl acetate and water. The separated organic layer was washed with a saturated aqueous sodium chloride solution and dried over anhydrous sodium sulfate. The solvent was removed in vacuo, and the residue was purified by chromatography on silica gel using a mixture of ethyl acetate and hexane (3:7 to 7:3), then a mixture of methanol and dichloromethane (1:19 to 2:18) as the eluent to afford a mixture of (Z)-4-(acetylsulfanyl)-3-{[1H-pyrazol-3(5)-yl]methylidene}-1-(triphenylmethyl)piperidine and its (E)-isomer as brown amorphous solids (3.42 g).

To a solution of the above mixture in dichloromethane (60 ml) was added trifluoroacetic acid (5.5 ml) at 0° C. The resulting mixture was stirred at 0° C. for 0.5 hour, concentrated in vacuo, and the residue was purified by chromatography on silica gel using a mixture of methanol and dichloromethane (5:95 to 50:50) as the eluent to afford a mixture of the title compound and its (E)-isomer (1.56 g). The product was purified further by preparative HPLC (YMC-Pack ODS-A; YMC, eluent: acetonitrile/0.026 N aqueous trifluoroacetic acid, 15/85, v/v) to afford the title compound as a colourless solid (261 mg, overall yield: 4%).

$^1$H NMR (500 MHz, DMSO-$d_6$) δ ppm: 1.86-1.95 (1H, m), 2.10-2.22 (1H, m), 2.38 (3H, s), 3.09-3.63 (3H, m), 3.90 (1H, d, J=14.0), 5.50 (1H, bs), 6.26 (1H, s), 6.56 (1H, s), 7.73 (1H, s).

(b) (Z)-4-(Acetylsulfanyl)-1-[2-cyclopropyl-1-(2-fluorophenyl)-2-oxoethyl]-3-{[1H-pyrazol-3(5)-yl]methylidene}piperidine hydrochloride (Z)-4-(Acetylsulfanyl)-3-{[1H-pyrazol-3(5)-yl]methylidene}piperidine bis(hydrogen trifluoroacetate) (261 mg) was treated with 2-bromo-2-(2-fluorophenyl)-1-cyclopropylethanone (140 mg) and triethylamine (230 μl) in acetonitrile (6 ml) in a similar manner to that described in Example 132(g), and the crude residue obtained by extraction as usual was purified by chromatography on silica gel using a mixture of ethyl acetate and hexane (2:8 to 6:4) as the eluent to afford the free base of the title compound as a yellow oil (165 mg with impurities). The product was purified further by preparative HPLC [YMC-Pack ODS-A; YMC, eluent: acetonitrile/aqueous acetic acid (0.5%), then acetonitrile/aqueous triethylamine (0.5%) 60/40 to 65/35, v/v]. The product was extracted from the fractions using ethyl acetate. The extract was dried over anhydrous sodium sulfate, and the solvent was removed in vacuo to afford the free base of the title compound (134 mg). The base was dissolved in acetonitrile (4 ml), and 4 N HCl in dioxane (400 μl) was added to the solution, the solvent and excess HCl were removed in vacuo to afford the title hydrochloride as a colourless amorphous solid (155 mg, overall yield: 43%).

$^1$H NMR (400 MHz, CDCl$_3$) δ ppm: 0.76-0.92 (2H, m), 0.98-1.10 (2H, m), 1.71-1.88 (1H, m), 2.11-2.27 (2H, m), 2.36 (3H, s), 2.52-2.64 (1H, m), 2.83 (1H, d, J=12.0), 3.02 (1H, d, J=12.0), 3.33 and 3.46 (total 1H, each d, J=12.0), 4.71-4.80 (1H, m), 5.19 (1H, bs), 6.22-6.36 (2H, m), 7.06-7.58 (5H, m);

IR (KBr, cm$^{-1}$): 1697, 1494.

Example 209

(Z)-1-[2-Cyclopropyl-1-(2-fluorophenyl)-2-oxoethyl]-3-{[1H-pyrazol-3(5)-yl]methylidene}-4-sulfanylpiperidine hydrochloride (Exemplification Compound No. 4-1)

(Z)-4-(Acetylsulfanyl)-1-[2-cyclopropyl-1-(2-fluorophenyl)-2-oxoethyl]-3-{[1H-pyrazol-3(5)-yl]methylidene}piperidine (266.8 mg) was allowed to react with HCl in ethanol (7 ml) in a similar manner to that described in Example 133. The reaction mixture was concentrated in vacuo, and the residue was purified by preparative HPLC (YMC-Pack ODS-A; YMC, eluent: acetonitrile/0.024 N aqueous hydrochloric acid, 20/80 to 25/75, v/v) to afford the title compound as a colourless amorphous solid (170 mg, yield: 65%).

$^1$H NMR (400 MHz, CDCl$_3$) δ ppm: 0.75-0.93 (2H, m), 0.98-1.11 (2H, m), 1.65-1.81 (1H, m), 2.11-2.34 (2H, m), 2.49-2.97 (2H, m), 3.15-3.27 (1H, m), 3.31-3.46 (1H, m), 4.73-4.83 (2H, m), 6.09 and 6.21 (total 1H, each s), 6.36 and 6.39 (total 1H, each s), 7.08-7.49 (4H, m), 7.53-7.60 (1H, m);

IR (KBr, cm$^{-1}$): 2654, 1710, 1494.

Example 210

(E)-4-(Acetylsulfanyl)-1-[2-cyclopropyl-1-(2-fluorophenyl)-2-oxoethyl]-3-({2-[3-(ethoxycarbonyl)propyl]-2H-tetrazol-5-yl}methylidene)piperidine (Exemplification Compound No. 2-1634)

(a) Ethyl 4-(5-formyl-2H-tetrazol-2-yl)butanoate

To a solution of [1(2)H-tetrazol-5-yl]methanol (10 g) in acetonitrile (80 ml) were added triethylamine (27.7 ml) and ethyl 4-bromobutanoate (28.9 ml). The resulting mixture was stirred at room temperature for 24 hours, concentrated in vacuo, and the residue was purified by chromatography on silica gel using a mixture of ethyl acetate and methanol (19:1) as the eluent to afford crude ethyl 4-[5-(hydroxymethyl)-2H-tetrazol-2-yl]butanoate as a yellow oil (25.9 g).

To a solution of this crude product in acetone (100 ml) was added active manganese dioxide (86.9 g) at room temperature. The resulting mixture was stirred at room temperature for 15 hours, filtrated, and the filtrate was concentrated in vacuo. The residue was purified by chromatography on silica gel using a mixture of dichloromethane and methanol (20:1, then 10:1) as the eluent to afford the title compound as a yellow oil (4.94 g, yield: 23%)

$^1$H NMR (400 MHz, CDCl$_3$) δ ppm: 1.25-1.29 (3H, m), 2.24-2.31 (2H, m), 2.26-2.39 (2H, m), 4.11-4.17 (2H, m), 4.54 (2H, t, J=7.0), 8.64 (1H, s).

(b) (E)-3-({2-[3-(Ethoxycarbonyl)propyl]-2H-tetrazol-5-yl}methylidene)-1-(triphenylmethyl)piperidin-4-one To a solution of 1-(triphenylmethyl)piperidin-4-one (7.63 g) in benzene (200 ml) was added pyrrolidine (1.9 ml), and the resulting mixture was heated under reflux for 2.5 hours removing water using a Dean-Staak apparatus. The reaction mixture was cooled to room temperature and ethyl 4-(5-formyl-2H-tetrazol-2-yl)butanoate (4.74 g) was added. The resulting mixture was heated to reflux for 3 hours, cooled, and diluted with water. The product was extracted with ethyl acetate, the solvent was dried over anhydrous sodium sulfate, and concentrated in vacuo. The residue was purified by chromatography on silica gel using a mixture of ethyl acetate and hexane (5:95 to 14:6) as the eluent to afford the title compound as a light yellow oil (3.86 g, yield: 32%).

$^1$H NMR (400 MHz, CDCl$_3$) δ ppm: 1.27 (3H, t, J=7.0), 2.11-2.27 (4H, m), 2.62-2.84 (4H, m), 3.74-3.86 (2H, m), 4.16 (2H, q, J=7.0), 4.59 (2H, t, J=6.5), 7.11-7.33 (10H, m), 7.45-7.58 (6H, m).

(c) (E)-3-({2-[3-(Ethoxycarbonyl)propyl]-2H-tetrazol-5-yl}methylidene)-1-(triphenylmethyl)piperidin-4-ol (E)-3-({2-[3-(Ethoxycarbonyl)propyl]-2H-tetrazol-5-yl}methylidene)-1-(triphenylmethyl)piperidin-4-one (3.93 g) was reduced with sodium borohydride (281 mg) in a mixed solvent of dichloromethane (30 ml) and ethanol (30 ml) in a similar manner to that mentioned in Example 138 (c), and the crude product obtained by conventional extraction procedures was purified by chromatography on silica gel using a mixture of ethyl acetate and hexane (1:9 to 7:3) as the eluent to afford the title compound as a yellow oil (1.46 g, yield: 37%).

¹H NMR (500 MHz, CDCl₃) δ ppm: 1.27 (3H, t, J=7.0), 1.69-1.99 (3H, m), 2.08-2.33 (5H, m), 2.89-3.00 (1H, m), 4.09-4.20 (4H, m), 4.38-4.55 (2H, m), 6.72 (1H, s), 7.05-7.46 (15H, m).

(d) (E)-4-(Acetylsulfanyl)-3-({2-[3-(ethoxycarbonyl) propyl]-2H-tetrazol-5-yl}methylidene)piperidine bis(hydrogen trifluoroacetate)

Using (E)-3-({2-[3-(ethoxycarbonyl)propyl]-2H-tetrazol-5-yl}methylidene)-1-(triphenylmethyl)piperidin-4-ol (3.51 g) as the starting material, a similar process to that mentioned in Example 132(e) afforded (E)-4-(acetylsulfanyl)-3-({2-[3-(ethoxycarbonyl)propyl]-2H-tetrazol-5-yl}methylidene)-1-(triphenylmethyl)piperidine as a yellow oil (3.10 g). This compound was treated with trifluoroacetic acid (1.2 ml) in a mixed solvent of dichloromethane (36 ml) and ethanol (4 ml) in a similar manner to that described in Example 132 (f). The reaction mixture was concentrated, and the residue was purified by chromatography on silica gel using a mixture of ethanol and dichloromethane (2:98 to 10:90) as the eluent to afford the title compound (1.41 g, yield: 46%) as a brown oil.

¹H NMR (500 MHz, CDCl₃) δ ppm: 1.26 (3H, t, J=7.0), 2.11-2.19 (1H, m), 2.25-2.42 (7H, m), 2.49-2.60 (1H, m), 3.22-3.32 (1H, m), 3.45-3.53 (1H, m), 4.03 (1H, d, J=14.0), 4.14 (2H, q, J=7.0), 4.61-4.72 (3H, m), 5.20 (1H, d, J=14.0), 6.89 (1H, s).

(e) (E)-4-(Acetylsulfanyl)-1-[2-cyclopropyl-1-(2-fluorophenyl)-2-oxoethyl]-3-({2-[3-(ethoxycarbonyl) propyl]-2H-tetrazol-5-yl}methylidene)piperidine (E)-4-(Acetylsulfanyl)-3-({2-[3-(ethoxycarbonyl)propyl]-2H-tetrazol-5-yl}methylidene)piperidine bis(hydrogen trifluoroacetate) (1.51 g) was treated with 2-bromo-2-(2-fluorophenyl)-1-cyclopropylethanone (1.01 g) and triethylamine (1.41 ml) in acetonitrile (25 ml) in a similar manner to that described in Example 132(g), and the crude products extracted using the conventional procedures was purified by chromatography on silica gel using a mixture of ethyl acetate and hexane (1:4 to 2:3) as the eluent to afford the title compound as a light yellow oil (1.13 g, yield: 66%).

¹H NMR (400 MHz, CDCl₃) δ ppm: 0.68-1.06 (4H, m), 1.27 (3H, t, J=7.0), 1.86-1.97 (1H, m), 2.15-2.39 (9H, m), 2.46-2.71 (1H, m), 2.77-2.86 (1H, m), 3.42 and 3.50 (total 1H, each d, J=13.5), 4.15 (2H, q, J=7.0), 4.25 and 4.33 (total 1H, each d, J=13.5), 4.48-4.66 (3H, m), 4.75 and 4.76 (total 1H, each s), 6.66 (1H, s), 7.04-7.19 (2H, m), 7.25-7.43 (2H, m).

Example 211

(E)-1-[2-Cyclopropyl-1-(2-fluorophenyl)-2-oxoethyl]-3-({2-[3-(ethoxycarbonyl)propyl]-2H-tetrazol-5-yl}methylidene)-4-sulfanylpiperidine hydrochloride (Exemplification Compound No. 2-1633)

(E)-4-(Acetylsulfanyl)-1-[2-cyclopropyl-1-(2-fluorophenyl)-2-oxoethyl]-3-({2-[3-(ethoxycarbonyl)propyl]-2H-tetrazol-5-yl}methylidene}piperidine (1.08 g) was treated with hydrogen chloride in ethanol (20 ml) in a similar manner to that described in Example 133. The reaction mixture was concentrated in vacuo, and the residue was purified by chromatography on silica gel using a mixture of ethanol and dichloromethane (2:98 to 10:90) as the eluent to afford the title compound as a pale yellow amorphous solid (976 mg, yield: 91%).

¹H NMR (500 MHz, CDCl₃) δ ppm: 0.69-1.09 (4H, m), 1.27 (3H, t, J=7.0), 1.81-1.93 (1H, m), 2.08-2.43 (6H, m), 2.61-3.01 (2H, m), 3.81-4.22 (5H, m), 4.51-4.66 (2H, m), 4.81 (1H, bs), 6.66 (1H, s), 7.01-7.19 (2H, m), 7.23-7.48 (2H, m);

IR (KBr, cm⁻¹): 2609, 1730, 1494.

Example 212

(E)-3-{[2-(3-Carboxypropyl)-2H-tetrazol-5-yl]methylidene}-1-[2-cyclopropyl-1-(2-fluorophenyl)-2-oxoethyl]-4-sulfanylpiperidine hydrochloride (Exemplification Compound No. 2-1603)

(E)-1-[2-Cyclopropyl-1-(2-fluorophenyl)-2-oxoethyl]-3-({2-[3-(ethoxycarbonyl)propyl]-2H-tetrazol-5-yl}methylidene)-4-sulfanylpiperidine hydrochloride (854 mg) was treated with 3 N aqueous hydrochloric acid solution (16 ml) at 50° C. for one hour in a similar manner to that described in Example 134. The reaction mixture was concentrated in vacuo, and the residue was purified by preparative HPLC (YMC-Pack ODS-A; YMC, eluent: acetonitrile/0.024 N aqueous hydrochloric acid, 30/70 to 35/65, v/v) to afford the title compound as a colourless amorphous solid (801 mg, yield: 99%).

¹H NMR (500 MHz, pyridine-d₅) δ ppm: 0.64-0.79 (2H, m), 0.93-1.19 (2H, m), 1.85-1.97 (1H, m), 2.29-2.51 (4H, m), 2.56-2.66 (2H, m), 2.72-2.93 (2H, m), 2.93-3.09 (1H, m), 4.03-4.11 (1H, m), 4.20 and 4.34 (total 1H, each d, J=13.0), 4.75-4.88 (2H, m), 5.02 (1H, s), 6.96 (1H, s), 7.16-7.27 (2H, m), 7.30-7.40 (1H, m), 7.65-7.74 (1H, m);

IR (KBr, cm⁻¹): 2622, 1712, 1494.

Example 213

(E)-4-(Acetylsulfanyl)-1-[2-cyclopropyl-1-(2-fluorophenyl)-2-oxoethyl]-3-({1-[3-(ethoxycarbonyl) propyl]-1H-tetrazol-5-yl}methylidene)piperidine (Exemplification Compound No. 2-1570)

(a) (E)-4-(t-Butyldimethylsilyloxy)-3-(cyanomethylidene)-1-(triphenylmethyl)piperidine To a solution of (E)-4-(t-butyldimethylsilyloxy)-3-(formylmethylidene)-1-(triphenylmethyl)piperidine (Example 36(b), 46.81 g) in tetrahydrofuran (150 ml) were added sodium hydroxide (9.0 g) in water (150 ml) and hydroxylamine hydrochloride (7.8 g). After the resulting mixture was stirred at room temperature for 3 hours, further hydroxylamine hydrochloride (2 g) was added. The resulting mixture was stirred at room temperature for additional 1.5 hours, and 50% aqueous hydroxylamine solution (4.0 ml) was added. The resulting mixture was stirred at room temperature for additional 1 hour, and further 50% aqueous hydroxylamine solution (4.0 ml) was added. The resulting mixture was stirred at room temperature for 40 minutes, the solvent was removed in vacuo, and the residue was extracted with ethyl acetate. The organic layer was washed with water and saturated aqueous sodium chloride solution successively, dried over anhydrous sodium sulfate, and concentrated in vacuo to afford crude oxime as a yellow oil.

To a solution of the above compound in acetonitrile (300 ml) were added triphenylphosphine (25.0 g), triethylamine (19.5 ml), and carbon tetrachloride (14.9 ml). The resulting mixture was stirred at room temperature for 6 hours and partitioned between ethyl acetate and water. The separated organic layer was washed with water and saturated aqueous sodium chloride solution successively, and dried over anhydrous sodium sulfate. The solvent was removed in vacuo, and the residue was purified by chromatography on silica gel using a mixture of hexane and ethyl acetate (15:1) as the eluent to afford the title compound as light yellow powdery crystals (28.8 g, yield: 62%).

$^1$H NMR (400 MHz, CDCl$_3$) δ ppm: 0.03 (6H, s), 0.90 (9H, s), 1.89-1.98 (4H, m), 3.13-3.17 (1H, m), 3.87-3.92 (1H, m), 4.16-4.20 (1H, m), 5.59 (1H, s), 7.17-7.20 (4H, m), 7.26-7.31 (5H, m), 7.47 (6H, bs).

(b) (E)-4-(t-Butyldimethylsilyloxy)-3-{[1(2)H-tetrazol-5-yl]methylidene}-1-(triphenylmethyl)piperidine To a solution of (E)-4-(t-butyldimethylsilyloxy)-3-(cyanomethylidene)-1-(triphenylmethyl)piperidine (28.8 g) in 1,2-dimethoxyethane (300 ml) was added tributyltin azide (30.0 g) The resulting mixture was heated under reflux for 2 days, cooled to room temperature, and further tributyltin azide (10.0 g) was added. The resulting mixture was heated under reflux for another day, cooled to room temperature, and the solvent was removed in vacuo. The residue was partitioned between ethyl acetate and water. The organic layer partitioned was washed with water and saturated aqueous sodium chloride successively, and dried over anhydrous sodium sulfate. The solvent was removed in vacuo, and the residue was purified by chromatography on silica gel using a mixture of hexane and ethyl acetate (15:1~10:1~1:1) as eluents to afford the title compound as a light yellow amorphous solid (7.63 g, yield 24%).

$^1$H NMR (400 MHz, CDCl$_3$) δ ppm: 0.03 and 0.05 (total 6H, each s), 0.92 (9H, s), 1.36-1.41 (2H, m), 1.65-1.68 (2H, m), 1.95-1.99 (1H, m), 3.08 (1H, bs), 4.04-4.07 (1H, m), 6.68 (1H, s), 7.10 (10H, bs), 7.84 (6H, bs).

(c) (E)-4-(t-Butyldimethylsilyloxy)-3-({1-[3-ethoxycarbonyl]propyl]-1H-tetrazol-5-yl}methylidene)-1-(triphenylmethyl)piperidine A mixture of (E)-4-(t-butyldimethylsilyloxy)-3-{[1(2)H-tetrazol-5-yl]methylidene}-1-(triphenylmethyl)piperidine (7.63 g), acetonitrile (100 ml), N,N-dimethylformamide (20 ml), triethylamine (3.8 ml) and ethyl 4-bromobutylate (2 ml) was stirred at room temperature for 21.5 hours. To the resulting reaction mixture were added 1,8-diazabicyclo[5.4.0]undec-7-ene (DBU) (2.1 ml) and ethyl 4-bromobutylate (2 ml) successively. The resulting mixture was stirred at room temperature for one hour and the solvent was removed in vacuo. The residue was partitioned between ethyl acetate and water. The separated organic layer was washed with water and saturated aqueous sodium chloride successively, and dried over anhydrous sodium sulfate. The solvent was removed in vacuo, and the residue was purified by chromatography on silica gel using a mixture of hexane and ethyl acetate (4:1) as the eluent to afford the title compound as a yellow amorphous solid (980 mg, yield 11%).

$^1$H NMR (400 MHz, CDCl$_3$) δ ppm: 0.04 and 0.08 (total 6H, each s), 0.95 (9H, s), 1.28 (3H, t, J=7.0), 1.63-1.69 (2H, m), 1.96-2.03 (3H, m), 2.27-2.84 (2H, m), 2.47 (2H, t, J=7.0), 3.12-3.15 (1H, m), 4.06-4.10 (1H, m), 4.18 (2H, q, J=7.0), 4.45-4.50 (2H, m), 6.50 (1H, s), 7.14 (10H, bs), 7.86-7.87 (5H, m).

(d) (E)-3-({1-[3-Ethoxycarbonyl]propyl]-1H-tetrazol-5-yl}methylidene)-1-(triphenylmethyl)piperidin-4-ol To a solution of (E)-4-(t-butyldimethylsilyloxy)-3-({1-[3-ethoxycarbonyl]propyl]-1H-tetrazol-5-yl}methylidene)-1-(triphenylmethyl)piperidine (980 mg) in tetrahydrofuran (15 ml) was added 75% aqueous tetrabutylammonium fluoride (617 mg). The resulting mixture was stirred at room temperature for 30 minutes, diluted with ethyl acetate, and washed with water and saturated aqueous sodium chloride successively. The organic solvent was dried over anhydrous sodium sulfate, and removed in vacuo. The residue was purified by chromatography on silica gel using a mixture of ethyl acetate and hexane (1:9 to 10:0) as the eluent to afford the title compound as a colourless amorphous solid (716 mg, yield 89%).

$^1$H NMR (400 MHz, CDCl$_3$) δ ppm: 1.29 (3H, t, J=7.0), 1.72-1.83 (1H, m), 1.86-2.00 (1H, m), 2.13-2.34 (4H, m), 2.44-2.51 (2H, m), 3.04-3.13 (1H, m), 4.20 (2H, q, J=7.0), 4.39-4.61 (4H, m), 6.52 (1H, s), 7.06-7.20 (9H, m), 7.30-7.40 (6H, m).

(e) (E)-4-(Acetylsulfanyl)-3-({1-[3-ethoxycarbonyl]propyl]-1H-tetrazol-5-yl}methylidene)piperidine trifluoroacetate To a solution of (E)-3-({1-[3-ethoxycarbonyl]propyl]-1H-tetrazol-5-yl}methylidene)-1-(triphenylmethyl)piperidin-4-ol (715.6 mg) in N,N-dimethylformamide (10 ml) were added thioacetic acid (950 μl) and N,N-dimethylformamide dineopentyl acetal (3.7 ml). The resulting mixture was stirred at room temperature for one hour. Then, thioacetic acid (950 μl) and N,N-dimethylformamide dineopentyl acetal (3.7 ml) were added further, and the reaction mixture was stirred at room temperature for 30 minutes. The reaction mixture was partitioned between ethyl acetate and water. The organic layer partitioned was washed with water and saturated aqueous sodium chloride successively, and dried over anhydrous sodium sulfate. The solvent was removed in vacuo, and the residue was purified by chromatography on silica gel using a mixture of ethyl acetate and hexane (1:9 to 3:7) as the eluent to afford crude (E)-4-(acetylsulfanyl)-3-({1-[3-ethoxycarbonyl]propyl]-1H-tetrazol-5-yl}methylidene)-1-(triphenylmethyl)piperidine (419 mg) as a yellow oil.

To a solution of the above product in a mixed solvent of dichloromethane and ethanol (9:1, 7 ml) was added trifluoroacetic acid (160 μl) at 0° C. The resulting mixture was stirred at 0° C. for 15 minutes, and dichloromethane (33 ml) was added to the reaction mixture. The solution was subjected to chromatography on silica gel. Using a mixture of ethanol and dichloromethane (2:98 to 10:90) as eluent, the title compound was obtained as a yellow oil (220 mg, overall yield: 36%).

$^1$H NMR (400 MHz, CDCl$_3$) δ ppm: 1.27 (3H, t, J=7.0), 2.12-2.27 (3H, m), 2.36-2.45 (5H, m), 2.58-2.71 (1H, m), 3.17-3.28 (1H, m), 3.51-3.60 (1H, m), 3.98 (1H, d, J=15.0), 4.16 (2H, q, J=7.0), 4.43 (2H, t, J=7.0), 4.66 (1H, bs), 5.26 (1H, d, J=15.0), 6.71 (1H, s).

(f) (E)-4-(Acetylsulfanyl)-1-[2-cyclopropyl-1-(2-fluorophenyl)-2-oxoethyl]-3-({1-[3-(ethoxycarbonyl)propyl]-1H-tetrazol-5-yl}methylidene)piperidine To a solution of (E)-4-(acetylsulfanyl)-3-({1-[3-ethoxycarbonyl]propyl]-1H-tetrazol-5-yl}methylidene)piperidine trifluoroacetate (220 mg) in acetonitrile (5 ml) were added 2-bromo-2-(2-fluorophenyl)-1-cyclopropylethanone (190 mg) and triethylamine (200 μl) at 0° C. The resulting mixture was stirred at 0° C. for 20 minutes, then at room temperature for one hour. The reaction mixture was partitioned between ethyl acetate and water. The separated organic layer was washed with water and a saturated aqueous sodium chloride solution successively, and dried over anhydrous sodium sulfate. The solvent was removed in vacuo, and the residue was purified by chromatography on silica gel using a mixture of ethyl acetate and hexane (1:4 to 1:0), then a mixture of ethanol and dichloromethane (1:19) as the eluent to afford the title compound as a colourless oil (139 mg, yield: 56%).

$^1$H NMR (400 MHz, CDCl$_3$) δ ppm: 0.70-1.09 (4H, m), 1.27 and 1.28 (total 3H, each t, J=7.0), 1.85-1.98 (1H, m), 2.01-2.44 (9H, m), 2.67-2.99 (2H, m), 3.35 and 3.48 (total 1H, each d, J=13.5), 4.07-4.58 (6H, m), 4.79 and 4.80 (total 1H, each s), 6.39 and 6.40 (total 1H, each s), 7.02-7.21 (2H, m), 7.27-7.43 (2H, m).

Example 214

(E)-1-[2-Cyclopropyl-1-(2-fluorophenyl)-2-oxoethyl]-3-({1-[3-(ethoxycarbonyl)propyl]-1H-tetrazol-5-yl}methylidene)-4-sulfanylpiperidine hydrochloride (Exemplification Compound No. 2-1569)

Hydrogen chloride was passed through a solution of (E)-4-(acetylsulfanyl)-1-[2-cyclopropyl-1-(2-fluorophenyl)-2-oxoethyl]-3-({1-[3-(ethoxycarbonyl)propyl]-1H-tetrazol-5-yl}methylidene)piperidine (139 mg) in ethanol (4 ml) at 0° C. The mixture was stirred under tightly sealed condition at room temperature for 3.5 hours. The solvent and excess amount of hydrogen chloride were removed in vacuo, and the residue was purified by chromatography on silica gel using a mixture of ethanol and dichloromethane (2:98 to 12:88) as the eluent to afford the title compound as a pale yellow amorphous solid (136 mg, yield 99%)

$^1$H NMR (500 MHz, CDCl$_3$) δ ppm: 0.72-0.84 (2H, m), 0.93-1.04 (2H, m), 1.27 (3H, t, J=7.0), 1.81-1.93 (1H, m), 2.03-2.10 (1H, m), 2.18-2.43 (5H, m), 2.53-3.07 (2H, m), 3.56-4.03 (2H, m), 4.12-4.23 (3H, m), 4.41 (2H, t, J=7.0), 4.79 and 4.80 (total 1H, each s), 6.44 and 6.51 (total 1H, each s), 7.03-7.19 (2H, m), 7.28-7.38 (2H, m).

Example 215

(E)-3-{[1-(3-Carboxypropyl)-1H-tetrazol-5-yl]methylidene}-1-[2-cyclopropyl-1-(2-fluorophenyl)-2-oxoethyl]-4-sulfanylpiperidine hydrochloride (Exemplification Compound No. 2-1537)

A solution of (E)-1-[2-cyclopropyl-1-(2-fluorophenyl)-2-oxoethyl]-3-({1-[3-(ethoxycarbonyl)propyl]-1H-tetrazol-5-yl}methylidene)-4-sulfanylpiperidine hydrochloride (134 mg) in 3 N HCl (4 ml) was stirred at 50° C. for 2 hours. The solvent and excess HCl were removed in vacuo, and the residue was purified by preparative HPLC (YMC-Pack ODS-A; YMC, eluent: acetonitrile/0.024 N aqueous HCl, 30/70, v/v) to afford the title compound as a colourless amorphous solid (91 mg, yield: 72%).

$^1$H NMR (500 MHz, C$_5$D$_5$N) δ ppm: 0.67-0.78 (2H, m), 0.95-1.04 (1H, m), 1.09-1.19 (1H, m), 1.88-1.96 (1H, m), 2.28-2.46 (4H, m), 2.58 (2H, t, J=7.0), 2.66-2.86 (1H, m), 2.89-3.13 (1H, m), 4.02-4.14 (1H, m), 4.21 and 4.28 (total 1H, each d, J=13.0), 4.43 (1H, d, J=13.0), 4.63 (2H, t, J=7.0), 5.03 and 5.04 (total 1H, each s), 6.88 and 6.91 (total 1H, each s), 7.13-7.35 (3H, m), 7.62-7.70 (1H, m);

IR (KBr, cm$^{-1}$): 2557, 1713, 1495.

Example 216

(E)-3-{[1-(2-Aminoethyl)-1H-pyrazol-3-yl]methylidene}-1-[2-cyclopropyl-1-(2-fluorophenyl)-2-oxoethyl]-4-sulfanylpiperidine dihydrochloride (Exemplification Compound No. 2-1661)

(a) (E)-3-({1-[2-(t-Butoxycarbonylamino)ethyl]-1H-pyrazol-3-yl}methylidene)-1-(triphenylmethyl)piperidin-4-one To a solution of 2-(t-butoxycarbonylamino)ethanol (5.0 ml) in dichloromethane (100 ml) were added triethylamine (13.5 ml) and methanesulfonic anhydrous (8.35 g). The resulting mixture was stirred at 0° C. for 45 minutes, water was added to the mixture, and the product was extracted with dichloromethane. The separated organic layer was dried over anhydrous sodium sulfate, and the solvent was removed in vacuo to afford crude 2-(t-butoxycarbonylamino)ethyl methanesulfonate as a brown oil.

To a solution of the above product in N,N-dimethylformamide (100 ml) were added (E)-3-{[1H-pyrazol-3(5)-yl]methylidene}-1-(triphenylmethyl)piperidin-4-one (Example 73-(a), 6.85 g) and 1,8-diazabicyclo[5.4.0]undec-7-ene (DBU) (5.0 ml). After the resulting mixture was stirred at 60° C. for 6 hours, DBU (2.5 ml) and tetrabutylammonium iodide (1.20 g) were added and the mixture was stirred further for 4.5 hours. The reaction mixture was cooled to room temperature, diluted with ethyl acetate, and the organic layer was washed with water and saturated aqueous sodium chloride successively. The solvent was removed in vacuo, and the residue was purified by chromatography on silica gel using a mixture of ethyl acetate and hexane (2:8 to 4:6) as the eluent to afford the title compound as a pale yellow amorphous solid (6.41 g, yield from the starting pyrazole derivative: 35%).

$^1$H NMR (400 MHz, CDCl$_3$) δ ppm: 1.44 (9H, s), 2.59-2.80 (6H, m), 3.29-3.72 (2H, m), 4.06-4.17 (2H, m), 6.20 (1H, s), 7.11-7.61 (17H, m).

(b) (E)-3-({1-[2-(t-Butoxycarbonylamino)ethyl]-1H-pyrazol-3-yl}methylidene)-1-(triphenylmethyl)piperidin-4-ol To a solution of (E)-3-({1-[2-(t-butoxycarbonylamino)ethyl]-1H-pyrazol-3-yl}methylidene)-1-(triphenylmethyl)piperidin-4-one (6.41 g) in a mixed solvent of dichloromethane (40 ml) and methanol (40 ml) was added sodium borohydride (436 mg) at 0° C. After the resulting mixture was stirred at 0° C. for 30 minutes, water was added to the mixture to stop the reaction and the product was extracted with ethyl acetate. The organic layer was washed with water and saturated aqueous sodium chloride successively, and dried over anhydrous sodium sulfate. The solvent was removed in vacuo, and the residue was purified by chromatography on silica gel using a mixture of ethyl acetate and hexane (3:7 to 7:3) as eluents to afford the title compound as a colourless solid (5.35 g, yield: 84%)

$^1$H NMR (400 MHz, CDCl$_3$) δ ppm: 1.46 (9H, s), 1.83-2.21 (4H, m), 2.55-2.80 (1H, m), 3.25-3.36 (2H, m), 3.96-4.21 (4H, m), 6.08 (1H, s), 6.50 (1H, s), 7.05-7.47 (16H, m).

(c) (E)-4-(Acetylsulfanyl)-3-({1-[2-(t-butoxycarbonylamino)ethyl]-1H-pyrazol-3-yl}methylidene)piperidine bis(hydrogen trifluoroacetate)

To a solution of (E)-3-({1-[2-(t-butoxycarbonylamino)ethyl]-1H-pyrazol-3-yl}methylidene)-1-(triphenylmethyl)piperidin-4-ol (3.67 g) in N,N-dimethylformamide (50 ml) were added thioacetic acid (4.6 ml) and N,N-dimethylformamide dineopentylacetal (18 ml). The resulting mixture was stirred at room temperature overnight. The reaction mixture was diluted with ethyl acetate. The organic layer was washed with water and saturated aqueous sodium chloride successively, and dried over anhydrous sodium sulfate. The solvent was removed in vacuo, and the residue was purified by chromatography on silica gel using a mixture of ethyl acetate and hexane (1:9 to 1:1) as the eluent to afford crude (E)-4-(acetylsulfanyl)-3-({1-[2-(t-butoxycarbonylamino)ethyl]-1H-pyrazol-3-yl}methylidene)-1-(triphenylmethyl)piperidine (4.29 g) as a brown oil. To a solution of the above oil in dichloromethane (50 ml) was added trifluoroacetic acid (1.5 ml) at 0° C. The resulting mixture was stirred at room temperature for 30 minutes, and the solvent was removed in vacuo. The residue was purified twice by chromatography on silica gel using a mixture of methanol and dichloromethane (1:99 to 7:93) as the eluent to afford the title compound as a brown oil (1.46 g, overall yield: 37%).

$^1$H NMR (400 MHz, CDCl$_3$) δ ppm: 1.41 (9H, s), 2.03-2.11 (1H, m), 2.36 (3H, s), 2.37-2.49 (1H, m), 3.13-3.57 (4H, m), 3.76 (1H, d, J=14.5), 4.08-4.25 (2H, m), 4.53-4.62 (1H, m), 5.13 (1H, d, J=14.5), 6.18 (1H, s), 6.63 (1H, s), 7.29 (1H, s).

(d) (E)-4-(Acetylsulfanyl)-3-({1-[2-(t-butoxycarbonylamino)ethyl]-1H-pyrazol-3-yl}methylidene)-1-[2-cyclopropyl-1-(2-fluorophenyl)-2-oxoethyl]piperidine To a solution of (E)-4-(acetylsulfanyl)-3-({1-[2-(t-butoxycarbonylamino)ethyl]-1H-pyrazol-3-yl}methylidene)piperidine bis(hydrogen trifluoroacetate) (619 mg) in acetonitrile (9 ml) were added 2-bromo-2-(2-fluorophenyl)-1-cyclopropylethanone (392 mg) and triethylamine (430 μl), and the resulting mixture was stirred at 0° C. for 2 hours. The reaction mixture was diluted with ethyl acetate. The organic layer was washed with water and saturated aqueous sodium chloride solution successively, and dried over anhydrous sodium sulfate. The solvent was removed in vacuo, and the residue was purified by chromatography on silica gel using a mixture of ethyl acetate and hexane (3:7 to 6:4) as the eluent to afford the title compound as a yellow amorphous solid (478 mg, yield: 84%).

$^1$H NMR (400 MHz, CDCl$_3$) δ ppm: 0.63-1.02 (4H, m), 1.44 (9H, s), 1.82-1.93 (1H, m), 2.06-2.28 (2H, m), 2.29 and 2.31 (total 3H, each s), 2.42-2.63 (1H, m), 2.66-2.86 (1H, m), 2.98 and 3.31 (total 1H, each d, J=13.5), 3.42-3.59 (2H, m), 4.04-4.43 (3H, m), 4.46-4.55 (1H, m), 4.73 and 4.77 (total 1H, each s), 6.07 and 6.13 (total 1H, each s), 6.49 (1H, s), 7.03-7.44 (5H, m).

(e) (E)-3-{[1-(2-Aminoethyl)-1H-pyrazol-3-yl]methylidene}-1-[2-cyclopropyl-1-(2-fluorophenyl)-2-oxoethyl]-4-sulfanylpiperidine dihydrochloride A solution of (E)-4-(acetylsulfanyl)-3-({1-[2-(t-butoxycarbonylamino)ethyl]-1H-pyrazol-3-yl}methylidene)-1-[2-cyclopropyl-1-(2-fluorophenyl)-2-oxoethyl]piperidine (479 mg) in 4 N hydrogen chloride (in dioxane, 8 ml) was stirred at room temperature for one hour. The solvent and hydrogen chloride were removed in vacuo, and the residue was purified by chromatography on silica gel using a mixture of in ethanol and dichloromethane (2:98 to 20:80) as eluents to afford (E)-4-(acetylsulfanyl)-3-{[1-(2-aminoethyl)-1H-pyrazol-3-yl]methylidene}-1-[2-cyclopropyl-1-(2-fluorophenyl)-2-oxoethyl]piperidine dihydrochloride as a pale brown amorphous solid (450 mg). A part of the above compound (104.2 mg) was dissolved in ethanol (4 ml), and hydrogen chloride gas was passed therethrough with stirring at 0° C., and the resulting mixture was stirred under tightly sealed condition at room temperature for 5 hours. The solvent was removed in vacuo, and the residue was purified by chromatography on silica gel using a mixture of ethanol and dichloromethane (5:95 to 25:75) as the eluent to afford the title compound as a colourless amorphous solid (86.3 mg, overall yield: 90%).

$^1$H NMR (400 MHz, CDCl$_3$) δ ppm: 0.65-1.02 (4H, m), 1.66-1.72 (1H, m), 2.17-2.38 (2H, m), 2.59-2.92 (2H, m), 3.05-3.15 (2H, m), 3.56 and 3.65 (total 1H, each d, J=12.5), 3.80-3.98 (2H, m), 4.01-4.13 (2H, m), 4.74 and 4.76 (total 1H, each s), 6.07 and 6.16 (total 1H, each s), 6.46 and 6.47 (total 1H, each s), 7.03-7.46 (5H, m);

IR (KBr, cm$^{-1}$): 2556, 1710, 1494.

Example 217

(E)-4-(Acetylsulfanyl)-1-[2-cyclopropyl-1-(2-fluorophenyl)-2-oxoethyl]-3-({1-[4-(ethoxycarbonyl)butyl]-1H-1,2,3-triazol-4-yl}methylidene)piperidine (Exemplification Compound No. 2-1190)

(a) Ethyl 5-(4-formyl-1H-1,2,3-triazol-1-yl)pentanoate, and ethyl 5-(5-formyl-1H-1,2,3-triazol-1-yl)pentanoate To a solution of ethyl 5-azidopentanoate (32.93 g) in toluene (250 ml) was added propargyl alcohol (10.5 ml). The resulting mixture was heated under reflux for 8 hours, cooled to room temperature, and concentrated in vacuo to afford a pale yellow oil (40.29 g). Since 5-azidopentanoate was still remaining in the crude product, the product was dissolved in toluene (250 ml), and propargyl alcohol (4.2 ml) was added to the resulting mixture. Then the resulting mixture was heated under reflux for 2 hours. When the mixture was cooled to room temperature, the reaction mixture was concentrated in vacuo to afford a crude mixture of ethyl 5-[4-(hydroxymethyl)-1H-1,2,3-triazol-1-yl]pentanoate and ethyl 5-[5-(5-hydroxymethyl)-1H-1,2,3-triazol-1-yl)pentanoate as a pale yellow oil (42.81 g).

To a solution of the product (37.27 g) mentioned above in dichloromethane (300 ml) was added active manganese dioxide. The resulting mixture was stirred at room temperature for 18 hours, filtrated, and the filtrate was evaporated in vacuo. The residue was purified by chromatography on silica gel using a mixture of ethyl acetate and hexane (2:8 to 5:5) as the eluent to afford a mixture of the two title compounds as a pale yellow oil (22.73 g, overall yield: 62%).

$^1$H NMR (400 MHz, CDCl$_3$) δ ppm: 1.23-1.29 (3H, m), 1.62-1.73 (2H, m), 1.90-2.07 (2H, m), 2.35 and 2.37 (total 2H, each t, J=7.0), 4.12 and 4.14 (total 2H, each q, J=7.0), 4.47 and 4.74 (total 2H, each t, J=7.0), 8.13 and 8.26 (total 1H, each s), 10.01 and 10.15 (total 1H, each s).

(b) (E)-3-({1-[4-(Ethoxycarbonyl)butyl]-1H-1,2,3-triazol-4-yl}methylidene)-1-(triphenylmethyl)piperidin-4-one and (E)-3-({1-[4-(ethoxycarbonyl)butyl]-1H-1,2,3-triazol-5-yl}methylidene)-1-(triphenylmethyl)piperidin-4-one The regioisomeric mixture of the two aldehydes (22.73 g) obtained as mentioned above was treated with 1-(triphenylmethyl)piperidin-4-one (34.23 g) and pyrrolidine (8.4 ml) in benzene (500 ml) in a similar manner to that described in Example 132 (c). The crude products extracted using conventional procedures were purified by chromatography on silica gel using a mixture of hexane and ethyl acetate (2:8 to 6:4) as the eluent and by crystallization (only less polar isomer was obtained by the crystallization, solvent: a mixed solvent of ethyl acetate and hexane) to afford the two regio isomers.

Less polar isomer: (E)-3-({1-[4-(ethoxycarbonyl)butyl]-1H-1,2,3-triazol-5-yl}methylidene)-1-(triphenylmethyl)piperidin-4-one (4.87 g, yield: 9%, colourless crystalline solids).

$^1$H NMR (400 MHz, CDCl$_3$) δ ppm: 1.25 (3H, t, J=7.5), 1.60-1.70 (2H, m), 1.88-2.00 (2H, m), 2.35 (2H, t, J=7.5), 2.65-2.85 (4H, m), 3.31-3.44 (2H, m), 4.13 (2H, q, J=7.5), 4.44 (2H, t, J=7.5), 7.11-7.56 (17H, m).

More polar isomer: (E)-3-({1-[4-(ethoxycarbonyl)butyl]-1H-1,2,3-triazol-4-yl}methylidene)-1-(triphenylmethyl)piperidin-4-one as yellow amorphous solids (18.87 g, yield: 34%).

$^1$H NMR (400 MHz, CDCl$_3$) δ ppm: 1.26 (3H, t, J=7.5), 1.53-1.64 (2H, m), 1.85-1.96 (2H, m), 2.33 (2H, t, J=7.0), 2.62-2.80 (4H, m), 3.58-3.70 (2H, m), 4.14 (2H, q, J=7.5), 4.32 (2H, t, J=7.0), 7.12-7.57 (17H, m).

(c) (E)-3-({1-[4-(Ethoxycarbonyl)butyl]-1H-1,2,3-triazol-4-yl}methylidene)-1-(triphenylmethyl)piperidin-4-ol (E)-3-({1-[4-(Ethoxycarbonyl)butyl]-1H-1,2,3-triazol-4-yl}methylidene)-1-(triphenylmethyl)piperidin-4-one (18.87 g) was allowed to react with sodium borohydride (1.32 g) in a similar manner to that described in Example 132 (d). The crude product obtained by extraction was purified by chromatography on silica gel using a mixture of ethyl acetate and hexane (4:6 to 6:4), followed by a mixture of methanol and dichloromethane (5:9 to 10:90) as eluents to afford the title compound as a pale brown amorphous solid (18.59 g).

$^1$H NMR (400 MHz, CDCl$_3$) δ ppm: 1.26 (3H, t, J=7.0), 1.57-1.68 (2H, m), 1.80-1.96 (3H, m), 2.06-2.21 (1H, m), 2.34 (2H, t, J=7.0), 2.58-2.84 (2H, m), 3.53-3.69 (1H, m), 4.07-4.28 (6H, m), 6.63 (1H, s), 7.07-7.47 (16H, m).

(d) (E)-4-(Acetylsulfanyl)-3-({1-[4-(ethoxycarbonyl)butyl]-1H-1,2,3-triazol-4-yl}methylidene)piperidine hydrogen trifluoroacetate Using (E)-3-({1-[4-(ethoxycarbonyl)butyl]-1H-1,2,3-triazol-4-yl}methylidene)-1-(triphenylmethyl)piperidin-4-ol (18.59 g) as the starting material, thioacetylation and removal of triphenylmethyl group were conducted in a similar manner to that described in Examples 132(e) and (f). The crude product was purified by preparative HPLC (YMC-Pack ODS-A; YMC, eluent: acetonitrile/0.026 N aqueous trifluoroacetic acid, 30/70, v/v) to afford the title compound (2.29 g, Yield: 23%) as a brown oil.

$^1$H NMR (400 MHz, CDCl$_3$) δ ppm: 1.25 (3H, t, J=7.0), 1.56-1.69 (2H, m), 1.87-2.00 (2H, m), 2.09-2.21 (1H, m), 2.31-2.59 (6H, m), 3.26-3.32 (1H, m), 3.47-3.60 (1H, m), 3.96 (1H, d, J=14.5), 4.13 (2H, q, J=7.0), 4.37 (2H, t, J=6.5), 4.60 (1H, bs), 5.07 (1H, d, J=14.5), 6.71 (1H, s), 7.62 (1H, s).

(e) (E)-4-(Acetylsulfanyl)-1-[2-cyclopropyl-1-(2-fluorophenyl)-2-oxoethyl]-3-({1-[4-(ethoxycarbonyl)butyl]-1H-1,2,3-triazol-4-yl}methylidene)piperidine In a similar manner to that described in Example 132(g), (E)-4-(acetylsulfanyl)-({1-[4-(ethoxycarbonyl)butyl]-1H-1,2,3-triazol-4-yl}methylidene)piperidine hydrogen trifluoroacetate (2.29 g) was subjected to a reaction with 2-bromo-2-(2-fluorophenyl)-1-cyclopropylethanone (1.59 g). The crude extract was purified by chromatography on silica gel using a mixture of ethyl acetate and hexane (35:65 to 65:35) as the eluent to afford the title compound as a yellow oil (1.58 g, yield: 76%).

$^1$H NMR (400 MHz, CDCl$_3$) δ ppm: 0.68-1.05 (4H, m), 1.26 (3H, t, J=7.5), 1.57-1.71 (2H, m), 1.82-2.00 (3H, m), 2.08-2.16 (1H, m), 2.17-2.39 (6H, m), 2.42-2.67 (1H, m), 2.69-2.84 (1H, m), 3.13 and 3.24 (total 1H, each d, J=13.5), 3.88 and 3.96 (total 1H, each d, J=13.5), 4.14 (2H, q, J=7.5), 4.31 and 4.34 (total 2H, each t, J=7.0), 4.43-4.52 (1H, m), 4.76 and 4.78 (total 1H, each s), 6.57 and 6.58 (total 1H, each s), 7.05-7.20 (2H, m), 7.27-7.44 (2H, m), 7.50 and 7.59 (total 1H, each s).

Example 218

(E)-1-[2-Cyclopropyl-1-(2-fluorophenyl)-2-oxoethyl]-3-({1-[4-(ethoxycarbonyl)butyl]-1H-1,2,3-triazol-4-yl}methylidene)-4-sulfanylpiperidine hydrochloride (Exemplification Compound No. 2-1189)

In a similar manner to that described in Example 133, (E)-4-(acetylsulfanyl)-1-[2-cyclopropyl-1-(2-fluorophenyl)-2-oxoethyl]-3-({1-[4-(ethoxycarbonyl)butyl]-1H-1,2,3-triazol-4-yl}methylidene)piperidine (1.32 g) was treated with hydrogen chloride. The crude product was purified by chromatography on silica gel using a mixture of methanol and dichloromethane (1:99 to 10:90) as the eluent to afford the title compound as a pale yellow amorphous solid (1.44 g, yield: 92%).

$^1$H NMR (400 MHz, CDCl$_3$) δ ppm: 0.68-1.04 (4H, m), 1.26 (3H, t, J=7.0), 1.61-1.72 (2H, m), 1.88-2.15 (3H, m), 2.19-2.40 (4H, m), 2.56-2.90 (2H, m), 3.50-3.70 (2H, m), 3.87-3.95 (1H, m), 4.14 (2H, q, J=7.0), 4.32 and 4.35 (total 2H, each t, J=7.0), 4.80 (1H, bs), 6.58 (1H, s), 7.06-7.21 (2H, m), 7.28-7.45 (2H, m), 7.54 and 7.63 (total 1H, each s);

IR (KBr, cm$^{-1}$): 2515, 1726, 1495.

Example 219

(E)-3-{[1-(4-Carboxybutyl)-1H-1,2,3-triazol-4-yl]methylidene}-1-[2-cyclopropyl-1-(2-fluorophenyl)-2-oxoethyl]-4-sulfanylpiperidine hydrochloride (Exemplification Compound No. 2-1157)

In a similar manner to that described in Example 134, (E)-1-[2-cyclopropyl-1-(2-fluorophenyl)-2-oxoethyl]-3-({1-[4-(ethoxycarbonyl)butyl]-1H-1,2,3-triazol-4-yl}methylidene)-4-sulfanylpiperidine hydrochloride (1.32 g) was treated with 3 N HCl. The crude product was purified by preparative HPLC (YMC-Pack ODS-A; YMC, eluent: acetonitrile/0.024 N HCl, 20/80, v/v) to afford the title compound as a colourless amorphous solid (1.22 g, yield: 97%).

$^1$H NMR (500 MHz, pyridine-d$_5$) δ ppm: 0.65-0.78 (2H, m), 0.95-1.05 (1H, m), 1.07-1.19 (1H, m), 1.72-2.05 (5H, m), 2.28-2.47 (2H, m), 2.53 (2H, t, J=7.0), 2.63-2.80 (1H, m), 2.88-3.08 (1H, m), 3.99-4.11 (2H, m), 4.22-4.45 (3H, m), 5.00 and 5.01 (total 1H, each s), 6.83 and 6.87 (total 1H, each s), 7.17-7.28 (2H, m), 7.29-7.40 (1H, m), 7.65-7.75 (1H, m), 7.85 and 7.94 (total 1H, each s);

IR (KBr, cm$^{-1}$): 2612, 1711, 1494.

Example 220

(E)-4-(Acetylsulfanyl)-3-{[1-(4-carboxybutyl)-1H-1, 2,3-triazol-4-yl]methylidene}-1-[2-cyclopropyl-1-(2-fluorophenyl)-2-oxoethyl]piperidine (Exemplification Compound No. 2-1158)

In a similar manner to that described in Example 183, (E)-3-{[1-(4-carboxybutyl)-1H-1,2,3-triazol-4-yl]methylidene}-1-[2-cyclopropyl-1-(2-fluorophenyl)-2-oxoethyl]-4-sulfanylpiperidine hydrochloride (190 mg) was treated with acetic anhydride. The crude product extracted using conventional procedures was purified by chromatography on silica gel using a mixture of methanol and dichloromethane (1:99 to 7:93) as the eluent to afford the title compound as a colourless oil (190 mg, yield: 99%).

$^1$H NMR (400 MHz, CDCl$_3$) δ ppm: 0.67-1.05 (4H, m), 1.60-1.73 (2H, m), 1.82-2.13 (4H, m), 2.18-2.34 (4H, m), 2.40 (2H, t, J=7.0), 2.44-2.84 (2H, m), 3.13 and 3.26 (total 1H, each d, J=12.5), 3.88 and 3.91 (total 1H, each d, J=12.5), 4.33 and 4.36 (total 2H, each t, J=7.0), 4.46 and 4.48 (total 1H, each t, J=4.5), 4.80 and 4.83 (total 1H, each s), 6.59 and 6.60 (total 1H, each s), 7.06-7.20 (2H, m), 7.30-7.42 (2H, m), 7.56 and 7.63 (total 1H, each s).

Example 221

(E)-4-(Acetylsulfanyl)-1-[2-cyclopropyl-1-(2-fluorophenyl)-2-oxoethyl]-3-({1-[4-(N-methoxycarbamoyl)butyl]-1H-1,2,3-triazol-4-yl}methylidene)piperidine (Exemplification Compound No. 2-1694)

Using (E)-4-(acetylsulfanyl)-3-{[1-(4-carboxybutyl)-1H-1,2,3-triazol-4-yl]methylidene}-1-[2-cyclopropyl-1-(2-fluorophenyl)-2-oxoethyl]piperidine (478 mg) as the starting material, similar reaction to that mentioned in Example 191 was conducted. The crude product extracted as usual was purified by chromatography on silica gel using a mixture of methanol and dichloromethane (1:99 to 5:95) as the eluent to afford the title compound (154.4 mg, yield: 31%) as a colourless oil.

$^1$H NMR (400 MHz, CDCl$_3$) δ ppm: 0.68-1.05 (4H, m), 1.62-2.34 (12H, m), 2.41-2.83 (2H, m), 3.14-3.28 (1H, m), 3.74 (3H, s), 3.90 and 3.97 (total 1H, each d, J=13.0), 4.33 and 4.35 (total 2H, each t, J=6.5), 4.47 and 4.48 (total 1H, each t, J=5.0), 4.76 and 4.80 (total 1H, each s), 6.57 and 6.58 (total 1H, each s), 7.05-7.21 (2H, m), 7.27-7.43 (2H, m), 7.50 and 7.59 (total 1H, each s).

Example 222

(E)-1-[2-Cyclopropyl-1-(2-fluorophenyl)-2-oxoethyl]-3-({1-[4-(N-methoxycarbamoyl)butyl]-1H-1,2,3-triazol-4-yl}methylidene)-4-sulfanylpiperidine hydrochloride (Exemplification Compound No. 2-1693)

To a solution of (E)-4-(acetylsulfanyl)-1-[2-cyclopropyl-1-(2-fluorophenyl)-2-oxoethyl]-3-({1-[4-(N-methoxycarbamoyl)butyl]-1H-1,2,3-triazol-4-yl}methylidene)piperidine (154 mg) in methanol (4 ml) was added potassium carbonate (157 mg) at 0° C. The resulting mixture was stirred at room temperature for 30 minutes, and partitioned between ethyl acetate and water. The separated organic layer was washed with a saturated aqueous sodium chloride solution, and dried over anhydrous sodium sulfate. The solvent was removed in vacuo, and the residue was purified by chromatography on silica gel using a mixture of methanol and dichloromethane (1:99 to 5:95) as the eluent to afford the free base of title compound (89.4 mg, yield: 63%).

To a solution of the free base as above in acetonitrile (3 ml) was added 4 N HCl in dioxane. Removal of the solvent and excess hydrogen chloride in vacuo gave the title compound as a colourless amorphous solid (97.7 mg).

$^1$H NMR (400 MHz, CDCl$_3$) δ ppm: 0.68-1.05 (4H, m), 1.63-1.84 (3H, m), 1.88-2.38 (6H, m), 2.41-2.93 (2H, m), 3.49-3.68 (2H, m), 3.74 (3H, s), 3.87-3.95 (1H, m), 4.29-4.41 (2H, m), 4.81 (1H, s), 6.58 (1H, s), 7.06-7.21 (2H, m), 7.29-7.44 (2H, m), 7.53 and 7.62 (total 1H, each s);

IR (KBr, cm$^{-1}$): 2625, 1712, 1494.

Example 223

(E)-1-[2-Cyclopropyl-1-(2-fluorophenyl)-2-oxoethyl]-3-({1-[4-(N-hydroxycarbamoyl)butyl]-1H-1,2,3-triazol-4-yl}methylidene)-4-sulfanylpiperidine hydrochloride (Exemplification Compound No. 2-1205)

(a) (E)-4-(Acetylsulfanyl)-3-({1-[4-(N-t-butyldimethylsilyloxy)carbamoyl)butyl]-1H-1,2,3-triazol-4-yl}methylidene)-1-[2-cyclopropyl-1-(2-fluorophenyl)-2-oxoethyl]piperidine In a similar manner to that described below in Example 262, (E)-4-(acetylsulfanyl)-3-{[1-(4-carboxybutyl)-1H-1,2,3-triazol-4-yl]methylidene}-1-[2-cyclopropyl-1-(2-fluorophenyl)-2-oxoethyl]piperidine (190 mg) as the starting material was allowed to react with O-(t-butyldimethylsilyl) hydroxylamine (71.7 mg). The crude product obtained by the extraction using conventional procedures was purified by chromatography on silica gel using a mixture of ethyl acetate and dichloromethane (1:9 to 6:4) as the eluent to afford the title compound as a colourless amorphous solid (148 mg, yield: 62%).

$^1$H NMR (400 MHz, CDCl$_3$) δ ppm: 0.18 (6H, s), 0.67-1.05 (13H, m), 1.60-1.71 (2H, m), 1.81-2.35 (10H, s), 2.41-2.84 (2H, m), 3.06-3.28 (1H, m), 3.81-4.02 (1H, m), 4.31 and 4.34 (total 2H, each t, J=6.5), 4.47 and 4.49 (total 1H, each t, J=4.5), 4.76 and 4.79 (total 1H, each s), 6.57 and 6.58 (total 1H, each s), 7.05-7.21 (2H, m), 7.29-7.43 (2H, m), 7.48 and 7.57 (total 1H, each s).

(b) (E)-1-[2-Cyclopropyl-1-(2-fluorophenyl)-2-oxoethyl]-3-({1-[4-(N-hydroxycarbamoyl)butyl]-1H-1,2,3-triazol-4-yl}methylidene)-4-sulfanylpiperidine hydrochloride To a solution of (E)-4-(acetylsulfanyl)-3-[(1-{4-[N-(t-butyldimethylsilyloxy)carbamoyl]butyl}-1H-1,2,3-triazol-4-yl)methylidene]-1-[2-cyclopropyl-1-(2-fluorophenyl)-2-oxoethyl]piperidine (148 mg) in dichloromethane (3 ml) was added 4N solution of hydrogen chloride in dioxane (230 µl) at 0° C. The resulting mixture was stirred at room temperature for 15 minutes. The solvent and excess hydrogen chloride were removed in vacuo, and the residue was purified by chromatography on silica gel using a mixture of methanol and dichloromethane (3:97 to 15:85) as the eluent to afford (E)-4-(acetylsulfanyl)-1-[2-cyclopropyl-1-(2-fluorophenyl)-2-oxoethyl]-3-({1-[4-(N-hydroxycarbamoyl)butyl]-1H-1,2,3-triazol-4-yl}methylidene)piperidine hydrochloride (110 mg).

To a solution of the compound mentioned above in methanol (2 ml) was added potassium carbonate (103 mg) at 0° C. The resulting mixture was stirred at room temperature for 0.5 hour, to which was added 4N solution of hydrogen chloride in dioxane (0.39 ml). The solvent was evaporated in vacuo and the residue was purified by chromatography on silica gel using a mixture of methanol and dichloromethane (3:97 to 25:75) as the eluent, followed by preparative HPLC (YMC-Pack ODS-A; YMC, eluent: acetonitrile/0.024 N HCl, 22/78, v/v) to afford the title compound as a colourless amorphous solid (39.6 mg, yield: 26%).

$^1$H NMR (400 MHz, pyridine-$d_5$) δ ppm: 0.64-0.78 (2H, m), 0.93-1.19 (2H, m), 1.75-2.02 (5H, m), 2.24-2.48 (4H, m), 2.62-2.80 (2H, m), 2.83-3.10 (1H, m), 3.98-4.11 (2H, m), 4.24-4.37 (2H, m), 5.01 (1H, s), 6.80 and 6.84 (total 1H, each s), 7.23-7.40 (2H, m), 7.53-7.88 (3H, m);

IR (KBr, cm$^{-1}$): 2562, 1711, 1494.

Example 224

(E)-4-(Acetylsulfanyl)-1-[2-cyclopropyl-1-(2-fluorophenyl)-2-oxoethyl]-3-({1-[4-(ethoxycarbonyl)butyl]-1H-1,2,3-triazol-5-yl}methylidene)piperidine (Exemplification Compound No. 2-1254)

(a) (E)-3-({1-[4-(Ethoxycarbonyl)butyl]-1H-1,2,3-triazol-5-yl}methylidene)-1-(triphenylmethyl)piperidin-4-ol Using (E)-3-({1-[4-(ethoxycarbonyl)butyl]-1H-1,2,3-triazol-5-yl}methylidene)-1-(triphenylmethyl)piperidin-4-one (Example 217(b), 4.87 g) as the starting material, a similar reaction to that mentioned in Example 217(c) gave the title compound (4.91 g, yield: quantitative) as a colourless amorphous solid.

$^1$H NMR (400 MHz, CDCl$_3$) δ ppm: 1.26 (3H, t, J=7.5), 1.71-2.08 (6H, m), 2.12-2.47 (5H, m), 2.93-3.06 (1H, m), 3.69-3.85 (1H, m), 4.06-4.21 (2H, m), 4.29-4.49 (2H, m), 6.42 (1H, s), 7.08-7.45 (16H, m).

(b) (E)-4-(Acetylsulfanyl)-3-({1-[4-(ethoxycarbonyl)butyl]-1H-1,2,3-triazol-5-yl}methylidene)piperidine hydrogen trifluoroacetate Using (E)-3-({1-[4-(ethoxycarbonyl)butyl]-1H-1,2,3-triazol-5-yl}methylidene)-1-(triphenylmethyl)piperidin-4-ol (4.91 g) as the starting material, a similar reaction to that mentioned in Example 217(d) gave the title compound (1.62 g, yield: 31%) as a pale brown oil.

$^1$H NMR (400 MHz, CDCl$_3$) δ ppm: 1.24 (3H, t, J=7.0), 1.44-1.59 (2H, m), 1.86-1.94 (2H, m), 2.12-2.24 (1H, m), 2.34 (2H, t, J=7.5), 2.41 (3H, s), 2.45-2.59 (1H, m), 3.23-3.36 (1H, m), 3.48-3.59 (1H, m), 3.93 (1H, d, J=14.5), 4.10 (2H, q, J=7.0), 4.17-4.48 (3H, m), 4.65 (1H, bs), 6.68 (1H, s), 7.88 (1H, s).

(c) (E)-4-(Acetylsulfanyl)-1-[2-cyclopropyl-1-(2-fluorophenyl)-2-oxoethyl]-3-({1-[4-(ethoxycarbonyl)butyl]-1H-1,2,3-triazol-5-yl}methylidene)piperidine Using (E)-4-(acetylsulfanyl)-3-({1-[4-(ethoxycarbonyl)butyl]-1H-1,2,3-triazol-5-yl}methylidene)piperidine hydrogen trifluoroacetate (1.62 g) as the starting material, a similar process to that mentioned in Example 217(e) gave the title compound (1.00 g, yield: 55%) as a colourless oil.

$^1$H NMR (400 MHz, CDCl$_3$) δ ppm: 0.69-0.87 (2H, m), 0.96-1.06 (2H, m), 1.26 (3H, t, J=7.5), 1.57-1.70 (2H, m), 1.81-2.06 (3H, m), 2.21-2.38 (7H, m), 2.43-2.61 (1H, m), 2.74-2.93 (1H, m), 2.91 and 3.18 (total 1H, each d, J=13.0), 3.49-3.59 (1H, m), 4.06-4.30 (4H, m), 4.49 (1H, bs), 4.75 (1H, s), 6.33 (1H, s), 7.06-7.22 (2H, m), 7.25-7.40 (2H, m), 7.41 and 7.48 (total 1H, each s).

Example 225

(E)-1-[2-Cyclopropyl-1-(2-fluorophenyl)-2-oxoethyl]-3-({1-[4-(ethoxycarbonyl)butyl]-1H-1,2,3-triazol-5-yl}methylidene)-4-sulfanylpiperidine hydrochloride (Exemplification Compound No. 2-1253)

Using (E)-4-(acetylsulfanyl)-1-[2-cyclopropyl-1-(2-fluorophenyl)-2-oxoethyl]-3-({1-[4-(ethoxycarbonyl)butyl]-1H-1,2,3-triazol-5-yl}methylidene)piperidine (1.00 g) as the starting material, a similar process to that mentioned in Example 218 gave the title compound (884 mg, yield: 89%) as a pale yellow amorphous solid.

$^1$H NMR (400 MHz, CDCl$_3$) δ ppm: 0.69-0.86 (2H, m), 0.93-1.06 (2H, m), 1.25 (3H, t, J=7.0), 1.59-1.70 (2H, m), 1.78-2.05 (4H, m), 2.24-2.39 (3H, m), 2.61-2.71 (1H, m), 2.82-2.94 (1H, m), 3.16 and 3.25 (total 1H, each d, J=13.0), 3.43 and 3.58 (total 1H, each d, J=13.0), 3.80-3.88 (1H, m), 4.13 (2H, q, J=7.0), 4.24-4.34 (2H, m), 4.76 (1H, s), 6.32 and 6.34 (total 1H, each s), 7.05-7.21 (2H, m), 7.23-7.38 (2H, m), 7.40 and 7.47 (total 1H, each s).

Example 226

(E)-3-{[1-(4-Carboxybutyl)-1H-1,2,3-triazol-5-yl]methylidene}-1-[2-cyclopropyl-1-(2-fluorophenyl)-2-oxoethyl]-4-sulfanylpiperidine hydrochloride (Exemplification Compound No. 2-1221)

Using (E)-1-[2-cyclopropyl-1-(2-fluorophenyl)-2-oxoethyl]-3-({1-[4-(ethoxycarbonyl)butyl]-1H-1,2,3-triazol-5-yl}methylidene)-4-sulfanylpiperidine hydrochloride (874 mg) as the starting material, a similar process to that mentioned in Example 219 gave the title compound (640 mg, yield: 77%) as a colourless amorphous solid.

$^1$H NMR (400 MHz, pyridine-$d_5$) δ ppm: 0.62-0.77 (2H, m), 0.94-1.09 (2H, m), 1.69-2.07 (5H, m), 2.25-2.56 (4H, m), 2.65-3.05 (2H, m), 3.58 (1H, d, J=12.0), 3.77 and 3.84 (total 1H, each d, J=12.0), 4.02-4.11 (1H, m), 4.42 (2H, t, J=7.5), 4.98 (1H, s), 6.68 and 6.69 (total 1H, each s), 7.15-7.37 (2H, m), 7.55-7.70 (2H, m), 7.90 and 7.96 (total 1H, each s);

IR (KBr, cm$^{-1}$): 2530, 1712, 1494.

Example 227

(E)-4-(Acetylsulfanyl)-3-{[1-(4-carboxybutyl)-1H-1,2,3-triazol-5-yl]methylidene}-1-[2-cyclopropyl-1-(2-fluorophenyl)-2-oxoethyl]piperidine (Exemplification Compound No. 2-1222)

Using (E)-3-{[1-(4-carboxybutyl)-1H-1,2,3-triazol-5-yl]methylidene}-1-[2-cyclopropyl-1-(2-fluorophenyl)-2-oxoethyl]-4-sulfanylpiperidine hydrochloride (509 mg) as the starting material, a similar process to that mentioned in Example 220 gave the title compound (233 mg, yield: quantitative) as a colourless oil.

$^1$H NMR (400 MHz, CDCl$_3$) δ ppm: 0.68-0.88 (2H, m), 0.97-1.05 (2H, m), 1.45-1.71 (2H, m), 1.74-2.12 (3H, m), 2.18-2.42 (7H, m), 2.66-2.88 (1H, m), 3.00-3.47 (2H, m), 3.69 (1H, d, J=13.0), 4.24-4.54 (3H, m), 4.83 (1H, s), 6.33 and 6.35 (total 1H, each s), 7.12-7.47 (5H, m).

Example 228

(E)-4-(Acetylsulfanyl)-1-[2-cyclopropyl-1-(2-fluorophenyl)-2-oxoethyl]-3-({1-[4-(N-methoxycarbamoyl)butyl]-1H-1,2,3-triazol-5-yl}methylidene)piperidine (Exemplification Compound No. 2-1722)

Using (E)-4-(acetylsulfanyl)-3-{[1-(4-carboxybutyl)-1H-1,2,3-triazol-5-yl]methylidene}-1-[2-cyclopropyl-1-(2-fluorophenyl)-2-oxoethyl]piperidine (233 mg) as the starting material, a similar process to that mentioned in Example 221 gave the title compound (172 mg, yield: 80%) as a colourless oil.

$^1$H NMR (400 MHz, CDCl$_3$) δ ppm: 0.68-1.06 (4H, m), 1.59-1.72 (2H, m), 1.81-2.13 (3H, m), 2.19-2.39 (7H, m), 2.44-2.61 (1H, m), 2.71-3.25 (2H, m), 3.42-3.60 (1H, m), 3.74 (3H, s), 4.21-4.34 (2H, m), 4.42-4.53 (1H, m), 4.76 and 4.77 (total 1H, each s), 6.33 (1H, s), 7.07-7.49 (5H, m).

Example 229

(E)-1-[2-Cyclopropyl-1-(2-fluorophenyl)-2-oxoethyl]-3-({1-[4-(N-methoxycarbamoyl)butyl]-1H-1,2,3-triazol-5-yl}methylidene)-4-sulfanylpiperidine hydrochloride (Exemplification Compound No. 2-1721)

Using (E)-4-(acetylsulfanyl)-1-[2-cyclopropyl-1-(2-fluorophenyl)-2-oxoethyl]-3-({1-[4-(N-methoxycarbamoyl)butyl]-1H-1,2,3-triazol-5-yl}methylidene)piperidine (172 mg) as the starting material, a similar process to that described for example 222 gave the title compound (44 mg, yield: 26%) as a colourless amorphous solid.

$^1$H NMR (400 MHz, CDCl$_3$) δ ppm: 0.67-0.90 (2H, m), 0.92-1.04 (2H, m), 1.56-2.14 (8H, m), 2.23-2.38 (1H, m), 2.57-2.72 (1H, m), 2.79-2.95 (1H, m), 3.03-3.63 (2H, m), 3.74 (3H, s), 3.79-3.92 (1H, m), 4.23-4.38 (2H, m), 4.77 and 4.78 (total 1H, each s), 6.32 and 6.35 (total 1H, each s), 7.08-7.47 (5H, m);

IR (KBr, cm$^{-1}$): 2522, 1711, 1494.

Example 230

(E)-1-[2-Cyclopropyl-1-(2-fluorophenyl)-2-oxoethyl]-3-({1-[4-(N-hydroxycarbamoyl)butyl]-1H-1,2,3-triazol-5-yl}methylidene)-4-sulfanylpiperidine hydrochloride (Exemplification Compound No. 2-1269)

(a) (E)-4-(Acetylsulfanyl)-3-({1-[4-(N-t-butyldimethylsilyloxy)carbamoyl)butyl]-1H-1,2,3-triazol-5-yl}methylidene)-1-[2-cyclopropyl-1-(2-fluorophenyl)-2-oxoethyl]piperidine Using (E)-4-(acetylsulfanyl)-3-{[1-(4-carboxybutyl)-1H-1,2,3-triazol-5-yl]methylidene}-1-[2-cyclopropyl-1-(2-fluorophenyl)-2-oxoethyl]piperidine (291 mg) as the starting material, a similar process to that mentioned in Example 223 (a) gave the title compound (336 mg, yield: 92%) as a colourless oil.

$^1$H NMR (400 MHz, CDCl$_3$) δ ppm: 0.18 (6H, s), 0.70-1.07 (13H, m), 1.57-1.71 (2H, m), 1.82-2.16 (6H, m), 2.18-2.39 (4H, m), 2.41-2.61 (1H, m), 2.72-3.23 (2H, m), 3.44-3.57 (1H, m), 4.18-4.33 (2H, m), 4.42-4.51 (1H, m), 4.75 and 4.76 (total 1H, each s), 6.32 (1H, s), 7.06-7.50 (5H, m).

(b) (E)-1-[2-Cyclopropyl-1-(2-fluorophenyl)-2-oxoethyl]-3-({1-[4-(N-hydroxycarbamoyl)butyl]-1H-1,2,3-triazol-5-yl}methylidene)-4-sulfanylpiperidine hydrochloride Using (E)-4-(acetylsulfanyl)-3-({1-[4-(N-t-butyldimethylsilyloxy)carbamoyl)butyl]-1H-1,2,3-triazol-5-yl}methylidene)-1-[2-cyclopropyl-1-(2-fluorophenyl)-2-oxoethyl]piperidine (336 mg) as the starting material, a similar process to that described in Example 223(b) gave, via (E)-4-(acetylsulfanyl)-1-[2-cyclopropyl-1-(2-fluorophenyl)-2-oxoethyl]-3-({1-[4-(N-hydroxycarbamoyl)butyl]-1H-1,2,3-triazol-5-yl}methylidene)piperidine hydrochloride, the title compound (66 mg, yield: 24%) as a colourless amorphous solid.

$^1$H NMR (400 MHz, pyridine-d$_5$) δ ppm: 0.63-0.80 (2H, m), 0.93-1.10 (2H, m), 1.78-2.05 (5H, m), 2.24-2.48 (4H, m), 2.66-3.07 (2H, m), 3.60 (1H, d, J=12.5), 3.74 and 3.83 (total 1H, each d, J=12.5), 4.09 (1H, bs), 4.34-4.45 (2H, m), 4.98 (1H, m), 6.66 (1H, s), 7.16-7.37 (3H, m), 7.57-7.68 (1H, m), 7.88 and 7.94 (total 1H, each s);

IR (KBr, cm$^{-1}$): 2661, 1711, 1494.

Example 231

(Z)-4-(Acetylsulfanyl)-1-[2-cyclopropyl-1-(2-fluorophenyl)-2-oxoethyl]-3-({1-[2-(methoxycarbonyl)ethyl]-1H-1,2,3-triazol-5-yl}methylidene)piperidine hydrochloride (Exemplification Compound No. 4-148)

(a) (Z)-4-(Acetylsulfanyl)-3-({1-[2-(methoxycarbonyl)ethyl]-1H-1,2,3-triazol-5-yl}methylidene)piperidine hydrogen trifluoroacetate salt and its (E)-isomer To a solution of 5-(acetylsulfanyl){1-[2-(methoxycarbonyl)ethyl]-1H-1,2,3-triazol-5-yl}methyl)-1-(triphenylmethyl)-1,2,3,6-tetrahydropyridine [Example 132(d), 8.15 g] in dimethyl sulfoxide (100 ml), potassium thioacetate (16.5 g) was added. The resulting mixture was stirred at 80° C. for 4 hours, cooled to room temperature, and partitioned between water and ethyl acetate. The separated organic layer was washed with a saturated aqueous sodium chloride solution, dried over anhydrous sodium sulfate The solvent was removed in vacuo, and the residue was purified by chromatography on silica gel using a mixture of hexane, ethyl acetate and dichloromethane (1:1:1) as the eluent to afford a mixture of (Z)-4-(acetylsulfanyl)-3-({1-[2-(methoxycarbonyl)ethyl]-1H-1,2,3-triazol-5-yl}methylidene)-1-(triphenylmethyl)piperidine and its (E)-isomer, the isomeric ratio being approximately 1:1 (6.65 g, yield: 81.6%).

A portion of the above mixture (6.43 g) was treated with trifluoroacetic acid in a similar manner to that described in Example 132 (f). The residue obtained by the concentration was purified by chromatography on silica gel using a mixture of dichloromethane and methanol (10:1) as the eluent. Then, the isomeric mixture obtained was separated by preparative HPLC (YMC-Pack ODS-A; YMC, eluent: acetonitrile/0.026 N aqueous trifluoroacetic acid, 20/80, v/v) to afford the two title isomers, both as a yellow amorphous solid.

More mobile isomer: (E)-4-(Acetylsulfanyl)-3-({1-[2-(methoxycarbonyl)ethyl]-1H-1,2,3-triazol-5-yl}methylidene)piperidine hydrogen trifluoroacetate: 1.5 g, yield: 30%. $^1$H NMR: Identical with that described in Example 132 (f).

Less mobile isomer: (Z)-4-(Acetylsulfanyl)-3-({1-[2-(methoxycarbonyl)ethyl]-1H-1,2,3-triazol-5-yl}methylidene)piperidine hydrogen trifluoroacetate: 1.2 g, yield: 24%. $^1$H NMR (400 MHz, CDCl$_3$) δ ppm: 2.02-2.13 (1H, m), 2.32-2.47 (1H, m), 2.40 (3H, s), 2.96-3.10 (2H, m), 3.27-3.45 (1H, m), 3.54 (1H, d, J=13.0), 3.64 (3H, s), 3.82-3.92 (1H, m), 4.07 (1H, d, J=14.0), 4.46-4.61 (2H, m), 4.76-4.80 (1H, m), 6.59 (1H, s), 7.82 (1H, s).

(b) (Z)-4-(Acetylsulfanyl)-1-[2-cyclopropyl-1-(2-fluorophenyl)-2-oxoethyl]-3-({1-[2-(methoxycarbonyl)ethyl]-1H-1,2,3-triazol-5-yl}methylidene)piperidine hydrochloride Using (Z)-4-(acetylsulfanyl)-3-({1-[2-(methoxycarbonyl)ethyl]-1H-1,2,3-triazol-5-yl}methylidene)piperidine hydrogen trifluoroacetate (1.2 g) as the starting material, a similar process to that mentioned in Example 132(g) gave the title compound (820 mg, yield: 56%) as a pale yellow amorphous solid.

$^1$H NMR (400 MHz, CDCl$_3$) δ ppm: 0.71-0.94 (2H, m), 0.97-1.10 (2H, m), 1.70-1.87 (1H, m), 2.01-2.32 (2H, m), 2.29 and 2.30 (total 3H, each s), 2.29-2.41 and 2.51-2.63 (total 1H, each m), 2.72-2.86 (1H, m), 2.88-3.12 (3H, m), 3.41 and 3.50 (total 1H, each d, J=13.5), 3.67 and 3.69 (total 3H, each s), 4.42-4.59 (2H, m), 4.72-4.81 (1H, m), 4.76 and 4.79 (total 1H, each s), 6.10 and 6.18 (total 1H, each s), 7.08-7.24 (2H, m), 7.29-7.40 (2H, m), 7.57 and 7.58 (total 1H, each s);

IR (KBr, cm$^{-1}$): 2954, 2496, 1737, 1698.

Example 232

(Z)-1-[2-Cyclopropyl-1-(2-fluorophenyl)-2-oxoethyl]-3-({1-[2-(ethoxycarbonyl)ethyl]-1H-1,2,3-triazol-5-yl}methylidene)-4-sulfanylpiperidine hydrochloride (Exemplification Compound No. 4-147)

Using (Z)-4-(acetylsulfanyl)-1-[2-cyclopropyl-1-(2-fluorophenyl)-2-oxoethyl]-3-({1-[2-(methoxycarbonyl)ethyl]-1H-1,2,3-triazol-5-yl}methylidene)piperidine hydrochloride (760 mg) as the starting material, a similar process to that mentioned in Example 133 gave the title compound (540 mg, yield: 75%) as a colourless amorphous solid.

$^1$H NMR (400 MHz, CDCl$_3$) δ ppm: 0.73-0.95 (2H, m), 0.96-1.12 (2H, m), 1.22 and 1.24 (total 3H, each t, J=7.5), 1.62-1.82 (1H, m), 1.99-2.33 (2H, m), 2.53-3.13 (4H, m), 3.24 and 3.29 (total 1H, each d, J=13.0), 3.38 and 3.44 (total 1H, each d, J=13.0), 4.06-4.18 (2H, m), 4.23-4.29 (1H, m), 4.40-4.60 (2H, m), 4.82 and 4.84 (total 1H, each s), 6.00 and 6.08 (total 1H, each s), 7.09-7.23 (2H, m), 7.30-7.40 (2H, m), 7.79 and 7.83 (total 1H, each s).

IR (KBr, cm$^{-1}$): 2978, 2447, 1730.

Example 233

(Z)-3-{[1-(4-Carboxyethyl)-1H-1,2,3-triazol-5-yl]methylidene}-1-[2-cyclopropyl-1-(2-fluorophenyl)-2-oxoethyl]-4-sulfanylpiperidine hydrochloride (Exemplification Compound No. 4-139)

Using (Z)-1-[2-cyclopropyl-1-(2-fluorophenyl)-2-oxoethyl]-3-({1-[2-(ethoxycarbonyl)ethyl]-1H-1,2,3-triazol-5-yl}methylidene)-4-sulfanylpiperidine hydrochloride (420 mg) as the starting material, a similar process to that mentioned in Example 134 gave the title compound (230 mg, yield: 58%) as a colourless amorphous solid.

$^1$H NMR (400 MHz, pyridine-d$_5$) δ ppm: 0.69-0.92 (2H, m), 0.95-1.17 (2H, m), 1.64-1.83 (1H, m), 2.16-2.37 (1H, m), 2.37-2.52 (1H, m), 2.70-3.08 (2H, m), 3.16-3.39 (2H, m), 3.52 (1H, s), 3.63 (1H, s), 4.48-4.56 (1H, m), 4.68-4.87 (2H, m), 4.96 and 5.00 (total 1H, each s), 6.46 and 6.52 (total 1H, each s), 7.13-7.34 (3H, m), 7.61-7.70 (1H, m), 8.28 and 8.30 (total 1H, each s).

IR (KBr, cm$^{-1}$): 2926, 2549, 1711.

Example 234

(E)-4-(Acetylsulfanyl)-1-[2-cyclopropyl-1-(2-fluorophenyl)-2-oxoethyl]-3-{[1(2)H-1,2,3-triazol-4(5)-yl]methylidene}piperidine (Exemplification Compound No. 1-50)

(a) 1-(4-Methoxybenzyl)-1H-1,2,3-triazole-4-carbaldehyde

To tetrahydrofuran (THF, 500 ml) was added carefully lithium aluminium hydride (7.3 g) with stirring. The resulting mixture was stirred at 0° C., to which was added dropwise a solution of ethyl 1-(4-methoxybenzyl)-1H-1,2,3-triazole-4-carboxylate (50.0 g) in THF (500 ml). The resulting mixture was stirred at room temperature for 30 minutes, and the reaction was stopped by careful addition of sodium sulfate decahydrate. The slurry mixture was stirred at room temperature for 2 hours further, filtered to remove solids, and the filtrate was concentrated in vacuo to afford [1-(4-methoxybenzyl)-1H-1,2,3-triazol-4-yl]methanol (39.51 g, yield: 94%).

To a solution of the above compound in dichloromethane (600 ml) was added molecular sieves 4A (80.0 g) and pyridinium dichromate (80.0 g). The resulting mixture was stirred at room temperature for 50 minutes, filtrated to remove solids, and the filtrate was concentrated in vacuo. The residue was purified by chromatography on silica gel using a mixture of hexane, ethyl acetate and dichloromethane (1:1:1) as the eluent to afford the title compound as a colourless oil (12.35 g, yield: 32%).

$^1$H NMR (400 MHz, CDCl$_3$) δ ppm: 3.81 (3H, s), 5.52 (2H, s), 6.92 (2H, d, J=9.0), 7.27 (2H, d, J=9.0), 7.96 (1H, s), 10.11 (1H, s).

(b) (E)-3-{[1-(4-Methoxybenzyl)-1H-1,2,3-triazol-4-yl]methylidene}-1-(triphenylmethyl)piperidin-4-one To a solution of 1-(triphenylmethyl)piperidin-4-one (19.4 g) in benzene (500 ml) was added pyrrolidine (4.7 ml). The resulting mixture was heated under reflux for 3 hours removing water using a Dean-Staak apparatus. The reaction mixture was cooled to room temperature, and 1-(4-methoxybenzyl)-1H-1,2,3-triazole-4-carbaldehyde (12.35 g) was added thereto. The resulting mixture was heated under reflux for 7 hours, cooled, diluted with water, and products were extracted with ethyl acetate. The organic layer was washed with a saturated aqueous sodium chloride solution, and dried over anhydrous sodium sulfate. The solvent was evaporated in vacuo, and the residue was purified by chromatography on silica gel using a mixture of hexane, ethyl acetate and dichloromethane (2:1:1) as the eluent to afford the title compound as a yellow amorphous solid (17.64 g, yield: 57%).

$^1$H NMR (400 MHz, CDCl$_3$) δ ppm: 2.66 (2H, bs), 2.75 (2H, t, J=5.5), 3.45 (2H, bs), 3.86 (3H, s), 5.41 (2H, s), 6.91 (2H, d, J=8.5), 7.10-7.30 (15H, m), 7.44-7.55 (4H, m).

(c) (E)-3-{[1-(4-Methoxybenzyl)-1H-1,2,3-triazol-4-yl]methylidene}-1-(triphenylmethyl)piperidin-4-ol Using (E)-3-{[1-(4-methoxybenzyl)-1H-1,2,3-triazol-4-yl]methylidene}-1-(triphenylmethyl)piperidin-4-one (17.64 g) as the starting material, a similar process to that mentioned in Example 132(d) gave the title compound (17.45 g, yield: quantitative) as a pale yellow amorphous solid.

$^1$H NMR (400 MHz, CDCl$_3$) δ ppm: 1.96-2.33 (3H, m), 2.61 (1H, bs), 2.89 (1H, bs), 3.65 (1H, bs), 3.95 (3H, s), 4.27 (1H, bs), 5.45 (2H, d, J=15.0), 6.75 (1H, s), 7.00 (2H, d, J=8.5), 7.10 (1H, s), 7.19 (2H, d, J=8.5), 7.21-7.30 (8H, m), 7.46-7.53 (7H, m).

(d) (E)-4-(Acetylsulfanyl)-3-{[1-(4-methoxybenzyl)-1H-1,2,3-triazol-4-yl]methylidene}piperidine hydrogen trifluoroacetate and its (Z)-isomer To a solution of (E)-3-{[1-(4-methoxybenzyl)-1H-1,2,3-triazol-4-yl]methylidene}-1-(triphenylmethyl)piperidin-4-ol (17.45 g) in toluene (300 ml) were added thioacetic acid (4.6 ml) and N,N-dimethylformamide dineopentylacetal (18 ml). The resulting solution was stirred at room temperature for 15 minutes, and the reaction was stopped by an addition of a saturated aqueous sodium chloride solution. The products were extracted with ethyl acetate, and the extract was dried over anhydrous sodium sulfate and concentrated in vacuo. The residue was purified by chromatography on silica gel using a mixture of hexane, ethyl acetate and dichloromethane (1:1:1) as the eluent to afford an approximately 1:3 mixture of (E)-4-(acetylsulfanyl)-3-{[1-(4-methoxybenzyl)-1H-1,2,3-triazol-4-yl]methylidene}-1-(triphenylmethyl)piperidine and 5-(acetylsulfanyl){[1-(4-methoxybenzyl)-1H-1,2,3-triazol-4-yl]methylidene}methyl)-1-(triphenylmethyl)-1,2,3,6-tetrahydropyridine (17.83 g, yield: 92%).

To a solution of the whole amount of above mixture in dimethyl sulfoxide (200 ml) was added potassium thioacetate (25 g). The resulting mixture was stirred at 80° C. for 4 hours, cooled to room temperature, and the reaction was stopped by addition of water. The products were extracted with ethyl acetate. The organic layer was washed with a saturated aqueous sodium chloride solution and dried over anhydrous sodium sulfate. Solvents were evaporated in vacuo, and the residue was purified by chromatography on silica gel using a mixture of hexane, ethyl acetate and dichloromethane (1:1:1) as the eluent to afford an approximately 2:1 mixture of (E)-4-(acetylsulfanyl)-3-{[1-(4-methoxybenzyl)-1H-1,2,3-triazol-4-yl]methylidene}-1-(triphenylmethyl)piperidine and its (Z)-isomer (19.3 g).

To a solution of a portion of the above mixture (17.83 g) in dichloromethane (400 ml) was added trifluoroacetic acid (6.0 ml). The resulting mixture was stirred at room temperature for 15 minutes, and concentrated in vacuo. The residue was purified by chromatography on silica gel using a mixture of dichloromethane and methanol (10:1) as the eluent to afford (E)-4-(acetylsulfanyl)-3-{[1-(4-methoxybenzyl)-1H-1,2,3-triazol-4-yl]methylidene}piperidine hydrogen trifluoroacetate (6.03 g, yield: 43%) as the less polar isomer and (Z)-4-(acetylsulfanyl)-3-{[1-(4-methoxybenzyl)-1H-1,2,3-triazol-4-yl]methylidene}piperidine hydrogen trifluoroacetate (3.86 g, yield: 28%) as the more polar one, both as yellow amorphous solids.

Less polar isomer (E)-4-acetylsulfanyl)-3-{[1-(4-methoxybenzyl)-1H-1,2,3-triazol-4-yl]methylidene}piperidine hydrogen trifluoroacetate: $^1$H NMR (400 MHz, DMSO-d$_6$) δ ppm: 1.89-2.01 (1H, m), 2.17-2.31 (1H, m), 2.37 (3H, s), 3.06-3.19 (1H, m), 3.27-3.41 (1H, m), 3.72 (3H, s), 4.01 (1H, d, J=14.0), 4.54 (1H, t, J=4.5), 4.81 (1H, d, J=14.0), 5.52 (2H, s), 6.67 (1H, s), 6.92 (2H, d, J=8.5), 7.27 (2H, d, J=8.5), 8.28 (1H, s).

More polar isomer (Z)-4-(acetylsulfanyl)-3-{[1-(4-methoxybenzyl)-1H-1,2,3-triazol-4-yl]methylidene}piperidine hydrogen trifluoroacetate: $^1$H NMR (400 MHz, DMSO-d$_6$) δ ppm: 1.88-1.98 (1H, m), 2.10-2.13 (1H, m), 2.34 (3H, s), 3.07-3.21 (1H, m), 3.26-3.40 (1H, m), 3.61 (1H, d, J=14.0), 3.73 (3H, s), 3.90 (1H, d, J=14.0), 5.52 (2H, s), 5.62 (1H, bs), 6.57 (1H, s), 6.93 (2H, d, J=8.5), 7.29 (2H, d, J=8.5), 8.12 (1H, s).

(e) (E)-4-(Acetylsulfanyl)-1-[2-cyclopropyl-1-(2-fluorophenyl)-2-oxoethyl]-3-{[1-(4-methoxybenzyl)-1H-1,2,3-triazol-4-yl]methylidene}piperidine To a solution of (E)-4-(acetylsulfanyl)-3-{[1-(4-methoxybenzyl)-1H-1,2,3-triazol-4-yl]methylidene}piperidine hydrogen trifluoroacetate (6.03 g) in acetonitrile (100 ml) were added 2-bromo-2-(2-fluorophenyl)-1-cyclopropylethanone (5.0 g) and triethylamine (3.5 ml). The resulting mixture was stirred at room temperature for 15 minutes. Then, the reaction was stopped by addition of a saturated aqueous sodium chloride solution, and the products were extracted with ethyl acetate. The organic layer was washed with a saturated aqueous sodium chloride solution and dried over anhydrous sodium sulfate. The residue was purified by chromatography on silica gel using a mixture of hexane, ethyl acetate and dichloromethane (1:1:1) as the eluent to afford the title compound as a pale yellow amorphous solid (5.11 g, yield: 75%).

$^1$H NMR (400 MHz, CDCl$_3$) δ ppm: 0.62-1.04 (4H, m), 1.78-1.93 (1H, m), 2.05-2.15 (1H, m), 2.15-2.32 (1H, m), 2.30 (3H, s), 2.39-2.50 and 2.55-2.67 (total 1H, each m), 2.67-2.82 (1H, m), 3.09 and 3.20 (total 1H, each d, J=13.0), 3.81 (3H, s), 3.86 and 3.93 (total 1H, each d, J=13.0), 4.41-4.49 (1H, m), 4.72 and 4.76 (total 1H, each s), 5.36-5.48 (2H, m), 6.54 and 6.55 (total 1H, each s), 6.89 (2H, d, J=8.5), 7.03-7.40 (6H, m), 7.44 and 7.50 (total 1H, each s).

(f) (E)-4-(Acetylsulfanyl)-1-[2-cyclopropyl-1-(2-fluorophenyl)-2-oxoethyl]-3-{[1(2)H-1,2,3-triazol-4 (5)-yl}methylidene)piperidine To a solution of (E)-4-(acetylsulfanyl)-1-[2-cyclopropyl-1-(2-fluorophenyl)-2-oxoethyl]-3-{[1-(4-methoxybenzyl)-1H-1,2,3-triazol-4-yl]methylidene}piperidine (5.01 g) in trifluoroacetic acid (250 ml) was added anisole (50 ml). The resulting mixture was stirred at 80° C. for 2.5 days and cooled to room temperature, and the solvents were evaporated in vacuo. To the residue, a saturated aqueous sodium hydrogen carbonate solution was added, and the products were extracted with ethyl acetate. The organic layer was washed with a saturated aqueous sodium chloride solution and dried over anhydrous sodium sulfate. Solvents were evaporated in vacuo, and the residue was purified by chromatography on silica gel using a mixture of hexane and ethyl acetate (1:1) as the eluent to afford the title compound as a pale yellow amorphous solid (3.5 g, yield: 90%).

$^1$H NMR (400 MHz, CDCl$_3$) δ ppm: 0.65-0.90 (2H, m), 0.99-1.16 (2H, m), 1.81-1.93 (1H, m), 1.92-2.07 (1H, m), 2.15-2.36 (1H, m), 2.28 and 2.32 (total 3H, each s), 2.47-2.62 (1H, m), 2.64-2.88 (1H, m), 3.30 (1H, d, J=13.0), 4.39 (1H, bs), 4.47 (1H, t, J=4.5), 4.83 and 4.90 (total 1H, each s), 6.50 and 6.51 (1H, s), 7.07-7.19 (2H, m), 7.27-7.39 (2H, m), 7.54 and 7.58 (total 1H, each s).

Example 235

(E)-1-[2-Cyclopropyl-1-(2-fluorophenyl)-2-oxoethyl]-4-sulfanyl-3-{[1(2)H-1,2,3-triazol-4(5)-yl]methylidene}piperidine hydrochloride (Exemplification Compound No. 1-49)

To a solution of (E)-4-(acetylsulfanyl)-1-[2-cyclopropyl-1-(2-fluorophenyl)-2-oxoethyl]-3-{[1(2)H-1,2,3-triazol-4(5)-yl]methylidene}piperidine hydrochloride (HCl salt of the product in Example 234, 670 mg) in methanol (20 ml) was added potassium carbonate (620 mg). The resulting mixture was stirred at room temperature for 15 minutes, the reaction was stopped by the addition of water, and the products were extracted with ethyl acetate. The organic layer was washed with a saturated aqueous sodium chloride solution, dried over anhydrous sodium sulfate, and the solvent was evaporated in vacuo. The residue was purified by preparative HPLC (YMC-Pack ODS-A; YMC, eluent: acetonitrile/0.024 N HCl, 27/73, v/v) to afford the title compound as a colourless amorphous solid (510 mg, yield: 84%).

$^1$H NMR (400 MHz, pyridine-d$_5$) δ ppm: 0.57-0.77 (2H, m), 0.86-1.00 (1H, m), 1.01-1.14 (1H, m), 1.80-1.95 (1H, m), 2.23-2.50 (2H, m), 2.64-2.80 (1H, m), 2.84-3.06 (1H, m), 3.98-4.29 (3H, m), 4.97 and 4.99 (total 1H, each s), 6.86 and 6.88 (total 1H, each s), 7.09-7.31 (3H, m), 7.63-7.73 (1H, m), 7.93 and 7.99 (total 1H, each s);

IR (KBr, cm$^{-1}$): 2914, 2643, 1709.

Example 236

(Z)-4-(Acetylsulfanyl)-1-[2-cyclopropyl-1-(2-fluorophenyl)-2-oxoethyl]-3-{[1(2)H-1,2,3-triazol-4(5)-yl]methylidene}piperidine (Exemplification Compound No. 4-92)

(a) (Z)-4-(Acetylsulfanyl)-1-[2-cyclopropyl-1-(2-fluorophenyl)-2-oxoethyl]-3-{[1-(4-methoxybenzyl)-1H-1,2,3-triazol-4-yl]methylidene}piperidine Using (Z)-4-(acetylsulfanyl)-3-{[1-(4-methoxybenzyl)-1H-1,2,3-triazol-4-yl]methylidene}piperidine hydrogen trifluoroacetate [Example 234 (d), 3.86 g] as the starting material, a similar process to that mentioned in Example 234 (e) gave the title compound (3.01 g, yield: 69%) as a pale yellow amorphous solid.

$^1$H NMR (400 MHz, CDCl$_3$) δ ppm: 0.72-0.92 (2H, m), 0.91-1.09 (2H, m), 1.66-0.180 (1H, m), 2.11-2.34 (2H, m), 2.25 and 2.26 (total 3H, each s), 2.46-2.85 (2H, m), 2.94 (1H, d, J=12.0), 3.27 and 3.44 (total 1H, each d, J=12.0), 3.79 (3H, s), 4.62 and 4.66 (total 1H, each s), 5.03 (1H, bs), 5.35-5.51 (2H, m), 6.29 and 6.39 (total 1H, each s), 6.89 (2H, d, J=9.0), 7.04-7.21 (2H, m), 7.24 (2H, d, J=9.0), 7.27-7.35 (1H, m), 7.39-7.47 (2H, m).

(b) (Z)-4-(Acetylsulfanyl)-1-[2-cyclopropyl-1-(2-fluorophenyl)-2-oxoethyl]-3-{[1(2)H-1,2,3-triazol-4(5)-yl]methylidene}piperidine Using (Z)-4-(acetylsulfanyl)-1-[2-cyclopropyl-1-(2-fluorophenyl)-2-oxoethyl]-3-{[1-(4-methoxybenzyl)-1H-1,2,3-triazol-4-yl]methylidene}piperidine (3.01 g) as the starting material, a similar process to that mentioned in Example 234(f) gave the title compound (2.14 g, yield: 92%) as a pale yellow amorphous solid.

$^1$H NMR (400 MHz, CDCl$_3$) δ ppm: 0.73-0.94 (2H, m), 0.96-1.11 (2H, m), 1.72-1.89 (1H, m), 2.07-2.65 (3H, m), 2.33 (3H, s), 2.82 (1H, d, J=12.0), 3.02 (1H, d, J=12.0), 3.33 and 3.48 (1H, d, J=12.5), 4.73 and 4.77 (total 1H, each s), 5.22 (1H, bs), 6.26 and 6.35 (total 1H, each s), 7.08-7.24 (2H, m), 7.29-7.44 (2H, m), 7.63 and 7.64 (total 1H, each s);

IR (KBr, cm$^{-1}$): 2912, 2537, 1696.

Example 237

(Z)-1-[2-Cyclopropyl-1-(2-fluorophenyl)-2-oxoethyl]-3-([1(2)H-1,2,3-triazol-4(5)-yl]methylidene)-4-sulfanylpiperidine hydrochloride (Exemplification Compound No. 4-91)

Using (Z)-4-(acetylsulfanyl)-1-[2-cyclopropyl-1-(2-fluorophenyl)-2-oxoethyl]-3-{[1(2)H-1,2,3-triazol-4(5)-yl]methylidene}piperidine hydrochloride (HCl salt of the product in Example 236, 540 mg) as the starting material, a similar process to that mentioned in Example 235 gave the title compound (430 mg, yield: 88%) as a colourless amorphous solid.

$^1$H NMR (400 MHz, pyridine-d$_5$) δ ppm: 0.69-0.85 (2H, m), 0.94-1.17 (2H, m), 1.70-1.90 (1H, m), 2.18-2.44 (1H, m), 2.46-2.55 (1H, m), 2.70-3.08 (2H, m), 3.42 and 3.59 (total 1H, each d, J=12.5), 3.53 and 3.69 (total 1H, each d, J=12.5), 4.94 and 4.96 (total 1H, each s), 5.39-5.46 (1H, m), 6.39 and 6.50 (total 1H, each s), 7.17-7.35 (3H, m), 7.68-7.76 (1H, m), 8.12 and 8.16 (total 1H, each s);

IR (KBr, cm$^{-1}$): 2911, 2543, 1709.

Example 238

(Z)-4-(Acetylsulfanyl)-1-[2-cyclopropyl-1-(2-fluorophenyl)-2-oxoethyl]-3-{[2-(methoxycarbonylmethyl)-2H-1,2,3-triazol-4-yl]methylidene}piperidine (Exemplification Compound No. 2-1418)

To a solution of (E)-4-(acetylsulfanyl)-1-[2-cyclopropyl-1-(2-fluorophenyl)-2-oxoethyl]-3-{[1(2)H-1,2,3-triazol-4(5)-yl]methylidene}piperidine (1.0 g) in acetonitrile (15 ml) were added methyl bromoacetate (1.1 g) and 1,8-diazabicyclo[5.4.0]undec-7-ene (DBU) (1.0 ml). The resulting solution was stirred at room temperature for 15 minutes, and the reaction was stopped by addition of a saturated aqueous sodium chloride solution. The products were extracted with ethyl acetate and the extract was dried over anhydrous sodium sulfate. The solvent was evaporated in vacuo, and the residue was purified by chromatography on silica gel using a mixture of hexane, ethyl acetate and dichloromethane (1:1:1) as the eluent to afford the title compound (550 mg, yield: 47%) as a pale yellow amorphous solid.

$^1$H NMR (400 MHz, CDCl$_3$) δ ppm: 0.63-0.84 (2H, m), 0.84-1.04 (2H, m), 1.80-1.94 (1H, m), 2.11-2.39 (2H, m), 2.30 (3H, s), 2.44-2.60 (1H, m), 2.68-2.79 and 2.81-2.92 (total 1H, each m), 3.01 and 3.30 (total 1H, each d, J=13.5), 3.76 (3H, s), 3.97 and 4.05 (total 1H, each d, J=13.5), 4.45-

4.52 (1H, m), 4.69 and 4.70 (total 1H, each s), 5.03 and 5.11 (total 2H, each s), 6.46 and 6.48 (total 1H, each s), 7.02-7.16 (2H, m), 7.25-7.34 (1H, m), 7.36-7.42 (1H, m), 7.43 and 7.51 (total 1H, each s).

Example 239

(E)-1-[2-Cyclopropyl-1-(2-fluorophenyl)-2-oxoethyl]-3-{[2-(methoxycarbonylmethyl)-2H-1,2,3-triazol-4-yl]methylidene}-4-sulfanylpiperidine hydrochloride (Exemplification Compound No. 2-1417)

Using (E)-4-(acetylsulfanyl)-1-[2-cyclopropyl-1-(2-fluorophenyl)-2-oxoethyl]-3-{[2-(methoxycarbonylmethyl)-2H-1,2,3-triazol-4-yl]methylidene}piperidine (550 mg) as the starting material, conduction of a similar reaction to that described in Example 151 gave the title compound (260 mg, yield: 48%) as a colourless amorphous solid.

$^1$H NMR (400 MHz, pyridine-$d_5$) δ ppm: 0.60-0.76 (2H, m), 0.88-0.99 (1H, m), 1.01-1.11 (1H, m), 1.79-1.91 (1H, m), 2.22-2.45 (2H, m), 2.62-2.71 and 2.73-2.83 (total 1H, each m), 2.89-3.01 (total 1H, each s), 3.55-3.63 (3H, m), 3.80 and 3.95 (total 1H, each d, J=13.0), 3.96-4.02 (1H, m), 4.04 and 4.11 (total 1H, each d, J=13.0), 4.93 and 4.94 (total 1H, each s), 5.48-5.55 (2H, m), 6.63 and 6.68 (total 1H, each s), 7.13-7.22 (2H, m), 7.26-7.33 (1H, m), 7.62-7.69 (1H, m), 7.81-7.88 (total 1H, each s);
IR (KBr, cm$^{-1}$): 2954, 2452, 1754, 1712.

Example 240

(E)-3-{[2-(Carboxymethyl)-2H-1,2,3-triazol-4-yl]methylidene}-1-[2-cyclopropyl-1-(2-fluorophenyl)-2-oxoethyl]-4-sulfanylpiperidine hydrochloride (Exemplification Compound No. 2-1401)

Using (E)-3-{[2-(methoxycarbonylmethyl)-2H-1,2,3-triazol-4-yl]methylidene}-1-[2-cyclopropyl-1-(2-fluorophenyl)-2-oxoethyl]-4-sulfanylpiperidine hydrochloride (106 mg) as the starting material, a similar process to that mentioned in Example 134 gave the title compound (86.0 mg, yield: 84%) as a colourless amorphous solid.

$^1$H NMR (400 MHz, pyridine-$d_5$) δ ppm: 0.60-0.76 (2H, m), 0.85-0.99 (1H, m), 0.99-1.14 (1H, m), 1.75-1.94 (1H, m), 2.21-2.47 (2H, m), 2.61-2.74 and 2.74-2.86 (total 1H, each m), 2.87-3.02 (1H, m), 3.80 and 4.00 (total 1H, each d, J=13.0), 3.96-4.04 (1H, m), 4.08 and 4.19 (total 1H, each d, J=13.0), 4.93 and 4.94 (total 1H, each s), 5.52-5.61 (2H, m), 6.65 and 6.71 (total 1H, each s), 7.13-7.37 (3H, m), 7.63-7.71 (1H, m), 7.82 and 7.89 (total 1H, each s);
IR (KBr, cm$^{-1}$): 2929, 1743, 1711.

Example 241

(E)-1-[2-Cyclopropyl-1-(2-fluorophenyl)-2-oxoethyl]-3-({2-[2-(ethoxycarbonyl)ethyl]-2H-1,2,3-triazol-4-yl}methylidene)-4-sulfanylpiperidine hydrochloride (Exemplification Compound No. 2-1437)

To a solution of (E)-4-(acetylsulfanyl)-1-[2-cyclopropyl-1-(2-fluorophenyl)-2-oxoethyl]-3-{[1(2)H-1,2,3-triazol-4(5)-yl]methylidene}piperidine (900 mg) in acetonitrile (10 ml) were added ethyl acrylate (660 mg) and 1,8-diazabicyclo[5.4.0]undec-7-ene (DBU) (1.0 ml). The resulting solution was stirred at room temperature for 30 minutes, and the reaction was stopped by the addition of a saturated aqueous sodium chloride solution. The products were extracted with ethyl acetate, and the extract was dried over anhydrous sodium sulfate. The solvent was evaporated in vacuo, and the residue was purified by chromatography on silica gel using a mixture of hexane, ethyl acetate and dichloromethane (1:1:1) as the eluent to afford crude (E)-4-(acetylsulfanyl)-1-[2-cyclopropyl-1-(2-fluorophenyl)-2-oxoethyl]-3-({2-[2-(ethoxycarbonyl)ethyl]-2H-1,2,3-triazol-4-yl]methyliden}piperidine (300 mg). To a solution of this compound in ethanol (30 ml) was introduced HCl gas at 0° C. for 30 minutes. The flask was stoppered, the mixture was stirred for one hour, and the solvent and excess HCl were removed in vacuo. The residue was purified by preparative HPLC (YMC-Pack ODS-A; YMC, eluent: acetonitrile/0.024 N HCl, 35/65, v/v) to afford a fraction containing the product. This fraction was treated with a saturated aqueous sodium hydrogen carbonate solution, and the liberated base was extracted with ethyl acetate to afford the free base of the title compound.

$^1$H NMR (400 MHz, CDCl$_3$) δ ppm: 0.63-0.86 (2H, m), 0.87-1.05 (2H, m), 1.26 (3H, t, J=7.0), 1.75-1.89 (1H, m), 2.09-2.22 (1H, m), 2.22-2.41 (1H, m), 2.62-2.70 and 2.72-2.79 (total 1H, each m), 2.81-2.97 (3H, m), 3.55 and 3.70 (total 1H, each d, J=13.0), 3.78 and 3.82 (total 1H, each d, J=13.0), 3.86-3.96 (1H, m), 4.18 (2H, q, J=7.0), 4.58 and 4.61 (total 2H, each t, J=7.5), 4.78 and 4.79 (total 1H, each s), 6.42 and 6.46 (total 1H, each s), 7.04-7.18 (2H, m), 7.28-7.36 (1H, m), 7.36 and 7.43 (total 1H, each s), 7.39-7.46 (1H, m);
IR (Thin film, cm$^{-1}$): 2932, 2458, 1732.

The free base thus obtained was treated with 4 N solution of hydrogen chloride in dioxane, and the solvent and excess hydrogen chloride were removed in vacuo to afford the title compound as a colourless amorphous solid (200 mg, overall yield: 18%).

Example 242

(E)-3-{[2-(Carboxyethyl)-2H-1,2,3-triazol-4-yl]methylidene}-1-[2-cyclopropyl-1-(2-fluorophenyl)-2-oxoethyl]-4-sulfanylpiperidine hydrochloride (Exemplification Compound No. 2-1405)

Using (E)-1-[2-cyclopropyl-1-(2-fluorophenyl)-2-oxoethyl]-3-({2-[2-(ethoxycarbonyl)ethyl]-2H-1,2,3-triazol-4-yl}methylidene)-4-sulfanylpiperidine hydrochloride (160 mg) as the starting material, a similar process to that mentioned in Example 134 gave the title compound (70 mg, yield: 46%) as a colourless amorphous solid.

$^1$H NMR (400 MHz, pyridine-$d_5$) δ ppm: 0.57-0.79 (2H, m), 0.89-0.99 (1H, m), 1.00-1.14 (1H, m), 1.76-1.95 (1H, m), 2.23-2.45 (2H, m), 2.63-2.74 and 2.76-2.85 (total 1H, each m), 2.91-3.02 (1H, m), 3.19-3.30 (2H, m), 3.81 and 3.99 (total 1H, each d, J=13.0), 3.96-4.05 (1H, m), 4.06 and 4.14 (total 1H, each d, J=13.0), 4.82-4.92 (2H, m), 4.97 (1H, s), 6.62 and 6.66 (total 1H, each s), 7.14-7.25 (2H, m), 7.29-7.38 (1H, m), 7.64-7.72 (1H, m), 7.75 and 7.76 (total 1H, each s);
IR (Thin film, cm$^{-1}$): 3405, 2957, 2569, 1713.

Example 243

(E)-4-(Acetylsulfanyl)-1-[2-cyclopropyl-1-(2-fluorophenyl)-2-oxoethyl]-3-({2-[3-(ethoxycarbonyl)propyl]-2H-1,2,3-triazol-4-yl}methylidene)piperidine (Exemplification Compound No. 2-1442)

To a solution of (E)-4-(acetylsulfanyl)-1-[2-cyclopropyl-1-(2-fluorophenyl)-2-oxoethyl]-3-{[1(2)H-1,2,3-triazol-4(5)-yl]methylidene}piperidine (900 mg) in acetonitrile (10 ml) were added ethyl 4-bromobutylate (1.3 g) and 1,8-diazabicyclo[5.4.0]undec-7-ene (DBU) (1.0 ml). The resulting mixture was stirred at room temperature for 30 minutes, and the reaction was stopped by the addition of a saturated aqueous sodium chloride solution. The products were extracted with ethyl acetate, and the extract was dried over anhydrous sodium sulfate. The solvent was evaporated in vacuo, and the residue was purified by chromatography on silica gel using a mixture of hexane, ethyl acetate and dichloromethane (1:1:1) as the eluent to afford the title compound as a pale yellow amorphous solid (570 mg, yield: 50%).

$^1$H NMR (400 MHz, CDCl$_3$) δ ppm: 0.62-0.86 (2H, m), 0.88-1.05 (2H, m), 1.22-1.29 (3H, m), 1.82-1.96 (1H, m), 2.11-2.38 (6H, m), 2.31 (3H, s), 2.46-2.63 (1H, m), 2.73-2.81 and 2.83-2.91 (total 1H, each m), 3.06 and 3.29 (total 1H, each d, J=13.0), 4.01 and 4.05 (total 1H, each d, J=13.0), 4.07-4.19 (2H, m), 4.29-4.43 (2H, m), 4.46-4.54 (1H, m), 4.72 and 4.74 (total 1H, each s), 6.46 and 6.48 (total 1H, each s), 7.04-7.18 (2H, m), 7.26-7.44 (2H, m), 7.34 and 7.43 (total 1H, each s).

Example 244

(E)-1-[2-Cyclopropyl-1-(2-fluorophenyl)-2-oxoethyl]-3-({2-[3-(ethoxycarbonyl)propyl]-2H-1,2,3-triazol-4-yl}methylidene)-4-sulfanylpiperidine hydrochloride (Exemplification Compound No. 2-1441)

To a solution of (E)-4-(acetylsulfanyl)-1-[2-cyclopropyl-1-(2-fluorophenyl)-2-oxoethyl]-3-({2-[3-(ethoxycarbonyl)propyl]-2H-1,2,3-triazol-4-yl}methylidene)piperidine (570 mg) in ethanol (50 ml) was introduced HCl gas at 0° C. for 30 minutes. The mixture was stirred under tightly sealed condition for 2 hours, and the solvent and excess hydrogen chloride were removed in vacuo. The residue was purified by preparative HPLC (YMC-Pack ODS-A; YMC, eluent: acetonitrile/ 0.024 N HCl, 35/65, v/v) to afford a fraction containing the product. This fraction was treated with a saturated aqueous sodium hydrogen carbonate solution, and the liberated base was extracted with ethyl acetate to afford the free base of the title compound.

$^1$H NMR (400 MHz, CDCl$_3$) δ ppm: 0.77-0.96 (2H, m), 1.00-1.16 (2H, m), 1.37 (3H, t, J=7.0), 1.88-1.99 (1H, m), 2.23-2.48 (6H, m), 2.73-2.88 (1H, m), 2.91-3.03 (1H, m), 3.65 and 3.79 (total 1H, each d, J=13.0), 3.86 and 3.87 (total 1H, each d, J=13.0), 3.98-4.07 (1H, m), 4.25 (2H, q, J=7.0), 4.44-4.53 (2H, m), 4.88 (1H, s), 6.55 and 6.58 (total 1H, each s), 7.16-7.28 (2H, m), 7.39-7.47 (1H, m), 7.47 and 7.54 (total 1H, each s), 7.49-7.55 (1H, m).

IR (KBr, cm$^{-1}$): 2935, 2459, 1729.

The free base as above was treated with 4 N solution of hydrogen chloride in dioxane, and the solvent and excess hydrogen chloride were removed in vacuo to afford the title compound as a colourless amorphous solid (420 mg, overall yield: 75%).

Example 245

(E)-3-{[2-(Carboxypropyl)-2H-1,2,3-triazol-4-yl] methylidene}-1-[2-cyclopropyl-1-(2-fluorophenyl)-2-oxoethyl]-4-sulfanylpiperidine hydrochloride (Exemplification Compound No. 2-1409)

Using (E)-1-[2-cyclopropyl-1-(2-fluorophenyl)-2-oxoethyl]-3-({2-[3-(ethoxycarbonyl)propyl]-2H-1,2,3-triazol-4-yl}methylidene)-4-sulfanylpiperidine hydrochloride (380 mg) as the starting material, a similar process to that mentioned in Example 134 gave the title compound (290 mg, yield: 81%) as a colourless amorphous solid.

$^1$H NMR (400 MHz, pyridine-d$_5$) δ ppm: 0.53-0.81 (2H, m), 0.88-1.13 (2H, m), 1.79-1.96 (1H, m), 2.23-2.64 (6H, m), 2.65-3.08 (2H, m), 3.80-4.18 (3H, m), 4.50-4.62 (2H, m), 5.01 (1H, s), 6.66 and 6.70 (total 1H, each s), 7.14-7.26 (2H, m), 7.29-7.38 (1H, m), 7.65-7.73 (1H, m), 7.76 (1H, s);

IR (KBr, cm$^{-1}$): 3349, 2939, 2560, 1711.

Example 246

(E)-4-(Acetylsulfanyl)-1-[2-cyclopropyl-1-(2-fluorophenyl)-2-oxoethyl]-3-{[1-(ethoxycarbonylmethyl)-1H-pyrazol-4-yl]methylidene}piperidine (Exemplification Compound No. 2-214)

(a) (E)-3-[(1H-Pyrazol-4-yl)methylidene]-1-(triphenylmethyl)piperidin-4-one

A mixture of 1H-pyrazole-4-carbaldehyde (14.5 g), acetonitrile (300 ml), di(t-butyl)dicarbonate (36.0 g) and tetramethylammonium hydroxide was stirred at room temperature for 30 minutes. The reaction was stopped by addition of a saturated aqueous sodium chloride solution, and the products were extracted with ethyl acetate. The organic layer was washed with a saturated aqueous sodium chloride solution, and dried over anhydrous sodium sulfate. The solvent was evaporated in vacuo, and the residue was purified by chromatography on silica gel using a mixture of hexane and ethyl acetate (2:1) as the eluent to afford 1-(t-butoxycarbonyl)-1H-pyrazol-4-carbaldehyde (24.74 g, yield: 84%).

To a solution of 1-(triphenylmethyl)piperidin-4-one (42.8 g) in benzene (800 ml) was added pyrrolidine (10.4 ml), and the resulting mixture was heated under reflux for 3 hours removing water using a Dean-Staak apparatus. The reaction mixture was cooled to room temperature, and 1-(t-butoxycarbonyl)-1H-pyrazol-4-carbaldehyde (24.6 g) obtained as mentioned above was added thereto. The resulting mixture was heated under reflux for 5 hours, cooled, diluted with a saturated aqueous sodium chloride solution, and the products were extracted with ethyl acetate. The organic layer was washed with a saturated aqueous sodium chloride solution, and dried over anhydrous sodium sulfate. The solvent was evaporated in vacuo, and the residue was purified by chromatography on silica gel. Elution by a mixed solvent of hexane, ethyl acetate and dichloromethane (3:1:1) gave (E)-3-{[1-(t-butoxycarbonyl)-1H-pyrazol-4-yl]methylidene}-1-(tri phenylmethyl)piperidin-4-one (16.07 g, yield: 25% from the aldehyde) firstly. Then, elution by a mixed solvent of hexane and ethyl acetate (1:2) gave the title compound as a yellow amorphous solid (15.25 g, yield: 29% from the aldehyde).

$^1$H NMR (400 MHz, CDCl$_3$) δ ppm: 2.61-2.78 (4H, m), 3.21-3.43 (2H, m), 7.10-7.32 (9H, m), 7.44-7.57 (9H, m).

To a solution of (E)-3-{[1-(t-butoxycarbonyl)-1H-pyrazol-4-yl]methylidene}-1-(triphenylmethyl)piperidin-4-one (16.0 g) obtained as mentioned above in methanol (200 ml) was added potassium carbonate (12.8 g). The resulting mixture was stirred at room temperature for 30 minutes, and partitioned between water and ethyl acetate. The separated organic layer was washed with a saturated aqueous sodium chloride solution, and dried over anhydrous sodium sulfate. The solvent was removed in vacuo to afford the title compound further (8.85 g, yield: 68% from the Boc compound).

(b) (E)-3-{[1-(Ethoxycarbonylmethyl)-1H-pyrazol-4-yl]methylidene}-1-(triphenylmethyl)piperidin-4-one To a solution of (E)-3-[(1H-pyrazol-4-yl)methylidene]-1-(triphenylmethyl)piperidin-4-one (6.0 g) in acetonitrile (100 ml) were added ethyl bromoacetate (7.2 g) and 1,8-diazabicyclo[5.4.0]undec-7-ene (DBU) (6.4 ml). The resulting mixture was stirred at room temperature for one hour, and the reaction was stopped by addition of a saturated aqueous sodium chloride solution. The products were extracted with ethyl acetate, and the organic layer was dried over anhydrous sodium sulfate. The solvent was evaporated in vacuo, and the residue was purified by chromatography on silica gel using a mixture of hexane, ethyl acetate and dichloromethane (2:1:1) as the eluent to afford the title compound as a yellow amorphous solid (6.08 g, yield: 84%).

$^1$H NMR (400 MHz, CDCl$_3$) δ ppm: 1.27 (3H, t, J=7.0), 2.60-2.78 (4H, m), 3.37 (2H, bs), 4.23 (2H, q, J=7.0), 4.84 (2H, s), 7.14-7.31 (9H, m), 7.39 (1H, s), 7.43-7.56 (8H, m).

(c) (E)-3-{[1-(Ethoxycarbonylmethyl)-1H-pyrazol-4-yl]methylidene}-1-(triphenylmethyl)piperidin-4-ol To a solution of (E)-3-{[1-(ethoxycarbonylmethyl)-1H-pyrazol-4-yl]methylidene}-1-(triphenylmethyl)piperidin-4-one (6.08 g) in ethanol (100 ml) was added sodium borohydride (230 mg). The resulting mixture was stirred at room temperature for 30 minutes, and the reaction was stopped by addition of a saturated aqueous ammonium chloride solution. The products were extracted with ethyl acetate, and the organic layer was washed with a saturated aqueous sodium chloride solution and dried over anhydrous sodium sulfate. The solvent was evaporated in vacuo to afford the title compound as a yellow amorphous solid (6.2 g, yield: quantitative).

$^1$H NMR (400 MHz, CDCl$_3$) δ ppm: 1.28 (3H, t, J=7.0), 1.80-1.95 (1H, m), 2.06-2.21 (2H, m), 2.57-2.84 (2H, m), 3.40 (1H, bs), 4.07-4.17 (1H, m), 4.22 (2H, q, J=7.0), 4.74 (2H, d, J=3.5), 6.34 (1H, s), 7.07-7.23 (10H, m), 7.37 (1H, s), 7.39-7.47 (6H, m).

(d) (E)-4-(Acetylsulfanyl)-3-{[1-(ethoxycarbonylmethyl)-1H-pyrazol-4-yl]methylidene}piperidine hydrogen trifluoroacetate To a solution of (E)-3-{[1-(ethoxycarbonylmethyl)-1H-pyrazol-4-yl]methylidene}-1-(triphenylmethyl)piperidin-4-ol (6.2 g) in toluene (100 ml) were added thioacetic acid (1.8 ml) and N,N-dimethylformamide dineopentylacetal (6.8 ml). The resulting mixture was stirred at room temperature for 15 minutes, and the reaction was stopped by the addition of a saturated aqueous sodium chloride solution. The products were extracted with ethyl acetate. The organic layer was washed with a saturated aqueous sodium chloride solution, and dried over anhydrous sodium sulfate. Solvents were evaporated in vacuo and the residue was purified by chromatography on silica gel using a mixture of hexane, ethyl acetate and dichloromethane (1:1:1) as the eluent to afford a mixture of (E)-4-(acetylsulfanyl)-3-{[1-(ethoxycarbonylmethyl)-1H-pyrazol-4-yl]methylidene}-1-(triphenylmethyl)piperidine and 5-{(acetylsulfanyl)[1-(ethoxycarbonylmethyl)-1H-pyrazol-4-yl]methyl}-1-(triphenylmethyl)-1,2,3,6-tetrahydropyridine (6.11 g).

To a solution of the mixture as above in dimethyl sulfoxide (100 ml), was added potassium thioacetate (12.3 g). The resulting mixture was stirred at 80° C. for 15 hours, cooled to room temperature, and diluted with water to stop the reaction. The products were extracted with ethyl acetate. The organic layer was washed with a saturated aqueous sodium chloride solution. The organic layer was dried over anhydrous aqueous sodium chloride, and solvents were evaporated in vacuo. The residue was purified by chromatography on silica gel using a mixture of hexane, ethyl acetate and dichloromethane (2:1:1) as the eluent to afford an approximately 7:6:1 mixture of (E)-4-(acetylsulfanyl)-3-{[1-(ethoxycarbonylmethyl)-1H-pyrazol-4-yl]methylidene}-1-(triphenylmethyl)piperidine, its (Z)-isomer and 5-{(acetylsulfanyl)[1-(ethoxycarbonylmethyl)-1H-pyrazol-4-yl]methyl}-1-(triphenylmethyl)-1,2,3,6-tetrahydropyridine (5.52 g). To a solution of the above mixture in dichloromethane (300 ml) was added trifluoroacetic acid (1.9 ml). The resulting mixture was stirred at room temperature for 15 minutes. The solvent was evaporated in vacuo, and the residue was purified by chromatography on silica gel using a mixture of dichloromethane and methanol (10:1) as the eluent to afford the title compound as a yellow amorphous solid (1.75 g, overall yield: 33%).

$^1$H NMR (400 MHz, CDCl$_3$) δ ppm: 1.26 (3H, t, J=7.0), 2.00-2.09 (1H, m), 2.32-2.53 (2H, m), 2.34 (3H, s), 3.08-3.22 (1H, m), 3.31 (1H, d, J=14.0), 3.65 (1H, d, J=14.0), 4.20 (2H, q, J=7.0), 4.56 (1H, t, J=4.0), 4.84 (2H, s), 6.62 (1H, s), 7.45 (1H, s), 7.49 (1H, s).

(e) (E)-4-(Acetylsulfanyl)-1-[2-cyclopropyl-1-(2-fluorophenyl)-2-oxoethyl]-3-{[1-(ethoxycarbonylmethyl)-1H-pyrazol-4-yl]methylidene}piperidine Using (E)-4-(acetylsulfanyl)-3-{[1-(ethoxycarbonylmethyl)-1H-pyrazol-4-yl]methylidene}piperidine hydrogen trifluoroacetate (1.75 g) as the starting material, a similar process to that mentioned in Example 132(g) gave the title compound (1.0 g, yield: 50%) as a pale yellow amorphous solid.

$^1$H NMR (400 MHz, CDCl$_3$) δ ppm: 0.64-0.86 (2H, m), 0.87-1.04 (2H, m), 1.22-1.30 (3H, m), 1.77-1.91 (1H, m), 2.11-2.20 (1H, m), 2.22-2.33 (1H, m), 2.29 and 2.30 (3H, s), 2.39-2.47 and 2.49-2.58 (total 1H, each m), 2.67-2.75 and 2.80-2.88 (total 1H, each m), 2.89 and 3.06 (total 1H, each d, J=13.0), 3.63 and 3.69 (total 1H, each d, J=13.0), 4.18-4.26 (2H, m), 4.43-4.49 (1H, m), 4.68 and 4.70 (total 1H, each s), 4.76-4.84 (2H, m), 6.34 and 6.36 (total 1H, each s), 7.03-7.18 (2H, m), 7.26-7.44 (4H, m).

Example 247

(E)-1-[2-Cyclopropyl-1-(2-fluorophenyl)-2-oxoethyl]-3-{[1-(ethoxycarbonylmethyl)-1H-pyrazol-4-yl]methylidene}-4-sulfanylpiperidine hydrochloride (Exemplification Compound No. 2-213)

Using (E)-4-(acetylsulfanyl)-1-[2-cyclopropyl-1-(2-fluorophenyl)-2-oxoethyl]-3-{[1-(ethoxycarbonylmethyl)-1H-pyrazol-4-yl]methylidene}piperidin (1.0 g) as the starting material, a similar process to that mentioned in Example 133 gave the title compound (780 mg, yield: 79%) as a colourless amorphous solid.

$^1$H NMR (400 MHz, CDCl$_3$) δ ppm: 0.62-0.87 (2H, m), 0.87-1.05 (2H, m), 1.18-1.34 (3H, m), 1.70-1.84 (1H, m), 2.11 (1H, bs), 2.27 (1H, bs), 2.56-2.96 (2H, m), 3.29-3.58 (2H, m), 3.84-3.95 (1H, m), 4.22 (2H, m), 4.75-4.85 (3H, m), 6.31 and 6.34 (total 1H, each s), 7.04-7.18 (2H, m), 7.26-7.48 (2H, m), 7.34 (1H, s), 7.40 (1H, s);

IR (KBr, cm$^{-1}$): 2926, 2460, 1750, 1711.

Example 248

(E)-1-[2-Cyclopropyl-1-(2-fluorophenyl)-2-oxoethyl]-3-({1-[2-(ethoxycarbonyl)ethyl]-1H-pyrazol-4-yl}methylidene)-4-sulfanylpiperidine hydrochloride (Exemplification Compound No. 2-217)

(a) (E)-3-({1-[2-(ethoxycarbonyl)ethyl]-1H-pyrazol-4-yl}methylidene)-1-(triphenylmethyl)piperidin-4-one To a solution of (E)-3-[(1H-pyrazol-4-yl)methylidene]-1-(triphenylmethyl)piperidin-4-one (Example 98(a), 6.0 g) in acetonitrile (100 ml) were added ethyl acrylate (4.7 ml) and 1,8-diazabicyclo[5.4.0]undec-7-ene (DBU) (6.4 ml). The resulting mixture was stirred at room temperature for 15 minutes, and the reaction was stopped by an addition of a saturated aqueous sodium chloride solution. The products were extracted with ethyl acetate. The organic layer was dried over anhydrous sodium sulfate, and solvents were evaporated in vacuo. The residue was purified by chromatography on silica gel using a mixture of hexane, ethyl acetate and dichloromethane (2:1:1) as the eluent to afford the title compound as a yellow amorphous solid (6.12 g, yield: 82%).

$^1$H NMR (400 MHz, CDCl$_3$) δ ppm: 1.20 (3H, t, J=7.0), 2.62-2.76 (4H, m), 2.82 (2H, t, J=6.0), 3.32 (2H, bs), 4.07 (2H, q, J=7.0), 4.35 (2H, t, J=6.0), 7.13-7.58 (18H, m).

(b) (E)-3-({1-[2-(Ethoxycarbonyl)ethyl]-1H-pyrazol-4-yl}methylidene]-1-(triphenylmethyl)piperidin-4-ol Using (E)-3-({1-[2-(ethoxycarbonyl)ethyl]-1H-pyrazol-4-yl}methylidene)-1-(triphenylmethyl)piperidin-4-one (6.12 g) as the starting material, a similar process to that mentioned in Example 246(c) gave the title compound (6.19 g, yield: 100%) as a pale yellow amorphous solid.

$^1$H NMR (400 MHz, CDCl$_3$) δ ppm: 1.24 (3H, t, J=7.0), 1.80-1.94 (1H, m), 2.06-2.22 (2H, m), 2.55-2.82 (2H, m), 2.79 (2H, t, J=7.0), 3.36 (1H, bs), 4.06-4.16 (1H, m), 4.13 (2H, q, J=7.0), 4.25 (2H, t, J=7.0), 6.32 (1H, s), 7.07-7.22 (10H, m), 7.32 (1H, s), 7.38-7.46 (6H, m).

(c) (E)-1-[2-Cyclopropyl-1-(2-fluorophenyl)-2-oxoethyl]-3-({1-[2-(ethoxycarbonyl)ethyl]-1H-pyrazol-4-yl}methylidene)-4-sulfanylpiperidine hydrochloride Using (E)-3-({1-[2-(ethoxycarbonyl)ethyl]-1H-pyrazol-4-yl}methylidene)-1-(triphenylmethyl)piperidin-4-ol (6.19 g) as the starting material, successive processes similar to those mentioned in Examples 246(d) and (e) gave the title compound (540 mg, yield: 10%) as a colourless amorphous solid.

$^1$H NMR (400 MHz, CDCl$_3$) δ ppm: 0.64-0.87 (2H, m), 0.89-1.06 (2H, m), 1.24 (3H, t, J=7.0), 1.70-1.84 (1H, m), 2.05-2.18 (1H, m), 2.18-2.39 (1H, m), 2.59-2.95 (4H, m), 3.31-3.58 (2H, m), 3.84-3.97 (1H, m), 4.15 (2H, q, J=7.0), 4.31 and 4.34 (total 2H, each t, J=7.0), 4.78 and 4.80 (total 1H, each s), 6.29 and 6.32 (total 1H, each s), 7.05-7.21 (2H, m), 7.27-7.50 (4H, m);

IR (KBr, cm$^{-1}$): 2927, 2460, 1730, 1714.

Example 249

(E)-3-{[2-(Carboxyethyl)-1H-pyrazol-4-yl]methylidene}-1-[2-cyclopropyl-1-(2-fluorophenyl)-2-oxoethyl]-4-sulfanylpiperidine hydrochloride (Exemplification Compound No. 2-185)

Using (E)-1-[2-cyclopropyl-1-(2-fluorophenyl)-2-oxoethyl]-3-({1-[2-(ethoxycarbonyl)ethyl]-1H-pyrazol-4-yl}methylidene)-4-sulfanylpiperidine hydrochloride (520 mg) as the starting material, a similar process to that mentioned in Example 134 gave the title compound (480 mg, yield: 98%) as a colourless amorphous solid.

$^1$H NMR (400 MHz, pyridine-d$_5$) δ ppm: 0.56-0.77 (2H, m), 0.88-1.12 (2H, m), 1.73-1.90 (1H, m), 2.18-2.43 (2H, m), 2.63-2.83 (1H, m), 2.86-3.01 (1H, m), 3.09-3.23 (2H, m), 3.57-3.79 (2H, m), 3.95-4.06 (1H, m), 4.53-4.62 (2H, m), 4.94 (1H, s), 6.48 and 6.49 (total 1H, each s), 7.16-7.24 (2H, m), 7.29-7.36 (1H, m), 7.62-7.77 (3H, m);

IR (KBr, cm$^{-1}$): 2922, 2617, 2540, 1729, 1711.

Example 250

(E)-1-[2-Cyclopropyl-1-(2-fluorophenyl)-2-oxoethyl]-3-({1-[3-(ethoxycarbonyl)propyl]-1H-pyrazol-4-yl}methylidene)-4-sulfanylpiperidine hydrochloride (Exemplification Compound No. 2-221)

(a) (E)-3-({1-[3-(Ethoxycarbonyl)propyl]-1H-pyrazol-4-yl}methylidene)-1-(triphenylmethyl)piperidin-4-one To a solution of (E)-3-[(1H-pyrazol-4-yl)methylidene]-1-(triphenylmethyl)piperidin-4-one (Example 98(a), 6.0 g) in acetonitrile (100 ml) were added ethyl 4-bromobutylate (8.4 g) and 1,8-diazabicyclo[5.4.0]undec-7-ene (DBU) (6.4 ml). The resulting mixture was stirred at room temperature for one hour, and the reaction was stopped by addition of a saturated aqueous sodium chloride solution. The products were extracted with ethyl acetate and the extract was dried over anhydrous sodium sulfate. The solvent was evaporated in vacuo, and the residue was purified by chromatography on silica gel using a mixture of hexane, ethyl acetate and dichloromethane (2:1:1) as the eluent to afford the title compound as a yellow amorphous solid (5.45 g, yield: 71%).

$^1$H NMR (400 MHz, CDCl$_3$) δ ppm: 1.14 (3H, t, J=7.0), 2.00 (2H, t, J=7.0), 2.09 (2H, t, J=7.0), 2.52-2.64 (4H, m), 3.22 (2H, bs), 4.01 (4H, q, J=7.0), 7.03-7.44 (18H, m).

(b) (E)-3-({1-[3-(Ethoxycarbonyl)propyl]-1H-pyrazol-4-yl}methylidene)-1-(triphenylmethyl)piperidin-4-ol Using (E)-3-({1-[3-(ethoxycarbonyl)propyl]-1H-pyrazol-4-yl}methylidene)-1-(triphenylmethyl)piperidin-4-one (5.45 g) as the starting material, a similar process to that mentioned in Example 246(c) gave the title compound (5.54 g, yield: 100%) as a pale yellow amorphous solid.

$^1$H NMR (400 MHz, CDCl$_3$) δ ppm: 1.25 (3H, t, J=7.0), 1.81-1.93 (1H, m), 2.06 (2H, t, J=7.0), 2.06-2.19 (2H, m), 2.19 (2H, t, J=7.0), 2.53-2.87 (2H, m), 3.35 (1H, bs), 4.01 (2H, t, J=7.0), 4.09-4.16 (3H, m), 6.32 (1H, s), 7.06 (1H, s), 7.09-7.22 (8H, m), 7.33 (1H, s), 7.38-7.46 (7H, m).

(c) (E)-1-[2-Cyclopropyl-1-(2-fluorophenyl)-2-oxo-
ethyl]-3-({1-[3-(ethoxycarbonyl)propyl]-1H-pyrazol-
4-yl}methylidene)-4-sulfanylpiperidine hydrochloride Using (E)-3-({1-[3-(ethoxycarbonyl)propyl]-1H-pyrazol-4-yl}methylidene)-1-(triphenylmethyl)piperidin-4-ol as the starting material, similar sequential processes to those shown in Examples 246(d) and (e) gave the title compound (430 mg, yield: 8%) as a colourless amorphous solid.

$^1$H NMR (500 MHz, CDCl$_3$) δ ppm: 0.65-0.87 (2H, m), 0.90-1.06 (2H, m), 1.25 (3H, t, J=7.0), 1.73-1.84 (1H, m), 2.00-2.20 (3H, m), 2.21-2.43 (3H, m), 2.66-3.00 (2H, m), 3.34-3.69 (2H, m), 3.85-3.99 (1H, m), 4.04-4.18 (4H, m), 4.84 and 4.88 (total 1H, each s), 6.33 and 6.36 (total 1H, each s), 7.04-7.21 (2H, m), 7.26-7.39 (3H, m), 7.42-7.54 (1H, m);
IR (KBr, cm$^{-1}$): 2935, 2514, 1727, 1716.

Example 251

(E)-3-{[1-(Carboxypropyl)-1H-pyrazol-4-yl]meth-
ylidene}-1-[2-cyclopropyl-1-(2-fluorophenyl)-2-
oxoethyl]-4-sulfanylpiperidine hydrochloride (Exemplification Compound No. 2-189)

Using (E)-1-[2-cyclopropyl-1-(2-fluorophenyl)-2-oxoethyl]-3-({1-[3-(ethoxycarbonyl)propyl]-1H-pyrazol-4-yl}methylidene)-4-sulfanylpiperidine hydrochloride (350 mg) as the starting material, similar a process to that mentioned in Example 134 gave the title compound (280 mg, yield: 85%) as a colourless amorphous solid.

$^1$H NMR (500 MHz, pyridine-d$_5$) δ ppm: 0.60-0.81 (2H, m), 0.89-1.12 (2H, m), 1.76-1.93 (1H, m), 2.21-2.42 (4H, m), 2.45-2.58 (2H, m), 2.63-2.73 and 2.77-2.87 (total 1H, each m), 2.89-3.02 (1H, m), 3.62 and 3.73 (total 1H, each d, J=12.5), 3.77 (1H, s), 3.99-4.07 (1H, m), 4.20-4.31 (2H, m), 4.96 and 4.97 (total 1H, each s), 6.50 and 6.53 (total 1H, each s), 7.15-7.26 (2H, m), 7.29-7.39 (1H, m), 7.64 (1H, s), 7.65-7.73 (1H, m), 7.71 (1H, s).
IR (KBr, cm$^{-1}$): 2636, 2616, 2535, 1711.

Example 252

(E)-3-(Acetylsulfanyl)-1-[2-cyclopropyl-1-(2-fluo-
rophenyl)-2-oxoethyl]-4-{[1-(ethoxycarbonylm-
ethyl)-1H-pyrazol-4-yl]methylidene}pyrrolidine
hydrochloride (Exemplification Compound No. 6-28)

(a) Ethyl(4-formyl-1H-pyrazol-1-yl)acetate

To a mixture of 1H-pyrazole-4-carbaldehyde (5.5 g) and ethyl bromoacetate (19.0 g) in dichloromethane (150 ml), was added 1,8-diazabicyclo[5.4.0]undec-7-ene (DBU) (10 ml) at 0° C. The resulting mixture was stirred at room temperature for 30 minutes, and the reaction was stopped by addition of a saturated aqueous sodium chloride solution. The products were extracted with ethyl acetate, and the extract was dried over anhydrous sodium sulfate. The solvent was evaporated in vacuo, and the residue was purified by chromatography on silica gel using a mixture of hexane and ethyl acetate (1:3) as the eluent to afford the title compound as a colourless oil (8.09 g, yield: 78%).

$^1$H NMR (400 MHz, CDCl$_3$) δ ppm: 1.28 (3H, t, J=7.0), 4.24 (2H, q, J=7.0), 4.95 (2H, s), 7.99 (1H, s), 8.03 (1H, s), 9.87 (1H, s).

(b) (E)-1-(t-Butoxycarbonyl)-4-{[1-(ethoxycarbonyl-
methyl)-1H-pyrazol-4-yl]methylidene}pyrrolidin-3-
one To a solution of 1-(t-butoxycarbonyl)pyrrolidin-3-one (6.8 g) in ethanol (200 ml) were added ethyl(4-formyl-1H-pyrazol-1-yl)acetate (8.0 g) and pyrrolidine (600 μl). The resulting mixture was stirred at 80° C. for 45 minutes, cooled to room temperature, and the solvent was evaporated in vacuo. The residue was purified by chromatography on silica gel using a mixture of hexane, ethyl acetate and dichloromethane (2:1:1) as the eluent to afford the title compound as a yellow amorphous solid (4.47 g, yield: 35%).

$^1$H NMR (400 MHz, CDCl$_3$) δ ppm: 1.28 (3H, t, J=7.0), 1.48 (9H, s), 3.93 (2H, s), 4.24 (2H, q, J=7.0), 4.47 (2H, s), 4.92 (2H, s), 7.41 (1H, s), 7.69 (1H, s), 7.71 (1H, s).

(c) (E)-1-(t-Butoxycarbonyl)-4-{[1-(ethoxycarbonyl-
methyl)-1H-pyrazol-4-yl]methylidene}pyrrolidin-3-
ol Using (E)-1-(t-butoxycarbonyl)-4-{[1-(ethoxycarbonylmethyl)-1H-pyrazol-4-yl]methylidene}pyrrolidin-3-one (4.47 g) as the starting material, a similar process to that mentioned in Example 246(c) gave the title compound (1.55 g, yield: 35%) as a pale yellow amorphous solid.

$^1$H NMR (400 MHz, CDCl$_3$) δ ppm: 1.27 (3H, t, J=7.0), 1.47 (9H, s), 3.41 (1H, dd, J=11.5, 4.0), 3.57-3.72 (1H, m), 4.05-4.15 (1H, m), 4.23 (2H, q, J=7.0), 4.21-4.31 (1H, m), 4.67-4.75 (1H, m), 4.88 (2H, bs), 6.49 (1H, s), 7.42 (1H, bs), 7.51 (1H, s).

(d) (E)-3-(Acetylsulfanyl)-1-[2-cyclopropyl-1-(2-
fluorophenyl)-2-oxoethyl]-4-{[1-(ethoxycarbonylm-
ethyl)-1H-pyrazol-4-yl]methylidene}pyrrolidine
hydrochloride Using (E)-1-(t-butoxycarbonyl)-4-{[1-(ethoxycarbonylmethyl)-1H-pyrazol-4-yl]methylidene}pyrrolidin-3-ol (1.55 g) as the starting material, a similar process to that shown in Examples 246(d) and (e) gave the free base of the title compound. The free base was purified by preparative HPLC (YMC-Pack ODS-A; YMC, eluent acetonitrile/0.024 N HCl, 35/65, v/v) to afford the title hydrochloride (205 mg, overall yield: 9%) as a pale yellow amorphous solid.

$^1$H NMR (400 MHz, CDCl$_3$) δ ppm: 0.77-0.93 (2H, m), 0.95-1.07 (2H, m), 1.26 (3H, t, J=7.0), 2.15-2.27 (1H, m), 2.34 (3H, s), 2.72-2.85 (1H, m), 2.98-3.11 (1H, m), 3.27 and 3.73 (total 1H, each d, J=14.0), 3.46 (1H, s), 4.18-4.26 (2H, m), 4.62-4.69 (1H, m), 4.71 and 4.75 (total 1H, each s), 4.84 and 4.86 (total 2H, each s), 6.34-6.41 (1H, m), 7.07-7.21 (2H, m), 7.24-7.42 (3H, m), 7.43-7.55 (1H, m).

Example 253

(E)-1-[2-Cyclopropyl-1-(2-fluorophenyl)-2-oxoet-
hyl]-4-{[1-(ethoxycarbonyl)methyl]-1H-pyrazol-4-
yl]methylidene}-3-sulfanylpyrrolidine hydrochloride
(Exemplification Compound No. 6-27)

Using (E)-3-(acetylsulfanyl)-1-[2-cyclopropyl-1-(2-fluorophenyl)-2-oxoethyl]-4-{[1-(ethoxycarbonylmethyl)-1H-pyrazol-4-yl]methylidene}pyrrolidine hydrochloride (205 mg) as the starting material, a similar process to that mentioned in Example 133 gave the title compound (180 mg, yield: 96%) as a colourless amorphous solid.

¹H NMR (500 MHz, pyridine-d₅) δ ppm: 0.60-0.78 (2H, m), 0.91-1.10 (5H, m), 2.26-2.42 (1H, m), 2.72-2.78 and 2.78-2.84 (total 1H, each m), 3.18-3.28 (1H, m), 3.61 and 3.65 (total 1H, each d, J=14.0), 3.83 and 3.94 (total 1H, each d, J=14.0), 4.00-4.08 (2H, m), 4.09-4.16 (1H, m), 4.90 and 4.93 (total 1H, each s), 5.18 and 5.19 (total 2H, each s), 6.64-6.70 (1H, m), 7.11-7.34 (4H, m), 7.72 and 7.75 (total 1H, each s), 7.85 and 7.87 (total 1H, each s);
IR (KBr, cm⁻¹): 2931, 2512, 1747, 1711.

Example 254

(E)-4-{[1-(Carboxymethyl)-1H-pyrazol-4-yl]methylidene}-1-[2-cyclopropyl-1-(2-fluorophenyl)-2-oxoethyl]-3-sulfanylpyrrolidine hydrochloride (Exemplification Compound No. 6-31)

Using (E)-1-[2-cyclopropyl-1-(2-fluorophenyl)-2-oxoethyl]-4-{[1-(ethoxycarbonyl)methyl]-1H-pyrazol-4-yl]methylidene}-3-sulfanylpyrrolidine (110 mg) as the starting material, a similar process to that mentioned in Example 134 gave the title compound (87 mg, yield: 84%) as a colourless amorphous solid.
¹H NMR (500 MHz, pyridine-d₅) δ ppm: 0.58-0.77 (2H, m), 0.89-1.08 (2H, m), 2.29-2.40 (1H, m), 2.70-2.77 and 2.78-2.84 (total 1H, each m), 3.16-3.27 (1H, m), 3.58-3.68 (1H, m), 3.85 and 3.96 (total 1H, each d, J=14.5), 4.06-4.18 (1H, m), 4.90 and 4.92 (total 1H, each s), 5.26 and 5.27 (total 2H, each s), 6.65-6.72 (1H, each s), 7.08-7.33 (4H, m), 7.74 and 7.76 (total 1H, each s), 7.90 and 7.91 (total 1H, each s);
IR (KBr, cm⁻¹): 3404, 2925, 2528, 1744, 1710.

Example 255

(E)-4-(Acetylsulfanyl)-3-{[1-(carboxymethyl)-1H-1,2,3-triazol-5-yl]methylidene}-1-[2-cyclopropyl-1-(2-fluorophenyl)-2-oxoethyl]piperidine hydrochloride (Exemplification Compound No. 2-1210)

Using (E)-3-{[1-(carboxymethyl)-1H-1,2,3-triazol-5-yl]methylidene}-1-[2-cyclopropyl-1-(2-fluorophenyl)-2-oxoethyl]-4-sulfanylpiperidine hydrochloride as the starting material, a similar process to that mentioned in Example 198 gave the title compound (44 mg, yield: 23%) as a colourless amorphous solid.
¹H NMR (400 MHz, CDCl₃) δ ppm: 0.70-0.76 (2H, m), 0.98-1.08 (2H, m), 1.85-1.92 (1H, m), 2.21 and 2.23 (total 3H, each s), 2.24-2.34 (1H, m), 2.55-2.60 and 2.65-2.70 (total 1H, each m), 2.80-2.83 and 2.89-2.92 (total 1H, each m), 3.28 and 3.46 (total 1H, each d, J=12.5), 3.68-3.71 (1H, m), 3.91-4.11 (1H, m), 4.66 (1H, dd, J=8.0, 4.5), 4.97 and 4.99 (total 1H, each s), 5.64-5.66 (2H, m), 6.88 and 6.89 (total 1H, each s), 7.18-7.25 (1H, m), 7.31-7.36 (1H, m), 7.57-7.62 (2H, m), 8.02 and 8.06 (total 1H, each s);
IR (KBr, cm⁻¹): 1699, 1474.

Example 256

(E)-4-(Acetylsulfanyl)-1-[2-cyclopropyl-1-(2-fluorophenyl)-2-oxoethyl]-3-({2-[2-(ethoxycarbonyl)ethyl]-2H-tetrazol-5-yl}methylidene)piperidine (Exemplification Compound No. 2-1630) and (E)-4-(acetylsulfanyl)-1-[2-cyclopropyl-1-(2-fluorophenyl)-2-oxoethyl]-3-({2-[2-(ethoxycarbonyl)ethyl]-1H-tetrazol-5-yl}methylidene)piperidine (Exemplification Compound No. 2-1566)

A mixture of (E)-4-(acetylsulfanyl)-3-{[1(2)H-tetrazol-5-yl]methylidene}-1-[2-cyclopropyl-1-(2-fluorophenyl)-2-oxoethyl]piperidine hydrogen trifluoroacetate (Example 156, 2.0 g), 2-propanol (25 ml), ethyl acrylate (4.1 ml) and triethylamine (2.6 ml) was heated to reflux for one hour. After being cooled, the reaction solution was concentrated in vacuo, and the residue was partitioned between ethyl acetate and water. The separated organic layer was washed with water and saturated aqueous sodium chloride, successively. The organic layer was dried over anhydrous sodium sulfate and concentrated in vacuo. The residue was purified by chromatography on silica gel using a mixture of hexane and ethyl acetate (2:1, then 1.5:1, and finally 1:1) as the eluent to afford each of the two title isomers.

Less polar isomer (E)-4-(Acetylsulfanyl)-1-[2-cyclopropyl-1-(2-fluorophenyl)-2-oxoethyl]-3-({2-[2-(ethoxycarbonyl)ethyl]-2H-tetrazol-5-yl}methylidene)piperidine: yellow oil (674 mg, yield: 35%). ¹H NMR (400 MHz, CDCl₃) δ ppm: 0.68-0.82 (2H, m), 0.89-1.01 (2H, m), 1.22-1.25 (3H, m), 1.97-1.99 (1H, m), 2.15-2.21 (1H, m), 2.24-2.27 (1H, m), 2.29 and 2.30 (total 3H, each s), 2.47-2.53 and 2.61-2.67 (total 1H, each m), 2.76-2.83 (1H, m), 2.94 and 3.00 (total 2H, t, each J=7.0), 3.37 and 3.48 (total 1H, each d, J=14.0), 4.17 (2H, dd, J=14.0, 7.0), 4.22-4.30 (1H, m), 4.50 (1H, m), 4.74 (2H, m), 4.77-4.81 (1H, m), 6.63 (1H, s), 7.04-7.14 (2H, m), 7.27-7.32 (1H, m), 7.36-7.40 (1H, m).

More polar isomer (E)-4-(Acetylsulfanyl)-1-[2-cyclopropyl-1-(2-fluorophenyl)-2-oxoethyl]-3-({1-[2-(ethoxycarbonyl)ethyl]-1H-tetrazol-5-yl}methylidene)piperidine: colourless oil (311 mg, yield: 16%). ¹H NMR (400 MHz, CDCl₃) δ ppm: 0.75-0.86 (2H, m), 0.96-1.05 (2H, m), 1.23-1.28 (3H, m), 1.89-1.97 (1H, m), 2.06-2.11 (1H, m), 2.26-2.29 (1H, m), 2.82 and 2.84 (total 3H, each s), 2.72-2.81 (1H, m), 2.91-2.95 (1H, m), 3.00-3.04 (2H, m), 3.37 and 3.51 (total 1H, each d, J=13.5), 4.10-4.19 (2H, m), 4.36 (1H, d, J=13.5), 4.51-4.57 (3H, m), 4.79 (1H, d, J=6.0), 6.50 (1H, s), 7.05-7.18 (2H, m), 7.31-7.37 (2H, m).

Example 257

(E)-3-{[2-(2-Carboxyethyl)-2H-tetrazol-5-yl]methylidene}-1-[2-cyclopropyl-1-(2-fluorophenyl)-2-oxoethyl]-4-sulfanylpiperidine hydrochloride (Exemplification Compound No. 2-1597)

The title compound (232 mg) was synthesized in a yield of 37% as a colourless amorphous solid using (E)-4-(acetylsulfanyl)-1-[2-cyclopropyl-1-(2-fluorophenyl)-2-oxoethyl]-3-({2-[2-(ethoxycarbonyl)ethyl]-2H-tetrazol-5-yl}methylidene)piperidine (674 mg) by conducting similar procedure to that mentioned in Examples 133 and 134 successively.
¹H NMR (400 MHz, CDCl₃) δ ppm: 0.70-0.76 (2H, m), 0.95-1.01 (1H, m), 1.11-1.16 (1H, m), 1.88-1.95 (1H, m), 2.28-2.37 (1H, m), 2.41-2.50 (1H, m), 2.72-2.80 (2H, m), 2.93-3.05 (1H, m), 3.30-3.37 (2H, m), 4.04 (1H, bs), 4.18 and 4.32 (total 1H, each d, J=13.0), 4.30 (1H, s), 5.00 (1H, s), 5.06-5.12 (2H, m), 6.92 (1H, s), 7.18-7.24 (1H, m), 7.31-7.38 (1H, m), 7.66-7.71 (1H, m).
IR (KBr, cm⁻¹): 1712, 1191.

Example 258

(E)-3-{[1-(2-Carboxyethyl)-1H-tetrazol-5-yl]methylidene}-1-[2-cyclopropyl-1-(2-fluorophenyl)-2-oxoethyl]-4-sulfanylpiperidine hydrochloride (Exemplification Compound No. 2-1533)

The title compound (108.6 mg) was synthesized in a yield of 38% as a colourless amorphous solid using (E)-4-(acetylsulfanyl)-1-[2-cyclopropyl-1-(2-fluorophenyl)-2-oxoethyl]-

3-({1-[2-(ethoxycarbonyl)ethyl]-1H-tetrazol-5-yl}methylidene)piperidine (Example 256, more polar isomer, 311 mg) by conducting a similar procedure to that mentioned in Examples 133 and 134 successively.

$^1$H NMR (400 MHz, CDCl$_3$) δ ppm: 0.67-0.72 (2H, m), 0.94-1.00 (1H, m), 1.08-1.16 (1H, m), 1.87-1.96 (1H, m), 2.29-2.37 (1H, m), 2.38-2.44 (1H, m), 2.65-2.70 and 2.78-2.83 (total 1H, each m), 2.88-2.94 (1H, m), 3.05-3.11 (1H, m), 3.29 (2H, t, J=6.5), 4.02-4.05 and 4.09-4.12 (total 1H, each m), 4.17 and 4.23 (total 1H, each d, J=13.0), 4.40 (1H, dd, J=13.0, 8.0), 4.82 (2H, d, J=6.5), 5.01 and 5.02 (total 1H, each s), 6.99 and 7.04 (total 1H, each s), 7.14-7.20 (1H, m), 7.26-7.31 (1H, m), 7.60-7.65 (1H, m);

IR (KBr, cm$^{-1}$): 1712, 1190.

Example 259

(Z)-4-(Acetylsulfanyl)-1-[2-cyclopropyl-1-(2-fluorophenyl)-2-oxoethyl]-3-{[1(2)H-tetrazol-5-yl]methylidene)piperidine hydrogen trifluoroacetate (Exemplification Compound No. 4-170)

(a) (E)-3-(2-Acetoxyethylidene)-1-(t-butoxycarbonyl)-4-(t-butyldimethylsilyloxy)piperidine To a solution of (E)-4-(t-butyldimethylsilyloxy)piperidin-3-(2-hydroxyethylidene)-1-(triphenylmethyl)piperidine [Example 36(b), 20 g] in dichloromethane (100 ml) were added triethylamine (17 ml) and acetic anhydride (11 ml) at 0° C. The resulting mixture was stirred at room temperature overnight, and partitioned between water and ethyl acetate. The separated organic layer was washed with a saturated aqueous sodium chloride solution, and dried over anhydrous sodium sulfate. The solvent was evaporated in vacuo to afford crude (E)-3-(2-acetoxyethylidene)-4-(t-butyldimethylsilyloxy)-1-(triphenylmethyl)piperidine (22.6 g).

To a solution of above compound in dichloromethane (100 ml) was added trifluoroacetic acid (3.2 ml) at 0° C. The resulting mixture was stirred at room temperature for 3.5 hours, and trifluoroacetic acid (3.2 ml) was added further. The solvent was evaporated in vacuo, and the residue was purified by chromatography on silica gel using a mixture of dichloromethane and methanol (19:1 to 9:1) as the eluent to afford crude (E)-3-(2-acetoxyethylidene)-4-(t-butyldimethylsilyloxy)piperidine hydrogen trifluoroacetate (12.9 g) as a yellow oil.

To a solution of above salt in dichloromethane (100 ml) were added triethylamine (9.5 ml) and di(t-butyl)dicarbonate (7.5 g) at 0° C. The resulting mixture was concentrated in vacuo, and the residue was purified by chromatography on silica gel using a mixture of hexane and ethyl acetate (5:1 to 1:1) as the eluent to afford the title compound as a colourless oil (13.8 g, yield: 77%).

$^1$H NMR (400 MHz, CDCl$_3$) δ ppm: 0.04 (3H, s), 0.07 (3H, s), 0.90 (9H, s), 1.45 (9H, s), 1.57-1.66 (1H, m), 1.75-1.86 (1H, m), 2.05 (3H, s), 3.34-3.42 (1H, m), 3.63-3.75 (1H, m), 3.78-3.90 (1H, m), 4.15-4.24 (2H, m), 4.62-4.73 (2H, m), 5.56-5.61 (1H, m).

(b) 1-(t-Butoxycarbonyl)-4-(t-butyldimethylsilyloxy)piperidin-3-one

To a solution of (E)-3-(2-acetoxyethylidene)-1-(t-butoxycarbonyl)-4-(t-butyldimethylsilyloxy)piperidine (9.9 g) in dichloromethane (100 ml) was introduced gaseous ozone at −78° C. for 2 hours. After the excess ozone was removed by bubbling nitrogen gas for 1 hour, triphenylphosphine (13 g) was added at the same temperature. The resulting mixture was stirred at room temperature for one hour, and concentrated in vacuo. The residue was purified by chromatography on silica gel using a mixture of hexane, ethyl acetate and dichloromethane (5:1:1 to 1:1:1) as the eluent to afford the title compound as a light yellow oil (4.6 g, yield: 56%).

$^1$H NMR (500 MHz, CDCl$_3$) δ ppm: 0.07 (3H, s), 0.12 (3H, s), 0.90 (9H, s), 1.45 (9H, s), 1.90-2.00 (1H, m), 2.11-2.19 (1H, m), 3.50 (1H, m), 3.76-4.01 (2H, m), 4.15-4.21 (2H, m).

(c) (Z)-1-(t-Butoxycarbonyl)-4-(t-butyldimethylsilyloxy)-3-(cyanomethylidene)piperidine To a solution of trimethylsilylacetonitrile (1.3 ml) in tetrahydrofuran (THF) (30 ml) was added at −78° C. lithium diisopropylamide (2.0 M in hexane, 4.7 ml). The resulting mixture was stirred at −78° C. for 0.5 hours, and then a solution of 1-(t-butoxycarbonyl)-4-(t-butyldimethylsilyloxy)piperidin-3-one (3 g) in THF (10 ml) was added at the same temperature. The resulting mixture was stirred for one hour while the temperature was raised to room temperature. The mixture was concentrated in vacuo, and the residue was purified by chromatography on silica gel using a mixture of hexane and ethyl acetate (9:1) as the eluent to afford the title compound (880 mg, yield: 27%) as the less polar isomer as a yellow oil.

$^1$H NMR (500 MHz, CDCl$_3$) δ ppm: 0.10 (3H, s), 0.15 (3H, s), 0.90 (9H, s), 1.45 (9H, s), 1.68-1.86 (2H, m), 3.25-3.40 (1H, m), 3.68-4.01 (2H, m), 4.15-4.45 (1H, m), 4.85 (1H, m), 5.19-5.29 (1H, m).

Further elution gave the geometrical isomer (E)-1-(t-butoxycarbonyl)-4-(t-butyldimethylsilyloxy)-3-(cyanomethylidene)piperidine (1040 mg, yield: 32%).

(d) (Z)-1-(t-Butoxycarbonyl)-4-(t-butyldimethylsilyloxy)-3-{[1(2)H-tetrazol-5-yl]methylidene}piperidine A mixture of (Z)-1-(t-butoxycarbonyl)-4-(t-butyldimethylsilyloxy)-3-(cyanomethylidene)piperidine (1.09 g), 1,2-dimethoxyethane (30 ml) and tributyltin azide (1.3 ml) was stirred at 110° C. for 7 days. After the reaction mixture was cooled, the solvent was evaporated in vacuo. The residue was purified by chromatography on silica gel using a mixture of hexane and ethyl acetate (4:1) as the eluent to afford the title compound as a colourless solid (750 mg, yield: 61%).

$^1$H NMR (400 MHz, CDCl$_3$) δ ppm: 0.10 (3H, s), 0.19 (3H, s), 0.96 (9H, s), 1.60 (9H, s), 1.85-2.02 (2H, m), 3.53-3.66 (1H, m), 3.97-4.08 (1H, m), 4.12-4.23 (1H, m), 4.45-4.56 (1H, m), 6.19-6.29 (1H, m), 6.48 (1H, bs).

(e) (Z)-1-(t-Butoxycarbonyl)-4-(t-butyldimethylsilyloxy)-3-{[2-(4-methoxybenzyl)-2H-tetrazol-5-yl]methylidene}piperidine and (Z)-1-(t-butoxycarbonyl)-4-(t-butyldimethylsilyloxy)-3-{[1-(4-methoxybenzyl)-1H-tetrazol-5-yl]methylidene}piperidine To a solution of (Z)-1-(t-butoxycarbonyl)-4-(t-butyldimethylsilyloxy)-3-{[1(2)H-tetrazol-5-yl]methylidene}piperidine (750 mg) in a mixed solvent of dichloromethane (10 ml) and acetonitrile (10 ml) were added triethylamine (530 μl) and 4-methoxybenzyl chloride (520 μl). The resulting mixture was stirred at 80° C. for 2.5 hours, and triethylamine (530 μl) and 4-methoxybenzylchloride (260 μl) were added further. After the reaction mixture was cooled, it was concentrated in vacuo, and the residue was purified by chromatography on silica gel using a mixture of hexane and ethyl acetate (3:1) as the eluent to afford each of the two title isomers (which product corresponds to which isomer is not yet determined).

Less polar isomer: 500 mg, yield: 51%, an yellow oil. $^1$H NMR (500 MHz, CDCl$_3$) δ ppm: 0.16 (3H, s), 0.22 (3H, s), 1.04 (9H, s), 1.66 (9H, s), 1.90-2.01 (2H, m), 3.46-3.65 (1H, m), 4.01 (3H, s), 4.05-4.28 (2H, m), 4.41-4.69 (1H, m), 5.85 (1H, d, J=14.5), 5.93 (1H, d, J=14.5), 6.01 (1H, m), 6.50-6.62 (1H, m), 7.10 (2H, d, J=8.5), 7.54 (2H, d, J=8.5).

More polar isomer: 330 mg, yield: 33%.

(f) (Z)-1-(t-Butoxycarbonyl)-3-{[2-(4-methoxybenzyl)-2H-tetrazol-5-yl]methylidene}piperidin-4-ol, or (Z)-1-(t-butoxycarbonyl)-3-{[1-(4-methoxybenzyl)-1H-tetrazol-5-yl]methylidene}piperidin-4-ol To a solution of the less polar isomer obtained as above (500 mg) in tetrahydrofuran (THF, 5 ml) was added tetrabutylammonium fluoride (1.0 M in THF, 2.0 ml). The resulting mixture was stirred at room temperature for 1.75 hours, and tetrabutylammonium fluoride M in THF, 0.5 ml) was added further. The reaction mixture was stirred at room temperature for 0.25 hours, and tetrabutylammonium fluoride (1.0 M in THF, 0.5 ml) was added still further. The reaction mixture was stirred for 0.25 hours, and concentrated in vacuo. The residue was purified by chromatography on silica gel using a mixture of dichloromethane and methanol (19:1) as the eluent to afford either one of the two title compounds as a yellow oil (460 mg, yield: quantitative).

$^1$H NMR (500 MHz, CDCl$_3$) δ ppm: 1.46 (9H, s), 1.90-2.02 (2H, m), 3.44-3.69 (2H, m), 3.80 (3H, s), 4.21-4.37 (1H, m), 5.03-5.16 (1H, m), 5.67 (1H, d, J=14.0), 5.71 (1H, d, J=14.0), 6.44-6.55 (1H, m), 6.90 (2H, d, J=8.5), 7.35 (2H, d, J=8.5).

(g) (Z)-4-(Acetylsulfanyl)-3-{[2-(4-methoxybenzyl)-2H-tetrazol-5-yl]methylidene}piperidine hydrochloride, or (Z)-4-(acetylsulfanyl)-3-{[1-(4-methoxybenzyl)-1H-tetrazol-5-yl]methylidene}piperidine hydrochloride A solution of the compound obtained as above (480 mg), dichloromethane (10 ml), triethylamine (400 µl) and methanesulfonylchloride (220 µl) was stirred at room temperature for 2 hours. The reaction mixture was partitioned between water and dichloromethane, the separated organic layer was washed with water, and dried over anhydrous sodium sulfate. The solvent was evaporated in vacuo to afford crude mesilate. To a solution of the mesilate in dimethyl sulfoxide was added potassium thioacetate (680 mg). The reaction mixture was stirred at 50° C. for 30 minutes, and partitioned between water and ethyl acetate. The separated organic layer was washed with water and saturated aqueous sodium chloride successively, and dried over anhydrous sodium chloride. The solvent was evaporated in vacuo to afford crude thioacetate as a brown oil (520 mg). The above oil was treated with 4 N solution of hydrogen chloride in dioxane (10 ml) at room temperature for 0.5 hour. The solvent and excess hydrogen chloride were evaporated in vacuo, and the residue was purified by chromatography on silica gel using a mixture of dichloromethane and methanol (19:1 to 9:1) as the eluent to afford either one of the two title compounds as a yellow solid (190 mg, overall yield: 39%).

$^1$H NMR (500 MHz, DMSO-d$_6$) δ ppm: 1.93-2.00 (1H, m), 2.18-2.27 (1H, m), 2.35 (3H, s), 3.10-3.18 (1H, m), 3.27-3.37 (1H, m), 3.68 (1H, d, J=14.0), 3.74 (3H, s), 4.02 (1H, d, J=14.0), 5.75 (1H, m), 5.82 (1H, d, J=14.5), 5.87 (1H, d, J=14.5), 6.80 (1H, bs), 6.94 (2H, d, J=8.5), 7.36 (2H, d, J=8.5).

(h) (Z)-4-(Acetylsulfanyl)-1-[2-cyclopropyl-1-(2-fluorophenyl)-2-oxoethyl]-3-{[1(2)H-tetrazol-5-yl}methylidene)piperidine hydrogen trifluoroacetate A solution of the compound obtained in (g) (190 mg), acetonitrile (5 ml), N,N-dimethylformamide (5 ml), 2-bromo-2-(2-fluorophenyl)-1-cyclopropylethanone (225 mg) and triethylamine (240 µl) was stirred at room temperature for 1.5 hours. The reaction mixture was concentrated in vacuo, and the obtained yellow oily residue was partitioned between ethyl acetate and water. The separated organic layer was concentrated, and the residue was purified by chromatography on silica gel using a mixture of hexane, ethyl acetate and dichloromethane (2:1:1) as the eluent to afford the desired alkylated product as a yellow amorphous solid (150 mg).

The above product was treated with trifluoroacetic acid (8 ml) at 60~70° C. for 3 hours. After the reaction mixture was cooled to room temperature, it was concentrated in vacuo, and the residue was purified by chromatography on silica gel using a mixture of dichloromethane and methanol (9:1) as the eluent to afford the title product as a yellow oil (150 mg, overall yield: 58%).

$^1$H NMR (400 MHz, pyridine-d$_5$) δ ppm: 0.75-0.90 (2H, m), 1.00-1.17 (2H, m), 2.01-2.12 (1H, m), 2.21 (3H, s), 2.37-2.52 (2H, m), 2.54-2.63 and 2.76-2.85 (total 1H, each m), 2.95-3.02 and 3.05-3.13 (total 1H, each m), 3.13 and 3.29 (total 1H, each d, J=12.5), 3.65 and 3.75 (total 1H, each d, J=12.5), 4.96 and 5.01 (total 1H, each s), 6.50 (1H, m), 6.78 and 6.83 (total 1H, each bs), 7.22-7.28 (2H, m), 7.31-7.38 (1H, m), 7.61-7.69 (1H, m).

Example 260

(Z)-3-{[1(2)H-Tetrazol-5-yl]methylidene}-1-[2-cyclopropyl-1-(2-fluorophenyl)-2-oxoethyl]-4-sulfanylpiperidine hydrochloride (Exemplification Compound No. 4-169)

The title compound (70 mg) was synthesized in a yield of 60% as a colourless amorphous solid using (Z)-4-(acetylsulfanyl)-1-[2-cyclopropyl-1-(2-fluorophenyl)-2-oxoethyl]-3-{[1(2)H-tetrazol-5-yl}methylidene)piperidine hydrogen trifluoroacetate (150 mg) as the starting material by conducting a similar procedure to that mentioned in Example 133.

$^1$H NMR (500 MHz, pyridine-d$_5$) δ ppm: 0.76-0.92 (2H, m), 0.99-1.15 (2H, m), 1.82-1.96 (1H, m), 2.28-2.51 (2H, m), 2.62-2.70 and 2.85-2.95 and 2.98-3.04 (total 2H, each m), 3.50 and 3.60 (total 1H, each d, J=12.5), 3.61 and 3.73 (total 1H, each d, J=12.5), 4.94 and 5.00 (total 1H, each s), 5.83-5.87 (1H, m), 6.56 and 6.64 (total 1H, each s), 7.22-7.29 (2H, m), 7.34-7.41 (1H, m), 7.64-7.69 (1H, m);

IR (KBr, cm$^{-1}$): 2560, 1711.

Example 261

(E)-4-(Acetylsulfanyl)-3-{[1-(3-carboxypropyl)-1H-1,2,3-triazol-5-yl]methylidene}-1-[2-cyclopropyl-1-(2-fluorophenyl)-2-oxoethyl]piperidine (Exemplification Compound No. 2-1217)

To a solution of (E)-3-{[1-(3-carboxypropyl)-1H-1,2,3-triazol-5-yl]methylidene}-1-[2-[2-cyclopropyl-1-(2-fluororophenyl)-2-oxoethyl]-4-sulfanylpiperidine hydrochloride (Example 140, 510 mg) in dichloromethane (5 ml) were added pyridine (250 μl) and acetic anhydride (150 μl). The resulting mixture was stirred at room temperature for 2 hours while further pyridine (98 μl) and acetic anhydride (113 μl) were added. The reaction mixture was concentrated in vacuo, and the residue was purified by chromatography on silica gel using a mixture of dichloromethane and methanol (29:1) as the eluent to afford the title product as a colourless oil (450 mg, yield: 83%).

$^1$H NMR (500 MHz, pyridine-$d_5$) δ ppm: 0.63-0.79 (2H, m), 0.95-1.10 (2H, m), 1.87-1.98 (1H, m), 2.15 (3H, s), 2.24-2.41 (4H, m), 2.57 (2H, t, J=7.0), 2.60 and 2.69 (total 1H, each m), 2.81-2.88 and 2.90-2.98 (total 1H, each m), 3.26 and 3.44 (total 1H, each d, J=13.0), 3.90 (1H, d, J=13.0), 4.58 (2H, t, J=7.0), 4.70-4.74 (1H, m), 4.98 and 5.00 (total 1H, each s), 6.75 and 6.76 (total 1H, each bs), 7.18-7.26 (2H, m), 7.30-7.37 (1H, m), 7.55-7.66 (1H, m), 7.94 and 7.99 (total 1H, each bs).

Example 262

(E)-1-[2-Cyclopropyl-1-(2-fluorophenyl)-2-oxoethyl]-3-({1-[3-(N-hydroxycarbamoyl)propyl]-1H-1,2,3-triazol-5-yl}methylidene)-4-sulfanylpiperidine hydrochloride (Exemplification Compound No. 2-1265)

To a solution of (E)-4-(acetylsulfanyl)-3-{[1-(3-carboxypropyl)-1H-1,2,3-triazol-5-yl]methylidene}-1-[2-[2-cyclopropyl-1-(2-fluorophenyl)-2-oxoethyl]piperidine (450 mg) in dichloromethane (5 ml) were added isobutyl chloroformate (270 μl) and triethylamine (375 μl) at 0° C. The resulting mixture was stirred at room temperature for 10 minutes, and O-(t-butyldimethylsilyl)hydroxylamine (300 mg) was added. The resulting mixture was stirred at room temperature for one hour, concentrated in vacuo, and the residue was purified by chromatography on silica gel using a mixture of dichloromethane and methanol (19:1) as the eluent to afford (E)-4-(acetylsulfanyl)-3-[(1-{3-[N-(t-butyldimethylsilyloxy)carbamoyl]propyl}-1H-1,2,3-triazol-5-yl)methylidene]-1-[2-cyclopropyl-1-(2-fluorophenyl)-2-oxoethyl]piperidine (330 mg, with some impurities) as a colourless oil.

To a solution of above oil in dichloromethane (5 ml) was added 4 N solution of hydrogen chloride in dioxane (530 μl). The resulting mixture was stirred at room temperature for 30 minutes, and concentrated in vacuo to afford crude (E)-4-(acetylsulfanyl)-1-[2-cyclopropyl-1-(2-fluorophenyl)-2-oxoethyl]-3-({1-[3-(N-hydroxycarbamoyl)propyl]-1H-1,2,3-triazol-5-yl}methylidene)piperidine hydrochloride.

To a solution of above compound in methanol (5 ml) was added sodium carbonate (150 mg). The solution was stirred at room temperature for 30 minutes and 4 N solution of hydrogen chloride in dioxane (800 μl) was also added. The resulting reaction mixture was concentrated in vacuo and the residue was purified by preparative HPLC (YMC-Pack ODS-A; YMC, eluent: acetonitrile/0.024 N HCl, 20/80, v/v) to afford the title compound as a colourless amorphous solid (60 mg, overall yield: 13%).

$^1$H NMR (500 MHz, pyridine-$d_5$) δ ppm: 0.63-0.81 (2H, m), 0.92-1.06 (2H, m), 1.84-1.95 (1H, m), 2.23-2.48 (6H, m), 2.65-2.78 (1H, m), 2.83-3.01 (1H, m), 3.59 (1H, d, J=12.5), 3.70 and 3.78 (total 1H, each d, J=12.5), 4.09-4.14 (1H, m), 4.53 (2H, t, J=7.0), 4.96 and 4.97 (total 1H, each s), 6.72 and 6.73 (total 1H, each bs), 7.20-7.27 (2H, m), 7.32-7.39 (1H, m), 7.59-7.66 (1H, m), 7.85 and 7.91 (total 1H, each bs)

IR (KBr, cm$^{-1}$): 2558, 1710, 1651..

Example 263

(E)-4-(Acetylsulfanyl)-3-{[1-(3-carboxypropyl)-1H-1,2,3-triazol-4-yl]methylidene}-1-[2-cyclopropyl-1-(2-fluorophenyl)-2-oxoethyl]piperidine (Exemplification Compound No. 2-1154)

The title compound (410 mg) was synthesized in a yield of 85% as a colourless oil using (E)-3-{[1-(3-carboxypropyl)-1H-1,2,3-triazol-4-yl]methylidene}-1-[2-cyclopropyl-1-(2-fluorophenyl)-2-oxoethyl]-4-sulfanylpiperidine hydrochloride (Example 143, 500 mg) as the starting material by conducting a similar procedure to that mentioned in Example 261.

$^1$H NMR (500 MHz, pyridine-$d_5$) δ ppm: 0.66-0.79 (2H, m), 0.98-1.06 (1H, m), 1.09-1.22 (1H, m), 1.90-2.01 (1H, m), 2.15 (3H, s), 2.28-2.47 (4H, m), 2.54 (2H, m), 2.69 and 2.75 (total 1H, each m), 2.88-2.98 (1H, m), 3.52 and 3.57 (total 1H, each d, J=12.5), 4.46-4.57 (3H, m), 4.76 (1H, m), 5.00 and 5.02 (total 1H, each s), 6.90 and 6.92 (total 1H, each bs), 7.18-7.26 (2H, m), 7.30-7.39 (1H, m), 7.63-7.71 (1H, m), 7.86 and 7.95 (total 1H, each bs).

Example 264

(E)-1-[2-Cyclopropyl-1-(2-fluorophenyl)-2-oxoethyl]-3-({1-[3-(N-hydroxycarbamoyl)propyl]-1H-1,2,3-triazol-4-yl}methylidene)-4-sulfanylpiperidine hydrochloride (Exemplification Compound No. 2-1201)

The title compound (70 mg) was synthesized in a yield of 16% as a colourless amorphous solid using (E)-4-(acetylsulfanyl)-3-{[1-(3-carboxypropyl)-1H-1,2,3-triazol-4-yl]methylidene}-1-[2-cyclopropyl-1-(2-fluorophenyl)-2-oxoethyl]piperidine (410 mg) as the starting material by conducting a similar procedure to that mentioned in Example 262.

$^1$H NMR (500 MHz, pyridine-$d_5$) δ ppm: 0.64-0.80 (2H, m), 0.94-1.04 (1H, m), 1.07-1.18 (1H, m), 1.84-1.95 (1H, m), 2.29-2.51 (6H, m), 2.73-2.82 (1H, m), 2.90-2.98 and 3.00-3.08 (total 1H, each m), 3.97-4.10 and 4.23-4.31 (total 3H, each m), 4.48-4.58 (2H, m), 5.02 (1H, bs), 6.78 and 6.81 (total 1H, each bs), 7.18-7.29 (2H, m), 7.34-7.44 (1H, m), 7.65-7.75 (1H, m), 7.86 and 7.97 (total 1H, each bs).

IR (KBr, cm$^{-1}$): 1710, 1653.

Example 265

(Z)-4-(Acetylsulfanyl)-1-[2-cyclopropyl-1-(2-fluorophenyl)-2-oxoethyl]-3-{[5-(ethoxycarbonyl)-1H-1,2,3-triazol-4-yl]methylidene)piperidine hydrochloride (Exemplification Compound No. 1-213)

(a) Ethyl 5-formyl-1-(4-methoxybenzyl)-1H-1,2,3-triazole-4-carboxylate, and ethyl 4-formyl-1-(4-methoxybenzyl)-1H-1,2,3-triazole-5-carboxylate To a solution of trimethyl(prop-2-ynyloxy)silane (15 ml) in tetrahydrofuran (100 ml) was added butyllithium (2.6 M in hexane, 38 ml) at −78° C. The resulting mixture was stirred at the same temperature for 0.5 hour, and ethyl chloroformate (10 ml) was added thereto. The resulting mixture was stirred at −78° C. for 1.5 hours, and poured into ice water. The resulting materials were extracted with ethyl acetate. The organic layer was washed with water and saturated aqueous sodium chloride solution successively. The extract was dried over anhydrous sodium sulfate, and the solvents were evaporated in vacuo to afford ethyl 4-(trimethylsilyloxy)but-2-ynoate (16.5 g).

A solution of the above compound (16.5 g) and 4-methoxybenzyl azide in toluene (200 ml) was stirred at 120° C. for 8 hours. When the reaction mixture was cooled to room temperature, tetrabutylammonium fluoride (1.0 M in tetrahydrofuran) was added to the mixture, and the resulting mixture was stirred at room temperature for 0.5 hour. The mixture was partitioned between water and ethyl acetate. The separated organic layer was washed with water and saturated aqueous sodium chloride solution successively, dried over anhydrous sodium sulfate. Solvents were evaporated in vacuo to afford a mixture of ethyl 5-(hydroxymethyl)-1-(4-methoxybenzyl)-1H-1,2,3-triazole-4-carboxylate and ethyl 4-(hydroxymethyl)-1-(4-methoxybenzyl)-1H-1,2,3-triazole-5-carboxylate (25 g) as a brown oil.

The above-described crude product (26 g, including the product similarly obtained in another study) was dissolved in dichloromethane (500 ml), and molecular sieves 4A (50 g) was added thereto. While the mixture was being stirred at 20° C., pyridinium dichromate (47 g) was added over a period of 30 minutes. The resulting mixture was stirred at room temperature for 1.5 hours, and filtrated. The precipitate was washed with dichloromethane. The filtrate and the washing liquid were combined. Solvents were evaporated in vacuo, and the residue was purified by chromatography on silica gel using a mixture of dichloromethane and methanol (19:1) as the eluent to afford a mixture of the two title compounds as a brown oil. The mixture was purified again by chromatography on silica gel to obtain the less polar isomer of the two title compounds as a yellow oil (10.9 g).

$^1$H NMR (500 MHz, CDCl$_3$) δ ppm: 1.44 (3H, t, J=7.0), 3.77 (3H, s), 4.50 (2H, q, J=7.0), 5.85 (2H, s), 6.84 (2H, d, J=9.0), 7.33 (2H, d, J=9.0), 10.47 (1H, s).

(b) (E)-3-{[4-(Ethoxycarbonyl)-1-(4-methoxybenzyl)-1H-1,2,3-triazol-5-yl]methylidene}-1-(triphenylmethyl)piperidin-4-one, or (E)-3-{[5-(Ethoxycarbonyl)-1-(4-methoxybenzyl)-1H-1,2,3-triazol-4-yl]methylidene}-1-(triphenylmethyl)piperidin-4-one By treating the less polar isomer obtained in Example 265 (a) (10.9 g) with 1-(triphenylmethyl)piperidin-4-one (14.0 g) in a similar manner to that described in Example 132 (c), one of the two title compounds (the regioisomer corresponding to the starting material used, 7.2 g, yield: 31%) was obtained as a pale yellow solid.

$^1$H NMR (400 MHz, CDCl$_3$) δ ppm: 1.30 (3H, t, J=7.0), 2.59 (2H, bs), 2.75 (2H, t, J=6.0), 2.92 (2H, bs), 3.77 (3H, s), 4.28 (2H, q, J=7.0), 5.40 (2H, s), 6.86 (2H, d, J=8.5), 7.10-7.23 (12H, m), 7.24-7.32 (6H, m).

(c) (E)-3-{[4-(Ethoxycarbonyl)-1-(4-methoxybenzyl)-1H-1,2,3-triazol-5-yl]methylidene}-1-(triphenylmethyl)piperidin-4-ol, or (E)-3-{[5-(ethoxycarbonyl)-1-(4-methoxybenzyl)-1H-1,2,3-triazol-4-yl]methylidene}-1-(triphenylmethyl)piperidin-4-ol Using the compound obtained in (b) (3.6 g) as the starting material, one of the two title compounds (the corresponding regioisomer to the starting material used in (b), 3.6 g, yield: quantitative) was obtained as a colourless solid.

$^1$H NMR (500 MHz, CDCl$_3$) δ ppm: 1.32 (3H, m), 1.81-1.93 (2H, m), 1.95-2.03 (1H, m), 2.06-2.14 (1H, m), 2.83-2.99 (1H, m), 3.09-3.34 (1H, m), 3.77 (3H, s), 4.05-4.16 (1H, m), 4.33 (2H, m), 5.44 (2H, m), 6.39 (1H, bs), 6.82-6.92 (2H, m), 6.97-7.22 (17H, m).

(d) (E)-4-(Acetylsulfanyl)-3-{[4-(ethoxycarbonyl)-1-(4-methoxybenzyl)-1H-1,2,3-triazol-5-yl] methylidene}piperidine hydrogen trifluoroacetate, or (E)-4-(acetylsulfanyl)-3-{[5-(ethoxycarbonyl)-1-(4-methoxybenzyl)-1H-1,2,3-triazol-4-yl] methylidene}piperidine hydrogen trifluoroacetate Using the compound (3.6 g) obtained in (c) as the starting material, the reaction was conducted in a similar manner to that described in Example 132(e). The crude products were purified by chromatography on silica gel using a mixture of hexane and ethyl acetate (1:1) as the eluent to afford either one (the regioisomer corresponding to the starting material used in (b)) of (E)-4-(acetylsulfanyl)-3-{[4-(ethoxycarbonyl)-1-(4-methoxybenzyl)-1H-1,2,3-triazol-5-yl]methylidene}-1-(triphenylmethyl)piperidine, or (E)-4-(acetylsulfanyl)-3-{[5-(ethoxycarbonyl)-1-(4-methoxybenzyl)-1H-1,2,3-triazol-4-yl]methylidene}-1-(triphenylmethyl) piperidine (2.6 g, yield: 65%) as an orange amorphous solid.

The triphenylmethyl group of the above compound was removed in a similar manner to that described in Example 132 (f), and the crude product was purified by chromatography on silica gel using a mixture of dichloromethane and methanol (19:1 to 9:1) as the eluent to afford either of the two title compounds (the regioisomer corresponding to the starting material used in (b), 1.7 g, yield in the removal step of the triphenylmethyl group: 52%) as an orange amorphous solid.

$^1$H NMR (400 MHz, CDCl$_3$) δ ppm: 1.39 (3H, t, J=7.0), 2.11-2.20 (1H, m), 2.36-2.52 (1H, m), 2.40 (3H, s), 3.21-3.31 (1H, m), 3.33-3.42 (1H, m), 3.52 (1H, d, J=14.5), 3.63 (1H, d, J=14.5), 3.80 (3H, s), 4.37 (2H, q, J=7.0), 4.54 (1H, m), 5.39 (1H, d, J=15.0), 5.45 (1H, d, J=15.0), 6.38 (1H, s), 6.87 (2H, d, J=8.5), 7.17 (2H, d, J=8.5).

(e) (Z)-4-(Acetylsulfanyl)-1-[2-cyclopropyl-1-(2-fluorophenyl)-2-oxoethyl]-3-{[5-(ethoxycarbonyl)-1H-1,2,3-triazol-4-yl}methylidene)piperidine hydrochloride The compound (1.7 g) obtained in (d) was treated with 2-bromo-2-(2-fluorophenyl)-1-cyclopropylethanone (1.0 g) in a similar manner to that described in Example 132 (g). The crude product was purified by chromatography on silica gel using a mixture of hexane and ethyl acetate (1:1) as the eluent to afford either one (the regioisomer corresponding to the starting material used in (b)) of (E)-4-(acetylsulfanyl)-3-{[4-(ethoxycarbonyl)-1-(4-methoxybenzyl)-1H-1,2,3-triazol-5-yl}methylidene)-1-[2-cyclopropyl-1-(2-fluorophenyl)-2-oxoethyl]piperidine, or (E)-4-(acetylsulfanyl)-3-{[5-(ethoxycarbonyl)-1-(4-methoxybenzyl)-1H-1,2,3-triazol-4-yl}methylidene)-1-[2-cyclopropyl-1-(2-fluorophenyl)-2-oxoethyl]piperidine (2.0 g with some impurities) as a yellow amorphous solid.

The compound obtained as above was treated with trifluoroacetic acid at 80° C. for one hour. After the mixture was cooled to room temperature, saturated aqueous sodium hydrogencarbonate was added to the reaction mixture, and the products were extracted with ethyl acetate. The organic layer was washed with a saturated aqueous sodium chloride solution and dried over anhydrous sodium sulfate. The solvent was evaporated in vacuo, and the residue was purified by chromatography on silica gel using a mixture of dichloromethane and methanol (19:1) as the eluent to afford the free base of the title compound. This free base was treated with 4N hydrogen chloride in dioxane (0.5 ml), and the solvent and excess HCl were removed in vacuo to afford the title compound as a pale yellow amorphous solid (440 mg, overall yield: 23%).

$^1$H NMR (500 MHz, pyridine-$d_5$) δ ppm: 0.61-0.75 (2H, m), 0.90-0.98 (1H, m), 1.04-1.15 (1H, m), 1.30 (3H, t, J=7.0), 1.94-2.06 (1H, m), 2.30 (3H, s), 2.35-2.54 (2H, m), 2.57-2.65 and 2.76-2.83 (total 1H, each m), 2.87-2.95 (1H, m), 3.77 and 3.80 (total 1H, each d, J=13.0), 4.40 and 4.41 (total 2H, each q, J=7.0), 4.65 and 4.82 (total 1H, each d, J=13.0), 4.85 and 4.88 (total 1H, each m), 4.98 and 5.00 (total 1H, each s), 7.12-7.30 (3H, m), 7.55 and 7.56 (total 1H, each s), 7.64-7.72 (1H, m).

IR (KBr, cm$^{-1}$): 1713.

Example 266

(E)-3-{[5-Carboxy-(1H-1,2,3-triazol-4-yl)methyliden-1-[2-cyclopropyl-1-(2-fluorophenyl)-2-oxoethyl]-4-sulfanylpiperidine hydrochloride (Exemplification Compound No. 1-210)

Using (E)-4-(acetylsulfanyl)-1-[2-cyclopropyl-1-(2-fluorophenyl)-2-oxoethyl]-3-{[5-(ethoxycarbonyl)-1H-1,2,3-triazol-4-yl}methylidene)piperidine hydrochloride (380 mg) as the starting material, removal of acetyl and ethyl groups was conducted in a manner similar to that mentioned in Examples 133 and 134. The crude products were purified by preparative HPLC (YMC-Pack ODS-A; YMC, eluent: acetonitrile/0.024 N HCl, 25/75, v/v) to afford the title compound (170 mg, yield: 52%) as a colourless amorphous solid.

$^1$H NMR (500 MHz, pyridine-$d_5$) δ ppm: 0.62-0.76 (2H, m), 0.89-0.97 (1H, m), 1.07-1.18 (1H, m), 1.85-1.99 (1H, m), 2.32-2.43 (1H, m), 2.47-2.57 (1H, m), 2.72-2.83 (1H, m), 2.87-2.95 and 3.01-3.10 (total 1H, each m), 4.15 and 4.21 (total 1H, each m), 4.16 and 4.26 (total 1H, each d, J=13.0), 4.47 and 4.68 (total 1H, each d, J=13.0), 4.98 and 5.00 (total 1H, each s), 7.13-7.32 (3H, m), 7.62 and 7.64 (total 1H, each s), 7.67-7.75 (1H, m).

IR (KBr, cm$^{-1}$): 2565, 1713.

Example 267

(E)-3-{[5-Carboxy-2-(3-carboxypropyl)-2H-1,2,3-triazol-4-yl]methylidene}-1-[2-cyclopropyl-1-(2-fluorophenyl)-2-oxoethyl]-4-sulfanylpiperidine hydrochloride (Exemplification Compound No. 1-214)

A mixture of (E)-4-(acetylsulfanyl)-1-[2-cyclopropyl-1-(2-fluorophenyl)-2-oxoethyl]-3-{[5-(ethoxycarbonyl)-1H-1,2,3-triazol-4-yl}methylidene)piperidine hydrochloride (680 mg), acetonitrile (20 ml), ethyl 4-bromobutylate (300 µl) and 1,8-diazabicyclo[5.4.0]undec-7-ene (DBU) (310 µl) was stirred at room temperature for one hour, and then at 50° C. for 1.5 hours. The solvent was evaporated in vacuo, and the residue was purified by chromatography on silica gel using a mixture of hexane, ethyl acetate and dichloromethane (1:1:1) as the eluent to afford (E)-4-(acetylsulfanyl)-1-[2-cyclopropyl-1-(2-fluorophenyl)-2-oxoethyl]-3-{[5-(ethoxycarbonyl)-2-[3-(ethoxycarbonyl)propyl]-2H-1,2,3-triazol-4-yl}methylidene)piperidine (630 mg with some impurities) as a yellow oil.

The above compound was deacetylated in a similar manner to that described in Example 133. The reaction mixture was concentrated in vacuo to afford crude (E)-1-[2-cyclopropyl-1-(2-fluorophenyl)-2-oxoethyl]-3-{[5-(ethoxycarbonyl)-2-[3-(ethoxycarbonyl)propyl]-2H-1,2,3-triazol-4-yl}methylidene)-4-sulfanylpiperidine hydrochloride (620 mg with some impurities) as a yellow oil. This compound was de-ethylated in a similar manner to that described in Example 134. The residue obtained by concentration of the reaction mixture was purified by preparative HPLC (YMC-Pack ODS-A; YMC, eluent: acetonitrile/0.024 N HCl, 25/75, v/v) to afford the title compound (200 mg, overall yield: 27%) as a colourless amorphous solid.

$^1$H NMR (500 MHz, pyridine-$d_5$) δ ppm: 0.63-0.81 (2H, m), 0.91-1.00 (1H, m), 1.05-1.13 (1H, m), 1.86-1.99 (1H, m), 2.33-2.54 (4H, m), 2.59-2.68 (2H, m), 2.74-2.81 and 2.86-2.93 (total 1H, each m), 2.97-3.07 (1H, m), 3.90 and 4.19 (total 1H, each d, J=13.0), 4.13-4.20 (1H, m), 4.32 and 4.48 (total 1H, each d, J=13.0), 4.54-4.70 (2H, m), 5.00 and 5.03 (total 1H, each s), 7.18-7.30 (2H, m), 7.35-7.45 (1H, m), 7.57 and 7.60 (total 1H, each s), 7.70-7.76 (1H, m).

IR (KBr, cm$^{-1}$): 2564, 1713.

Example 268

(E)-4-(Acetylsulfanyl)-1-[2-cyclopropyl-1-(2-fluorophenyl)-2-oxoethyl]-3-({5-(ethoxycarbonyl)-2-[3-(ethoxycarbonyl)propyl]-2H-1,2,3-triazol-4-yl}methylidene)piperidine hydrochloride (Exemplification Compound No. 1-219)

Hydrogen chloride was passed through a solution of (E)-3-{[5-carboxy-2-(3-carboxypropyl)-2H-1,2,3-triazol-4-yl]methylidene}-1-[2-cyclopropyl-1-(2-fluorophenyl)-2-oxoethyl]-4-sulfanylpiperidine hydrochloride (140 mg) in ethanol (20 ml) under ice-cooling for 3 hours. The mixture was stirred under tightly sealed condition at room temperature overnight. The solvent and excess hydrogen chloride were removed in vacuo. Water was added to the residue and the resulting mixture was concentrated in vacuo to remove further solvents and hydrogen chloride. The residue was purified by chromatography on silica gel using a mixture of dichloromethane and methanol (19:1) as the eluent to afford (E)-1-[2-cyclopropyl-1-(2-fluorophenyl)-2-oxoethyl]-3-({1-(ethoxycarbonyl)-2-[3-(ethoxycarbonyl)propyl]-2H-1,2,3-triazol-3-yl}methylidene)-4-sulphanylpiperidine hydrochloride (80 mg with some impurities) as a colourless oil. To a solution of this compound in dichloromethane (5 ml) were added triethylamine (50 µl) and acetyl chloride (151). While the resulting mixture was stirred at room temperature for one hour, further triethylamine (50 µl) and acetyl chloride (15 µl) were added. The reaction mixture was concentrated in vacuo, and the residue was purified by chromatography on silica gel using a mixture of hexane, ethyl acetate, and dichloromethane (3:2:3) as the eluent to afford the free base of the title compound. To a solution of the free base in dichloromethane was added 4N hydrogen chloride in dioxane (70 µl), and the solvent and excess hydrogen chloride were removed under reduced pressure. Further purification by azeotropic evaporation with water gave the title compound as a pale yellow amorphous solid (70 mg, yield 42%).

$^1$H NMR (500 MHz, pyridine-$d_5$) δ ppm: 0.65-0.83 (2H, m), 0.94-1.02 (1H, m), 1.06-1.12 (1H, m), 1.14 and 1.15 (total 3H, each t, J=7.0), 1.31 and 1.32 (total 3H, each t, J=7.0), 1.94-2.05 (1H, m), 2.24-2.50 (6H, m), 2.32 and 2.33 (total 3H, each s), 2.69-2.78 (1H, m), 2.85-2.93 and 2.97-3.03 (total 1H, each m), 3.51 and 3.80 (total 1H, each d, J=13.5), 4.10 and 4.11 (total 2H, each q, J=7.0), 4.40 and 4.41 (total 2H, each q, J=7.0), 4.44-4.61 (3H, m), 4.78-4.83 (1H, m), 4.98 and 5.04 (total 1H, each s), 7.22-7.33 (2H, m), 7.37-7.46 (2H, m), 7.67-7.73 (1H, m).

IR (KBr, cm$^{-1}$): 1730.

Test Example 1

Confirmation of Inhibitory Activities of Test Compounds Against Platelet Coagulation In Vitro Three to four male Sprague-Dawley rats (8 weeks of age, Japan SLC., Inc.) per group were used in the present test. Platelet coagulation was determined by platelet aggregometer (MCM Hema Tracer 313M, MC Medical, Inc.) according to modified methods described by Born et al. (Journal of Physiology, vol. 168, 178 (1963)). Blood (6.3 ml) was collected from abdominal aorta of rats anesthetized with pentobarbital sodium (40 mg/kg) with a microsyringe containing 0.7 ml of sodium citrate at a concentration of 3.8% as anti-coagulant. The obtained blood containing sodium citrate was centrifuged (230×g for 15 min at room temperature) and plate-rich plasma (hereinafter referred to as PRP) fraction was isolated. Furthermore, after PRP was isolated, the blood was further centrifuged (2,000×g for 10 min at room temperature) and platelet-poor plasma (hereinafter referred to as PPP) fraction was isolated. Platelet count in PRP was determined by automated hematology analyzer (KX-21N, SYSMEX CORPORATION) and adjusted as 5×10$^8$/ml. After PRP (239 µl) was put into each cuvette, the test substance dissolved in dimethyl sulfoxide (DMSO, 1 µl) was added to the PRP solution and assessed by automated hematology analyzer. In the control group, DMSO solution (1 µl) instead of the test substance solution was added to the PRP solution. After warming at 37° C. for 1.5 min, 10 µl of adenosine-5'-diphosphate (ADP) solution (final concentration: 10 µl) was added, and platelet coagulation was induced. Platelet coagulation was determined for 5 min and the maximum rate of plate coagulation determined. The results are shown in Table 7.

TABLE 7

| Test Substance | Test Example 1 (% inhibition) (10 µg/ml) |
|---|---|
| Example 77 | 76 |
| Example 112 | 75 |
| Example 117 | 70 |
| Example 121 | 55 |
| Example 134 | 85 |
| Example 143 | 81 |
| Example 192 | 84 |
| Example 235 | 77 |
| Example 242 | 75 |
| Example 249 | 81 |
| Example 257 | 87 |
| Example 258 | 85 |
| Example 262 | 71 |

As shown in Table 7, the present invention compounds exhibited remarkable inhibiting activities against platelet coagulation. Thus compounds of the present invention may be useful as anti-coagulant agents.

Test Example 2

Confirmation of Inhibitory Activities of the Test Compounds Against Platelet Coagulation Ex Vivo Three to four male Sprague-Dawley rats (8 weeks of age, Japan SLC., Inc.) per group were used in the present test. Platelet coagulation was determined by platelet aggregometer (MCM Hema Tracer 313M, MC Medical, Inc.) according to modified methods described by Born et al. (Journal of Physiology, vol. 168, 178 (1963)). The test compounds dissolved in 5% arabic gum solution or suspended in mixed solution of 10% dimethylacetoamide, 6.4% polyethyleneglycol 400, and 16% Tween 80 solution were orally administered to the rats at a volume of 1 mL/kg 4 hrs prior to the blood collection. In the control group, the vehicle was similarly and orally administered at the rate of 1 mL/kg 4 hrs prior to the blood collection. Blood (6.3 ml) was collected from abdominal aorta of rats anesthetized with pentobarbital sodium (40 mg/kg) with a microsyringe containing 0.7 ml of sodium citrate at a concentration of 3.8% as anti-coagulant. The obtained blood containing sodium citrate was centrifuged (230×g for 15 min at room temperature) and PRP fraction was isolated. Furthermore, after PRP was isolated, the blood was further centrifuged (2,000×g for 10 min at room temperature) and PPP fraction was isolated. Platelet count in PRP was determined by automated hematology analyzer (KX-21N, SYSMEX CORPORATION) and adjusted as 5×10$^8$/ml. After PRP (240 µl) was put into each cuvette, the platelet coagulation was assessed by automated hematology analyzer. After warming at 37° C. for 1.5 min, 10 µl of ADP solution (final concentration: 3 µl) was added, and platelet coagulation was induced. Platelet coagulation was determined for 5 min and the maximum rate of plate coagulation determined. The results are shown in Table 8.

TABLE 8

| Test Substance | Test Example 2 (% inhibition) (10 µg/ml) |
|---|---|
| Example 77 | 77 |
| Example 112 | 91 |
| Example 114 | 81 |
| Example 117 | 63 |
| Example 121 | 72 |
| Example 134 | 85 |
| Example 143 | 69 |
| Example 154 | 79 |
| Example 192 | 81 |
| Example 203 | 84 |
| Example 235 | 54 |
| Example 242 | 82 |
| Example 249 | 88 |
| Example 257 | 51 |
| Example 258 | 76 |
| Example 262 | 91 |

As shown in above Table 8, the present invention compounds exhibited remarkable inhibiting activities against platelet coagulation. Thus compounds of the present invention may be useful as anti-coagulant agents.

Formulation Example 1

Hard Capsules

Single capsules are manufactured by adding 100 mg of the compound of Example 1, 150 mg of lactose, 50 mg of cellulose, and 6 mg of magnesium stearate into conventionally designated two-piece hard gelatin capsules, and after washing, the capsules are dried.

Formulation Example 2

Soft Capsules

Single soft capsules are manufactured by adding the compound of Example 2 mixed with digestive oily substance, for example lincoln bean oil, cottonseed oil, or olive oil and injecting into a gelatin capsule by positive displacement pump, and after washing, the capsules are dried.

Formulation Example 3

Tablets

According to conventional methods, tablets are prepared using 100 mg of the compound of Example 3, 0.2 mg of colloidal silica dioxide, 5 mg of magnesium stearate, 275 mg of microcrystalline cellulose, 11 mg of starch, and 98.8 mg of lactose.

When desired, the tablets are coated.

Formulation Example 4

Suspended Solution

Suspended solution is prepared with 100 mg of the micronized compound of Example 4, 100 mg of carboxymethylcellulose, 5 mg of sodium benzoate, 1.0 g of sorbitol solution (Japanese Pharmacopoeia), and 0.025 ml of vanillin.

Formulation Example 5

Cream

Cream is preparing by mixing 5 g of the micronized compound of Example 5 into cream containing white petrolatum, microcrystallized wax, lanolin, Span 20, Tween 20, and water at concentrations of 40, 3, 10, 5, 0.3, and 41.7%, respectively.

Formulation Example 6

Injection

Injection is prepared by stirring 1.5% by weight of the compound in Example 6 in 10% by weight of polyethyleneglycol, adjusting the volume to be consistent for injection, followed by sterilization.

ADVANTAGE OF THE INVENTION

The compounds of the present invention are chemically stable and exert excellent platelet anticoagulation activities and inhibiting action against thrombosis formation. Furthermore, the compounds of the present invention exert the said actions with short onset latencies and exhibit low toxicities. Thus the compounds of the present invention may be useful in the prophylactic, prevention of recurrence, and therapeutic settings (particularly the latter) against diseases induced by platelet activation such as thrombosis formation and platelet coagulation and releasing responses of platelets, for example in percutaneous coronary intervention (PCI), angioplasty, endarterectomy, restenosis after stenting, acute coronary syndrome, stable and unstable angina, myocardial infarction, atrial fibrillation, cerebral ischemic attack, cerebral infarction, and atherosclerosis and diseases induced by thrombosis formation or embolus formation that are associated with diabetes mellitus, peripheral arterial disease, heparin-induced thrombocytopenia (HIT), thrombotic thrombocytopenic purpura (TTP), antiphospholipid antibody syndrome, venous thrombosis, and ichorrhemia.

The invention claimed is:

1. A compound having the general formula (I) shown below,

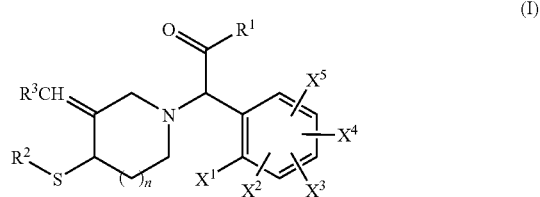

wherein, $R^1$ represents a hydrogen atom, a C1-C6 alkyl group which may be substituted (said substituent group represents a halogen atom or a C1-C6 alkoxy group), a C3-C6 cycloalkyl group which may be substituted (said substituent group represents a halogen atom or a C1-C6 alkoxy group), a C1-C6 alkoxy group which may be substituted (said substituent group represents a halogen atom or a C1-C6 alkoxy group) or a C6-C10 aryl group which may be substituted (said substituent group represents a halogen atom, a C1-C6 alkyl group, a C1-C6 alkoxy group, a cyano group or a nitro group);

$R^2$ represents a hydrogen atom, a C1-C7 alkanoyl group, a C7-C11 arylcarbonyl group, a group of formula $R^4$—$(CH_2)_l$—CO— (wherein $R^4$ represents a C1-C6 alkoxy group, an amino group, a C1-C6 alkylamino group, a di-(C1-C6 alkyl)amino group or a carboxyl group, and l represents an integer of from 0 to 4), a C6-C10 arylsulfonyl group, a C7-C16 alkylarylsulfonyl group, a C1-C6 alkylsulfanyl group or a C1-C6 alkylsulfanyl group substituted with 1 or 2 substituents selected from a group consisting of an amino group, a carboxyl group, a C1-C6 acylamino group and a C2-C7 alkoxycarbonyl group;

$R^3$ represents a C6-C10 aryl group, a C6-C10 aryl group substituted with from 1 to 5 substituents selected from <Substituent group α>, a heteroaryl group or a heteroaryl group substituted with from 1 to 5 substituents selected from <Substituent group α>;

$X^1, X^2, X^3, X^4$ and $X^5$ represent independently a hydrogen atom, a halogen atom, an amino group, a carboxyl group, a carbamoyl group, a cyano group, a nitro group, a C1-C6 alkyl group, a halogeno C1-C6 alkyl group, a C1-C6 alkoxy group or a halogeno C1-C6 alkoxy group;

n represents an integer of from 0 to 2; and

<Substituent group α> is defined by:

a halogen atom, an amino group, a carboxyl group, a carbamoyl group, a cyano group, a nitro group, a C1-C6 alkyl group, a halogeno C1-C6 alkyl group, a C1-C6 alkyl group substituted with heteroaryl group(s), a C1-C6 alkoxy group, a halogeno C1-C6 alkoxy group, a hydroxy C1-C6 alkyl group, a C2-C12 alkoxyalkyl group, a C2-C7 alkanoyl group, a C4-C7 cycloalkylcarbonyl group, a C1-C6 alkylamino group, a di-(C1-C6 alkyl)amino group, a C2-C7 alkylcarbamoyl group, a di-(C1-C6 alkyl)carbamoyl group, a group of formula $R^5$—CO—CHR$^6$—$(CH_2)_m$— (wherein $R^5$ represents a hydroxyl group, an amino group, a C1-C6 alkyl group, a C1-C6 alkylamino group, a di-(C1-C6 alkyl)amino group, a hydroxyamino group, a C1-C6 alkoxyamino group or a C1-C6 alkoxy group;

$R^6$ represents a hydrogen atom, a C1-C6 alkyl group, a C2-C7 carboxyalkyl group or a C3-C13 alkoxycarbonylalkyl group; and m represents an integer of from 0 to 5) and a sulfamoyl C1-C6 alkyl group, or pharmacologically acceptable salts thereof.

2. A compound according to claim 1 wherein $R^1$ represents a C1-C6 alkyl group, a halogeno C1-C6 alkyl group, a C3-C6 cycloalkyl group, a halogeno C3-C6 cycloalkyl group or a C1-C6 alkoxy group, or pharmacologically acceptable salts thereof.

3. A compound according to claim 1 wherein $R^1$ represents a C3-C6 cycloalkyl group, a halogeno C3-C6 cycloalkyl group or a C1-C6 alkoxy group, or pharmacologically acceptable salts thereof.

4. A compound according to claim 1 wherein $R^1$ represents a C3-C6 cycloalkyl group or a C1-C6 alkoxy group, or pharmacologically acceptable salts thereof.

5. A compound according to claim 1 wherein $R^1$ represents a cyclopropyl group or a methoxy group, or pharmacologically acceptable salts thereof.

6. A compound according to claim 1 wherein $R^1$ represents a cyclopropyl group, or pharmacologically acceptable salts thereof.

7. A compound according to claim 1 wherein $R^2$ represents a hydrogen atom or a C2-C7 alkanoyl group, or pharmacologically acceptable salts thereof.

8. A compound according to claim 1 wherein $R^2$ represents a hydrogen atom or an acetyl group, or pharmacologically acceptable salts thereof.

9. A compound according to claim 1 wherein $R^2$ represents a hydrogen atom, or pharmacologically acceptable salts thereof.

10. A compound according to claim 1 wherein $R^3$ represents a heteroaryl group or a heteroaryl group substituted with 1 or 2 substituents selected from <Substituent group α>, or pharmacologically acceptable salts thereof.

11. A compound according to claim 1 wherein $R^3$ represents a heteroaryl group or a heteroaryl group substituted with one substituent selected from <Substituent group α>, or pharmacologically acceptable salts thereof.

12. A compound according to claim 1 wherein $R^3$ represents a heteroaryl group substituted with one substituent selected from <Substituent group α>, or pharmacologically acceptable salts thereof.

13. A compound according to claim 1 wherein $R^3$ represents a heteroaryl group substituted with one substituent selected from <Substituent group α>, and said substituent selected from <Substituent group α> represents a group of formula $R^5$—CO—$CHR^6$—$(CH_2)_m$— (wherein $R^5$ represents a hydroxyl group, an amino group, a C1-C6 alkyl group, a C1-C6 alkylamino group, a di-(C1-C6 alkyl)amino group, a hydroxyamino group, a C1-C6 alkoxyamino group or a C1-C6 alkoxy group; $R^6$ represents a hydrogen atom; and m represents an integer of from 0 to 5), or pharmacologically acceptable salts thereof.

14. A compound according to claim 1 wherein $R^3$ represents a heteroaryl group substituted with one substituent selected from <Substituent group α>, and said substituent selected from <Substituent group α> represents a group of formula $R^5$—CO—$CHR^6$—$(CH_2)_m$— (wherein $R^5$ represents a hydroxyl group, a hydroxyamino group, a C1-C6 alkoxyamino group or a C1-C6 alkoxy group; $R^6$ represents a hydrogen atom; and m represents an integer of from 0 to 5), or pharmacologically acceptable salts thereof.

15. A compound according to claim 1 wherein $R^3$ represents a heteroaryl group substituted with one substituent selected from <Substituent group α>, and said substituent selected from <Substituent group α> represents a group of formula $R^5$—CO—$CHR^6$—$(CH_2)_m$— (wherein $R^5$ represents a hydroxyl group; $R^6$ represents a hydrogen atom; and m represents an integer of from 0 to 2), or pharmacologically acceptable salts thereof.

16. A compound according to claim 1 wherein a heteroaryl group of $R^3$ represents a furyl group, thienyl group, pyrrolyl group, pyrazolyl group, imidazolyl group, oxazolyl group, isoxazolyl group, thiazolyl group, triazolyl group, tetrazolyl group, thiadiazolyl group, oxadiazolyl group, pyridyl group, pyridazinyl group, pyrimidinyl group, pyrazinyl group, indolyl group or quinolyl group, or pharmacologically acceptable salts thereof.

17. A compound according to claim 1 wherein a heteroaryl group of $R^3$ represents a pyrrolyl group, pyrazolyl group, imidazolyl group, triazolyl group or tetrazolyl group, or pharmacologically acceptable salts thereof.

18. A compound according to claim 1 wherein a heteroaryl group of $R^3$ represents a pyrazolyl group, triazolyl group or tetrazolyl group, or pharmacologically acceptable salts thereof.

19. A compound according to claim 1 wherein $X^1$, $X^2$, $X^3$, $X^4$ and $X^5$ represent independently a hydrogen atom or a halogen atom, or pharmacologically acceptable salts thereof.

20. A compound according to claim 1 wherein $X^1$ and $X^2$ represent independently a hydrogen atom or a halogen atom and $X^3$, $X^4$ and $X^5$ represent a hydrogen atom, or pharmacologically acceptable salts thereof.

21. A compound according to claim 1 wherein $X^1$ represents a halogen atom, and $X^2$, $X^3$, $X^4$ and $X^5$ represent a hydrogen atom, or pharmacologically acceptable salts thereof.

22. A compound according to claim 1 wherein $X^1$ represents a fluorine atom, and $X^2$, $X^3$, $X^4$ and $X^5$ represent a hydrogen atom, or pharmacologically acceptable salts thereof.

23. A compound according to claim 1 wherein n represents 0 or 1, or pharmacologically acceptable salts thereof.

24. A compound according to claim 1 wherein n represents 1, or pharmacologically acceptable salts thereof.

25. A compound according to claim 1 wherein said compound is selected from the following compounds, or pharmacologically acceptable salts thereof:

(E)-3-{[1-(carboxymethyl)-1H-pyrazol-3-yl]methylidene}-1-[2-cyclopropyl-1-(2-fluorophenyl)-2-oxoethyl]-4-sulfanylpiperidine, (E)-3-{[1-(2-carboxyethyl)-1H-pyrazol-3-yl]methylidene}-1-[2-cyclopropyl-1-(2-fluorophenyl)-2-oxoethyl]-4-sulfanylpiperidine, (E)-3-{[1-(3-carboxypropyl)-1H-pyrazol-3-yl]methylidene}-1-[2-cyclopropyl-1-(2-fluorophenyl)-2-oxoethyl]-4-sulfanylpiperidine, (E)-3-{[1-(carboxymethyl)-1H-pyrazol-4-yl]methylidene}-1-[2-cyclopropyl-1-(2-fluorophenyl)-2-oxoethyl]-4-sulfanylpiperidine, (E)-3-[1-(2-carboxyethyl)-1H-pyrazol-4-yl]methylidene 1-[2-cyclopropyl-1-(2-fluorophenyl)-2-oxoethyl]-4-sulfanylpiperidine, (E)-3-{[1-(3-carboxypropyl)-1H-pyrazol-4-yl]methylidene}-1-[2-cyclopropyl-1-(2-fluorophenyl)-2-oxoethyl]-4-sulfanylpiperidine, (E)-3-{[1-(carboxymethyl)-1H-1,2,3-triazol-4-yl]methylidene}-1-[2-cyclopropyl-1-(2-fluorophenyl)-2-oxoethyl]-4-sulfanylpiperidine, (E)-3-{[1-(2-carboxyethyl)-1H-1,2,3-triazol-4-yl]methylidene}-1-[2-cyclopropyl-1-(2-fluorophenyl)-2-oxoethyl]-4-sulfanylpiperidine, (E)-3-{[1-(3-carboxypropyl)-1H-1,2,3-triazol-4-yl]methylidene}-1-[2-cyclopropyl-1-(2-fluorophenyl)-2-oxoethyl]-4-sulfanylpiperidine, (E)-3-{[1-(4-carboxybutyl)-1H-1,2,3-triazol-4-yl]methylidene}1-[2-cyclopropyl-1-(2-fluorophenyl)-2-oxoethyl]-4-sulfanylpiperidine, (E)-3-{[1-(carboxymethyl)-1H-1,2,3-triazol-5-yl]methylidene}-1-[2-cyclopropyl-1-(2-fluorophenyl)-2-oxoethyl]-4-sulfanylpiperidine, (E)-3-{[1-(2-carboxyethyl)-1H-1,2,3-triazol-5-yl]methylidene}-1-[2-cyclopropyl-1-(2-fluorophenyl)-2-oxoethyl]-4-sulfanylpiperidine, (E)-3-{[1-(3-carboxypropyl)-1H-1,2,3-triazol-5-yl]methylidene}-1-[2-cyclopropyl-1-(2-fluorophenyl)-2-oxoethyl]-4-sulfanylpiperidine, (E)-3-{[1-(4-carboxybutyl)-1H-1,2,3-triazol-5-yl]methylidene}-1-[2-cyclopropyl-1-(2-fluorophenyl)-2-oxoethyl]-4-sulfanylpiperidine, (E)-3-{[2-(carboxymethyl)-2H-1,2,3-triazol-4-yl]methylidene}-1-[2-cyclopropyl-1-(2-fluorophenyl)-2-oxoethyl]-4-sulfanylpiperidine, (E)-3-{[2-(2-carboxyethyl)-2H-1,2,3-triazol-4-yl]methylidene}-1-[2-cyclopropyl-1-(2-fluorophenyl)-2-oxoethyl]-4-sulfanylpiperidine, (E)-3-{[3-(3-carboxypropyl)-2H-1,2,3-triazol-4-yl]methylidene}-1-[2-cyclopropyl-1-(2-fluorophenyl)-2-oxoethyl]-4-sulfanylpiperidine, (E)-3-{[1-(carboxymethyl)-1H-tetrazol-5-yl]methylidene}-1-[2-cyclopropyl-1-(2-fluorophenyl)-2-oxoethyl]-4-sulfanylpiperidine, (E)-3-{[1-(2-carboxyethyl)-1H-tetrazol-5-yl]methylidene}-1-[2-cyclopropyl-1-(2-fluorophenyl)-2-oxoethyl]-4-sulfanylpiperidine, (E)-3-{[1-(3-carboxypropyl)-1H-tetrazol-5-yl]methylidene}-1-[2-cyclopropyl-1-(2-fluorophenyl)-2-oxoethyl]-4-sulfanylpiperidine, (E)-3-{[1-(4-carboxybutyl)-1H-tetrazol-5-yl]methylidene}-1-[2-cyclopropyl-1-(2-fluorophenyl)-2-oxoethyl]-4-sulfanylpiperidine, (E)-3-{[2-(carboxymethyl)-2H-tetrazol-5-yl]methylidene}-1-[2-cyclopropyl-1-(2-fluorophenyl)-2-oxoethyl]-4-sulfanylpiperidine, (E)-3-{[2-(2-carboxyethyl)-2H-tetrazol-5-yl]methylidene}-1-[2-cyclopropyl-1-(2-fluorophenyl)-2-oxoethyl]-4-sulfanylpiperidine, (E)-3-{[2-(3-carboxypropyl)-2H-tetrazol-5-yl]methylidene}-1-[2-cyclopropyl-1-(2-fluorophenyl)-2-oxoethyl]-4-sulfanylpiperidine, (E)-3-{[2-(4-carboxybutyl)-2H-tetrazol-5-yl]methylidene}-1-[2-cyclopropyl-1-(2-fluorophenyl)-2-oxoethyl]-4-sulfanylpiperidine, (E)-1-{[1-(2-fluorophenyl)-2-methoxy-2-oxoethyl]-3-[1-(2-carboxyethyl)-1H-pyrazol-3-yl]methylidene}-4-sulfanylpiperidine, (E)-1-[1-(2-fluorophenyl)-2-methoxy-2-oxoethyl]-3-[1-(3-carboxypropyl)-1H-pyrazol-3-yl]methylidene-4-sulfanylpiperidine, (E)-1-{[1-(2-fluorophenyl)-2-methoxy-2-oxoethyl]-3-[1-(2-carboxyethyl)-1H-pyrazol-4-yl]methylidene}-4-sulfanylpiperidine, (E)-1-[1-(2-fluorophenyl)-2-methoxy-2-oxoethyl]-3-[1-(3-carboxypropyl)-1H-pyrazol-4-yl]methylidene-4-sulfanylpiperidine, (E)-1-{[1-(2-fluorophenyl)-2-methoxy-2-oxoethyl]-3-{[1-(2-carboxyethyl)-1H-pyrazol-5-yl]methylidene-4-sulfanylpiperidine, (E)-1-[1-(2-fluorophenyl)-2-methoxy-2-oxoethyl]-3-{[1-(3-carboxypropyl)-1H-pyrazol-5-yl]methylidene}-4-sulfanylpiperidine, (E)-1-[1-(2-fluorophenyl)-2-methoxy-2-oxoethyl]-3-{[1-(2-carboxyethyl)-1H-1,2,3-triazol-4-yl]methylidene}-4-sulfanylpiperidine, (E)-1-{[1-(2-fluorophenyl)-2-methoxy-2-oxoethyl]-3-[1-(3-carboxypropyl)-1H-1,2,3-triazol-4-yl]methylidene}-4-sulfanylpiperidine, (E)-1-{[1-(2-fluorophenyl)-2-methoxy-2-oxoethyl]-3-[1-(2-carboxyethyl)-1H-1,2,3-triazol-5-yl]methylidene}-4-sulfanylpiperidine, (E)-1-[1-(2-fluorophenyl)-2-methoxy-2-oxoethyl]-3-{[1-(3-carboxypropyl)-1H-1,2,3-triazol-5-yl]methylidene}-4-sulfanylpiperidine, (E)-1-[1-(2-fluorophenyl)-2-methoxy-2-oxoethyl]-3-{[1-(2-carboxyethyl)-1H-tetrazol-5-yl]methylidene}-4-sulfanylpiperidine, (E)-1-[1-(2-fluorophenyl)-2-methoxy-2-oxoethyl]-3-{[1-(3-carboxypropyl)-1H-tetrazol-5-yl]methylidene}-4-sulfanylpiperidine, (E)-1-[1-(2-fluorophenyl)-2-methoxy-2-oxoethyl]-3-{[2-(2-carboxyethyl)-2H-tetrazol-5-yl]methylidene}-4-sulfanylpiperidine, and (E)-1-{[1-(2-fluorophenyl)-2-methoxy-2-oxoethyl]-3-[2-(3-carboxypropyl)-2H-tetrazol-5-yl]methylidene}-4-sulfanylpiperidine.

26. A pharmaceutical composition containing an effective amount of a compound according to any one of claims 1 to 25, or pharmacologically acceptable salts thereof or prodrugs thereof and a pharmaceutically acceptable carrier.

27. A pharmaceutical composition according to claim 26 wherein the pharmaceutical composition comprising the effective amount is for inhibiting against thrombus or embolus formation.

28. A method for inhibiting against thrombosis formation comprising administering an anticoagulating effective amount of a compound according to any one of claims 1 to 25, or pharmacologically acceptable salts thereof to warm-blooded animals.

29. A method according to claim 28 wherein the inhibition is against embolus formation.

30. A method according to claim 28 wherein the warm-blooded animals are humans.

31. The compound according to claim 1, wherein said compound is (E)-4-(acetylsulfanyl)-3-{1-(carboxymethyl)-1H-pyrazol-3-yl]methylidene}-1-[2-cyclopropyl-1-(2-fluorophenyl)-2-oxoethyl]piperidine or pharmacologically acceptable salts thereof.

32. A pharmaceutical composition comprising an effective amount of the compound according to claim 31 and a pharmaceutically acceptable carrier.

33. The pharmaceutical composition according to claim 32, wherein the pharmaceutical composition comprising the effective amount is for inhibiting against thrombus or embolus formation.

34. A method for inhibiting against thrombosis formation comprising administering an anticoagulating effective amount of the compound according to claim 31 to a warm-blooded animal in need thereof.

35. The method according to claim 34, wherein the inhibition is against embolus formation.

36. The method according to claim 35, wherein the warm-blooded animal is human.

37. The compound according to claim 1, wherein said compound is (E)-3-[1-(carboxymethyl)-1H-pyrazol-3-yl]methylidene)-1-[2-cyclopropyl-1-(2-fluorophenyl)-2-oxoethyl]-4-sulfanylpiperidine or pharmacologically acceptable salts thereof.

38. A pharmaceutical composition comprising an effective amount of the compound according to claim 37 and a pharmaceutically acceptable carrier.

39. The pharmaceutical composition according to claim 38, wherein the pharmaceutical composition comprising the effective amount is for inhibiting against thrombus or embolus formation.

40. A method for inhibiting against thrombosis formation comprising administering an anticoagulating effective amount of the compound according to claim 37 to a warm-blooded animal in need thereof.

41. The method according to claim 40, wherein the inhibition is against embolus formation.

42. The method according to claim 41, wherein the warm-blooded animal is human.

43. The compound according to claim 1, wherein said compound is (E)-3-[[1-(2-carboxyethyl)-1H-pyrazol-3-yl]methylidene)-1-[2-cyclopropyl-1-(2-fluorophenyl)-2-oxoethyl]4-sulfanylpiperidine or pharmacologically acceptable salts thereof.

44. A pharmaceutical composition comprising an effective amount of the compound according to claim 43 and a pharmaceutically acceptable carrier.

45. The pharmaceutical composition according to claim 44 wherein the pharmaceutical composition comprising the effective amount is for inhibiting against thrombus or embolus formation.

46. A method for inhibiting against thrombosis formation comprising administering an anticoagulating effective amount of the compound according to claim 43 to a warm-blooded animal in need thereof.

47. The method according to claim 46, wherein the inhibition is against thrombus or embolus formation.

48. The method according to claim 47, wherein the warm-blooded animal is human.

49. The compound according to claim 1, wherein said compound is (E)-4-(acetylsulfanyl)-3-{[1-(2-carboxyethyl)-1H-pyrazol-3-yl]methylidene}-1-[2-cyclopropyl-1-(2-fluorophenyl)-2-oxoethyl]piperidine or pharmacologically acceptable salts thereof.

50. A pharmaceutical composition comprising an effective amount of the compound according to claim 49 and a pharmaceutically acceptable carrier.

51. The pharmaceutical composition according to claim 50 wherein the pharmaceutical composition comprising the effective amount is for inhibiting, against thrombus or embolus formation.

52. A method for inhibiting against thrombosis formation comprising administering an anticoagulating effective amount of the compound according to claim 49 to a warm-blooded animal in need thereof.

53. The method according to claim 52, wherein the inhibition is against embolus formation.

54. The method according to claim 53, wherein the warm-blooded animal is human.

55. The compound according to claim 1, wherein said compound is (E)-3-{[1-(2-carboxyethyl)-1H-1,2,3-triazol-5-yl]methylidene}-[2-cyclopropyl-1-(2-fluorophenyl)-2-oxo-ethyl]-4-sulfanylpiperidine or pharmacologically acceptable salts thereof.

56. A pharmaceutical composition comprising an effective amount of the compound according to claim 55 and a pharmaceutically acceptable carrier.

57. The pharmaceutical composition according to claim 56 wherein the pharmaceutical composition comprising the effective amount is for inhibiting thrombus or embolus formation.

58. A method for inhibiting against thrombosis formation comprising administering an anticoagulating effective amount of the compound according to claim 55 to a warm-blooded animal in need thereof.

59. The method according to claim 58, wherein the inhibition is against embolus formation.

60. The method according to claim 59, wherein the warm-blooded animal is human.

61. The compound according to claim 1, wherein said compound is (E)-3-{[1-(3-carboxypropyl)-1H-1,2,3-triazol-4yl]methylidene}-1-[2-cyclopropyl-1-(2-fluorophenyl)-2-oxoethyl]-4-sulfanylpiperidine or pharmacologically acceptable salts thereof.

62. A pharmaceutical composition comprising an effective amount of the compound according to claim 61 and a pharmaceutically acceptable carrier.

63. The pharmaceutical composition according to claim 62 wherein the pharmaceutical composition comprising the effective amount is for inhibiting against thrombus or embolus formation.

64. A method for inhibiting against thrombosis formation comprising administering an anticoagulating effective amount of the compound according to claim 61 to a warm-blooded animal in need thereof.

65. The method according to claim 64, wherein the inhibition is against embolus formation.

66. The method according to claim 65, wherein the warm-blooded animal is human.

67. The compound according to claim 1, wherein said compound is (E)-4-(acetylsulfanyl)-3-{[1-(3-carboxypropyl)-1H-1,2,3-triazol-4-yl]methylidene}-1-[2-cyclopropyl-1-(2-fluorophenyl)-2-oxoethyl]piperidine or pharmacologically acceptable salts thereof.

68. A pharmaceutical composition comprising an effective amount of the compound according to claim 67 and a pharmaceutically acceptable carrier.

69. The pharmaceutical composition according to claim 68 wherein the pharmaceutical composition comprising the effective amount is for inhibiting against thrombus or embolus formation.

70. A method for inhibiting against thrombosis formation comprising administering an anticoagulating effective amount of the compound according to claim 67 to a warm-blooded animal in need thereof.

71. The method according to claim 70, wherein the inhibition is against embolus formation.

72. The method according to claim 71, wherein the warm-blooded animal is human.

* * * * *

UNITED STATES PATENT AND TRADEMARK OFFICE
CERTIFICATE OF CORRECTION

PATENT NO.         : 7,829,580 B2
APPLICATION NO.    : 11/442429
DATED              : November 9, 2010
INVENTOR(S)        : Tomio Kimura et al.

It is certified that error appears in the above-identified patent and that said Letters Patent is hereby corrected as shown below:

On page 2, in the OTHER PUBLICATIONS considered by the Examiner, the following two (2) references should be included:

-- Copy of English Translation of the International Preliminary Report on Patentability together with the Written Opinion of the International Search Authority as issued in Application PCT/JP2006/310556, dated November 29, 2007; which is the International application of the related US application No. 11/915,522 --

-- Copy of International Search Report as issued in Application PCT/JP2006/310556, dated July 25, 2006; which is the International application of the related US application No. 11/915,522 --

In Claim 25, Column 292, lines 59-61, the compound name should appear as follows:
(E)-3-{[1-(2-carboxyethyl)-1H-pyrazol-4-yl]
methylidene}-1-[2-cyclopropyl-1-(2-fluorophenyl)-2-oxoethyl]-4-sulfanylpiperidine, In claim 25, Column 293, lines 56-58, the compound name should appear as follows:
(E)-1-[1-(2-fluorophenyl)-2-methoxy-2-oxoethyl]-3-{[1-(2-carboxyethyl)-1H-pyrazol-3-yl]
methylidene}-4-sulfanylpiperidine, In Claim 25, Column 293, lines 62-64, the compound name should appear as follows:
(E)-1-[1-(2-fluorophenyl)-2-methoxy-2-oxoethyl]-3-{[1-(2-carboxyethyl)-1H-pyrazol-4-yl]
methylidene}-4-sulfanylpiperidine, In Claim 25, Column 294, lines 1-3, the compound name should appear as follows:
(E)-1-[1-(2-fluorophenyl)-2-methoxy-2-oxoethyl]-3-{[1-(2-carboxyethyl)-1H-pyrazol-5-yl]
methylidene}-4-sulfanylpiperidine, Signed and Sealed this
Fifth Day of April, 2011

David J. Kappos
*Director of the United States Patent and Trademark Office*

CERTIFICATE OF CORRECTION (continued)
U.S. Pat. No. 7,829,580 B2

In Claim 25, Column 294, lines 10-12, the compound name should appear as follows:
(E)-1-[1-(2-fluorophenyl)-2-methoxy-2-oxoethyl]-3-{[1-(3-carboxypropyl)-1H-1,2,3-triazol-4-yl]
methylidene}-4-sulfanylpiperidine, In Claim 25, Column 294, lines 13-15, the compound name should appear as follows:
(E)-1-[1-(2-fluorophenyl)-2-methoxy-2-oxoethyl]-3-{[1-(2-carboxyethyl)-1H-1,2,3-triazol-5-yl]
methylidene}-4-sulfanylpiperidine, In Claim 25, Column 294, lines 28-30, the compound name should appear as follows:
(E)-1-[1-(2-fluorophenyl)-2-methoxy-2-oxoethyl]-3-{[2-(3-carboxypropyl)-2H-tetrazol-5-yl]
methylidene}-4-sulfanylpiperidine, In Claim 26, Column 294, lines 33-34, delete "or prodrugs thereof".

In Claim 37, Column 295, lines 2-4, the compound name should appear as follows:
(E)-3-{[1-(carboxymethyl)-1H-pyrazol-3-yl]
methylidene}-1-[2-cyclopropyl-1-(2-fluorophenyl)-2-oxoethyl]-4-sulfanylpiperidine In Claim 43, Column 295, lines 22-24, the compound name should appear as follows:
(E)-3-{[1-(2-carboxyethyl)-1H-pyrazol-3-yl]
methylidene}-1-[2-cyclopropyl-1-(2-fluorophenyl)-2-oxoethyl]-4-sulfanylpiperidine In Claim 55, Column 296, lines 2-4, the compound name should appear as follows:
(E)-3-{[1-(2-carboxyethyl)-1H-1,2,3-triazol-5-yl]
methylidene}-1-[2-cyclopropyl-1-(2-fluorophenyl)-2-oxoethyl]-4-sulfanylpiperidine